United States Patent
Lim et al.

(10) Patent No.: US 11,098,056 B2
(45) Date of Patent: Aug. 24, 2021

(54) UDP GLYCOSYLTRANSFERASE INHIBITORS AND METHODS OF USE

(71) Applicant: GENZYME CORPORATION, Cambridge, MA (US)

(72) Inventors: Sungtaek Lim, Bridgewater, NJ (US); Robert H. Barker, Jr., Bridgewater, NJ (US); Mary A. Cromwell, Bridgewater, NJ (US); Elina Makino, Bridgewater, NJ (US); Bradford Hirth, Bridgewater, NJ (US); John Jiang, Bridgewater, NJ (US); Sachin Maniar, Bridgewater, NJ (US); Mark Munson, Bridgewater, NJ (US); Yong-Mi Choi, Bridgewater, NJ (US); Sukanthini Thurairatnam, Bridgewater, NJ (US); Kwon Yon Musick, Bridgewater, NJ (US); James Pribish, Bridgewater, NJ (US); Michael Angelastro, Bridgewater, NJ (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 16/590,027

(22) Filed: Oct. 1, 2019

(65) Prior Publication Data

US 2020/0102324 A1 Apr. 2, 2020

Related U.S. Application Data

(60) Provisional application No. 62/739,405, filed on Oct. 1, 2018.

(51) Int. Cl.
 *C07D 495/04* (2006.01)
 *C07D 519/00* (2006.01)
(52) U.S. Cl.
 CPC ......... *C07D 495/04* (2013.01); *C07D 519/00* (2013.01)

(58) Field of Classification Search
 CPC .......................... C07D 495/04; C07D 519/00
 See application file for complete search history.

(56) References Cited

U.S. PATENT DOCUMENTS

| | | | | |
|---|---|---|---|---|
| 3,763,156 A | * | 10/1973 | Narr et al. | C07D 495/04 544/117 |
| 2011/0092499 A1 | | 4/2011 | Bourke et al. | |
| 2017/0355702 A1 | | 12/2017 | Skerlj et al. | |
| 2019/0022074 A1 | | 1/2019 | Hadari et al. | |
| 2019/0134005 A1 | | 5/2019 | Wang | |
| 2019/0218229 A1 | | 7/2019 | Hadari et al. | |
| 2019/0322676 A1 | | 10/2019 | Wang | |

FOREIGN PATENT DOCUMENTS

| | | |
|---|---|---|
| WO | WO 2001/10842 | 2/2001 |
| WO | WO2001/010842 A1 * | 2/2015 |
| WO | WO 2018/203298 | 11/2018 |

OTHER PUBLICATIONS

CAS Registry, entered Apr. 29, 2009, RN: 677706-92-2.

\* cited by examiner

*Primary Examiner* — Timothy R Rozof
(74) *Attorney, Agent, or Firm* — Hoxie & Associates LLC

(57) ABSTRACT

Described herein is a compound of Formula (I),

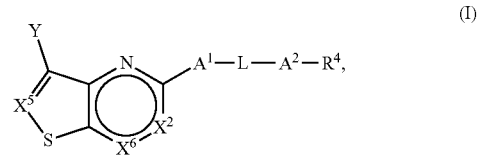

and pharmaceutically acceptable salts thereof. Also described herein are compositions and the use of such compositions in methods of treating a variety of diseases and conditions, in particular Krabbe's Disease (KD) and Metachromatic leukodystrophy (MLD).

30 Claims, No Drawings

UDP GLYCOSYLTRANSFERASE INHIBITORS AND METHODS OF USE

This application is national application under 35 U.S.C. § 111(a) claiming priority to and the benefit of U.S. Provisional Application No. 62/739,405, filed on Oct. 1, 2018, the contents of which are hereby incorporated by reference in its entirety.

BACKGROUND

UDP Glycosyltransferase 8 (UGT8) is an enzyme within the UDP-glycosyltransferase enzyme family. UGT8 catalyzes the transfer of galactose to ceramide, a key enzymatic step in the biosynthesis of galactoyslceramides. These molecules are abundant sphingolipids of the myelin membrane of the central and peripheral nervous systems. Galactocerebrosides also serve as precursors in the glycosphingolipid biosynthetic pathway and are further modified by cerebroside sulfotransferase, an enzyme which converts Galactocerebrosides to sulfatides. Sulfatides are also important components of the central nervous system (CNS) and peripheral nervous system (PNS) as a component of myelin, which is a crucial insulator sheath that surrounds axons as a bilayer membrane. The inappropriate recycling of sulfatides can result in the alteration of the myelin structure, affecting the physiological transmission of electrical impulse between nerve cells.

Krabbe's disease (KD) is a lysosomal storage disorder in which galactosylceramide (a specific galactocerebroside) and psychosine cannot be adequately degraded because of a deficiency in the galactosylceramidase enzyme. To allow for the correction of the balance between formation and degradation of galactosylceramide and psychosine, a reduced biosynthesis of glycosphingolipids by the inhibition of UGT8 is considered a validated therapeutic approach.

Metachromatic leukodystrophy (MLD) is an autosomal recessive lysosomal storage disorder caused by the deficiency of arylsulfatase A (ASA), a lysosomal sulfatase that hydrolyzes the 3-O ester bond from sulfatides including 3-O-sulfogalactosylceramide and 3-O-sulfolactosylceramide. The deficiency expressed in MLD causes a buildup of sulfatides within the CNS and PNS. To allow for correction of the resulting sulfatide buildup, a therapeutic approach similar to Krabbe's via the inhibition of UGT8 (and the resulting production of sulfatides) has been proposed.

Despite the awareness and research conducted on both Krabbe's and MLD, there are no cures for these fatal and debilitating diseases. Thus, identification of new compounds and new methods of therapy are needed as well as new methods for treating or lessening the severity of Krabbe's, MLD and other conditions and disease related to UGT8 in a patient.

SUMMARY

In one aspect, the present application is directed to a compound of Formula (I):

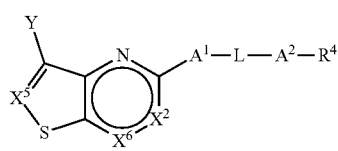

(I)

or a pharmaceutically acceptable salt or prodrug thereof, wherein:
(a) $X^2$ is $CR^2$ or N;
(b) $X^5$ is $CR^7$ or N;
(c) $X^6$ is $CR^1$ or N;
(d) Y is —CN, $C_{1-4}$ alkyl, —C(O)NR$^a$R$^b$, —NR$^a$—C(O)—R$^b$, —C(O)OR$^a$, —C(O)R$^a$, heteroaryl or —S(O)$_2$NR$^a$R$^b$, wherein the $C_{1-4}$ alkyl or heteroaryl may be substituted with 0-3 occurrences of R$^z$;
(e) each R$^a$ is independently H, $C_{1-4}$ alkyl, $C_{1-4}$ haloalkyl, $C_{1-4}$ alkyl-$C_{3-9}$ cycloalkyl or $C_{3-9}$ cycloalkyl;
(f) each R$^b$ is independently $C_{1-4}$ alkyl, $C_{1-4}$ alkoxy, $C_{3-9}$ cycloalkyl or $C_{1-4}$ alkyl-$C_{1-4}$ alkoxy; or
  when Y is —C(O)NR$^a$R$^b$, R$^a$ and R$^b$ can be taken together with the nitrogen atom to which they are attached to form a heterocycloalkyl ring substituted with 0-3 occurrences of R$^x$;
(g) $R^7$ is hydrogen, $C_{1-4}$ alkyl, $C_{1-4}$ alkoxy, —S(O)$_2$—NR$^a$R$^b$— or heteroaryl;
(h) $R^1$ is hydrogen, halo, —OH, $C_{1-4}$ alkyl, $C_{1-4}$ alkoxy, $C_{1-4}$ haloalkyl, $C_{1-4}$ haloalkoxy, —NH$_3$, —NH($C_{1-4}$ alkyl) or —N($C_{1-4}$ alkyl)$_2$, $C_{3-9}$ cycloalkyl or heterocycloalkyl, wherein each —NH($C_{1-4}$ alkyl), cycloalkyl or heterocycloalkyl is substituted with 0-5 occurrences of R$^x$;
(i) $R^2$ is hydrogen, halo, —OH, $C_{1-4}$ alkyl, $C_{1-4}$ alkoxy or $C_{3-9}$ cycloalkyl;
(j) $A^1$ is a bond, $C_{1-4}$ alkylene, —O—, —O—$C_{1-4}$ alkylene, —$C_{2-4}$ alkenylene, —$C_{2-4}$ alkynylene, —NR$^a$, —NR$^a$—$C_{1-4}$ alkylene-, —S—, —S(O)—, —S(O)$_2$—, —C(O)—, —C(O)—O— or —O—C(O)—;
(k) L is aryl, heteroaryl, $C_{3-12}$ cycloalkyl, a 3-12 membered heterocycloalkyl or a 3-12 membered heterocycloalkenyl each of which may be substituted with 0-3 occurrences of R$^x$;
(l) $A^2$ is a bond, —O—, —NR$^a$—, —$C_{1-4}$-alkyl-NR$^a$—, —C(O)—, —$C_{1-4}$ alkyl-C(O)—, —O—C(O)—, —$C_{1-4}$ alkyl-O—C(O)—, —C(O)—O—, —$C_{1-4}$ alkyl-C(O)—O—, —O—C(O)—O—, —S(O)$_2$—, —NR$^a$—S(O)—, —$C_{1-4}$-alkyl-NR$^a$—S(O)—, —NR$^a$—S(O)$_2$—, —$C_{1-4}$-alkyl-NR$^a$—S(O)$_2$—, —C(O)—NR$^a$—, —$C_{1-4}$ alkyl-C(O)—NR$^a$—, —NR$^a$—C(O)—, —$C_{1-4}$-alkyl-NR$^a$—C(O)—, —O—C(O)—NR$^a$—, —$C_{1-4}$-alkyl-O—C(O)—NR$^a$—, —NR$^a$—C(O)—O— or —NR$^a$—C(O)—NR$^a$—, —NR$^a$—CH$_2$—C(O)—NR$^a$—, —O—CH$_2$—C(O)—NR$^a$—, —C(O)—O—CH$_2$—C(O)—, —C(O)—NR$^a$—CH$_2$—C(O)—;
(m) $R^4$ is hydrogen, —OH, $C_{1-6}$ alkyl, $C_{2-6}$ alkenyl, $C_{2-6}$ alkynyl, $C_{3-9}$ cycloalkyl, heterocycloalkyl, aryl or heteroaryl, wherein each alkyl, cycloalkyl, heterocycloalkyl, aryl or heteroaryl of R$^4$ is substituted with 0-5 occurrences of R$^5$;
(n) $R^5$ is OH, halo, CO$_2$H, $C_{1-4}$ alkyl, $C_{2-6}$ alkynyl, $C_{1-4}$ alkoxy, $C_{1-4}$ haloalkyl, —O—$C_{1-4}$ haloalkyl, —$C_{1-4}$ alkyl-O—$C_{1-4}$ alkyl, —S—$C_{1-4}$ alkyl, —S(O)$_2$—$C_{1-4}$ alkyl, —S(O)—$C_{1-4}$ alkyl, —N(R$^a$)$_2$, —CH$_2$N(R$^a$)$_2$, —N(R$^a$)—S(O)—$C_{1-4}$ alkyl, —N—(R$^a$)—S(O)$_2$—$C_{1-4}$ alkyl, —NO$_2$, —CN, —CH$_2$CN, $C_{3-9}$ cycloalkyl, —O—$C_{3-9}$ cycloalkyl, —$C_{1-4}$ alkyl-$C_{3-9}$ cycloalkyl, —O—$C_{1-4}$ alkyl-$C_{3-9}$ cycloalkyl, —$C_{1-4}$ alkyl-O—$C_{1-4}$ haloalkyl, heterocycloalkyl, —$C_{1-4}$ alkyl-heterocycloalkyl, aryl, —O-aryl, heteroaryl, —O-heteroaryl, $C_{1-4}$-alkyl-heteroaryl, aralkyl or —O-aralkyl, wherein each alkyl, aryl, heteroaryl, cycloalkyl or heterocycloalkyl is substituted with 0-3 occurrences of R$^w$;

(o) each $R^w$ is independently halo, —OH, $C_{1-4}$ alkyl, $C_{1-4}$ haloalkyl or —$C_{1-4}$ alkoxy;

(p) each $R^x$ is independently halo, —OH, $C_{1-4}$ alkyl, —$C_{1-4}$ alkoxy, —$C_{1-4}$ alkyl-O—$C_{1-4}$ alkyl, —C(O)—N(R$^a$)$_2$, —O—C(O)—N(R$^a$)$_2$, —N(R$^a$)$_2$, —CH$_2$N(R$^a$)$_2$, heterocycloalkyl, —O-heterocycloalkyl, —O-aryl or —O-heteroaryl; and (q) each $R^z$ is independently hydrogen, halo, —OH, $C_{1-4}$ alkyl, $C_{1-4}$ alkoxy or $C_{3-9}$ cycloalkyl.

Various embodiments of the application are described herein. It will be recognized that features specified in each embodiment may be combined with other specified features to provide further embodiments.

In some embodiments of the present disclosure, the compound of Formula I may be a compound of Formula Ia, as shown below:

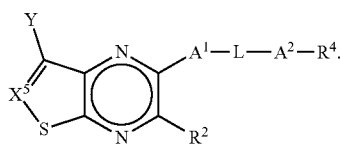
(Ia)

In some embodiments of the present disclosure, the compound of Formula I may be a compound of Formula Ib, as shown below:

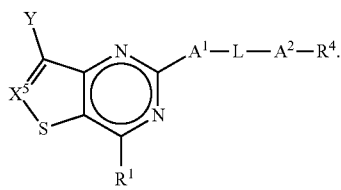
(Ib)

In some embodiments of the present disclosure, the compound of Formula I may be a compound of Formula Ic, as shown below:

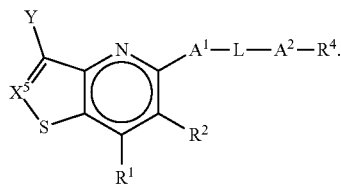
(Ic)

In some embodiments of the present disclosure, the compound of Formula I may be a compound of Formula Id, as shown below:

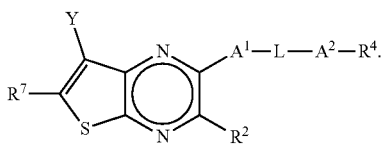
(Id)

In some embodiments of the present disclosure, the compound of Formula I may be a compound of Formula Ie, as shown below:

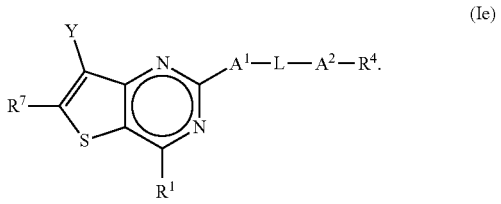
(Ie)

In some embodiments of the present disclosure, the compound of Formula I may be a compound of Formula If, as shown below:

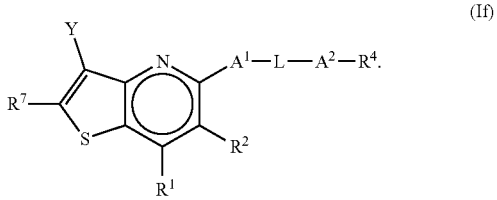
(If)

In some embodiments of the present disclosure, the compound of Formula I may be a compound of Formula II, IIa, IIb, or IIc, as shown below:

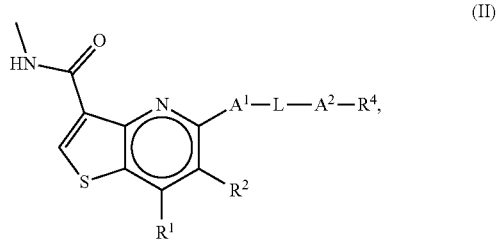
(II)

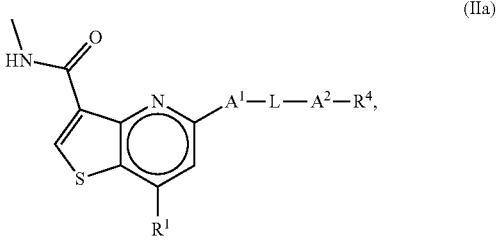
(IIa)

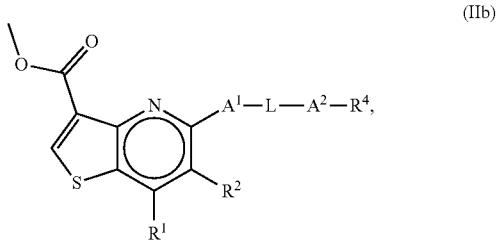
(IIb)

-continued

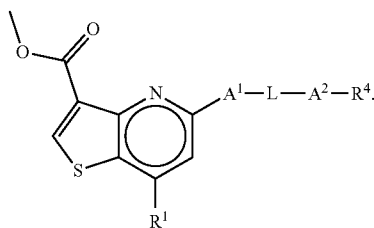
(IIc)

In some embodiments of the present disclosure, the compound of Formula I may be a compound of Formula III, IIIa, IIIb, or IIIc, as shown below:

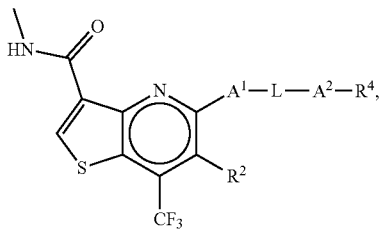
(III)

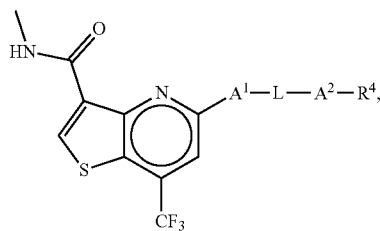
(IIIa)

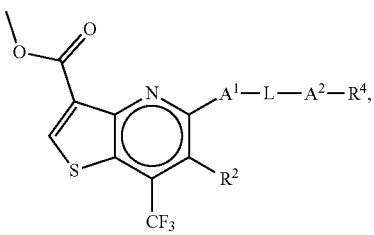
(IIIb)

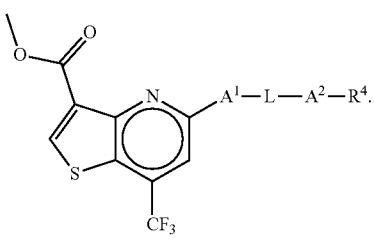
(IIIc)

DETAILED DESCRIPTION

A description of embodiments of the application follows.
In one aspect, the present application is directed to a compound (Compound 1) of Formula (I):

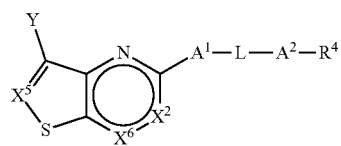
(I)

or a pharmaceutically acceptable salt or prodrug thereof, wherein:

(a) $X^2$ is $CR^2$ or N;
(b) $X^5$ is $CR^7$ or N;
(c) $X^6$ is $CR^1$ or N;
(d) Y is —CN, $C_{1-4}$ alkyl, —C(O)NR$^a$R$^b$, —NR$^a$—C(O)—R$^b$, —C(O)OR$^a$, —C(O)R$^a$, heteroaryl or —S(O)$_2$NR$^a$R$^b$, wherein the $C_{1-4}$ alkyl or heteroaryl may be substituted with 0-3 occurrences of R$^z$;
(e) each R$^a$ is independently H, $C_{1-4}$ alkyl, $C_{1-4}$ haloalkyl, —$C_{1-4}$ alkyl-$C_{3-9}$ cycloalkyl or $C_{3-9}$ cycloalkyl;
(f) Each R$^b$ is independently $C_{1-4}$ alkyl, $C_{1-4}$ alkoxy, $C_{3-9}$ cycloalkyl or —$C_{1-4}$ alkyl-$C_{1-4}$ alkoxy; or when Y is —C(O)NR$^a$R$^b$, R$^a$ and R$^b$ can be taken together with the nitrogen atom to which they are attached to form a heterocycloalkyl ring substituted with 0-3 occurrences of R$^x$;
(g) $R^7$ is hydrogen, $C_{1-4}$ alkyl, $C_{1-4}$ alkoxy, —S(O)$_2$—NR$^a$R$^b$— or heteroaryl;
(h) $R^1$ is hydrogen, halo, —OH, $C_{1-4}$ alkyl, $C_{1-4}$ alkoxy, $C_{1-4}$ haloalkyl, $C_{1-4}$ haloalkoxy, —NH$_3$, —NH($C_{1-4}$ alkyl) or —N($C_{1-4}$ alkyl)$_2$, $C_{3-9}$ cycloalkyl or heterocycloalkyl, wherein each —NH($C_{1-4}$ alkyl), cycloalkyl or heterocycloalkyl is substituted with 0-5 occurrences of R$^x$;
(i) $R^2$ is hydrogen, halo, —OH, $C_{1-4}$ alkyl, $C_{1-4}$ alkoxy or $C_{3-9}$ cycloalkyl;
(j) $A^1$ is a bond, $C_{1-4}$ alkylene, —O—, —O—$C_{1-4}$ alkylene, —$C_{2-4}$ alkenylene, —$C_{2-4}$ alkynylene, —NR$^a$—, —NR$^a$—$C_{1-4}$ alkylene-, —S—, —S(O)—, —S(O)$_2$—, —C(O)—, —C(O)—O— or —O—C(O)—;
(k) L is aryl, heteroaryl, $C_{3-12}$ cycloalkyl, a 3-12 membered heterocycloalkyl or a 3-12 membered heterocycloalkenyl each of which may be substituted with 0-3 occurrences of R$^x$;
(l) $A^2$ is a bond, —O—, —NR$^a$—, —$C_{1-4}$-alkyl-NR$^a$—, —C(O)—, —$C_{1-4}$ alkyl-C(O)—, —O—C(O)—, —$C_{1-4}$ alkyl-O—C(O)—, —C(O)—O—, —$C_{1-4}$ alkyl-C(O)—O—, —O—C(O)—O—, —S(O)$_2$—, —NR$^a$—S(O)—, —$C_{1-4}$-alkyl-NR$^a$—S(O)—, —NR$^a$—S(O)$_2$—, —$C_{1-4}$-alkyl-NR$^a$—S(O)$_2$—, —C(O)—NR$^a$—, —$C_{1-4}$ alkyl-C(O)—NR$^a$—, —NR$^a$—C(O)—, —$C_{1-4}$-alkyl-NR$^a$—C(O)—, —O—C(O)—NR$^a$—, —$C_{1-4}$-alkyl-O—C(O)—NR$^a$—, —NR$^a$—C(O)—O— or —NR$^a$—C(O)—NR$^a$—, —NR$^a$—CH$_2$—C(O)—NR$^a$—, —O—CH$_2$—C(O)—NR$^a$—, —C(O)—O—CH$_2$—C(O)—, —C(O)—NR$^a$—CH$_2$—C(O)—;
(m) $R^4$ is hydrogen, —OH, $C_{1-6}$ alkyl, $C_{2-6}$ alkenyl, $C_{2-6}$ alkynyl, $C_{3-9}$ cycloalkyl, heterocycloalkyl, aryl or heteroaryl, wherein each alkyl, cycloalkyl, heterocycloalkyl, aryl or heteroaryl of $R^4$ is substituted with 0-5 occurrences of $R^5$;

(n) $R^5$ is OH, halo, $CO_2H$, $C_{1-4}$ alkyl, $C_{2-6}$ alkynyl, $C_{1-4}$ alkoxy, $C_{1-4}$ haloalkyl, —O—$C_{1-4}$ haloalkyl, —$C_{1-4}$ alkyl-O—$C_{1-4}$ alkyl, —S—$C_{1-4}$ alkyl, —S(O)$_2$—$C_{1-4}$ alkyl, —S(O)—$C_{1-4}$ alkyl, —N(R$^a$)$_2$, —CH$_2$N(R$^a$)$_2$, —N(R$^a$)—S(O)—$C_{1-4}$ alkyl, —N—(R$^a$)—S(O)$_2$—$C_{1-4}$ alkyl, —NO$_2$, —CN, —CH$_2$CN, $C_{3-9}$ cycloalkyl, —O—$C_{3-9}$ cycloalkyl, —$C_{1-4}$ alkyl-$C_{3-9}$ cycloalkyl, —O—$C_{1-4}$ alkyl-$C_{3-9}$ cycloalkyl, —$C_{1-4}$ alkyl-O—$C_{1-4}$ haloalkyl, heterocycloalkyl, —$C_{1-4}$ alkyl-heterocycloalkyl, aryl, —O-aryl, heteroaryl, —O-heteroaryl, $C_{1-4}$-alkyl-heteroaryl, aralkyl or —O-aralkyl, wherein each alkyl, aryl, heteroaryl, cycloalkyl or heterocycloalkyl is substituted with 0-3 occurrences of $R^w$;

(o) each $R^w$ is independently halo, —OH, $C_{1-4}$ alkyl, $C_{1-4}$ haloalkyl or —$C_{1-4}$ alkoxy;

(p) each $R^x$ is independently halo, —OH, $C_{1-4}$ alkyl, —$C_{1-4}$ alkoxy, —$C_{1-4}$ alkyl-O—$C_{1-4}$ alkyl, —C(O)—N(R$^a$)$_2$, —O—C(O)—N(R$^a$)$_2$, —N(R$^a$)$_2$, —CH$_2$N(R$^a$)$_2$, heterocycloalkyl, —O— heterocycloalkyl, —O-aryl or —O-heteroaryl; and (q) each $R^z$ is independently hydrogen, halo, —OH, $C_{1-4}$ alkyl, $C_{1-4}$ alkoxy or $C_{3-9}$ cycloalkyl.

In particular embodiments of the first aspect, the present application further provides:

1.1 Compound 1, wherein $X^6$ is N.
1.2 Compound 1, wherein $X^6$ is $CR^1$.
1.3 Compound 1, 1.1 or 1.2, wherein $X^2$ is N.
1.4 Compound 1, 1.1 or 1.2, wherein $X^2$ is $CR^2$.
1.5 Any of Compound 1, or 1.1 et seq., wherein $X^2$ is $CR^2$ and $X^6$ is N (formula Ia).
1.6 Any of Compound 1, or 1.1 et seq., wherein $X^2$ is N and $X^6$ is $CR^1$ (formula Ib).
1.7 Any of Compound 1, or 1.1 et seq., wherein $X^2$ is $CR^2$ and $X^6$ is $CR^1$ (formula Ic).
1.8 Any of Compound 1, or 1.1 et seq., wherein $X^2$ is $CR^2$ and $X^6$ is N and $X^5$ is $CR^7$ (formula Id).
1.9 Any of Compound 1, or 1.1 et seq., wherein $X^2$ is N and $X^6$ is $CR^1$ and $X^5$ is $CR^7$ (formula Ie).
1.10 Any of Compound 1, or 1.1 et seq., wherein $X^2$ is $CR^2$ and $X^6$ is $CR^1$ and $X^5$ is $CR^7$ (formula If).
1.11 Any of Compound 1, or 1.1 et seq., wherein $R^2$ is hydrogen, $C_{1-4}$ alkyl (e.g., methyl) or halo (e.g., fluoro, chloro or bromo).
1.12 Any of Compound 1, or 1.1-1.11, wherein $R^2$ is hydrogen.
1.13 Any of Compound 1, or 1.1-1.11, wherein $R^2$ is halo, optionally wherein $R^2$ is selected from fluoro, chloro and bromo.
1.14 Any of Compound 1, or 1.1-1.11, wherein $R^2$ is $C_{1-4}$ alkyl, optionally wherein $R^2$ is methyl.
1.15 Any of Compound 1, or 1.1-1.11, wherein $R^2$ is $C_{1-4}$ alkoxy, optionally wherein $R^2$ is methoxy.
1.16 Any of Compound 1, or 1.1-1.11, wherein $R^2$ is $C_{3-9}$ cycloalkyl, optionally wherein $R^2$ is cyclopropyl.
1.17 Any of Compound 1, or 1.1-1.11, wherein $R^2$ is hydroxyl.
1.18 Any of Compound 1, or 1.1 et seq., wherein $R^7$ is $C_{1-4}$ alkyl, optionally wherein $R^7$ is methyl.
1.19 Any of Compound 1, or 1.1-1.17, wherein $R^7$ is hydrogen.
1.20 Any of Compound 1, or 1.1 et seq., wherein Y is CN.
1.21 Any of Compound 1, or 1.1 et seq., wherein Y is —C(O)R$^a$.
1.22 Compound 1.21, wherein R$^a$ is hydrogen.
1.23 Compound 1.21, wherein R$^a$ is $C_{1-4}$ alkyl, optionally wherein R$^a$ is methyl or R$^a$ is ethyl.
1.24 Any of Compound 1, or 1.1 et seq., wherein Y is —NR$^a$—C(O)—R$^b$.
1.25 Compound 1.24, wherein R$^a$ is hydrogen and R$^b$ is $C_{1-4}$ alkyl or $C_{1-4}$ alkoxy.
1.26 Compound 1.24, wherein R$^a$ is hydrogen and R$^b$ is $C_{1-4}$ alkyl, optionally wherein R$^b$ is methyl.
1.27 Compound 1.24, wherein R$^a$ is hydrogen and R$^b$ is $C_{1-4}$ alkoxy, optionally wherein R$^b$ is methoxy or R$^b$ is t-butoxy.
1.28 Any of Compound 1, or 1.1 et seq., wherein Y is heteroaryl substituted with 0-3 occurrences of $R^2$, e.g., wherein Y is heteroaryl substituted with 0 occurrences of $R^2$, or Y is heteroaryl substituted with 1 occurrence of $R^2$, optionally wherein any one or more of the $R^2$ are the same or different.
1.29 Compound 1.28, wherein Y is oxazolyl (e.g., 2-oxazolyl) substituted with 1 occurrence of $R^2$, optionally wherein Y is 4-methyl-2-oxazolyl or 5-methyl-2-oxazolyl.
1.30 Any of Compound 1, or 1.1 et seq., wherein Y is —C(O)OR$^a$.
1.31 Compound 1.30, wherein R$^a$ is hydrogen
1.32 Compound 1.30, wherein R$^a$ is $C_{1-4}$ alkyl (e.g., methyl or t-butyl), optionally wherein Y is —C(O)OMe.
1.33 Any of Compound 1, or 1.1 et seq., wherein Y is $C_{1-4}$ alkyl substituted with 0-3 occurrences of $R^2$, optionally wherein any one or more of the $R^2$ are the same or different.
1.34 Compound 1.33, wherein Y is $C_{1-4}$ alkyl (e.g., methyl or propyl) substituted with 0 occurrences of $R^2$ or with 1 occurrence of $R^2$, optionally wherein Y is methyl or propyl substituted with 0 occurrences of $R^2$ or with 1 occurrence of $R^2$.
1.35 Compound 1.34, wherein $R^2$ is —OH, optionally wherein Y is 1-hydroxypropyl.
1.36 Any of Compound 1, or 1.1 et seq., wherein Y is —C(O)NR$^a$R$^b$.
1.37 Compound 1.36, wherein R$^a$ is $C_{1-4}$ alkyl (e.g., methyl) and R$^b$ is $C_{1-4}$ alkyl (e.g., methyl).
1.38 Compound 1.36, wherein R$^a$ and R$^b$ are taken together with the nitrogen atom to which they are attached to form a heterocycloalkyl ring substituted with 0-3 occurrences of $R^x$, optionally 0 or 1 occurrences of $R^x$.
1.39 Compound 1.38, wherein R$^a$ and R$^b$ are taken together with the nitrogen atom to which they are attached to form an azetidine ring substituted with 0 or 1 occurrences of $R^x$, or to form a morpholine ring substituted with 0 or 1 occurrences of $R^x$.
1.40 Compound 1.38 or 1.39, wherein $R^x$ is halo (e.g., chloro).
1.41 Compound 1.38 or 1.39, wherein $R^x$ is $C_{1-4}$ alkoxy (e.g., methoxy).
1.42 Compound 1.38 or 1.39, wherein $R^x$ is —O-heteroaryl (e.g., —O-2-pyridyl).
1.43 Compound 1.36, wherein R$^a$ is hydrogen and R$^b$ is $C_{1-4}$ alkyl, $C_{1-4}$ alkoxy, $C_{3-9}$ cycloalkyl, or $C_{1-4}$ alkyl-$C_{1-4}$ alkoxy.
1.44 Compound 1.43, wherein R$^a$ is hydrogen and R$^b$ is $C_{1-4}$ alkoxy (e.g., methoxy).
1.45 Compound 1.43, wherein R$^a$ is hydrogen and R$^b$ is $C_{3-9}$ cycloalkyl (e.g., cyclopropyl).
1.46 Compound 1.43, wherein R$^a$ is hydrogen and R$^b$ is $C_{1-4}$ alkyl-$C_{1-4}$ alkoxy (e.g., 2-methoxyethyl).

1.47 Compound 1.43, wherein $R^a$ is hydrogen and $R^b$ is $C_{1-4}$ alkyl (e.g., methyl, ethyl, propyl, isopropyl or n-butyl), optionally wherein $R^a$ is hydrogen and $R^b$ is ethyl, or $R^a$ is hydrogen and $R^b$ is isopropyl, or $R^a$ is hydrogen and $R^b$ is n-butyl, or $R^a$ is hydrogen and $R^b$ is methyl.

1.48 Any of Compound 1, or 1.1 et seq., wherein $X^2$ is $CR^2$, $X^6$ is $CR^1$, $X^5$ is $CR^7$ and $R^7$ is hydrogen, and Y is —C(O)NR$^a$R$^b$ and $R^a$ is hydrogen and $R^b$ is methyl (formula II).

1.49 Compound 1.48, wherein $R^2$ is hydrogen (formula IIa).

1.50 Any of Compound 1, or 1.1 et seq., wherein $X^2$ is $CR^2$, $X^6$ is $CR^1$, $X^5$ is $CR^7$ and $R^7$ is hydrogen, and Y is —C(O)OR$^a$ and $R^a$ is methyl (formula IIb).

1.51 Compound 1.50, wherein $R^2$ is hydrogen (formula IIc).

1.52 Any of Compound 1, or 1.1 et seq., wherein $R^1$ is hydrogen, halo, (e.g., chloro), $C_{1-4}$ haloalkyl (e.g., difluoromethyl or trifluoromethyl).

1.53 Compound 1.52, wherein $R^1$ is hydrogen.

1.54 Compound 1.52, wherein $R^1$ is halo, optionally, wherein $R^1$ is chloro.

1.55 Any of Compound 1, or 1.1 et seq., wherein $R^1$ is —OH.

1.56 Any of Compound 1, or 1.1 et seq., wherein $R^1$ is —NH($C_{1-4}$ alkyl) (e.g., —NHMe).

1.57 Any of Compound 1, or 1.1 et seq., wherein $R^1$ is —N($C_{1-4}$ alkyl)$_2$ (e.g., —N(Me)$_2$).

1.58 Any of Compound 1, or 1.1 et seq., wherein $R^1$ is $C_{3-9}$ cycloalkyl substituted with 0-3 occurrences of $R^x$, optionally wherein $R^1$ is $C_{3-9}$ cycloalkyl substituted with 0 occurrences of $R^x$.

1.59 Compound 1.58, wherein $R^1$ is cyclopropyl or cyclopentyl substituted with 0 occurrences of $R^x$.

1.60 Any of Compound 1, or 1.1 et seq., wherein $R^1$ is heterocycloalkyl (e.g., azetidinyl) substituted with 0-3 occurrences of $R^x$.

1.61 Compound 1.60, wherein $R^1$ is azetidinyl substituted with 0-3 occurrences of $R^x$, optionally wherein $R^1$ is azetidinyl substituted with 0 or 2 occurrences of $R^x$.

1.62 Any of compounds 1.58-1.61, wherein each $R^x$ is independently halo (e.g., fluoro), for example, wherein $R^1$ is 2,2-difluoroazetidinyl.

1.63 Any of Compound 1, or 1.1 et seq., wherein $R^1$ is $C_{1-4}$ alkyl (e.g., methyl, isopropyl or t-butyl), optionally wherein $R^1$ is methyl, or $R^1$ is isopropyl, or $R^1$ is t-butyl.

1.64 Any of Compound 1, or 1.1 et seq., wherein $R^1$ is $C_{1-4}$ alkoxy, optionally wherein $R^1$ is methoxy.

1.65 Any of Compound 1, or 1.1 et seq., wherein $R^1$ is $C_{1-4}$ haloalkoxy (e.g., difluoromethoxy or 2,2,2-trifluoroethoxy), optionally wherein $R^1$ is difluoromethoxy or wherein $R^1$ is 2,2,2-trifluoroethoxy.

1.66 Any of Compound 1, or 1.1 et seq., wherein $R^1$ is $C_{1-4}$ haloalkyl, optionally wherein $R^1$ is trifluoromethyl or difluoromethyl or 1,1-difluoroethyl.

1.67 Any of Compound 1, or 1.1 et seq., wherein $X^2$ is $CR^2$, $X^6$ is $CR^1$ and $R^1$ is trifluoromethyl, $X^5$ is $CR^7$ and $R^7$ is hydrogen, and Y is —C(O)NR$^a$R$^b$ and $R^a$ is hydrogen and $R^b$ is methyl (formula III).

1.68 Compound 1.67, wherein $R^2$ is hydrogen (formula IIIa).

1.69 Any of Compound 1, or 1.1 et seq., wherein $X^2$ is $CR^2$, $X^6$ is $CR^1$ and $R^1$ is trifluoromethyl, $X^5$ is $CR^7$ and $R^7$ is hydrogen, and Y is —C(O)OR$^a$ and $R^a$ is methyl (formula IIIb).

1.70 Compound 1.69, wherein $R^2$ is hydrogen (formula IIIc).

1.71 Any of Compound 1, or 1.1 et seq., wherein $A^1$ is —O—, $C_{1-4}$ alkylene, —O—$C_{1-4}$ alkylene, a bond, —O—C(O)—, —C(O)—, —S—, —S(O)—, —S(O)$_2$—, $C_{2-4}$ alkynylene, —NR$^a$— or —NR$^a$—$C_{1-4}$ alkylene.

1.72 Compound 1.71, wherein $A^1$ is a bond, —O—, —O—$C_{1-4}$ alkylene or $C_{1-4}$ alkylene.

1.73 Compound 1.72, wherein $A^1$ is a bond or —O—.

1.74 Compound 1.73, wherein $A^1$ is a bond.

1.75 Compound 1.73, wherein $A^1$ is —O—.

1.76 Compound 1.72, wherein $A^1$ is $C_{1-4}$ alkylene, optionally wherein $A^1$ is —CH$_2$— or —CH(CH$_3$)—.

1.77 Any of Compound 1, or 1.1 et seq., wherein $A^1$ is —O—C(O)—.

1.78 Any of Compound 1, or 1.1 et seq., wherein $A^1$ is —S—, or $A^1$ is —S(O)$_2$—, or $A^1$ is —S(O)—.

1.79 Any of Compound 1, or 1.1 et seq., wherein $A^1$ is $C_{2-4}$ alkynylene, optionally wherein $A^1$ is —C≡C— or —C≡C—CH$_2$—.

1.80 Any of Compound 1, or 1.1 et seq., wherein $A^1$ is —NR$^a$—. 1.81 Any of Compound 1, or 1.1 et seq., wherein $A^1$ is —NR$^a$—$C_{1-4}$ alkylene-.

1.82 Any of Compound 1, or 1.1 et seq., wherein $A^1$ is —NR$^a$—CH$_2$—.

1.83 Any of Compound 1, or 1.1 et seq., wherein L is aryl or heteroaryl, each optionally substituted with 0-3 occurrences of $R^x$.

1.84 Any of Compound 1, or 1.1 et seq., wherein L is $C_{3-12}$ cycloalkyl, optionally substituted with 0-3 occurrences of $R^x$.

1.85 Any of Compound 1, or 1.1 et seq., wherein L is a 3-12 membered heterocycloalkyl or a 3-12 membered heterocycloalkenyl, optionally substituted with 0-3 occurrences of $R^x$.

1.86 Any of Compound 1, or 1.1 et seq., wherein L is selected from:

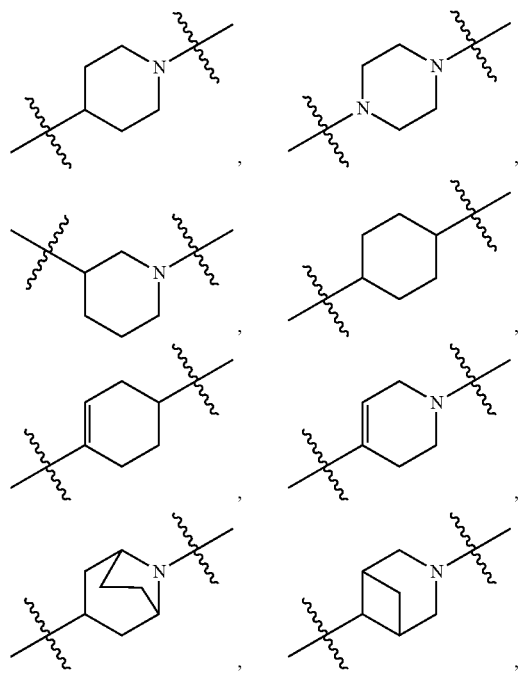

-continued
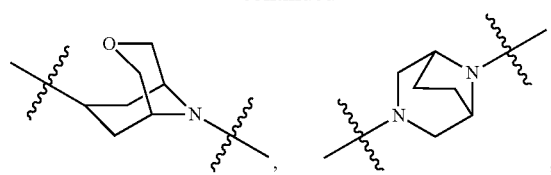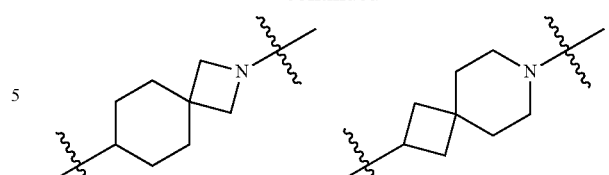
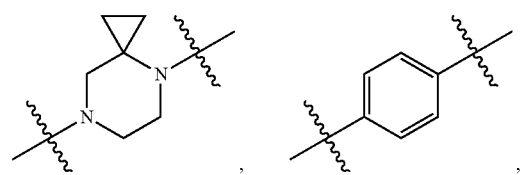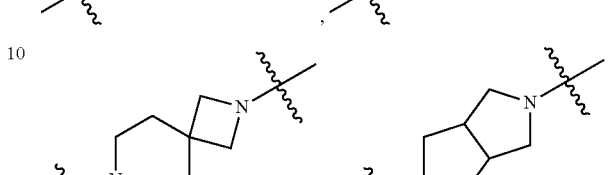
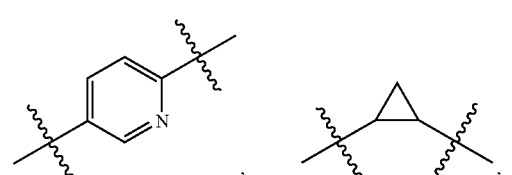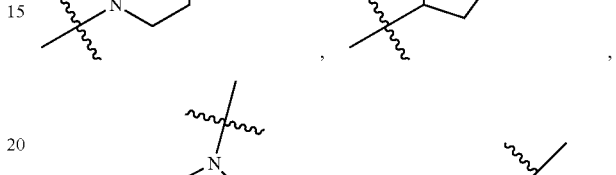
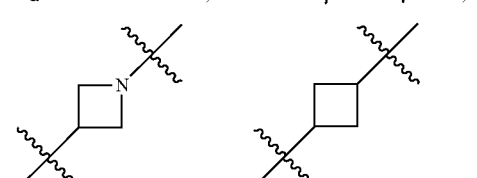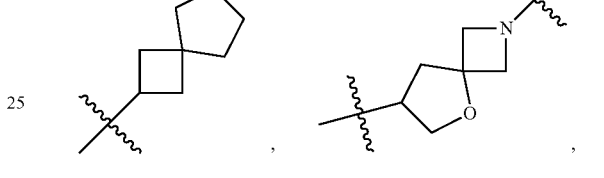
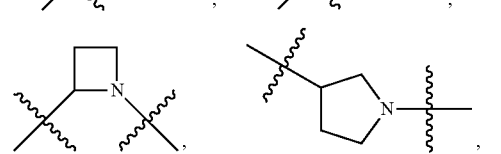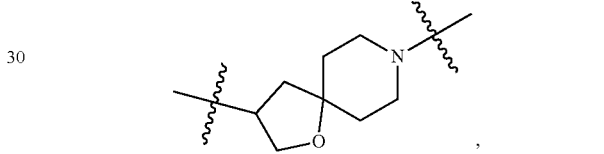
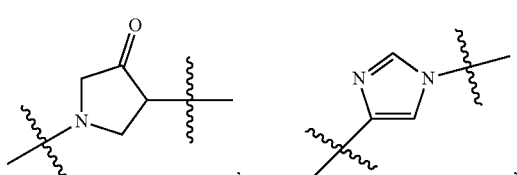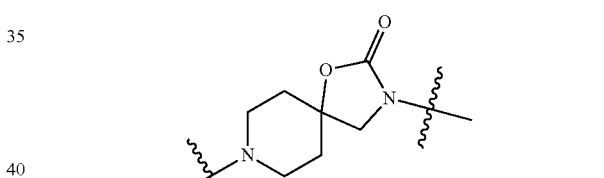
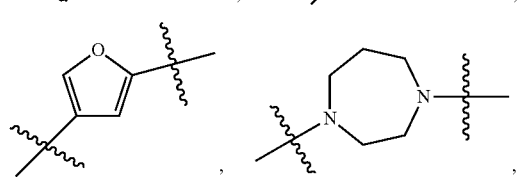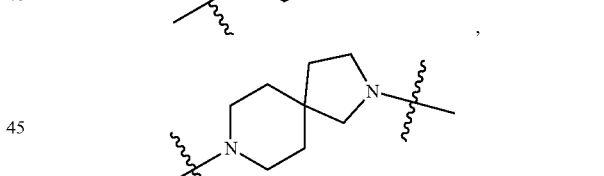
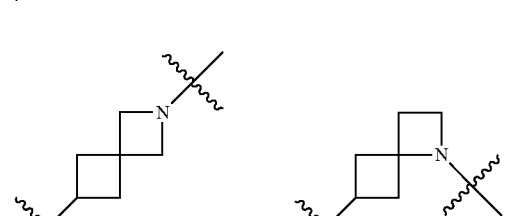
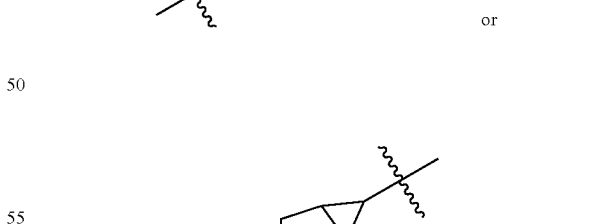
or
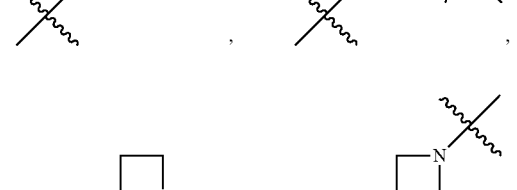
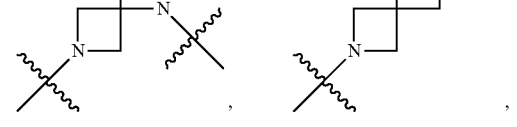
and wherein each of which L moiety is substituted with 0-5 occurrences of $R^x$.
1.87 Any of Compound 1, or 1.1 et seq., wherein L is substituted with 1 occurrence of $R^x$, or with 2 occurrences of $R^x$, or with 3 occurrences of $R^x$, or with 4 occurrences of $R^x$.

1.88 Any of Compound 1, or 1.1 et seq., wherein L is selected from any one of:
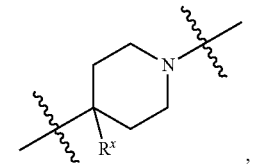 , 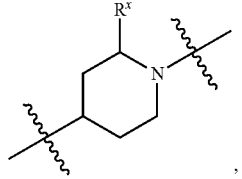 ,
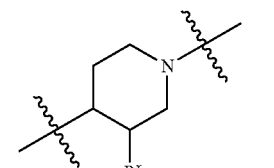 , 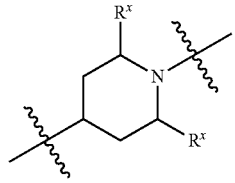 ,
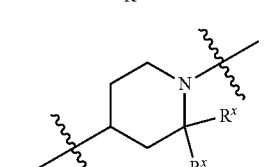 , 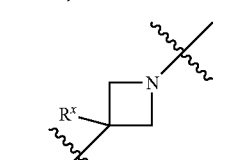 ,
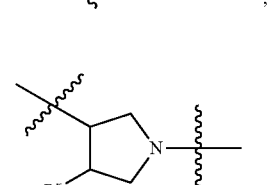 , 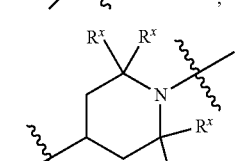 ,
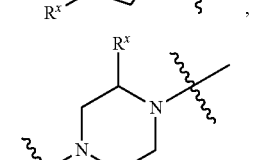 , 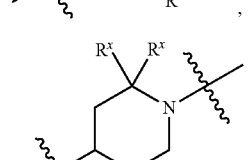 ,
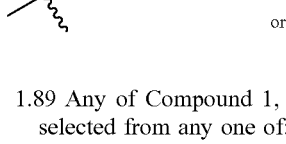 or 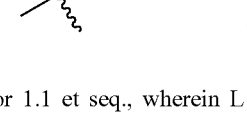 .
1.89 Any of Compound 1, or 1.1 et seq., wherein L is selected from any one of:
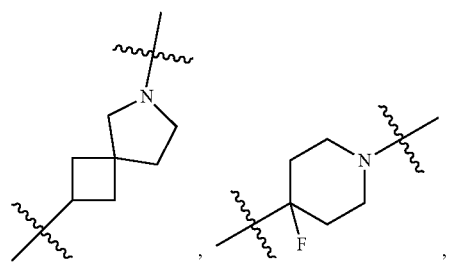
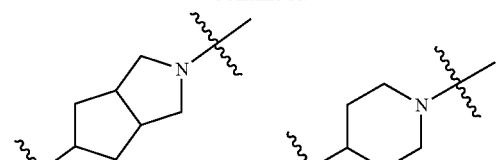
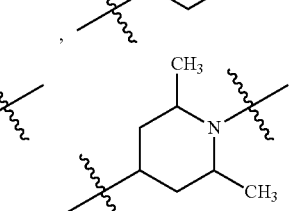
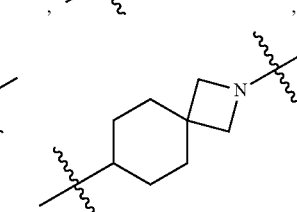
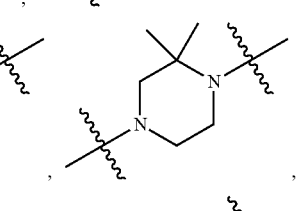
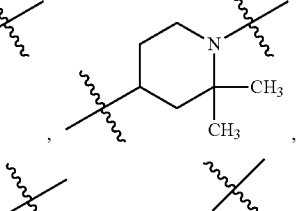
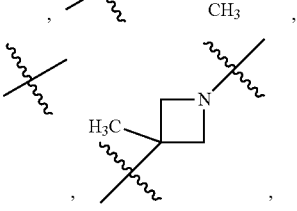

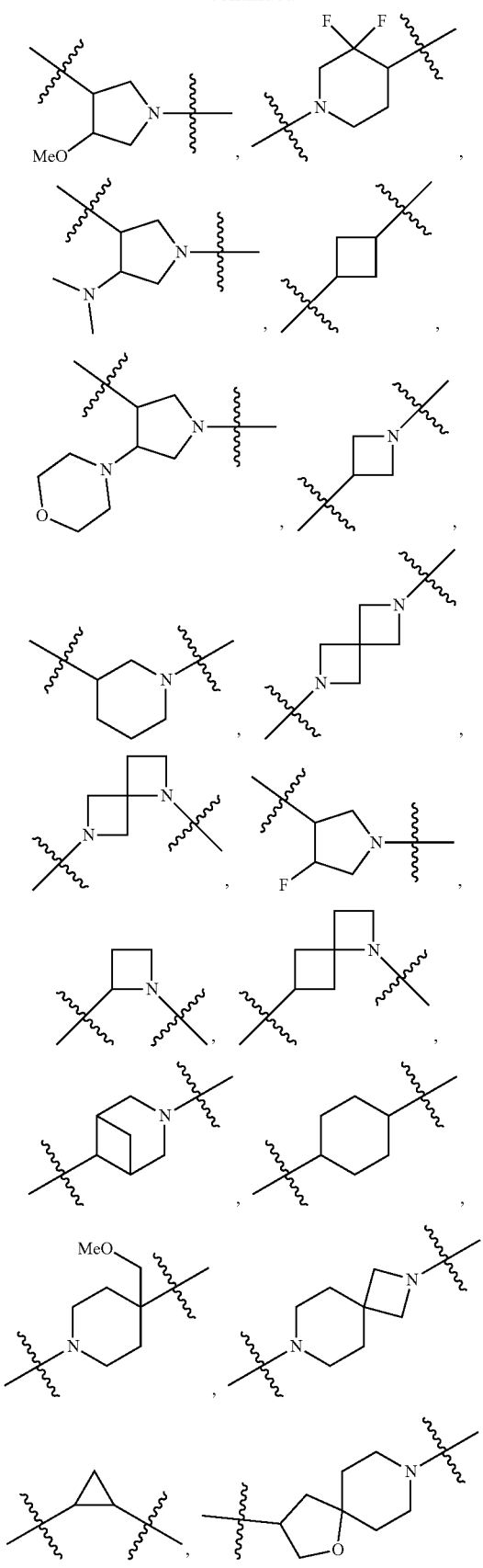
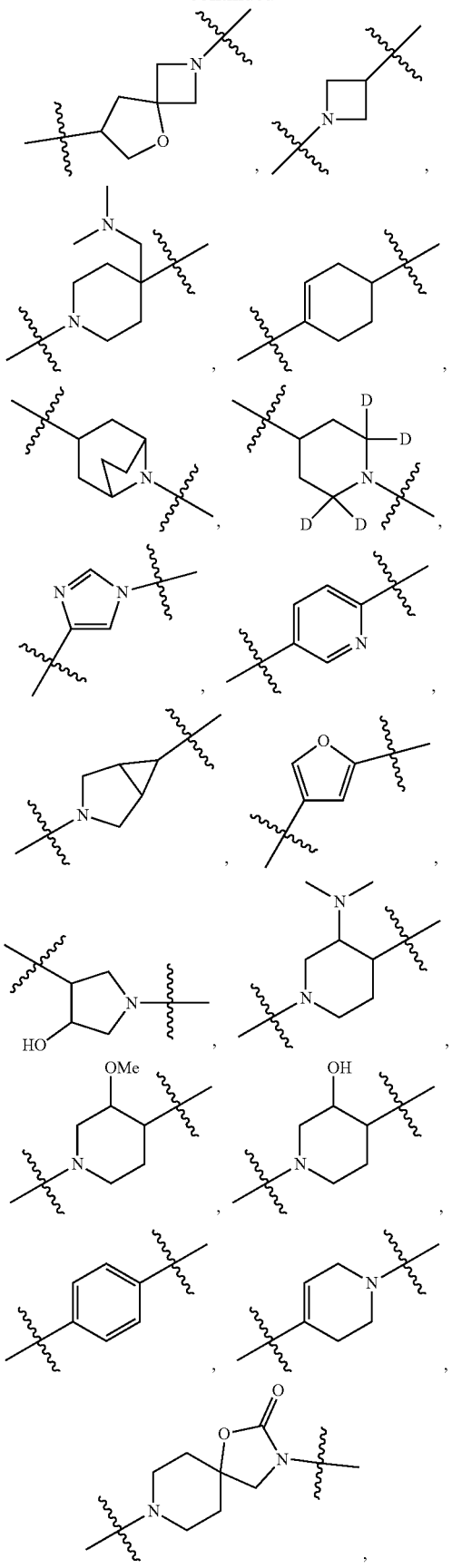

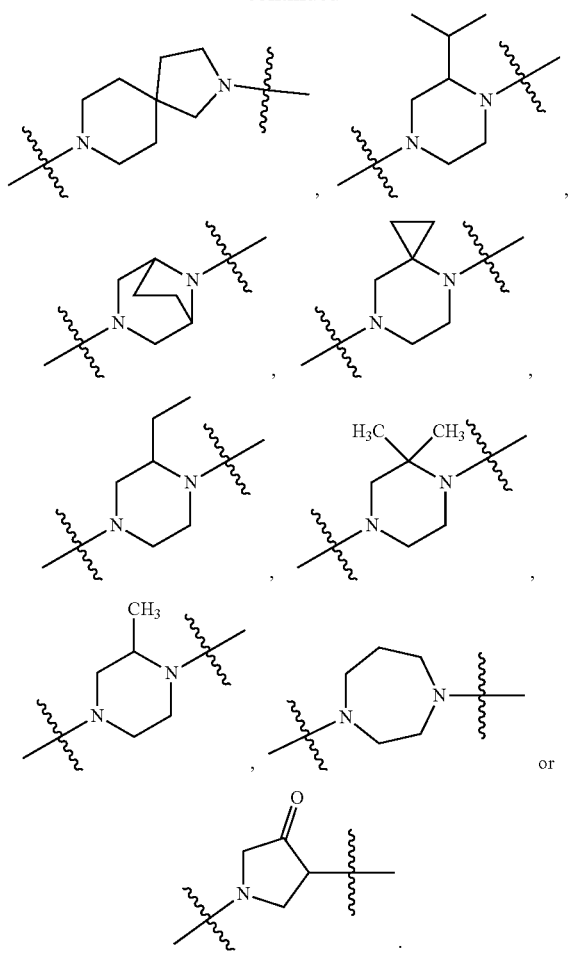
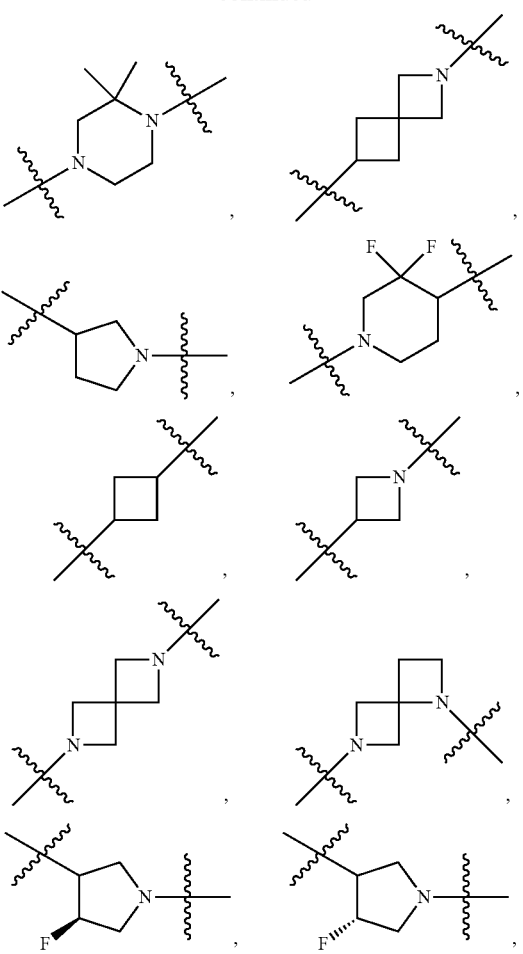
1.90 Any of Compound 1, or 1.1 et seq., wherein L is selected from any one of:
1.91 Any of Compound 1, or 1.1 et seq., wherein L is selected from any one of:
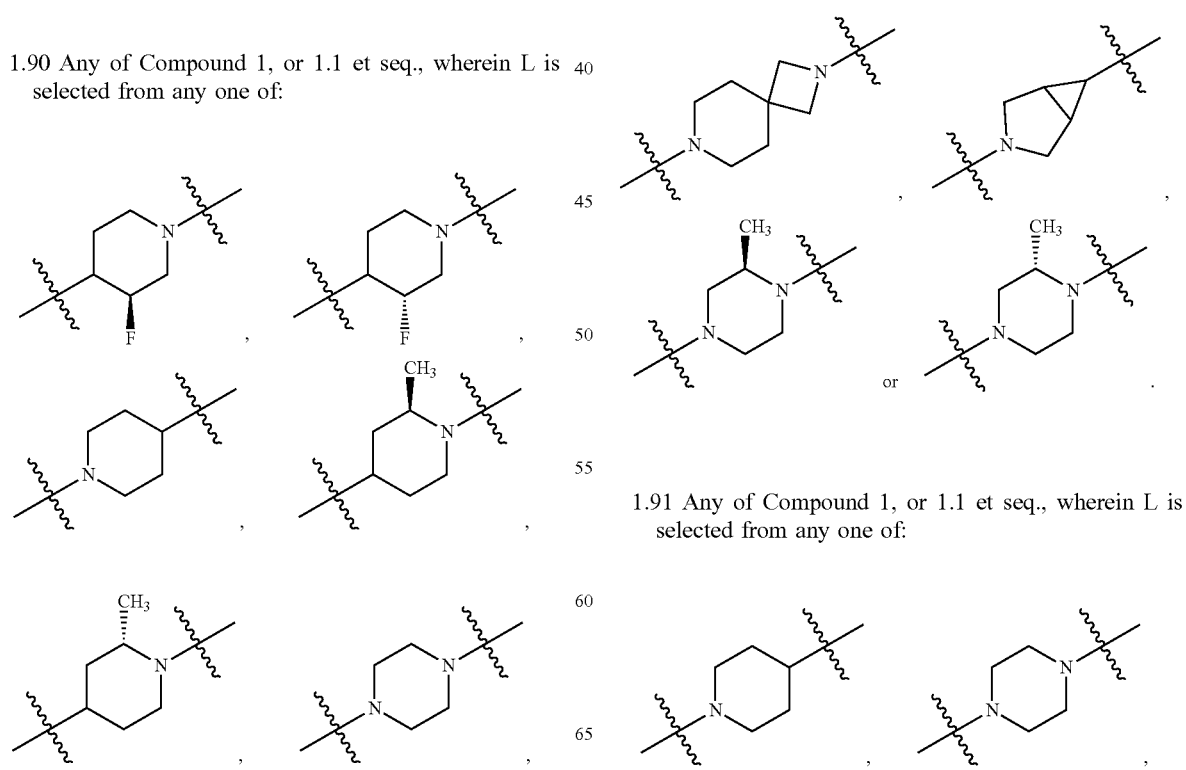

-continued
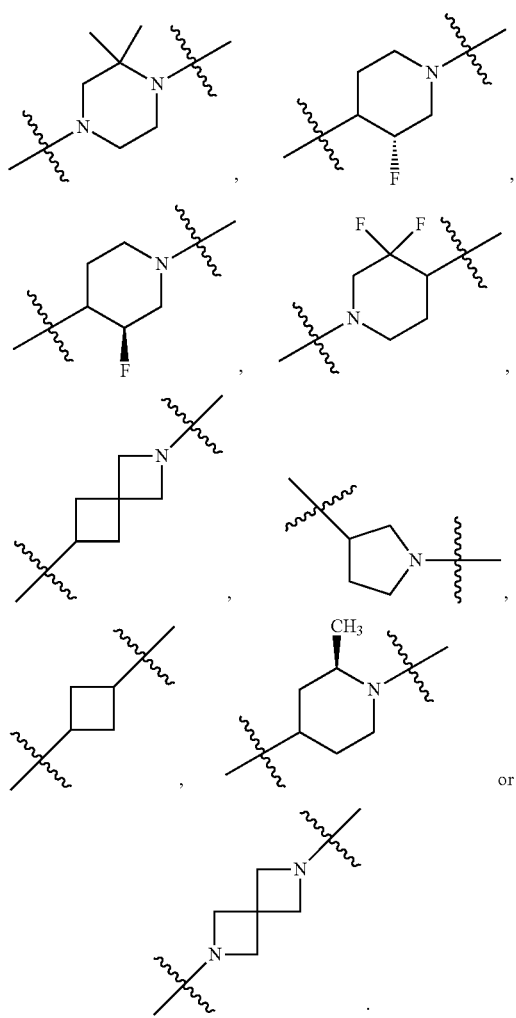
1.92 Any of Compound 1, or 1.1 et seq., wherein L is selected from any one of:
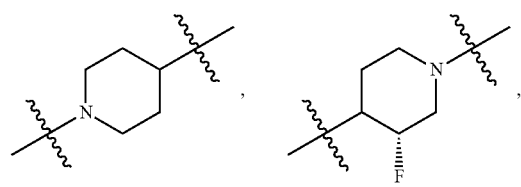
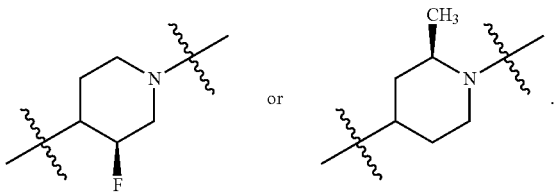
1.93 Any of Compound 1, or 1.1 et seq., wherein L is
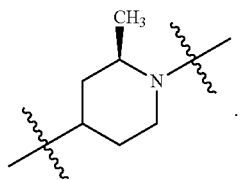 [SMILES: *C1CCN(*)[C@H](C)C1]
1.94 Any of Compound 1, or 1.1 et seq., wherein L is
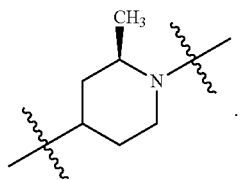 [SMILES: *C1CCN(*)[C@H](C)C1]
1.95 Any of Compound 1, or 1.1 et seq., wherein L is
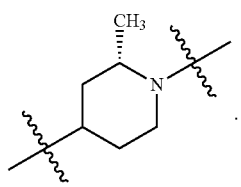 [SMILES: *C1CCN(*)[C@@H](C)C1]
1.96 Any of Compound 1, or 1.1 et seq., wherein L is
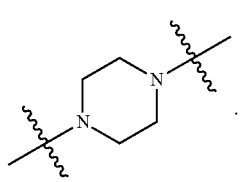 [SMILES: *N1CCN(*)CC1]
1.97 Any of Compound 1, or 1.1 et seq., wherein L is
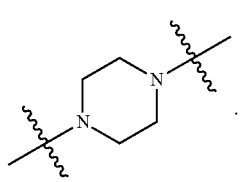 [SMILES: *N1CCN(*)CC1]
1.98 Any of Compound 1, or 1.1 et seq., wherein L is 1.99 Any of Compound 1, or 1.1 et seq., wherein L is

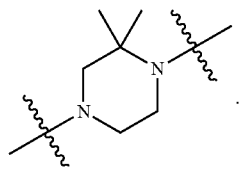 [SMILES: *N1CCN(*)C(C)(C)C1]

1.100 Any of Compound 1, or 1.1 et seq., wherein L is

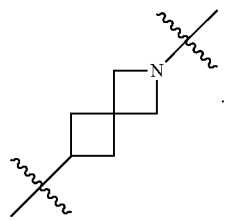 [SMILES: *C1CC2(C1)CN(*)C2]

1.101 Any of Compound 1, or 1.1 et seq., wherein L is

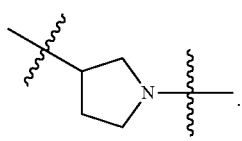 [SMILES: *C1CCN(*)C1]

1.102 Any of Compound 1, or 1.1 et seq., wherein L is

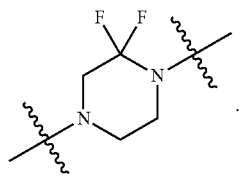 [SMILES: *N1CCN(*)C(F)(F)C1]

1.103 Any of Compound 1, or 1.1 et seq., wherein L is

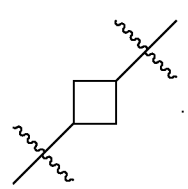

1.104 Any of Compound 1, or 1.1 et seq., wherein L is

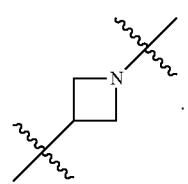

1.105 Any of Compound 1, or 1.1 et seq., wherein L is

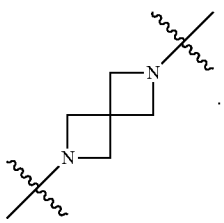 [SMILES: *N1CC2(C1)CN(*)C2]

1.106 Any of Compound 1, or 1.1 et seq., wherein L is

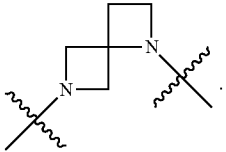

1.107 Any of Compound 1, or 1.1 et seq., wherein L is

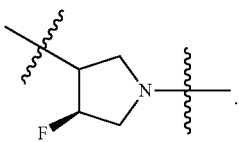 [SMILES: *C1CN(*)C[C@H]1F]

1.108 Any of Compound 1, or 1.1 et seq., wherein L is

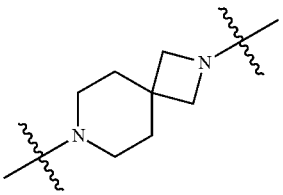

1.109 Any of Compound 1, or 1.1 et seq., wherein L is

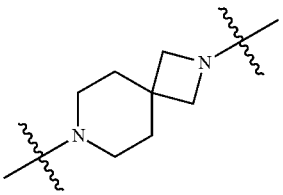

1.110 Any of Compound 1, or 1.1 et seq., wherein L is

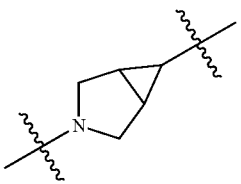

1.111 Any of Compound 1, or 1.1 et seq., wherein L is

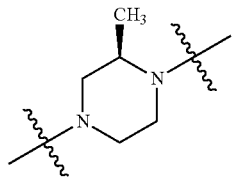

1.112 Any of Compound 1, or 1.1 et seq., wherein L is

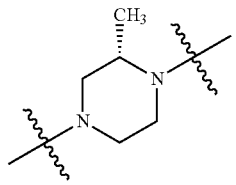

1.113 Any of Compound 1, or 1.1 et seq., wherein $A^2$ is a bond, —C(O)—O—, —OC(O)—$NR^a$—, —OC(O)—, —O—, —C(O)—, —$NR^a$—C(O)—O—, —$NR^a$—C(O)—$NR^a$—, —C(O)—$NR^a$—, —$C_{1-4}$ alkyl-C(O)—$NR^a$—, —$C_{1-4}$ alkyl-O—C(O)—$NR^a$—, —O—C(O)—O—, —$NR^a$—C(O)—, —$NR^a$—, —S(O)$_2$—, —$C_{1-4}$ alkyl-C(O)—, —$C_{1-4}$ alkyl-$NR^a$—, —$C_{1-4}$ alkyl-$NR^a$—S(O)— or —$C_{1-4}$ alkyl-C(O)—O—.
1.114 Compound 1.113, wherein $A^2$ is a bond, —C(O)—O—, —OC(O)—$NR^a$—, —OC(O)—, —O—, —$NR^a$—C(O)—O—, —$C_{1-4}$ alkyl-C(O)—$NR^a$—, —$C_{1-4}$ alkyl-O—C(O)—$NR^a$— or —$NR^a$—.
1.115 Compound 1.113, wherein $A^2$ is —O—C(O)—O.
1.116 Compound 1.113, wherein $A^2$ is —$NR^a$—C(O)—, optionally wherein $R^a$ is H.
1.117 Compound 1.113, wherein $A^2$ is —$NR^a$—, optionally wherein $R^a$ is H.
1.118 Compound 1.113, wherein $A^2$ is —S(O)$_2$—.
1.119 Compound 1.113, wherein $A^2$ is —C(O)—$NR^a$—, optionally wherein $R^a$ is H, or optionally wherein $R^a$ is $C_{1-4}$ alkyl (e.g., methyl or ethyl).
1.120 Compound 1.119, wherein $A^2$ is —C(O)—NH—, —C(O)—N(Me)-, or —C(O)—N(Et)-.
1.121 Compound 1.113, wherein $A^2$ is —$NR^a$—C(O)—$NR^a$—, optionally wherein both $R^a$ are H.
1.122 Compound 1.113, wherein $A^2$ is —$C_{1-4}$ alkyl-C(O)—, optionally wherein $A^2$ is —CH$_2$—C(O)— or $A^2$ is —CH(CH$_3$)—C(O)—.
1.123 Compound 1.113, wherein $A^2$ is —$C_{1-4}$ alkyl-$NR^a$—.
1.124 Compound 1.123, wherein $R^a$ is H, for example wherein $A^2$ is —CH$_2$—NH—.
1.125 Compound 1.123, wherein $R^a$ is $C_{1-4}$ alkyl, optionally wherein $R^a$ is methyl, for example, wherein $A^2$ is —$C_{1-4}$ alkyl-N(Me)-, e.g., $A^2$ is —CH$_2$—N(Me)-.
1.126 Compound 1.113, wherein $A^2$ is —$C_{1-4}$ alkyl-$NR^a$—S(O)—, optionally wherein $R^a$ is H, for example, wherein $A^2$ is —CH$_2$—NH—S(O)—.
1.127 Compound 1.113, wherein $A^2$ is —$C_{1-4}$ alkyl-C(O)—O—, optionally wherein $A^2$ is —CH$_2$—C(O)—O— or —CH(CH$_3$)—C(O)—O—.
1.128 Compound 1.113, wherein $A^2$ is —$C_{1-4}$ alkyl-O—C(O)—$NR^a$—, optionally wherein $R^a$ is H, for example, wherein $A^2$ is —CH$_2$—O—C(O)—NH—.
1.129 Compound 1.113, wherein $A^2$ is —$C_{1-4}$ alkyl-C(O)—$NR^a$—.
1.130 Compound 1.129, wherein $R^a$ is H, for example, wherein $A^2$ is —CH$_2$—C(O)—NH— or $A^2$ is —CH(CH$_3$)—C(O)—NH— or $A^2$ is —C(CH$_3$)$_2$—C(O)—NH— or $A^2$ is —CH(CH$_2$CH$_3$)—C(O)—NH—.
1.131 Compound 1.129, wherein $R^a$ is $C_{1-4}$ alkyl (e.g., methyl), for example, wherein $A^2$ is —CH$_2$—C(O)—N(Me)-,
1.132 Compound 1.113, wherein or $A^2$ is —C(O)—.
1.133 Compound 1.113, wherein $A^2$ is —O—.
1.134 Compound 1.113, wherein $A^2$ is —$NR^a$—C(O)—O—, optionally wherein $R^a$ is H, or wherein $R^a$ is $C_{1-4}$ alkyl, for example, wherein $A^2$ is —N(Me)-C(O)—O—.
1.135 Compound 1.113, wherein $A^2$ is a bond.
1.136 Compound 1.113, wherein $A^2$ is —O—C(O)—.
1.137 Compound 1.113, wherein $A^2$ is —O—C(O)—$NR^a$—, optionally wherein $R^a$ is H, or wherein $R^a$ is $C_{1-4}$ alkyl (e.g., methyl, ethyl or isopropyl), for example, wherein $A^2$ is —O—C(O)—N(Me)-, or $A^2$ is —O—C(O)—N(Et)-, or $A^2$ is —O—C(O)—N(iPr)-.
1.138 Compound 1.113, wherein $A^2$ is —C(O)—O—.
1.139 Any of Compound 1, or 1.1 et seq., wherein $R^4$ is hydrogen.
1.140 Any of Compound 1, or 1.1 et seq., wherein $R^4$ is —OH.
1.141 Any of Compound 1, or 1.1 et seq., wherein $R^4$ is $C_{1-6}$ alkyl, $C_{2-6}$ alkynyl, heterocycloalkyl, $C_{3-9}$ cycloalkyl or heteroaryl, each optionally substituted with 0-5 occurrences of $R^5$, optionally wherein any one or more of the $R^5$ are the same or different.
1.142 Compound 1.141, wherein $R^4$ is $C_{1-6}$ alkyl substituted with 0-5 occurrences of $R^5$.
1.143 Compound 1.142, wherein $R^4$ is $C_{1-6}$ alkyl substituted with 0 occurrences of $R^5$, or with 1 occurrence of $R^5$, or with 2 occurrences of $R^5$, or with 3 occurrences of $R^5$, or with 4 occurrences of $R^5$, or with 5 occurrences of $R^5$.
1.144 Compound 1.142 or 1.143, wherein the $C_{1-6}$ alkyl of $R^4$ is selected from methyl, ethyl, n-propyl, isopropyl, n-butyl, sec-butyl, t-butyl, isobutyl, n-pentyl, isopentyl, neopentyl, 3,3-dimethylbutyl or 4-methylpentan-2-yl.
1.145 Compound 1.142 or 1.143, wherein the $C_{1-6}$ alkyl of $R^4$ is methyl.
1.146 Compound 1.142 or 1.143, wherein the $C_{1-6}$ alkyl of $R^4$ is ethyl.
1.147 Compound 1.142 or 1.143, wherein the $C_{1-6}$ alkyl of $R^4$ is n-propyl.
1.148 Compound 1.142 or 1.143, wherein the $C_{1-6}$ alkyl of $R^4$ is isopropyl.
1.149 Compound 1.142 or 1.143, wherein the $C_{1-6}$ alkyl of $R^4$ is isobutyl.
1.150 Compound 1.142 or 1.143, wherein the $C_{1-6}$ alkyl of $R^4$ is sec-butyl.
1.151 Compound 1.142 or 1.143, wherein the $C_{1-6}$ alkyl of $R^4$ is t-butyl.
1.152 Compound 1.142 or 1.143, wherein the $C_{1-6}$ alkyl of $R^4$ is isopentyl.
1.153 Compound 1.142 or 1.143, wherein the $C_{1-6}$ alkyl of $R^4$ is n-pentyl.
1.154 Compound 1.142 or 1.143, wherein the $C_{1-6}$ alkyl of $R^4$ is neopentyl.
1.155 Compound 1.142 or 1.143, wherein the $C_{1-6}$ alkyl of $R^4$ is 4-methylpentan-2-yl.

1.156 Compound 1.142 or 1.143, wherein the $C_{1-6}$ alkyl of $R^4$ is 3,3-dimethylbutyl.
1.157 Any of Compounds 1.144-1.156, wherein said $C_{1-6}$ alkyl of $R^4$ is substituted with 0 occurrences of $R^5$.
1.158 Any of Compounds 1.144-1.156, wherein said $C_{1-6}$ alkyl of $R^4$ is substituted with 1 occurrence of $R^5$.
1.159 Any of Compounds 1.144-1.156, wherein said $C_{1-6}$ alkyl of $R^4$ is substituted with 2 occurrences of $R^5$.
1.160 Any of Compounds 1.144-1.156, wherein said $C_{1-6}$ alkyl of $R^4$ is substituted with 3 occurrences of $R^5$.
1.161 Compound 1.141, wherein $R^4$ is $C_{2-6}$ alkynyl substituted with 0-5 occurrences of $R^5$.
1.162 Compound 1.161, wherein $R^4$ is $C_{2-6}$ alkynyl substituted with 0 occurrences of $R^5$, or with 1 occurrence of $R^5$, or with 2 occurrences of $R^5$, or with 3 occurrences of $R^5$, or with 4 occurrences of $R^5$, or with 5 occurrences of $R^5$.
1.163 Compound 1.161 or 1.162, wherein the $C_{2-6}$ alkynyl of $R^4$ is selected from ethynyl, 2-propynyl, 1-butynyl, 2-butynyl, 2-pentynyl, and 1-hexa-1,3-diynyl.
1.164 Compound 1.161 or 1.162, wherein the $C_{2-6}$ alkynyl of $R^4$ is ethynyl.
1.165 Compound 1.161 or 1.162, wherein the $C_{2-6}$ alkynyl of $R^4$ is 2-propynyl.
1.166 Compound 1.161 or 1.162, wherein the $C_{2-6}$ alkynyl of $R^4$ is 1-butynyl.
1.167 Compound 1.161 or 1.162, wherein the $C_{2-6}$ alkynyl of $R^4$ is 2-butynyl
1.168 Compound 1.161 or 1.162, wherein the $C_{2-6}$ alkynyl of $R^4$ is 2-pentynyl.
1.169 Compound 1.161 or 1.162, wherein the $C_{2-6}$ alkynyl of $R^4$ is 1-hexa-1,3-diynyl.
1.170 Any of Compounds 1.163-1.169, wherein said $C_{2-6}$ alkynyl of $R^4$ is substituted with 0 occurrences of $R^5$.
1.171 Any of Compounds 1.163-1.169, wherein said $C_{2-6}$ alkynyl of $R^4$ is substituted with 1 occurrence of $R^5$.
1.172 Any of Compounds 1.163-1.169, wherein said $C_{2-6}$ alkynyl of $R^4$ is substituted with 2 occurrences of $R^5$.
1.173 Any of Compounds 1.163-1.169, wherein said $C_{2-6}$ alkynyl of $R^4$ is substituted with 3 occurrences of $R^5$.
1.174 Compound 1.141, wherein $R^4$ is $C_{3-9}$ cycloalkyl substituted with 0-5 occurrences of $R^5$.
1.175 Compound 1.174, wherein $R^4$ is $C_{3-9}$ cycloalkyl substituted with 0 occurrences of $R^5$, or with 1 occurrence of $R^5$, or with 2 occurrences of $R^5$, or with 3 occurrences of $R^5$, or with 4 occurrences of $R^5$, or with 5 occurrences of $R^5$.
1.176 Compound 1.174 or 1.175, wherein the $C_{3-9}$ cycloalkyl of $R^4$ is selected from cyclopropyl, cyclobutyl and cyclohexyl.
1.177 Compound 1.174 or 1.175, wherein the $C_{3-9}$ cycloalkyl of $R^4$ is cyclopropyl.
1.178 Compound 1.174 or 1.175, wherein the $C_{3-9}$ cycloalkyl of $R^4$ is cyclobutyl.
1.179 Compound 1.174 or 1.175, wherein the $C_{3-9}$ cycloalkyl of $R^4$ is cyclohexyl.
1.180 Any of Compounds 1.176-1.179, wherein said $C_{3-9}$ cycloalkyl of $R^4$ is substituted with 0 occurrences of $R^5$.
1.181 Any of Compounds 1.176-1.179, wherein said $C_{3-9}$ cycloalkyl of $R^4$ is substituted with 1 occurrence of $R^5$.
1.182 Any of Compounds 1.176-1.179, wherein said $C_{3-9}$ cycloalkyl of $R^4$ is substituted with 2 occurrences of $R^5$.
1.183 Compound 1.141, wherein $R^4$ is aryl substituted with 0-5 occurrences of $R^5$.
1.184 Compound 1.183, wherein $R^4$ is aryl substituted with 0 occurrences of $R^5$, or with 1 occurrence of $R^5$, or with 2 occurrences of $R^5$, or with 3 occurrences of $R^5$, or with 4 occurrences of $R^5$, or with 5 occurrences of $R^5$.
1.185 Compound 1.183 or 1.184, wherein the aryl of $R^4$ is phenyl.
1.186 Compound 1.185, wherein said aryl is aryl substituted with 0 occurrences of $R^5$.
1.187 Compound 1.185, wherein said aryl is aryl substituted with 1 occurrence of $R^5$.
1.188 Compound 1.185, wherein said aryl is aryl substituted with 2 occurrences of $R^5$.
1.189 Compound 1.141, wherein $R^4$ is heteroaryl substituted with 0-5 occurrences of $R^5$.
1.190 Compound 1.189, wherein $R^4$ is heteroaryl substituted with 0 occurrences of $R^5$, or with 1 occurrence of $R^5$, or with 2 occurrences of $R^5$, or with 3 occurrences of $R^5$, or with 4 occurrences of $R^5$, or with 5 occurrences of $R^5$.
1.191 Compound 1.189 or 1.190, wherein the heteroaryl of $R^4$ is selected from imidazolyl, pyrimidinyl, pyridinyl, pyrazinyl, oxadiazolyl, thiadiazolyl, thiazolyl, and thiophenyl.
1.192 Compound 1.189 or 1.190, wherein the heteroaryl of $R^4$ is imidazolyl, e.g., 2-imidazolyl.
1.193 Compound 1.189 or 1.190, wherein the heteroaryl of $R^4$ is pyrimidinyl, e.g., 2-pyrimidinyl, 2-pyrimidinyl, 4-pyrimidinyl, or 5-pyrimidinyl.
1.194 Compound 1.189 or 1.190, wherein the heteroaryl of $R^4$ is pyridinyl, e.g., 2-pyridinyl, 3-pyridinyl, or 4-pyridinyl.
1.195 Compound 1.189 or 1.190, wherein the heteroaryl of $R^4$ is pyrazinyl, e.g., 2-pyrazinyl.
1.196 Compound 1.189 or 1.190, wherein the heteroaryl of $R^4$ is oxadiazolyl, e.g., 2-(1,3,4-oxadiazolyl).
1.197 Compound 1.189 or 1.190, wherein the heteroaryl of $R^4$ is thiadiazolyl, e.g., 5-(1,2,4-thiadiazolyl).
1.198 Compound 1.189 or 1.190, wherein the heteroaryl of $R^4$ is thiazolyl, e.g., 2-thiazolyl, or 4-thiazolyl.
1.199 Compound 1.189 or 1.190, wherein the heteroaryl of $R^4$ is thiophenyl, e.g., 2-thiophenyl.
1.200 Any of Compounds 1.191-1.199, wherein said heteroaryl of $R^4$ is substituted with 0 occurrences of $R^5$.
1.201 Any of Compounds 1.191-1.199, wherein said heteroaryl of $R^4$ is substituted with 1 occurrence of $R^5$.
1.202 Any of Compounds 1.191-1.199, wherein said heteroaryl of $R^4$ is substituted with 2 occurrences of $R^5$.
1.203 Compound 1.141, wherein $R^4$ is heterocycloalkyl substituted with 0-5 occurrences of $R^5$.
1.204 Compound 1.203, wherein $R^4$ is heterocycloalkyl substituted with 0 occurrences of $R^5$, or with 1 occurrence of $R^5$, or with 2 occurrences of $R^5$, or with 3 occurrences of $R^5$, or with 4 occurrences of $R^5$, or with 5 occurrences of $R^5$.
1.205 Compound 1.203 or 1.204, wherein the heterocycloalkyl of $R^4$ is selected from azetidinyl, oxetanyl, pyrrolidinyl, tetrahydrofuranyl, dioxanyl, piperidinyl, piperazinyl, morpholinyl, thiomorpholinyl, pyranyl, azaspiro[2.3]hexanyl, diazaspiro[3.3]heptanyl, oxaazaspiro[3.3]heptanyl, oxaspiro[3.3]heptanyl, oxaazaspiro[3.4]octanyl, dioxaazaspiro[3.4]octanyl, oxaazaspiro[3.5]nonanyl, diazabicyclo[4.1.0]heptanyl, 3-(tetrahydrothiophene-1,1-dioxide), 2-(octahydropyrrolo[3,4-c]pyrrolyl), 7-(5,6,7,8-tetrahydro[1,2,4]triazolo[1,5]pyrazinyl), 5-(4,5,6,7-tetrahydropyrazolo[1,5]pyrazinyl), 7-(5,6,7,8-tetrahydroimidazo[1,5] pyrazinyl, 7-(5,6,7,8-tetrahydroimidazo[1,2]pyrazinyl, 3-pyrrolindin-2-onyl, and 3-(oxazolidine-2-onyl).

1.206 Compound 1.203 or 1.204, wherein the heterocycloalkyl of $R^4$ is azetidinyl, e.g., 2-azetidinyl or 3-azetidinyl.
1.207 Compound 1.203 or 1.204, wherein the heterocycloalkyl of $R^4$ is oxetanyl, e.g., 2-oxetanyl or 3-oxetanyl.
1.208 Compound 1.203 or 1.204, wherein the heterocycloalkyl of $R^4$ is pyranyl, e.g., 4-pyranyl.
1.209 Compound 1.203 or 1.204, wherein the heterocycloalkyl of $R^4$ is pyrrolidinyl, e.g., 1-pyrrolidinyl, 2-pyrrolidinyl, or 3-pyrrolidinyl.
1.210 Compound 1.203 or 1.204, wherein the heterocycloalkyl of $R^4$ is 3-pyrrolidin-2-onyl.
1.211 Compound 1.203 or 1.204, wherein the heterocycloalkyl of $R^4$ is piperidinyl, e.g., 3-piperidinyl or 4-piperidinyl.
1.212 Compound 1.203 or 1.204, wherein the heterocycloalkyl of $R^4$ is piperazinyl, e.g., piperazin-3-onyl.
1.213 Compound 1.203 or 1.204, wherein the heterocycloalkyl of $R^4$ is tetrahydrofuranyl, e.g., 2-tetrahydrofuranyl or 3-tetrahydrofuranyl.
1.214 Compound 1.203 or 1.204, wherein the heterocycloalkyl of $R^4$ is dioxanyl, e.g., 5-(1,3-dioxanyl).
1.215 Compound 1.203 or 1.204, wherein the heterocycloalkyl of $R^4$ is morpholinyl, e.g., 2-morpholinyl.
1.216 Compound 1.203 or 1.204, wherein the heterocycloalkyl of $R^4$ is azaspiro[2.3]hexanyl, e.g., 5-(5-azaspiro[2.3]hexanyl).
1.217 Compound 1.203 or 1.204, wherein the heterocycloalkyl of $R^4$ is oxaspiro[3.3]heptanyl, e.g., 6-(2-oxaspiro[3.3]heptanyl).
1.218 Compound 1.203 or 1.204, wherein the heterocycloalkyl of $R^4$ is diazaspiro[3.3]heptanyl, e.g., 6-(1,6-diazaspiro[3.3]heptanyl), or 1-(1,6-diazaspiro[3.3]heptanyl), or 2-(2,6-diazaspiro[3.3]heptanyl).
1.219 Compound 1.203 or 1.204, wherein the heterocycloalkyl of $R^4$ is oxaazaspiro[3.3]heptanyl, e.g., 6-(1-oxa-6-azaspiro[3.3]heptanyl), or 1-(6-oxa-1-azaspiro[3.3]heptanyl), or 6-(2-oxa-6-azaspiro[3.3]heptanyl).
1.220 Compound 1.203 or 1.204, wherein the heterocycloalkyl of $R^4$ is diazabicyclo[4.1.0]heptanyl, e.g., 2-(2,5-diazabicyclo[4.1.0]heptanyl).
1.221 Compound 1.203 or 1.204, wherein the heterocycloalkyl of $R^4$ is oxaazaspiro[3.4]octanyl, e.g., 2-(5-oxa-2-azaspiro[3.4]octanyl).
1.222 Compound 1.203 or 1.204, wherein the heterocycloalkyl of $R^4$ is dioxaazaspiro[3.4]octanyl, e.g., 2-(5,8-dioxa-2-azaspiro[3.4]octanyl).
1.223 Compound 1.203 or 1.204, wherein the heterocycloalkyl of $R^4$ is oxaazaspiro[3.5]nonanyl, e.g., 7-(1-oxa-7-azaspiro[3.5]nonanyl).
1.224 Compound 1.203 or 1.204, wherein the heterocycloalkyl of $R^4$ is thiomorpholinyl, e.g., thiomorpholinyl-1-oxide or thiomorpholinyl-1,1-dioxide.
1.225 Any of Compounds 1.205-1.224, wherein said heterocycloalkyl of $R^4$ is substituted with 0 occurrences of $R^5$.
1.226 Any of Compounds 1.205-1.224, wherein said heterocycloalkyl of $R^4$ is substituted with 1 occurrence of $R^5$.
1.227 Any of Compounds 1.205-1.224, wherein said heterocycloalkyl of $R^4$ is substituted with 2 occurrences of $R^5$.
1.228 Any of Compound 1, or 1.1 et seq., wherein each $R^5$ is independently selected from OH, halo, $CO_2H$, $C_{1-4}$ alkyl, $C_{1-4}$ alkoxy, $C_{1-4}$ haloalkyl, —O—$C_{1-4}$ haloalkyl, —$C_{1-4}$ alkyl-O—$C_{1-4}$ alkyl, —S—$C_{1-4}$ alkyl, —S(O)$_2$—$C_{1-4}$ alkyl, —S(O)—$C_{1-4}$ alkyl, —N(R$^a$)$_2$, —CH$_2$N(R$^a$)$_2$, —N(R$^a$)—S(O)—$C_{1-4}$ alkyl, —NO$_2$, —CN, —CH$_2$CN, $C_{3-9}$ cycloalkyl, —$C_{1-4}$ alkyl-$C_{3-9}$ cycloalkyl, —O—$C_{1-4}$ alkyl-$C_{3-9}$ cycloalkyl, heterocycloalkyl, aryl, heteroaryl, —O-heteroaryl, and —O-aralkyl, wherein each alkyl, aryl, heteroaryl, cycloalkyl or heterocycloalkyl is substituted with 0-3 occurrences of $R^w$, optionally wherein any one or more of the $R^w$ are the same or different.
1.229 Compound 1.228, wherein $R^5$ is halo, $C_{1-4}$ alkyl, $C_{1-4}$ alkoxy, $C_{1-4}$ haloalkyl, O—$C_{1-4}$ haloalkyl, —CN, $C_{3-9}$ cycloalkyl, $C_{1-4}$ alkyl-$C_{3-9}$ cycloalkyl, —O—$C_{1-4}$ alkyl-$C_{3-9}$ cycloalkyl, —$C_{1-4}$ alkyl-O—$C_{1-4}$ haloalkyl, or heterocycloalkyl, and wherein each of said cycloalkyl, aryl, heteroaryl or heterocycloalkyl is substituted with 0-3 occurrences of $R^w$.
1.230 Compound 1.228, wherein each $R^5$ is independently selected from halo, $C_{1-4}$ alkyl, $C_{1-4}$ alkoxy, $C_{1-4}$ haloalkyl, —O—$C_{1-4}$ haloalkyl, N(R$^a$)$_2$, —N(R$^a$)—S(O)—$C_{1-4}$ alkyl, —CN, $C_{3-9}$ cycloalkyl, —$C_{1-4}$ alkyl-$C_{3-9}$ cycloalkyl, —O—$C_{1-4}$ alkyl-$C_{3-9}$ cycloalkyl, and heterocycloalkyl, wherein each alkyl, aryl, heteroaryl, cycloalkyl or heterocycloalkyl is substituted with 0-3 occurrences of $R^w$.
1.231 Compound 1.228, wherein each $R^5$ is independently selected from halo, OH, $C_{1-4}$ alkoxy, —O—$C_{1-4}$ haloalkyl, N(R$^a$)$_2$, —CH$_2$—N(R$^a$)$_2$, —CN, $C_{3-9}$ cycloalkyl, —$C_{1-4}$ alkyl-$C_{3-9}$ cycloalkyl, heteroaryl, and heterocycloalkyl, wherein each alkyl, heteroaryl, cycloalkyl or heterocycloalkyl is substituted with 0-3 occurrences of $R^w$.
1.232 Compound 1.228, wherein each $R^5$ is independently selected from OH, $CO_2H$, $C_{1-4}$ alkoxy, $C_{1-4}$ haloalkyl, —O—$C_{1-4}$ haloalkyl, —S(O)$_2$—$C_{1-4}$ alkyl, —N(R$^a$)$_2$, $C_{3-9}$ cycloalkyl, heterocycloalkyl, heteroaryl, wherein each alkyl, heteroaryl, cycloalkyl or heterocycloalkyl is substituted with 0-3 occurrences of $R^w$.
1.233 Compound 1.228, wherein $R^5$ is independently selected from OH, halo, —CN, $C_{1-4}$ alkoxy, S—$C_{1-4}$ alkyl, —S(O)$_2$—$C_{1-4}$ alkyl, —S(O)—$C_{1-4}$ alkyl, $C_{3-9}$ cycloalkyl, heterocycloalkyl, and heteroaryl, wherein each alkyl, cycloalkyl, heterocycloalkyl, or heteroaryl is substituted with 0-3 occurrences of $R^w$.
1.234 Compound 1.228, wherein each $R^5$ is independently selected from halo, OH, $C_{1-4}$ alkoxy, —O—$C_{1-4}$ haloalkyl, N(R$^a$)$_2$, —S(O)$_2$—$C_{1-4}$ alkyl, —CN, and O-aralkyl, wherein each alkyl or aryl is substituted with 0-3 occurrences of $R^w$.
1.235 Compound 1.228, wherein each $R^5$ is independently selected from OH, halo, $C_{1-4}$ alkyl, $C_{1-4}$ alkoxy, $C_{1-4}$ haloalkyl, N(R$^a$)$_2$, and O-heterocycloalkyl, wherein each alkyl or heterocycloalkyl is substituted with 0-3 occurrences of $R^w$.
1.236 Compound 1.228, wherein $R^5$ is independently selected from $C_{1-4}$ alkyl, $C_{1-4}$ haloalkyl, S—$C_{1-4}$ alkyl, —S(O)$_2$—$C_{1-4}$ alkyl, —S(O)—$C_{1-4}$ alkyl, $C_{3-9}$ cycloalkyl, and heteroaryl, wherein each alkyl, cycloalkyl or heteroaryl is substituted with 0-3 occurrences of $R^w$.
1.237 Compound 1.228, wherein $R^5$ is independently selected from $C_{1-4}$ alkyl, $C_{1-4}$ alkoxy, —CH$_2$CN, and —S(O)$_2$—$C_{1-4}$ alkyl, wherein each alkyl, cycloalkyl or heteroaryl is substituted with 0-3 occurrences of $R^w$.
1.238 Compound 1.228, wherein $R^5$ is independently selected from OH, halo, $C_{1-4}$ alkyl, —CN, —CH$_2$CN, and heteroaryl, wherein each alkyl or heteroaryl is substituted with 0-3 occurrences of $R^w$.

1.239 Compound 1.228, wherein $R^5$ is independently selected from $C_{1-4}$ alkyl, $C_{1-4}$ haloalkyl, and $C_{3-9}$ cycloalkyl, wherein each alkyl or cycloalkyl is substituted with 0-3 occurrences of $R^w$.

1.240 Compound 1.228, wherein $R^5$ is independently selected from $C_{1-4}$ haloalkyl, $C_{3-9}$ cycloalkyl, aryl, heteroaryl and heterocycloalkyl, wherein each alkyl, aryl, heteroaryl, cycloalkyl or heterocycloalkyl is substituted with 0-3 occurrences of $R^w$.

1.241 Compound 1.228, wherein $R^5$ is independently selected from $C_{3-9}$ cycloalkyl, aryl, heteroaryl and heterocycloalkyl, wherein each alkyl, aryl, heteroaryl, cycloalkyl or heterocycloalkyl is substituted with 0-3 occurrences of $R^w$.

1.242 Compound 1.228, wherein each $R^5$ is independently selected from halo, $C_{1-4}$ alkoxy, and —O—$C_{1-4}$ haloalkyl, wherein each alkyl is substituted with 0-3 occurrences of $R^w$.

1.243 Compound 1.228, wherein each $R^5$ is independently selected from OH, $C_{1-4}$ alkyl, and $C_{3-9}$ cycloalkyl, wherein each alkyl is substituted with 0-3 occurrences of $R^w$.

1.244 Compound 1.228, wherein each $R^5$ is independently selected from $C_{1-4}$ haloalkyl and —O—$C_{1-4}$ alkoxy, wherein each alkyl is substituted with 0-3 occurrences of $R^w$.

1.245 Compound 1.228, wherein $R^5$ is independently selected from $C_{3-9}$ cycloalkyl and heteroaryl, wherein each cycloalkyl or heteroaryl is substituted with 0-3 occurrences of $R^w$.

1.246 Compound 1.228, wherein each $R^5$ is independently selected from OH and $C_{1-4}$ alkyl, wherein each alkyl is substituted with 0-3 occurrences of $R^w$.

1.247 Compound 1.228, wherein each $R^5$ is independently selected from $C_{1-4}$ alkyl, $C_{3-9}$ cycloalkyl, and $C_{1-4}$ alkyl-$C_{3-9}$ cycloalkyl, wherein each alkyl is substituted with 0-3 occurrences of $R^w$.

1.248 Compound 1.228, wherein each $R^5$ is independently selected from $C_{1-4}$ alkyl and $C_{1-4}$ alkyl-O—$C_{1-4}$ alkyl, wherein each alkyl is substituted with 0-3 occurrences of $R^w$.

1.249 Compound 1.228, wherein $R^5$ is independently OH.

1.250 Compound 1.228, wherein $R^5$ is independently halo, optionally selected from fluoro, chloro or bromo.

1.251 Compound 1.228, wherein $R^5$ is independently $CO_2H$.

1.252 Compound 1.228, wherein $R^5$ is independently $C_{1-4}$ alkyl substituted with 0, 1, 2 or 3 occurrences of $R^w$, optionally wherein said $C_{1-4}$ alkyl is selected from methyl, ethyl, and isopropyl.

1.253 Compound 1.228, wherein $R^5$ is independently $C_{1-4}$ alkoxy substituted with 0, 1, 2 or 3 occurrences of $R^w$, optionally wherein said $C_{1-4}$ alkoxy is selected from methoxy, ethoxy, isopropoxy and t-butoxy.

1.254 Compound 1.228, wherein $R^5$ is independently $C_{1-4}$ haloalkyl substituted with 0, 1, 2 or 3 occurrences of $R^w$, optionally wherein said $C_{1-4}$ haloalkyl is selected from trifluoromethyl, difluoromethyl, 2-fluoroethyl, 2,2-difluoroethyl, 2,2,2,-trifluoroethyl, 3-fluoropropyl, 1,1,1-trifluoroisopropyl, and 1,3-difluoroisopropyl.

1.255 Compound 1.228, wherein $R^5$ is independently —O—$C_{1-4}$ haloalkyl substituted with 0, 1, 2 or 3 occurrences of $R^w$, optionally wherein said —O—$C_{1-4}$ haloalkyl is selected from fluoromethoxy, difluoromethoxy, 2,2-difluoroethoxy, trifluoromethoxy, and 2,2,2-trifluoroethoxy.

1.256 Compound 1.228, wherein $R^5$ is independently —$C_{1-4}$ alkyl-O—$C_{1-4}$ alkyl substituted with 0, 1, 2 or 3 occurrences of $R^w$, optionally wherein said —$C_{1-4}$ alkyl-O—$C_{1-4}$ alkyl is $CH_2$—O—$CH_3$.

1.257 Compound 1.228, wherein $R^5$ is independently —$C_{1-4}$ alkyl-O—$C_{1-4}$ haloalkyl substituted with 0, 1, 2 or 3 occurrences of $R^w$, optionally wherein said —$C_{1-4}$ alkyl-O—$C_{1-4}$ haloalkyl is $CH_2$—O—$CF_3$.

1.258 Compound 1.228, wherein $R^5$ is independently —S—$C_{1-4}$ alkyl substituted with 0, 1, 2 or 3 occurrences of $R^w$, optionally wherein said —S—$C_{1-4}$ alkyl is —S—$CH_3$.

1.259 Compound 1.228, wherein $R^5$ is independently —$S(O)_2$—$C_{1-4}$ alkyl substituted with 0, 1, 2 or 3 occurrences of $R^w$, optionally wherein said —$S(O)_2$—$C_{1-4}$ alkyl is —$S(O)_2$—$CH_3$.

1.260 Compound 1.228, wherein $R^5$ is independently —$S(O)$—$C_{1-4}$ alkyl substituted with 0, 1, 2 or 3 occurrences of $R^w$, optionally wherein said —$S(O)$—$C_{1-4}$ alkyl is —$S(O)$—$CH_3$.

1.261 Compound 1.228, wherein $R^5$ is independently —$N(R^a)_2$.

1.262 Compound 1.261, wherein each $R^a$ is independently H, $C_{1-4}$alkyl, or $C_{3-9}$ cycloalkyl, optionally wherein said $R^a$ is methyl or cyclopropyl, and further optionally wherein each $R^a$ is the same or each $R^a$ is different.

1.263 Compound 1.228, wherein $R^5$ is independently —$CH_2N(R^a)_2$.

1.264 Compound 1.263, wherein each $R^a$ is independently H, $C_{1-4}$alkyl, or $C_{3-9}$ cycloalkyl, optionally wherein said $R^a$ is methyl or cyclopropyl, and further optionally wherein each $R^a$ is the same or each $R^a$ is different.

1.265 Compound 1.228, wherein $R^5$ is independently —$N(R^a)$—$S(O)$—$C_{1-4}$ alkyl substituted with 0, 1, 2 or 3 occurrences of $R^w$, optionally wherein said —$N(R^a)$—$S(O)$—$C_{1-4}$ alkyl is —$N(R^a)$—$S(O)$-t-butyl.

1.266 Compound 1.228, wherein $R^5$ is independently —$NO_2$.

1.267 Compound 1.228, wherein $R^5$ is independently —CN.

1.268 Compound 1.228, wherein $R^5$ is independently —$CH_2CN$.

1.269 Compound 1.228, wherein $R^5$ is independently $C_{3-9}$ cycloalkyl substituted with 0, 1, 2 or 3 occurrences of $R^w$, optionally wherein said $C_{3-9}$ cycloalkyl is selected from cyclopropyl, cyclobutyl, and cyclohexyl.

1.270 Compound 1.228, wherein $R^5$ is independently —$C_{1-4}$ alkyl-$C_{3-9}$ cycloalkyl substituted with 0, 1, 2 or 3 occurrences of $R^w$, optionally wherein said —$C_{1-4}$ alkyl-$C_{3-9}$ cycloalkyl is methylcyclopropyl.

1.271 Compound 1.228, wherein $R^5$ is independently —O—$C_{1-4}$ alkyl-$C_{3-9}$ cycloalkyl substituted with 0, 1, 2 or 3 occurrences of $R^w$, optionally wherein said —O—$C_{1-4}$ alkyl-$C_{3-9}$ cycloalkyl is O-methyl-cyclopropyl.

1.272 Compound 1.228, wherein $R^5$ is independently heterocycloalkyl substituted with 0, 1, 2 or 3 occurrences of $R^w$, optionally wherein said heterocycloalkyl is selected from azetidinyl (e.g., 2-azetidinyl or 3-azetidinyl), oxetanyl (e.g., 2-oxetanyl or 3-oxetanyl), tetrahydrofuranyl (e.g., 2-tetrahydrofuranyl), pyrrolidinyl, dioxanyl (e.g., 1,4-dioxanyl), morpholinyl (e.g., 2-morpholinyl), piperidinyl, and dihydrooxazolyl (e.g., 2-(4,5-dihydrooxazolyl).

1.273 Compound 1.228, wherein $R^5$ is independently aryl substituted with 0, 1, 2 or 3 occurrences of $R^w$, optionally wherein said aryl is phenyl.

1.274 Compound 1.228, wherein $R^5$ is independently heteroaryl substituted with 0, 1, 2 or 3 occurrences of $R^w$, optionally wherein said heteroaryl is selected from imidazolyl (e.g., 2-imidazolyl), oxazolyl (e.g., 2-oxazolyl, or 4-oxazolyl), isoxazolyl (e.g., 3-isoxazolyl), thiazolyl (e.g., 2-thiazolyl or 4-thiazolyl), pyrazolyl (e.g., 1-pyrazolyl, 2-pyrazolyl), triazolyl (e.g., 1,2,3-triazolyl or 1,2,4-triazolyl), thiophenyl (e.g., 2-thiophenyl), oxadiazolyl (e.g., 2-(1,3,4-oxadiazolyl), pyridyl (e.g., 2-pyridyl, 3-pyridyl, or 4-pyridyl), pyrazinyl (e.g., 2-pyrazinyl), and pyrimidinyl (e.g., 2-pyrimidyl, or 4-pyrimidyl).

1.275 Compound 1.228, wherein $R^5$ is independently —O-heteroaryl substituted with 0, 1, 2 or 3 occurrences of $R^w$, optionally wherein said O-heteroaryl is O-pyridiyl (e.g., O-3-pyridyl).

1.276 Compound 1.228, wherein $R^5$ is independently —O-aralkyl substituted with 0, 1, 2 or 3 occurrences of $R^w$, optionally wherein said —O-aralkyl is O-benzyl (benzoxy).

1.277 Compound 1, or any of 1.1 et seq., wherein $R^4$ is substituted with 2 occurrences of $R^5$, and both occurrences of $R^5$ are the same.

1.278 Compound 1, or any of 1.1 et seq., wherein $R^4$ is substituted with 2 occurrences of $R^5$, and the two occurrences of $R^5$ are different.

1.279 Compound 1, or any of 1.1 et seq., wherein $R^4$ is substituted with 3 occurrences of $R^5$, and all three occurrences of $R^5$ are the same.

1.280 Compound 1, or any of 1.1 et seq., wherein $R^4$ is substituted with 3 occurrences of $R^5$, and all two of the three occurrences of $R^5$ are the same.

1.281 Compound 1, or any of 1.1 et seq., wherein $R^4$ is substituted with 3 occurrences of $R^5$, and all three occurrences of $R^5$ are different from each other.

1.282 Compound 1, or any of 1.1 et seq., wherein the alkyl, aryl, heteroaryl, cycloalkyl, or heterocycloalkyl of any $R^5$ is independently substituted with 0 $R^w$, or with 1 $R^w$, or with 2 $R^w$, or with 3 $R^w$.

1.283 Compound 1.282, wherein each $R^w$ is independently halo, optionally selected from fluoro, chloro and bromo.

1.284 Compound 1.282, wherein each $R^w$ is independently —OH.

1.285 Compound 1.282, wherein each $R^w$ is independently $C_{1-4}$ alkyl, optionally selected from methyl, ethyl, and isopropyl.

1.286 Compound 1.282, wherein each $R^w$ is independently $C_{1-4}$ alkoxy, optionally selected from methoxy and isopropoxy.

1.287 Compound 1.282, wherein each $R^w$ is independently $C_{1-4}$ haloalkyl, optionally selected from trifluoromethyl and 2,2-difluoroethyl.

1.288 Any of Compounds 1.282-1.287, wherein any one or more $R^5$ is substituted with 2 occurrences of $R^w$, and the two occurrences of $R^w$ on the $R^5$ are the same.

1.289 Any of Compounds 1.282-1.287, wherein any one or more $R^5$ is substituted with 2 occurrences of $R^w$, and the two occurrences of $R^w$ on the $R^5$ are different from each other.

1.290 Any of Compounds 1.282-1.287, wherein any one or more $R^5$ is substituted with 3 occurrences of $R^w$, and the three occurrences of $R^w$ on the $R^5$ are the same.

1.291 Any of Compounds 1.282-1.287, wherein any one or more $R^5$ is substituted with 3 occurrences of $R^w$, and the two of the three occurrences of $R^w$ on the $R^5$ are the same.

1.292 Any of Compounds 1.282-1.287, wherein any one or more $R^5$ is substituted with 3 occurrences of $R^w$, and the all three occurrences of $R^w$ on the $R^5$ are different from each other.

1.293 Compound 1 or any of 1.1-1.292, wherein: $X^2$ is $CR^2$ and $R^2$ is hydrogen, halo (e.g., fluoro) or $C_{1-4}$ alkyl (e.g., methyl); $X^5$ is $CR^7$ and $R^7$ is hydrogen; $X^6$ is $CR^1$ and $R^1$ is $C_{1-4}$ haloalkyl (e.g., trifluoromethyl); Y is —C(O)NR$^a$R$^b$, and R$^a$ is H, and R$^b$ is $C_{1-4}$alkyl (e.g., methyl), or R$^a$ and R$^b$ are taken together with the nitrogen atom to which they are attached to form a heterocycloalkyl ring substituted with 0 occurrences of $R^x$ (e.g., R$^a$ and R$^b$ form 1-azetidinyl); $A^1$ is a bond, $C_{1-4}$alkyene (e.g., $CH_2$) or —O—; L is a 3-12 membered heterocycloalkyl substituted with 0, 1 or 2 occurrences of $R^x$, and $R^x$ is halo (e.g., fluoro) or $C_{1-4}$ alkyl (e.g., methyl); $A^2$ is selected from —O—, —NR$^a$—, —O—C(O)—, —C(O)—O—, $CH_2$—C(O)—NR$^a$, —O—C(O)—NR$^a$, and NR$^a$—C(O)—O—, and R$^a$ is hydrogen; $R^4$ is $C_{1-4}$ alkyl (e.g., methyl, ethyl, propyl, isopropyl, or butyl), $C_{3-9}$ cycloalkyl (e.g., cyclopropyl or cyclohexyl), heterocycloalkyl (e.g., azetidinyl), or heteroaryl (e.g., 2-pyridyl), each substituted with 0 or 1 occurrences of $R^5$, and each $R^5$ is independently selected from halo (e.g., fluoro), $C_{1-4}$ alkyl (e.g., methyl or isopropyl), $C_{1-4}$ alkoxy (e.g., methoxy), $C_{1-4}$ haloalkyl (e.g., trifluoromethyl), —O$C_{1-4}$ haloalkyl (e.g., trifluoromethoxy), CN, $C_{3-9}$ cycloalkyl (e.g., cyclopropyl), heteroaryl (e.g., 2-thiazolyl), or heterocycloalkyl (e.g., 1-pyrrolidinyl) and said heteroaryl or heterocycloalkyl is substituted with 0, 1, or 2 halo (e.g., fluoro) or $C_{1-4}$ alkyl (e.g., isopropyl).

1.294 Compound 1.293, wherein L is selected from one of the following moieties, each substituted with 0, 1 or 2 occurrences of $R^x$, and wherein $R^x$ is halo (e.g., fluoro) or $C_{1-4}$ alkyl (e.g., methyl):

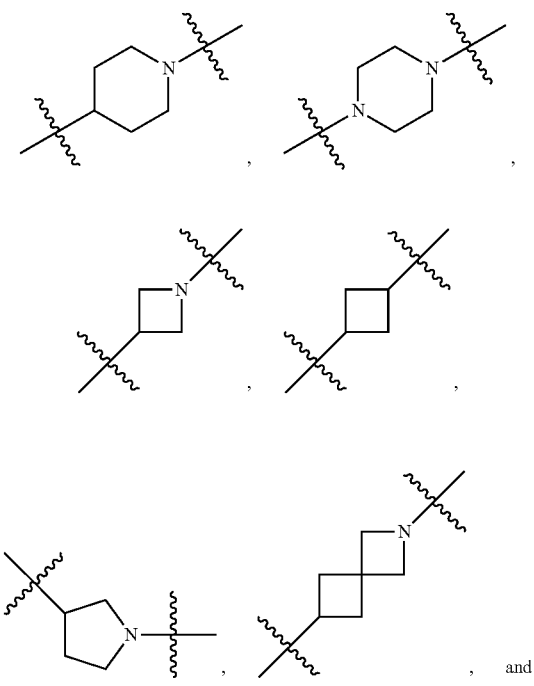

, and

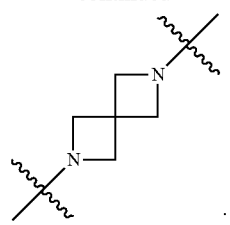

1.295 Compound 1.294, wherein L is the following moiety substituted with 0 occurrences of $R^x$:

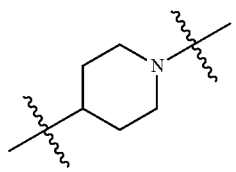

1.296 Compound 1.295, wherein $X^2$ is $CR^2$ and $R^2$ is hydrogen; $X^5$ is $CR^7$ and $R^7$ is hydrogen; $X^6$ is $CR^1$ and $R^1$ is trifluoromethyl; Y is —C(O)$NR^aR^b$, and $R^a$ is H, and $R^b$ is methyl; $A^1$ is a bond; $A^2$ is selected from —O—C(O)—, —C(O)—O—, $CH_2$—C(O)—$NR^a$, —O—C(O)—$NR^a$, and $NR^a$—C(O)—O—, and $R^a$ is hydrogen; $R^4$ is $C_{1-4}$ alkyl (e.g., methyl, ethyl, propyl, isopropyl, or butyl), $C_{3-9}$ cycloalkyl (e.g., cyclopropyl or cyclohexyl), or heterocycloalkyl (e.g., azetidinyl), each substituted with 0 or 1 occurrences of $R^5$, and each $R^5$ is independently selected from halo (e.g., fluoro), $C_{1-4}$ alkyl (e.g., methyl or isopropyl), $C_{1-4}$ alkoxy (e.g., methoxy), $C_{1-4}$ haloalkyl (e.g., trifluoromethyl), —$OC_{1-4}$ haloalkyl (e.g., trifluoromethoxy), and $C_{3-9}$ cycloalkyl (e.g., cyclopropyl).

1.297 Compound 1.296, wherein $A^2$ is selected from —O—C(O)—$NR^a$, and $NR^a$—C(O)—O—, and $R^a$ is hydrogen;

1.298 Compound 1.296 or 1.297, wherein $R^4$ is $C_{1-4}$ alkyl (e.g., methyl, ethyl, propyl, isopropyl, or butyl), $C_{3-9}$ cycloalkyl (e.g., cyclopropyl or cyclohexyl), each substituted with 0 or 1 occurrences of $R^5$, and each $R^5$ is independently selected from halo (e.g., fluoro), $C_{1-4}$ alkyl (e.g., methyl or isopropyl), $C_{1-4}$ alkoxy (e.g., methoxy), $C_{1-4}$ haloalkyl (e.g., trifluoromethyl), —$OC_{1-4}$ haloalkyl (e.g., trifluoromethoxy), and $C_{3-9}$ cycloalkyl (e.g., cyclopropyl).

1.299 Compound 1.298, wherein $R^4$ is substituted with 0 occurrences of $R^5$.

1.300 Compound 1 or any of 1.1-1.298, or any group of such compounds, comprising any one of, any two of, any three of, any four of, any five of, any six of, any seven of, any eight of, any nine of, or any ten of, the compounds of Example 1 to Example 870.

In further embodiments, the present application provides Compound 1 or any of Compounds 1.1 to 1.300, wherein the compound is selected from one or more of the following compounds represented in Table 1 below:

TABLE 1-continued
| Compound | # |
|---|---|
| 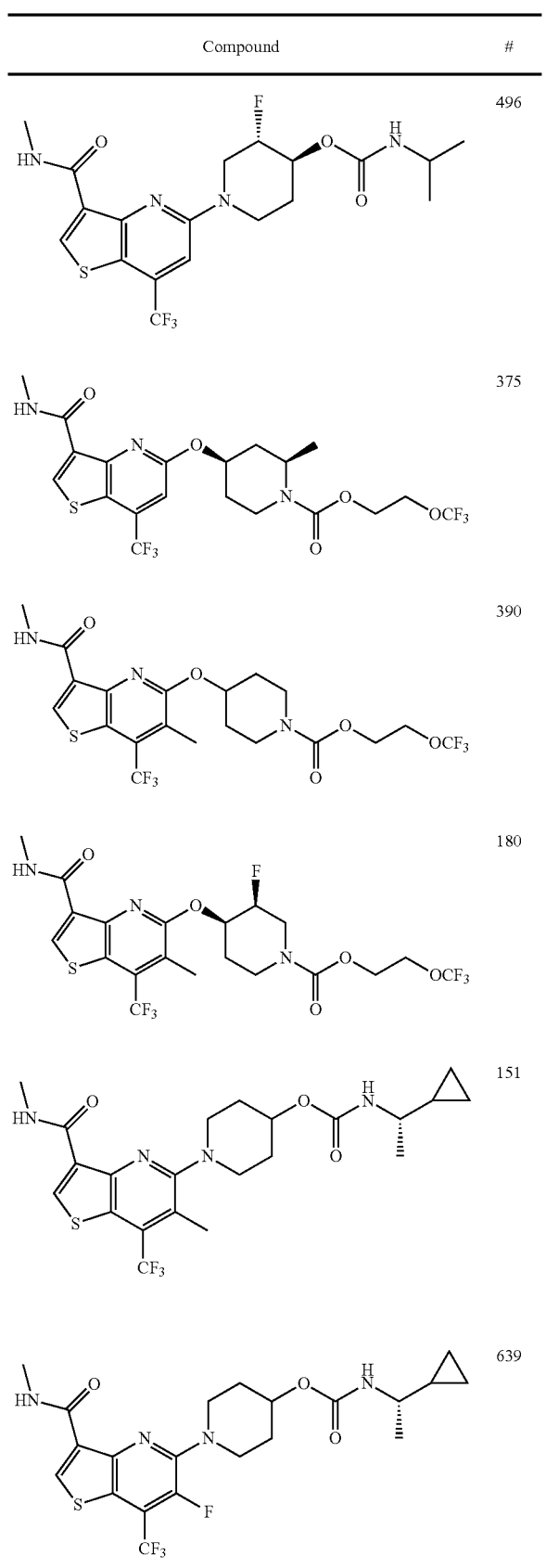 | 496, 375, 390, 180, 151, 639 |
| 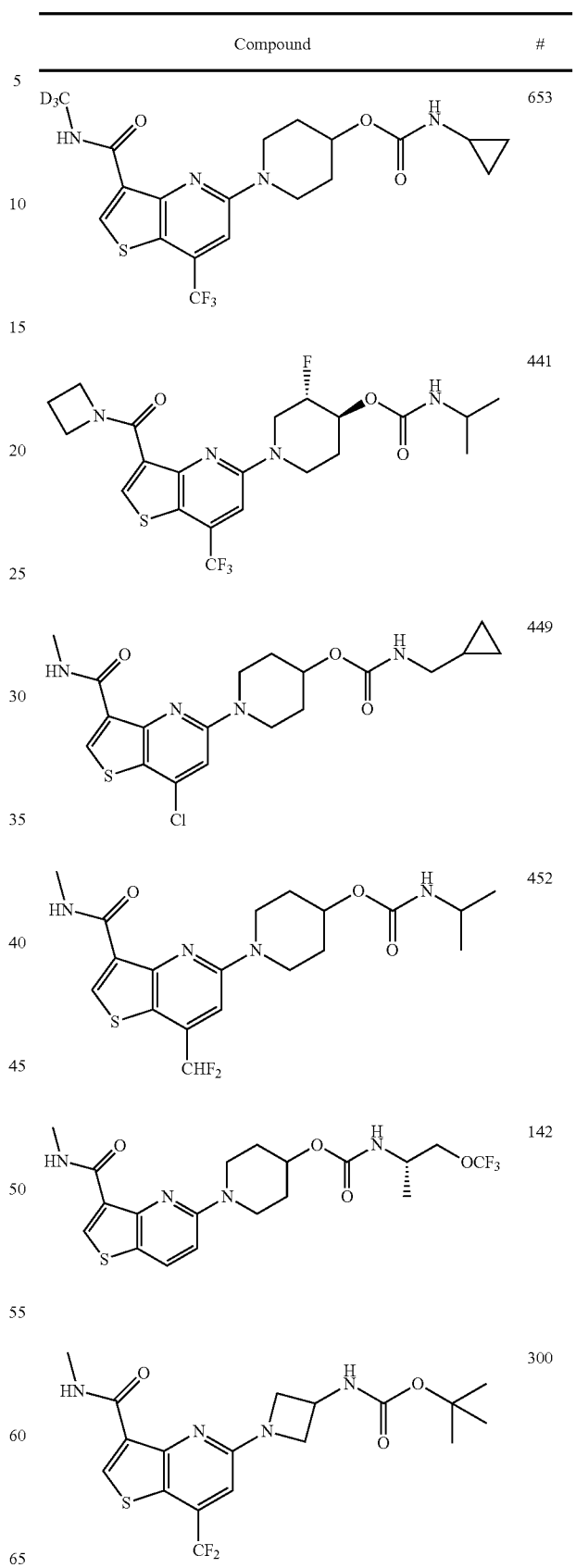 | 653, 441, 449, 452, 142, 300 |

TABLE 1-continued

| Compound | # |
|---|---|
| (structure) | 49 |
| (structure) | 475 |
| CF₃CO₂H | |
| (structure) | 692 |
| (structure) | 63 |
| (structure) | 806 |
| (structure) | 490 |
| (structure) | 492 |
| (structure) | 418 |
| (structure) | 91 |
| (structure) | 816 |
| (structure) | 520 |
| (structure) | 528 |

TABLE 1-continued

| Compound | # |
|---|---|
| (structure) | 145 |
| (structure) | 780 |
| (structure) | 361 |
| (structure) | 350 |
| (structure) | 632 |
| (structure) | 576 |
| (structure) | 256 |
| (structure) | 853 |
| (structure) | 833 |
| (structure) | 220 |
| (structure) | 600 |
| (structure) | 611 |
| (structure) | 171 |

TABLE 1-continued

| Compound | # |
|---|---|
| (structure) | 371 |
| (structure) | 866 |
| (structure) | 176 |
| (structure) | 181 |
| (structure) | 183 |
| (structure) | 186 |
| (structure) | 187 |

TABLE 1-continued

| Compound | # |
|---|---|
| (structure) | 636 |
| (structure) | 637 |
| (structure) | 408 |
| (structure) | 415 |
| (structure) | 47 |
| (structure) | 638 |

TABLE 1-continued

| Compound | # |
|---|---|
| (structure) | 640 |
| (structure) | 641 |
| (structure) | 419 |
| (structure) | 473 |
| (structure) HCl | 669 |

TABLE 2

| Compound | # |
|---|---|
| (structure) | 474 |
| (structure) | 109 |
| (structure) | 76 |
| (structure) | 693 |
| (structure) | 90 |
| (structure) | 88 |

In further embodiments, the present application provides Compound 1 or any of Compounds 1.1 to 1.300, wherein the compound is selected from one or more of the following compounds represented in Table 2 below:

TABLE 2-continued

| Compound | # |
|---|---|
| 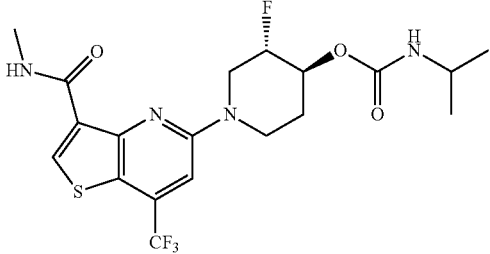 [SMILES: CNC(=O)c1csc2c(C(F)(F)F)cc(N3CC[C@H](OC(=O)NC(C)C)[C@@H](F)C3)nc12] | 496 |
| 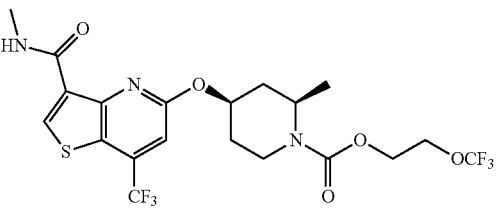 [SMILES: CNC(=O)c1csc2c(C(F)(F)F)cc(O[C@@H]3CCN(C(=O)OCCOC(F)(F)F)[C@H](C)C3)nc12] | 375 |
| 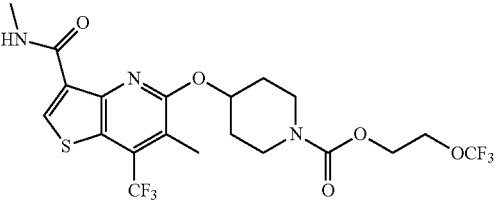 [SMILES: CNC(=O)c1csc2c(C(F)(F)F)c(C)c(OC3CCN(C(=O)OCCOC(F)(F)F)CC3)nc12] | 390 |
| 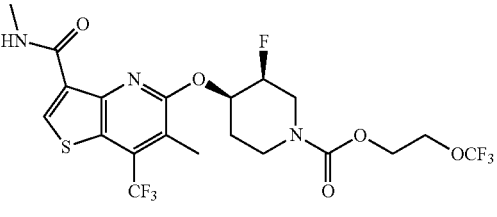 [SMILES: CNC(=O)c1csc2c(C(F)(F)F)c(C)c(O[C@@H]3CCN(C(=O)OCCOC(F)(F)F)C[C@@H]3F)nc12] | 180 |
| 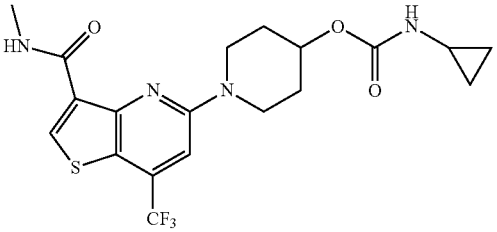 [SMILES: CNC(=O)c1csc2c(C(F)(F)F)cc(N3CCC(OC(=O)NC4CC4)CC3)nc12] | 473 |
| 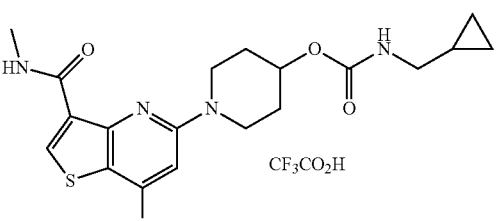 | 475 |

In further embodiments, the present application provides Compound 1 or any of Compounds 1.1 to 1.300, wherein the compound is selected from the following named compounds below:

N-Methyl-5-(4-((5-methylpyridin-2-yl)methyl)piperazin-1-yl)-7-(trifluoromethyl)thieno[3,2-b]pyridine-3-carboxamide;
5-(4-Benzylpiperazin-1-yl)-N-methyl-7-(trifluoromethyl)thieno[3,2-b]pyridine-3-carboxamide;
N-Methyl-5-(4-((2-methylpyrimidin-4-yl)methyl)piperazin-1-yl)-7-(trifluoromethyl)thieno[3,2-b]pyridine-3-carboxamide;
5-(4-((6-Ethylpyridin-2-yl)methyl)piperazin-1-yl)-N-methyl-7-(trifluoromethyl)thieno[3,2-b]pyridine-3-carboxamide;
5-(4-((6-(Methoxymethyl)pyridin-2-yl)methyl)piperazin-1-yl)-N-methyl-7-(trifluoromethyl)thieno[3,2-b]pyridine-3-carboxamide;
N-Methyl-5-(4-((4-methylpyridin-2-yl)methyl)piperazin-1-yl)-7-(trifluoromethyl)thieno[3,2-b]pyridine-3-carboxamide;
N-Methyl-5-(4-((3-methylpyridin-2-yl)methyl)piperazin-1-yl)-7-(trifluoromethyl)thieno[3,2-b]pyridine-3-carboxamide;
5-(4-((6-Methoxypyridin-2-yl)methyl)piperazin-1-yl)-N-methyl-7-(trifluoromethyl)thieno[3,2-b]pyridine-3-carboxamide;
N-Methyl-5-(4-((6-methylpyridin-2-yl)methyl)piperazin-1-yl)-7-(trifluoromethyl)thieno[3,2-b]pyridine-3-carboxamide;
Methyl 5-(4-(2-(isopropylamino)-2-oxoethyl)piperazin-1-yl)-7-(trifluoromethyl)thieno[3,2-b]pyridine-3-carboxylate;
5-(4-(2-(Isopropylamino)-2-oxoethyl)piperazin-1-yl)-N-methyl-7-(trifluoromethyl)thieno[3,2-b]pyridine-3-carboxamide;
5-(4-(2-(Isopropylamino)-2-oxoethyl)piperazin-1-yl)-N,N-dimethyl-7-(trifluoromethyl)thieno[3,2-b]pyridine-3-carboxamide;
Methyl 5-(4-(2-(benzylamino)-2-oxoethyl)piperazin-1-yl)-7-(trifluoromethyl)thieno[3,2-b]pyridine-3-carboxylate;
Methyl 5-(4-(2-oxo-2-(phenylamino)ethyl)piperazin-1-yl)-7-(trifluoromethyl)thieno[3,2-b]pyridine-3-carboxylate;
Methyl 5-(4-(2-(cyclohexylamino)-2-oxoethyl)piperazin-1-yl)-7-(trifluoromethyl)thieno[3,2-b]pyridine-3-carboxylate;
Methyl 5-(4-(2-oxo-2-(piperidin-1-yl)ethyl)piperazin-1-yl)-7-(trifluoromethyl)thieno[3,2-b]pyridine-3-carboxylate;
Methyl 5-(4-(2-oxo-2-(pyrrolidin-1-yl)ethyl)piperazin-1-yl)-7-(trifluoromethyl)thieno[3,2-b]pyridine-3-carboxylate;
Methyl 5-(4-(2-(methylamino)-2-oxoethyl)piperazin-1-yl)-7-(trifluoromethyl)thieno[3,2-b]pyridine-3-carboxylate;
Methyl 5-(4-(4-methylpentanoyl)piperazin-1-yl)-7-(trifluoromethyl)thieno[3,2-b]pyridine-3-carboxylate;
Methyl 5-(4-(4-methylpentyl)piperazin-1-yl)-7-(trifluoromethyl)thieno[3,2-b]pyridine-3-carboxylate;
Isobutyl 4-(3-(methylcarbamoyl)-7-(trifluoromethyl)thieno[3,2-b]pyridin-5-yl)piperazine-1-carboxylate;
N-Methyl-5-(4-(pyridin-2-ylmethyl)piperazin-1-yl)-7-(trifluoromethyl)thieno[3,2-b]pyridine-3-carboxamide;
N-Methyl-5-(4-(pyridin-3-ylmethyl)piperazin-1-yl)-7-(trifluoromethyl)thieno[3,2-b]pyridine-3-carboxamide;
N-Methyl-5-(4-(pyridin-4-ylmethyl)piperazin-1-yl)-7-(trifluoromethyl)thieno[3,2-b]pyridine-3-carboxamide;
5-(4-(2-(Ethylamino)-2-oxoethyl)piperazin-1-yl)-N-methyl-7-(trifluoromethyl)thieno[3,2-b]pyridine-3-carboxamide;
5-(4-(2-(Cyclopropylamino)-2-oxoethyl)piperazin-1-yl)-N-methyl-7-(trifluoromethyl)thieno[3,2-b]pyridine-3-carboxamide;
5-(4-(2-(Isobutylamino)-2-oxoethyl)piperazin-1-yl)-N-methyl-7-(trifluoromethyl)thieno[3,2-b]pyridine-3-carboxamide;

(+/−)-5-(4-(1-(Isopropylamino)-1-oxobutan-2-yl)piperazin-1-yl)-N-methyl-7-(trifluoromethyl)thieno[3,2-b]pyridine-3-carboxamide;

5-(4-(1-(Isopropylamino)-2-methyl-1-oxopropan-2-yl)piperazin-1-yl)-N-methyl-7-(trifluoromethyl)thieno[3,2-b]pyridine-3-carboxamide;

tert-Butyl 2-(4-(3-(methylcarbamoyl)-7-(trifluoromethyl)thieno[3,2-b]pyridin-5-yl)piperazin-1-yl)acetate;

(+/−)-tert-Butyl 2-(4-(3-(methylcarbamoyl)-7-(trifluoromethyl)thieno[3,2-b]pyridin-5-yl)piperazin-1-yl)propanoate;

(+/−)-Isopropyl 2-(4-(3-(methylcarbamoyl)-7-(trifluoromethyl)thieno[3,2-b]pyridin-5-yl)piperazin-1-yl)propanoate;

(+/−)-5-(4-(1-(Isopropylamino)-1-oxopropan-2-yl)piperazin-1-yl)-N-methyl-7-(trifluoromethyl)thieno[3,2-b]pyridine-3-carboxamide;

Isopropyl 2-(4-(3-(methylcarbamoyl)-7-(trifluoromethyl)thieno[3,2-b]pyridin-5-yl)piperazin-1-yl)acetate;

5-(4-(2-(tert-butylamino)-2-oxoethyl)piperazin-1-yl)-N-methyl-7-(trifluoromethyl)thieno[3,2-b]pyridine-3-carboxamide;

(S)-5-(4-(1-(Isopropylamino)-1-oxopropan-2-yl)piperazin-1-yl)-N-methyl-7-(trifluoromethyl)thieno[3,2-b]pyridine-3-carboxamide;

(R)-5-(4-(1-(Isopropylamino)-1-oxopropan-2-yl)piperazin-1-yl)-N-methyl-7-(trifluoromethyl)thieno[3,2-b]pyridine-3-carboxamide;

N-Methyl-5-(4-((6-methylpyrazin-2-yl)methyl)piperazin-1-yl)-7-(trifluoromethyl)thieno[3,2-b]pyridine-3-carboxamide;

(+/−)-5-(4-(2-(Cyclopropylmethoxy)propyl)piperazin-1-yl)-N-methyl-7-(trifluoromethyl)thieno[3,2-b]pyridine-3-carboxamide;

(+/−)-5-(4-(1-(Cyclopropylmethoxy)propan-2-yl)piperazin-1-yl)-N-methyl-7-(trifluoromethyl)thieno[3,2-b]pyridine-3-carboxamide;

5-(4-(2-(Cyclopropylmethoxy)ethyl)piperazin-1-yl)-N-methyl-7-(trifluoromethyl)thieno[3,2-b]pyridine-3-carboxamide;

5-(4-(2-Cyclopropoxyethyl)piperazin-1-yl)-N-methyl-7-(trifluoromethyl)thieno[3,2-b]pyridine-3-carboxamide;

5-(4-(2-Isopropoxyethyl)piperazin-1-yl)-N-methyl-7-(trifluoromethyl)thieno[3,2-b]pyridine-3-carboxamide;

5-(4-(2-Isopropoxyacetyl)piperazin-1-yl)-N-methyl-7-(trifluoromethyl)thieno[3,2-b]pyridine-3-carboxamide;

5-(4-(2-(Isopropyl(methyl)amino)-2-oxoethyl)piperazin-1-yl)-N-methyl-7-(trifluoromethyl)thieno[3,2-b]pyridine-3-carboxamide;

5-(4-(1-isopropyl-2-oxopyrrolidin-3-yl)piperazin-1-yl)-N-methyl-7-(trifluoromethyl)thieno[3,2-b]pyridine-3-carboxamide;

5-(4-(2-(Isopropylamino)-2-oxoethyl)piperazin-1-yl)-N,6-dimethyl-7-(trifluoromethyl)thieno[3,2-b]pyridine-3-carboxamide;

5-(4-(2-(Isopropylamino)-2-oxoethyl)piperazin-1-yl)-N,7-dimethylthieno[3,2-b]pyridine-3-carboxamide;

5-(4-(2-(Isopropylamino)-2-oxoethyl)-3,3-dimethylpiperazin-1-yl)-N-methyl-7-(trifluoromethyl)thieno[3,2-b]pyridine-3-carboxamide;

(+/−)-5-(3-Isopropyl-4-(2-(isopropylamino)-2-oxoethyl)piperazin-1-yl)-N-methyl-7-(trifluoromethyl)thieno[3,2-b]pyridine-3-carboxamide;

(+/−)-5-(3-Ethyl-4-(2-(isopropylamino)-2-oxoethyl)piperazin-1-yl)-N-methyl-7-(trifluoromethyl)thieno[3,2-b]pyridine-3-carboxamide;

(+/−)-5-(4-(2-(Isopropylamino)-2-oxoethyl)-2-methylpiperazin-1-yl)-N-methyl-7-(trifluoromethyl)thieno[3,2-b]pyridine-3-carboxamide;

5-(8-(2-(Isopropylamino)-2-oxoethyl)-3,8-diazabicyclo[3.2.1]octan-3-yl)-N-methyl-7-(trifluoromethyl)thieno[3,2-b]pyridine-3-carboxamide;

5-(4-(2-(isopropylamino)-2-oxoethyl)-4,7-diazaspiro[2.5]octan-7-yl)-N-methyl-7-(trifluoromethyl)thieno[3,2-b]pyridine-3-carboxamide;

(+/−)-5-(4-(2-(Isopropylamino)-2-oxoethyl)-3-methylpiperazin-1-yl)-N-methyl-7-(trifluoromethyl)thieno[3,2-b]pyridine-3-carboxamide;

5-(4-(2-(Isopropylamino)-2-oxoethyl)-1,4-diazepan-1-yl)-N-methyl-7-(trifluoromethyl)thieno[3,2-b]pyridine-3-carboxamide;

N-Isopropyl-2-(4-(3-isopropyl-7-(trifluoromethyl)thieno[3,2-b]pyridin-5-yl)piperazin-1-yl)acetamide;

2-(4-(3-(Hydroxymethyl)-7-(trifluoromethyl)thieno[3,2-b]pyridin-5-yl)piperazin-1-yl)-N-isopropylacetamide;

5-(4-(2-(Isopropylamino)-2-oxoethyl)piperazin-1-yl)-7-(trifluoromethyl)thieno[3,2-b]pyridine-3-carboxylic acid;

1-(3-(Methylcarbamoyl)-7-(trifluoromethyl)thieno[3,2-b]pyridin-5-yl)piperidin-4-yl azetidine-1-carboxylate;

1-(3-(Methylcarbamoyl)-7-(trifluoromethyl)thieno[3,2-b]pyridin-5-yl)piperidin-4-yl (S)-pentan-2-ylcarbamate;

1-(3-(Methylcarbamoyl)-7-(trifluoromethyl)thieno[3,2-b]pyridin-5-yl)piperidin-4-yl (S)-(3-methylbutan-2-yl)carbamate;

1-(3-(Methylcarbamoyl)-7-(trifluoromethyl)thieno[3,2-b]pyridin-5-yl)piperidin-4-yl (S)-sec-butylcarbamate;

1-(3-(Methylcarbamoyl)-7-(trifluoromethyl)thieno[3,2-b]pyridin-5-yl)piperidin-4-yl cyclobutylcarbamate;

1-(3-(Methylcarbamoyl)-7-(trifluoromethyl)thieno[3,2-b]pyridin-5-yl)piperidin-4-yl (2-(trifluoromethoxy)ethyl)carbamate;

1-(3-(Methylcarbamoyl)-7-(trifluoromethyl)thieno[3,2-b]pyridin-5-yl)piperidin-4-yl 5-azaspiro[2.3]hexane-5-carboxylate;

1-(3-(Methylcarbamoyl)-7-(trifluoromethyl)thieno[3,2-b]pyridin-5-yl)piperidin-4-yl 1,1-difluoro-5-azaspiro[2.3]hexane-5-carboxylate;

1-(3-(Methylcarbamoyl)-7-(trifluoromethyl)thieno[3,2-b]pyridin-5-yl)piperidin-4-yl 3-(methoxymethyl)azetidine-1-carboxylate;

1-(3-(Methylcarbamoyl)-7-(trifluoromethyl)thieno[3,2-b]pyridin-5-yl)piperidin-4-yl 3-(dimethylamino)-3-methylazetidine-1-carboxylate;

1-(3-(Methylcarbamoyl)-7-(trifluoromethyl)thieno[3,2-b]pyridin-5-yl)piperidin-4-yl 3-((dimethylamino)methyl)azetidine-1-carboxylate;

1-(3-(Methylcarbamoyl)-7-(trifluoromethyl)thieno[3,2-b]pyridin-5-yl)piperidin-4-yl 3-(oxetan-3-yl)azetidine-1-carboxylate;

1-(3-(Methylcarbamoyl)-7-(trifluoromethyl)thieno[3,2-b]pyridin-5-yl)piperidin-4-yl 3-hydroxy-3-(trifluoromethyl)azetidine-1-carboxylate;

1-(3-(Methylcarbamoyl)-7-(trifluoromethyl)thieno[3,2-b]pyridin-5-yl)piperidin-4-yl (1R,6S)-5-methyl-2,5-diazabicyclo[4.1.0]heptane-2-carboxylate;

1-(3-(Methylcarbamoyl)-7-(trifluoromethyl)thieno[3,2-b]pyridin-5-yl)piperidin-4-yl (1S,6R)-5-methyl-2,5-diazabicyclo[4.1.0]heptane-2-carboxylate;

1-(3-(Methylcarbamoyl)-7-(trifluoromethyl)thieno[3,2-b]pyridin-5-yl)piperidin-4-yl 3-cyclopropylazetidine-1-carboxylate;

1-(3-(Methylcarbamoyl)-7-(trifluoromethyl)thieno[3,2-b]pyridin-5-yl)piperidin-4-yl isopropylcarbamate;

1-(3-(Methylcarbamoyl)-7-(trifluoromethyl)thieno[3,2-b]pyridin-5-yl)piperidin-4-yl (cyclobutylmethyl)carbamate;

1-(3-(Methylcarbamoyl)-7-(trifluoromethyl)thieno[3,2-b]pyridin-5-yl)piperidin-4-yl (S)-but-3-yn-2-ylcarbamate;

1-(3-(Methylcarbamoyl)-7-(trifluoromethyl)thieno[3,2-b]pyridin-5-yl)piperidin-4-yl (3S,5S)-3,5-dimethylmorpholine-4-carboxylate;

1-(3-(Methylcarbamoyl)-7-(trifluoromethyl)thieno[3,2-b]pyridin-5-yl)piperidin-4-yl (S)-2-methylpiperidine-1-carboxylate;

1-(3-(Methylcarbamoyl)-7-(trifluoromethyl)thieno[3,2-b]pyridin-5-yl)piperidin-4-yl (S)-2-methylpyrrolidine-1-carboxylate;

1-(3-(Methylcarbamoyl)-7-(trifluoromethyl)thieno[3,2-b]pyridin-5-yl)piperidin-4-yl (S)-(1-cyanoethyl)carbamate;

1-(3-(Methylcarbamoyl)-7-(trifluoromethyl)thieno[3,2-b]pyridin-5-yl)piperidin-4-yl 5,6,7,8-tetrahydro-[1,2,4]triazolo[1,5-a]pyrazine-7-carboxylate;

1-(3-(Methylcarbamoyl)-7-(trifluoromethyl)thieno[3,2-b]pyridin-5-yl)piperidin-4-yl 6-oxa-1-azaspiro[3.3]heptane-1-carboxylate;

1-(3-(Methylcarbamoyl)-7-(trifluoromethyl)thieno[3,2-b]pyridin-5-yl)piperidin-4-yl isopropyl(methyl)carbamate;

(1α,5α,6α)-3-(3-(Methylcarbamoyl)-7-(trifluoromethyl)thieno[3,2-b]pyridin-5-yl)-3-azabicyclo[3.1.0]hexan-6-yl (cyclopropylmethyl)carbamate;

1-(3-(Methylcarbamoyl)-7-(trifluoromethyl)thieno[3,2-b]pyridin-5-yl)piperidin-4-yl 3-(difluoromethoxy)azetidine-1-carboxylate;

1-(3-(Methylcarbamoyl)-7-(trifluoromethyl)thieno[3,2-b]pyridin-5-yl)piperidin-4-yl 3-(trifluoromethoxy)azetidine-1-carboxylate;

1-(3-(Methylcarbamoyl)-7-(trifluoromethyl)thieno[3,2-b]pyridin-5-yl)piperidin-4-yl 3-((trifluoromethoxy)methyl)azetidine-1-carboxylate;

1-(3-(Methylcarbamoyl)-7-(trifluoromethyl)thieno[3,2-b]pyridin-5-yl)piperidin-4-yl (S)-(1-(trifluoromethoxy)propan-2-yl)carbamate;

3,3-Difluoro-1-(3-(methylcarbamoyl)-7-(trifluoromethyl)thieno[3,2-b]pyridin-5-yl)piperidin-4-yl isopropylcarbamate;

3,3-Difluoro-1-(3-(methylcarbamoyl)-7-(trifluoromethyl)thieno[3,2-b]pyridin-5-yl)piperidin-4-yl 4-cyclopropylpiperazine-1-carboxylate;

3,3-Difluoro-1-(3-(methylcarbamoyl)-7-(trifluoromethyl)thieno[3,2-b]pyridin-5-yl)piperidin-4-yl (2S)-2,4-dimethylpiperazine-1-carboxylate;

3,3-Dimethyl-1-(3-(methylcarbamoyl)-7-(trifluoromethyl)thieno[3,2-b]pyridin-5-yl)piperidin-4-yl 4-methylpiperazine-1-carboxylate;

1-(3-(Methylcarbamoyl)-7-(trifluoromethyl)thieno[3,2-b]pyridin-5-yl)piperidin-4-yl 6,7-dihydropyrazolo[1,5-a]pyrazine-5(4H)-carboxylate;

1-(3-(methylcarbamoyl)-7-(trifluoromethyl)thieno[3,2-b]pyridin-5-yl)piperidin-4-yl 5,6-dihydroimidazo[1,5-a]pyrazine-7(8H)-carboxylate;

1-(3-(methylcarbamoyl)-7-(trifluoromethyl)thieno[3,2-b]pyridin-5-yl)piperidin-4-yl 5,6-dihydroimidazo[1,5-a]pyrazine-7(8H)-carboxylate;

1-(3-(Methylcarbamoyl)-7-(trifluoromethyl)thieno[3,2-b]pyridin-5-yl)piperidin-4-yl (3aR,6aS)-5-methylhexahydropyrrolo[3,4-c]pyrrole-2(1H)-carboxylate;

1-(3-(Methylcarbamoyl)-7-(trifluoromethyl)thieno[3,2-b]pyridin-5-yl)piperidin-4-yl 3-(dimethylamino)azetidine-1-carboxylate;

1-(3-(Methylcarbamoyl)-7-(trifluoromethyl)thieno[3,2-b]pyridin-5-yl)piperidin-4-yl (S)-(1-(thiazol-2-yl)ethyl)carbamate;

1-(3-(Methylcarbamoyl)-7-(trifluoromethyl)thieno[3,2-b]pyridin-5-yl)piperidin-4-yl (S)-2-ethyl-4-methylpiperazine-1-carboxylate;

(+/−)-trans-1-(3-(Methylcarbamoyl)-7-(trifluoromethyl)thieno[3,2-b]pyridin-5-yl)piperidin-4-yl 4-methoxy-1-methylpyrrolidin-3-yl)carbamate;

1-(3-(Methylcarbamoyl)-7-(trifluoromethyl)thieno[3,2-b]pyridin-5-yl)piperidin-4-yl (R)-2,4-dimethylpiperazine-1-carboxylate;

1-(3-(Methylcarbamoyl)-7-(trifluoromethyl)thieno[3,2-b]pyridin-5-yl)piperidin-4-yl (S)-2,4-dimethylpiperazine-1-carboxylate;

1-(3-(Methylcarbamoyl)-7-(trifluoromethyl)thieno[3,2-b]pyridin-5-yl)piperidin-4-yl (2-(pyrrolidin-1-yl)ethyl)carbamate;

(+/−)-1-(3-(Methylcarbamoyl)-7-(trifluoromethyl)thieno[3,2-b]pyridin-5-yl)piperidin-4-yl (2-(3-fluoropyrrolidin-1-yl)ethyl)carbamate;

1-(3-(Methylcarbamoyl)-7-(trifluoromethyl)thieno[3,2-b]pyridin-5-yl)piperidin-4-yl (2-(3,3-difluoropyrrolidin-1-yl)ethyl)carbamate;

1-(3-(Methylcarbamoyl)-7-(trifluoromethyl)thieno[3,2-b]pyridin-5-yl)piperidin-4-yl (R)-(1-cyclopropylethyl)carbamate;

1-(3-(Methylcarbamoyl)-7-(trifluoromethyl)thieno[3,2-b]pyridin-5-yl)piperidin-4-yl (S)-(1-cyclopropylethyl)carbamate;

1-(3-(Methylcarbamoyl)-7-(trifluoromethyl)thieno[3,2-b]pyridin-5-yl)piperidin-4-yl pyrrolidin-1-ylcarbamate;

1-(3-(Methylcarbamoyl)-7-(trifluoromethyl)thieno[3,2-b]pyridin-5-yl)piperidin-4-yl (cyclopropylmethyl)(methyl)carbamate;

1-(3-(Methylcarbamoyl)-7-(trifluoromethyl)thieno[3,2-b]pyridin-5-yl)piperidin-4-yl 4-(cyclopropylmethyl)piperazine-1-carboxylate;

1-(3-(Methylcarbamoyl)-7-(trifluoromethyl)thieno[3,2-b]pyridin-5-yl)piperidin-4-yl (2-isopropoxyethyl)carbamate;

1-(3-(Methylcarbamoyl)-7-(trifluoromethyl)thieno[3,2-b]pyridin-5-yl)piperidin-4-yl 4-methylpiperazine-1-carboxylate;

1-(3-(Methylcarbamoyl)-7-(trifluoromethyl)thieno[3,2-b]pyridin-5-yl)piperidin-4-yl ((4-methylmorpholin-2-yl)methyl)carbamate;

1-(3-(Methylcarbamoyl)-7-(trifluoromethyl)thieno[3,2-b]pyridin-5-yl)piperidin-4-yl (R)-3,4-dimethylpiperazine-1-carboxylate;

1-(3-(Methylcarbamoyl)-7-(trifluoromethyl)thieno[3,2-b]pyridin-5-yl)piperidin-4-yl (S)-3,4-dimethylpiperazine-1-carboxylate;

1-(3-(Methylcarbamoyl)-7-(trifluoromethyl)thieno[3,2-b]pyridin-5-yl)piperidin-4-yl (R)-2-(hydroxymethyl)-4-methylpiperazine-1-carboxylate;

1-(3-(Methylcarbamoyl)-7-(trifluoromethyl)thieno[3,2-b]pyridin-5-yl)piperidin-4-yl ((2S,3R)-3-hydroxybutan-2-yl)carbamate;

1-(3-(Methylcarbamoyl)-7-(trifluoromethyl)thieno[3,2-b]pyridin-5-yl)piperidin-4-yl (S)-3-methylmorpholine-4-carboxylate;

1-(3-(Methylcarbamoyl)-7-(trifluoromethyl)thieno[3,2-b]pyridin-5-yl)piperidin-4-yl cis-3-hydroxycyclobutyl)carbamate;

1-(3-(Methylcarbamoyl)-7-(trifluoromethyl)thieno[3,2-b]pyridin-5-yl)piperidin-4-yl trans-3-hydroxycyclobutyl)carbamate;
1-(3-(Methylcarbamoyl)-7-(trifluoromethyl)thieno[3,2-b]pyridin-5-yl)piperidin-4-yl (S)-(1-cyanopropan-2-yl)carbamate;
1-(3-(Methylcarbamoyl)-7-(trifluoromethyl)thieno[3,2-b]pyridin-5-yl)piperidin-4-yl (S)-(1-hydroxypropan-2-yl)carbamate;
1-(3-(Methylcarbamoyl)-7-(trifluoromethyl)thieno[3,2-b]pyridin-5-yl)piperidin-4-yl 3-hydroxyazetidine-1-carboxylate;
1-(3-(Methylcarbamoyl)-7-(trifluoromethyl)thieno[3,2-b]pyridin-5-yl)piperidin-4-yl (S)-(1-methoxypropan-2-yl)carbamate;
(+/−)-1-(3-(Methylcarbamoyl)-7-(trifluoromethyl)thieno[3,2-b]pyridin-5-yl)piperidin-4-yl trans-4-hydroxy-1-methylpyrrolidin-3-yl)carbamate;
1-(3-(Methylcarbamoyl)-7-(trifluoromethyl)thieno[3,2-b]pyridin-5-yl)piperidin-4-yl (2-hydroxy-2-methylpropyl)carbamate;
1-(3-(Methylcarbamoyl)-7-(trifluoromethyl)thieno[3,2-b]pyridin-5-yl)piperidin-4-yl (S)-2-methylpiperazine-1-carboxylate;
4-((Dimethylamino)methyl)-1-(3-(methylcarbamoyl)-7-(trifluoromethyl)thieno[3,2-b]pyridin-5-yl)piperidin-4-yl (S)-2-methylpyrrolidine-1-carboxylate;
4-((Dimethylamino)methyl)-1-(3-(methylcarbamoyl)-7-(trifluoromethyl)thieno[3,2-b]pyridin-5-yl)piperidin-4-yl isopropylcarbamate;
4-(Methoxymethyl)-1-(3-(methylcarbamoyl)-7-(trifluoromethyl)thieno[3,2-b]pyridin-5-yl)piperidin-4-yl isopropylcarbamate;
1-(3-(Dimethylcarbamoyl)-7-(trifluoromethyl)thieno[3,2-b]pyridin-5-yl)piperidin-4-yl (S)-(1-cyanopropan-2-yl)carbamate;
1-(3-(Azetidine-1-carbonyl)-7-(trifluoromethyl)thieno[3,2-b]pyridin-5-yl)piperidin-4-yl (S)-(1-cyanopropan-2-yl)carbamate;
(+/−)-trans-3-(Dimethylamino)-1-(3-(methylcarbamoyl)-7-(trifluoromethyl)thieno[3,2-b]pyridin-5-yl)piperidin-4-yl (cyclopropylmethyl)carbamate;
(+/−)-cis-3-Methyl-1-(3-(methylcarbamoyl)-7-(trifluoromethyl)thieno[3,2-b]pyridin-5-yl)piperidin-4-yl 4-methylpiperazine-1-carboxylate;
1-(3-(Methoxycarbamoyl)-7-(trifluoromethyl)thieno[3,2-b]pyridin-5-yl)piperidin-4-yl (cyclopropylmethyl)carbamate;
(+/−)-trans-1-(3-(Methylcarbamoyl)-7-(trifluoromethyl)thieno[3,2-b]pyridin-5-yl)piperidin-4-yl 4-fluoro-1-methylpyrrolidin-3-yl)carbamate;
(+/−)-cis-1-(3-(Methylcarbamoyl)-7-(trifluoromethyl)thieno[3,2-b]pyridin-5-yl)piperidin-4-yl 4-fluoro-1-methylpyrrolidin-3-yl)carbamate;
5-(3-Isopropyl-2-oxo-1-oxa-3,8-diazaspiro[4.5]decan-8-yl)-N-methyl-7-(trifluoromethyl)thieno[3,2-b]pyridine-3-carboxamide;
5-(2-Isopropyl-2,8-diazaspiro[4.5]decan-8-yl)-N-methyl-7-(trifluoromethyl)thieno[3,2-b]pyridine-3-carboxamide;
1-(3-(Methylcarbamoyl)thieno[3,2-b]pyridin-5-yl)piperidin-4-yl (S)-(1-(trifluoromethoxy)propan-2-yl)carbamate;
1-(7-Methyl-3-(methylcarbamoyl)thieno[3,2-b]pyridin-5-yl)piperidin-4-yl isopropylcarbamate;
1-(7-Methyl-3-(methylcarbamoyl)thieno[3,2-b]pyridin-5-yl)piperidin-4-yl (S)-(1-(trifluoromethoxy)propan-2-yl)carbamate;
N-Methyl-5-(4-((6-methylpyridin-2-yl)oxy)piperidin-1-yl)-7-(trifluoromethyl)thieno[3,2-b]pyridine-3-carboxamide;
5-(4-((6-Ethylpyridin-2-yl)oxy)piperidin-1-yl)-N-methyl-7-(trifluoromethyl)thieno[3,2-b]pyridine-3-carboxamide;
N-Methyl-5-(4-((2-methylpyrimidin-4-yl)oxy)piperidin-1-yl)-7-(trifluoromethyl)thieno[3,2-b]pyridine-3-carboxamide;
(+/−)-N-Methyl-5-(cis-3-methyl-4-((2-methylpyrimidin-4-yl)oxy)piperidin-1-yl)-7-(trifluoromethyl)thieno[3,2-b]pyridine-3-carboxamide;
(+/−)-N-Methyl-5-(trans-3-methyl-4-((2-methylpyrimidin-4-yl)oxy)piperidin-1-yl)-7-(trifluoromethyl)thieno[3,2-b]pyridine-3-carboxamide;
5-(4-((3-Cyclopropyl-1,2,4-thiadiazol-5-yl)oxy)piperidin-1-yl)-N-methyl-7-(trifluoromethyl)thieno[3,2-b]pyridine-3-carboxamide;
1-(6-Methyl-3-(methylcarbamoyl)-7-(trifluoromethyl)thieno[3,2-b]pyridin-5-yl)piperidin-4-yl (S)-(1-cyclopropylethyl)carbamate;
1-(3-(Methylcarbamoyl)-7-(trifluoromethyl)thieno[3,2-b]pyridin-5-yl)piperidin-4-yl (S)-(1-cyanopropan-2-yl)(methyl)carbamate;
1-(3-(Methylcarbamoyl)-7-(trifluoromethyl)thieno[3,2-b]pyridin-5-yl)piperidin-4-yl ((1-(2,2-difluoroethyl)azetidin-3-yl)methyl)carbamate;
Methyl 5-(4-(2-(isopropylamino)-2-oxoethyl)piperidin-1-yl)-7-(trifluoromethyl)thieno[3,2-b]pyridine-3-carboxylate;
5-(4-(2-(Isopropylamino)-2-oxoethyl)piperidin-1-yl)-N-methyl-7-(trifluoromethyl)thieno[3,2-b]pyridine-3-carboxamide;
5-(4-(2-((1-Methoxypropan-2-yl)amino)-2-oxoethyl)piperidin-1-yl)-N-methyl-7-(trifluoromethyl)thieno[3,2-b]pyridine-3-carboxamide;
5-(4-(2-((1,3-Dimethoxypropan-2-yl)amino)-2-oxoethyl)piperidin-1-yl)-N-methyl-7-(trifluoromethyl)thieno[3,2-b]pyridine-3-carboxamide;
(S)-1-Methoxypropan-2-yl (1-(3-(methylcarbamoyl)-7-(trifluoromethyl)thieno[3,2-b]pyridin-5-yl)piperidin-4-yl) carbonate;
Isopropyl (1-(3-(methylcarbamoyl)-7-(trifluoromethyl)thieno[3,2-b]pyridin-5-yl)piperidin-4-yl) carbonate;
(R)-1-Cyclopropylethyl 4-((3-(methylcarbamoyl)-7-(trifluoromethyl)thieno[3,2-b]pyridin-5-yl)oxy)piperidine-1-carboxylate;
(S)-1-Cyclopropylethyl 4-((3-(methylcarbamoyl)-7-(trifluoromethyl)thieno[3,2-b]pyridin-5-yl)oxy)piperidine-1-carboxylate;
Isopropyl 4-((3-(methylcarbamoyl)-7-(trifluoromethyl)thieno[3,2-b]pyridin-5-yl)oxy)piperidine-1-carboxylate;
tert-Butyl 3,3-difluoro-4-((3-(methylcarbamoyl)-7-(trifluoromethyl)thieno[3,2-b]pyridin-5-yl)oxy)piperidine-1-carboxylate;
N-Methyl-5-((1-(6-methylpyridin-2-yl)piperidin-4-yl)oxy)-7-(trifluoromethyl)thieno[3,2-b]pyridine-3-carboxamide;
2-Cyanoethyl 4-((3-(methylcarbamoyl)-7-(trifluoromethyl)thieno[3,2-b]pyridin-5-yl)oxy)piperidine-1-carboxylate;
2-Isopropoxyethyl 4-((3-(methylcarbamoyl)-7-(trifluoromethyl)thieno[3,2-b]pyridin-5-yl)oxy)piperidine-1-carboxylate;
2-(tert-Butoxy)ethyl 4-((3-(methylcarbamoyl)-7-(trifluoromethyl)thieno[3,2-b]pyridin-5-yl)oxy)piperidine-1-carboxylate;
(3-Fluoroazetidin-3-yl)methyl 4-((3-(methylcarbamoyl)-7-(trifluoromethyl)thieno[3,2-b]pyridin-5-yl)oxy)piperidine-1-carboxylate;

1-(Prop-2-yn-1-yl)azetidin-3-yl 4-((3-(methylcarbamoyl)-7-(trifluoromethyl)thieno[3,2-b]pyridin-5-yl)oxy)piperidine-1-carboxylate;

1-(Cyanomethyl)azetidin-3-yl 4-((3-(methylcarbamoyl)-7-(trifluoromethyl)thieno[3,2-b]pyridin-5-yl)oxy)piperidine-1-carboxylate;

2-(Trifluoromethoxy)ethyl 4-((3-(methylcarbamoyl)-7-(trifluoromethyl)thieno[3,2-b]pyridin-5-yl)oxy)piperidine-1-carboxylate;

2-(Trifluoromethoxy)ethyl 4-((6-chloro-3-(methylcarbamoyl)thieno[3,2-b]pyridin-5-yl)oxy)piperidine-1-carboxylate;

2-(Trifluoromethoxy)ethyl 4-((6-bromo-3-(methylcarbamoyl)thieno[3,2-b]pyridin-5-yl)oxy)piperidine-1-carboxylate;

2-(Trifluoromethoxy)ethyl 4-((6-cyclopropyl-3-(methylcarbamoyl)thieno[3,2-b]pyridin-5-yl)oxy)piperidine-1-carboxylate;

(S)-1-(Trifluoromethoxy)propan-2-yl (2R,4R)-2-methyl-4-((3-(methylcarbamoyl)-7-(trifluoromethyl)thieno[3,2-b]pyridin-5-yl)oxy)piperidine-1-carboxylate;

(S)-1-(Trifluoromethoxy)propan-2-yl (2R,4R)-2-methyl-4-((6-methyl-3-(methylcarbamoyl)-7-(trifluoromethyl)thieno[3,2-b]pyridin-5-yl)oxy)piperidine-1-carboxylate;

2-(Trifluoromethoxy)ethyl (2R,4R)-2-methyl-4-((6-methyl-3-(methylcarbamoyl)-7-(trifluoromethyl)thieno[3,2-b]pyridin-5-yl)oxy)piperidine-1-carboxylate;

(S)-1-(Trifluoromethoxy)propan-2-yl 4-((6-methyl-3-(methylcarbamoyl)-7-(trifluoromethyl)thieno[3,2-b]pyridin-5-yl)oxy)piperidine-1-carboxylate;

2-(Trifluoromethoxy)ethyl (2R,4S)-2-methyl-4-((6-methyl-3-(methylcarbamoyl)-7-(trifluoromethyl)thieno[3,2-b]pyridin-5-yl)oxy)piperidine-1-carboxylate;

2-(Trifluoromethoxy)ethyl (3S,4R)-3-fluoro-4-((6-methyl-3-(methylcarbamoyl)-7-(trifluoromethyl)thieno[3,2-b]pyridin-5-yl)oxy)piperidine-1-carboxylate;

(S)-1-(Trifluoromethoxy)propan-2-yl (3S,4R)-3-fluoro-4-((6-methyl-3-(methylcarbamoyl)-7-(trifluoromethyl)thieno[3,2-b]pyridin-5-yl)oxy)piperidine-1-carboxylate;

2-(Trifluoromethoxy)ethyl (3R,4S)-3-fluoro-4-((6-methyl-3-(methylcarbamoyl)-7-(trifluoromethyl)thieno[3,2-b]pyridin-5-yl)oxy)piperidine-1-carboxylate;

(S)-1-(Trifluoromethoxy)propan-2-yl (3R,4S)-3-fluoro-4-((6-methyl-3-(methylcarbamoyl)-7-(trifluoromethyl)thieno[3,2-b]pyridin-5-yl)oxy)piperidine-1-carboxylate;

(S)-1-(Trifluoromethoxy)propan-2-yl (2R,4S)-2-methyl-4-((6-methyl-3-(methylcarbamoyl)-7-(trifluoromethyl)thieno[3,2-b]pyridin-5-yl)oxy)piperidine-1-carboxylate;

1-(3-(Methylcarbamoyl)-7-(trifluoromethyl)isothiazolo[4,5-b]pyridin-5-yl)piperidin-4-yl (cyclopropylmethyl)carbamate;

1-(7-(Methylcarbamoyl)-4-(trifluoromethyl)thieno[3,2-d]pyrimidin-2-yl)piperidin-4-yl (S)-(1-methoxypropan-2-yl)carbamate;

1-(7-(Methylcarbamoyl)-4-(trifluoromethyl)thieno[3,2-d]pyrimidin-2-yl)piperidin-4-yl (S)-(1-cyclopropylethyl)carbamate;

1-(7-(Methylcarbamoyl)-4-(trifluoromethyl)thieno[3,2-d]pyrimidin-2-yl)piperidin-4-yl (S)-2,4-dimethylpiperazine-1-carboxylate;

1-(3-Propionyl-7-(trifluoromethyl)thieno[3,2-b]pyridin-5-yl)piperidin-4-yl 4-methylpiperazine-1-carboxylate dihydrochloride;

5-(3-((5-Fluoropyridin-3-yl)oxy)azetidin-1-yl)-N-methyl-7-(trifluoromethyl)thieno[3,2-b]pyridine-3-carboxamide;

N-Methyl-5-(3-((3-methylpyridin-2-yl)oxy)azetidin-1-yl)-7-(trifluoromethyl)thieno[3,2-b]pyridine-3-carboxamide;

5-(3-((3-Fluoropyridin-2-yl)oxy)azetidin-1-yl)-N-methyl-7-(trifluoromethyl)thieno[3,2b]pyridine-3-carboxamide;

N-Methyl-5-(3-((2-methylpyridin-3-yl)oxy)azetidin-1-yl)-7-(trifluoromethyl)thieno[3,2-b]pyridine-3-carboxamide;

Isopentyl 3-(3-(methylcarbamoyl)-7-(trifluoromethyl)thieno[3,2-b]pyridin-5-yl)azetidine-1-carboxylate;

Cyclopropylmethyl 3-(3-(methylcarbamoyl)-7-(trifluoromethyl)thieno[3,2-b]pyridin-5 yl)azetidine-1-carboxylate;

Isopropyl 6-((3-(methylcarbamoyl)-7-(trifluoromethyl)thieno[3,2-b]pyridin-5-yl)oxy)-2-azaspiro[3.3]heptane-2-carboxylate;

1-Fluoropropan-2-yl 6-((3-(methylcarbamoyl)-7-(trifluoromethyl)thieno[3,2-b]pyridin-5-yl)oxy)-2-azaspiro[3.3]heptane-2-carboxylate;

1-Methoxy-2-methylpropan-2-yl 6-((3-(methylcarbamoyl)-7-(trifluoromethyl)thieno[3,2-b]pyridin-5-yl)oxy)-2-azaspiro[3.3]heptane-2-carboxylate;

2,2-Difluoroethyl 6-((3-(methylcarbamoyl)-7-(trifluoromethyl)thieno[3,2-b]pyridin-5-yl)oxy)-2-azaspiro[3.3]heptane-2-carboxylate;

Oxetan-3-ylmethyl 6-((3-(methylcarbamoyl)-7-(trifluoromethyl)thieno[3,2-b]pyridin-5-yl)oxy)-2-azaspiro[3.3]heptane-2-carboxylate;

Cyclopropyl 6-((3-(methylcarbamoyl)-7-(trifluoromethyl)thieno[3,2-b]pyridin-5-yl)oxy)-2-azaspiro[3.3]heptane-2-carboxylate;

Oxetan-3-yl 6-((3-(methylcarbamoyl)-7-(trifluoromethyl)thieno[3,2-b]pyridin-5-yl)oxy)-2-azaspiro[3.3]heptane-2-carboxylate;

2-(Trifluoromethoxy)ethyl 6-((3-(methylcarbamoyl)-7-(trifluoromethyl)thieno[3,2-b]pyridin-5-yl)oxy)-2-azaspiro[3.3]heptane-2-carboxylate;

(R)-1-Cyclopropylethyl 6-((3-(methylcarbamoyl)-7-(trifluoromethyl)thieno[3,2-b]pyridin-5-yl)oxy)-2-azaspiro[3.3]heptane-2-carboxylate;

(S)-1-Cyclopropylethyl 6-((3-(methylcarbamoyl)-7-(trifluoromethyl)thieno[3,2-b]pyridin-5-yl)oxy)-2-azaspiro[3.3]heptane-2-carboxylate;

5-((2-(3-Fluoro-2,2-dimethylpropanoyl)-2-azaspiro[3.3]heptan-6-yl)oxy)-N-methyl-7-(trifluoromethyl)thieno[3,2-b]pyridine-3-carboxamide;

5-((2-(2,2-Dimethyl-3-(trifluoromethoxy)propanoyl)-2-azaspiro[3.3]heptan-6-yl)oxy)-N-methyl-7-(trifluoromethyl)thieno[3,2-b]pyridine-3-carboxamide;

5-((2-Isobutyryl-2-azaspiro[3.3]heptan-6-yl)oxy)-N-methyl-7-(trifluoromethyl)thieno[3,2-b]pyridine-3-carboxamide;

5-((2-(5-Fluoropyridin-3-yl)-2-azaspiro[3.3]heptan-6-yl)oxy)-N-methyl-7-(trifluoromethyl)thieno[3,2-b]pyridine-3-carboxamide;

5-((2-(6-Fluoropyridin-2-yl)-2-azaspiro[3.3]heptan-6-yl)oxy)-N-methyl-7(trifluoromethyl)thieno[3,2-b]pyridine-3-carboxamide;

N-Methyl-5-((2-(2,2,2-trifluoroethyl)-2-azaspiro[3.3]heptan-6-yl)oxy)-7-(trifluoromethyl)thieno[3,2-b]pyridine-3-carboxamide;

2-(Trifluoromethoxy)ethyl 6-((3-(methylcarbamoyl)-7-(trifluoromethyl)thieno[3,2-b]pyridin-5-yl)oxy)-1-azaspiro[3.3]heptane-1-carboxylate;

tert-Butyl 2-((3-(methylcarbamoyl)-7-(trifluoromethyl)thieno[3,2-b]pyridin-5-yl)oxy)-7-azaspiro[3.5]nonane-7-carboxylate;

2-(Trifluoromethoxy)ethyl 6-((3-(methylcarbamoyl)-7-(trifluoromethyl)thieno[3,2-b]pyridin-5-yl)oxy)-3-azabicyclo[3.1.1]heptane-3-carboxylate;

2-(Trifluoromethoxy)ethyl 3-((6-methyl-3-(methylcarbamoyl)-7-(trifluoromethyl)thieno[3,2-b]pyridin-5-yl)oxy)azetidine-1-carboxylate;

2-(Trifluoromethoxy)ethyl 6-((6-methyl-3-(methylcarbamoyl)-7-(trifluoromethyl)thieno[3,2-b]pyridin-5-yl)oxy)-2-azaspiro[3.3]heptane-2-carboxylate;

(S)-1-Cyclopropylethyl 6-((6-methyl-3-(methylcarbamoyl)-7-(trifluoromethyl)thieno[3,2-b]pyridin-5-yl)oxy)-2-azaspiro[3.3]heptane-2-carboxylate;

Cyclopropylmethyl ((1s,3s)-3-((6-methyl-3-(methylcarbamoyl)-7-(trifluoromethyl)thieno[3,2-b]pyridin-5-yl)oxy)cyclobutyl)carbamate;

Isopropyl ((1s,3s)-3-((6-methyl-3-(methylcarbamoyl)-7-(trifluoromethyl)thieno[3,2-b]pyridin-5-yl)oxy)cyclobutyl)carbamate;

(S)-1-Cyclopropylethyl ((1s,3R)-3-((6-methyl-3-(methylcarbamoyl)-7 (trifluoromethyl)thieno[3,2-b]pyridin-5-yl)oxy)cyclobutyl)carbamate;

(R)-1-Cyclopropylethyl ((1s,3S)-3-((6-methyl-3-(methylcarbamoyl)-7 (trifluoromethyl)thieno[3,2-b]pyridin-5-yl)oxy)cyclobutyl)carbamate;

Cyclopropylmethyl ((1r,3r)-3-((6-methyl-3-(methylcarbamoyl)-7-(trifluoromethyl)thieno[3,2-b]pyridin-5-yl)oxy)cyclobutyl)carbamate;

2-(Trifluoromethoxy)ethyl (2R,4R)-4-((6-chloro-3-(methylcarbamoyl)-7-(trifluoromethyl)thieno[3,2-b]pyridin-5-yl)oxy)-2-methylpiperidine-1-carboxylate;

2-(Trifluoromethoxy)ethyl (2S,4S)-4-((6-chloro-3-(methylcarbamoyl)-7-(trifluoromethyl)thieno[3,2-b]pyridin-5-yl)oxy)-2-methylpiperidine-1-carboxylate;

2-(Trifluoromethoxy)ethyl 4-((6-chloro-3-(methylcarbamoyl)-7-(trifluoromethyl)thieno[3,2-b]pyridin-5-yl)oxy)piperidine-1-carboxylate;

tert-Butyl (2R,4R)-4-((6-fluoro-3-(methylcarbamoyl)-7-(trifluoromethyl)thieno[3,2-b]pyridin-5-yl)oxy)-2-methylpiperidine-1-carboxylate;

2-(Trifluoromethoxy)ethyl 6-((6-chloro-3-(methylcarbamoyl)-7-(trifluoromethyl)thieno[3,2-b]pyridin-5-yl)oxy)-2-azaspiro[3.3]heptane-2-carboxylate;

(S)-1-Cyclopropylethyl 6-((6-chloro-3-(methylcarbamoyl)-7-(trifluoromethyl)thieno[3,2-b]pyridin-5-yl)oxy)-2-azaspiro[3.3]heptane-2-carboxylate;

2-(Trifluoromethoxy)ethyl 6-((2-methyl-3-(methylcarbamoyl)-7-(trifluoromethyl)thieno[3,2-b]pyridin-5-yl)oxy)-2-azaspiro[3.3]heptane-2-carboxylate;

5-(cis-3-(3-(Cyclopropylmethyl)ureido)cyclobutoxy)-N,2-dimethyl-7 (trifluoromethyl)thieno[3,2-b]pyridine-3-carboxamide;

(S)-1-cyclopropylethyl ((1s,3R)-3-((3-(methylcarbamoyl)-7-(trifluoromethyl)thieno[3,2-b]pyridin-5-yl)oxy)cyclobutyl)carbamate;

(R)-1-cyclopropylethyl ((1s,3S)-3-((3-(methylcarbamoyl)-7-(trifluoromethyl)thieno[3,2-b]pyridin-5-yl)oxy)cyclobutyl)carbamate;

Oxetan-3-yl (cis-3-((3-(methylcarbamoyl)-7-(trifluoromethyl)thieno[3,2-b]pyridin-5-yl)oxy)cyclobutyl)carbamate;

(S)-1-Methoxypropan-2-yl (cis-3-((3-(methylcarbamoyl)-7-(trifluoromethyl)thieno[3,2-b]pyridin-5-yl)oxy)cyclobutyl)carbamate;

(R)-1-Methoxypropan-2-yl (cis-3-((3-(methylcarbamoyl)-7-(trifluoromethyl)thieno[3,2-b]pyridin-5-yl)oxy)cyclobutyl)carbamate;

2-(Trifluoromethoxy)ethyl (cis-3-((3-(methylcarbamoyl)-7-(trifluoromethyl)thieno[3,2-b]pyridin-5-yl)oxy)cyclobutyl)carbamate;

2,2-Difluoroethyl (cis-3-((3-(methylcarbamoyl)-7-(trifluoromethyl)thieno[3,2-b]pyridin-5-yl)oxy)cyclobutyl)carbamate;

2-(4-Chloro-1H-pyrazol-1-yl)ethyl (cis-3-((3-(methylcarbamoyl)-7-(trifluoromethyl)thieno[3,2-b]pyridin-5-yl)oxy)cyclobutyl)carbamate;

Thiazol-2-ylmethyl (cis-3-((3-(methylcarbamoyl)-7-(trifluoromethyl)thieno[3,2-b]pyridin-5-yl)oxy)cyclobutyl)carbamate;

Cyclopropylmethyl (cis-3-((3-(methylcarbamoyl)-7-(trifluoromethyl)thieno[3,2-b]pyridin-5-yl)oxy)cyclobutyl)carbamate;

Isopropyl (cis-3-((3-(methylcarbamoyl)-7-(trifluoromethyl)thieno[3,2-b]pyridin-5-yl)oxy)cyclobutyl)carbamate;

(+/−)-trans-4-Fluoro-1-methylpyrrolidin-3-yl (cis-3-((3-(methylcarbamoyl)-7-(trifluoromethyl)thieno [3,2-b]pyridin-5-yl)oxy)cyclobutyl)carbamate;

2-Chloroethyl (cis-3-((3-(methylcarbamoyl)-7-(trifluoromethyl)thieno[3,2-b]pyridin-5-yl)oxy)cyclobutyl)carbamate;

cis-3-((3-(Methylcarbamoyl)-7-(trifluoromethyl)thieno[3,2-b]pyridin-5-yl)oxy)cyclobutyl 3,3-difluoroazetidine-1-carboxylate;

cis-3-((3-(Methylcarbamoyl)-7-(trifluoromethyl)thieno[3,2-b]pyridin-5-yl)oxy)cyclobutyl (2-(trifluoromethoxy)ethyl)carbamate;

cis-3-((3-(Methylcarbamoyl)-7-(trifluoromethyl)thieno[3,2-b]pyridin-5-yl)oxy)cyclobutyl 1-oxa-7-azaspiro[3.5]nonane-7-carboxylate;

cis-3-((3-(Methylcarbamoyl)-7-(trifluoromethyl)thieno[3,2-b]pyridin-5-yl)oxy)cyclobutyl (S)-2,4-dimethylpiperazine-1-carboxylate;

cis-3-((3-(Methylcarbamoyl)-7-(trifluoromethyl)thieno[3,2-b]pyridin-5-yl)oxy)cyclobutyl ((S)-1-cyclopropylethyl)carbamate;

cis-3-((3-(Methylcarbamoyl)-7-(trifluoromethyl)thieno[3,2-b]pyridin-5-yl)oxy)cyclobutyl 5,6-dihydro-[1,2,4]triazolo[1,5-a]pyrazine-7(8H)-carboxylate;

cis-3-((3-(Methylcarbamoyl)-7-(trifluoromethyl)thieno[3,2-b]pyridin-5-yl)oxy)cyclobutyl 3-chloroazetidine-1-carboxylate;

cis-3-((3-(Methylcarbamoyl)-7-(trifluoromethyl)thieno[3,2-b]pyridin-5-yl)oxy)cyclobutyl (S)-3-methylmorpholine-4-carboxylate;

cis-3-((3-(Methylcarbamoyl)-7-(trifluoromethyl)thieno[3,2-b]pyridin-5-yl)oxy)cyclobutyl (cyclopropylmethyl)carbamate;

N-Methyl-5-(cis-3-(pyridin-2-yloxy)cyclobutoxy)-7-(trifluoromethyl)thieno[3,2-b]pyridine-3-carboxamide;

2-(Trifluoromethoxy)ethyl 3-methyl-3-((3-(methylcarbamoyl)-7-(trifluoromethyl)thieno[3,2-b]pyridin-5-yl)oxy)azetidine-1-carboxylate;

3-(Trifluoromethoxy)propyl 3-methyl-3-((3-(methylcarbamoyl)-7-(trifluoromethyl)thieno[3,2-b]pyridin-5-yl)oxy)azetidine-1-carboxylate;

2-(Trifluoromethoxy)ethyl 3-((3-(methylcarbamoyl)-7-(trifluoromethyl)thieno[3,2-b]pyridin-5-yl)oxy)azetidine-1-carboxylate;

2-(Trifluoromethoxy)ethyl 2-(((3-(methylcarbamoyl)-7-(trifluoromethyl)thieno[3,2-b]pyridin-5-yl)oxy)methyl)azetidine-1-carboxylate;

(1-(Trifluoromethyl)cyclopropyl)methyl 4-((3-(methylcarbamoyl)-7-(trifluoromethyl)thieno[3,2-b]pyridin-5-yl)oxy)piperidine-1-carboxylate;

Cyclopropylmethyl (trans-3-((3-(methylcarbamoyl)-7-(trifluoromethyl)thieno[3,2-b]pyridin-5-yl)oxy)cyclobutyl)carbamate;

trans-3-((3-(Methylcarbamoyl)-7-(trifluoromethyl)thieno[3,2-b]pyridin-5-yl)oxy)cyclobutyl (cyclopropylmethyl)carbamate;

3-((3-(Methylcarbamoyl)-7-(trifluoromethyl)thieno[3,2-b]pyridin-5-yl)oxy)cyclobutyl (cyclopropylmethyl)carbamate;

3-(Methylcarbamoyl)-7-(trifluoromethyl)thieno[3,2-b]pyridin-5-yl 4-(3,3,3-trifluoropropoxy)piperidine-1-carboxylate;

1-(tert-Butyl) 4-(3-(methylcarbamoyl)-7-(trifluoromethyl)thieno[3,2-b]pyridin-5-yl) piperazine-1,4-dicarboxylate;

tert-Butyl (2R,4R)-4-((6-chloro-3-(methylcarbamoyl)-7-(trifluoromethyl)thieno[3,2-b]pyridin-5-yl)oxy)-2-methylpiperidine-1-carboxylate;

tert-Butyl 6-((3-(methylcarbamoyl)-7-(trifluoromethyl)thieno[3,2-b]pyridin-5-yl)oxy)-2-azaspiro[3.3]heptane-2-carboxylate;

tert-Butyl 6-((6-methyl-3-(methylcarbamoyl)-7-(trifluoromethyl)thieno[3,2-b]pyridin-5-yl)oxy)-2-azaspiro[3.3]heptane-2-carboxylate;

tert-Butyl 6-((2-methyl-3-(methylcarbamoyl)-7-(trifluoromethyl)thieno[3,2-b]pyridin-5-yl)oxy)-2-azaspiro[3.3]heptane-2-carboxylate;

tert-Butyl 6-((6-chloro-3-(methylcarbamoyl)-7-(trifluoromethyl)thieno[3,2-b]pyridin-5-yl)oxy)-2-azaspiro[3.3]heptane-2-carboxylate;

tert-Butyl 3-methyl-3-((3-(methylcarbamoyl)-7-(trifluoromethyl)thieno[3,2-b]pyridin-5-yl)oxy)azetidine-1-carboxylate;

tert-Butyl 4-((6-chloro-3-(methylcarbamoyl)-7-(trifluoromethyl)thieno[3,2-b]pyridin-5-yl)oxy)piperidine-1-carboxylate;

2-(Trifluoromethoxy)ethyl 4-((5-chloro-3-(methylcarbamoyl)-7 (trifluoromethyl)thieno[3,2-b]pyridin-6-yl)oxy)piperidine-1-carboxylate;

Methyl 6-fluoro-5-((1-((2-(trifluoromethoxy)ethoxy)carbonyl)piperidin-4-yl)oxy)-7-(trifluoromethyl)thieno[3,2-b]pyridine-3-carboxylate;

2-(Trifluoromethoxy)ethyl 4-((6-fluoro-3-(methylcarbamoyl)-7-(trifluoromethyl)thieno[3,2-b]pyridin-5-yl)oxy)piperidine-1-carboxylate;

Methyl 5-(1-(tert-butoxycarbonyl)piperidin-4-yl)-7-(trifluoromethyl)thieno[3,2-b]pyridine-3-carboxylate;

Isobutyl 4-(3-(methylcarbamoyl)-7-(trifluoromethyl)thieno[3,2-b]pyridin-5-yl)piperidine-1-carboxylate;

5-(1-(4-Fluorophenethyl)piperidin-4-yl)-N-methyl-7-(trifluoromethyl)thieno[3,2-b]pyridine-3-carboxamide hydrochloride;

Benzyl 4-(3-(methylcarbamoyl)-7-(trifluoromethyl)thieno[3,2-b]pyridin-5-yl)piperidine-1-carboxylate;

N-Methyl-5-(1-(4-methylpentyl)piperidin-4-yl)-7-(trifluoromethyl)thieno[3,2-b]pyridine-3-carboxamide;

5-(1-(2-(Benzyloxy)ethyl)piperidin-4-yl)-N-methyl-7-(trifluoromethyl)thieno[3,2-b]pyridine-3-carboxamide hydrochloride;

Isopentyl 4-(3-(methylcarbamoyl)-7-(trifluoromethyl)thieno[3,2-b]pyridin-5-yl)piperidine-1-carboxylate;

Isopropoxyethyl 4-(3-(methylcarbamoyl)-7-(trifluoromethyl)thieno[3,2-b]pyridin-5-yl)piperidine-1-carboxylate;

tert-Butyl 2,6-dimethyl-4-((3-(methylcarbamoyl)-7-(trifluoromethyl)thieno[3,2-b]pyridin-5-yl)oxy)piperidine-1-carboxylate;

tert-Butyl (2S,4r,6R)-2,6-dimethyl-4-((3-(methylcarbamoyl)-7-(trifluoromethyl)thieno[3,2-b]pyridin-5-yl)oxy)piperidine-1-carboxylate;

2-(Trifluoromethoxy)ethyl (2S,4r,6R)-2,6-dimethyl-4-((3-(methylcarbamoyl)-7-(trifluoromethyl)thieno[3,2-b]pyridin-5-yl)oxy)piperidine-1-carboxylate;

(+/−)-tert-Butyl (2R,6R)-2,6-dimethyl-4-((3-(methylcarbamoyl)-7-(trifluoromethyl)thieno[3,2-b]pyridin-5-yl)oxy)piperidine-1-carboxylate;

(+/−)-2-Trifluoromethoxy)ethyl (2R,6R)-2,6-dimethyl-4-((3-(methylcarbamoyl)-7-(trifluoromethyl)thieno[3,2-b]pyridin-5-yl)oxy)piperidine-1-carboxylate;

2-(Trifluoromethoxy)ethyl (2R,6R)-2,6-dimethyl-4-((3-(methylcarbamoyl)-7-(trifluoromethyl)thieno[3,2-b]pyridin-5-yl)oxy)piperidine-1-carboxylate;

2-(Trifluoromethoxy)ethyl (2S,6S)-2,6-dimethyl-4-((3-(methylcarbamoyl)-7-(trifluoromethyl)thieno[3,2-b]pyridin-5-yl)oxy)piperidine-1-carboxylate;

4-Nitrophenyl (2S,4r,6R)-2,6-dimethyl-4-((3-(methylcarbamoyl)-7-(trifluoromethyl)thieno[3,2-b]pyridin-5-yl)oxy)piperidine-1-carboxylate;

tert-Butyl 4-((7-methoxy-3-(methylcarbamoyl)thieno[3,2-b]pyridin-5-yl)oxy)piperidine-1-carboxylate;

Methyl 5-(4-(((cyclopropylmethyl)carbamoyl)oxy)piperidin-1-yl)-7-methoxythieno[3,2-b]pyridine-3-carboxylate;

Methyl 5-(4-(((cyclopropylcarbamoyl)oxy)piperidin-1-yl)-7-methoxythieno[3,2-b]pyridine-3-carboxylate;

Isobutyl 4-((7-methoxy-3-(methylcarbamoyl)thieno[3,2-b]pyridin-5-yl)oxy)piperidine-1-carboxylate;

2-(Trifluoromethoxy)ethyl 4-((7-hydroxy-3-(methylcarbamoyl)thieno[3,2-b]pyridin-5-yl)oxy)piperidine-1-carboxylate;

2-(Trifluoromethoxy)ethyl 4-((7-(difluoromethoxy)-3-(methylcarbamoyl)thieno[3,2-b]pyridin-5-yl)oxy)piperidine-1-carboxylate;

tert-Butyl (1-(3-(methylcarbamoyl)-7-(trifluoromethyl)thieno[3,2-b]pyridin-5-yl)piperidin-4-yl)carbamate;

Isobutyl (1-(3-(methylcarbamoyl)-7-(trifluoromethyl)thieno[3,2-b]pyridin-5-yl)piperidin-4-yl) carbamate;

Cyclopropylmethyl (1-(3-(methylcarbamoyl)-7-(trifluoromethyl)thieno[3,2-b]pyridin-5-yl)piperidin-4-yl)carbamate;

Neopentyl (1-(3-(methylcarbamoyl)-7-(trifluoromethyl)thieno[3,2-b]pyridin-5-yl)piperidin-4-yl)carbamate;

tert-Butyl (1-(3-(methylcarbamoyl)-7-(trifluoromethyl)thieno[3,2-b]pyridin-5-yl)azetidin-3-yl)carbamate;

Isobutyl (1-(3-(methylcarbamoyl)-7-(trifluoromethyl)thieno[3,2-b]pyridin-5-yl)azetidin-3-yl) carbamate;

Cyclopropylmethyl (1-(3-(methylcarbamoyl)-7-(trifluoromethyl)thieno[3,2-b]pyridin-5-yl)azetidin-3-yl)carbamate;

Neopentyl (1-(3-(methylcarbamoyl)-7-(trifluoromethyl)thieno[3,2-b]pyridin-5-yl)azetidin-3-yl)carbamate;

tert-Butyl methyl(1-(3-(methylcarbamoyl)-7-(trifluoromethyl) thieno[3,2-b]pyridin-5-yl) piperidin-4-yl)carbamate;

Isobutyl methyl(1-(3-(methylcarbamoyl)-7-(trifluoromethyl)thieno[3,2-b]pyridin-5-yl) piperidin-4-yl) carbamate;

1-(7-Cyclopentyl-3-(methylcarbamoyl)thieno[3,2-b]pyridin-5-yl)piperidin-4-yl (cyclopropylmethyl)carbamate;

tert-Butyl (1-(7-cyclopentyl-3-(methylcarbamoyl)thieno[3,2-b]pyridin-5-yl)azetidin-3-yl)carbamate;

1-(7-(tert-Butyl)-3-(methylcarbamoyl)thieno[3,2-b]pyridin-5-yl)piperidin-4-yl (cyclopropylmethyl)carbamate;

1-(7-Isopropyl-3-(methylcarbamoyl)thieno[3,2-b]pyridin-5-yl)piperidin-4-yl (cyclopropylmethyl)carbamate;

tert-Butyl 4-fluoro-4-(((3-(methylcarbamoyl)-7-(trifluoromethyl)thieno[3,2-b]pyridin-5-yl)oxy)methyl)piperidine-1-carboxylate;

Isobutyl 4-fluoro-4-(((3-(methylcarbamoyl)-7-(trifluoromethyl)thieno[3,2-b]pyridin-5-yl)oxy)methyl)piperidine-1-carboxylate;

2,2,2-trifluoroethyl 4-fluoro-4-(((3-(methylcarbamoyl)-7-(trifluoromethyl)thieno[3,2-b]pyridin-5-yl)oxy)methyl)piperidine-1-carboxylate;

2-(Trifluoromethoxy)ethyl 4-fluoro-4-(((3-(methylcarbamoyl)-7-(trifluoromethyl)thieno[3,2-b]pyridin-5-yl)oxy)methyl)piperidine-1-carboxylate;

tert-Butyl 3-fluoro-3-(((3-(methylcarbamoyl)-7-(trifluoromethyl)thieno[3,2-b]pyridin-5-yl)oxy)methyl)azetidine-1-carboxylate;

Isobutyl 3-fluoro-3-(((3-(methylcarbamoyl)-7-(trifluoromethyl)thieno[3,2-b]pyridin-5-yl)oxy)methyl)azetidine-1-carboxylate;

2,2,2-Trifluoroethyl 3-fluoro-3-(((3-(methylcarbamoyl)-7-(trifluoromethyl)thieno[3,2-b]pyridin-5-yl)oxy)methyl)azetidine-1-carboxylate;

2-(Trifluoromethoxy)ethyl 3-fluoro-3-(((3-(methylcarbamoyl)-7-(trifluoromethyl)thieno[3,2-b]pyridin-5-yl)oxy)methyl)azetidine-1-carboxylate;

tert-Butyl 3-methyl-3-(((3-(methylcarbamoyl)-7-(trifluoromethyl)thieno[3,2-b]pyridin-5-yl)oxy)methyl)azetidine-1-carboxylate;

Isobutyl 3-methyl-3-(((3-(methylcarbamoyl)-7-(trifluoromethyl)thieno[3,2-b]pyridin-5-yl)oxy)methyl)azetidine-1-carboxylate;

2,2,2-Trifluoroethyl 3-methyl-3-(((3-(methylcarbamoyl)-7-(trifluoromethyl)thieno[3,2-b]pyridin-5-yl)oxy)methyl)azetidine-1-carboxylate;

2-(Trifluoromethoxy)ethyl 3-methyl-3-(((3-(methylcarbamoyl)-7-(trifluoromethyl)thieno[3,2-b]pyridin-5-yl)oxy)methyl)azetidine-1-carboxylate;

tert-Butyl 4-(((3-(methylcarbamoyl)-7-(trifluoromethyl)thieno[3,2-b]pyridin-5-yl)oxy)methyl)piperidine-1-carboxylate;

2,2,2-Trifluoroethyl 4-(((3-(methylcarbamoyl)-7-(trifluoromethyl)thieno[3,2-b]pyridin-5-yl)oxy)methyl)piperidine-1-carboxylate;

2-(Trifluoromethoxy)ethyl 4-(((3-(methylcarbamoyl)-7-(trifluoromethyl)thieno[3,2-b]pyridin-5-yl)oxy)methyl)piperidine-1-carboxylate;

tert-Butyl 4-methyl-4-(((3-(methylcarbamoyl)-7-(trifluoromethyl)thieno[3,2-b]pyridin-5-yl)oxy)methyl)piperidine-1-carboxylate;

2-(Trifluoromethoxy)ethyl 4-methyl-4-(((3-(methylcarbamoyl)-7-(trifluoromethyl)thieno[3,2-b]pyridin-5-yl)oxy)methyl)piperidine-1-carboxylate;

tert-Butyl (2r,4s)-2-((3-(methylcarbamoyl)-7-(trifluoromethyl)thieno[3,2-b]pyridin-5-yl)oxy)-6-azaspiro[3.4]octane-6-carboxylate;

tert-Butyl (2s,4r)-2-((3-(methylcarbamoyl)-7-(trifluoromethyl)thieno[3,2-b]pyridin-5-yl)oxy)-6-azaspiro[3.4]octane-6-carboxylate;

2-(Trifluoromethoxy)ethyl (2s,4r)-2-((3-(methylcarbamoyl)-7-(trifluoromethyl)thieno[3,2-b]pyridin-5-yl)oxy)-6-azaspiro[3.4]octane-6-carboxylate;

2-(Trifluoromethoxy)ethyl (2r,4s)-2-((3-(methylcarbamoyl)-7-(trifluoromethyl)thieno[3,2-b]pyridin-5-yl)oxy)-6-azaspiro[3.4]octane-6-carboxylate;

tert-Butyl (3aR,5r,6aS)-5-((3-(methylcarbamoyl)-7-(trifluoromethyl)thieno[3,2-b]pyridin-5-yl)oxy)hexahydrocyclopenta[c]pyrrole-2(1H)-carboxylate;

2-(Trifluoromethoxy)ethyl (3aR,5r,6aS)-5-((3-(methylcarbamoyl)-7-(trifluoromethyl)thieno[3,2-b]pyridin-5-yl)oxy)hexahydrocyclopenta[c]pyrrole-2(1H)-carboxylate;

trans-3-(Trifluoromethoxy)cyclobutyl (2R,4R)-4-((6-chloro-3-(methylcarbamoyl)-7-(trifluoromethyl)thieno[3,2-b]pyridin-5-yl)oxy)-2-methylpiperidine-1-carboxylate;

trans-3-((Trifluoromethoxy)methyl)cyclobutyl 4-((3-(methylcarbamoyl)-7-(trifluoromethyl)thieno[3,2-b]pyridin-5-yl)oxy)piperidine-1-carboxylate;

trans-3-(Trifluoromethoxy)cyclobutyl (2R,4R)-2-methyl-4-((3-(methylcarbamoyl)-7-(trifluoromethyl)thieno[3,2-b]pyridin-5-yl)oxy)piperidine-1-carboxylate;

cis-3-Hydroxycyclobutyl 4-((3-(methylcarbamoyl)-7-(trifluoromethyl)thieno[3,2-b]pyridin-5-yl)oxy)piperidine-1-carboxylate;

trans-3-(Trifluoromethoxy)cyclobutyl 4-((3-(methylcarbamoyl)-7-(trifluoromethyl)thieno[3,2-b]pyridin-5-yl)oxy)piperidine-1-carboxylate;

cis-3-(Trifluoromethoxy)cyclobutyl 4-((3-(methylcarbamoyl)-7-(trifluoromethyl)thieno[3,2-b]pyridin-5-yl)oxy)piperidine-1-carboxylate;

Oxetan-3-yl 6-(3-(methylcarbamoyl)-7-(trifluoromethyl)thieno[3,2-b]pyridin-5-yl)-2,6-diazaspiro[3.3]heptane-2-carboxylate;

N-Methyl-5-(6-(2-morpholinoacetyl)-2,6-diazaspiro[3.3]heptan-2-yl)-7-(trifluoromethyl)thieno[3,2-b]pyridine-3-carboxamide;

3-Methyloxetan-3-yl 6-(3-(methylcarbamoyl)-7-(trifluoromethyl)thieno[3,2-b]pyridin-5-yl)-2,6-diazaspiro[3.3]heptane-2-carboxylate;

1-Cyclopropylethyl 6-(3-(methylcarbamoyl)-7-(trifluoromethyl)thieno[3,2-b]pyridin-5-yl)-2,6-diazaspiro[3.3]heptane-2-carboxylate;

(R)-5-(6-(2-Methoxypropanoyl)-2,6-diazaspiro[3.3]heptan-2-yl)-N-methyl-7-(trifluoromethyl)thieno[3,2-b]pyridine-3-carboxamide;

(S)-5-(6-(2-Methoxypropanoyl)-2,6-diazaspiro[3.3]heptan-2-yl)-N-methyl-7-(trifluoromethyl)thieno[3,2-b]pyridine-3-carboxamide;

1-Methoxypropan-2-yl 6-(3-(methylcarbamoyl)-7-(trifluoromethyl)thieno[3,2-b]pyridin-5-yl)-2,6-diazaspiro[3.3]heptane-2-carboxylate;

Oxetan-3-ylmethyl 6-(3-(methylcarbamoyl)-7-(trifluoromethyl)thieno[3,2-b]pyridin-5-yl)-2,6-diazaspiro[3.3]heptane-2-carboxylate;

1-Methylpiperidin-3-yl 6-(3-(methylcarbamoyl)-7-(trifluoromethyl)thieno[3,2-b]pyridin-5-yl)-2,6-diazaspiro[3.3]heptane-2-carboxylate;

1-(1-Methylazetidin-3-yl)ethyl 6-(3-(methylcarbamoyl)-7-(trifluoromethyl)thieno[3,2-b]pyridin-5-yl)-2,6-diazaspiro[3.3]heptane-2-carboxylate;

1-Methylazetidin-3-yl 6-(3-(methylcarbamoyl)-7-(trifluoromethyl)thieno[3,2-b]pyridin-5-yl)-2,6-diazaspiro[3.3]heptane-2-carboxylate;

1-Cyanopropan-2-yl 6-(3-(methylcarbamoyl)-7-(trifluoromethyl)thieno[3,2-b]pyridin-5-yl)-2,6-diazaspiro[3.3]heptane-2-carboxylate;

1-(2-Fluoroethyl)azetidin-3-yl 6-(3-(methylcarbamoyl)-7-(trifluoromethyl)thieno[3,2-b]pyridin-5-yl)-2,6-diazaspiro[3.3]heptane-2-carboxylate;

1-(Cyanomethyl)azetidin-3-yl 6-(3-(methylcarbamoyl)-7-(trifluoromethyl)thieno[3,2-b]pyridin-5-yl)-2,6-diazaspiro[3.3]heptane-2-carboxylate;

2-(Trifluoromethoxy)ethyl 6-(3-(methylcarbamoyl)-7-(trifluoromethyl)thieno[3,2-b]pyridin-5-yl)-2,6-diazaspiro[3.3]heptane-2-carboxylate;

5-(4-((1-Isopropylpyrrolidin-3-yl)oxy)piperidin-1-yl)-N-methyl-7-(trifluoromethyl)thieno[3,2-b]pyridine-3-carboxamide;

5-(4-((1-(2,2-Difluoroethyl)pyrrolidin-3-yl)oxy)piperidin-1-yl)-N-methyl-7-(trifluoromethyl)thieno[3,2-b]pyridine-3-carboxamide;

5-(4-((1-(2-Fluoroethyl)pyrrolidin-3-yl)oxy)piperidin-1-yl)-N-methyl-7-(trifluoromethyl)thieno[3,2-b]pyridine-3-carboxamide;

5-(4-((1-(1,3-Difluoropropan-2-yl)pyrrolidin-3-yl)oxy)piperidin-1-yl)-N-methyl-7-(trifluoromethyl)thieno[3,2-b]pyridine-3-carboxamide;

5-(4-((1-(2,2-Difluoroethyl)azetidin-3-yl)oxy)piperidin-1-yl)-N-methyl-7-(trifluoromethyl)thieno[3,2-b]pyridine-3-carboxamide;

5-(4-((1-(2-Fluoroethyl)azetidin-3-yl)oxy)piperidin-1-yl)-N-methyl-7-(trifluoromethyl)thieno[3,2-b]pyridine-3-carboxamide;

5-(4-((1-(1,3-Difluoropropan-2-yl)azetidin-3-yl)oxy)piperidin-1-yl)-N-methyl-7-(trifluoromethyl)thieno[3,2-b]pyridine-3-carboxamide;

5-(4-(2-(3,3-Difluoropyrrolidin-1-yl)ethoxy)piperidin-1-yl)-N-methyl-7-(trifluoromethyl)thieno[3,2-b]pyridine-3-carboxamide;

5-(4-(2-(3-Fluoropyrrolidin-1-yl)ethoxy)piperidin-1-yl)-N-methyl-7-(trifluoromethyl)thieno[3,2-b]pyridine-3-carboxamide;

5-(4-(2-(4,4-Difluoropiperidin-1-yl)ethoxy)piperidin-1-yl)-N-methyl-7-(trifluoromethyl)thieno[3,2-b]pyridine-3-carboxamide;

5-(4-(2-(3-Hydroxypyrrolidin-1-yl)ethoxy)piperidin-1-yl)-N-methyl-7-(trifluoromethyl)thieno[3,2-b]pyridine-3-carboxamide;

5-(4-(2-(trans-3-Fluoro-4-hydroxypyrrolidin-1-yl)ethoxy)piperidin-1-yl)-N-methyl-7-(trifluoromethyl)thieno[3,2-b]pyridine-3-carboxamide;

N-Methyl-5-(4-(2-morpholinoethoxy)piperidin-1-yl)-7-(trifluoromethyl)thieno[3,2-b]pyridine-3-carboxamide;

5-(4-((6-Isopropylpyridin-2-yl)oxy)piperidin-1-yl)-N-methyl-7-(trifluoromethyl)thieno[3,2-b]pyridine-3-carboxamide;

(+/−)-tert-Butyl trans-2-methyl-4-((3-(methylcarbamoyl)-7-(trifluoromethyl)thieno[3,2-b]pyridin-5-yl)oxy)piperidine-1-carboxylate;

(+/−)-trans-2-(Trifluoromethoxy)ethyl-2-methyl-4-((3-(methylcarbamoyl)-7-(trifluoromethyl)thieno[3,2-b]pyridin-5-yl)oxy)piperidine-1-carboxylate;

(+/−)-tert-Butyl cis-2-methyl-4-((3-(methylcarbamoyl)-7-(trifluoromethyl)thieno[3,2-b]pyridin-5-yl)oxy)piperidine-1-carboxylate;

(+/−)-cis-2-(Trifluoromethoxy)ethyl-2-methyl-4-((3-(methylcarbamoyl)-7-(trifluoromethyl)thieno[3,2-b]pyridin-5-yl)oxy)piperidine-1-carboxylate;

(S)-1-Cyclopropylethyl (2R,4R)-2-methyl-4-((3-(methylcarbamoyl)-7-(trifluoromethyl)thieno[3,2-b]pyridin-5-yl)oxy)piperidine-1-carboxylate;

(S)-1-Cyclopropylethyl (2S,4S)-2-methyl-4-((3-(methylcarbamoyl)-7-(trifluoromethyl)thieno[3,2-b]pyridin-5-yl)oxy)piperidine-1-carboxylate;

tert-Butyl (2R,4R)-2-methyl-4-((3-(methylcarbamoyl)-7-(trifluoromethyl)thieno[3,2-b]pyridin-5-yl)oxy)piperidine-1-carboxylate;

tert-Butyl (2S,4S)-2-methyl-4-((3-(methylcarbamoyl)-7-(trifluoromethyl)thieno[3,2-b]pyridin-5-yl)oxy)piperidine-1-carboxylate;

2-(Trifluoromethoxy)ethyl (2R,4R)-2-methyl-4-((3-(methylcarbamoyl)-7-(trifluoromethyl)thieno[3,2-b]pyridin-5-yl)oxy)piperidine-1-carboxylate;

2-(Trifluoromethoxy)ethyl (2S,4S)-2-methyl-4-((3-(methylcarbamoyl)-7-(trifluoromethyl)thieno[3,2-b]pyridin-5-yl)oxy)piperidine-1-carboxylate;

(+/−)-tert-Butyl trans-3-fluoro-4-((3-(methylcarbamoyl)-7-(trifluoromethyl)thieno[3,2-b]pyridin-5-yl)oxy)piperidine-1-carboxylate;

(+/−)-2-(Trifluoromethoxy)ethyl trans-3-fluoro-4-((3-(methylcarbamoyl)-7-(trifluoromethyl)thieno[3,2-b]pyridin-5-yl)oxy)piperidine-1-carboxylate;

(S)-1-Cyclopropylethyl (3R,4R)-3-fluoro-4-((3-(methylcarbamoyl)-7-(trifluoromethyl)thieno[3,2-b]pyridin-5-yl)oxy)piperidine-1-carboxylate;

(S)-1-Cyclopropylethyl (3S,4S)-3-fluoro-4-((3-(methylcarbamoyl)-7-(trifluoromethyl)thieno[3,2-b]pyridin-5-yl)oxy)piperidine-1-carboxylate;

(+/−)-tert-Butyl cis-3-fluoro-4-((3-(methylcarbamoyl)-7-(trifluoromethyl)thieno[3,2-b]pyridin-5-yl)oxy)piperidine-1-carboxylate;

(+/−)-cis-2-(Trifluoromethoxy)ethyl-3-fluoro-4-((3-(methylcarbamoyl)-7-(trifluoromethyl)thieno[3,2-b]pyridin-5-yl)oxy)piperidine-1-carboxylate;

(S)-1-cyclopropylethyl (3R,4S)-3-fluoro-4-((3-(methylcarbamoyl)-7-(trifluoromethyl)thieno[3,2-b]pyridin-5-yl)oxy)piperidine-1-carboxylate;

(S)-1-cyclopropylethyl (3S,4R)-3-fluoro-4-((3-(methylcarbamoyl)-7-(trifluoromethyl)thieno[3,2-b]pyridin-5-yl)oxy)piperidine-1-carboxylate;

tert-Butyl (3S,4R)-3-fluoro-4-((3-(methylcarbamoyl)-7-(trifluoromethyl)thieno[3,2-b]pyridin-5-yl)oxy)piperidine-1-carboxylate;

tert-Butyl (3R,4S)-3-fluoro-4-((3-(methylcarbamoyl)-7-(trifluoromethyl)thieno[3,2-b]pyridin-5-yl)oxy)piperidine-1-carboxylate;

2-(Trifluoromethoxy)ethyl (3S,4R)-3-fluoro-4-((3-(methylcarbamoyl)-7-(trifluoromethyl)thieno[3,2-b]pyridin-5-yl)oxy)piperidine-1-carboxylate;

2-(Trifluoromethoxy)ethyl (3R,4S)-3-fluoro-4-((3-(methylcarbamoyl)-7-(trifluoromethyl)thieno[3,2-b]pyridin-5-yl)oxy)piperidine-1-carboxylate;

(+/−)-tert-Butyl cis-3-fluoro-4-((6-methyl-3-(methylcarbamoyl)-7-(trifluoromethyl)thieno[3,2-b]pyridin-5-yl)oxy)piperidine-1-carboxylate;

(+/−)-cis-2-(Trifluoromethoxy)ethyl-3-fluoro-4-((6-methyl-3-(methylcarbamoyl)-7-(trifluoromethyl)thieno[3,2-b]pyridin-5-yl)oxy)piperidine-1-carboxylate;

tert-Butyl 4-((6-methyl-3-(methylcarbamoyl)-7-(trifluoromethyl)thieno[3,2-b]pyridin-5-yl)oxy)piperidine-1-carboxylate;

2-(Trifluoromethoxy)ethyl 4-((6-methyl-3-(methylcarbamoyl)-7-(trifluoromethyl)thieno[3,2-b]pyridin-5-yl)oxy)piperidine-1-carboxylate;

tert-Butyl (2R,4R)-2-ethyl-4-((3-(methylcarbamoyl)-7-(trifluoromethyl)thieno[3,2-b]pyridin-5-yl)oxy)piperidine-1-carboxylate;

2-(Trifluoromethoxy)ethyl (2R,4R)-2-ethyl-4-((3-(methylcarbamoyl)-7-(trifluoromethyl)thieno[3,2-b]pyridin-5-yl)oxy)piperidine-1-carboxylate;

tert-Butyl (2R,4S)-2-ethyl-4-((3-(methylcarbamoyl)-7-(trifluoromethyl)thieno[3,2-b]pyridin-5-yl)oxy)piperidine-1-carboxylate;

2-(Trifluoromethoxy)ethyl-(2R,4S)-2-ethyl-4-((3-(methylcarbamoyl)-7-(trifluoromethyl)thieno[3,2-b]pyridin-5-yl)oxy)piperidine-1-carboxylate;

2-Hydroxyethyl 4-((3-(methylcarbamoyl)-7-(trifluoromethyl)thieno[3,2-b]pyridin-5-yl)oxy)piperidine-1-carboxylate;

tert-Butyl 7-((3-(methylcarbamoyl)-7-(trifluoromethyl)thieno[3,2-b]pyridin-5-yl)oxy)-2-azaspiro[3.5]nonane-2-carboxylate;
(R)-5-(4-(2-Cyclopropoxyethyl)-3-methylpiperazin-1-yl)-N-methyl-7-(trifluoromethyl)thieno[3,2-b]pyridine-3-carboxamide;
(S)-5-(4-(2-Cyclopropoxyethyl)-3-methylpiperazin-1-yl)-N-methyl-7-(trifluoromethyl)thieno[3,2-b]pyridine-3-carboxamide;
5-(cis-4-(2-Cyclopropoxyethyl)-3,5-dimethylpiperazin-1-yl)-N-methyl-7-(trifluoromethyl)thieno[3,2-b]pyridine-3-carboxamide;
5-(4-((4-Methoxy-6-methylpyridin-2-yl)methyl)piperazin-1-yl)-N-methyl-7-(trifluoromethyl)thieno[3,2-b]pyridine-3-carboxamide;
5-(4-(3-((Dimethylamino)methyl)benzyl)piperazin-1-yl)-N-methyl-7-(trifluoromethyl)thieno[3,2-b]pyridine-3-carboxamide;
5-(4-(1-((4-Methoxycyclohexyl)amino)-1-oxopropan-2-yl)piperazin-1-yl)-N-methyl-7-(trifluoromethyl)thieno[3,2-b]pyridine-3-carboxamide;
N-Methyl-5-(4-(1-oxo-1-((tetrahydro-2H-pyran-4-yl)amino)propan-2-yl)piperazin-1-yl)-7-(trifluoromethyl)thieno[3,2-b]pyridine-3-carboxamide;
N-Methyl-5-(4-((2-morpholinoethyl)sulfonyl)piperazin-1-yl)-7-(trifluoromethyl)thieno[3,2-b]pyridine-3-carboxamide;
N-Methyl-5-(4-((3-morpholinopropyl)sulfonyl)piperazin-1-yl)-7-(trifluoromethyl)thieno[3,2-b]pyridine-3-carboxamide;
(R)—N-(Cyclopropylmethyl)-2-(2-methyl-4-(3-propionyl-7-(trifluoromethyl)thieno[3,2-b]pyridin-5-yl)piperazin-1-yl)acetamide;
(S)—N-(Cyclopropylmethyl)-2-(2-methyl-4-(3-propionyl-7-(trifluoromethyl)thieno[3,2-b]pyridin-5-yl)piperazin-1-yl)acetamide;
5-(4-(2-(Isopropylamino)-2-oxoethyl)piperazin-1-yl)-N,2-dimethyl-7-(trifluoromethyl)thieno[3,2-b]pyridine-3-carboxamide;
5-(4-(2-(3-Fluoropyrrolidin-1-yl)-1-hydroxyethyl)piperidin-1-yl)-N-methyl-7-(trifluoromethyl)thieno[3,2-b]pyridine-3-carboxamide;
5-(4-(2-(4,4-Difluoropiperidin-1-yl)-1-hydroxyethyl)piperidin-1-yl)-N-methyl-7-(trifluoromethyl)thieno[3,2-b]pyridine-3-carboxamide;
5-(4-(1-Hydroxy-2-morpholinoethyl)piperidin-1-yl)-N-methyl-7-(trifluoromethyl)thieno[3,2-b]pyridine-3-carboxamide;
5-(4-(3-(4,4-Difluoropiperidin-1-yl)-2-hydroxypropyl)piperidin-1-yl)-N-methyl-7-(trifluoromethyl)thieno[3,2-b]pyridine-3-carboxamide;
5-(4-(3-(3,3-Difluoropyrrolidin-1-yl)-2-hydroxypropyl)piperidin-1-yl)-N-methyl-7-(trifluoromethyl)thieno[3,2-b]pyridine-3-carboxamide;
5-(4-(2-(1-(2,2-Difluoroethyl)pyrrolidin-3-yl)-2-hydroxyethyl)piperazin-1-yl)-N-methyl-7-(trifluoromethyl)thieno[3,2-b]pyridine-3-carboxamide;
1-(2-Methyl-3-(methylcarbamoyl)-7-(trifluoromethyl)thieno[3,2-b]pyridin-5-yl)piperidin-4-yl (cyclopropylmethyl)carbamate;
1-(3-(Methylcarbamoyl)-7-(trifluoromethyl)thieno[3,2-b]pyridin-5-yl)piperidin-4-yl (R)-2-(methoxymethyl)pyrrolidine-1-carboxylate;
1-(3-(Methylcarbamoyl)-7-(trifluoromethyl)thieno[3,2-b]pyridin-5-yl)piperidin-4-yl (S)-(1-(2,2-difluoroethoxy)propan-2-yl)carbamate;
(+/−)-trans-3-Fluoro-1-(3-(methylcarbamoyl)-7-(trifluoromethyl)thieno[3,2-b]pyridin-5-yl)piperidin-4-yl ((S)-1-(trifluoromethoxy)propan-2-yl)carbamate;
N-Isopropyl-7-(trifluoromethyl)-5-(3-((4-(trifluoromethyl)cyclohexyl)amino)pyrrolidin-1-yl)thieno[3,2-b]pyridine-3-carboxamide;
7-Cyclopropyl-N-ethyl-5-(4-(2-(isopropylamino)-2-oxoethyl)piperazin-1-yl)thieno[3,2-b]pyridine-3-carboxamide;
N-Butyl-7-cyclopropyl-5-(4-(2-(isopropylamino)-2-oxoethyl)piperazin-1-yl)thieno[3,2-b]pyridine-3-carboxamide;
1-(3-(Azetidine-1-carbonyl)-7-(trifluoromethyl)thieno[3,2-b]pyridin-5-yl)piperidin-4-yl tert-butylcarbamate;
1-(3-(3-Methoxyazetidine-1-carbonyl)-7-(trifluoromethyl)thieno[3,2-b]pyridin-5-yl)piperidin-4-yl tert-butylcarbamate;
1-(3-((3-Chloropropyl)carbamoyl)-7-(trifluoromethyl)thieno[3,2-b]pyridin-5-yl)piperidin-4-yl tert-butylcarbamate hydrochloride;
2-(4-(3-Acetamido-7-(trifluoromethyl)thieno[3,2-b]pyridin-5-yl)piperazin-1-yl)-N-isopropylacetamide;
1-(3-Acetamido-7-(trifluoromethyl)thieno[3,2-b]pyridin-5-yl)piperidin-4-yl (cyclopropylmethyl)carbamate;
1-(3-Acetyl-7-(trifluoromethyl)thieno[3,2-b]pyridin-5-yl)piperidin-4-yl (cyclopropylmethyl)carbamate;
Methyl 5-(4-((((cyclopropylmethyl)carbamoyl)oxy)piperidin-1-yl)-7-(trifluoromethyl)thieno[3,2-b]pyridine-3-carboxylate;
1-(3-(Ethylcarbamoyl)-7-(trifluoromethyl)thieno[3,2-b]pyridin-5-yl)piperidin-4-yl (cyclopropylmethyl)carbamate;
1-(3-(Cyclopropylcarbamoyl)-7-(trifluoromethyl)thieno[3,2-b]pyridin-5-yl)piperidin-4-yl (cyclopropylmethyl)carbamate;
2-(4-(3-Acetyl-7-(trifluoromethyl)thieno[3,2-b]pyridin-5-yl)piperazin-1-yl)-N-isopropylacetamide;
1-(3-(Azetidine-1-carbonyl)-7-(trifluoromethyl)thieno[3,2-b]pyridin-5-yl)piperidin-4-yl (cyclopropylmethyl)carbamate;
1-(3-((2-Methoxyethyl)carbamoyl)-7-(trifluoromethyl)thieno[3,2-b]pyridin-5-yl)piperidin-4-yl (cyclopropylmethyl)carbamate;
1-(3-Propionyl-7-(trifluoromethyl)thieno[3,2-b]pyridin-5-yl)piperidin-4-yl (S)-(1-cyclopropylethyl)carbamate;
1-(3-(1-Hydroxypropyl)-7-(trifluoromethyl)thieno[3,2-b]pyridin-5-yl)piperidin-4-yl ((S)-1-cyclopropylethyl)carbamate;
tert-Butyl 7-(3-acetyl-7-(trifluoromethyl)thieno[3,2-b]pyridin-5-yl)-2,7-diazaspiro[3.5]nonane-2-carboxylate;
1-(7-(3-Acetyl-7-(trifluoromethyl)thieno[3,2-b]pyridin-5-yl)-2,7-diazaspiro[3.5]nonan-2-yl)-3-methylbutan-1-one;
1-(3-(Azetidine-1-carbonyl)-7-(trifluoromethyl)thieno[3,2-b]pyridin-5-yl)piperidin-4-yl 3-fluoroazetidine-1-carboxylate;
1-(3-(Azetidine-1-carbonyl)-7-(trifluoromethyl)thieno[3,2-b]pyridin-5-yl)piperidin-4-yl 3-chloroazetidine-1-carboxylate;
1-(3-(3-Chloroazetidine-1-carbonyl)-7-(trifluoromethyl)thieno[3,2-b]pyridin-5-yl)piperidin-4-yl 3-chloroazetidine-1-carboxylate;
(+/−)-trans-1-(3-(Azetidine-1-carbonyl)-7-(trifluoromethyl)thieno[3,2-b]pyridin-5-yl)-3-fluoropiperidin-4-yl isopropylcarbamate;
7-Cyclopropyl-5-(4-(2-(isopropylamino)-2-oxoethyl)piperazin-1-yl)-N-methylthieno[3,2-b]pyridine-3-carboxamide;

7-Ethyl-5-(4-(2-(isopropylamino)-2-oxoethyl)piperazin-1-yl)-N-methylthieno[3,2-b]pyridine-3-carboxamide;

7-Chloro-5-(4-(2-(isopropylamino)-2-oxoethyl)piperazin-1-yl)-N-methylthieno[3,2-b]pyridine-3-carboxamide;

5-(4-(2-(Isopropylamino)-2-oxoethyl)piperazin-1-yl)-7-methoxy-N-methylthieno[3,2-b]pyridine-3-carboxamide;

7-(Difluoromethyl)-5-(4-(2-(isopropylamino)-2-oxoethyl)piperazin-1-yl)-N-methylthieno[3,2-b]pyridine-3-carboxamide;

7-(Dimethylamino)-5-(4-(2-(isopropylamino)-2-oxoethyl)piperazin-1-yl)-N-methylthieno[3,2-b]pyridine-3-carboxamide;

5-(4-(2-(Isopropylamino)-2-oxoethyl)piperazin-1-yl)-N-methyl-7-(2,2,2-trifluoroethoxy)thieno[3,2-b]pyridine-3-carboxamide;

1-(7-Chloro-3-(methylcarbamoyl)thieno[3,2-b]pyridin-5-yl)piperidin-4-yl (cyclopropylmethyl)carbamate;

1-(7-(Dimethylamino)-3-(methylcarbamoyl)thieno[3,2-b]pyridin-5-yl)piperidin-4-yl (cyclopropylmethyl)carbamate;

1-(7-(Difluoromethyl)-3-(methylcarbamoyl)thieno[3,2-b]pyridin-5-yl)piperidin-4-yl (cyclopropylmethyl)carbamate;

1-(7-(Difluoromethyl)-3-(methylcarbamoyl)thieno[3,2-b]pyridin-5-yl)piperidin-4-yl isopropylcarbamate;

1-(7-(Difluoromethyl)-3-(methylcarbamoyl)thieno[3,2-b]pyridin-5-yl)piperidin-4-yl cyclopropylcarbamate;

1-(7-Methoxy-3-(methylcarbamoyl)thieno[3,2-b]pyridin-5-yl)piperidin-4-yl isopropylcarbamate;

1-(3-(Methylcarbamoyl)-7-(trifluoromethyl)thieno[3,2-b]pyridin-5-yl)azetidin-3-yl (cyclopropylmethyl)carbamate trifluoroacetate;

5-(3-(2,2-Diethoxyethoxy)azetidin-1-yl)-N-methyl-7-(trifluoromethyl)thieno[3,2-b]pyridine-3-carboxamide;

5-(3-(2-Hydroxy-2-methylpropoxy)azetidin-1-yl)-N-methyl-7-(trifluoromethyl)thieno[3,2-b]pyridine-3-carboxamide trifluoroacetate;

5-(3-(2-(Cyclopropylmethoxy)ethoxy)azetidin-1-yl)-N-methyl-7-(trifluoromethyl)thieno[3,2-b]pyridine-3-carboxamide;

(1-(3-(Methylcarbamoyl)-7-(trifluoromethyl)thieno[3,2-b]pyridin-5-yl)azetidin-3-yl)methyl (cyclopropylmethyl)carbamate;

(1-(3-(Methylcarbamoyl)-7-(trifluoromethyl)thieno[3,2-b]pyridin-5-yl)azetidin-3-yl)methyl (1-cyanopropan-2-yl)carbamate;

5-(3-((2-(Isopropylamino)-2-oxoethyl)amino)pyrrolidin-1-yl)-N-methyl-7-(trifluoromethyl)thieno[3,2-b]pyridine-3-carboxamide;

5-(3-(2-(Isopropylamino)-2-oxoethoxy)pyrrolidin-1-yl)-N-methyl-7-(trifluoromethyl)thieno[3,2-b]pyridine-3-carboxamide;

5-(3-((2-(Isopropylamino)-2-oxoethyl)(methyl)amino)pyrrolidin-1-yl)-N-methyl-7-(trifluoromethyl)thieno[3,2-b]pyridine-3-carboxamide;

5-(3-(3-(tert-Butyl)ureido)pyrrolidin-1-yl)-N-methyl-7-(trifluoromethyl)thieno[3,2-b]pyridine-3-carboxamide;

5-(3-(((5-Isopropyloxazol-2-yl)methyl)amino)pyrrolidin-1-yl)-N-methyl-7-(trifluoromethyl)thieno[3,2-b]pyridine-3-carboxamide;

N-Methyl-5-(3-(((4-methylthiazol-2-yl)methyl)amino)pyrrolidin-1-yl)-7-(trifluoromethyl)thieno[3,2-b]pyridine-3-carboxamide;

1-(3-(Methylcarbamoyl)-7-(trifluoromethyl)thieno[3,2-b]pyridin-5-yl)pyrrolidin-3-yl (cyclopropylmethyl)carbamate;

5-(4-(2-(Cyclopropylamino)-2-oxoethyl)piperazin-1-yl)-N-methyl-7-(trifluoromethyl)thieno[3,2-b]pyridine-3-carboxamide hydrogen chloride;

5-(4-(3-(tert-Butyl)ureido)piperidin-1-yl)-N-methyl-7-(trifluoromethyl)thieno[3,2-b]pyridine-3-carboxamide;

5-(4-(3,3-Dimethyl-2-oxobutyl)piperazin-1-yl)-N-methyl-7-(trifluoromethyl)thieno[3,2-b]pyridine-3-carboxamide;

5-(4-(1-(Cyclopropylamino)-1-oxopropan-2-yl)piperazin-1-yl)-N-methyl-7-(trifluoromethyl)thieno[3,2-b]pyridine-3-carboxamide;

1-(3-(Methylcarbamoyl)-7-(trifluoromethyl)thieno[3,2-b]pyridin-5-yl)piperidin-4-yl tert-butylcarbamate;

1-(3-(Methylcarbamoyl)-7-(trifluoromethyl)thieno[3,2-b]pyridin-5-yl)piperidin-4-yl cyclopropylcarbamate;

1-(3-(Methylcarbamoyl)-7-(trifluoromethyl)thieno[3,2-b]pyridin-5-yl)piperidin-4-yl (cyclopropylmethyl)carbamate;

1-(3-(Methylcarbamoyl)-7-(trifluoromethyl)thieno[3,2-b]pyridin-5-yl)piperidin-4-yl (cyclopropylmethyl)carbamate trifluoroacetate;

((+/−)-cis-1-(3-(Methylcarbamoyl)-7-(trifluoromethyl)thieno[3,2-b]pyridin-5-yl)piperidine-3,4-diyl bis((cyclopropylmethyl)carbamate);

(+/−)-cis-4-Hydroxy-1-(3-(methylcarbamoyl)-7-(trifluoromethyl)thieno[3,2-b]pyridin-5-yl)piperidin-3-yl (cyclopropylmethyl)carbamate;

(+/−)-cis-3-Hydroxy-1-(3-(methylcarbamoyl)-7-(trifluoromethyl)thieno[3,2-b]pyridin-5-yl)piperidin-4-yl (cyclopropylmethyl)carbamate;

3-Fluoro-1-(3-(methylcarbamoyl)-7-(trifluoromethyl)thieno[3,2-b]pyridin-5-yl)piperidin-4-yl (cyclopropylmethyl)carbamate;

1-(3-(Methylcarbamoyl)-7-(trifluoromethyl)thieno[3,2-b]pyridin-5-yl)piperidin-4-yl ((tetrahydrofuran-2-yl)methyl)carbamate;

(+/−)-cis-3-methoxy-1-(3-(methylcarbamoyl)-7-(trifluoromethyl)thieno[3,2-b]pyridin-5-yl)piperidin-4-yl (cyclopropylmethyl)carbamate;

1-(3-(Methylcarbamoyl)-7-(trifluoromethyl)thieno[3,2-b]pyridin-5-yl)piperidin-4-yl (2-hydroxy-3-methoxypropyl)carbamate;

1-(3-(Methylcarbamoyl)-7-(trifluoromethyl)thieno[3,2-b]pyridin-5-yl)piperidin-4-yl 3-cyanoazetidine-1-carboxylate;

1-(3-(Methylcarbamoyl)-7-(trifluoromethyl)thieno[3,2-b]pyridin-5-yl)piperidin-4-yl 3-cyanomorpholine-4-carboxylate;

1-(3-(Methylcarbamoyl)-7-(trifluoromethyl)thieno[3,2-b]pyridin-5-yl)piperidin-4-yl ((1,4-dioxan-2-yl)methyl)carbamate;

1-(3-(Methylcarbamoyl)-7-(trifluoromethyl)thieno[3,2-b]pyridin-5-yl)piperidin-4-yl (5-fluoropyridin-3-yl)carbamate trifluoroacetate;

1-(3-(Methylcarbamoyl)-7-(trifluoromethyl)thieno[3,2-b]pyridin-5-yl)piperidin-4-yl 3-chloroazetidine-1-carboxylate;

(+/−)-trans-3-Fluoro-1-(3-(methylcarbamoyl)-7-(trifluoromethyl)thieno[3,2-b]pyridin-5-yl)piperidin-4-yl diisopropylcarbamate;

(+/−)-trans-3-Fluoro-1-(3-(methylcarbamoyl)-7-(trifluoromethyl)thieno[3,2-b]pyridin-5-yl)piperidin-4-yl oxetan-3-ylcarbamate;

(+/−)-tran-3-Fluoro-1-(3-(methylcarbamoyl)-7-(trifluoromethyl)thieno[3,2-b]pyridin-5-yl)piperidin-4-yl isopropylcarbamate;

(+/−)-trans-3-Fluoro-1-(3-(methylcarbamoyl)-7-(trifluoromethyl)thieno[3,2-b]pyridin-5-yl)piperidin-4-yl 3-methoxyazetidine-1-carboxylate;

(+/−)-trans-3-Fluoro-1-(3-(methylcarbamoyl)-7-(trifluoromethyl)thieno[3,2-b]pyridin-5-yl)piperidin-4-yl cyclopropylcarbamate;

(+/−)-trans-3-Fluoro-1-(3-(methylcarbamoyl)-7-(trifluoromethyl)thieno[3,2-b]pyridin-5-yl)piperidin-4-yl 4-methylpiperazine-1-carboxylate;

(+/−)-trans-3-Fluoro-1-(3-(methylcarbamoyl)-7-(trifluoromethyl)thieno[3,2-b]pyridin-5-yl)piperidin-4-yl ((S)-1-cyclopropylethyl)carbamate;

(3R,4R)-3-Fluoro-1-(3-(methylcarbamoyl)-7-(trifluoromethyl)thieno[3,2-b]pyridin-5-yl)piperidin-4-yl isopropylcarbamate;

(3S,4S)-3-Fluoro-1-(3-(methylcarbamoyl)-7-(trifluoromethyl)thieno[3,2-b]pyridin-5-yl)piperidin-4-yl isopropylcarbamate;

(+/−)-trans-3-Fluoro-1-(3-(methylcarbamoyl)-7-(trifluoromethyl)thieno[3,2-b]pyridin-5-yl)piperidin-4-yl (3-fluorocyclobutyl)carbamate;

(+/−)-cis-3-Fluoro-1-(3-(methylcarbamoyl)-7-(trifluoromethyl)thieno[3,2-b]pyridin-5-yl)piperidin-4-yl isopropylcarbamate;

(+/−)-trans-3-Fluoro-1-(3-(methylcarbamoyl)-7-(trifluoromethyl)thieno[3,2-b]pyridin-5-yl)piperidin-4-yl cyclopropylcarbamate;

(+/−)-trans-3-Fluoro-1-(3-(methylcarbamoyl)-7-(trifluoromethyl)thieno[3,2-b]pyridin-5-yl)piperidin-4-yl (2-(trifluoromethoxy)ethyl)carbamate;

(3R,4R)-3-Fluoro-1-(3-(methylcarbamoyl)-7-(trifluoromethyl)thieno[3,2-b]pyridin-5-yl)piperidin-4-yl cyclopropylcarbamate;

(3S,4S)-3-Fluoro-1-(3-(methylcarbamoyl)-7-(trifluoromethyl)thieno[3,2-b]pyridin-5-yl)piperidin-4-yl cyclopropylcarbamate;

(+/−)-trans-3-Fluoro-1-(3-(methylcarbamoyl)-7-(trifluoromethyl)thieno[3,2-b]pyridin-5-yl)piperidin-4-yl (2-(trifluoromethoxy)ethyl)carbamate;

(+/−)-trans-3-Fluoro-1-(3-(methylcarbamoyl)-7-(trifluoromethyl)thieno[3,2-b]pyridin-5-yl)piperidin-4-yl 3-(trifluoromethoxy)azetidine-1-carboxylate;

2-Cyanoethyl (1-(3-(methylcarbamoyl)-7-(trifluoromethyl)thieno[3,2-b]pyridin-5-yl)piperidin-4-yl)carbamate;

3-Cyanocyclobutyl (1-(3-(methylcarbamoyl)-7-(trifluoromethyl)thieno[3,2-b]pyridin-5-yl)piperidin-4-yl)carbamate;

1-Cyanopropan-2-yl (1-(3-(methylcarbamoyl)-7-(trifluoromethyl)thieno[3,2-b]pyridin-5-yl)piperidin-4-yl)carbamate;

4-Methyl-N-(1-(3-(methylcarbamoyl)-7-(trifluoromethyl)thieno[3,2-b]pyridin-5-yl)piperidin-4-yl)morpholine-2-carboxamide;

1-Methoxypropan-2-yl (1-(3-(methylcarbamoyl)-7-(trifluoromethyl)thieno[3,2-b]pyridin-5-yl)piperidin-4-yl)carbamate;

1,3-Dimethoxypropan-2-yl (1-(3-(methylcarbamoyl)-7-(trifluoromethyl)thieno[3,2-b]pyridin-5-yl)piperidin-4-yl)carbamate;

(1,4-Dioxan-2-yl)methyl (1-(3-(methylcarbamoyl)-7-(trifluoromethyl)thieno[3,2-b]pyridin-5-yl)piperidin-4-yl)carbamate;

Oetan-3-ylmethyl (1-(3-(methylcarbamoyl)-7-(trifluoromethyl)thieno[3,2-b]pyridin-5-yl)piperidin-4-yl)carbamate;

(4-Methylmorpholin-3-yl)methyl (1-(3-(methylcarbamoyl)-7-(trifluoromethyl)thieno[3,2-b]pyridin-5-yl)piperidin-4-yl)carbamate;

1-Methylpyrrolidin-3-yl (1-(3-(methylcarbamoyl)-7-(trifluoromethyl)thieno[3,2-b]pyridin-5-yl)piperidin-4-yl)carbamate trifluoroacetate;

Oxetan-3-yl (1-(3-(methylcarbamoyl)-7-(trifluoromethyl)thieno[3,2-b]pyridin-5-yl)piperidin-4-yl)carbamate;

4-Methylpentan-2-yl (1-(3-(methylcarbamoyl)-7-(trifluoromethyl)thieno[3,2-b]pyridin-5-yl)piperidin-4-yl)carbamate;

(S)-1-Cyclopropylethyl (1-(3-(methylcarbamoyl)-7-(trifluoromethyl)thieno[3,2-b]pyridin-5-yl)piperidin-4-yl)carbamate;

(R)-1-Cyclopropylethyl (1-(3-(methylcarbamoyl)-7-(trifluoromethyl)thieno[3,2-b]pyridin-5-yl)piperidin-4-yl)carbamate trifluoroacetate;

1-Cyclopropylpropan-2-yl (1-(3-(methylcarbamoyl)-7-(trifluoromethyl)thieno[3,2-b]pyridin-5-yl)piperidin-4-yl)carbamate;

2-(Trifluoromethoxy)ethyl (1-(3-(methylcarbamoyl)-7-(trifluoromethyl)thieno[3,2-b]pyridin-5-yl)piperidin-4-yl)carbamate;

N-Methyl-5-(4-((4-methylthiazol-2-yl)methyl)piperazin-1-yl)-7-(trifluoromethyl)thieno[3,2-b]pyridine-3-carboxamide;

5-(4-((4,5-Dimethyloxazol-2-yl)methyl)piperazin-1-yl)-N-methyl-7-(trifluoromethyl)thieno[3,2-b]pyridine-3-carboxamide;

5-(4-((5-Isopropyloxazol-2-yl)methyl)piperazin-1-yl)-N-methyl-7-(trifluoromethyl)thieno[3,2-b]pyridine-3-carboxamide;

5-(4-((5-Isopropyl-1,3,4-oxadiazol-2-yl)methyl)piperazin-1-yl)-N-methyl-7-(trifluoromethyl)thieno[3,2-b]pyridine-3-carboxamide;

5-(4-((4,5-Dimethyl-1H-imidazol-2-yl)methyl)piperazin-1-yl)-N-methyl-7-(trifluoromethyl)thieno[3,2-b]pyridine-3-carboxamide;

5-(4-((1-((4,5-dimethyl-1H-imidazol-2-yl)methyl)-4,5-dimethyl-1H-imidazol-2-yl)methyl)piperazin-1-yl)-N-methyl-7-(trifluoromethyl)thieno[3,2-b]pyridine-3-carboxamide;

N-Methyl-5-(4-((5-methyl-1,3,4-oxadiazol-2-yl)methyl)piperazin-1-yl)-7-(trifluoromethyl)thieno[3,2-b]pyridine-3-carboxamide;

5-(4-((4-Isopropylthiazol-2-yl)methyl)piperazin-1-yl)-N-methyl-7-(trifluoromethyl)thieno[3,2-b]pyridine-3-carboxamide;

N-Methyl-5-(4-(1-(4-methylthiazol-2-yl)ethyl)piperazin-1-yl)-7-(trifluoromethyl)thieno[3,2-b]pyridine-3-carboxamide;

N-Methyl-5-(4-(1-(5-methylthiazol-2-yl)ethyl)piperazin-1-yl)-7-(trifluoromethyl)thieno[3,2-b]pyridine-3-carboxamide;

N-Methyl-5-(1-((4-methylthiazol-2-yl)methyl)piperidin-4-yl)-7-(trifluoromethyl)thieno[3,2-b]pyridine-3-carboxamide;

N-Methyl-5-(4-((5-methyl-1,3,4-oxadiazol-2-yl)methoxy)piperidin-1-yl)-7-(trifluoromethyl)thieno[3,2-b]pyridine-3-carboxamide;

N-Methyl-5-(4-(1-(6-methylpyridin-2-yl)ethyl)piperazin-1-yl)-7-(trifluoromethyl)thieno[3,2-b]pyridine-3-carboxamide;

N-Methyl-5-(4-(2-methylthiazole-4-carbonyl)piperazin-1-yl)-7-(trifluoromethyl)thieno[3,2-b]pyridine-3-carboxamide;

5-(4-(5-Cyclopropyl-1,3,4-oxadiazol-2-yl)piperidin-1-yl)-N-methyl-7-(trifluoromethyl)thieno[3,2-b]pyridine-3-carboxamide;

5-(4-((2-(Cyclopropylamino)ethyl)sulfonyl)piperazin-1-yl)-N-methyl-7-(trifluoromethyl)thieno[3,2-b]pyridine-3-carboxamide trifluoroacetate;

5-(4-((2-Isopropoxyethyl)sulfonyl)piperazin-1-yl)-N-methyl-7-(trifluoromethyl)thieno[3,2-b]pyridine-3-carboxamide;

5-(4-((2-(Cyclopropylmethoxy)ethyl)sulfonyl)piperazin-1-yl)-N-methyl-7-(trifluoromethyl)thieno[3,2-b]pyridine-3-carboxamide;

5-(4-((2-(Cyclopropyl(methyl)amino)ethyl)sulfonyl)piperazin-1-yl)-N-methyl-7-(trifluoromethyl)thieno[3,2-b]pyridine-3-carboxamide;

5-(4-((2-(3-Methoxyazetidin-1-yl)ethyl)sulfonyl)piperazin-1-yl)-N-methyl-7-(trifluoromethyl)thieno[3,2-b]pyridine-3-carboxamide;

5-(4-((2-((Isopropylamino)-2-oxoethyl)amino)piperidin-1-yl)-N-methyl-7-(trifluoromethyl)thieno[3,2-b]pyridine-3-carboxamide trifluoroacetate;

5-(4-(((tert-Butylsulfinyl)amino)methyl)piperidin-1-yl)-N-methyl-7-(trifluoromethyl)thieno[3,2-b]pyridine-3-carboxamide;

5-(4-((((Cyclopropylmethyl)amino)methyl)piperidin-1-yl)-N-methyl-7-(trifluoromethyl)thieno[3,2-b]pyridine-3-carboxamide trifluoroacetate;

5-(4-(2-Isopropoxyethoxy)piperidin-1-yl)-N-methyl-7-(trifluoromethyl)thieno[3,2-b]pyridine-3-carboxamide;

5-(4-(1-(Cyclopropylmethoxy)-3-hydroxypropan-2-yl)piperazin-1-yl)-N-methyl-7-(trifluoromethyl)thieno[3,2-b]pyridine-3-carboxamide;

5-(4-(3-Formamidopropyl)piperazin-1-yl)-N-methyl-7-(trifluoromethyl)thieno[3,2-b]pyridine-3-carboxamide;

5-(4-(2-(Bis(cyclopropylmethyl)amino)ethyl)piperazin-1-yl)-N-methyl-7-(trifluoromethyl)thieno[3,2-b]pyridine-3-carboxamide;

5-(4-(3-(Cyclopropanecarboxamido)propyl)piperazin-1-yl)-N-methyl-7-(trifluoromethyl)thieno[3,2-b]pyridine-3-carboxamide trifluoroacetate;

5-(4-(2-(Cyclopropylmethoxy)ethoxy)piperidin-1-yl)-N-methyl-7-(trifluoromethyl)thieno[3,2-b]pyridine-3-carboxamide;

5-(4-(2-(Isopropylsulfonyl)ethyl)piperazin-1-yl)-N-methyl-7-(trifluoromethyl)thieno[3,2-b]pyridine-3-carboxamide;

5-(4-(2-Hydroxy-3-morpholinopropoxy)piperidin-1-yl)-N-methyl-7-(trifluoromethyl)thieno[3,2-b]pyridine-3-carboxamide;

5-(4-((4-Isopropylmorpholin-2-yl)methyl)piperazin-1-yl)-N-methyl-7-(trifluoromethyl)thieno[3,2-b]pyridine-3-carboxamide trifluoroacetate;

Methyl 5-(4-((3-isopropoxyazetidin-1-yl)methyl)piperidin-1-yl)-7-(trifluoromethyl)thieno[3,2-b]pyridine-3-carboxylate;

5-(4-((3-Isopropoxyazetidin-1-yl)methyl)piperidin-1-yl)-N-methyl-7-(trifluoromethyl)thieno[3,2-b]pyridine-3-carboxamide;

5-(4-(3-(3,3-Difluoropyrrolidin-1-yl)-2-hydroxypropoxy)piperidin-1-yl)-N-methyl-7-(trifluoromethyl)thieno[3,2-b]pyridine-3-carboxamide;

5-(4-(2-hydroxy-3-isopropoxypropoxy)piperidin-1-yl)-N-methyl-7-(trifluoromethyl)thieno[3,2-b]pyridine-3-carboxamide;

5-(4-((5-Isopropyl-1,3,4-oxadiazol-2-yl)methoxy)piperidin-1-yl)-N-methyl-7-(trifluoromethyl)thieno[3,2-b]pyridine-3-carboxamide;

(S)-1-Cyclopropylethyl 7-(3-(methylcarbamoyl)-7-(trifluoromethyl)thieno[3,2-b]pyridin-5-yl)-2,7-diazaspiro[3.5]nonane-2-carboxylate;

Cyclopropyl 7-(3-(methylcarbamoyl)-7-(trifluoromethyl)thieno[3,2-b]pyridin-5-yl)-2,7-diazaspiro[3.5]nonane-2-carboxylate;

Oxetan-3-yl 7-(3-(methylcarbamoyl)-7-(trifluoromethyl)thieno[3,2-b]pyridin-5-yl)-2,7-diazaspiro[3.5]nonane-2-carboxylate;

Isopropyl 7-(3-(methylcarbamoyl)-7-(trifluoromethyl)thieno[3,2-b]pyridin-5-yl)-2,7-diazaspiro[3.5]nonane-2-carboxylate;

5-(2-(Ethyl(isopropyl)carbamoyl)-2,7-diazaspiro[3.5]nonan-7-yl)-N-methyl-7-(trifluoromethyl)thieno[3,2-b]pyridine-3-carboxamide;

tert-Butyl 4-(3-(methylcarbamoyl)-7-(trifluoromethyl)thieno[3,2-b]pyridin-5-yl)piperidine-1-carboxylate;

5-(1-(1-(Cyclopropylamino)-1-oxopropan-2-yl)piperidin-4-yl)-N-methyl-7-(trifluoromethyl)thieno[3,2-b]pyridine-3-carboxamide;

N-Methyl-5-(1-((4-methylthiazol-2-yl)methyl)piperidin-4-yl)-7-(trifluoromethyl)thieno[3,2-b]pyridine-3-carboxamide hydrogen chloride;

(S)-1-Cyclopropylethyl 4-(3-(methylcarbamoyl)-7-(trifluoromethyl)thieno[3,2-b]pyridin-5-yl)piperidine-1-carboxylate;

4-Methylpentan-2-yl 4-(3-(methylcarbamoyl)-7-(trifluoromethyl)thieno[3,2-b]pyridin-5-yl)piperidine-1-carboxylate;

4-(3-(Methylcarbamoyl)-7-(trifluoromethyl)thieno[3,2-b]pyridin-5-yl)cyclohex-3-en-1-yl (cyclopropylmethyl)carbamate;

2-Cyclopropylethyl 4-(3-(methylcarbamoyl)-7-(trifluoromethyl)thieno[3,2-b]pyridin-5-yl)piperidine-1-carboxylate;

tert-Butyl (3S,4S)-3,4-dihydroxy-4-(3-(methylcarbamoyl)-7-(trifluoromethyl)thieno[3,2-b]pyridin-5-yl)piperidine-1-carboxylate;

2-Cyclopropyl-2-oxoethyl 4-(3-(methylcarbamoyl)-7-(trifluoromethyl)thieno[3,2-b]pyridin-5-yl)piperidine-1-carboxylate;

4-(3-(Methylcarbamoyl)-7-(trifluoromethyl)thieno[3,2-b]pyridin-5-yl)cyclohexyl (cyclopropylmethyl)carbamate;

2-(Trifluoromethoxy)ethyl 4-(3-(methylcarbamoyl)-7-(trifluoromethyl)thieno[3,2-b]pyridin-5-yl)piperidine-1-carboxylate;

tert-Butyl 6-(3-(methylcarbamoyl)-7-(trifluoromethyl)thieno[3,2-b]pyridin-5-yl)-2-azaspiro[3.3]heptane-2-carboxylate;

tert-Butyl 2-(3-(methylcarbamoyl)-7-(trifluoromethyl)thieno[3,2-b]pyridin-5-yl)-7-azaspiro[3.5]nonane-7-carboxylate;

2-(Trifluoromethoxy)ethyl 6-(3-(methylcarbamoyl)-7-(trifluoromethyl)thieno[3,2-b]pyridin-5-yl)-2-azaspiro[3.3]heptane-2-carboxylate;

2-(Trifluoromethoxy)ethyl 2-(3-(methylcarbamoyl)-7-(trifluoromethyl)thieno[3,2-b]pyridin-5-yl)-7-azaspiro[3.5]nonane-7-carboxylate;

tert-Butyl 4-((3-(methylcarbamoyl)-7-(trifluoromethyl)thieno[3,2-b]pyridin-5-yl)thio)piperidine-1-carboxylate;

tert-Butyl 4-((3-(methylcarbamoyl)-7-(trifluoromethyl)thieno[3,2-b]pyridin-5-yl) sulfinyl)piperidine-1-carboxylate;

tert-butyl 4-((3-(methylcarbamoyl)-7-(trifluoromethyl)thieno[3,2-b]pyridin-5-yl) sulfonyl)piperidine-1-carboxylate;

5-(4-(2-(Cyclopropylamino)-2-oxoethoxy)phenyl)-N-methyl-7-(trifluoromethyl)thieno[3,2-b]pyridine-3-carboxamide;

(1-(3-(Methylcarbamoyl)-7-(trifluoromethyl)thieno[3,2-b]pyridin-5-yl)-1H-imidazol-4-yl)methyl (cyclopropylmethyl)carbamate;

tert-Butyl 3-(((3-(methylcarbamoyl)-7-(trifluoromethyl)thieno[3,2-b]pyridin-5-yl)oxy)methyl)pyrrolidine-1-carboxylate;

tert-Butyl 3-(((3-(methylcarbamoyl)-7-(trifluoromethyl)thieno[3,2-b]pyridin-5-yl)oxy)methyl)azetidine-1-carboxylate;

5-((6-Methoxypyridin-3-yl)methoxy)-N-methyl-7-(trifluoromethyl)thieno[3,2-b]pyridine-3-carboxamide trifluoroacetate;

5-((1-(Cyclopropylcarbamoyl)azetidin-3-yl)methoxy)-N-methyl-7-(trifluoromethyl)thieno[3,2-b]pyridine-3-carboxamide;

tert-Butyl 3-((3-(methylcarbamoyl)-7-(trifluoromethyl)thieno[3,2-b]pyridin-5-yl)oxy)azetidine-1-carboxylate;

tert-Butyl 3-((3-(methylcarbamoyl)-7-(trifluoromethyl)thieno[3,2-b]pyridin-5-yl)oxy)pyrrolidine-1-carboxylate;

5-((1-((Cyclopropylmethyl)carbamoyl)pyrrolidin-3-yl)oxy)-N-methyl-7-(trifluoromethyl)thieno[3,2-b]pyridine-3-carboxamide;

tert-Butyl (R)-3-((3-(methylcarbamoyl)-7-(trifluoromethyl)thieno[3,2-b]pyridin-5-yl)oxy)pyrrolidine-1-carboxylate;

(R)-5-((1-((Cyclopropylmethyl)carbamoyl)pyrrolidin-3-yl)oxy)-N-methyl-7-(trifluoromethyl)thieno[3,2-b]pyridine-3-carboxamide;

tert-Butyl (S)-3-((3-(methylcarbamoyl)-7-(trifluoromethyl)thieno[3,2-b]pyridin-5-yl)oxy)pyrrolidine-1-carboxylate;

(S)-5-((1-((Cyclopropylmethyl)carbamoyl)pyrrolidin-3-yl)oxy)-N-methyl-7-(trifluoromethyl)thieno[3,2-b]pyridine-3-carboxamide;

Cyclopropylmethyl (S)-3-((3-(methylcarbamoyl)-7-(trifluoromethyl)thieno[3,2-b]pyridin-5-yl)oxy)pyrrolidine-1-carboxylate;

1-Methoxypropan-2-yl (3S)-3-((3-(methylcarbamoyl)-7-(trifluoromethyl)thieno[3,2-b]pyridin-5-yl)oxy)pyrrolidine-1-carboxylate;

1-Cyanoethyl (3R)-3-((3-(methylcarbamoyl)-7-(trifluoromethyl)thieno[3,2-b]pyridin-5-yl)oxy)pyrrolidine-1-carboxylate;

1,3-Difluoropropan-2-yl (S)-3-((3-(methylcarbamoyl)-7-(trifluoromethyl)thieno[3,2-b]pyridin-5-yl)oxy)pyrrolidine-1-carboxylate;

tert-Butyl 3-hydroxy-4-((3-(methylcarbamoyl)-7-(trifluoromethyl)thieno[3,2-b]pyridin-5-yl)oxy)pyrrolidine-1-carboxylate;

2-(Trifluoromethoxy)ethyl (S)-3-((3-(methylcarbamoyl)-7-(trifluoromethyl)thieno[3,2-b]pyridin-5-yl)oxy)pyrrolidine-1-carboxylate;

Isopropyl (S)-3-((3-(methylcarbamoyl)-7-(trifluoromethyl)thieno[3,2-b]pyridin-5-yl)oxy)pyrrolidine-1-carboxylate;

(S)-1-Cyclopropylethyl (S)-3-((3-(methylcarbamoyl)-7-(trifluoromethyl)thieno[3,2-b]pyridin-5-yl)oxy)pyrrolidine-1-carboxylate;

3-(Trifluoromethoxy)propyl (S)-3-((3-(methylcarbamoyl)-7-(trifluoromethyl)thieno[3,2-b]pyridin-5-yl)oxy)pyrrolidine-1-carboxylate;

2,2,2-Trifluoroethyl (S)-3-((3-(methylcarbamoyl)-7-(trifluoromethyl)thieno[3,2-b]pyridin-5-yl)oxy)pyrrolidine-1-carboxylate;

tert-Butyl (+/−)-trans-3-fluoro-4-((3-(methylcarbamoyl)-7-(trifluoromethyl)thieno[3,2-b]pyridin-5-yl)oxy)pyrrolidine-1-carboxylate;

2-(Trifluoromethoxy)ethyl (+/−)-trans-3-fluoro-4-((3-(methylcarbamoyl)-7-(trifluoromethyl)thieno[3,2-b]pyridin-5-yl)oxy)pyrrolidine-1-carboxylate;

Cyclopropylmethyl (+/−)-trans-3-fluoro-4-((3-(methylcarbamoyl)-7-(trifluoromethyl)thieno[3,2-b]pyridin-5-yl)oxy)pyrrolidine-1-carboxylate;

2-Cyclopropylethyl (S)-3-((3-(methylcarbamoyl)-7-(trifluoromethyl)thieno[3,2-b]pyridin-5-yl)oxy)pyrrolidine-1-carboxylate;

tert-Butyl (+/−)-cis-3-fluoro-4-((3-(methylcarbamoyl)-7-(trifluoromethyl)thieno[3,2-b]pyridin-5-yl)oxy)pyrrolidine-1-carboxylate;

Cyclopropylmethyl (+/−)-cis-3-fluoro-4-((3-(methylcarbamoyl)-7-(trifluoromethyl)thieno[3,2-b]pyridin-5-yl)oxy)pyrrolidine-1-carboxylate;

2-(Trifluoromethoxy)ethyl (+/−)-cis-3-fluoro-4-((3-(methylcarbamoyl)-7-(trifluoromethyl)thieno[3,2-b]pyridin-5-yl)oxy)pyrrolidine-1-carboxylate;

3,3,3-Trifluoropropyl (S)-3-((3-(methylcarbamoyl)-7-(trifluoromethyl)thieno[3,2-b]pyridin-5-yl)oxy)pyrrolidine-1-carboxylate;

(2,2-Difluorocyclopropyl)methyl (3S)-3-((3-(methylcarbamoyl)-7-(trifluoromethyl)thieno[3,2-b]pyridin-5-yl)oxy)pyrrolidine-1-carboxylate;

4,4,4-Trifluorobutyl (S)-3-((3-(methylcarbamoyl)-7-(trifluoromethyl)thieno[3,2-b]pyridin-5-yl)oxy)pyrrolidine-1-carboxylate;

tert-Butyl (+/−)-trans-3-((3-(methylcarbamoyl)-7-(trifluoromethyl)thieno[3,2-b]pyridin-5-yl)oxy)-4-morpholinopyrrolidine-1-carboxylate;

(5-(Trifluoromethyl)isoxazol-3-yl)methyl (S)-3-((3-(methylcarbamoyl)-7-(trifluoromethyl)thieno[3,2-b]pyridin-5-yl)oxy)pyrrolidine-1-carboxylate;

2-(Trifluoromethoxy)ethyl (R)-3-((3-(methylcarbamoyl)-7-(trifluoromethyl)thieno[3,2-b]pyridin-5-yl)oxy)pyrrolidine-1-carboxylate;

tert-Butyl ((+/−)-trans-3-(dimethylamino)-4-((3-(methylcarbamoyl)-7-(trifluoromethyl)thieno[3,2-b]pyridin-5-yl)oxy)pyrrolidine-1-carboxylate;

2-(Trifluoromethoxy)ethyl (+/−)-trans-3-(dimethylamino)-4-((3-(methylcarbamoyl)-7-(trifluoromethyl)thieno[3,2-b]pyridin-5-yl)oxy)pyrrolidine-1-carboxylate;

tert-Butyl (S)-3-((6-methyl-3-(methylcarbamoyl)-7-(trifluoromethyl)thieno[3,2-b]pyridin-5-yl)oxy)pyrrolidine-1-carboxylate;

tert-Butyl (+/−)-trans-3-methoxy-4-((3-(methylcarbamoyl)-7-(trifluoromethyl)thieno[3,2-b]pyridin-5-yl)oxy)pyrrolidine-1-carboxylate;

2-(Trifluoromethoxy)ethyl ((+/−)-trans-3-methoxy-4-((3-(methylcarbamoyl)-7-(trifluoromethyl)thieno[3,2-b]pyridin-5-yl)oxy)pyrrolidine-1-carboxylate;

2-(Trifluoromethoxy)ethyl (S)-3-((6-methyl-3-(methylcarbamoyl)-7-(trifluoromethyl)thieno[3,2-b]pyridin-5-yl)oxy)pyrrolidine-1-carboxylate;

tert-Butyl 4-((3-(methylcarbamoyl)-7-(trifluoromethyl)thieno[3,2-b]pyridin-5-yl)oxy)piperidine-1-carboxylate;

5-((1-(2-(Isopropylamino)-2-oxoethyl)piperidin-4-yl)oxy)-N-methyl-7-(trifluoromethyl)thieno[3,2-b]pyridine-3-carboxamide;

tert-Butyl (+/−)-cis-4-((3-(methylcarbamoyl)-7-(trifluoromethyl)thieno[3,2-b]pyridin-5-yl)oxy)cyclohexyl)carbamate;

Isopropyl (+/−)-cis-4-((3-(methylcarbamoyl)-7-(trifluoromethyl)thieno[3,2-b]pyridin-5-yl)oxy)cyclohexyl)carbamate;

tert-Butyl (+/−)-endo7-((3-(methylcarbamoyl)-7-(trifluoromethyl)thieno[3,2-b]pyridin-5-yl)oxy)-3-oxa-9-azabicyclo[3.3.1]nonane-9-carboxylate;
2-(Trifluoromethoxy)ethyl (+/−)-endo7-((3-(methylcarbamoyl)-7-(trifluoromethyl)thieno[3,2-b]pyridin-5-yl)oxy)-3-oxa-9-azabicyclo[3.3.1]nonane-9-carboxylate;
tert-Butyl (+/−)-exo-3-((3-(methylcarbamoyl)-7-(trifluoromethyl)thieno[3,2-b]pyridin-5-yl)oxy)-8-azabicyclo[3.2.1]octane-8-carboxylate;
tert-Butyl (+/−)-endo3-((3-(methylcarbamoyl)-7-(trifluoromethyl)thieno[3,2-b]pyridin-5-yl)oxy)-8-azabicyclo[3.2.1]octane-8-carboxylate;
2-(Trifluoromethoxy)ethyl 4-((3-(methylcarbamoyl)-7-(trifluoromethyl)thieno[3,2-b]pyridin-5-yl)methyl)piperidine-1-carboxylate;
5-(4-((Cyclopropylmethyl)carbamoyl)piperazin-1-yl)-N-methyl-7-(trifluoromethyl)thieno[3,2-b]pyridine-3-carboxamide trifluoroacetate;
tert-Butyl 4-((3-(methylcarbamoyl)-7-(trifluoromethyl)thieno[3,2-b]pyridin-5-yl)methyl)piperidine-1-carboxylate;
2-(Trifluoromethoxy)ethyl (+/−)-exo-3-((3-(methylcarbamoyl)-7-(trifluoromethyl)thieno[3,2-b]pyridin-5-yl)oxy)-8-azabicyclo[3.2.1]octane-8-carboxylate;
6-Chloro-5-[4-[2-(isopropylamino)-2-oxo-ethyl]piperazin-1-yl]-N-methyl-7-(trifluoromethyl)thieno[3,2-b]pyridine-3-carboxamide;
6-Chloro-5-[4-[2-(isopropylamino)-2-oxo-ethyl]piperazin-1-yl]-2-methoxy-N-methyl-7-(trifluoromethyl)thieno[3,2-b]pyridine-3-carboxamide;
[1-[6-Chloro-3-(methylcarbamoyl)-7-(trifluoromethyl)thieno[3,2-b]pyridin-5-yl]-4-piperidyl]N-(cyclopropylmethyl)carbamate;
[1-[6-Fluoro-3-(methylcarbamoyl)-7-(trifluoromethyl)thieno[3,2-b]pyridin-5-yl]-4-piperidyl]N-[(1S)-1-cyclopropylethyl]carbamate;
[1-[6-Chloro-3-(methylcarbamoyl)-7-(trifluoromethyl)thieno[3,2-b]pyridin-5-yl]-4-piperidyl]N-cyclopropylcarbamate;
[1-[6-fluoro-3-(methylcarbamoyl)-7-(trifluoromethyl)thieno[3,2-b]pyridin-5-yl]-4-piperidyl]N-cyclopropylcarbamate;
tert-Butyl N-[1-[3-(isopropylcarbamoyl)-7-(trifluoromethyl)thieno[3,2-b]pyridin-5-yl]pyrrolidin-3-yl]carbamate;
N-Isopropyl-2-[4-[3-(5-methyloxazol-2-yl)-7-(trifluoromethyl)thieno[3,2-b]pyridin-5-yl]piperazin-1-yl]acetamide;
N-[(4-Fluorophenyl)methyl]-5-[4-[2-(isopropylamino)-2-oxo-ethyl]piperazin-1-yl]-7-(trifluoromethyl)thieno[3,2-b]pyridine-3-carboxamide;
5-[4-[2-(Isopropylamino)-2-oxo-ethyl]piperazin-1-yl]-7-(trifluoromethyl)thieno[3,2-b]pyridine-3-carboxamide;
N-Isopropyl-2-[4-[3-(4-methyloxazol-2-yl)-7-(trifluoromethyl)thieno[3,2-b]pyridin-5-yl]piperazin-1-yl]acetamide;
2-[4-[3-(1-Hydroxypropyl)-7-(trifluoromethyl)thieno[3,2-b]pyridin-5-yl]piperazin-1-yl]-N-isopropyl-acetamide;
N-Isopropyl-2-[4-[3-propanoyl-7-(trifluoromethyl)thieno[3,2-b]pyridin-5-yl]piperazin-1-yl]acetamide;
2-[4-[3-(Azetidine-1-carbonyl)-7-(trifluoromethyl)thieno[3,2-b]pyridin-5-yl]piperazin-1-yl]-N-isopropyl-acetamide;
N-Isopropyl-2-[4-[3-(methoxymethyl)-7-(trifluoromethyl)thieno[3,2-b]pyridin-5-yl]piperazin-1-yl]acetamide;
N-Isopropyl-2-[4-[3-methyl-7-(trifluoromethyl)thieno[3,2-b]pyridin-5-yl]piperazin-1-yl]acetamide;
[1-[3-Propanoyl-7-(trifluoromethyl)thieno[3,2-b]pyridin-5-yl]-4-piperidyl] N-(cyclopropylmethyl)carbamate;
[1-[3-(Trideuteriomethylcarbamoyl)-7-(trifluoromethyl)thieno[3,2-b]pyridin-5-yl]-4-piperidyl] N-cyclopropylcarbamate;
7-(1-Difluoroethyl)-5-[4-[2-(isopropylamino)-2-oxo-ethyl]piperazin-1-yl]-N-methylthieno[3,2-b]pyridine-3-carboxamide;
[1-[7-(1,1-Difluoroethyl)-3-(methylcarbamoyl)thieno[3,2-b]pyridin-5-yl]-4-piperidyl] N-(cyclopropylmethyl)carbamate hydrochloride;
[1-[3-(Methylcarbamoyl)-7-(2,2,2-trifluoroethoxy)thieno[3,2-b]pyridin-5-yl]-4-piperidyl] N-isopropylcarbamate;
5-[3-(4-Hydroxy-4-methyl-pent-2-ynoxy)azetidin-1-yl]-N-methyl-7-(trifluoromethyl)thieno[3,2-b]pyridine-3-carboxamide;
5-[3-[3-(Cyclopropylmethoxy)azetidin-1-yl]azetidin-1-yl]-N-methyl-7-(trifluoromethyl)thieno[3,2-b]pyridine-3-carboxamide;
Methyl 5-[3-(tert-butoxycarbonylamino)pyrrolidin-1-yl]-7-(trifluoromethyl)thieno[3,2-b]pyridine-3-carboxylate;
5-[3-[[(1R,2R)-2-Hydroxycyclohexyl]amino]pyrrolidin-1-yl]-N-methyl-7-(trifluoromethyl)thieno[3,2-b]pyridine-3-carboxamide;
5-[3-(2-Isopropoxyethylamino)pyrrolidin-1-yl]-N-methyl-7-(trifluoromethyl)thieno[3,2-b]pyridine-3-carboxamide;
5-[3-(3-Hydroxy-3-methyl-but-1-ynyl)pyrrolidin-1-yl]-N-methyl-7-(trifluoromethyl)thieno[3,2-b]pyridine-3-carboxamide;
5-[3-(Cyclopropylmethoxy)pyrrolidin-1-yl]-N-methyl-7-(trifluoromethyl)thieno[3,2-b]pyridine-3-carboxamide;
Methyl 5-[4-(tert-butoxycarbonylamino)-1-piperidyl]-7-(trifluoromethyl)thieno[3,2-b]pyridine-3-carboxylate;
5-[4-[2-[(2-Hydroxy-1,1-dimethyl-ethyl)amino]-1-methyl-2-oxo-ethyl]piperazin-1-yl]-N-methyl-7-(trifluoromethyl)thieno[3,2-b]pyridine-3-carboxamide;
[1-[3-(Methylcarbamoyl)-7-(trifluoromethyl)thieno[3,2-b]pyridin-5-yl]-4-piperidyl] N-(2-methoxy-2-methyl-propyl)carbamate;
[1-[3-(Methylcarbamoyl)-7-(trifluoromethyl)thieno[3,2-b]pyridin-5-yl]-4-piperidyl] N-(3-methoxy-2,2-dimethyl-propyl)carbamate;
[1-[3-(Methylcarbamoyl)-7-(trifluoromethyl)thieno[3,2-b]pyridin-5-yl]-4-piperidyl]3,3-dimethylpiperazine-1-carboxylate;
[1-[3-(Methylcarbamoyl)-7-(trifluoromethyl)thieno[3,2-b]pyridin-5-yl]-4-piperidyl] N-(cyclopropylmethyl)carbamate hydrochloride;
[1-[3-(Methylcarbamoyl)-7-(trifluoromethyl)thieno[3,2-b]pyridin-5-yl]-4-piperidyl] N-(2,2-difluoro-1-methyl-ethyl)carbamate;
[1-[3-(Methylcarbamoyl)-7-(trifluoromethyl)thieno[3,2-b]pyridin-5-yl]-4-piperidyl] N-(2-fluoro-1-methyl-ethyl)carbamate;
[1-[3-(Methylcarbamoyl)-7-(trifluoromethyl)thieno[3,2-b]pyridin-5-yl]-4-piperidyl] N-[2-hydroxy-1-(hydroxymethyl)ethyl]carbamate;
[1-[3-(Methylcarbamoyl)-7-(trifluoromethyl)thieno[3,2-b]pyridin-5-yl]-4-piperidyl] N-tetrahydrofuran-3-ylcarbamate;
[1-[3-(Methylcarbamoyl)-7-(trifluoromethyl)thieno[3,2-b]pyridin-5-yl]-4-piperidyl] N-(oxetan-3-yl)carbamate;
[1-[3-(Methylcarbamoyl)-7-(trifluoromethyl)thieno[3,2-b]pyridin-5-yl]-4-piperidyl] N-(3-methyloxetan-3-yl)carbamate;

[1-[3-(methylcarbamoyl)-7-(trifluoromethyl)thieno[3,2-b]pyridin-5-yl]-4-piperidyl]3-methylthiomorpholine-4-carboxylate;

[1-[3-(Methylcarbamoyl)-7-(trifluoromethyl)thieno[3,2-b]pyridin-5-yl]-4-piperidyl] 3-methyl-1-oxo-1,4-thiazinane-4-carboxylate;

[1-[3-(Methylcarbamoyl)-7-(trifluoromethyl)thieno[3,2-b]pyridin-5-yl]-4-piperidyl] 3-methyl-1,1-dioxo-1,4-thiazinane-4-carboxylate;

[1-[3-(Methylcarbamoyl)-7-(trifluoromethyl)thieno[3,2-b]pyridin-5-yl]-4-piperidyl] N-[(1S)-1-methyl-2-methylsulfanyl-ethyl]carbamate;

[1-[3-(Methylcarbamoyl)-7-(trifluoromethyl)thieno[3,2-b]pyridin-5-yl]-4-piperidyl] N-[(1S)-1-methyl-2-methylsulfinyl-ethyl]carbamate;

[1-[3-(methylcarbamoyl)-7-(trifluoromethyl)thieno[3,2-b]pyridin-5-yl]-4-piperidyl] N—[(S)-1-methyl-2-methylsulfonyl-ethyl]carbamate;

[1-[3-(Methylcarbamoyl)-7-(trifluoromethyl)thieno[3,2-b]pyridin-5-yl]-4-piperidyl] N-(1,1-dioxothiolan-3-yl)carbamate;

[1-[3-(Methylcarbamoyl)-7-(trifluoromethyl)thieno[3,2-b]pyridin-5-yl]-4-piperidyl] 3-(3-pyridyloxy)azetidine-1-carboxylate;

[1-[3-(Methylcarbamoyl)-7-(trifluoromethyl)thieno[3,2-b]pyridin-5-yl]-4-piperidyl] 3-(2-pyridyl)azetidine-1-carboxylate;

[1-[3-(Methylcarbamoyl)-7-(trifluoromethyl)thieno[3,2-b]pyridin-5-yl]-4-piperidyl] N-(1-cyclopropyl-1-deuterio-ethyl)carbamate;

[1-[3-(Methylcarbamoyl)-7-(trifluoromethyl)thieno[3,2-b]pyridin-5-yl]-4-piperidyl] N-(1-deuterio-1-methyl-ethyl)carbamate;

[2,2,6,6-Tetradeuterio-1-[3-(methylcarbamoyl)-7-(trifluoromethyl)thieno[3,2-b]pyridin-5-yl]-4-piperidyl] N-cyclopropylcarbamate;

[2,2,6,6-Tetradeuterio-1-[3-(methylcarbamoyl)-7-(trifluoromethyl)thieno[3,2-b]pyridin-5-yl]-4-piperidyl] N-isopropylcarbamate;

[(1R,5S)-8-[3-(Methylcarbamoyl)-7-(trifluoromethyl)thieno[3,2-b]pyridin-5-yl]-8-azabicyclo[3.2.1]octan-3-yl] N-cyclopropylcarbamate;

[1-[3-(Methylcarbamoyl)-7-(trifluoromethyl)thieno[3,2-b]pyridin-5-yl]-4-piperidyl] N-[(1S)-2,2-dideuterio-1-methyl-2-(trideuteriomethoxy)ethyl]carbamate;

[(1R,5S)-8-[3-(Methylcarbamoyl)-7-(trifluoromethyl)thieno[3,2-b]pyridin-5-yl]-8-azabicyclo[3.2.1]octan-3-yl] N-cyclopropylcarbamate;

[1-[3-(Methylcarbamoyl)-7-(trifluoromethyl)thieno[3,2-b]pyridin-5-yl]-4-piperidyl] N-[(1R)-2-fluoro-1-methyl-ethyl]carbamate;

[1-[3-(Methylcarbamoyl)-7-(trifluoromethyl)thieno[3,2-b]pyridin-5-yl]-4-piperidyl] N-[(1S)-2-fluoro-1-methyl-ethyl]carbamate;

[1-[3-(methylcarbamoyl)-7-(trifluoromethyl)thieno[3,2-b]pyridin-5-yl]-4-piperidyl] N-[cyclopropyl(dideuterio)methyl]carbamate;

[1-[3-(Methylcarbamoyl)-7-(trifluoromethyl)thieno[3,2-b]pyridin-5-yl]-4-piperidyl] N-[2-fluoro-1-(fluoromethyl)ethyl]carbamate;

[1-[3-(Methylcarbamoyl)-7-(trifluoromethyl)thieno[3,2-b]pyridin-5-yl]-4-piperidyl] 6-hydroxy-8-oxa-2-azaspiro[3.4]octane-2-carboxylate;

[1-[3-(Methylcarbamoyl)-7-(trifluoromethyl)thieno[3,2-b]pyridin-5-yl]-4-piperidyl] 6-[(2,2,2-trifluoro-1-methyl-ethyl)amino]-8-oxa-2-azaspiro[3.4]octane-2-carboxylate;

[1-[3-(Methylcarbamoyl)-7-(trifluoromethyl)thieno[3,2-b]pyridin-5-yl]-4-piperidyl] 3-(2,2,2-trifluoroethoxy)azetidine-1-carboxylate;

[2-Fluoro-1-(fluoromethyl)ethyl] N-[1-[3-(methylcarbamoyl)-7-(trifluoromethyl)thieno[3,2-b]pyridin-5-yl]-4-piperidyl]carbamate;

5-[4-[(2-Ethylthiazol-4-yl)methyl]piperazin-1-yl]-N-methyl-7-(trifluoromethyl)thieno[3,2-b]pyridine-3-carboxamide;

N-Methyl-5-[4-[(4-methyl-2-thienyl)methyl]piperazin-1-yl]-7-(trifluoromethyl)thieno[3,2-b]pyridine-3-carboxamide;

N-Methyl-5-[4-[(2-methyloxazol-4-yl)methyl]piperazin-1-yl]-7-(trifluoromethyl)thieno[3,2-b]pyridine-3-carboxamide;

5-[4-(Isobutylcarbamoyl)-1-piperidyl]-N-methyl-7-(trifluoromethyl)thieno[3,2-b]pyridine-3-carboxamide;

5-[4-(2-Hydroxy-4,4-dimethyl-pentyl)piperazin-1-yl]-N-methyl-7-(trifluoromethyl)thieno[3,2-b]pyridine-3-carboxamide;

5-[4-[1-(4,4-Dimethyl-5H-oxazol-2-yl)ethyl]piperazin-1-yl]-N-methyl-7-(trifluoromethyl)thieno[3,2-b]pyridine-3-carboxamide;

5-[4-[3-(Cyclopropylmethoxy)pyrrolidin-1-yl]-1-piperidyl]-N-methyl-7-(trifluoromethyl)thieno[3,2-b]pyridine-3-carboxamide;

5-[4-(2-Hydroxy-3-isopropoxy-propyl)piperazin-1-yl]-N-methyl-7-(trifluoromethyl)thieno[3,2-b]pyridine-3-carboxamide;

5-[4-(2-Isopropoxyethylamino)-1-piperidyl]-N-methyl-7-(trifluoromethyl)thieno[3,2-b]pyridine-3-carboxamide;

5-[4-(3-tert-Butoxy-2-hydroxy-propyl)piperazin-1-yl]-N-methyl-7-(trifluoromethyl)thieno[3,2-b]pyridine-3-carboxamide;

5-[4-(3-Isopropoxypyrrolidin-1-yl)-1-piperidyl]-N-methyl-7-(trifluoromethyl)thieno[3,2-b]pyridine-3-carboxamide;

5-[4-(4-Hydroxy-4-methyl-pent-2-ynyl)piperazin-1-yl]-N-methyl-7-(trifluoromethyl)thieno[3,2-b]pyridine-3-carboxamide;

5-[4-(3-Hydroxy-3-methyl-but-1-ynyl)-1-piperidyl]-N-methyl-7-(trifluoromethyl)thieno[3,2-b]pyridine-3-carboxamide;

5-[4-(5-Hydroxy-5-methyl-hexa-1,3-diynyl)-1-piperidyl]-N-methyl-7-(trifluoromethyl)thieno[3,2-b]pyridine-3-carboxamide;

5-[4-(4-Hydroxy-4-methyl-pent-2-ynoxy)-1-piperidyl]-N-methyl-7-(trifluoromethyl)thieno[3,2-b]pyridine-3-carboxamide;

[1,1-Dimethyl-4-[[1-[3-(methylcarbamoyl)-7-(trifluoromethyl)thieno[3,2-b]pyridin-5-yl]-4-piperidyl]oxy]but-2-ynyl]acetate;

5-[4-Hydroxy-4-(5-hydroxy-5-methyl-hexa-1,3-diynyl)-1-piperidyl]-N-methyl-7-(trifluoromethyl)thieno[3,2-b]pyridine-3-carboxamide;

5-[2-(Cyclopropylmethoxy)-4-oxa-8-azaspiro[4.5]decan-8-yl]-N-methyl-7-(trifluoromethyl)thieno[3,2-b]pyridine-3-carboxamide;

5-[2-(2-Hydroxy-2-methyl-propoxy)-4-oxa-8-azaspiro[4.5]decan-8-yl]-N-methyl-7-(trifluoromethyl)thieno[3,2-b]pyridine-3-carboxamide;

5-(2-Hydroxy-4-oxa-8-azaspiro[4.5]decan-8-yl)-N-methyl-7-(trifluoromethyl)thieno[3,2-b]pyridine-3-carboxamide;

5-[6-(Cyclopropylmethoxy)-8-oxa-2-azaspiro[3.4]octan-2-yl]-N-methyl-7-(trifluoromethyl)thieno[3,2-b]pyridine-3-carboxamide;

5-[6-(3,3-Difluoropyrrolidin-1-yl)-8-oxa-2-azaspiro[3.4]oc tan-2-yl]-N-methyl-7-(trifluoromethyl)thieno[3,2-b]pyri dine-3-carboxamide;

N-Methyl-7-(trifluoromethyl)-5-[6-[(2,2,2-trifluoro-1-methyl-ethyl)amino]-8-oxa-2-azaspiro[3.4]octan-2-yl] thieno[3,2-b]pyridine-3-carboxamide trifluoroacetate;

tert-Butyl 2-[3-(methylcarbamoyl)-7-(trifluoromethyl) thieno[3,2-b]pyridin-5-yl]-2,6-diazaspiro[3.3]heptane-6-carboxylate;

tert-Butyl 7-[3-(Methylcarbamoyl)-7-(trifluoromethyl) thieno[3,2-b]pyridin-5-yl]-2,7-diazaspiro[3.5]nonane-2-carboxylate;

5-[6-(2-tert-Butoxyacetyl)-2,6-diazaspiro[3.3]heptan-2-yl]-N-methyl-7-(trifluoromethyl)thieno[3,2-b]pyridine-3-carboxamide;

5-[2-(2-tert-Butoxyacetyl)-2,7-diazaspiro[3.5]nonan-7-yl]-N-methyl-7-(trifluoromethyl)thieno[3,2-b]pyridine-3-carboxamide;

tert-butyl 2-[3-(Methylcarbamoyl)-7-(trifluoromethyl) thieno[3,2-b]pyridin-5-yl]-2,7-diazaspiro[3.5]nonane-7-carboxylate;

5-[7-(2-tert-butoxyacetyl)-2,7-diazaspiro[3.5]nonan-2-yl]-N-methyl-7-(trifluoromethyl)thieno[3,2-b]pyridine-3-carboxamide;

5-[2-[2-(Isopropylamino)-2-oxo-ethyl]-2,7-diazaspiro[3.5] nonan-7-yl]-N-methyl-7-(trifluoromethyl)thieno[3,2-b] pyridine-3-carboxamide;

N-Methyl-5-[2-(4-methylpyrimidin-2-yl)-2,7-diazaspiro [3.5]nonan-7-yl]-7-(trifluoromethyl)thieno[3,2-b]pyri dine-3-carboxamide;

5-[2-(Cyclopropylmethylcarbamoyl)-2,7-diazaspiro[3.5] nonan-7-yl]-N-methyl-7-(trifluoromethyl)thieno[3,2-b] pyridine-3-carboxamide;

Cyclopropylmethyl 7-[3-(methylcarbamoyl)-7-(trifluorom ethyl)thieno[3,2-b]pyridin-5-yl]-2,7-diazaspiro[3.5] nonane-2-carboxylate;

N-Methyl-5-[2-[(2S)-1-methylpyrrolidine-2-carbonyl]-2,7-diazaspiro[3.5]nonan-7-yl]-7-(trifluoromethyl)thieno[3, 2-b]pyridine-3-carboxamide;

N-methyl-5-[2-(4-methylpiperazine-1-carbonyl)-2,7-diaz aspiro[3.5]nonan-7-yl]-7-(trifluoromethyl)thieno[3,2-b] pyridine-3-carboxamide;

5-[2-[2-(3,3-Difluoropyrrolidin-1-yl)acetyl]-2,7-diazaspiro [3.5]nonan-7-yl]-N-methyl-7-(trifluoromethyl)thieno[3, 2-b]pyridine-3-carboxamide;

5-[2-[2-[(3R)-3-Fluoropyrrolidin-1-yl]acetyl]-2,7-diaz aspiro[3.5]nonan-7-yl]-N-methyl-7-(trifluoromethyl) thieno[3,2-b]pyridine-3-carboxamide;

5-[2-(2-Hydroxy-3,3-dimethyl-butyl)-2,7-diazaspiro[3.5] nonan-7-yl]-N-methyl-7-(trifluoromethyl)thieno[3,2-b] pyridine-3-carboxamide;

5-[2-(3-Hydroxy-3-methyl-butanoyl)-2,7-diazaspiro[3.5] nonan-7-yl]-N-methyl-7-(trifluoromethyl)thieno[3,2-b] pyridine-3-carboxamide hydrochloride;

N-Methyl-5-[2-[2-(trifluoromethoxy)acetyl]-2,7-diazaspiro [3.5]nonan-7-yl]-7-(trifluoromethyl)thieno[3,2-b]pyri dine-3-carboxamide;

5-[2-(2-Methoxypropanoyl)-2,7-diazaspiro[3.5]nonan-7-yl]-N-methyl-7-(trifluoromethyl)thieno[3,2-b]pyridine-3-carboxamide;

(2-Methoxy-1,1-dimethyl-ethyl) 7-[3-(methylcarbamoyl)-7-(trifluoromethyl)thieno[3,2-b]pyridin-5-yl]-2,7-diaz aspiro[3.5]nonane-2-carboxylate;

N-Methyl-5-[6-(4-methylpiperazine-1-carbonyl)-2,6-diaz aspiro[3.3]heptan-2-yl]-7-(trifluoromethyl)thieno[3,2-b] pyridine-3-carboxamide;

N-Methyl-5-[2-(3,3,3-trifluoro-2-hydroxy-propanoyl)-2,7-diazaspiro[3.5]nonan-7-yl]-7-(trifluoromethyl)thieno[3, 2-b]pyridine-3-carboxamide;

(3-Hydroxy-3-methyl-butyl) 4-[3-(methylcarbamoyl)-7-(tri fluoromethyl)thieno[3,2-b]pyridin-5-yl]piperidine-1-car boxylate;

tert-Butyl 7-[3-(methylcarbamoyl)-7-(trifluoromethyl) thieno[3,2-b]pyridin-5-yl]-2-azaspiro[3.5]nonane-2-car boxylate;

2-(Trifluoromethoxy)ethyl 4-[1-[3-(methylcarbamoyl)-7-(trifluoromethyl)thieno[3,2-b]pyridin-5-yl]ethyl]pipera zine-1-carboxylate;

2-(Trifluoromethoxy)ethyl 7-[3-(methylcarbamoyl)-7-(trif luoromethyl)thieno[3,2-b]pyridin-5-yl]-2-azaspiro[3.5] nonane-2-carboxylate;

Methyl 5-[(1-tert-butoxycarbonyl-4-piperidyl)amino]-7-(trifluoromethyl)thieno[3,2-b]pyridine-3-carboxylate;

Methyl 5-[(1-tert-butoxycarbonylpyrrolidin-3-yl)amino]-7-(trifluoromethyl)thieno[3,2-b]pyridine-3-carboxylate;

Methyl 5-[(1-tert-butoxycarbonyl-4-piperidyl)methyl amino]-7-(trifluoromethyl)thieno[3,2-b]pyridine-3-car boxylate;

5-[2-(2-Isopropylthiazol-4-yl)ethylamino]-N-methyl-7-(tri fluoromethyl)thieno[3,2-b]pyridine-3-carboxamide;

Methyl 5-[2-(1-tert-butoxycarbonylpyrrolidin-3-yl)ethy nyl]-7-(trifluoromethyl)thieno[3,2-b]pyridine-3-carboxy late;

tert-Butyl 4-hydroxy-4-[2-[3-(methylcarbamoyl)-7-(trifluo romethyl)thieno[3,2-b]pyridin-5-yl]ethynyl]piperidine-1-carboxylate;

[(1S)-1-Cyclopropylethyl] 3-[[3-(methylcarbamoyl)-7-(trif luoromethyl)thieno[3,2-b]pyridin-5-yl]oxymethyl]azeti dine-1-carboxylate;

tert-Butyl 6-[3-(methylcarbamoyl)-7-(trifluoromethyl) thieno[3,2-b]pyridin-5-yl]oxy-8-oxa-2-azaspiro[3.4]oc tane-2-carboxylate;

tert-Butyl 2-[3-(methylcarbamoyl)-7-(trifluoromethyl) thieno[3,2-b]pyridin-5-yl]oxy-4-oxa-8-azaspiro[4.5]de cane-8-carboxylate;

N-Methyl-5-[5-[3-(3-pyridyl)azetidine-1-carbonyl]-3-fu ryl]-7-(trifluoromethyl)thieno[3,2-b]pyridine-3-carbox amide;

5-[4-[4-(2-Hydroxy-2-methyl-propyl)piperazin-1-yl]phe nyl]-N-methyl-7-(trifluoromethyl)thieno[3,2-b]pyridine-3-carboxamide;

5-[6-(6-Chloro-3-pyridyl)-3-pyridyl]-N-methyl-7-(trifluo romethyl)thieno[3,2-b]pyridine-3-carboxamide;

5-[6-(3-Isopropoxyazetidin-1-yl)-3-pyridyl]-N-methyl-7-(trifluoromethyl)thieno[3,2-b]pyridine-3-carboxamide; trifluoroacetate;

5-[6-[2-(1-hydroxycyclohexyl)ethynyl]-3-pyridyl]-N-methyl-7-(trifluoromethyl)thieno[3,2-b]pyridine-3-car boxamide; trifluoroacetate;

1-(3-(Methylcarbamoyl)-7-(trifluoromethyl)thieno[3,2-b] pyridin-5-yl)piperidin-4-yl (1-(1H-imidazol-1-yl)propan-2-yl)carbamate;

1-(3-(Methylcarbamoyl)-7-(trifluoromethyl)thieno[3,2-b] pyridin-5-yl)piperidin-4-yl 2-methyl-4-(1H-1,2,4-triazol-1-yl)piperidine-1-carboxylate;

1-(3-(Methylcarbamoyl)-7-(trifluoromethyl)thieno[3,2-b] pyridin-5-yl)piperidin-4-yl (1-(methylsulfonyl)azetidin-3-yl)carbamate;

1-(3-(Methylcarbamoyl)-7-(trifluoromethyl)thieno[3,2-b] pyridin-5-yl)piperidin-4-yl 2-methyl-4-(methylsulfonyl) piperazine-1-carboxylate;

1-(3-(Methylcarbamoyl)-7-(trifluoromethyl)thieno[3,2-b]pyridin-5-yl)piperidin-4-yl (S)-(1-cyclopropylpropan-2-yl)carbamate;

1-(3-(Methylcarbamoyl)-7-(trifluoromethyl)thieno[3,2-b]pyridin-5-yl)piperidin-4-yl (R)-(1-cyclopropylpropan-2-yl)carbamate;

1-(3-(Methylcarbamoyl)-7-(trifluoromethyl)thieno[3,2-b]pyridin-5-yl)piperidin-4-yl (oxetan-3-ylmethyl)carbamate;

1-(3-(Methylcarbamoyl)-7-(trifluoromethyl)thieno[3,2-b]pyridin-5-yl)piperidin-4-yl ((3-hydroxyoxetan-3-yl)methyl)carbamate;

1-(3-(Methylcarbamoyl)-7-(trifluoromethyl)thieno[3,2-b]pyridin-5-yl)piperidin-4-yl ((3-fluorooxetan-3-yl)methyl)carbamate;

1-(3-(Methylcarbamoyl)-7-(trifluoromethyl)thieno[3,2-b]pyridin-5-yl)piperidin-4-yl (R)-2-methylazetidine-1-carboxylate;

1-(3-(Methylcarbamoyl)-7-(trifluoromethyl)thieno[3,2-b]pyridin-5-yl)piperidin-4-yl (S)-2-methylazetidine-1-carboxylate;

1-(3-(Methylcarbamoyl)-7-(trifluoromethyl)thieno[3,2-b]pyridin-5-yl)piperidin-4-yl 3-methoxyazetidine-1-carboxylate;

1-(3-(Methylcarbamoyl)-7-(trifluoromethyl)thieno[3,2-b]pyridin-5-yl)piperidin-4-yl 2-oxa-6-azaspiro[3.3]heptane-6-carboxylate;

1-(3-(Methylcarbamoyl)-7-(trifluoromethyl)thieno[3,2-b]pyridin-5-yl)piperidin-4-yl 6-methyl-2,6-diazaspiro[3.3]heptane-2-carboxylate;

1-(3-(Methylcarbamoyl)-7-(trifluoromethyl)thieno[3,2-b]pyridin-5-yl)piperidin-4-yl 5,8-dioxa-2-azaspiro[3.4]octane-2-carboxylate;

1-(3-(methylcarbamoyl)-7-(trifluoromethyl)thieno[3,2-b]pyridin-5-yl)piperidin-4-yl (2S)-3-cyclopropyl-3-hydroxy-2-methylazetidine-1-carboxylate;

1-(3-(Methylcarbamoyl)-7-(trifluoromethyl)thieno[3,2-b]pyridin-5-yl)piperidin-4-yl (2S,3S)-3-hydroxy-2-methylpyrrolidine-1-carboxylate;

Cyclopropylmethyl 4-(3-(methylcarbamoyl)-7-(trifluoromethyl)thieno[3,2-b]pyridin-5-yl)piperazine-1-carboxylate;

1-(3-(Methylcarbamoyl)-7-(trifluoromethyl)thieno[3,2-b]pyridin-5-yl)piperidin-4-yl (2-fluoroethyl)carbamate;

1-(3-(Methylcarbamoyl)-7-(trifluoromethyl)thieno[3,2-b]pyridin-5-yl)piperidin-4-yl (2,2-difluoroethyl)carbamate;

1-(3-(Methylcarbamoyl)-7-(trifluoromethyl)thieno[3,2-b]pyridin-5-yl)piperidin-4-yl (methyl-d3)carbamate;

1-(3-(Methylcarbamoyl)-7-(trifluoromethyl)thieno[3,2-b]pyridin-5-yl)piperidin-4-yl (3-methoxycyclobutyl)carbamate;

(+/−)-1-(3-(Methylcarbamoyl)-7-(trifluoromethyl)thieno[3,2-b]pyridin-5-yl)piperidin-4-yl ((1r,3r)-3-cyanocyclobutyl)carbamate;

(+/−)-1-(3-(Methylcarbamoyl)-7-(trifluoromethyl)thieno[3,2-b]pyridin-5-yl)piperidin-4-yl ((1s,3s)-3-cyanocyclobutyl)carbamate;

1-(3-(Methylcarbamoyl)-7-(trifluoromethyl)thieno[3,2-b]pyridin-5-yl)piperidin-4-yl (3-ethoxycyclobutyl)carbamate;

(+/−)-1-(3-(Methylcarbamoyl)-7-(trifluoromethyl)thieno[3,2-b]pyridin-5-yl)piperidin-4-yl ((1r,3r)-3-(methylsulfonyl)cyclobutyl)carbamate;

(+/−)-1-(3-(Methylcarbamoyl)-7-(trifluoromethyl)thieno[3,2-b]pyridin-5-yl)piperidin-4-yl ((1s,3s)-3-(methylsulfonyl)cyclobutyl)carbamate;

1-(3-(Methylcarbamoyl)-7-(trifluoromethyl)thieno[3,2-b]pyridin-5-yl)piperidin-4-yl (2-oxaspiro[3.3]heptan-6-yl)carbamate;

1-(3-(Methylcarbamoyl)-7-(trifluoromethyl)thieno[3,2-b]pyridin-5-yl)piperidin-4-yl ((2-methyltetrahydrofuran-2-yl)methyl)carbamate;

Cyclopropyl (1-(3-(methylcarbamoyl)-7-(trifluoromethyl)thieno[3,2-b]pyridin-5-yl)piperidin-4-yl)carbamate;

1-(3-(Methylcarbamoyl)-7-(trifluoromethyl)thieno[3,2-b]pyridin-5-yl)piperidin-4-yl (2S,3S)-3-(dimethylamino)-2-methylazetidine-1-carboxylate;

1-(3-(Methylcarbamoyl)-7-(trifluoromethyl)thieno[3,2-b]pyridin-5-yl)piperidin-4-yl (2S,3R)-3-(dimethylamino)-2-methylazetidine-1-carboxylate;

1-(3-(Methylcarbamoyl)-7-(trifluoromethyl)thieno[3,2-b]pyridin-5-yl)piperidin-4-yl (S)-(1-(oxetan-3-yl)ethyl)carbamate;

1-(3-(Methylcarbamoyl)-7-(trifluoromethyl)thieno[3,2-b]pyridin-5-yl)piperidin-4-yl (R)-(1-(oxetan-3-yl)ethyl)carbamate;

1-(3-(Methylcarbamoyl)-7-(trifluoromethyl)thieno[3,2-b]pyridin-5-yl)piperidin-4-yl (2S,3S)-3-methoxy-2-methylazetidine-1-carboxylate;

1-(3-(Methylcarbamoyl)-7-(trifluoromethyl)thieno[3,2-b]pyridin-5-yl)piperidin-4-yl [1,3'-biazetidine]-1'-carboxylate;

1-(3-(Methylcarbamoyl)-7-(trifluoromethyl)thieno[3,2-b]pyridin-5-yl)piperidin-4-yl (2'S, 3'S)-2'-methyl-[1,3'-biazetidine]-1'-carboxylate;

1-(3-(Methylcarbamoyl)-7-(trifluoromethyl)thieno[3,2-b]pyridin-5-yl)piperidin-4-yl (2S,3R)-3-hydroxy-2-methylpyrrolidine-1-carboxylate;

1-(3-(Methylcarbamoyl)-7-(trifluoromethyl)thieno[3,2-b]pyridin-5-yl)piperidin-4-yl (2S,3S)-3-hydroxy-2,3-dimethylpyrrolidine-1-carboxylate;

1-(3-(Methylcarbamoyl)-7-(trifluoromethyl)thieno[3,2-b]pyridin-5-yl)piperidin-4-yl (2S,3S)-3-cyano-2-methylazetidine-1-carboxylate;

1-(3-(Methylcarbamoyl)-7-(trifluoromethyl)thieno[3,2-b]pyridin-5-yl)piperidin-4-yl 6-(cyanomethyl)-2,6-diazaspiro[3.3]heptane-2-carboxylate;

1-(3-(Methylcarbamoyl)-7-(trifluoromethyl)thieno[3,2-b]pyridin-5-yl)piperidin-4-yl (2S,3R)-3-(cyanomethyl)-2-methylazetidine-1-carboxylate;

1-(3-(Methylcarbamoyl)-7-(trifluoromethyl)thieno[3,2-b]pyridin-5-yl)piperidin-4-yl (2S,3S)-3-(cyanomethyl)-2-methylazetidine-1-carboxylate;

1-(3-(Methylcarbamoyl)-7-(trifluoromethyl)thieno[3,2-b]pyridin-5-yl)piperidin-4-yl 1-methyl-1,6-diazaspiro[3.3]heptane-6-carboxylate;

1-(3-(Methylcarbamoyl)-7-(trifluoromethyl)thieno[3,2-b]pyridin-5-yl)piperidin-4-yl (S)-pent-3-yn-2-ylcarbamate;

1-(3-(Methylcarbamoyl)-7-(trifluoromethyl)thieno[3,2-b]pyridin-5-yl)piperidin-4-yl (R)-pent-3-yn-2-ylcarbamate;

(2S,3S)-1,2-Dimethylpyrrolidin-3-yl (1-(3-(methylcarbamoyl)-7-(trifluoromethyl)thieno[3,2-b]pyridin-5-yl)piperidin-4-yl)carbamate;

(S)-1-(2,2-Difluoroethyl)pyrrolidin-3-yl (1-(3-(methylcarbamoyl)-7-(trifluoromethyl)thieno[3,2-b]pyridin-5-yl)piperidin-4-yl)carbamate;

1-(3-(Methylcarbamoyl)-7-(trifluoromethyl)thieno[3,2-b]pyridin-5-yl)piperidin-4-yl 6-methyl-1,6-diazaspiro[3.3]heptane-1-carboxylate;

1-(3-(Methylcarbamoyl)-7-(trifluoromethyl)thieno[3,2-b]pyridin-5-yl)piperidin-4-yl (2S,3R)-2-methyl-3-(1H-1,2,4-triazol-1-yl)azetidine-1-carboxylate;

1-(3-(methylcarbamoyl)-7-(trifluoromethyl)thieno[3,2-b]pyridin-5-yl)piperidin-4-yl (S)-(5-hydroxy-5-methylhex-3-yn-2-yl)carbamate;

1-(3-(Methylcarbamoyl)-7-(trifluoromethyl)thieno[3,2-b]pyridin-5-yl)piperidin-4-yl (R)-(5-hydroxy-5-methylhex-3-yn-2-yl)carbamate;

1-Methylazetidin-3-yl (1-(3-(methylcarbamoyl)-7-(trifluoromethyl)thieno[3,2-b]pyridin-5-yl)piperidin-4-yl)carbamate;

Isopropyl (1-(3-(methylcarbamoyl)-7-(trifluoromethyl)thieno[3,2-b]pyridin-5-yl)piperidin-4-yl)carbamate;

2,2-Difluoroethyl (1-(3-(methylcarbamoyl)-7-(trifluoromethyl)thieno[3,2-b]pyridin-5-yl)piperidin-4-yl)carbamate;

1-(1,3-Difluoropropan-2-yl)azetidin-3-yl (1-(3-(methylcarbamoyl)-7-(trifluoromethyl)thieno[3,2-b]pyridin-5-yl)piperidin-4-yl)carbamate;

Methyl-d₃ (1-(3-(methylcarbamoyl)-7-(trifluoromethyl)thieno[3,2-b]pyridin-5-yl)piperidin-4-yl)carbamate;

2-Fluoroethyl (1-(3-(methylcarbamoyl)-7-(trifluoromethyl)thieno[3,2-b]pyridin-5-yl)piperidin-4-yl)carbamate;

1-Fluoropropan-2-yl (1-(3-(methylcarbamoyl)-7-(trifluoromethyl)thieno[3,2-b]pyridin-5-yl)piperidin-4-yl)carbamate;

(+/−)-cis-(1s,3s)-3-((3-(Methylcarbamoyl)-7-(trifluoromethyl)thieno[3,2-b]pyridin-5-yl)oxy)cyclobutyl oxetan-3-ylcarbamate;

(1s,3s)-3-((3-(Methylcarbamoyl)-7-(trifluoromethyl)thieno[3,2-b]pyridin-5-yl)oxy)cyclobutyl 3-methoxyazetidine-1-carboxylate;

1-(3-(Methylcarbamoyl)-7-(trifluoromethyl)thieno[3,2-b]pyridin-5-yl)piperidin-4-yl 1-oxa-6-azaspiro[3.3]heptane-6-carboxylate;

1-(3-(Methylcarbamoyl)-7-(trifluoromethyl)thieno[3,2-b]pyridin-5-yl)piperidin-4-yl ((S)-1-((S)-oxetan-2-yl)ethyl)carbamate;

1-(3-(Methylcarbamoyl)-7-(trifluoromethyl)thieno[3,2-b]pyridin-5-yl)piperidin-4-yl ((R)-1-((S)-oxetan-2-yl)ethyl)carbamate;

1-(3-(Methylcarbamoyl)-7-(trifluoromethyl)thieno[3,2-b]pyridin-5-yl)piperidin-4-yl (2S,3R)-3-cyano-2-methylpyrrolidine-1-carboxylate;

(S)-1-((S)-Oxetan-2-yl)ethyl (1-(3-(methylcarbamoyl)-7-(trifluoromethyl)thieno[3,2-b]pyridin-5-yl)piperidin-4-yl)carbamate;

(S)-1-((R)-Oxetan-2-yl)ethyl (1-(3-(methylcarbamoyl)-7-(trifluoromethyl)thieno[3,2-b]pyridin-5-yl)piperidin-4-yl)carbamate;

(+/−)-cis-(1s,3s)-3-((3-(Methylcarbamoyl)-7-(trifluoromethyl)thieno[3,2-b]pyridin-5-yl)oxy)cyclobutyl isopropylcarbamate;

(+/−)-cis-(1s,3s)-3-((3-(Methylcarbamoyl)-7-(trifluoromethyl)thieno[3,2-b]pyridin-5-yl)oxy)cyclobutyl 3-(trifluoromethoxy)azetidine-1-carboxylate;

(+/−)-cis-(1s,3s)-3-((3-(Methylcarbamoyl)-7-(trifluoromethyl)thieno[3,2-b]pyridin-5-yl)oxy)cyclobutyl 3-hydroxy-3-methylazetidine-1-carboxylate;

(+/−)-cis-(1s,3R)-3-((3-(Methylcarbamoyl)-7-(trifluoromethyl)thieno[3,2-b]pyridin-5-yl)oxy)cyclobutyl ((S)-1-(trifluoromethoxy)propan-2-yl)carbamate;

(+/−)-cis-(1s,3s)-3-((3-(Methylcarbamoyl)-7-(trifluoromethyl)thieno[3,2-b]pyridin-5-yl)oxy)cyclobutyl 3-(dimethylamino)azetidine-1-carboxylate;

4-Fluoro-1-methylpyrrolidin-3-yl 4-((3-(methylcarbamoyl)-7-(trifluoromethyl)thieno[3,2-b]pyridin-5-yl)oxy)piperidine-1-carboxylate;

1-(3-(Methylcarbamoyl)-7-(trifluoromethyl)thieno[3,2-b]pyridin-5-yl)piperidin-4-yl 3-(1H-imidazol-1-yl)azetidine-1-carboxylate;

1-(3-(Methylcarbamoyl)-7-(trifluoromethyl)thieno[3,2-b]pyridin-5-yl)piperidin-4-yl 3-(1H-1,2,3-triazol-1-yl)azetidine-1-carboxylate;

1-(3-(Methylcarbamoyl)-7-(trifluoromethyl)thieno[3,2-b]pyridin-5-yl)piperidin-4-yl 3-(1H-1,2,4-triazol-1-yl)azetidine-1-carboxylate;

(+/−)-trans-3-Fluoro-1-(3-(methylcarbamoyl)-7-(trifluoromethyl)thieno[3,2-b]pyridin-5-yl)piperidin-4-yl 3-(1H-1,2,4-triazol-1-yl)azetidine-1-carboxylate;

(+/−)-cis-3-Fluoro-1-(3-(methylcarbamoyl)-7-(trifluoromethyl)thieno[3,2-b]pyridin-5-yl)piperidin-4-yl 3-(1H-1,2,4-triazol-1-yl)azetidine-1-carboxylate;

1-(3-(Methylcarbamoyl)-7-(trifluoromethyl)thieno[3,2-b]pyridin-5-yl)piperidin-4-yl 1-cyclopropyl-1,6-diazaspiro[3.3]heptane-6-carboxylate;

1-(3-(Methylcarbamoyl)-7-(trifluoromethyl)thieno[3,2-b]pyridin-5-yl)piperidin-4-yl 1-ethyl-1,6-diazaspiro[3.3]heptane-6-carboxylate;

1-(3-(Methylcarbamoyl)-7-(trifluoromethyl)thieno[3,2-b]pyridin-5-yl)piperidin-4-yl 1-(2,2,2-trifluoroethyl)-1,6-diazaspiro[3.3]heptane-6-carboxylate;

(+/−)-trans-2-(Trifluoromethoxy)ethyl 3-methyl-4-((3-(methylcarbamoyl)-7-(trifluoromethyl)thieno[3,2-b]pyridin-5-yl)oxy)piperidine-1-carboxylate;

(+/−)-cis-2-(Trifluoromethoxy)ethyl 3-methyl-4-((3-(methylcarbamoyl)-7-(trifluoromethyl)thieno[3,2-b]pyridin-5-yl)oxy)piperidine-1-carboxylate;

2-(Trifluoromethoxy)ethyl (R)-3-((3-(methylcarbamoyl)-7-(trifluoromethyl)thieno[3,2-b]pyridin-5-yl)oxy)piperidine-1-carboxylate;

2-(Trifluoromethoxy)ethyl (S)-3-((3-(methylcarbamoyl)-7-(trifluoromethyl)thieno[3,2-b]pyridin-5-yl)oxy)piperidine-1-carboxylate;

tert-Butyl 2,2-dimethyl-4-((3-(methylcarbamoyl)-7-(trifluoromethyl)thieno[3,2-b]pyridin-5-yl)oxy)piperidine-1-carboxylate;

(S)-1-(Trifluoromethoxy)propan-2-yl 4-((3-(methylcarbamoyl)-7-(trifluoromethyl)thieno[3,2-b]pyridin-5-yl)oxy)piperidine-1-carboxylate;

(R)-1-(Trifluoromethoxy)propan-2-yl 4-((3-(methylcarbamoyl)-7-(trifluoromethyl)thieno[3,2-b]pyridin-5-yl)oxy)piperidine-1-carboxylate;

(S)-2-(Trifluoromethoxy)propyl 4-((3-(methylcarbamoyl)-7-(trifluoromethyl)thieno[3,2-b]pyridin-5-yl)oxy)piperidine-1-carboxylate;

(R)-2-(Trifluoromethoxy)propyl 4-((3-(methylcarbamoyl)-7-(trifluoromethyl)thieno[3,2-b]pyridin-5-yl)oxy)piperidine-1-carboxylate;

(S)-1-(Trifluoromethoxy)propan-2-yl 6-((3-(methylcarbamoyl)-7-(trifluoromethyl)thieno[3,2-b]pyridin-5-yl)oxy)-2-azaspiro[3.3]heptane-2-carboxylate;

(S)-1-(Trifluoromethoxy)propan-2-yl (S)-3-((3-(methylcarbamoyl)-7-(trifluoromethyl)thieno[3,2-b]pyridin-5-yl)oxy)pyrrolidine-1-carboxylate;

(3S,4S)-3-Methyl-1-(3-(methylcarbamoyl)-7-(trifluoromethyl)thieno[3,2-b]pyridin-5-yl)piperidin-4-yl isopropylcarbamate;

(3R,4R)-3-Methyl-1-(3-(methylcarbamoyl)-7-(trifluoromethyl)thieno[3,2-b]pyridin-5-yl)piperidin-4-yl 3-(trifluoromethoxy)azetidine-1-carboxylate;

(S)-2-(Trifluoromethoxy)propyl (S)-3-((3-(methylcarbamoyl)-7-(trifluoromethyl)thieno[3,2-b]pyridin-5-yl)oxy)pyrrolidine-1-carboxylate;

(R)-2-(Trifluoromethoxy)propyl (S)-3-((3-(methylcarbamoyl)-7-(trifluoromethyl)thieno[3,2-b]pyridin-5-yl)oxy)pyrrolidine-1-carboxylate;

(S)-2-(Trifluoromethoxy)propyl 6-((3-(methylcarbamoyl)-7-(trifluoromethyl)thieno[3,2-b]pyridin-5-yl)oxy)-2-azaspiro[3.3]heptane-2-carboxylate;

(R)-2-(Trifluoromethoxy)propyl 6-((3-(methylcarbamoyl)-7-(trifluoromethyl)thieno[3,2-b]pyridin-5-yl)oxy)-2-azaspiro[3.3]heptane-2-carboxylate;

2-(Trifluoromethoxy)ethyl 2,2-dimethyl-4-((3-(methylcarbamoyl)-7-(trifluoromethyl)thieno[3,2-b]pyridin-5-yl)oxy)piperidine-1-carboxylate;

(3R,4S)-3-methyl-1-(3-(Methylcarbamoyl)-7-(trifluoromethyl)thieno[3,2-b]pyridin-5-yl)piperidin-4-yl isopropylcarbamate;

(3R,4S)-3-Methyl-1-(3-(methylcarbamoyl)-7-(trifluoromethyl)thieno[3,2-b]pyridin-5-yl)piperidin-4-yl 3-(trifluoromethoxy)azetidine-1-carboxylate;

(S)-1-Cyanopropan-2-yl 4-((3-(methylcarbamoyl)-7-(trifluoromethyl)thieno[3,2-b]pyridin-5-yl)oxy)piperidine-1-carboxylate;

(S)-1-Cyanopropan-2-yl (2R,4R)-2-methyl-4-((3-(methylcarbamoyl)-7-(trifluoromethyl)thieno[3,2-b]pyridin-5-yl)oxy)piperidine-1-carboxylate;

(S)-1-Cyclopropylethyl (2R,4R)-2-methyl-4-((6-methyl-3-(methylcarbamoyl)-7-(trifluoromethyl)thieno[3,2-b]pyridin-5-yl)oxy)piperidine-1-carboxylate;

2-Hydroxy-2-methylpropyl (2R,4R)-2-methyl-4-((3-(methylcarbamoyl)-7-(trifluoromethyl)thieno[3,2-b]pyridin-5-yl)oxy)piperidine-1-carboxylate;

1-(2,2,2-Trifluoroethyl)pyrrolidin-3-yl 4-((3-(methylcarbamoyl)-7-(trifluoromethyl)thieno[3,2-b]pyridin-5-yl)oxy)piperidine-1-carboxylate;

2-(Fluoromethoxy)ethyl 4-((3-(methylcarbamoyl)-7-(trifluoromethyl)thieno[3,2-b]pyridin-5-yl)oxy)piperidine-1-carboxylate; or (S)-1-(3-Fluoroazetidin-1-yl)propan-2-yl (2R,4R)-2-methyl-4-((3-(methylcarbamoyl)-7-(trifluoromethyl)thieno[3,2-b]pyridin-5-yl)oxy)piperidine-1-carboxylate.

In another aspect, the present application is directed to a pharmaceutical composition comprising a compound described herein and a pharmaceutically acceptable carrier or adjuvant.

In some embodiments, the pharmaceutical composition described herein further comprises one or more additional therapeutic agents.

In another aspect, the present application is directed to a method of treating or lessening the severity of metachromatic leukodystrophy in a patient, comprising administering to the patient an effective amount of a compound described herein or a pharmaceutical composition comprising a compound described herein.

In another aspect, the present application is directed to a method of lowering or reducing sulfatides in a patient, comprising administering to the patient an effective amount of a compound described herein or a pharmaceutical composition comprising a compound described herein.

In another aspect, the present application is directed to a method of treating or lessening the severity of Krabbe's disease in a patient, comprising administering to the patient an effective amount of a compound described herein or a pharmaceutical composition comprising a compound described herein.

Definitions

The following definitions apply unless otherwise indicated.

As used herein, each occurrence of any constituent variable anywhere in the present disclosure is intended to be independently selected from among its indicated options.

As used herein, the term "pharmaceutically acceptable salt" refers to either a pharmaceutically acceptable acid addition salt or a pharmaceutically acceptable base addition salt of a currently disclosed compound that may be administered without any resultant substantial undesirable biological effect(s) or any resultant deleterious interaction(s) with any other component of a pharmaceutical composition in which it may be contained.

As used herein, the term "prodrug" means a pharmacological derivative of a parent drug molecule that requires biotransformation, either spontaneous or enzymatic, within the organism to release the active drug. For example, prodrugs are variations or derivatives of the compounds of Formula I, or any of 1.1-1.300, that have groups cleavable under certain metabolic conditions, which when cleaved, become the compounds of Formula I, or any of 1.1-1.300. Such prodrugs then are pharmaceutically active in vivo, when they undergo solvolysis under physiological conditions or undergo enzymatic degradation. Prodrug compounds herein may be called single, double, triple, etc., depending on the number of biotransformation steps required to release the active drug within the organism, and the number of functionalities present in a precursor-type form. Prodrug forms often offer advantages of solubility, tissue compatibility, or delayed release in the mammalian organism (See, Bundgard, Design of Prodrugs, pp. 7-9, 21-24, Elsevier, Amsterdam 1985 and Silverman, The Organic Chemistry of Drug Design and Drug Action, pp. 352-401, Academic Press, San Diego, Calif., 1992). Prodrugs commonly known in the art include well-known acid derivatives, such as, for example, esters prepared by reaction of the parent acids with a suitable alcohol, amides prepared by reaction of the parent acid compound with an amine, basic groups reacted to form an acylated base derivative, etc. Of course, other prodrug derivatives may be combined with other features disclosed herein to enhance bioavailability. As such, those of skill in the art will appreciate that certain of the presently disclosed compounds having free amino, amido, hydroxy or carboxylic groups can be converted into prodrugs. Prodrugs include compounds having an amino acid residue, or a polypeptide chain of two or more (e.g., two, three or four) amino acid residues which are covalently joined through peptide bonds to free amino, hydroxy or carboxylic acid groups of the presently disclosed compounds. The amino acid residues include the 20 naturally occurring amino acids commonly designated by three letter symbols and also include 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds having a carbonate, carbamate, amide or alkyl ester moiety covalently bonded to any of the above substituents disclosed herein.

As used herein, a pharmaceutically acceptable carrier or excipient (adjuvant) refers to compositions included with the compound of Formula I, or any of 1.1-1.300, for delivery, stability or solubility of the compound in formulations, including but not limited to any and all solvents, diluents, or other liquid vehicle, dispersion or suspension aids, surface active agents, isotonic agents, thickening or emulsifying agents, preservatives, solid binders, lubricants and the like, as suited to the particular dosage form desired.

As used herein, "effective amount" of an enzyme or small molecule, when delivered to a patient in a combination therapy, is an amount sufficient to improve the clinical course of a lysosomal storage disease, where clinical improvement is measured by any of the variety of defined parameters well known to the skilled artisan.

As used herein, the terms, "patient", "subject" and "human" are used interchangeably.

As used herein, "UGT8" means UDP glycosyltransferase 8—the enzyme that with the co-factor Saposin 1 catalyzes the transfer of galactose from UDP-galactose to ceramide to make galactosyl ceramide (GalCer), also known as galactosyl cerebroside. Other names for UGT8 include UDP-galactose-ceramide galactosyltransferase, 2-hydroxyacyl-sphingosine 1-betagalactosyl transferase, ceramide UDP galactosyltransferase, ceramide galactosyl transferase and cerebroside synthase. GalCer, in turn, is the substrate for galactose-3-O-sulfotransferase 1 (GAL3ST1), which transfers sulfate to GalCer, yielding sulfatide (SFT), which is a major component of the myelin sheath. Other names for this enzyme include galactosylceramide sulfotransferase. Patients with mutations in arylsulfatase A (ARSA) are unable to degrade SFT back to GalCer and sulfate, resulting in Metachromatic Leukodystrophy (MLD) disease. MLD patients therefore accumulate SFT, which results in demyelination. Similarly, patients with mutations in galactosylcerebrosidase (GalC) are unable to break down GalCer to galactose and ceramide, resulting in Krabbe disease. Krabbe patients accumulate psychosine and to a lesser extent, GalCer, which also result in demyelination. For these two diseases, substrate reduction therapy (SRT) consists of inhibiting biosynthesis of GalCer by UGT8, thereby preventing accumulation of the toxic products SFT and psychosine, respectively, that are responsible for disease manifestations.

As used herein, the term "combination therapy" means treating a patient with two or more therapeutic platforms (e.g., enzyme replacement therapy and small molecule therapy) in rotating, alternating and/or simultaneous treatment schedules. Examples of treatment schedules may include, but are not limited to: (1) enzyme replacement therapy, then small molecule therapy; (2) small molecule therapy, then enzyme replacement therapy; (3) enzyme replacement therapy concurrent with small molecule therapy, and (4) and any combination of the foregoing. Combination therapy may provide a temporal overlap of therapeutic platforms, as needed, depending on the clinical course of a given storage disease in a given subject.

As used herein, the term "enzyme replacement therapy", or "ERT" means administering an exogenously-produced natural or recombinant enzyme to a patient who is in need thereof. In the case of a lysosomal storage disease, for example, the patient accumulates harmful levels of a substrate (i.e., material stored) in lysosomes due to a deficiency or defect in an enzyme responsible for metabolizing the substrate, or due to a deficiency in an enzymatic activator required for proper enzymatic function. Enzyme replacement therapy is provided to the patient to reduce the levels of (i.e., debulk) accumulated substrate in affected tissues. Enzyme replacement therapies for treating lysosomal storage diseases are known in the art.

The components of a disclosed combination may be administered to a patient simultaneously or sequentially. It will be appreciated that the components may be present in the same pharmaceutically acceptable carrier and, therefore, are administered simultaneously. Alternatively, the active ingredients may be present in separate pharmaceutical carriers, such as, conventional oral dosage forms, that can be administered either simultaneously or sequentially.

As used herein, "MLD" (Metachromatic Leukodystrophy) refers to a disease in patients with mutations in the enzyme aryl sulfatase A (ARSA) which results in the inability to degrade SFT back to GalCer and sulfate. As a result, SFT accumulates in the central and peripheral nervous tissues, which induces neuropathology leading to demyelination and death.

As used herein, "Krabbe disease" refers to a disease in patients with mutations in galactosylcerebrosidase (GalC) which results in the inability to degrade GalCer back to galactose and ceramide. The accumulation of UGT8 and psychosine (another substrate for GalC) in the central and peripheral nervous systems also induces neuropathy leading to demyelination and death.

As used herein, the term "alkyl" refers to monovalent saturated aliphatic free radical groups of up to 20 carbon atoms and a corresponding number of hydrogen atoms. The hydrocarbon chain may be straight chained or branched. The term "$C_{1-6}$ alkyl" means a saturated linear or branched free radical consisting essentially of 1 to 6 carbon atoms and a corresponding number of hydrogen atoms. Exemplary "$C_{1-6}$ alkyl" groups include methyl, ethyl, n-propyl, isopropyl, n-butyl, isobutyl, tert-butyl, etc. Of course, other "$C_{1-6}$ alkyl" groups will be readily apparent to those of skill in the art given the benefit of the present disclosure. The term "alkyl" also includes "cycloalkyl" groups as further described below.

As used herein, the term "cycloalkyl" means a nonaromatic saturated or unsaturated free radical forming at least one ring consisting essentially of 3 to 10 carbon atoms and a corresponding number of hydrogen atoms. The term "cycloalkyl" therefore includes cycloalkenyl groups, as further defined below. As such, cycloalkyl groups can be monocyclic or polycyclic. Individual rings of such polycyclic cycloalkyl groups can have different connectivities, e.g., fused, bridged, spiro, etc., in addition to covalent bond substitution. Exemplary cycloalkyl groups include cyclopropyl, cyclobutyl, cyclopentyl, cyclohexyl, norbornanyl, bicyclo[3.2.1]octanyl, octahydro-pentalenyl, spiro[4.5]decanyl, cyclopropyl, adamantyl, substituted with cyclobutyl, cyclobutyl substituted with cyclopentyl, cyclohexyl substituted with cyclopropyl, etc. Of course, other cycloalkyl groups will be readily apparent to those of skill in the art given the benefit of the present disclosure. As used herein, the term "heterocycloalkyl" means a nonaromatic free radical having 3 to 10 atoms (i.e., ring atoms) that form at least one ring, wherein 2 to 9 of the ring atoms are carbon and the remaining ring atom(s) (i.e., hetero ring atom(s)) is selected from the group consisting of nitrogen, sulfur, and oxygen. As such, heterocycloalkyl groups can be monocyclic or polycyclic. Individual rings of such polycyclic heterocycloalkyl groups can have different connectivities, e.g., fused, bridged, spiro, etc., in addition to covalent bond substitution. Exemplary heterocycloalkyl groups include pyrrolidinyl, tetrahydrofuranyl, dihydrofuranyl, tetrahydropyranyl, pyranyl, thiopyranyl, azindinyl, azetidinyl, oxiranyl, methylenedioxyl, chromenyl, barbituryl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, piperizin-2-onyl, piperizin-3-onyl, chromanyl, 2-pyrrolinyl, 3-pyrrolinyl, imidazolidinyl, 2-imidazolidinyl, 1,4-dioxanyl, 8-azabicyclo[3.2.1]octanyl, 3-azabicyclo[3.2.1]octanyl, 3,8-diazabicyclo[3.2.1]octanyl, 2,5-diazabicyclo[2.2.1]heptanyl, 2,5-diazabicyclo[2.2.2]octanyl, octahydro-2H-pyrido[1,2-a]pyrazinyl, 3-azabicyclo[4.1.0]heptanyl, 3-azabicyclo[3.1.0]hexanyl, 2-azaspiro[4.4]nonanyl, 7-oxa-1-aza-spiro[4.4]nonanyl, 7-azabicyclo[2.2.2]heptanyl, octahydro-1H-indolyl, etc. In general, the heterocycloalkyl group typically is attached to the main structure via a carbon atom or a nitrogen atom. Of course, other heterocycloalkyl groups will be readily apparent to those of skill in the art given the benefit of the present disclosure.

As used herein, the term "heteroaryl" means an aromatic free radical having 5 to 10 atoms (i.e., ring atoms) that form at least one ring, wherein 2 to 9 of the ring atoms are carbon and the remaining ring atom(s) (i.e., hetero ring atom(s)) is selected from the group consisting of nitrogen, sulfur, and oxygen. As such, heteroaryl groups can be monocyclic or polycyclic. Individual rings of such polycyclic heteroaryl groups can have different connectivities, e.g., fused, etc., in addition to covalent bond substitution. Exemplary heteroaryl groups include furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidinyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyridinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianapthenyl, isothianapthenyl, benzofuranyl, isobenzofuranyl, isoindolyl, indolyl, indolizinyl, indazolyl, isoquinolyl, quinolyl, phthalazinyl, quinoxalinyl, quinazolinyl and benzoxazinyl, etc. In general, the heteroaryl group typically is attached to the main structure via a carbon atom, However, those of skill in the art will realize when certain other atoms, e.g., hetero ring atoms, can be attached to the main structure. Of course, other heteroaryl groups will be readily apparent to those of skill in the art given the benefit of the present disclosure.

As used herein, the term "aryl" means phenyl or naphthyl.

As used herein, "alkenyl" means a linear or branched free radical having a specified number of carbon atoms and having at least one double bond.

As used herein, the term "cycloalkenyl" means an alkenyl free radical having at least one double bond that is contained in a closed ring of carbon atoms, but does not have aromatic character. The at least one cycloalkenyl ring may consist essentially of 3 to 10 carbon atoms and a corresponding number of hydrogen atoms. As such, cycloalkenyl groups can be monocyclic or polycyclic. Individual rings of such polycyclic cycloalkenyl groups can have different connectivities, e.g., fused, bridged, spiro, etc., in addition to covalent bond substitution. Exemplary cycloalkenyl groups include cyclopropenyl, cyclobutenyl, cyclopentenyl, cyclohexenyl, cycloheptenyl, 1,3-cyclohexadienyl, 1,4-cyclohexadienyl and 1,5-cyclooctadienyl, each of which may or may not be further substituted. Of course, other cycloalkenyl groups will be readily apparent to those of skill in the art given the benefit of the present disclosure.

As used herein, "alkynyl" means a linear or branched free radical having a specified number of carbon atoms and having at least one triple bond.

As used herein, the term "halo" or "halogen" means fluorine, chlorine, bromine, or iodine.

As used herein, the term "haloalkyl" refers to monovalent saturated aliphatic free radical groups of up to 20 carbon atoms and a corresponding number of hydrogen atoms, wherein one or more hydrogen atoms is replaced by a halogen atom. The hydrocarbon chain may be straight chained or branched. The "$C_{1-6}$ haloalkyl" means a saturated linear or branched free radical consisting essentially of 1 to 6 carbon atoms and a corresponding number of hydrogen atoms, wherein one or more hydrogen atoms is replaced by a halogen atom. Exemplary "$C_{1-6}$ haloalkyl" groups include trifluoromethyl, difluoromethyl, fluoromethyl, 2-fluoroethyl, 2,2-difluoroethyl, 2,2,2-trifluoroethyl etc. Of course, other haloalkyl groups will be readily apparent to those of skill in the art given the benefit of the present disclosure.

As used herein, the term "amino" means a free radical having a nitrogen atom and 0, 1 or 2 hydrogen atoms. As such, the term amino generally refers to primary and secondary amines. In that regard, as used herein and in the appended claims, a tertiary amine is represented by the general formula RR'N—, wherein R and R' are carbon radicals that may or may not be identical. Nevertheless, the term "amino" generally may be used herein to describe a primary, secondary, or tertiary amine, and those of skill in the art will readily be able to ascertain the identification of which in view of the context in which this term is used in the present disclosure.

Although specific embodiments of the present disclosure will now be described with reference to the preparations and schemes, it should be understood that such embodiments are by way of example only and merely illustrative of but a small number of the many possible specific embodiments which can represent applications of the principles of the present disclosure. Various changes and modifications will be obvious to those of skill in the art given the benefit of the present disclosure and are deemed to be within the spirit and scope of the present disclosure as further defined in the appended claims.

Unless defined otherwise, all technical and scientific terms used herein have the same meaning as commonly understood by one having ordinary skill in the art to which this disclosure belongs. Although other compounds or methods can be used in practice or testing, certain preferred methods are now described in the context of the following preparations and schemes.

A number of synthetic protocols were used to produce the compounds described herein. These synthetic protocols (see schemes below) have common intersections and can be used alternatively for synthesis of the compounds described herein.

Scheme 1

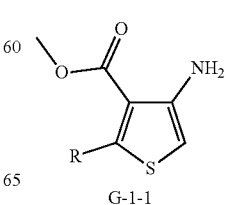

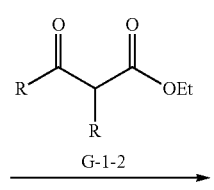

G-1-1

G-1-2

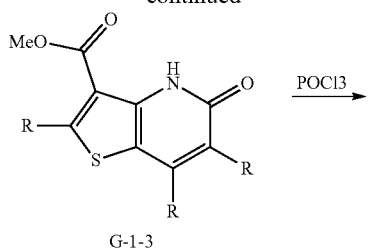

G-1-3

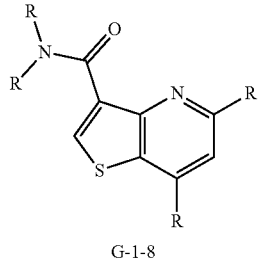

G-1-8

Scheme 1 provides a general scheme to arrive at the compounds described herein. The appropriate acetoacetate (G-1-2) is reacted with (2-substituted)-4-aminothiophene-3-carboxylate (G-1-1) at 130° C. to provide pyridone G-1-3. Chlorination with POCl₃ provided thienopyridine G-1-4. The methyl ester of G-1-4 undergoes amidation with an appropriate amine to provide G-1-5. The ester (G-1-6) is hydrolyzed by metal hydroxide to give acid (G-1-7) which is coupled with an appropriate amine, providing various amides (G-1-8).

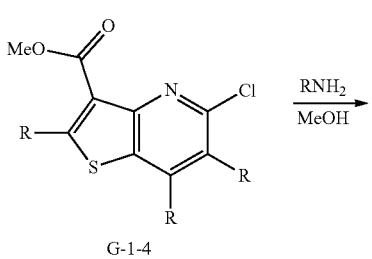

G-1-4

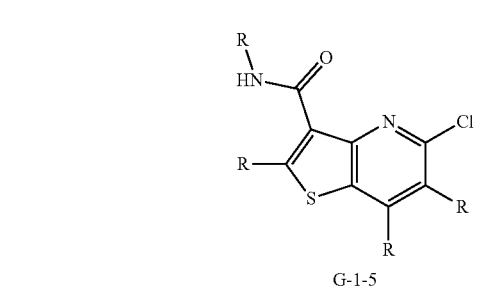

G-1-5

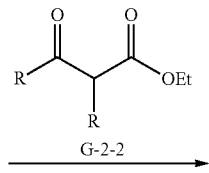

G-2-1

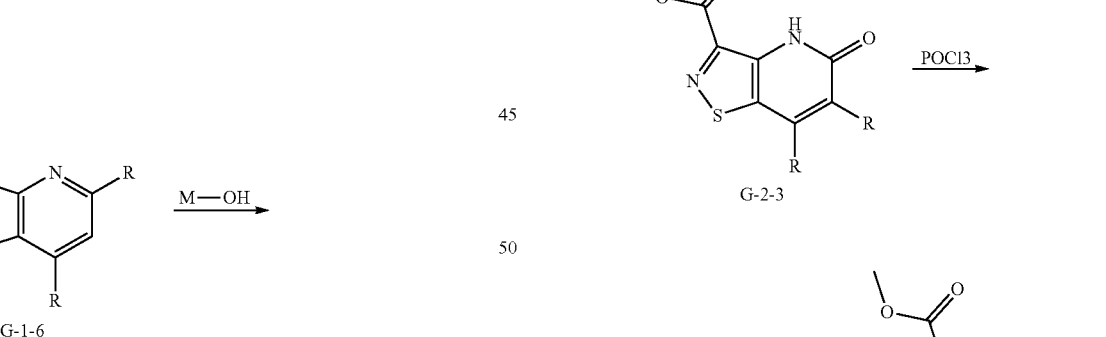

G-2-3

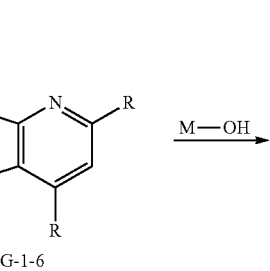

G-1-6

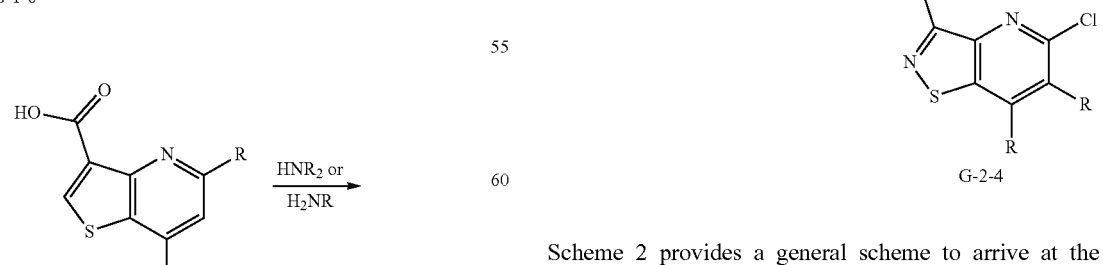

G-2-4

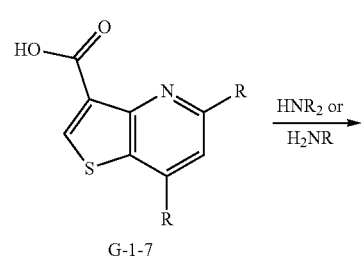

G-1-7

Scheme 2 provides a general scheme to arrive at the compounds described herein. The appropriate acetoacetate (G-2-2) is reacted with methyl 4-aminoisothiazole-3-carboxylate (G-2-1) to provide pyridone G-2-3. Chlorination with POCl₃ provided thienopyridine G-2-4.

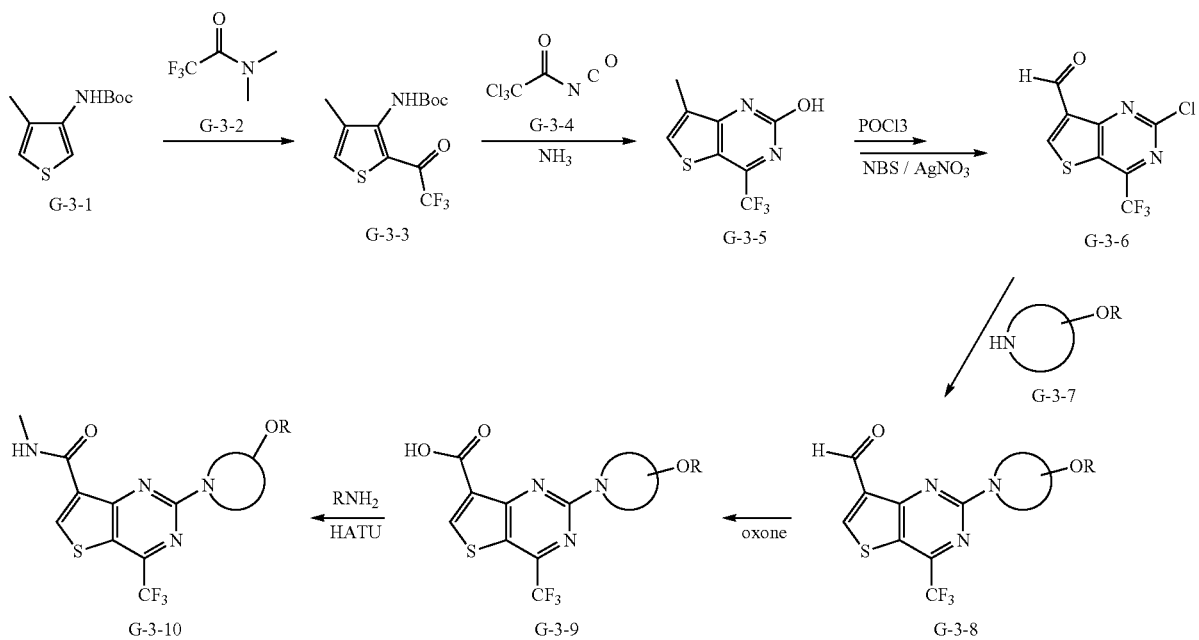

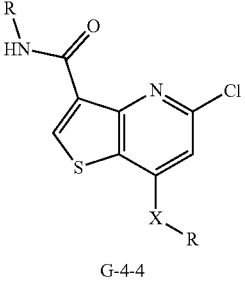

Scheme 3 provides a general scheme to arrive at the compounds described herein. tert-Butyl (4-methylthiophen-3-yl)carbamate (G-3-1) is reacted with 2,2,2-trifluoro-N,N-dimethylacetamide (G-3-2) to provide trifluoroacetyl thiophene G-3-3. Cyclization of de-Boc thiophene with isocyanate (G-3-4) provided thienopyrimidine G-3-5. Chlorination with $POCl_3$ and oxidation of methyl provided aldehyde (G-3-6). Nucleophilic aromatic substitution of the pyrimidinyl chloride (G-3-6) with an appropriate hydroxylated nitrogen containing heterocycle (G-3-7) provided G-3-8. Oxidation with oxone provided acid (G-3-9) which was coupled with an appropriate amine to provide amide (G-3-10).

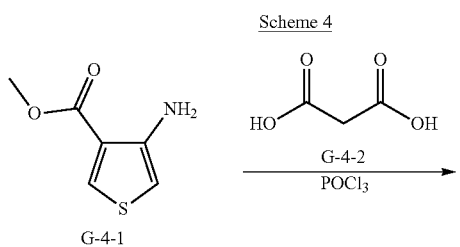

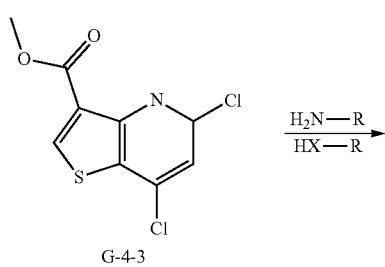

Scheme 4 provides a general scheme to arrive at the compounds described herein. Malonic acid (G-4-2) is reacted with 3-aminothiophene-4-carboxylate (G-4-1) to provide dichlorothienopyridine G-4-3. Amidation with an appropriate amine and substitution with amine/alcohol provided G-4-4. Pyridone (G-4-5) is chlorinated with NCS to provide chloropyridone (G-4-6). Chlorination with $POCl_3$ provided dichloro-thienopyridine G-4-7.

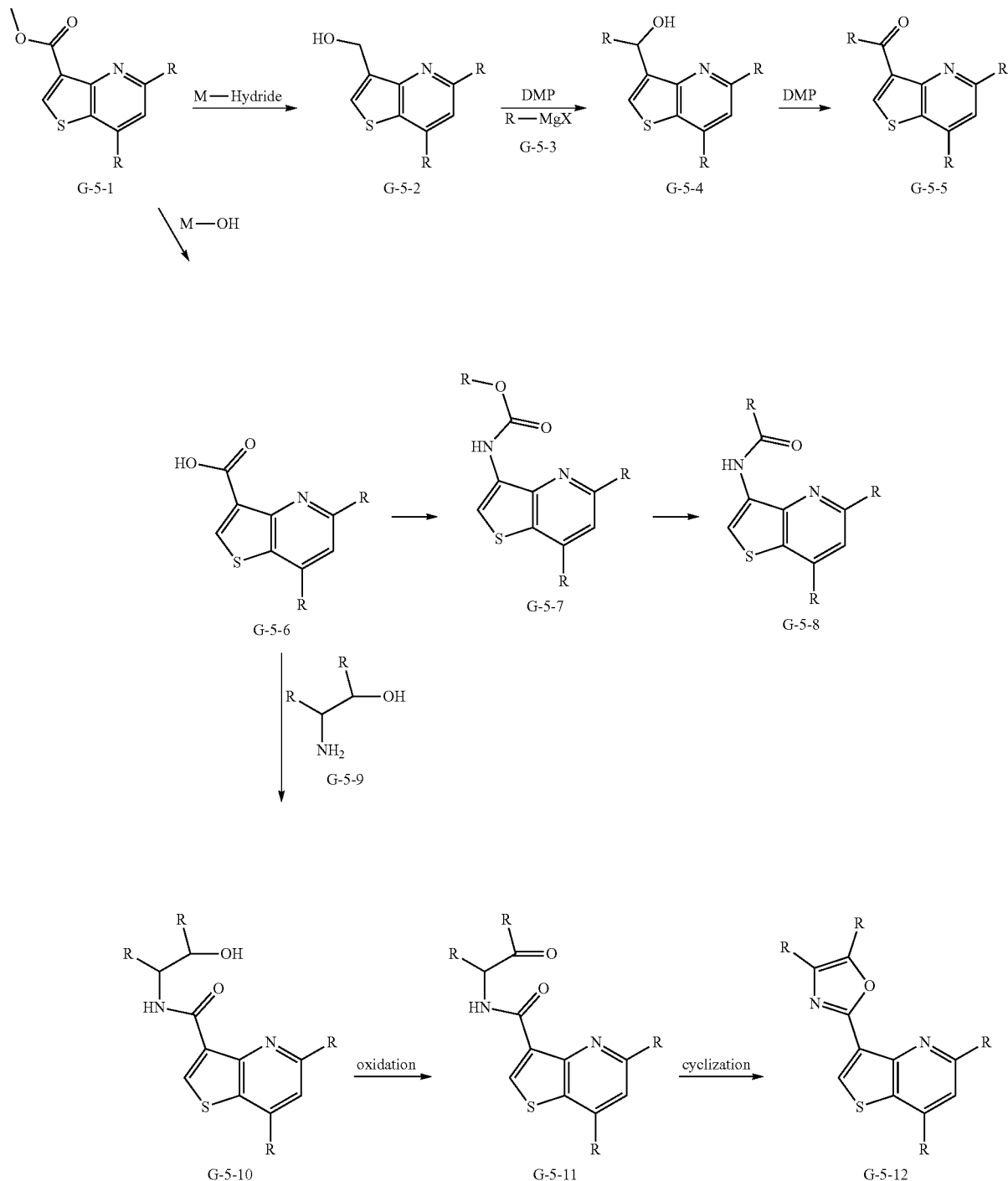

Scheme 5 provides a general scheme to arrive at the compounds described herein. Methyl ester (G-5-1) is reduced with metal hydrides to provide alcohol G-5-2. Oxidation with Dess-Martin Periodinate and reaction of corresponding aldehyde with an appropriate Grignard reagent (G-5-3) provided secondary alcohol G-5-4. The methyl ester of G-5-1 undergoes hydrolysis with an appropriate metal hydroxide to provide G-5-6. Rearrangement of acid (G-5-6) to carbamate (G-5-7) is carried with sodium azide in the presence of a tert-butyl alcohol. Removal of the BOC protecting group and acylation provided G-5-8. G-5-6 is coupled with the appropriate amino alcohol (G-5-9) to amide G-5-10. Oxidation with DMP provided ketone (G-5-11) which is cyclized by a dehydrating reagent to provide oxazole (G-5-12).

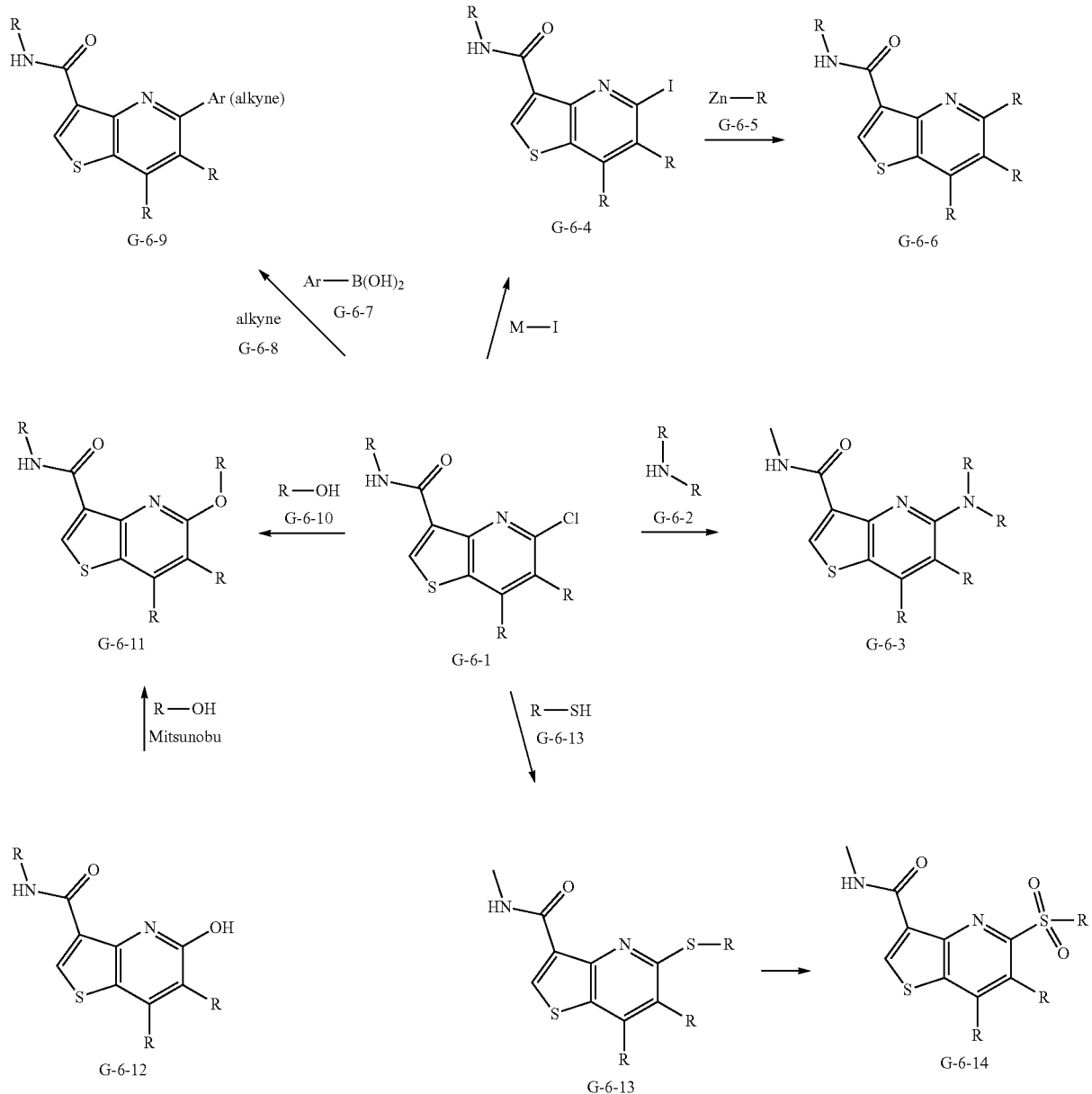

Scheme 6

Scheme 6 provides a general scheme to arrive at the compounds described herein. Nucleophilic aromatic substitution of the pyridinyl chloride (G-6-1) with an appropriate nitrogen containing heterocycle (G-6-2) provided N-substituted G-6-3. Iodination with metal iodide provided iodopyridine G-6-4. The iodine of G-6-4 is coupled with an appropriate zinc reagent (G-6-5) in the presence of palladium catalyst to provide C-substituted G-6-6. Pd-catalyzed Coupling reaction of the pyridinyl chloride (G-6-1) with an appropriate aryl boronic acid (G-6-7) or alkyne (G-6-8) provided aryl (alkyne)-substituted G-6-9. O-substituted G-6-11 is prepared by alkylation of the pyridinyl chloride (G-6-1) or Mitsunobu reaction of pyridone G-6-12. Nucleophilic aromatic substitution of the pyridinyl chloride (G-6-1) with an appropriate thiol (G-6-13) provided S-substituted G-6-13 which is oxidized to provide sulfoxide and sulfone (G-6-14).

Scheme 7

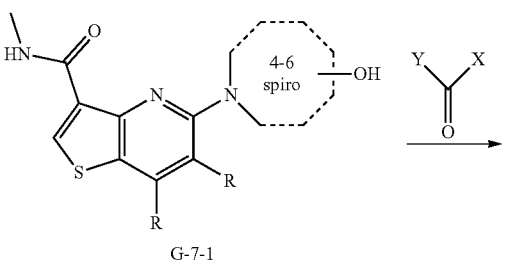

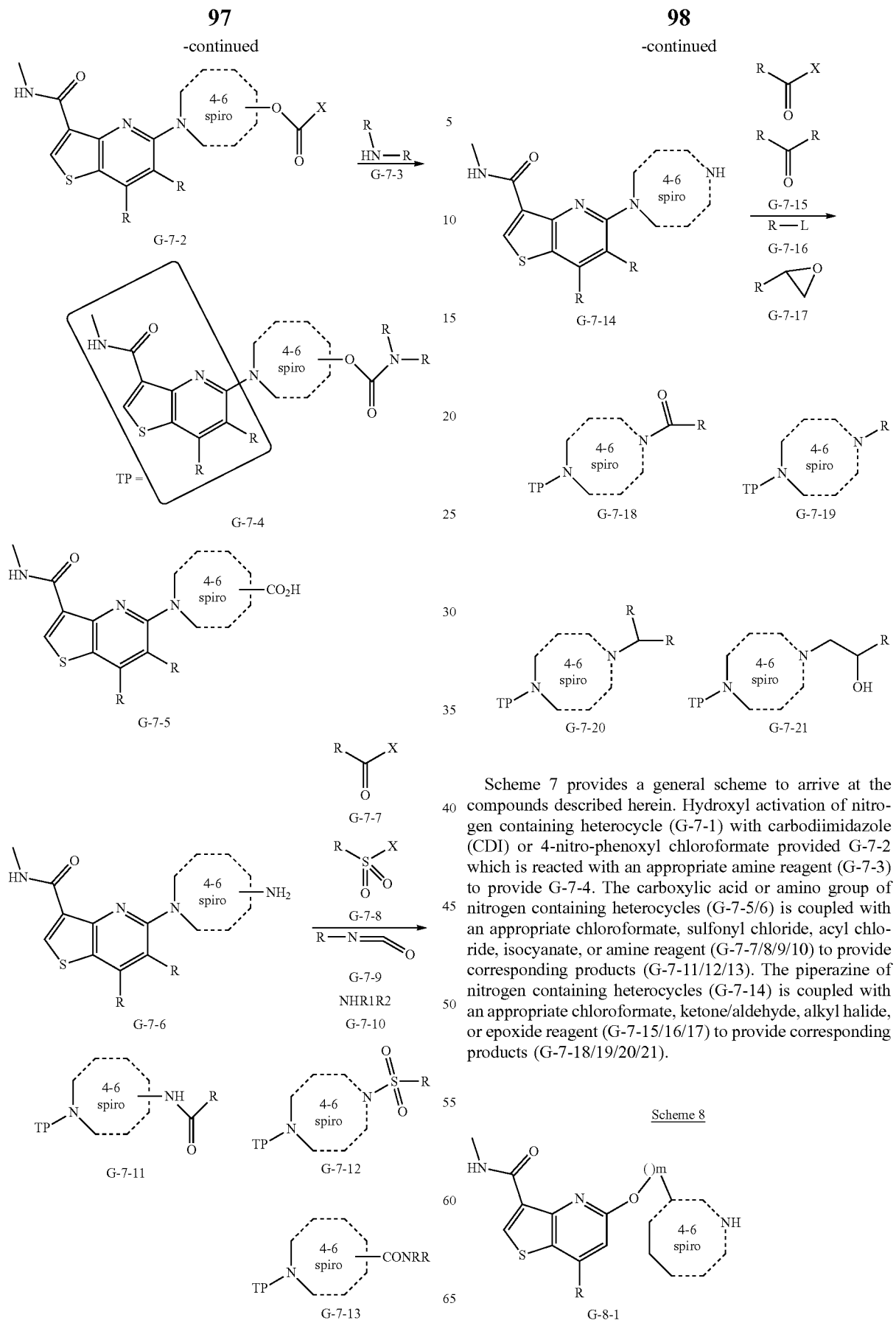

Scheme 7 provides a general scheme to arrive at the compounds described herein. Hydroxyl activation of nitrogen containing heterocycle (G-7-1) with carbodiimidazole (CDI) or 4-nitro-phenoxyl chloroformate provided G-7-2 which is reacted with an appropriate amine reagent (G-7-3) to provide G-7-4. The carboxylic acid or amino group of nitrogen containing heterocycles (G-7-5/6) is coupled with an appropriate chloroformate, sulfonyl chloride, acyl chloride, isocyanate, or amine reagent (G-7-7/8/9/10) to provide corresponding products (G-7-11/12/13). The piperazine of nitrogen containing heterocycles (G-7-14) is coupled with an appropriate chloroformate, ketone/aldehyde, alkyl halide, or epoxide reagent (G-7-15/16/17) to provide corresponding products (G-7-18/19/20/21).

Scheme 8

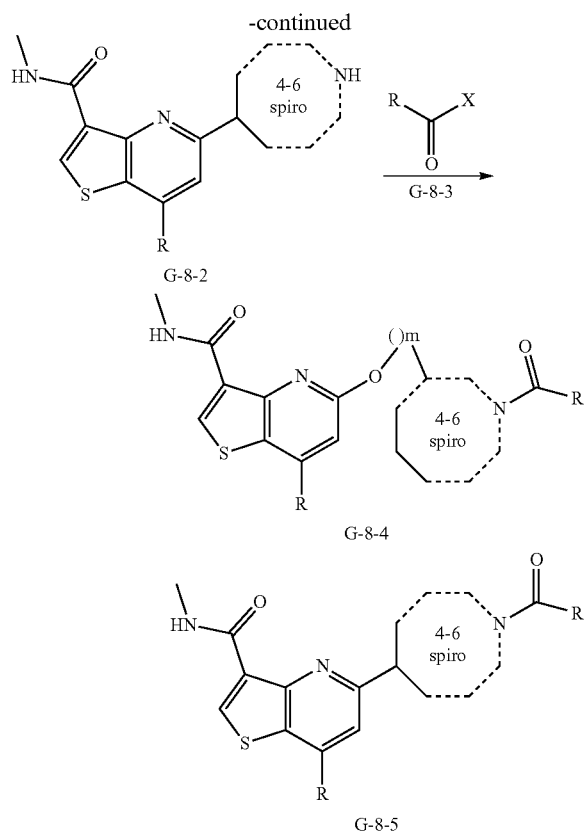

Scheme 8 provides a general scheme to arrive at the compounds described herein. The amine of O-linked nitrogen containing heterocycles (G-8-1) or C-linked nitrogen containing heterocycles (G-8-2) is coupled with an appropriate chloroformate or acyl halide (G-8-3) to provide corresponding products (G-8-4/5).

Unless otherwise stated, the structures depicted herein are also meant to include all isomeric forms of the structure. Certain compounds described herein contain one or more asymmetric centers and may give rise to isomers (e.g., enantiomers, diastereomers, racemates and other stereoisomeric forms that may be defined in terms of absolute chemistry, as (R)- or (S)-. The present disclosure is meant to include all such possible isomers, including racemic mixtures, optically pure forms and intermediate mixtures. The present application is meant to include all possible isomers, including racemic mixtures, optically pure forms and intermediate mixtures.

Any asymmetric atom (e.g., carbon or the like) of the compound(s) of the present application can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein, a compound of the present application can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present application into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Since the compounds of the application are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound described herein.

Compounds of the present application are either obtained in the free form, or as a salt thereof.

When both a basic group and an acid group are present in the same molecule, the compounds described herein may also form internal salts, e.g., zwitterionic molecules.

Atoms making up the compounds of the present disclosure also are intended to include isotopic forms of such atoms.

In an aspect of the present application, compounds of formula I, or any of 1.1-1.300, are described that contain isotope-labelled forms. An isotope-labelled form of a compound of formula I, or any of 1.1-1.300, is identical in structure to this compound apart from the fact that one or more atoms of the compound have been replaced by an atom or atoms having an atomic mass or mass number which differs from the atomic mass or mass number of the atom which usually occurs in greater natural abundance. Examples of isotopes which are readily commercially available and which can be incorporated into a compound of formula I, or any of 1.1-1.300, by well-known methods include isotopes of hydrogen, carbon, nitrogen, oxygen, phosphorus, fluorine and chlorine, for example $^2H$ (deuterium), $^3H$ (tritium), $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of formula I, or any of 1.1-1.300, or a prodrug thereof, or a pharmaceutically acceptable salt of either, which contains one or more of the above-mentioned isotopes and/or other isotopes of other atoms is intended to be part of the present application. An isotope-labelled compound of formula I, or any of 1.1-1.300, can be used in a number of beneficial ways. For example, an isotope-labelled compound of formula I into which, for example, a radioisotope, such as $^{14}C$, has been incorporated is suitable for medicament and/or substrate tissue distribution assays. These radioisotopes, i.e. tritium ($^3H$) and carbon-14 ($^{14}C$), are particularly preferred owing to simple preparation and excellent detectability. Incorporation of heavier isotopes, for example deuterium ($^2H$), into a compound of formula I may have therapeutic advantages owing to the higher metabolic stability of this isotope-labelled compound. Higher metabolic stability may translate directly into an increased in vivo half-life or reduced dosage requirements or an improvement in therapeutic index. An isotope-labelled compound of formula I can usually be prepared by carrying out the procedures disclosed in the synthesis schemes and the related description, in the example part and in the preparation part in the present text, replacing a non-isotope-labelled reactant by a readily available isotope-labelled reactant.

Deuterium ($^2$H or D) can also be incorporated into a compound of Formula I, or any of 1.1-1.300, in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of kM/kD=2-7 are typical. If this rate difference is successfully applied to a compound of formulas I, or any of 1.1-1.300, that is susceptible to oxidation, the pharmacodynamic profile of this compound in vivo can be drastically modified and result in improved pharmacokinetic properties. For a further discussion, see S. L. Harbeson and R. D. Tung, Deuterium In Drug Discovery and Development, Ann. Rep. Med. Chem. 2011, 46, 403-417, Foster, A. B., "Deuterium Isotope Effects in Studies of Drug Metabolism," Trends in Pharmacological Sciences, 5: 524-527 (1984) AND Foster, A. B., "Deuterium Isotope Effects in the Metabolism of Drugs and Xenobiotics: Implications for Drug Design," Advances in Drug Research, 14: 1-40 (1985) incorporated in their entirety herein by reference.

When discovering and developing therapeutic agents, the person skilled in the art attempts to optimize pharmacokinetic parameters while retaining desirable in vitro properties. In some cases, compounds with poor pharmacokinetic profiles are susceptible to oxidative metabolism. In vitro liver microsomal assays currently available may provide valuable information on the course of oxidative metabolism of this type, which in turn may permit the rational design of deuterated compounds of Formula I with improved stability through resistance to such oxidative metabolism. Significant improvements in the pharmacokinetic profiles of compounds of Formula I are thereby possible, and can be expressed quantitatively in terms of increases in the in vivo half-life (t½), concentration at maximum therapeutic effect (Cmax), area under the dose response curve (AUC), and bioavailability; and in terms of reduced clearance, dose and materials costs.

Deuterium-hydrogen exchange in a compound of formula I, or any of 1.1-1.300, can also be used to achieve a favorable modification of the metabolite spectrum of the starting compound in order to diminish or eliminate undesired toxic metabolites. For example, if a toxic metabolite arises through oxidative carbon-hydrogen (C—H) bond cleavage, it may be possible that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993. It is understood that deuterium in this context is regarded as a substituent of a compound of Formula I, or any of 1.1-1.300. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound described herein is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The following is intended to illustrate the above: a compound of formulas I, or any of 1.1-1.300, which has multiple potential sites of attack for oxidative metabolism, for example benzylic hydrogen atoms and hydrogen atoms bonded to a nitrogen atom, may be prepared as a series of analogues in which various combinations of hydrogen atoms are replaced by deuterium atoms, so that some, most or all of these hydrogen atoms have been replaced by deuterium atoms. Half-life determinations enable favorable and accurate determination of the extent to which the improvement in resistance to oxidative metabolism has improved. In this way, it may be determined that the half-life of the parent compound can be extended by up to 100% as the result of deuterium-hydrogen exchange of this type.

As indicated above, MLD disease results from mutations in the arylsulfatase A gene responsible for converting sulfatide (SFT) to galactosylceramide (GalCer) and sulfate. ARSA mutations leading to >90% reduction in ARSA activity result in accumulation of SFT, which in turn induces demyelination and death. By inhibiting the biosynthesis of SFT, compounds described herein can prevent the accumulation of SFT that causes MLD disease. Similarly, Krabbe disease results from mutations in galactosylcerebrosidase (GalC), the enzyme responsible for converting GalCer to galactose and ceramide. Mutations disrupting both alleles of GalC result in complete inactivation of GalC and the subsequent accumulation of GalCer and psychosine (another substrate for GalC). By inhibiting the biosynthesis of GalCer, compounds described herein can prevent the accumulation of GalCer and psychosine that cause Krabbe disease.

The compounds described herein can be used in combination with other UGT8 modulators or therapeutic agents for treating MLD, Krabbe disease and MLD- or Krabbe-related diseases and conditions. For MLD, other therapeutic modalities focus on ARSA, the enzyme that is defective in MLD patients. These include enzyme replacement therapy (ERT), gene replacement therapy and gene-transduced hematopoietic stem cell transfer. For ERT, recombinant human ARSA with full enzymatic activity is transfused into MLD patients either via the systemic circulation or by direct transfusion into the brain. In MLD, gene replacement therapy consists of delivering the functional form of the ARSA gene systemically or directly into the brain to augment the defective (or absent) mutant enzyme that causes MLD. In gene-transduced stem cell transfer, hematopoietic stem cells are transduced with copies of the fully functional ARSA gene and are then administered systemically back to the patients. An advantage of using the UGT8 inhibitor compounds described herein in combination with any of these modalities is that the inhibitors will immediately prevent further accumulation of toxic substrates such as SFT and Psychosine before the other therapeutics have become fully effective.

EXAMPLES

Preparation of Compounds

The preparation of exemplary compounds according to the present disclosure is described below. Other compounds within the scope of the disclosure may be made according to the general schemes described above and according to analogous methods and procedures to those described in detail below, and in conjunction with the skill of the art.

Analytical Methods

The 1H NMR spectra are run at 400 MHz on a Gemini 400 or Varian Mercury 400 spectrometer with an ASW 5 mm probe, and usually recorded at ambient temperature in a deuterated solvent, such as $D_2O$, DMSO-$d_6$ or $CDCl_3$ unless otherwise noted. Chemical shifts values (δ) are indicated in parts per million (ppm) with reference to tetramethylsilane (TMS) as the internal standard.

High Pressure Liquid Chromatography-Mass Spectrometry (LCMS) experiments to determine retention times (RT) and associated mass ions were performed using one of the following methods.

Mass Spectra (MS) were recorded using a Micromass mass spectrometer. Generally, the method used was positive electro-spray ionization, scanning mass m/z from 100 to 1000. Liquid chromatography was performed on a Hewlett Packard 1100 Series Binary Pump & Degasser; Auxiliary detectors used were: Hewlett Packard 1100 Series UV detector, wavelength=220 nm and Sedere SEDEX 75 Evaporative Light Scattering (ELS) detector temperature=46° C., $N_2$ pressure=4 bar.

LCT: Grad (AcN+0.05% TFA):($H_2O$+0.05% TFA)=5:95 (0 min) to 95:5 (2.5 min) to 95:5 (3 min). Column: YMC Jsphere 33×2 4 μM, 1 ml/min.

MUX: Column: YMC Jsphere 33×2, 1 ml/min.

Grad (AcN+0.05% TFA):($H_2O$+0.05% TFA)=5:95 (0 min) to 95:5 (3.4 min) to 95:5 (4.4 min).

LCT2: YMC Jsphere 33×2 4 μM, (AcN+0.05% TFA):($H_2O$+0.05% TFA)=5:95 (0 min) to 95:5 (3.4 min) to 95:5 (4.4 min).

QU: YMC Jsphere 33×2 1 ml/min, (AcN+0.08% formic acid):($H_2O$+0.1% formic acid)=5:95 (0 min) to 95:5 (2.5 min) to 95:5 (3.0 min).

Preparation of Intermediates

Intermediate 1: Methyl 5-oxo-7-(trifluoromethyl)-4,5-dihydrothieno[3,2-b]pyridine-3-carboxylate

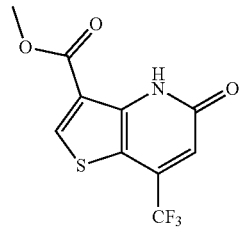 [SMILES: COC(=O)c1csc2c(C(F)(F)F)cc(=O)[nH]c12]

A stirred mixture of methyl 3-aminothiophene-4-carboxylate hydrochloride (180 g, 929 mmol) and ethyl 4,4,4-trifluoroacetoacetate (540 mL, 3.69 mol) was heated at 130° C. for 18 hours. The reaction was analyzed by LCMS and found to be complete. The mixture was concentrated and the resulting moist, brown solid was triturated with tert-butyl methyl ether (~300 mL). The suspended solid was collected by suction filtration, rinsed with additional tert-butyl methyl ether (2×~50 mL) and air dried on the frit under house vacuum. The title compound was obtained as a yellow solid (200 g, 74%). $^1$H NMR (400 MHz, DMSO-$d_6$) δ 11.10 (br s, 1H), 8.88 (s, 1H), 6.98 (s, 1H), 3.92 (s, 3H) ppm.

Intermediate 3: Methyl 5-chloro-7-(trifluoromethyl)thieno[3,2-b]pyridine-3-carboxylate

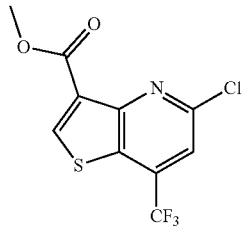 [SMILES: COC(=O)c1csc2c(C(F)(F)F)cc(Cl)nc12]

A stirred mixture of Intermediate 1 (100 g, 361 mmol) and phosphorus oxychloride (500 mL, 5.4 mol) was heated at 110° C. for five hours. The mixture was cooled to room temperature and then slowly poured into vigorously stirred and cooled (0° C.) water (~2 L). The resulting suspension was extracted with dichloromethane (2×~1 L). The combined organic layers were dried ($Na_2SO_4$), suction filtered through a pad of silica and concentrated under reduced pressure. The residue was then triturated with methanol (~300 mL) and recollected by suction filtration. The filtercake was air dried on the frit under house vacuum to afford the title compound as a white solid (91.0 g, 85%). $^1$H NMR (400 MHz, $CDCl_3$) δ 8.75 (s, 1H), 7.62 (s, 1H), 4.00 (s, 3H) ppm. MS: 296 m/z (M+H$^+$).

Intermediate 4: 5-Chloro-7-(trifluoromethyl)thieno[3,2-b]pyridine-3-carboxylic acid

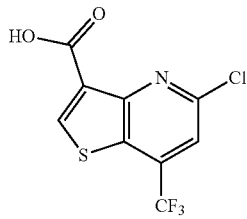 [SMILES: O=C(O)c1csc2c(C(F)(F)F)cc(Cl)nc12]

To a stirred solution of Intermediate 3 (40.0 g, 136 mmol) in tetrahydrofuran (300 mL) was added a solution of lithium hydroxide monohydrate (12.0 g, 286 mmol) in water (300 mL). After 30 minutes at room temperature, the reaction was analyzed by TLC and found to be complete. The mixture was diluted with water (500 mL) and then acidified (to pH 2-3) with the addition of 1.0 N hydrochloric acid. The resulting suspension was extracted with ethyl acetate (3×~500 mL) and the combined organic layers were dried (Na$_2$SO$_4$) and concentrated. The crude title compound, which was used without purification, was afforded as a pale red solid (38.0 g, 99%). $^1$H NMR (400 MHz, CDCl$_3$) δ 12.11 (br s, 1H), 8.98 (s, 1H), 7.71 (s, 1H) ppm. MS: 281 m/z (M+H$^+$).

Intermediate 5: 5-Chloro-N-methyl-7-(trifluoromethyl)thieno[3,2-b]pyridine-3-carboxamide

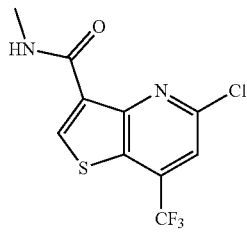 [SMILES: CNC(=O)c1csc2c(C(F)(F)F)cc(Cl)nc12]

Method 1 (from Intermediate 3):

Intermediate 3 (9.00 g, 30.4 mmol) and a 2.0 N solution of methylamine in methanol (75.0 mL, 150 mmol) were combined in a pressure vessel equipped with a stir bar. The vessel was sealed and the stirred solution was heated at 50° C. for 90 minutes. The mixture was stirred for an additional one hour at room temperature and then concentrated. The residue was subjected to automated flash chromatography (Combiflash instrument; 0 to 1% methanol in chloroform; 220 g silica column) to afford partially purified product (R$_f$=0.25 with 99:1 chloroform/methanol as the eluant) as a light amber solid (6.83 g, 76%). This material was triturated with diethyl ether (~40 mL) and recollected by suction filtration. The filtercake was rinsed with additional ether (2×~10 mL) and then air dried on the frit under house vacuum to afford the title compound as an off-white solid (6.51 g, 73%). $^1$H NMR (400 MHz, CDCl$_3$) δ 9.01-8.80 (m, 2H), 7.62 (s, 1H), 3.12 (d, J=4.9 Hz, 3H) ppm.

Method 2 (from Intermediate 4):

To a stirred and cooled (0° C.) solution of Intermediate 3 (38.0 g, 135 mmol) in dichloromethane (350 mL) was slowly added oxalyl chloride (18.0 mL, 213 mmol) followed by 2-3 drops of N,N-dimethylformamide. The cooling bath was removed and the reaction was allowed to warm to room temperature. After one hour, the reaction solution was concentrated to afford the crude acid chloride as an oil. To a stirred solution of this material in dichloromethane (300 mL) was slowly added a 2.0 M solution of methylamine in tetrahydrofuran (254 mL, 510 mmol). The mixture was stirred at room temperature for 30 minutes and then partitioned between dichloromethane (500 mL) and a saturated aqueous ammonium chloride solution (500 mL). The organic layer was removed, dried (Na$_2$SO$_4$) and concentrated to afford crude product as a yellow solid. This material was triturated with acetonitrile (~300 mL), recollected by suction filtration and air dried on the frit under house vacuum. The title compound was afforded as a light yellow solid (36.18 g, 91%). $^1$H NMR (400 MHz, CDCl$_3$) δ 8.89 (br s, 1H), 8.87 (s, 1H), 7.60 (s, 1H), 3.10 (d, J=4.8 Hz, 3H) ppm. MS: 295 m/z (M+H$^+$).

Intermediate 6: N-Methyl-5-(piperazin-1-yl)-7-(trifluoromethyl)thieno[3,2-b]pyridine-3-carboxamide

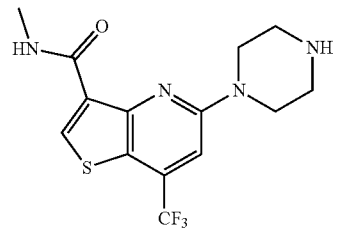 [SMILES: CNC(=O)c1csc2c(C(F)(F)F)cc(N3CCNCC3)nc12]

Step 1: Methyl 5-(4-(tert-butoxycarbonyl)piperazin-1-yl)-7-(trifluoromethyl)thieno[3,2-b]pyridine-3-carboxylate A 20 mL microwave reaction vessel equipped with a stir bar was loaded with Intermediate 3 (2.50 g, 8.46 mmol), tert-butyl piperazine-1-carboxylate (2.76 g, 14.8 mmol), N,N-diisopropylethylamine (3.00 mL, 17.2 mmol) and N-methyl-2-pyrrolidinone (10 mL). A second 20 mL microwave vial was prepared identically and both vessels were then sealed and heated in a microwave reactor for 1.5 hours at 130° C. The two reaction mixtures were combined and diluted with water (~50 mL). The resulting suspension was subjected to a combination of sonication and vigorous stirring (~30 mins) to disperse the larger solid aggregates. The resulting light brown precipitate was suction filtered off and rinsed with additional water (2×~25 mL). The filtercake was partially dried on the frit under house vacuum and then rinsed with diethyl ether (3×~20-25 mL). The solid was then dried in a vacuum oven (~50° C.) to afford the title compound as a tan solid (6.14 g, 82%). $^1$H NMR (400 MHz, CDCl$_3$) δ 8.57 (s, 1H), 6.99 (s, 1H), 3.96 (s, 3H), 3.79-3.70 (m, 4H), 3.64-3.56 (m, 4H), 1.50 (s, 9H) ppm.

Step 2: tert-Butyl 4-(3-(methylcarbamoyl)-7-(trifluoromethyl)thieno[3,2-b]pyridin-5-yl)piperazine-1-carboxylate A 20 mL microwave reaction vessel equipped with stir bar was loaded step 1 product (3.11 g, 6.98 mmol) and a 2.0 N solution of methylamine in methanol solution (12.0 mL, 24.0 mmol). The vessel was sealed and heated in a microwave reactor for 1.5 hours at 90° C. TLC analysis indicated that a small amount of ester starting material remained. Additional 2.0 N methylamine solution (4.0 mL, 8.0 mmol) was added and the reaction was heated for another one hour at 90° C. The reaction mixture was then concentrated to afford the title compound as a tan solid (3.04 g, 98%). $^1$H NMR (400 MHz, CDCl$_3$) δ 9.32 (br s, 1H), 8.67 (s, 1H), 7.04 (s, 1H), 3.66 (s, 8H), 3.09 (d, J=4.9 Hz, 3H), 1.51 (s, 9H) ppm.

Step 3: N-Methyl-5-(piperazin-1-yl)-7-(trifluoromethyl)thieno[3,2-b]pyridine-3-carboxamide Hydrogen chloride gas was bubbled through a stirred solution of step 2 product (4.06 g, 9.13 mmol) in ethyl acetate (120 mL) for approximately five minutes. The resulting thick yellow suspension was stirred at room temperature for one hour and then concentrated. The residue was partitioned between aqueous sodium carbonate solution (~100 mL) and 4:1 chloroform/isopropanol (~40 mL). The organic layer was combined with additional extracts (4:1 chloroform/isopropanol, 3×~40 mL), dried (Na$_2$SO$_4$) and concentrated. The title compound was afforded as a light yellow solid (3.18 g, 101%; $^1$H NMR analysis indicated that minor, residual isopropanol accounted for the excess yield). $^1$H NMR (400 MHz, CDCl$_3$) δ 9.42 (br s, 1H), 8.66 (s, 1H), 7.04 (s, 1H), 3.69-3.56 (m, 4H), 3.14-3.01 (m, 7H) ppm.

Intermediate 7: 5-(4-Hydroxypiperidin-1-yl)-N-methyl-7-(trifluoromethyl)thieno[3,2-b]pyridine-3-carboxamide

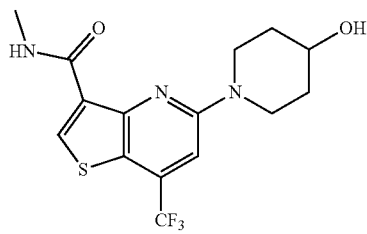 [SMILES: CNC(=O)c1csc2c(C(F)(F)F)cc(N3CCC(O)CC3)nc12]

Step 1: Methyl 5-(4-hydroxypiperidin-1-yl)-7-(trifluoromethyl)thieno[3,2-b]pyridine-3-carboxylate To a stirred solution of Intermediate 3 (10.0 g, 33.8 mmol) in N-methyl-2-pyrrolidinone (60 mL), was added piperidin-4-ol (6.00 g, 59.3 mmol, 1.75 eq) and N,N-diisopropylethylamine (11.8 mL, 67.7 mmol, 2.00 eq). The reaction was heated at 130° C. for three hours and then left to stir at room temperature overnight. LCMS analysis indicated that the reaction was complete. The mixture was concentrated to afford a moist brown solid. This material was taken up in water (~200 mL) and the suspended solid was dispersed through a combination of spatula agitation and sonication. When a nearly homogeneous suspension was achieved, the mixture was suction filtered. The filtercake was rinsed with water (2×~40 mL) and diethyl ether (2×~25 mL) and then air dried on the frit under house vacuum. The filtercake was further dried in a vacuum oven (~60° C.) to afford the title compound as a light brown solid (10.90 g, 89%). $^1$H NMR (400 MHz, CDCl$_3$) δ 8.54 (s, 1H), 7.02 (s, 1H), 4.30-4.20 (m, 2H), 4.08-3.88 (m, 4H), 3.48-3.29 (m, 2H), 2.10-1.99 (m, 1H), 1.67-1.56 (m, 2H) ppm.

Step 2: 5-(4-Hydroxypiperidin-1-yl)-N-methyl-7-(trifluoromethyl)thieno[3,2-b]pyridine-3-carboxamide To a stirred suspension of the product of step 1 (10.85 g, 30.11 mmol) in a 2.0 N solution of methylamine in methanol (75 mL, 150.00 mmol) was added sodium cyanide (0.221 g, 4.51 mmol). The vessel was sealed and heated overnight at 50° C. Following this time, the reaction was analyzed by LCMS and found to be complete. The mixture was cooled in an ice bath room (the reaction went from clear solution to a heavy suspension). The cold suspension was suction filtered and the collected solid was rinsed with cold methanol (1×~30 mL), water (2×~40 mL) and, finally, diethyl ether (2×~30 mL). The filtercake was further dried in a vacuum oven (~50° C.) to afford the title compound as a tan solid (9.60 g, 89%). $^1$H NMR (400 MHz, CDCl$_3$) δ 9.47 (s, 1H), 8.65 (s, 1H), 7.07 (s, 1H), 4.10-3.99 (m, 3H), 3.48-3.38 (m, 2H), 3.08 (d, J=4.8 Hz, 3H), 2.11-2.01 (m, 2H), 1.78-1.64 (m, 3H) ppm.

Intermediate 8: Methyl 5-(2,6-diazaspiro[3.3]heptan-2-yl)-7-(trifluoromethyl)thieno[3,2-b]pyridine-3-carboxylate

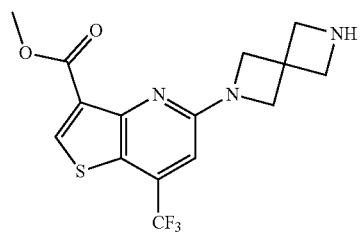 [SMILES: COC(=O)c1csc2c(C(F)(F)F)cc(N3CC4(CNC4)C3)nc12]

Step 1: Methyl 5-(6-(tert-butoxycarbonyl)-2,6-diazaspiro[3.3]heptan-2-yl)-7-(trifluoromethyl)thieno[3,2-b]pyridine-3-carboxylate A 20 mL microwave vial equipped with a stir was added Intermediate 3 (0.750 g, 2.54 mmol), tert-butyl-2,6-diazaspiro[3.3]heptane-2-carboxylate (0.920 g, 3.81 mmol), N,N-diisopropylethylamine (0.90 mL, 5.2 mmol) and N-methyl-2-pyrrolidinone (10 mL). The vessel was sealed and heated in a microwave reactor for two hours at 80° C. The mixture was then cooled and suction filtered to remove the solids, which were subsequently rinsed with ethyl acetate. The combined filtrate was concentrated and the residue was dissolved in 4:1 chloroform/isopropanol (50 mL). This solution was washed with aqueous sodium bicarbonate solution and brine, dried (Na$_2$SO$_4$) and concentrated. The crude product was purified by automated flash chromatography (Combiflash system; 0.3 to 3% methanol in dichloromethane eluant; 80 g silica column) to afford the title compound as an off-white solid (0.677 g, 58%). LC/MS: retention time=1.44 min; MS: 458 m/z (M+H$^+$).

Step 2: Methyl 5-(2,6-diazaspiro[3.3]heptan-2-yl)-7-(trifluoromethyl)thieno[3,2-b]pyridine-3-carboxylate To a stirred suspension of step 1 product (0.450 g, 0.984 mmol) in dichloromethane (2 mL) was added trifluoroacetic acid (2.0 mL, 26 mmol). After one hour at room temperature, the reaction was concentrated. The resulting gum was treated with solid sodium bicarbonate (400 mg) and then taken up in 98:2 dichloromethane/methanol solution (30 mL). The suspension was stirred vigorously for several minutes and then suction filtered to remove the solids. The filtercake was rinsed with a 4:1 chloroform/isopropanol solution (~10 mL) and the combined filtrate was washed with a saturated aqueous sodium bicarbonate solution and brine. The organic layer was then dried ($Na_2SO_4$) and concentrated to afford the title compound as an off-white solid (0.300 g, 85%). LC/MS: retention time=0.91 min; MS: 358 m/z (M+H$^+$).

Intermediate 11: 2-(Trifluoromethoxy)ethyl 1H-imidazole-1-carboxylate

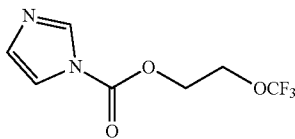 [SMILES: O=C(OCCOC(F)(F)F)n1ccnc1]

To a stirred solution of 2-(trifluoromethoxy)ethan-1-ol (1.20 g, 9.23 mmol) in dichloromethane (50 mL) was added 1,1'-carbonyldiimidazole (2.09 g, 12.9 mmol). The reaction was allowed to proceed overnight at room temperature and then washed into a separatory funnel with chloroform (~30 mL). The solution was washed with 0.1 N hydrochloric acid (1×~75 mL) and aqueous sodium bicarbonate solution (1×~75 mL). The organic layer was then dried ($Na_2SO_4$) and concentrated to afford crude title compound as a colorless oil (2.23 g, 108%; yield inflated by residual solvent). The crude product was used, without purification, in subsequent reactions and stored in a freezer. $^1$H NMR (400 MHz, CDCl$_3$) δ 8.16 (s, 1H), 7.46-7.41 (m, 1H), 7.10 (s, 1H), 4.69-4.61 (m, 2H), 4.35-4.27 (m, 2H) ppm. MS: 225 m/z (M+H$^+$).

Intermediate 12: (S)-1-(Trifluoromethoxy)propan-2-yl 1H-imidazole-1-carboxylate

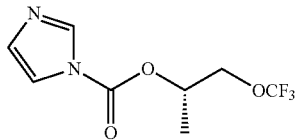 [SMILES: C[C@@H](COC(F)(F)F)OC(=O)n1ccnc1]

Step 1: (S)-(((1-(Trifluoromethoxy)propan-2-yl)oxy)methyl)benzene

Reaction based on: Liu, J.-B., Xu, X.-H., Qing, F.-L. *Org. Lett.* 2015, 17, 5048. (S)-2-(Benzyloxy)propan-1-ol (9.70 g, 58.4 mmol), silver trifluoromethanesulfonate (30.29 g, 116.7 mmol), potassium fluoride (10.27 g, 175.1 mmol) and SelectFluor (31.01 g, 87.53 mmol) were combined in a 1 L reaction flask. Ethyl acetate (275 mL) was then added and the mixture was stirred for several minutes before adding 2-fluoropyridine (10.1 mL, 117 mmol) and trifluoromethyl-trimethylsilane (17.6 mL, 117 mmol). The reaction, which slowly darkened over the first hour, was stirred overnight at room temperature. After this time, the mixture was suction filtered through a pad of silica gel. The silica was rinsed with additional ethyl acetate (6×~50 mL) and the combined filtrate was concentrated to afford a brown semi-solid (38.97 g). This material was taken up in ethyl acetate (~100 mL) and sonicated until a homogeneous suspension was achieved. The solid was suction filtered off and then rinsed with ethyl acetate (2×~25 mL). The combined filtrate was concentrated onto ~80 g of silica gel and the impregnated media was subjected to automated flash chromatography (Combiflash instrument; 0 to 15% ethyl acetate in heptane; 330 g silica column). Partially purified title compound (by $^1$H NMR analysis, purity was estimated to be 90-95%; R$_f$~0.6 in 85:15 heptane/ethyl acetate) was obtained as colorless oil (5.07 g, 37%). To avoid any possible product loss via evaporation, the oil was only briefly exposed to high vacuum (some minor residual solvent was accepted the product). $^1$H NMR (400 MHz, CDCl$_3$) δ 7.41-7.26 (m, 5H), 4.64-4.56 (m, 2H), 3.98 (dd, J=10.1, 6.1 Hz, 1H), 3.90 (dd, J=10.1, 4.4 Hz, 1H), 3.84-3.75 (m, 1H), 1.24 (d, J=6.4 Hz, 3H) ppm.

Step 2: (S)-1-(Trifluoromethoxy)propan-2-yl 1H-imidazole-1-carboxylate

The partially purified step 1 product (5.05 g, <21.6 mmol) was combined with 10% palladium on carbon (50% water) (2.00 g, 0.940 mmol) and taken up in ethyl acetate (150 mL). The stirred suspension was cycled between vacuum and a nitrogen atmosphere three times. The reaction vessel was then evacuated a final time and refilled with hydrogen (via balloon). The reaction was stirred under the hydrogen atmosphere overnight and then suction filtered through a plug of Celite. The filtering agent was rinsed with additional ethyl acetate (5×~30 mL) and the combined filtrate was stirred at room temperature and treated with 1,1'-carbonyldiimidazole (5.24 g, 32.3 mmol). The reaction was stirred overnight and then transferred to a separatory funnel and washed with 0.1 M hydrochloric acid (1×~150 mL) and aqueous sodium bicarbonate solution (1×~150 mL). The organic layer was dried ($Na_2SO_4$) and concentrated (only briefly under high vacuum) to afford a pale amber oil (3.41 g, 67%). $^1$H NMR analysis indicated that the acylation reaction was not complete (~7:3 ratio of the desired product to hydroxy intermediate was observed). The oil was taken up in tetrahydrofuran (80 mL), stirred at room temperature and treated with additional 1,1'-carbonyldiimidazole (2.00 g, 12.3 mmol). The reaction was then placed into a preheated (50° C.) oil bath. After three hours, a sample of the reaction was removed, concentrated and analyzed by $^1$H NMR. The reaction was determined to be complete. The mixture was concentrated and the residue was partitioned between an aqueous sodium bicarbonate solution (~100 mL) and chloroform (~60 mL). The organic layer was combined with additional extracts (chloroform, 2×~60 mL), dried ($Na_2SO_4$) and concentrated to afford crude, title compound as a pale amber oil (3.41 g, 67%, overall two steps). Despite the observation of minor impurity contaminating the desired product (by $^1$H NMR), the material was deemed sufficiently pure to use without purification in subsequent reactions. The intermediate was stored in a freezer to suppress decomposition. $^1$H NMR (400 MHz, CDCl$_3$) δ 8.14 (s, 1H), 7.44-7.40 (m, 1H), 7.10-7.08 (m, 1H), 5.39-5.29 (m, 1H), 4.19-4.08 (m, 2H), 1.49 (d, J=6.6 Hz, 3H) ppm. MS: 239 m/z (M+H$^+$).

Intermediate 13: Methyl 6-methyl-5-oxo-7-(trifluoromethyl)-4,5-dihydrothieno[3,2-b]pyridine-3-carboxylate

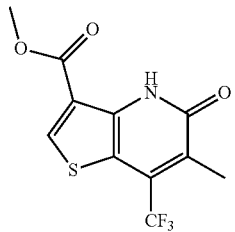

A stirred mixture of methyl 4-aminothiophene-3-carboxylate (8.23 g, 52.36 mmol), ethyl 4,4,4-trifluoro-2-methyl-3-oxobutanoate (16.5 mL, 104.76 mmol) and water (10 mL, 28 mmol) was heated overnight at 130° C. The reaction, which LCMS analysis indicated was a mixture of desired product and either the uncyclized amide or cyclized hydrate intermediate, was then cooled to room temperature and concentrated. The residue was dissolved in concentrated sulfuric acid (8 mL). After stirring the solution at room temperature for 45 minutes, the reaction was analyzed by LCMS and found to be complete. The mixture was poured into a stirred crushed ice/water slurry (~400 mL) along with ethyl acetate rinsings of the reaction vessel (~100 mL). After the ice had fully melted, the organic layer was removed and combined with additional ethyl acetate extracts (3×~100 mL). The pooled extracts were dried ($Na_2SO_4$) and concentrated to afford a moist, dirty orange solid. This material was taken up in mixture of heptane (~85 mL) and ethyl acetate (~15 mL) and sonicated for several minutes to disperse the larger chunks of solid. The suspension was then suction filtered and the collected solid was rinsed with heptane (3×~25 mL). The filtercake was further dried in a vacuum oven (~50° C.) to afford the title compound as an amber solid (7.85 g, 52%). $^1$H NMR (400 MHz, CDCl$_3$) δ 10.74 (br s, 1H), 8.29 (s, 1H), 3.97 (s, 3H), 2.40 (q, J=2.4 Hz, 3H) ppm. MS: 292 m/z (M+H$^+$).

Intermediate 14: Methyl 5-chloro-6-methyl-7-(trifluoromethyl)thieno[3,2-b]pyridine-3-carboxylate

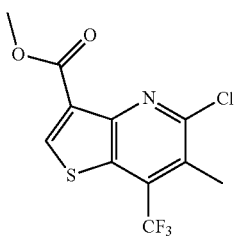

A stirred suspension of Intermediate 13 (11.00 g, 37.77 mmol) in phosphorus oxychloride (55.0 mL, 590 mmol, 17.5 eq) was heated at 110° C. for five hours. The mixture was cooled to room temperature and then slowly added, via pipet, to stirred and cooled (0° C.) water (500 mL). The resulting suspension was extracted with dichloromethane (2×~200 mL). The combined organic layers were dried ($Na_2SO_4$), filtered through a pad of silica gel and concentrated to afford the title compound as a yellow solid (10.00 g, 85%). $^1$H NMR (400 MHz, CDCl$_3$) δ 8.63 (s, 1H), 4.00 (s, 3H), 2.68 (s, 3H) ppm.

Intermediate 15: 5-Chloro-N,6-dimethyl-7-(trifluoromethyl)thieno[3,2-b]pyridine-3-carboxamide

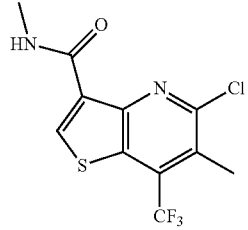

To a stirred suspension of Intermediate 14 (15.00 g, 48.4 mmol) in 2-methyltetrahydrofuran (60 mL) was added a 2.0 M solution of methylamine in methanol (57.0 mL, 114 mmol). The resulting suspension was stirred at room temperature for 24 hours and then partitioned between aqueous ammonium chloride solution (~500 mL) and dichloromethane (~300 mL). The organic layer was combined with an additional extract (dichloromethane, 1×~300 mL), dried ($Na_2SO_4$) and concentrated. The crude product was purified by trituration with acetonitrile (~40 mL) to afford the title compound as a white solid (19.60 g, 85%). $^1$H NMR (400 MHz CDCl$_3$) δ 8.88 (br, s, 1H), 8.70 (s, 1H), 3.04 (d, J=4.8 Hz, 3H), 2.61 (s, 3H) ppm. MS: 308 m/z (M+H$^+$).

Intermediate 16: Methyl 5-oxo-4,5-dihydrothieno[3,2-b]pyridine-3-carboxylate

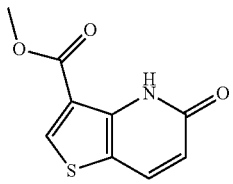

Step 1: 3-Ethoxyacrylic acid

To a stirred mixture of ethyl 3-ethoxyacrylate (20.00 g, 138.7 mmol) in water (160 mL) was added solid sodium hydroxide (13.32 g, 332.9 mmol). The reaction was heated at reflux for two hours and then cooled to room temperature. With stirring, the mixture was treated with sufficient concentrated hydrochloric acid to achieve pH 2-3 (~30 mL). The resulting yellow suspension was extracted with ethyl acetate (4×~100 mL). The combined organic layers were dried ($Na_2SO_4$) and concentrated to afford crude product as a bright yellow solid (9.21 g, 57%). This material was used, without purification, in the next step. $^1$H NMR (400 MHz, CDCl$_3$) δ 7.67 (d, J=12.6 Hz, 1H), 5.18 (d, J=12.6 Hz, 1H), 3.95 (q, J=7.1 Hz, 2H), 1.36 (t, J=7.1 Hz, 3H) ppm.

Step 2: Methyl 4-(3-ethoxyacrylamido)thiophene-3-carboxylate

To a stirred suspension of the step 1 crude product (9.21 g, 79.3 mmol) in toluene (130 mL) was added thionyl chloride (7.0 mL, 96 mmol). The mixture was heated at reflux for three hours and then cooled to room temperature and concentrated. Crude acid chloride was afforded as a brown oil. This material was taken up in dichloromethane (50 mL) and the resulting solution was slowly added, via pipet, to a stirred solution of methyl 4-aminothiophene-3-carboxylate hydrochloride (10.24 g, 52.88 mmol) and pyridine (12.8 mL, 159 mmol) in dichloromethane (250 mL). The mixture was stirred overnight at room temperature and then washed with ~0.2 N hydrochloric acid (1×~200 mL). The aqueous phase was back-extracted with chloroform (2×~40 mL) and the combined organic layers were washed with aqueous sodium bicarbonate solution (1×~200 mL). The organic solution was then dried ($Na_2SO_4$) and concentrated to provide the crude product which was subjected to automated flash chromatography (Combiflash instrument; 0 to 25% ethyl acetate in heptane; 330 g silica column). The title compound was obtained as a dirty yellow solid (10.38 g, 77% from the aminothiophene starting material). $^1$H NMR (400 MHz, $CDCl_3$) δ 9.83 (br s, 1H), 8.03 (s, 2H), 7.65 (d, J=12.2 Hz, 1H), 5.37 (d, J=12.2 Hz, 1H), 3.95 (q, J=7.1 Hz, 2H), 3.90 (s, 3H), 1.36 (t, J=7.1 Hz, 3H) ppm.

Step 3: Methyl 5-oxo-4,5-dihydrothieno[3,2-b]pyridine-3-carboxylate

Step 2 product (10.37 g, 40.62 mmol) was taken up in concentrated sulfuric acid (10 mL) and stirred at room temperature. After one hour, the reaction was analyzed by LCMS and found to be complete. The reaction was poured into ice water (~600 mL) and the resulting suspension was stirred until the ice had fully melted. The mixture was then extracted with chloroform (4×~150 mL) and the combined extracts were dried ($Na_2SO_4$) and concentrated. The resulting amber solid was taken up in diethyl ether (~60 mL) and sonicated until a near homogenous suspension was achieved. The suspension was then suction filtered and the collected solid was washed with additional diethyl ether (2×~20 mL). The filtercake was air dried on the frit under house vacuum to afford the title compound as a tan solid (7.90 g, 93%). $^1$H NMR (400 MHz, $CDCl_3$) δ 10.47 (br s, 1H), 8.29 (s, 1H), 7.73 (d, J=9.6 Hz, 1H), 6.60 (d, J=9.6 Hz, 1H), 3.96 (s, 3H) ppm. MS: 210 m/z (M+H$^+$).

Intermediate 17: N-Methyl-5-(piperidin-4-yloxy)-7-(trifluoromethyl)thieno[3,2-b]pyridine-3-carboxamide

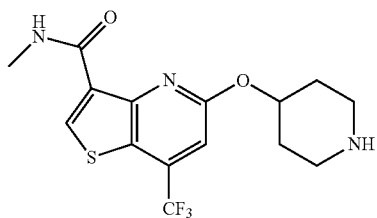 [SMILES: CNC(=O)c1csc2c(C(F)(F)F)cc(OC3CCNCC3)nc12]

Step 1: tert-Butyl 4-((3-(methylcarbamoyl)-7-(trifluoromethyl)thieno[3,2-b]pyridin-5-yl)oxy)piperidine-1-carboxylate A stirred solution of Intermediate 5 (8.00 g, 27.2 mmol) and tert-butyl 4-hydroxypiperidine-1-carboxylate (6.56 g, 32.58 mmol) in tetrahydrofuran (150 mL) was placed into an ambient temperature water bath and treated, in one portion, with sodium tert-butoxide (3.39 g, 35.3 mmol). The mixture was stirred at room temperature for two hours and then concentrated. The residue was partitioned between aqueous sodium bicarbonate solution (~300 mL) and chloroform (~150 mL). The organic layer was combined with a second extract (chloroform, 1×~100 mL), dried ($Na_2SO_4$) and concentrated onto of silica (~40 g). The impregnated media was subjected to automated flash chromatography (Combiflash instrument; 20 to 50% ethyl acetate in heptane; 330 g silica column). The target component ($R_f$=0.24 with 1:1 heptane/ethyl acetate as the eluant) was obtained as a gummy solid. This material was co-evaporated with diethyl ether to afford the title compound as a pale amber, foamy solid (10.43 g, 84%). $^1$H NMR (400 MHz, $CDCl_3$) δ 9.12-8.98 (m, 1H), 8.75 (s, 1H), 7.12 (s, 1H), 5.21 (tt, J=7.4, 3.6, 1H), 3.87-3.75 (m, 2H), 3.46-3.35 (m, 2H), 3.08 (d, J=4.9 Hz, 3H), 2.18-2.03 (m, 2H), 1.98-1.84 (m, 2H), 1.49 (s, 9H) ppm.

Step 2: N-Methyl-5-(piperidin-4-yloxy)-7-(trifluoromethyl)thieno[3,2-b]pyridine-3-carboxamide To a stirred solution of step 1 product (10.41 g, 22.66 mmol) in dichloromethane (100 mL) was added trifluoroacetic acid (25.0 mL, 326 mmol). After one hour, the mixture was concentrated and the resulting oil was partitioned between chloroform (~100 mL) and aqueous sodium carbonate solution (~150 mL). The organic layer was combined with a second extract (chloroform, 1×100 mL), dried ($Na_2SO_4$) and concentrated to afford a light brown solid. This material was taken up in diethyl ether (~60 mL) and sonicated until a fine, homogeneous suspension was achieved. The solid was suction filtered off, rinsed with additional diethyl ether (2×~20 mL) and air dried on the frit under house vacuum and a nitrogen funnel. The title compound was obtained as a sand colored solid (7.93 g, 97%). $^1$H NMR (400 MHz, $CDCl_3$) δ 9.26-9.06 (br s, 1H), 8.73 (s, 1H), 7.11 (s, 1H), 5.17-5.06 (m, 1H), 3.34-3.14 (m, 2H), 3.09 (d, J=4.9 Hz, 3H), 2.88-2.75 (m, 2H), 2.27-2.10 (m, 2H), 1.92-1.74 (m, 2H), 1.70 (br s, 1H) ppm. MS: 360 m/z (M+H$^+$).

Intermediate 18: (S)-1-(Trifluoromethoxy)propan-2-amine hydrochloride

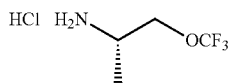

Step 1: tert-Butyl (S)-(1-(trifluoromethoxy)propan-2-yl)carbamate

Reaction based on: Liu, J.-B., Xu, X.-H., Qing, F.-L. Org. Lett. 2015, 17, 5048. A stirred suspension of N-Boc-L-alaninol (5.00 g, 28.5 mmol), silver trifluoromethanesulfonate (14.8 g, 57.1 mmol), potassium fluoride (5.02 g, 85.6 mmol), and SelectFluor (15.2 g, 42.8 mmol) in ethyl acetate (150 mL) was treated with 2-fluoropyridine (4.90 mL, 57.0 mmol) and trifluoromethyltrimethylsilane (8.60 mL, 57.0 mmol). The mixture was stirred overnight at room temperature and then suction filtered through a pad of silica.

The filtrate was concentrated and the residue was subjected to automated flash chromatography (Combiflash system; 0 to 20% ethyl acetate in heptane; 120 g silica column; ninhydrin staining solution was used to visualize TLC plates). The title compound was obtained as a colorless oil (2.20 g, 32%). ¹H NMR (400 MHz, CDCl₃) δ 4.58 (s, 1H), 4.00-3.87 (m, 3H), 1.45 (s, 9H), 1.22 (d, J=6.7 Hz, 3H) ppm.

Step 2: (S)-1-(Trifluoromethoxy)propan-2-amine hydrochloride

Hydrogen chloride gas was bubbled into a stirred solution of step 1 product (2.20 g, 9.05 mmol) in ethyl acetate (60 mL) for approximately three minutes. The reaction was maintained at room temperature for another 30 minutes and then concentrated to afford the title compound as a white solid. ¹H NMR (400 MHz, DMSO-d₆) δ 8.35 (br s, 3H), 4.29-4.12 (m, 2H), 3.55 (br s, 1H), 1.24 (d, J=6.8 Hz, 3H) ppm.

Intermediate 19: Methyl 5-chloro-2-methyl-7-(trifluoromethyl)thieno[3,2-b]pyridine-3-carboxylate

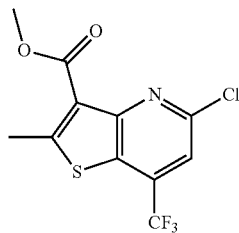 [SMILES: COC(=O)c1c(C)sc2c(C(F)(F)F)cc(Cl)nc12]

Step 1: Methyl 2-methyl-5-oxo-7-(trifluoromethyl)-4,5-dihydrothieno[3,2-b]pyridine-3-carboxylate A stirred mixture of methyl 4-amino-2-methylthiophene-3-carboxylate hydrochloride (5.00 g, 24.1 mmol) and ethyl 4,4,4-trifluoroacetoacetate (25.2 g, 137 mmol) was heated overnight at 130° C. The reaction mixture was then concentrated under reduced pressure to afford a moist, brown solid. This crude product was triturated with ethyl acetate (~20 mL). When a homogeneous suspension was achieved, the solid was collected by suction filtration, rinsed with additional ethyl acetate and air dried on the frit under house vacuum. The title compound was obtained as a yellow solid (5.00 g, 71%). ¹H NMR (400 MHz, DMSO-d₆) δ 10.79 (br s, 1H), 6.78 (s, 1H), 3.97 (s, 3H), 2.81 (s, 3H) ppm. MS: 292 m/z (M+H⁺).

Step 2: Methyl 5-chloro-2-methyl-7-(trifluoromethyl)thieno[3,2-b]pyridine-3-carboxylate Step 1 product (10.00 g, 34.33 mmol) was taken up in phosphorus oxychloride (43 mL, 460 mmol) and heated, with stirring, for five hours at 110° C. The mixture was cooled to room temperature and slowly added to stirred and cooled (0° C.) water (~200 mL). The resulting suspension was extracted with dichloromethane (3×150 mL). The combined organic layers were dried (Na₂SO₄) and concentrated. The resulting crude product was purified by automated flash chromatography (Combiflash system; 1 to 5% ethyl acetate in petroleum ether; 330 g silica column) to afford the title compound as a white solid (9.22 g, 87%). ¹H NMR (400 MHz, CDCl₃) δ 7.50 (s, 1H), 4.00 (s, 3H), 2.87 (s, 3H) ppm. MS: 310 m/z (M+H⁺).

Intermediate 20: 5-Chloro-N,2-dimethyl-7-(trifluoromethyl)thieno[3,2-b]pyridine-3-carboxamide

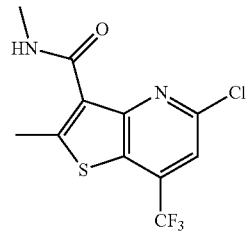 [SMILES: CNC(=O)c1c(C)sc2c(C(F)(F)F)cc(Cl)nc12]

Intermediate 19 (2.00 g, 6.46 mmol) and a 2.0 N solution of methylamine in methanol (24.0 mL, 48.0 mmol) were combined in a pressure vessel equipped with a stir bar. The vessel was sealed and the stirred solution was heated at 50° C. for seven hours and then allowed to cool to room temperature and stirred for an additional two days. After this time, the mixture was concentrated and the residue was subjected to automated flash chromatography (Combiflash instrument; 5 to 25% ethyl acetate in heptane; 80 g silica column). The title compound was obtained as a white solid (1.66 g, 83%). ¹H NMR (400 MHz, CDCl₃) δ 9.22 (s, 1H), 7.54 (s, 1H), 3.16-3.03 (m, 6H) ppm. MS: 309 m/z (M+H⁺).

Intermediate 21: 1-(3-(Methylcarbamoyl)-7-(trifluoromethyl)thieno[3,2-b]pyridin-5-yl)piperidin-4-yl (4-nitrophenyl) carbonate

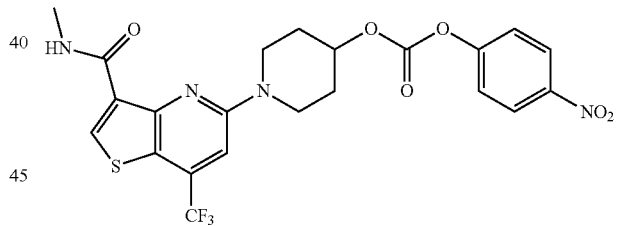

To a stirred solution of Intermediate 7 (5.00 g, 13.9 mmol) and triethylamine (2.30 mL, 16.5 mmol) in dichloromethane (40 mL) was added p-nitrophenyl chloroformate (2.89 g, 14.3 mmol) followed by several granules of 4-(dimethylamino)pyridine. The reaction was stirred at room temperature for seven hours and then diluted with sufficient dichloromethane to fully dissolve all solids (~200 mL). The clear solution was then concentrated onto ~25 g of silica and the impregnated media was subjected to automated flash chromatography (Combiflash instrument; 30 to 100% ethyl acetate in heptane; 120 g Gold silica column). The target component (R_f~0.6 with 7:3 ethyl acetate/heptane as the eluant) was obtained as a light brown solid (3.60 g). This material was further purified by trituration with a mixture of diethyl ether (~50 mL) and ethyl acetate (~5 mL). The solid was recollected via suction filtration, rinsed with additional diethyl ether (1×~25 mL) and then air dried on the frit under house vacuum. The title compound was obtained as a tan solid (3.44 g, 47%). ¹H NMR (400 MHz, CDCl₃) δ 9.37 (br s, 1H), 8.69 (s, 1H), 8.35-8.23 (m, 2H), 7.46-7.37 (m, 2H), 7.10 (s, 1H), 5.15-5.07 (m, 1H), 4.06-3.93 (m, 2H), 3.72-3.57 (m, 2H), 3.09 (d, J=4.9 Hz, 3H), 2.30-2.16 (m, 2H), 2.12-1.96 (m, 2H) ppm.

Intermediate 22: tert-Butyl 4-((chlorocarbonyl)oxy)piperidine-1-carboxylate

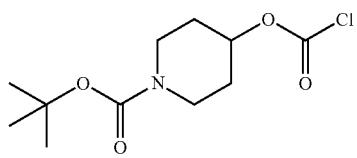 [SMILES: CC(C)(C)OC(=O)N1CCC(OC(=O)Cl)CC1]

To a stirred solution of tert-butyl 4-hydroxypiperidine-1-carboxylate (6.00 g, 29.8 mmol) in tetrahydrofuran (60 mL) was added a 15% (w/w) solution of phosgene in toluene (37.0 mL, 51.9 mmol). The reaction was stirred at room temperature for 90 minutes and then concentrated to afford the crude title compound as a colorless oil (8.04 g, 102%). $^1$H NMR analysis indicated that the material was sufficiently pure to use, without purification, in subsequent reactions. The intermediate was stored in a freezer, where it solidified. $^1$H NMR (400 MHz, CDCl$_3$) δ 5.06-4.97 (m, 1H), 3.78-3.64 (m, 2H), 3.34-3.22 (m, 2H), 2.02-1.89 (m, 2H), 1.82-1.70 (m, 2H), 1.46 (s, 9H) ppm.

Intermediate 23: Benzyl 4-((chlorocarbonyl)oxy)piperidine-1-carboxylate

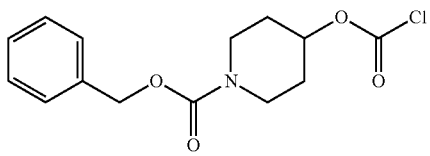 [SMILES: O=C(Cl)OC1CCN(C(=O)OCc2ccccc2)CC1]

To a stirred solution of benzyl 4-hydroxypiperidine-1-carboxylate (5.00 g, 21.3 mmol) in tetrahydrofuran (60 mL) was added a 15% (w/w) solution of phosgene in toluene (31.0 mL, 43.4 mmol). The reaction was stirred at room temperature for 90 minutes and then concentrated to afford the crude title compound as a colorless oil (6.50 g, 103%). $^1$H NMR analysis indicated that the material was sufficiently pure to use, without purification, in subsequent reactions. The intermediate was stored in a freezer, where it solidified. $^1$H NMR (400 MHz, CDCl$_3$) δ 7.45-7.29 (m, 5H), 5.13 (s, 2H), 5.08-4.99 (m, 1H), 3.83-3.70 (m, 2H), 3.46-3.34 (m, 2H), 2.04-1.89 (m, 2H), 1.87-1.71 (m, 2H) ppm.

Intermediate 24: Piperidin-4-yl (cyclopropylmethyl)carbamate

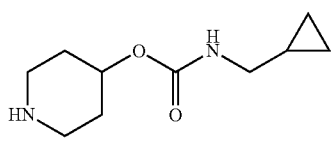 [SMILES: O=C(NCC1CC1)OC1CCNCC1]

Step 1: tert-Butyl 4-(((cyclopropylmethyl)carbamoyl)oxy)piperidine-1-carboxylate To a stirred and cooled (0° C.) solution of Intermediate 22 (31.65 g, 120.0 mmol) in chloroform (400 mL) was added (aminomethyl)cyclopropane (10.3 mL, 120 mmol) followed by triethylamine (25.1 mL, 180 mmol). The mixture was allowed to slowly warm to room temperature and stirring was continued overnight. The solution was then washed with 0.5 N hydrochloric acid (2×~200 mL) and aqueous sodium bicarbonate solution (1×~400 mL). The organic layer was dried (Na$_2$SO$_4$) and concentrated to afford crude title compound as an off-white solid (38.57 g, 108%; yield inflated by residual chloroform solvent). This material was used in the next step, without purification.

Step 2: Piperidin-4-yl (cyclopropylmethyl)carbamate

To a stirred solution of the step 1 product in dichloromethane (300 mL) was added trifluoroacetic acid (100 mL, 1.31 mmol). After 90 minutes at room temperature, the reaction was concentrated to afford a near colorless syrup. This material was partitioned between 1.0 N aqueous sodium hydroxide solution (~300 mL) and chloroform (~200 mL). The organic layer was combined with additional extracts (chloroform, 4×~200 mL), dried (Na$_2$SO$_4$) and concentrated to afford the crude title compound as an off-white solid (23.58 g, 99% overall yield). This intermediate was deemed sufficiently pure to use, without purification, in subsequent reactions. $^1$H NMR (400 MHz, CDCl$_3$) δ 4.96-4.55 (m, 2H), 3.17-2.95 (m, 4H), 2.82-2.64 (m, 2H), 2.36 (br s, 1H), 2.03-1.85 (m, 2H), 1.68-1.46 (m, 2H), 1.03-0.90 (m, 1H), 0.58-0.43 (m, 2H), 0.26-0.12 (m, 2H) ppm.

Intermediate 25: 5-((2-Azaspiro[3.3]heptan-6-yl)oxy)-N-methyl-7-(trifluoromethyl)thieno[3,2-b]pyridine-3-carboxamide

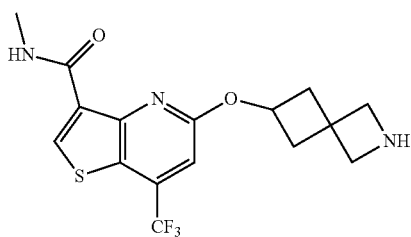 [SMILES: CNC(=O)c1csc2c(C(F)(F)F)cc(OC3CC4(CNC4)C3)nc12]

Step 1: tert-Butyl 6-((3-(methylcarbamoyl)-7-(trifluoromethyl)thieno[3,2-b]pyridin-5-yl)oxy)-2-azaspiro[3.3]heptane-2-carboxylate To a stirred mixture of Intermediate 5 (2.03 g, 6.89 mmol) and tert-butyl 6-hydroxy-2-azaspiro[3.3]heptane-2-carboxylate (2.17 g, 9.64 mmol) in tetrahydrofuran (30 mL) was added potassium tert-butoxide (0.928 g, 8.27 mmol). The reaction heated at 70° C. for two hours and then cooled to room temperature and concentrated. The residue was taken up in ethyl acetate and the solution was washed with aqueous sodium bicarbonate solution and brine. The organic layer was then dried (Na$_2$SO$_4$) and concentrated to afford the crude product which was purified by automated flash chromatography (Biotage system; 20 to 100% ethyl acetate in heptane followed by 5% methanol in dichloromethane; 100 g silica column). The title compound was obtained as a foamy, white solid (2.69 g, 83%). $^1$H NMR (400 MHz, CDCl$_3$) δ 9.11 (br s, 1H), 8.75 (s, 1H), 7.08 (s, 1H), 5.13 (p, J=6.9 Hz, 1H), 4.04 (s, 2H), 3.98 (s, 2H), 3.11 (d, J=4.9 Hz, 3H), 2.93-2.70 (m, 2H), 2.59-2.36 (m, 2H), 1.45 (s, 9H) ppm. MS: 472 m/z (M+H$^+$).

Step 2: 5-((2-Azaspiro[3.3]heptan-6-yl)oxy)-N-methyl-7-(trifluoromethyl)thieno[3,2-b]pyridine-3-carboxamide To a stirred and cooled (0° C.) solution of step 1 product (2.28 g, 4.84 mmol) in dichloromethane (5 mL) was added trifluoroacetic acid (3.7 mL, 48 mmol). The reaction was allowed to warm to room temperature and then stirred for another one hour before concentrating. The residue was partitioned between dichloromethane (200 mL) and aqueous 1.0 N sodium hydroxide solution 100 mL). The organic layer was combined with a backextract of the aqueous layer (dichloromethane, 1×~50 mL), dried (MgSO$_4$) and concentrated to afford the crude title compound as a beige solid (1.60 g, 89%). This intermediate was deemed sufficiently pure to use, without purification, in subsequent reactions. MS: 372 m/z (M+H$^+$).

Intermediate 27: 5-(cis-3-Aminocyclobutoxy)-N-methyl-7-(trifluoromethyl)thieno[3,2-b]pyridine-3-carboxamide

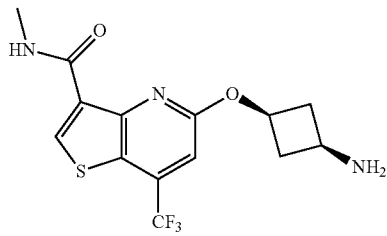 [SMILES: CNC(=O)c1csc2c(C(F)(F)F)cc(O[C@H]3C[C@@H](N)C3)nc12]

Step 1: tert-Butyl (cis-3-((3-(methylcarbamoyl)-7-(trifluoromethyl)thieno[3,2-b]pyridin-5-yl)oxy)cyclobutyl)carbamate To a stirred solution of Intermediate 5 (2.47 g, 8.38 mmol) and tert-butyl (cis-3 hydroxycyclobutyl)carbamate (1.88 g, 10.1 mmol) in tetrahydrofuran (60 mL) was added potassium tert-butoxide (1.03 g, 9.22 mmol). The reaction was heated at 90° C. for one hour, cooled to room temperature and concentrated. The residue was partitioned between ethyl acetate and aqueous ammonium chloride solution. The organic layer was dried (MgSO$_4$) and concentrated to afford crude product which was purified by automated flash chromatography (Combiflash instrument; 0 to 100% ethyl acetate in dichloromethane; 120 g silica column). The title compound was obtained as a white solid (2.50 g, 67%). MS: 446 m/z (M+H$^+$).

Step 2: 5-(cis-3-Aminocyclobutoxy)-N-methyl-7-(trifluoromethyl)thieno[3,2-b]pyridine-3-carboxamide To a stirred and cooled (0° C.) solution of step 1 product (1.89 g, 4.24 mmol) in dichloromethane (15 mL) was added trifluoroacetic acid (3.3 mL, 42 mmol). The reaction was allowed to warm to room temperature and stirred for another two hours before concentrating. The residue was partitioned between dichloromethane (200 mL) and an aqueous 0.5 N sodium hydroxide solution (100 mL). The organic layer was combined with additional extracts (dichloromethane, 2×~100 mL), dried (MgSO$_4$) and concentrated to afford the crude title compound as a white solid (1.13 g, 77%). $^1$H NMR (400 MHz, DMSO-d$_6$) δ 8.90 (s, 1H), 8.86 (d, J=4.9 Hz, 1H), 8.15 (s, 3H), 7.46 (s, 1H), 5.20 (q, 1H), 3.71-3.55 (m, 1H), 2.99 (d, J=4.9 Hz, 3H), 2.96-2.77 (m, 1H), 2.42-2.30 (m, 2H) ppm.

Intermediate 28: cis-3-((3-(Methylcarbamoyl)-7-(trifluoromethyl)thieno[3,2-b]pyridin-5-yl)oxy)cyclobutyl 1H-imidazole-1-carboxylate

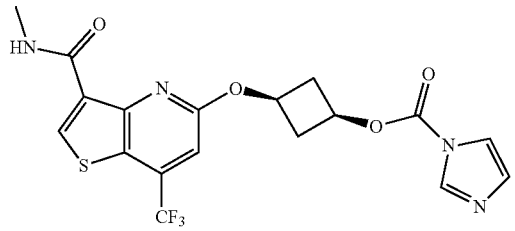 [SMILES: CNC(=O)c1csc2c(C(F)(F)F)cc(O[C@H]3C[C@@H](OC(=O)n4ccnc4)C3)nc12]

Step 1: 5-(cis-3-(Benzyloxy)cyclobutoxy)-N-methyl-7-(trifluoromethyl)thieno[3,2-b]pyridine-3-carboxamide To a stirred solution of cis-3-(benzyloxy)cyclobutanol (0.921 g, 5.17 mmol) in tetrahydrofuran (10 mL) was added potassium tert-butoxide (502 mg, 4.47 mmol). The mixture was stirred at room temperature for 15 minutes and then added, via syringe, to a stirred solution of Intermediate 5 (1.16 g, 3.94 mmol) in tetrahydrofuran (20 mL). The reaction was heated at reflux for one hour and then cooled to room temperature and concentrated. The residue was dissolved in ethyl acetate (~100 mL) and washed with aqueous ammonium chloride solution (1×~100 mL) and brine (1×~100 mL). The organic layer was then dried (MgSO$_4$) and concentrated to afford crude product which was purified by automated flash chromatography (Combiflash instrument; 0 to 100% ethyl acetate in dichloromethane followed by 0 to 5% methanol in dichloromethane; 40 g silica column) to afford the title compound as an amber oil (1.30 g, 76%). MS: 437 m/z (M+H$^+$).

Step 2: 5-(cis-3-Hydroxycyclobutoxy)-N-methyl-7-(trifluoromethyl)thieno[3,2-b]pyridine-3-carboxamide A stirred mixture of step 1 product (1.30 g, 2.98 mmol), ethanol (30 mL), acetic acid (171 μL, 2.98 mmol) and 20% palladium hydroxide on carbon (50% water) (0.500 g) was cycled between vacuum and a nitrogen atmosphere three times. The vessel was evacuated a final time and refilled with hydrogen (via balloon). The reaction was stirred under the hydrogen atmosphere overnight and then suction filtered through a plug of Celite and concentrated. The residue was partitioned between ethyl acetate and aqueous sodium bicarbonate solution. The organic layer was combined with an additional extract (ethyl acetate), dried (MgSO$_4$) and concentrated. The crude product was purified by automated flash chromatography (Biotage system; 0 to 100% ethyl acetate in dichloromethane; 25 g silica column) to afford the title compound as an off-white solid (0.495 g, 48%). $^1$H NMR (400 MHz, CDCl$_3$) δ 9.13 (br s, 1H), 8.74 (s, 1H), 7.11 (s, 1H), 4.99-4.73 (m, 1H), 4.36-4.17 (m, 1H), 3.10 (d, J=4.9 Hz, 3H), 3.08-2.99 (m, 2H), 2.34-2.21 (m, 2H), 1.98 (d, J=6.0 Hz, 1H) ppm. MS: 347 m/z (M+H$^+$).

Step 3: cis-3-((3-(Methylcarbamoyl)-7-(trifluoromethyl)thieno[3,2-b]pyridin-5-yl)oxy)cyclobutyl 1H-imidazole-1-carboxylate To a stirred solution of step 2 product (0.495 g, 1.43 mmol) in dichloromethane (15 mL) was added 1,1'-carbonyldiimidazole (0.301 g, 1.86 mmol). The mixture was stirred at room temperature for two hours and then diluted with additional dichloromethane and washed with water and brine. The organic layer was dried (MgSO$_4$) and concentrated to furnish crude product. This material was purified by flash chromatography (Combiflash instrument; 0 to 100% ethyl acetate in dichloromethane followed by 2 to 5% methanol in dichloromethane; 25 g silica column). The title compound was obtained as a white solid (0.458 g, 73%). MS: 441 m/z (M+H$^+$).

Intermediate 29: N-Methyl-5-(piperidin-4-yl)-7-(trifluoromethyl)thieno[3,2-b]pyridine-3-carboxamide hydrochloride

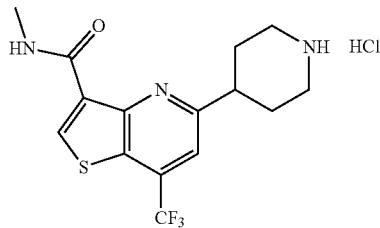 [SMILES: CNC(=O)c1csc2c(C(F)(F)F)cc(C3CCNCC3)nc12 ; Cl]

Step 1: tert-Butyl 4-(3-(methylcarbamoyl)-7-(trifluoromethyl)thieno[3,2-b]pyridin-5-yl)piperidine-1-carboxylate A 20 mL microwave reaction vial equipped with a stir bar was loaded the title compound of Example 274 (0.633 g, 1.42 mmol) and a 2.0 N methylamine in methanol solution (14.0 mL, 28.0 mmol). The vessel was sealed and heated in a microwave reactor for three hours at 90° C. The mixture was then concentrated to afford the crude title compound as a foamy, brown solid (0.631 g, 100%). $^1$H NMR (400 MHz, CDCl$_3$) δ 9.53 (br s, 1H), 8.82 (s, 1H), 7.49 (s, 1H), 4.33 (br s, 2H), 3.12 (d, J=5.1 Hz, 3H), 3.06-3.18 (m, 1H), 2.84-3.00 (m, 2H), 2.01-2.10 (m, 2H), 1.76-1.90 (m, 2H), 1.51 (s, 9H) ppm. $^{19}$F NMR (376 MHz, CDCl$_3$) δ −64.0 (s) ppm. MS: 444 m/z (M+H$^+$).

Step 2: N-Methyl-5-(piperidin-4-yl)-7-(trifluoromethyl)thieno[3,2-b]pyridine-3-carboxamide hydrochloride To a stirred solution of step 1 product (0.463 g, 1.04 mmol) in methanol (3.0 mL) was added a 1.2 M solution of hydrogen chloride in methanol (15.0 mL, 18.0 mmol). The reaction was allowed to proceed at room temperature over a weekend and then concentrated to afford a yellow oil. This material was redissolved in methanol (2.0 mL) and the solution was added to vigorously stirred diethyl ether (50 mL). The resulting suspension was briefly sonicated to disperse the aggregated solid and then suction filtered. The collected solid was rinsed with additional diethyl ether (~10 mL) and then dried under high vacuum to afford the title compound as a light yellow solid (0.338 g, 85%). $^1$H NMR (400 MHz, Methanol-d$_4$) δ 8.92 (s, 1H), 7.83 (s, 1H), 3.60 (d, J=12.5 Hz, 2H), 3.48 (tt, J=11.8, 3.5 Hz, 1H), 3.18-3.33 (m, 3H), 2.28-2.39 (m, 2H), 2.11-2.26 (m, 2H) ppm. $^{19}$F NMR (376 MHz, CDCl$_3$) δ −65.4 (s) ppm. MS: 344 m/z (M+H$^+$).

Intermediate 31: (+/−)-5-(trans-3-Fluoro-4-hydroxypiperidin-1-yl)-N-methyl-7-(trifluoromethyl)thieno[3,2-b]pyridine-3-carboxamide

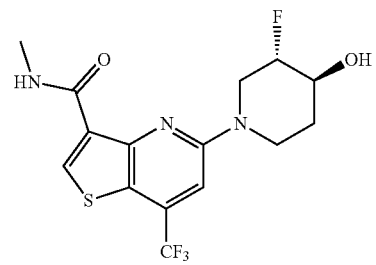 [SMILES: CNC(=O)c1csc2c(C(F)(F)F)cc(N3CC[C@H](O)[C@@H](F)C3)nc12]

A 20 mL microwave reaction vial equipped with a stir bar was loaded Intermediate 5 (1.20 g, 4.07 mmol), (+/−)-trans-3-fluoropiperidin-4-ol hydrochloride (0.824 g, 5.29 mmol), N-methyl-2-pyrrolidinone (14 mL) and N,N-diisopropylethylamine (2.1 mL, 12 mmol). The vessel was sealed and heated in a microwave reactor for three hours at 150° C. The mixture was then cooled and taken up in ethyl acetate (80 mL). The solution was washed with water (4×20 mL) and aqueous ammonium chloride solution (1×20 mL). The organic layer was dried (Na$_2$SO$_4$) and concentrated, yielding crude product as a brown solid. This material was taken up in diethyl ether and the resulting suspension was sonicated and suction filtered. The collected solid was air dried on the frit under house vacuum to afford the title compound as a reddish solid (1.26 g, 82%). $^1$H NMR (400 MHz, CDCl$_3$) δ 9.33 (s, 1H), 8.68 (s, 1H), 7.08 (d, J=1.2 Hz, 1H), 4.53 (dddd, J=49.0, 8.4, 7.1, 4.3 Hz, 1H), 4.44-4.30 (m, 1H), 4.21-3.99 (m, 2H), 3.53-3.31 (m, 2H), 3.09 (d, J=4.9 Hz, 3H), 2.48 (d, J=3.8 Hz, 1H), 2.33-2.11 (m, 1H), 1.76 (dtd, J=13.7, 9.7, 4.2 Hz, 1H) ppm. MS: 378 m/z (M+H$^+$).

Intermediate 32: Methyl 5,7-dichlorothieno[3,2-b]pyridine-3-carboxylate

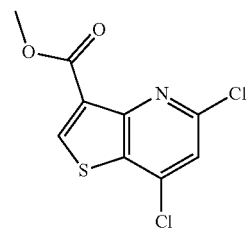

Methyl 4-aminothiophene-3-carboxylate hydrochloride (2.55 g, 13.2 mmol) and malonic acid (1.37 g, 13.2 mmol) were taken up in phosphorus oxychloride (40 mL, 430 mmol). The stirred mixture was heated overnight at 90° C. and then cooled to room temperature and slowly added to a vigorously stirred slurry of crushed ice and water (~250 mL). After the ice had fully melted, the mixture was neutralized by the slow, portionwise, addition of solid sodium bicarbonate. The resulting suspension was extracted with dichloromethane (3×75 mL). The combined organic layers were washed with water (1×100 mL), dried (MgSO$_4$) and filtered. Activated carbon (~1.0 g) was added to the solution and the mixture was stirred at room temperature for 20 minutes. After removing the carbon via suction filtration through Celite, the solution was concentrated. The crude, brown solid was purified by automated flash chromatography (Combiflash system; 0 to 80% ethyl acetate in heptane; 120 g silica column) to afford the title compound as pale amber solid (1.97 g, 57%). $^1$H NMR (400 MHz, CDCl$_3$) δ 8.67 (s, 1H), 7.44 (s, 1H), 4.00 (s, 3H) ppm. MS: 263 m/z (M+H$^+$).

Intermediate 33: 5,7-Dichloro-N-methylthieno[3,2-b]pyridine-3-carboxamide

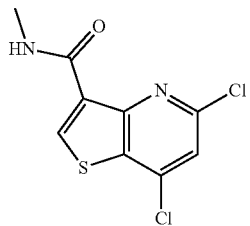

Intermediate 32 (3.10 g, 11.8 mmol) was combined with a 2.0 N solution of methylamine in methanol (25.0 mL, 50.0 mmol) in a sealed reaction flask. The mixture was stirred at room temperature for 20 hours and then concentrated. The resulting solid was purified by automated flash chromatography (Biotage system; 0 to 70% ethyl acetate in heptane; 120 g silica column) to afford the title compound as a pale yellow solid (1.93 g, 63%). $^1$H NMR (400 MHz, CDCl$_3$) δ 8.95 (s, 1H), 8.79 (s, 1H), 7.43 (s, 1H), 3.10 (d, J=4.8 Hz, 3H) ppm. MS: 262 m/z (M+H$^+$).

Intermediate 34: Methyl 5-chloro-7-(difluoromethyl)thieno[3,2-b]pyridine-3-carboxylate

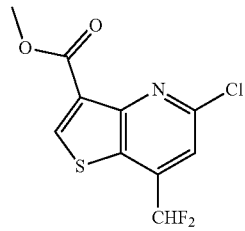 [SMILES: COC(=O)c1csc2c(C(F)F)cc(Cl)nc12]

A 20 mL microwave reaction vessel equipped with a stir bar was loaded methyl 4-aminothiophene-3-carboxylate hydrochloride (0.281 g, 1.45 mmol), ethyl 4,4-difluoro-3-oxobutanoate (0.482 g, 2.90 mmol) and phosphorus oxychloride (2.0 mL, 21 mmol). The vessel was sealed and heated in a microwave reactor for six hours at 90° C. The black mixture was cooled to room temperature and slowly added, via pipet, to a vigorously stirred slurry of crushed ice and water (~40 mL). After the ice had fully melted, the mixture was neutralized by the slow, portionwise, addition of solid sodium bicarbonate. The resulting suspension was extracted with ethyl acetate (1×40 mL). The organic layer was washed with water (2×20 mL) and brine (1×10 mL), dried (MgSO$_4$) and filtered. Activated carbon (~0.5 g) was added to the solution and the mixture was stirred at room temperature for 20 minutes. After removing the carbon via suction filtration through Celite, the solution was concentrated. The crude material obtained was purified by automated flash chromatography (Biotage system; 0 to 40% ethyl acetate in heptane; 40 g silica column) to afford the title compound as a pale yellow solid (0.125 g, 31%). MS: 278 m/z (M+H$^+$).

Preparation of Compounds

Example 10: Methyl 5-(4-(2-(isopropylamino)-2-oxoethyl)piperazin-1-yl)-7-(trifluoromethyl)thieno[3,2-b]pyridine-3-carboxylate

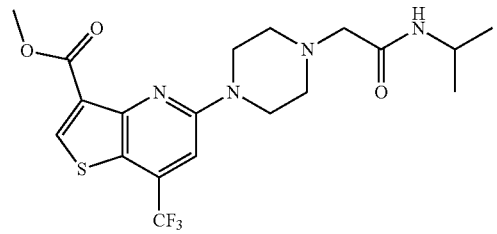 [SMILES: COC(=O)c1csc2c(C(F)(F)F)cc(N3CCN(CC(=O)NC(C)C)CC3)nc12]

Step 1: Methyl 5-(4-(2-(benzyloxy)-2-oxoethyl)piperazin-1-yl)-7-(trifluoromethyl)thieno[3,2-b]pyridine-3-carboxylate To a stirred solution of Intermediate 3 (0.642 g, 2.17 mmol) in N,N-dimethylformamide (15 mL) was added benzyl 2-(piperazin-1-yl)acetate dihydrochloride (800 mg, 2.60 mmol) followed potassium carbonate (0.900 g, 6.51 mmol). The reaction was heated overnight at 90° C. and then concentrated. The residue was partitioned between aqueous sodium bicarbonate solution (~60 mL) and ethyl acetate (~40 mL). The organic layer was combined with a back-extract of the aqueous layer (ethyl acetate, 1×~40 mL), dried (Na$_2$SO$_4$) and concentrated. The crude product was purified by automated flash chromatography (Combiflash system; 30 to 50% ethyl acetate in heptane; 40 g silica column) to afford the title compound (R$_f$~0.25 with 1:1 heptane/ethyl acetate as the eluant) as a pale yellow solid (0.611 g, 48%). $^1$H NMR (400 MHz, CDCl$_3$) δ 8.56 (s, 1H), 7.44-7.29 (m, 5H), 6.98 (s, 1H), 5.19 (s, 2H), 3.95 (s, 3H), 3.88-3.77 (m, 4H), 3.35 (s, 2H), 2.82-2.69 (m, 4H) ppm.

Step 2: 2-(4-(3-(Methoxycarbonyl)-7-(trifluoromethyl)thieno[3,2-b]pyridin-5-yl)piperazin-1-yl)acetic acid To a stirred solution of the of the step 1 product (0.610 g, 1.24 mmol) in a mixture of methanol (25 mL) and ethyl acetate (25 mL) was added 10% palladium on carbon (50% water; 0.300 g). The mixture was cycled between vacuum and a nitrogen atmosphere three times before evacuating a final time and backfilling the reaction vessel with hydrogen (via balloon). After 30 minutes the reaction was analyzed by TLC and found to be complete. The reaction was suction filtered through a plug of Celite which was subsequently rinsed with methanol. The combined filtrate was concentrated to afford crude title compound as a light yellow solid (0.489 g, 98%). This material was deemed to be of sufficient purity to use, without further processing, in the next step. $^1$H NMR (400 MHz, DMSO-$d_6$) δ 12.20 (s, 1H), 8.89 (s, 1H), 7.37 (s, 1H), 3.86 (s, 3H), 3.82-3.71 (m, 4H), 3.24 (s, 2H), 2.78-2.61 (m, 4H) ppm.

Step 3: Methyl 5-(4-(2-(isopropylamino)-2-oxo-ethyl)piperazin-1-yl)-7-(trifluoromethyl)thieno[3,2-b]pyridine-3-carboxylate To a stirred solution of the step 2 product (0.100 g, 0.247 mmol) and isopropylamine (0.021 g, 0.355 mmol) in N,N-dimethylformamide (5 mL) was added O-(7-azabenzotri-azol-1-yl)-N,N,N',N'-tetramethyluronium hexafluorophosphate (HATU; 0.104 g, 0.274 mmol). The mixture was cooled to 0° C. and treated, via dropwise addition, with triethylamine (0.15 mL, 1.1 mmol). The cooling bath was removed and the reaction was allowed to slowly warm to room temperature. Stirring was continued overnight. After this time, the reaction was concentrated and the residue was partitioned between aqueous sodium carbonate solution (~50 mL) and ethyl acetate (~40 mL). The organic layer was combined with an additional extract (ethyl acetate, 1×~40 mL), dried ($Na_2SO_4$) and concentrated. The crude product was purified by automated flash chromatography (Combi-flash system; 5 to 10% methanol in ethyl acetate; 40 g Gold silica column) to afford the title compound ($R_f$~0.65 with 9:1 ethyl acetate/methanol as the eluant) as a yellow solid (0.038 g, 35%). $^1$H NMR (400 MHz, $CDCl_3$) δ 8.57 (s, 1H), 7.01 (s, 1H), 6.94 (d, J=8.5 Hz, 1H), 4.19-4.08 (m, 1H), 3.96 (s, 3H), 3.83-3.75 (m, 4H), 3.06 (s, 2H), 2.74-2.65 (m, 4H), 1.19 (d, J=6.5 Hz, 6H) ppm. MS: 445 m/z (M+H$^+$).

Example 25: 5-(4-(2-(Ethylamino)-2-oxoethyl)piperazin-1-yl)-N-methyl-7-(trifluoromethyl)thieno[3,2-b]pyridine-3-carboxamide

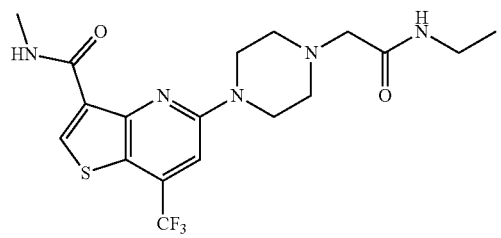 [SMILES: CCNC(=O)CN1CCN(c2cc(C(F)(F)F)c3scc(C(=O)NC)c3n2)CC1]

Step 1: Methyl 5-(4-(2-(ethylamino)-2-oxoethyl)piperazin-1-yl)-7-(trifluoromethyl)thieno[3,2-b]pyridine-3-carboxylate Using the procedure for HATU mediated amide coupling described in step 3 of Example 10, the step 2 product of Example 10 was condensed with ethylamine hydrochloride to afford the title compound as a light yellow solid. $^1$H NMR (400 MHz, $CDCl_3$) δ 8.57 (s, 1H), 7.12 (br s, 1H), 7.01 (s, 1H), 3.95 (s, 3H), 3.83-3.75 (m, 4H), 3.41-3.32 (m, 1H), 3.09 (s, 2H), 2.73-2.66 (m, 4H), 1.18 (t, J=7.3 Hz, 3H) ppm.

Step 2: 5-(4-(2-(Ethylamino)-2-oxoethyl)piperazin-1-yl)-N-methyl-7-(trifluoromethyl)thieno-[3,2-b]pyridine-3-carboxamide Into a 20 mL microwave reaction vial equipped with a stir bar was loaded step 1 product (0.150 g, 0.348 mmol) and 2.0 N solution of methylamine in methanol (8.0 mL, 16 mmol). The vessel was sealed and heated in a microwave reactor for one hour at 90° C. TLC analysis indicated that the reaction was complete. The reaction mixture was concentrated and the residue was purified by automated flash (Combiflash system; 0 to 5% methanol in dichloromethane; 40 g Gold silica column) to afford the title compound ($R_f$~0.35 with 19:1 dichloromethane/methanol as the eluant) as a faint yellow solid (0.129 g, 86%). $^1$H NMR (400 MHz, $CDCl_3$) δ 9.32 (br s, 1H), 8.68 (s, 1H), 7.11-6.99 (m, 2H), 3.73-3.66 (m, 4H), 3.42-3.32 (m, 2H), 3.12 (s, 2H), 3.08 (d, J=4.9 Hz, 3H), 2.79-2.71 (m, 4H), 1.20 (t, J=7.3 Hz, 3H) ppm. MS: 430 m/z (M+H$^+$).

Example 39. (+/−)-5-(4-(2-(Cyclopropylmethoxy)propyl)piperazin-1-yl)-N-methyl-7-(trifluoromethyl)thieno[3,2-b]pyridine-3-carboxamide

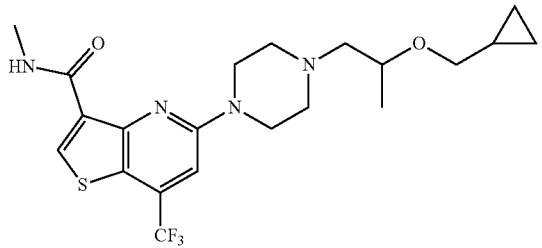 [SMILES: CNC(=O)c1csc2c(C(F)(F)F)cc(N3CCN(CC(C)OCC4CC4)CC3)nc12]

Step 1: (+/−)-tert-Butyl 4-(2-(cyclopropylmethoxy)propyl)piperazine-1-carboxylate To a stirred solution of tert-butyl 4-(2-hydroxypropyl)piperazine-1-carboxylate (0.750 g, 3.07 mmol) in tetrahydrofuran (30 mL) was added a 60% dispersion of sodium hydride in mineral oil (0.147 g, 3.68 mmol). The suspension was stirred at room temperature for one hour before adding (bromomethyl)cyclopropane (0.45 mL, 4.6 mmol) via syringe. The reaction was heated overnight at reflux. TLC analysis indicated that the reaction contained about equal portions of starting material and product, as judged by relative spot intensity (visualized by iodine staining). Additional sodium hydride (0.123 g, 3.08 mmol) and alkyl bromide (0.30 mL, 3.09 mmol) were added, ~30 minutes apart, to the stirred reaction. The mixture was returned to reflux for another night. After this time, the reaction was concentrated and partitioned between aqueous sodium carbonate solution (~40 mL) and chloroform (~40 mL). The organic layer was combined with additional extracts (chloroform, 2×~40 mL), dried (Na$_2$SO$_4$) and concentrated. The residue was subjected to automated flash chromatography (Combiflash system; isocratic 3% 2N ammonia/methanol in dichloromethane; 40 g Gold silica column) to afford the purified title compound (R$_f$~0.4 with 19:1 dichloromethane/2N ammonia in methanol as the eluant) as a colorless oil (0.781 g, 85%). $^1$H NMR (400 MHz, CDCl$_3$) δ 3.65-3.57 (m, 1H), 3.45-3.39 (m, 4H), 3.35 (dd, J=10.1, 6.8 Hz, 1H), 3.27 (dd, J=10.1, 6.8 Hz, 1H), 2.55-2.37 (m, 4H), 2.30 (dd, J=13.0, 5.0 Hz, 1H), 1.46 (s, 9H), 1.15 (d, J=6.2 Hz, 3H) ppm.

Step 2: (+/−)-1-(2-(Cyclopropylmethoxy)propyl)piperazine

To a stirred solution of the step 1 product (0.780 g, 2.61 mmol) in dichloromethane (12 mL) was added trifluoroacetic acid (4.0 mL, 52 mmol). After 2 hours, the reaction was analyzed by TLC and found to be complete. The mixture was concentrated and the residue was partitioned between aqueous sodium carbonate solution (~40 mL) and chloroform (~40 mL). The organic layer was combined with additional extracts (chloroform, 3×~40 mL), dried (Na$_2$SO$_4$) and concentrated to afford crude title compound as a colorless oil (0.527 g, 102%). $^1$H NMR (400 MHz, CDCl$_3$) δ 3.68-3.56 (m, 1H), 3.35 (dd, J=10.1, 6.8 Hz, 1H), 3.28 (dd, J=10.1, 6.9 Hz, 1H), 2.88 (t, J=4.9 Hz, 3H), 2.57-2.37 (m, 5H), 2.27 (dd, J=12.9, 5.1 Hz, 1H), 1.15 (d, J=6.2 Hz, 3H), 1.10-0.99 (m, 1H), 0.57-0.47 (m, 2H), 0.22-0.16 (m, 2H) ppm.

Step 3: (+/−)-5-(4-(3-Cyclopropoxy-2-methylpropyl)piperazin-1-yl)-N-methyl-7-(trifluoromethyl)thieno[3,2-b]pyridine-3-carboxamide A 20 mL microwave reaction vial equipped with a stir bar was loaded with Intermediate 5 (0.250 g, 0.848 mmol), step 2 product (0.294 g, 1.48 mmol), N,N-diisopropylethylamine (0.30 mL, 1.7 mmol) and N-methyl-2-pyrrolidinone (6 mL). The vessel was sealed and heated in a microwave reactor at 130° C. for two hours. TLC analysis indicated the reaction was complete. The mixture was concentrated and the residue was partitioned between chloroform (~30 mL) and aqueous sodium carbonate solution (~50 mL). The organic layer was combined with additional extracts (chloroform, 2×~30 mL), dried (Na$_2$SO$_4$) and concentrated. The crude material was subjected to automated flash chromatography (Combiflash system; isocratic, 2.5% methanol in dichloromethane; 40 g Gold silica column), providing the target component (R$_f$~0.4 with 19:1 dichloromethane/methanol as the eluant) as a viscous red-brown oil. This material was co-evaporated with ethyl acetate and vacuum oven dried (~70° C.) to afford the title compound as a red-brown gum (0.266 g, 69%). $^1$H NMR (400 MHz, CDCl$_3$) δ 9.44 (br s, 1H), 8.65 (s, 1H), 7.03 (s, 1H), 3.74-3.58 (m, 5H), 3.39 (dd, J=10.1, 6.9 Hz, 1H), 3.31 (dd, J=10.1, 6.9 Hz, 1H), 3.08 (d, J=4.9 Hz, 3H), 2.80-2.65 (m, 4H), 2.60 (dd, J=13.0, 6.8 Hz, 1H), 2.41 (dd, J=13.0, 4.8 Hz, 1H), 1.20 (d, J=6.2 Hz, 3H), 1.12-1.02 (m, 1H), 0.59-0.50 (m, 2H), 0.25-0.17 (m, 2H) ppm. MS: 457 m/z (M+H$^+$).

Example 44. 5-(4-(2-Isopropoxyacetyl)piperazin-1-yl)-N-methyl-7-(trifluoromethyl)thieno[3,2-b]pyridine-3-carboxamide

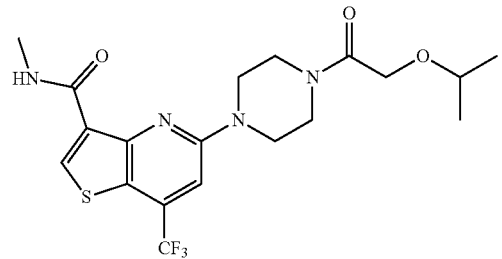 [SMILES: CNC(=O)c1csc2c(C(F)(F)F)cc(N3CCN(C(=O)COC(C)C)CC3)nc12]

Step 1: tert-Butyl 4-(2-bromoacetyl)piperazine-1-carboxylate

To a stirred and cooled (0° C.) solution of 2-bromoacetyl bromide (1.72 mL, 19.8 mmol) in dichloromethane (25 mL) was added a solution of tert-butyl piperazine-1-carboxylate (7.75 g, 41.6 mmol) in dichloromethane (20 mL), dropwise over ~20 minutes. The cooling bath was then removed and the reaction was allowed to stir another two hours before transferring to a separatory funnel along with a dichloromethane rinse of the reaction flask (~30 mL). The solution was washed with 1.0 N hydrochloric acid (2×~50 mL) and aqueous sodium bicarbonate solution (1×~50 mL). The organic layer was dried (Na$_2$SO$_4$) and concentrated to afford title compound as a clear, faint amber gum (5.68 g, 93%). The crude intermediate was deemed sufficiently pure to use, without purification, in the next step. $^1$H NMR (400 MHz, CDCl$_3$) δ 3.87 (s, 2H), 3.63-3.57 (m, 2H), 3.55-3.41 (m, 6H), 1.48 (s, 9H) ppm.

Step 2: tert-Butyl 4-(2-isopropoxyacetyl)piperazine-1-carboxylate

To a stirred and cooled (0° C.) solution of the step 1 product (2.00 g, 6.51 mmol) and isopropanol (0.50 mL, 6.5 mmol) in N,N-dimethylformamide (60 mL) was added a 60% dispersion of sodium hydride in mineral oil (0.290 g, 7.25 mmol). The mixture was allowed to slowly warm to room temperature and stirred overnight. The reaction was then concentrated and partitioned between water (~100 mL) and ethyl acetate (~50 mL). The organic layer was combined with a second extract (ethyl acetate, 1×~30 mL), dried (Na$_2$SO$_4$) and concentrated to afford a pale amber gum. The crude product subjected to automated flash chromatography (Combiflash system; 50 to 75% ethyl acetate in heptane; 80 g Gold silica column) to afford purified title compound (R$_f$~0.6 with 3:1 ethyl acetate/heptane as the eluant) as colorless gum which slowly solidified to a white solid (0.515 g, 28%; low yield was the result of failed triggering of automatic fraction collection due to the compound's weak UV activity). $^1$H NMR (400 MHz, CDCl$_3$) 4.13 (s, 2H), 3.67 (hept, J=6.1 Hz, 1H), 3.61-3.51 (m, 4H), 3.48-3.39 (m, 4H), 1.47 (s, 9H), 1.19 (d, J=6.1 Hz, 3H) ppm.

Step 3: 2-Isopropoxy-1-(piperazin-1-yl)ethan-1-one

Into a stirred solution of step 2 product (0.504 g, 1.76 mmol) in ethyl acetate (30 mL) was bubbled hydrogen chloride gas for approximately five minutes. After two hours, the reaction was analyzed by ¹H NMR and found to be complete. The reaction was concentrated and the residue was partitioned between aqueous sodium carbonate solution (~50 mL) and chloroform (~30 mL). The organic layer was combined with additional extracts (chloroform, 3×~30 mL), dried (Na₂SO₄) and concentrated to afford the title compound as a viscous, faint amber oil (0.317 g, 97%). The crude intermediate was deemed sufficiently pure to use, without purification, in the next step. ¹H NMR (400 MHz, CDCl₃) δ 4.13 (s, 2H), 3.63-3.57 (m, 2H), 2.98-2.86 (m, 4H), 1.19 (d, J=6.1 Hz, 6H) ppm.

Step 4: 5-(4-(2-Isopropoxyacetyl)piperazin-1-yl)-N-methyl-7-(trifluoromethyl)thieno[3,2-b]pyridine-3-carboxamide Using the conditions described in step 3 of Example 39, Intermediate 5 was subjected to S$_N$Ar displacement with a piperazine derivative, the step 3 product of the present Example, to afford the title compound as a light yellow solid. ¹H NMR (400 MHz, CDCl₃) δ 9.28 (br s, 1H), 8.69 (s, 1H), 7.06 (s, 1H), 4.22 (s, 2H), 3.89-3.80 (m, 4H), 3.77-3.64 (m, 5H), 3.09 (d, J=4.9 Hz, 3H), 1.23 (d, J=6.1 Hz, 6H) ppm. MS: 445 m/z (M+H⁺).

Example 47. 5-(4-(2-(Isopropylamino)-2-oxoethyl)piperazin-1-yl)-N,6-dimethyl-7-(trifluoromethyl)thieno[3,2-b]pyridine-3-carboxamide

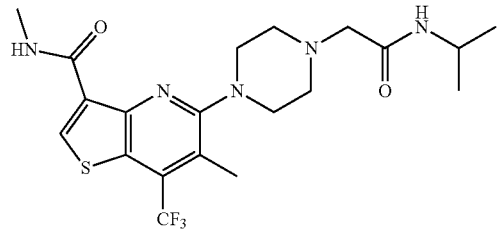 [SMILES: CNC(=O)c1csc2c(C(F)(F)F)c(C)c(N3CCN(CC(=O)NC(C)C)CC3)nc12]

Step 1: tert-Butyl 4-(2-(isopropylamino)-2-oxoethyl)piperazine-1-carboxylate

To a stirred solution of tert-butyl piperazine-1-carboxylate (5.85 g, 31.4 mmol) and 2-bromo-N-isopropylacetamide (5.94 g, 33.0 mmol) in acetonitrile (200 mL) was added sodium carbonate (4.99 g, 47.1 mmol). The mixture was heated at reflux overnight and then cooled to room temperature. TLC analysis indicated that the reaction was complete. The mixture was suction filtered to remove solids, which were then rinsed with ethyl acetate (3×~25 mL). The combined filtrate was concentrated to afford an oil. This material was partitioned between aqueous sodium carbonate solution (~100 mL) and ethyl acetate (~150 mL). The organic layer was combined with additional extracts (ethyl acetate, 2×~100 mL), dried (Na₂SO₄) and concentrated to afford crude product as an off-white solid (8.70 g, 97%). This material was deemed to be of sufficient purity to use, without further processing, in the next step. ¹H NMR (400 MHz, CDCl₃) δ 6.87 (d, J=6.2 Hz, 1H), 4.17-4.04 (m, 1H), 3.51-3.38 (m, 4H), 2.98 (s, 2H), 2.54-2.38 (m, 4H), 1.46 (s, 9H), 1.17 (d, J=6.6 Hz, 6H) ppm.

Step 2: N-isopropyl-2-(piperazin-1-yl)acetamide

The crude step 1 product was dissolved in ethyl acetate (300 mL). Into this stirred solution was bubbled hydrogen chloride for approximately five minutes. After another two hours the reaction was analyzed by TLC and found to still contain a minor portion of N-tert-butoxycarbonyl protected starting material. The reaction mixture was saturated with hydrogen chloride gas as before and stirred for another one hour. The mixture was then concentrated and the residue was partitioned between chloroform (~100 mL) and aqueous sodium carbonate solution (~200 mL). The organic layer was combined with additional extracts (chloroform, 5×~100 mL), dried (Na₂SO₄) and concentrated to afford crude product as an off-white solid. This material was subjected by automated flash chromatography (Combiflash system; 10% methanol in chloroform until the impurity spots had eluted and then 10 to 15% 2N ammonia/methanol in chloroform; 120 g silica column) to afford purified title compound (R$_f$~0.2 with 9:1 chloroform/2N ammonia in methanol as the eluant) as pale yellow solid (4.41 g, 77%). ¹H NMR (300 MHz, DMSO-d₆) δ 7.37 (d, J=8.1 Hz, 1H), 3.95-3.79 (m, 1H), 2.81 (s, 2H), 2.76-2.62 (m, 4H), 2.38-2.24 (m, 4H), 2.13 (br s, 1H), 1.07 (d, J=6.6 Hz, 6H) ppm.

Step 3: Methyl 5-(4-(2-(isopropylamino)-2-oxoethyl)piperazin-1-yl)-6-methyl-7-(trifluoromethyl)thieno[3,2-b]pyridine-3-carboxylate Into a 20 mL microwave reaction vial equipped with a stir bar was loaded Intermediate 14 (0.300 g, 0.969 mmol), step 2 product (0.314 g, 1.69 mmol), N-methyl-2-pyrrolidinone (6 mL) and N,N-diisopropylethylamine (0.34 mL, 2.0 mmol). The vessel was sealed and heated in a microwave reactor for two hours at 130° C. LCMS analysis indicated that significant step 2 product remained unreacted. Additional N-isopropyl-2-(piperazin-1-yl)acetamide (0.180 g, 0.972 mmol) was added to the reaction and microwave heating was continued for another two hours. The reaction was then concentrated and the residue was partitioned between aqueous sodium carbonate solution (~25 mL) and chloroform (~25 mL). The organic layer was combined with an additional extract (chloroform, 1×~25 mL), dried (Na₂SO₄) and concentrated. The crude material was subjected to automated flash chromatography (Combiflash system; 0 to 3% methanol in ethyl acetate; 40 g Gold silica column), providing the purified title compound (R$_f$~0.4 with 97:3 ethyl acetate/methanol as the eluant) as a tan solid (0.208 g, 47%). ¹H NMR (400 MHz, CDCl₃) δ 8.53 (s, 1H), 7.03 (d, J=8.2 Hz, 1H), 4.18-4.07 (m, 1H), 3.97 (s, 3H), 3.41-3.28 (m, 4H), 3.08 (s, 2H), 2.82-2.71 (m, 4H), 2.56-2.50 (m, 3H), 1.18 (d, J=6.5 Hz, 6H) ppm.

Step 4: 5-(4-(2-(Isopropylamino)-2-oxoethyl)piperazin-1-yl)-N,6-dimethyl-7-(trifluoromethyl)-thieno[3,2-b]pyridine-3-carboxamide Using the procedure described for step 2 of Example 25, the methyl ester functionality of the step 3 product was converted to the corresponding N-methyl carboxamide, affording the title compound as a tan solid. ¹H NMR (400 MHz, CDCl₃) δ 9.48 (br s, 1H), 8.64 (s, 1H), 6.90 (d, J=8.4 Hz, 1H), 4.21-4.08 (m, 1H), 3.37-3.21 (m, 4H), 3.18-3.03 (m, 5H), 2.87-2.72 (m, 3H), 2.61-2.49 (m, 2H), 1.20 (d, J=6.5 Hz, 6H) ppm. MS: 458 m/z (M+H⁺).

Example 48. 5-(4-(2-(Isopropylamino)-2-oxoethyl) piperazin-1-yl)-N,7-dimethylthieno[3,2-b]pyridine-3-carboxamide

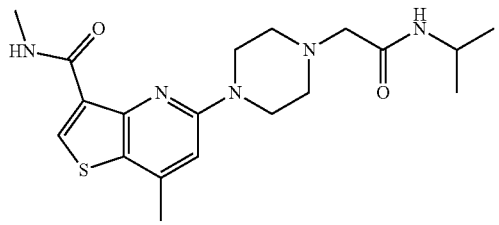 [SMILES: CNC(=O)c1csc2c(C)cc(N3CCN(CC(=O)NC(C)C)CC3)nc12]

Step 1: Methyl 7-methyl-5-oxo-4,5-dihydrothieno[3,2-b]pyridine-3-carboxylate Into a 100 mL round bottom flask equipped with a stir bar was loaded methyl 4-aminothiophene-3-carboxylate (4.99 g, 31.8 mmol), ethyl acetoacetate (7.70 mL, 60.9 mmol) and water (1 mL). The mixture was added stirred at room temperature for a few minutes and then placed into a preheated oil bath (125° C.). The reaction flask was fitted was a reflux condenser (no circulating coolant so volatile components could escape after the condenser warmed sufficiently). After six hours, additional portions of ethyl acetoacetate (2.00 mL, 15.8 mmol) and water (1.0 mL) were added to the mixture and the reaction was allowed to proceed over a weekend (~64 hours, total). After this time, the reaction analyzed by LCMS and found to be complete. The mixture was partitioned between chloroform (~200 mL) and aqueous sodium bicarbonate solution (~200 mL). The organic layer was combined with additional extracts (chloroform, 2×~100 mL), dried ($Na_2SO_4$) and concentrated to afford a moist, rust-colored solid. This material was taken up in a mixture of heptane (~120 mL) and ethyl acetate (~20 mL) and sonicated until a homogenous suspension was achieved. The suspended solid was suction filtered off and rinsed with additional heptane (2×~20 mL). The filtercake was air dried on the frit under house vacuum, affording an amber solid. The material was further purified by trituration with a mixture of diethyl ether (~75 mL) and ethyl acetate (~20 mL). Again, the suspended solid was collected by suction filtration and air dried on the frit under house vacuum. The title compound was afforded as a salmon colored solid (3.34 g, 50%). $^1$H NMR (400 MHz, DMSO-$d_6$) δ 10.39 (br s, 1H), 8.69 (s, 1H), 6.33 (s, 1H), 3.90 (s, 3H), 2.37 (s, 3H) ppm.

Step 2: Methyl 7-methyl-5-(((trifluoromethyl)sulfonyl)oxy)thieno[3,2-b]pyridine-3-carboxylate To a stirred and cooled (0° C.) solution of step 1 product (3.28 g, 14.7 mmol) in pyridine (40 mL) was added trifluoromethanesulfonic anhydride (3.10 mL, 18.4 mmol), dropwise over 4-5 minutes. The mixture was allowed to slowly warm to room temperature and stirred overnight. The reaction was then concentrated and the residue was partitioned between water (~125 mL) and chloroform (~75 mL). The organic layer was combined with additional extracts (chloroform, 2×~75 mL), dried ($Na_2SO_4$) and concentrated to afford crude title compound as a light brown solid (5.26 g, 100%). $^1$H NMR analysis indicated that the material was sufficiently pure to use, without purification, in subsequent reactions. $^1$H NMR (400 MHz, CDCl$_3$) δ 8.72 (s, 1H), 7.06 (s, 1H), 3.99 (s, 3H), 2.69 (s, 3H) ppm.

Step 3: Methyl 5-(4-(2-(isopropylamino)-2-oxoethyl)piperazin-1-yl)-6-methyl-7-(trifluoromethyl)thieno[3,2-b]pyridine-3-carboxylate Into a 10 mL microwave reaction vial equipped with a stir bar was loaded step 2 product (0.400 g, 1.13 mmol), N-isopropyl-2-(piperazin-1-yl)acetamide (0.375 g, 2.02 mmol; prepared as described in step 2 of Example 47), N-methyl-2-pyrrolidinone (2.5 mL) and N,N-diisopropylethylamine (0.40 mL, 2.3 mmol). The vessel was sealed and heated in a microwave reactor for two hours at 90° C. TLC analysis indicated that the reaction was complete. The mixture was concentrated and the residue was partitioned between ethyl acetate (~25 mL) and aqueous sodium bicarbonate solution (~50 mL). The organic layer was combined with additional extracts (ethyl acetate, 2×~25 mL), dried ($Na_2SO_4$) and concentrated. The crude material was subjected to automated flash chromatography (Combiflash system; 0 to 10% methanol in ethyl acetate; 40 g Gold silica column), affording the purified title compound ($R_f$~0.2 with 96:4 dichloromethane/methanol as the eluant) as an amber solid (0.330 g, 75%). $^1$H NMR (400 MHz, CDCl$_3$) δ 8.45 (s, 1H), 7.00 (d, J=8.2 Hz, 1H), 6.63 (s, 1H), 4.18-4.08 (m, 1H), 3.95 (s, 3H), 3.76-3.69 (m, 4H), 3.05 (s, 2H), 2.72-2.62 (m, 4H), 2.51 (s, 3H), 1.19 (d, J=6.6 Hz, 6H) ppm.

Step 4: 5-(4-(2-(Isopropylamino)-2-oxoethyl)piperazin-1-yl)-N,7-dimethylthieno[3,2-b]pyridine-3-carboxamide Using the procedure described for step 2 of Example 25, the methyl ester functionality of the step 3 product was converted to the corresponding N-methyl carboxamide, affording the title compound as an off-white solid. $^1$H NMR (400 MHz, CDCl$_3$) δ 9.48 (br s, 1H), 8.64 (s, 1H), 6.90 (d, J=8.4 Hz, 1H), 4.21-4.08 (m, 1H), 3.37-3.21 (m, 4H), 3.18-3.03 (m, 5H), 2.87-2.72 (m, 3H), 2.61-2.49 (m, 2H), 1.20 (d, J=6.5 Hz, 6H) ppm. MS: 390 m/z (M+H$^+$).

Example 49. 5-(4-(2-(Isopropylamino)-2-oxoethyl)-3,3-dimethylpiperazin-1-yl)-N-methyl-7-(trifluoromethyl)thieno[3,2-b]pyridine-3-carboxamide

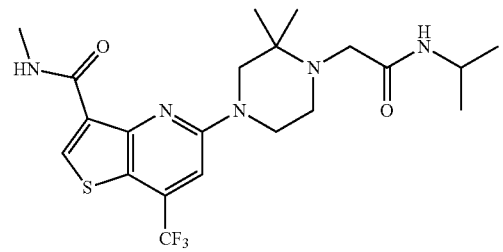 [SMILES: CNC(=O)c1csc2c(C(F)(F)F)cc(N3CCN(CC(=O)NC(C)C)C(C)(C)C3)nc12]

Step 1: tert-Butyl 4-(2-(isopropylamino)-2-oxoethyl)-3,3-dimethylpiperazine-1-carboxylate To a stirred solution of tert-butyl 3,3-dimethylpiperazine-1-carboxylate (1.00 g, 4.67 mmol) and 2-bromo-N-isopropylacetamide (0.882 g, 4.90 mmol) in butyronitrile (30 mL) was added sodium carbonate (0.742 g, 7.00 mmol). The mixture was heated at reflux overnight. TLC analysis indicated that the reaction was complete. The mixture was cooled to room temperature and suction filtered to remove the solids. The filtercake was rinsed with ethyl acetate (~30 mL) and the combined filtrate was concentrated. The residue was subjected to automated flash chromatography (Combiflash system; 0 to 5% 2N ammonia/methanol in dichloromethane; 80 g Gold silica column), affording the purified title compound ($R_f$~0.4 with 19:1 dichloromethane/2N ammonia in methanol as the eluant) as an off-white solid (1.37 g, 94%). $^1$H NMR (400 MHz, CDCl$_3$) δ 7.18 (d, J=8.4 Hz, 1H), 4.13-4.03 (m, 1H), 3.48-3.42 (m, 2H), 3.20 (br s, 2H), 2.96 (br s, 2H), 2.54-2.47 (m, 2H), 1.46 (s, 9H), 1.16 (d, J=6.6 Hz, 6H), 1.01 (s, 6H) ppm.

Step 2: 2-(2,2-Dimethylpiperazin-1-yl)-N-isopropylacetamide

Using the procedure described in step 3 of Example 44, the N-tert-butoxycarbonyl amine protecting group of the step 1 product was cleaved using an ethyl acetate solution of hydrogen chloride. The title compound was obtained as a pale amber gum. $^1$H NMR (400 MHz, CDCl$_3$) δ 7.26 (br s, 1H), 4.12-4.03 (m, 1H), 2.96 (br s, 2H), 2.93-2.87 (m, 2H), 2.66 (s, 2H), 2.53-2.46 (m, 2H), 1.16 (d, J=6.5 Hz, 6H), 1.04 (s, 6H) ppm.

Step 3: Methyl 5-(4-(2-(isopropylamino)-2-oxoethyl)-3,3-dimethylpiperazin-1-yl)-7-(trifluoromethyl)thieno[3,2-b]pyridine-3-carboxylate Into a 20 mL microwave reaction vial equipped with a stir bar was loaded Intermediate 3 (0.400 g, 1.35 mmol), step 2 product (0.460 g, 2.16 mmol), N-methyl-2-pyrrolidinone (6 mL), and N,N-diisopropylethylamine (0.47 mL, 2.7 mmol). The vessel was sealed and heated in a microwave reactor for two hours at 130° C. TLC analysis indicated that the reaction was nearly complete. The reaction was then concentrated and the residue was partitioned between aqueous sodium bicarbonate solution (~60 mL) and ethyl acetate (~30 mL). The organic layer was combined with an additional extracts (ethyl acetate, 2×~30 mL), dried (Na$_2$SO$_4$) and concentrated. The crude material was subjected to automated flash chromatography (Combiflash system; 25 to 60% ethyl acetate in heptane; 40 g Gold silica column), providing the purified title compound ($R_f$~0.3 with 6:4 heptane/ethyl acetate as the eluant) as an amber solid (0.287 g, 45%). $^1$H NMR (400 MHz, CDCl$_3$) δ 8.56 (s, 1H), 7.26 (d, J=8.3 Hz, 1H), 6.98 (s, 1H), 4.17-4.07 (m, 1H), 3.96 (s, 3H), 3.89-3.80 (m, 2H), 3.50 (br s, 2H), 3.05 (br s, 2H), 2.75-2.69 (m, 2H), 1.19 (d, J=6.5 Hz, 6H), 1.13 (s, 6H) ppm.

Step 4: 5-(4-(2-(Isopropylamino)-2-oxoethyl)-3,3-dimethylpiperazin-1-yl)-N-methyl-7-(trifluoromethyl)thieno[3,2-b]pyridine-3-carboxamide Using the procedure described for step 2 of Example 25, the methyl ester functionality of the step 3 product was converted to the corresponding N-methyl carboxamide, affording the title compound as a pale gold solid. $^1$H NMR (400 MHz, CDCl$_3$) δ 9.37 (br s, 1H), 8.67 (s, 1H), 7.18 (d, J=8.4 Hz, 1H), 7.01 (s, 1H), 4.18-4.08 (m, 1H), 3.74-3.67 (m, 2H), 3.47 (s, 2H), 3.09 (d, J=4.9 Hz, 3H), 3.07 (s, 1H), 2.81-2.74 (m, 2H), 1.20 (d, J=6.6 Hz, 6H), 1.15 (s, 6H) ppm. MS: 472 m/z (M+H$^+$).

Example 60. 1-(3-(Methylcarbamoyl)-7-(trifluoromethyl)thieno[3,2-b]pyridin-5-yl)piperidin-4-yl azetidine-1-carboxylate

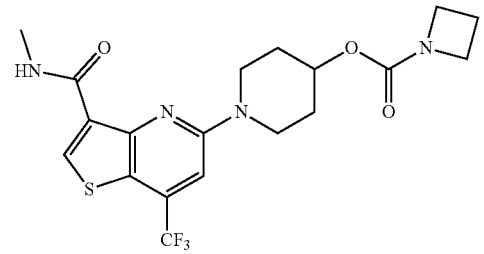 [SMILES: CNC(=O)c1csc2c(C(F)(F)F)cc(N3CCC(OC(=O)N4CCC4)CC3)nc12]

Into a 20 mL microwave reaction vial equipped with a stir bar was loaded Intermediate 21 (0.200 g, 0.381 mmol), N,N-dimethylformamide (6.0 mL), azetidine (77 μL, 1.14 mmol), triethylamine (0.21 mL, 1.5 mmol) and 4-(dimethylamino)pyridine (6 mg, 49 μmol). The vessel was sealed and heated in a microwave reactor for one hour at 90° C. The mixture was then concentrated and the residue was partitioned between chloroform (~20 mL) and aqueous sodium carbonate solution (~40 mL). The organic layer was combined with additional extracts (chloroform, 2×~20 mL), dried (Na$_2$SO$_4$) and concentrated. The crude material was subjected to automated flash chromatography (Combiflash system; 0-2% methanol in dichloromethane; 40 g Gold silica column). The target component ($R_f$~0.2 with 98:2 dichloromethane/methanol as the eluant) was obtained as a faint gold film. This material was co-evaporated with ethyl acetate and vacuum oven dried (~60° C.) to afford the title compound as a pale gold solid (0.144 g, 85%). $^1$H NMR (400 MHz, CDCl$_3$) δ 9.43 (s, 1H), 8.66 (s, 1H), 7.06 (s, 1H), 5.02-4.93 (m, 1H), 4.10-3.99 (m, 4H), 3.96-3.85 (m, 2H), 3.64-3.51 (m, 2H), 3.07 (d, J=4.9 Hz, 3H), 2.33-2.20 (m, 2H), 2.12-2.00 (m, 2H), 1.90-1.77 (m, 2H) ppm. MS: 443 m/z (M+H$^+$).

Example 63. 1-(3-(Methylcarbamoyl)-7-(trifluoromethyl)thieno[3,2-b]pyridin-5-yl)piperidin-4-yl (S)-sec-butylcarbamate

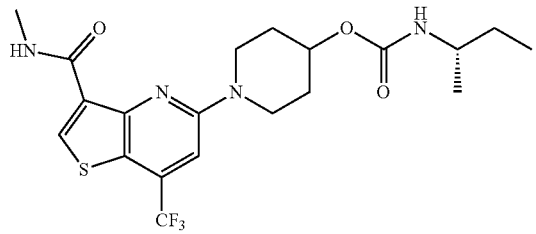 [SMILES: CC[C@H](C)NC(=O)OC1CCN(c2cc(C(F)(F)F)c3scc(C(=O)NC)c3n2)CC1]

Exchanging azetidine for (S)-sec-butylamine, the reaction procedure described in Example 60 was used to prepare the title compound as off-white solid. $^1$H NMR (400 MHz, CDCl$_3$) δ 9.43 (br s, 1H), 8.66 (s, 1H), 7.06 (s, 1H), 5.10-4.90 (m, 1H), 4.60-4.28 (m, 1H), 4.02-3.85 (m, 2H), 3.76-3.44 (m, 3H), 3.07 (d, J=4.9 Hz, 3H), 2.16-2.02 (m, 2H), 1.94-1.74 (m, 2H), 1.56-1.42 (m, 1H), 1.15 (d, J=6.6 Hz, 3H), 0.99-0.88 (m, 3H) ppm. MS: 459 m/z (M+H$^+$).

Example 76. 1-(3-(Methylcarbamoyl)-7-(trifluoromethyl)thieno[3,2-b]pyridin-5-yl)piperidin-4-yl isopropylcarbamate

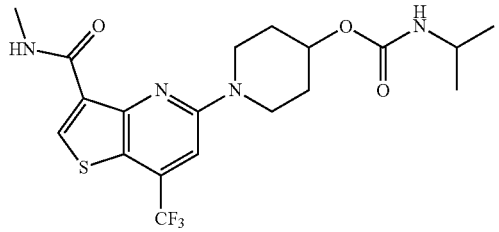 [SMILES: CNC(=O)c1csc2c(C(F)(F)F)cc(N3CCC(OC(=O)NC(C)C)CC3)nc12]

Exchanging azetidine for isopropylamine, the reaction procedure described in Example 60 was used to prepare the title compound as an off-white solid. $^1$H NMR (400 MHz, CDCl$_3$) δ 9.43 (br s, 1H), 8.66 (s, 1H), 7.06 (s, 1H), 4.97 (br s, 1H), 4.53 (br s, 1H), 4.00-3.73 (m, 3H), 3.64-3.36 (m, 2H), 3.07 (d, J=4.9 Hz, 3H), 2.14-2.02 (m, 2H), 1.92-1.74 (m, 2H), 1.18 (d, J=6.5 Hz, 6H) ppm. MS: 445 m/z (M+H$^+$).

Example 87. 1-(3-(Methylcarbamoyl)-7-(trifluoromethyl)thieno[3,2-b]pyridin-5-yl)piperidin-4-yl 3-(difluoromethoxy)azetidine-1-carboxylate

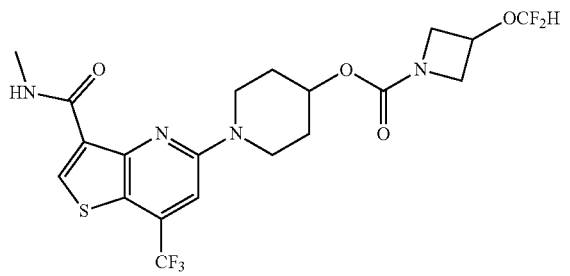

Step 1: 1-(3-(Methylcarbamoyl)-7-(trifluoromethyl)thieno[3,2-b]pyridin-5-yl)piperidin-4-yl 1H-imidazole-1-carboxylate To a stirred suspension of Intermediate 7 (2.50 g, 6.96 mmol) in dichloromethane (50 mL) was added 1,1'-carbonyldiimidazole (2.26 g, 13.9 mmol). The mixture quickly cleared to an amber solution. Stirring was continued overnight at room temperature. After this time, the mixture was diluted with additional dichloromethane (~100 mL) and washed with 0.1 N hydrochloric acid (1×~100 mL). The organic layer was dried (Na$_2$SO$_4$) and concentrated to afford crude the title compound as foamy, pale gold solid (3.26 g, 103%). The crude intermediate was deemed sufficiently pure to use, without purification, in the next step. $^1$H NMR (400 MHz, CDCl$_3$) δ 9.33 (br s, 1H), 8.69 (s, 1H), 8.18-8.15 (m, 1H), 7.44 (t, J=1.4 Hz, 1H), 7.13-7.07 (m, 2H), 5.38-5.30 (m, 1H), 4.07-3.97 (m, 2H), 3.70-3.59 (m, 2H), 3.08 (d, J=4.9 Hz, 3H), 2.31-2.21 (m, 2H), 2.10-1.98 (m, 2H) ppm.

Step 2: 1-(3-(Methylcarbamoyl)-7-(trifluoromethyl)thieno[3,2-b]pyridin-5-yl)piperidin-4-yl 3-(difluoromethoxy)azetidine-1-carboxylate Into a 20 mL microwave reaction vial equipped with a stir bar was loaded step 1 product (0.250 g, 0.551 mmol) and acetonitrile (10 mL). To this stirred solution was added 3-(difluoromethoxy)azetidine (0.082 g, 0.666 mmol) followed by N-hydroxysuccinimide (0.076 g, 0.660 mmol). The vessel was sealed and heated in a microwave reactor for one hour at 60° C. LCMS analysis indicated that the reaction was complete. The reaction was analyzed by LCMS and found to be complete. The mixture was concentrated and partitioned between chloroform (~30 mL) and aqueous sodium bicarbonate solution (~50 mL). The organic layer was combined with additional extracts (chloroform, 2×~30 mL), dried (Na$_2$SO$_4$) and concentrated. The residue was subjected to automated flash chromatography (Combiflash system; 40 to 70% ethyl acetate in heptane; 40 g Gold silica column). The target component (R$_f$~0.4 with 7:3 ethyl acetate/heptane as the eluant) was obtained as a near colorless film. This material was vacuum oven dried (~60° C.) and ground with a spatula to afford the title compound as a pale gold solid (0.270 g, 96%). $^1$H NMR (400 MHz, CDCl$_3$) δ 9.42 (br s, 1H), 8.67 (s, 1H), 7.06 (s, 1H), 6.25 (t, J=73 Hz, 1H), 5.04-4.90 (m, 2H), 4.28 (dd, J=9.9, 6.8 Hz, 2H), 4.07 (dd, J=10.2, 4.4 Hz, 2H), 3.98-3.85 (m, 2H), 3.63-3.49 (m, 2H), 3.08 (d, J=4.8 Hz, 3H), 2.13-2.01 (m, 2H), 1.90-1.77 (m, 2H) ppm. MS: 509 m/z (M+H$^+$).

Example 88. 1-(3-(Methylcarbamoyl)-7-(trifluoromethyl)thieno[3,2-b]pyridin-5-yl)piperidin-4-yl 3-(trifluoromethoxy)azetidine-1-carboxylate

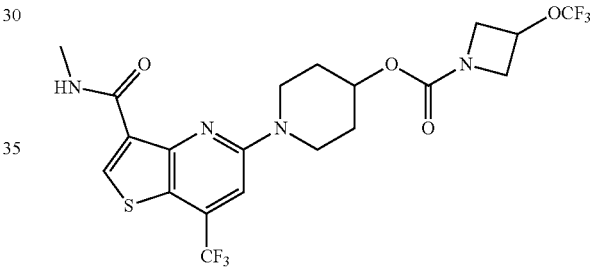

Exchanging 3-(difluoromethoxy)azetidine for equimolar quantities of 3-(trifluoromethoxy)azetidine hydrochloride and triethylamine, the same reaction procedure described for step 2 of Example 87 was used to prepare the title compound as a pale gold solid. $^1$H NMR (400 MHz, CDCl$_3$) δ 9.40 (br s, 1H), 8.66 (s, 1H), 7.07 (s, 1H), 5.07-4.90 (m, 2H), 4.32 (dd, J=10.2, 6.7 Hz, 2H), 4.14 (dd, J=10.2, 4.2 Hz, 2H), 4.02-3.86 (m, 2H), 3.08 (d, J=4.8 Hz, 3H), 2.16-2.02 (m, 2H), 1.92-1.76 (m, 2H) ppm. MS: 527 m/z (M+H$^+$).

Example 90. 1-(3-(Methylcarbamoyl)-7-(trifluoromethyl)thieno[3,2-b]pyridin-5-yl)piperidin-4-yl (S)-(1-(trifluoromethoxy)propan-2-yl)carbamate

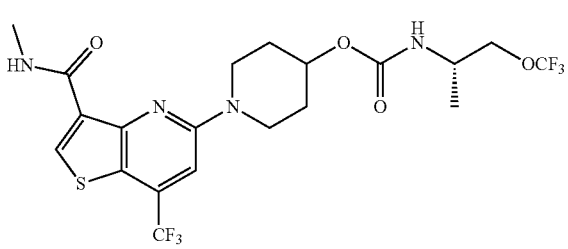 [SMILES: CNC(=O)c1csc2c(C(F)(F)F)cc(N3CCC(OC(=O)N[C@@H](C)COC(F)(F)F)CC3)nc12]

Exchanging 3-(difluoromethoxy)azetidine for equimolar quantities of Intermediate 18 and triethylamine, the same reaction procedure described for step 2 of Example 87 was used to prepare the title compound as a pale gold solid. $^1$H NMR (400 MHz, CDCl$_3$) δ 9.42 (br s, 1H), 8.67 (s, 1H), 7.07 (s, 1H), 5.07-4.92 (br s, 1H), 4.87-4.71 (br s, 1H), 4.13-3.84 (m, 5H), 3.62-3.49 (m, 2H), 3.07 (d, J=4.9 Hz, 3H), 2.16-2.02 (m, 2H), 1.90-1.76 (m, 2H), 1.28 (d, J=6.6 Hz, 3H) ppm. MS: 529 m/z (M+H$^+$).

Example 91. 3,3-Difluoro-1-(3-(methylcarbamoyl)-7-(trifluoromethyl)thieno[3,2-b]pyridin-5-yl)piperidin-4-yl isopropylcarbamate

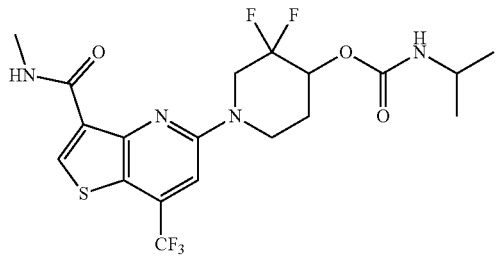 [SMILES: CNC(=O)c1csc2c(C(F)(F)F)cc(N3CCC(OC(=O)NC(C)C)C(F)(F)C3)nc12]

Step 1: Methyl 5-(3,3-difluoro-4-hydroxypiperidin-1-yl)-7-(trifluoromethyl)thieno[3,2-b]pyridine-3-carboxylate Into a 20 mL microwave reaction vial equipped with a stir bar was loaded Intermediate 3 (1.35 g, 4.57 mmol), N-methyl-2-pyrrolidinone (12 mL), 3,3-difluoropiperidin-4-ol (1.02 g, 7.44 mmol) and N,N-diisopropylethylamine (1.6 mL, 9.2 mmol). The vessel was sealed and heated in a microwave reactor for five hours at 130° C. Analysis by LCMS indicated that the reaction was incomplete (~73:27 ratio of product to starting material, by relative peak area). The reaction was heated for another five hours at 130° C. LCMS analysis indicated that the reaction had progressed sufficiently to proceed to the workup (~85/12 ratio of product and starting material). The solution was concentrated and the residue was partitioned between chloroform (~75 mL) and aqueous sodium bicarbonate solution (~100 mL). The organic layer was combined with additional extracts (chloroform, 2x~50 mL), dried (Na$_2$SO$_4$) and concentrated. The crude material was subjected to automated flash chromatography (Combiflash system; 40 to 60% ethyl acetate in heptane; 120 g silica column) to afford the title compound (R$_f$~0.4 with 6:4 heptane/ethyl acetate as the eluant) as a gold solid (1.07 g, 59%). $^1$H NMR (400 MHz, CDCl$_3$) δ 8.57 (s, 1H), 7.04 (s, 1H), 4.25-3.79 (m, 8H), 2.30 (d, J=3.7 Hz, 1H), 2.20-2.09 (m, 1H), 2.05-1.95 (m, 1H) ppm.

Step 2: 5-(3,3-Difluoro-4-hydroxypiperidin-1-yl)-N-methyl-7-(trifluoromethyl)thieno[3,2-b]pyridine-3-carboxamide Using the procedure described for step 2 of Example 25, the methyl ester functionality of the step 1 product was converted to the corresponding N-methyl carboxamide, affording the title compound as an off-white solid. $^1$H NMR (400 MHz, CDCl$_3$) δ 9.30 (br s, 1H), 8.69 (s, 1H), 7.08 (br s, 1H), 4.21-4.06 (m, 2H), 4.03-3.69 (m, 3H), 3.09 (d, J=4.8 Hz, 3H), 2.78 (br s, 1H), 2.22-2.11 (m, 1H), 2.10-2.00 (m, 1H) ppm.

Step 3: 3,3-Difluoro-1-(3-(methylcarbamoyl)-7-(trifluoromethyl)thieno[3,2-b]pyridin-5-yl)piperidin-4-yl 1H-imidazole-1-carboxylate To a stirred suspension of step 2 product (0.905 g, 2.29 mmol) in dichloromethane (12 mL) was added 1,1'-carbonyldiimidazole (0.557 g, 3.44 mmol). Stirring was continued overnight at room temperature. After this time, the reaction was diluted with chloroform (~80 mL). The solution was washed with 0.1 N hydrochloric acid (1x100 mL) and aqueous sodium bicarbonate solution (1x~80 mL). The organic layer was dried (Na$_2$SO$_4$) and concentrated to afford the title compound as a foamy, pale gold solid (1.12 g, 100%). This material was deemed sufficiently pure to use, without purification, in the next step. $^1$H NMR (400 MHz, CDCl$_3$) δ 9.11 (m, 1H), 8.73 (s, 1H), 8.21-8.18 (m, 1H), 7.47 (t, J=1.4 Hz, 1H), 7.15-7.10 (m, 1H), 5.52-5.43 (m, 1H), 4.31-4.18 (m, 1H), 4.07-3.92 (m, 2H), 3.83-3.73 (m, 1H), 3.10 (d, J=4.9 Hz, 3H), 2.46-2.37 (m, 1H), 2.34-2.23 (m, 1H) ppm.

Step 4: 3,3-Difluoro-1-(3-(methylcarbamoyl)-7-(trifluoromethyl)thieno[3,2-b]pyridin-5-yl)piperidin-4-yl isopropylcarbamate Exchanging the step 1 product of Example 87 for the step 3 product of the present Example and 3-(difluoromethoxy) azetidine for isopropylamine, the reaction procedure described for step 2 of Example 87 was used to prepare the title compound as a white solid. $^1$H NMR (400 MHz, CDCl$_3$) δ 9.21 (br s, 1H), 8.70 (s, 1H), 7.08 (s, 1H), 5.30-5.14 (m, 1H), 4.83-4.69 (m, 1H), 4.16-3.67 (m, 5H), 3.09 (d, J=4.9 Hz, 3H), 2.30-2.01 (m, 2H), 1.20 (t, J=6.5 Hz, 6H) ppm. MS: 481 m/z (M+H$^+$).

Example 95. 1-(3-(Methylcarbamoyl)-7-(trifluoromethyl)thieno[3,2-b]pyridin-5-yl)piperidin-4-yl 6,7-dihydropyrazolo[1,5-a]pyrazine-5(4H)-carboxylate

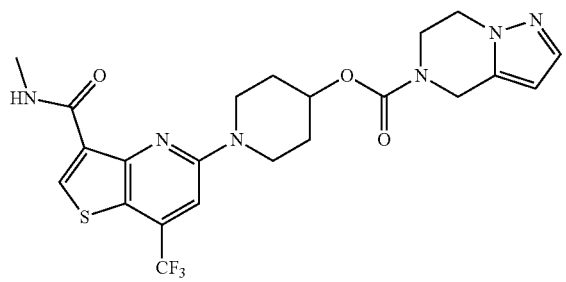 [SMILES: CNC(=O)c1csc2c(C(F)(F)F)cc(N3CCC(OC(=O)N4CCn5nccc5C4)CC3)nc12]

Step 1: Piperidin-4-yl 6,7-dihydropyrazolo[1,5-a]pyrazine-5(4H)-carboxylate

To a stirred and cooled (0° C.) solution of Intermediate 22 (1.35 g, 5.12 mmol) in chloroform (40 mL) was added 4,5,6,7-tetrahydropyrazolo[1,5-a]pyrazine dihydrochloride (1.00 g, 5.12 mmol) followed by triethylamine (2.9 mL, 21 mmol, 4.1 eq; the amount of triethylamine used in similar reactions utilizing Intermediate 22 was adjusted to at least two equivalents more than the number of acid equivalents introduced by the amine component, if in a salt form). The ice bath was removed and the reaction was allowed to warm to room temperature and stirred overnight. The mixture was then rinsed into a separatory funnel with chloroform (~20 mL) and washed with aqueous sodium carbonate solution (~50 mL). The organic layer was combined with additional extracts of the aqueous layer (chloroform, 2×~40 mL), dried (Na$_2$SO$_4$) and concentrated to afford the crude carbamate as a faint amber gum (2.13 g, 119%). This material was dissolved in dichloromethane (21 mL), stirred and treated with trifluoroacetic acid (7.0 mL, 92 mmol; the volume of dichloromethane and the number of equivalents of trifluoroacetic acid used in similar reactions with Intermediate 22 was adjusted so that a total of 17-20 equivalents of a 3.0-3.5 M trifluoroacetic acid solution was used). After two hours, the reaction was concentrated and the residue was partitioned between chloroform (~50 mL) and a 1.0 N aqueous sodium hydroxide solution (~50 mL). The organic layer was combined with additional extracts (chloroform, 3×~50 mL), dried (Na$_2$SO$_4$) and concentrated to afford the crude title compound as a faint amber gum (1.28 g, 100%). This material was deemed sufficiently pure to use, without purification, in the next step. $^1$H NMR (400 MHz, CDCl$_3$) δ 7.49 (s, 1H), 6.08 (s, 1H), 4.88-4.78 (m, 1H), 4.72 (s, 2H), 4.27-4.17 (m, 2H), 3.99-3.90 (m, 2H), 3.13-3.01 (m, 2H), 2.80-2.68 (m, 2H), 2.01-1.89 (m, 1H), 1.68-1.51 (m, 3H) ppm.

Step 2: 1-(3-(Methylcarbamoyl)-7-(trifluoromethyl) thieno[3,2-b]pyridin-5-yl)piperidin-4-yl 6,7-dihydropyrazolo[1,5-a]pyrazine-5(4H)-carboxylate Into a 20 mL microwave reaction vial equipped with a stir bar was loaded step 1 product (0.340 g, 1.36 mmol), Intermediate 5 (0.200 g, 0.679 mmol), N-methyl-2-pyrrolidinone (6 mL) and N,N-diisopropylethylamine (0.24 mL, 1.4 mmol). The vessel was sealed and heated in a microwave reactor for two hours at 130° C. The reaction was concentrated and the residue was partitioned between chloroform (~30 mL) and aqueous sodium bicarbonate solution (~50 mL). The organic layer was combined with additional extracts (chloroform, 2×~30 mL), dried (Na$_2$SO$_4$) and concentrated. The crude material was subjected to automated flash chromatography (Combiflash system; 3 to 8% methanol in ethyl acetate; 40 g Gold silica column). The target component (R$_f$~0.2 with 19:1 ethyl acetate/methanol as the eluant), component was obtained as an orange-yellow film (0.339 g, 98%). This material was triturated with diethyl ether/ethyl acetate (~1:1; ~25 mL) and recollected via suction filtration. The filtercake was rinsed with additional diethyl ether (1×~10 mL) and air-dried on the frit under house vacuum and a nitrogen funnel to afford the title compound as a yellow solid (0.274 g, 79%). $^1$H NMR (400 MHz, CDCl$_3$) δ 9.40 (br s, 1H), 8.67 (s, 1H), 7.50 (s, 1H), 7.08 (s, 1H), 6.08 (br s, 1H), 5.15-5.02 (m, 1H), 4.75 (s, 2H), 4.33-4.16 (m, 2H), 4.08-3.87 (m, 4H), 3.67-3.51 (m, 2H), 3.08 (d, J=4.7 Hz, 3H), 2.21-2.07 (m, 2H), 1.96-1.81 (m, 2H) ppm. MS: 509 m/z (M+H$^+$).

Example 109. 1-(3-(Methylcarbamoyl)-7-(trifluoromethyl)thieno[3,2-b]pyridin-5-yl)piperidin-4-yl (S)-(1-cyclopropylethyl)carbamate

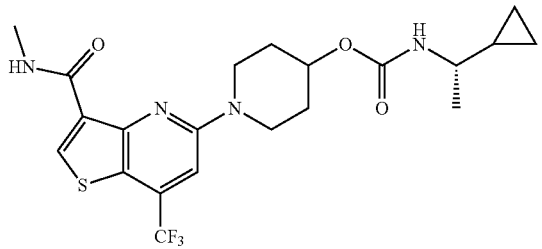

Exchanging 4,5,6,7-tetrahydropyrazolo[1,5-a]pyrazine dihydrochloride for (S)-1-cyclopropylethan-1-amine, the synthetic sequence described in Example 95 was used to prepare the title compound as a light yellow solid. $^1$H NMR (400 MHz, CDCl$_3$) δ 9.43 (br s, 1H), 8.66 (s, 1H), 7.06 (s, 1H), 4.97 (br s, 1H), 4.72 (br s, 1H), 4.02-3.85 (m, 2H), 3.62-3.45 (m, 2H), 3.22-3.02 (m, 1H), 3.07 (d, J=4.7 Hz, 3H), 2.16-2.00 (m, 2H), 1.91-1.68 (m, 2H), 1.23 (d, J=6.5 Hz, 3H), 0.88-0.76 (m, 1H), 0.57-0.30 (m, 3H), 0.28-0.14 (m, 1H) ppm. MS: 471 m/z (M+H$^+$).

Example 115. 1-(3-(Methylcarbamoyl)-7-(trifluoromethyl)thieno[3,2-b]pyridin-5-yl)piperidin-4-yl ((4-methylmorpholin-2-yl)methyl)carbamate

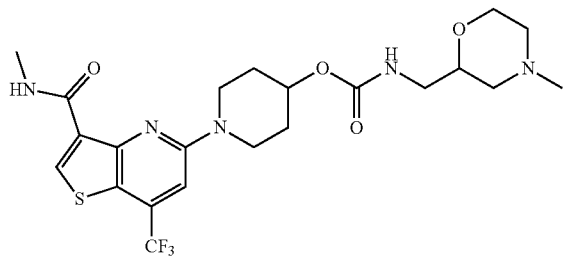

Step 1: Benzyl 4-(((((4-methylmorpholin-2-yl) methyl)carbamoyl)oxy)piperidine-1-carboxylate To a stirred and cooled (0° C.) solution of Intermediate 23 (1.46 g, 4.89 mmol) in chloroform (30 mL) was added 2-(aminomethyl)-4-methylmorpholine (0.636 g, 4.89 mmol) followed by triethylamine (1.40 mL, 10.0 mmol, 2.05 eq; the amount of triethylamine used in similar reactions utilizing Intermediate 23 was adjusted to at least 2.0 equivalents more than the number of acid equivalents introduced by the amine component, if in a salt form). The ice bath was removed and the reaction was allowed to warm to room temperature and stirred overnight. The mixture was then rinsed into a separatory funnel with chloroform (~20 mL) and washed with aqueous sodium carbonate solution (~50 mL). The organic layer was combined with additional extracts of the aqueous layer (chloroform, 2×~40 mL), dried (Na$_2$SO$_4$) and concentrated to afford the crude title compound as a faint amber gum (2.01 g, 105%; yield inflated by residual toluene). This material was deemed sufficiently pure to use, without purification, in the next step. $^1$H NMR (400 MHz, CDCl$_3$) δ

7.40-7.28 (m, 5H), 5.13 (s, 2H), 5.08-4.99 (m, 1H), 4.90-4.79 (m, 1H), 3.95-3.55 (m, 5H), 3.41-3.25 (m, 3H), 3.18-3.09 (m, 1H), 2.74-2.60 (m, 2H), 2.28 (s, 3H), 2.09 (td, J=11.5, 3.4 Hz, 1H), 1.95-1.79 (m, 3H), 1.71-1.53 (m, 2H) ppm.

Step 2: Piperidin-4-yl ((4-methylmorpholin-2-yl)methyl)carbamate

The crude step 1 product was combined with 10% palladium on carbon (0.400 g) and taken up in methanol (50 mL). The stirred mixture was cycled between vacuum and a nitrogen atmosphere three times. The reaction vessel was evacuated a final time and refilled with hydrogen (via balloon). The reaction was stirred at room temperature overnight and then analyzed by 1H NMR (a few drops of the settled suspension were removed and concentrated to supply the sample) and found to be complete. The mixture was suction filtered through a pad of Celite, which was subsequently rinsed with additional methanol (~80 mL). The combined filtrate was concentrated to afford crude product as an tacky colorless glass (1.32 g, 100%). The crude amine was deemed sufficiently pure to use, without purification, in the next step. $^1$H NMR (400 MHz, CDCl$_3$) δ 5.21-5.07 (m, 1H), 4.88-4.77 (m, 1H), 3.90-3.84 (m, 1H), 3.70-3.56 (m, 2H), 3.41-3.30 (m, 1H), 2.98-2.86 (m, 2H), 2.73-2.61 (m, 2H), 2.28 (s, 3H), 2.10 (td, J=11.5, 3.3 Hz, 1H), 2.09-1.99 (m, 2H), 1.85 (t, J=10.7 Hz, 1H), 1.80-1.69 (m, 2H) ppm.

Step 3: 1-(3-(Methylcarbamoyl)-7-(trifluoromethyl) thieno[3,2-b]pyridin-5-yl)piperidin-4-yl ((4-methylmorpholin-2-yl)methyl)carbamate Into a 20 mL microwave reaction vial equipped with a stir bar was loaded Intermediate 5 (0.200 g, 0.679 mmol), step 2 product (0.306 g, 1.19 mmol), N-methyl-2-pyrrolidinone (6 mL) and N,N-diisopropylethylamine (0.24 mL, 1.4 mmol). The vessel was sealed and heated in a microwave reactor for two hours at 130° C. The reaction was concentrated and the residue was partitioned between chloroform (~25 mL) and aqueous sodium carbonate solution (~40 mL). The organic layer was combined with additional extracts (chloroform, 2×~25 mL), dried (Na$_2$SO$_4$) and concentrated. The crude material was subjected to automated flash chromatography (Combiflash system; 0 to 10% methanol in chloroform; 80 g Gold silica column). The target component (R$_f$~0.36 with 9:1 chloroform/methanol as the eluant) was obtained as a foamy solid. This material was co-evaporated with ethyl acetate to afford the title compound as an amber solid (0.159 g, 45%). $^1$H NMR (400 MHz, CDCl$_3$) δ 9.48-9.39 (m, 1H), 8.66 (s, 1H), 7.06 (s, 1H), 5.17-4.88 (m, 2H), 3.99-3.83 (m, 3H), 3.74-3.49 (m, 4H), 3.46-3.35 (m, 1H), 3.22-3.12 (m, 1H), 3.07 (d, J=4.9 Hz, 3H), 2.74 (d, J=11.2 Hz, 1H), 2.66 (d, J=11.6 Hz, 1H), 2.30 (s, 1H), 2.17-2.01 (m, 3H), 1.92-1.77 (m, 3H) ppm. MS: 516 m/z (M+H$^+$).

Example 142. 1-(3-(Methylcarbamoyl)thieno[3,2-b]pyridin-5-yl)piperidin-4-yl (S)-(1-(trifluoromethoxy)propan-2-yl)carbamate

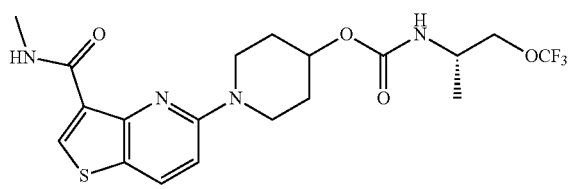 [SMILES: CNC(=O)c1csc2ccc(N3CCC(OC(=O)N[C@@H](C)COC(F)(F)F)CC3)nc12]

Step 1: Methyl 5-(((trifluoromethyl)sulfonyl)oxy)thieno[3,2-b]pyridine-3-carboxylate Exchanging the step 1 product of Example 48 for Intermediate 16, the reaction procedure described for step 2 of Example 48 was used to prepare the title compound as a brown solid. This material was deemed sufficiently pure to use, without purification, in the next step. $^1$H NMR (400 MHz, CDCl$_3$) δ 8.76 (s, 1H), 8.37 (d, J=8.6 Hz, 1H), 7.24 (d, J=8.6 Hz, 1H), 3.99 (s, 3H) ppm.

Step 2: Piperidin-4-yl (S)-(1-(trifluoromethoxy)propan-2-yl)carbamate

Exchanging 4,5,6,7-tetrahydropyrazolo[1,5-a]pyrazine dihydrochloride for Intermediate 18, the O-(piperidin-4-yl) carbamate preparation described in step 1 of Example 95 was used to prepare the crude title compound as a waxy, off-white solid. This material was deemed sufficiently pure to use, without purification, in the next step. $^1$H NMR (400 MHz, CDCl$_3$) δ 4.99-4.57 (m, 2H), 4.09-3.82 (m, 3H), 3.06 (dt, J=12.7, 4.5 Hz, 2H), 2.76-2.64 (m, 2H), 1.98-1.85 (m, 2H), 1.62-1.39 (m, 2H), 1.25 (d, J=6.7 Hz, 3H) ppm.

Step 3: Methyl (S)-5-(4-(((1-(trifluoromethoxy)propan-2-yl)carbamoyl)oxy)piperidin-1-yl)thieno[3,2-b]pyridine-3-carboxylate Into a 10 mL microwave reaction vial equipped with a stir bar was loaded step 2 product (0.220 g, 0.814 mmol), step 1 product (0.200 g, 0.586 mmol), N-methyl-2-pyrrolidinone (2.5 mL) and N,N-diisopropylethylamine (0.18 mL, 1.0 mmol). The reaction vessel was sealed and heated in a microwave reactor for five hours at 90° C. The reaction was analyzed by LCMS and found to incomplete (approximate 1:1 mixture of triflate starting material and putative product, as judged by relative peak size). Heating at was continued at 90° C. for another one hour, but no reaction advancement was observed by LCMS. The mixture was then concentrated and the residue was partitioned between chloroform (~30 mL) and aqueous sodium bicarbonate solution (~50 mL). The organic layer was combined with additional extracts (chloroform, 2×~15 mL), dried (Na$_2$SO$_4$) and concentrated. The crude material was subjected to automated flash chromatography (Combiflash system; 0 to 40% ethyl acetate in heptane; 40 g Gold silica column) to afford the title compound (R$_f$~0.35 with 6:4 heptane/ethyl acetate as the eluant) as a colorless solid (0.099 g, 37%). $^1$H NMR (400 MHz, CDCl$_3$) δ 8.45 (s, 1H), 7.89 (d, J=9.1 Hz, 1H), 6.81 (d, J=9.1 Hz, 1H), 5.00-4.87 (m, 1H), 4.85-4.71 (m, 1H), 4.16-3.87 (m, 8H), 3.56-3.39 (m, 2H), 2.10-1.98 (m, 2H), 1.84-1.68 (m, 2H), 1.26 (d, J=6.5 Hz, 3H) ppm.

Step 4: 1-(3-(Methylcarbamoyl)thieno[3,2-b]pyridin-5-yl)piperidin-4-yl (S)-(1-(trifluoromethoxy)propan-2-yl)carbamate Using the procedure described for step 2 of Example 25, the methyl ester functionality of the step 3 product was converted to the corresponding N-methyl carboxamide, affording the title compound as an off-white solid. $^1$H NMR (400 MHz, CDCl$_3$) δ 9.72-9.62 (m, 1H), 8.54 (s, 1H), 7.94 (d, J=9.1 Hz, 1H), 6.83 (d, J=9.1 Hz, 1H), 5.04-4.86 (s, 2H), 4.10-3.83 (m, 5H), 3.54-3.40 (m, 2H), 3.07 (d, J=4.8 Hz, 3H), 2.12-1.99 (m, 2H), 1.90-1.72 (m, 2H), 1.27 (d, J=6.6 Hz, 3H) ppm. MS: 461 m/z (M+H$^+$).

Example 145. N-Methyl-5-(4-((6-methylpyridin-2-yl)oxy)piperidin-1-yl)-7-(trifluoromethyl)thieno[3,2-b]pyridine-3-carboxamide

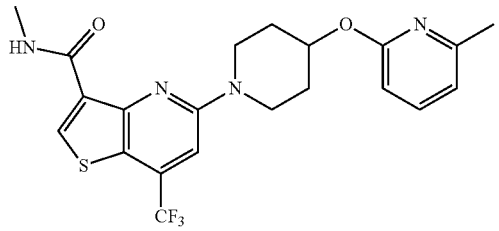

Using the conditions described in step 3 of Example 115, Intermediate 5 was subjected to SNAr displacement with a piperidine derivative, 2-methyl-6-(piperidin-4-yloxy)pyridine, to afford the title compound as a tan solid. $^{1}$H NMR (400 MHz, CDCl$_3$) δ 9.56-9.45 (m, 1H), 8.66 (s, 1H), 7.47 (dd, J=8.2, 7.3 Hz, 1H), 7.09 (s, 1H), 6.73 (d, J=7.3 Hz, 1H), 6.53 (d, J=8.2 Hz, 1H), 5.42 (tt, J=7.2, 3.6 Hz, 1H), 3.96 (ddd, J=13.2, 7.8, 3.7 Hz, 2H), 3.67 (ddd, J=13.2, 7.7, 3.7 Hz, 2H), 3.07 (d, J=4.9 Hz, 3H), 2.45 (s, 3H), 2.22-2.09 (m, 2H), 2.03-1.91 (m, 2H) ppm. MS: 451 m/z (M+H$^+$).

Example 151. 1-(6-Methyl-3-(methylcarbamoyl)-7-(trifluoromethyl)thieno[3,2-b]pyridin-5-yl)piperidin-4-yl (S)-(1-cyclopropylethyl)carbamate

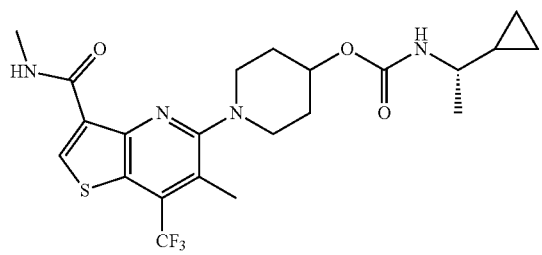 [SMILES: CNC(=O)c1csc2c(C(F)(F)F)c(C)c(N3CCC(OC(=O)N[C@@H](C)C4CC4)CC3)nc12]

Exchanging 4,5,6,7-tetrahydropyrazolo[1,5-a]pyrazine dihydrochloride for (S)-1-cyclopropylethan-1-amine and Intermediate 5 for Intermediate 15, the synthetic sequence described in Example 95 was used to prepare the title compound as an off-white solid. $^{1}$H NMR (400 MHz, CDCl$_3$) δ 9.60-9.44 (m, 1H), 8.62 (s, 1H), 5.03-4.84 (m, 1H), 4.80-4.56 (m, 1H), 3.49-3.33 (m, 2H), 3.28-2.90 (m, 6H), 2.54 (q, J=2.2 Hz, 3H), 2.25-2.05 (m, 2H), 2.00-1.81 (m, 2H), 1.24 (d, J=6.6 Hz, 3H), 0.90-0.76 (m, 1H), 0.57-0.32 (m, 3H), 0.28-0.17 (m, 1H) ppm. MS: 485 m/z (M+H$^+$).

Example 171. 2-(Trifluoromethoxy)ethyl 4-((3-(methylcarbamoyl)-7-(trifluoromethyl)thieno[3,2-b]pyridin-5-yl)oxy)piperidine-1-carboxylate

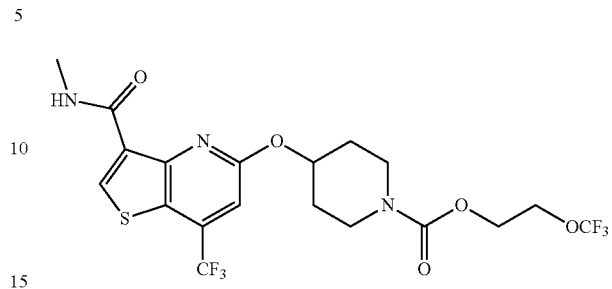

Into a 20 mL microwave reaction vial equipped with a stir bar was loaded Intermediate 11 (0.200 g, 0.892 mmol) and acetonitrile (10 mL). To this stirred solution was added Intermediate 17 (0.400 g, 1.11 mmol) and N-hydroxysuccimide (0.125 g, 1.09 mmol). The vessel was sealed and heated in a microwave reactor for one hour at 60° C. LCMS analysis indicated that the reaction was complete. The mixture was concentrated and the residue was partitioned between aqueous sodium bicarbonate solution (~100 mL) and chloroform (~75 mL). The organic layer was combined with a second extract (chloroform, 1×~50 mL), dried (Na$_2$SO$_4$) and concentrated. The crude material was subjected to automated flash chromatography (Combiflash system; 40 to 60% ethyl acetate in heptane; 80 g Gold silica column). The target component (Rf~0.25 with 6:4 ethyl acetate/heptane as the eluant) was obtained as a colorless foam. This material was vacuum oven dried (~60° C.) to afford the title compound as a colorless solid (0.392 g, 85%). $^{1}$H NMR (400 MHz, CDCl$_3$) δ 9.07-8.96 (m, 1H), 8.76 (s, 1H), 7.13 (s, 1H), 5.26 (tt, J=7.1, 3.5 Hz, 1H), 4.42-4.32 (m, 2H), 4.23-4.16 (m, 2H), 3.81 (ddd, J=13.7, 7.9, 3.8 Hz, 2H), 3.54 (ddd, J=13.7, 7.5, 3.9 Hz, 2H), 3.08 (d, J=4.9 Hz, 3H), 2.18-1.90 (m, 4H) ppm. MS: 516 m/z (M+H$^+$).

Example 175. (S)-1-(Trifluoromethoxy)propan-2-yl (2R,4R)-2-methyl-4-((3-(methylcarbamoyl)-7-(trifluoromethyl)thieno[3,2-b]pyridin-5-yl)oxy)piperidine-1-carboxylate

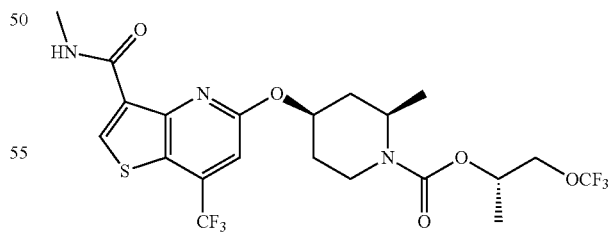

Step 1: tert-butyl (2R,4R)-2-methyl-4-((3-(methylcarbamoyl)-7-(trifluoromethyl)thieno[3,2-b]pyridin-5-yl)oxy)piperidine-1-carboxylate To a stirred solution of Intermediate 5 (1.35 g, 4.58 mmol) and tert-butyl (2R,4R)-4-hydroxy-2-methylpiperidine-1- carboxylate (1.00 g, 4.64 mmol) in tetrahydrofuran (30 mL) was added potassium tert-butoxide (0.668 g, 5.95 mmol). The mixture was heated at 70° C. for three hours and then analyzed by LCMS. Little or no chloropyridine starting was detected. The reaction was concentrated and the residue was partitioned between aqueous sodium bicarbonate solution (~100 mL) and chloroform (~60 mL). The organic layer was combined with additional extracts (chloroform, 2×~40 mL), dried (Na$_2$SO$_4$) and concentrated. The crude material was subjected to automated flash chromatography (Combiflash system; 20 to 50% ethyl acetate in heptane; 80 g Gold silica column) to afford the title compound (R$_f$~0.3 with 1:1 heptane/ethyl acetate as the eluant) as light amber solid (1.31 g, 60%). $^1$H NMR (400 MHz, CDCl$_3$) δ 9.08-9.01 (m, 1H), 8.75 (s, 1H), 7.11 (s, 1H), 5.38 (p, J=3.1 Hz, 1H), 4.50-4.40 (m, 1H), 4.00 (ddd, J=13.8, 4.7, 1.8 Hz, 1H), 3.29 (td, J=13.4, 2.8 Hz, 1H), 3.07 (d, J=4.9 Hz, 3H), 2.18-2.01 (m, 3H), 1.97-1.85 (m, 1H), 1.49 (s, 9H), 1.32 (d, J=7.1 Hz, 3H) ppm.

Step 2: N-methyl-5-(((2R,4R)-2-methylpiperidin-4-yl)oxy)-7-(trifluoromethyl)thieno[3,2-b]pyridine-3-carboxamide To a stirred solution of step 1 product (1.30 g, 2.75 mmol) in dichloromethane (10 mL) was added trifluoroacetic acid (3.0 mL, 39 mmol). After 75 minutes, the reaction was analyzed by 1H NMR (a few drops of the reaction solution were concentrated and partitioned between aqueous sodium carbonate solution and chloroform; the organic layer was concentrated to provide the sample) and found to be complete. The reaction was concentrated and the resulting oil was partitioned between chloroform (~40 mL) and aqueous sodium carbonate solution (~60 mL). The organic layer was combined with additional extracts (chloroform, 2×~40 mL), dried (Na$_2$SO$_4$) and concentrated to afford the crude title compound as a light amber solid (1.05 g, 102%). This material was deemed sufficiently pure to use, without purification, in the next step. $^1$H NMR (400 MHz, CDCl$_3$) δ 9.22-9.10 (m, 1H), 8.73 (s, 1H), 7.09 (s, 1H), 5.02 (tt, J=11.2, 4.4 Hz, 1H), 3.28 (ddd, J=12.6, 4.4, 2.6 Hz, 1H), 3.08 (d, J=4.9 Hz, 3H), 2.89-2.78 (m, 2H), 2.34-2.20 (m, 2H), 1.66 (dq, J=12.2, 4.4 Hz, 1H), 1.37 (q, J=11.4 Hz, 1H), 1.20 (d, J=6.3 Hz, 3H) ppm.

Step 3: (S)-1-(Trifluoromethoxy)propan-2-yl (2R,4R)-2-methyl-4-((3-(methylcarbamoyl)-7-(trifluoromethyl)thieno[3,2-b]pyridin-5-yl)oxy)piperidine-1-carboxylate Exchanging Intermediate 17 for the product of step 2 and Intermediate 11 for Intermediate 12, the reaction procedure described in Example 171 was used to prepare the title compound as a glassy, colorless solid. $^1$H NMR (400 MHz, CDCl$_3$) δ 9.01 (q, J=4.8 Hz, 1H), 8.76 (s, 1H), 7.11 (s, 1H), 5.40 (p, J=3.2 Hz, 1H), 5.14-5.04 (m, 1H), 4.56-4.45 (m, 1H), 4.12-3.96 (m, 3H), 3.43-3.31 (m, 1H), 3.07 (d, J=4.8 Hz, 3H), 2.21-2.02 (m, 3H), 1.99-1.86 (m, 1H), 1.40-1.30 (m, 6H) ppm. MS: 544 m/z (M+H$^+$).

Example 176. (S)-1-(Trifluoromethoxy)propan-2-yl (2R,4R)-2-methyl-4-((6-methyl-3-(methylcarbamoyl)-7-(trifluoromethyl)thieno[3,2-b]pyridin-5-yl)oxy)piperidine-1-carboxylate

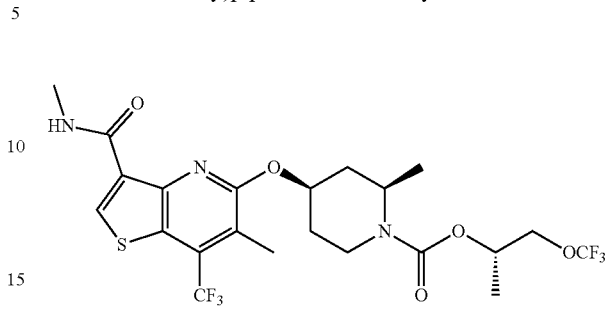

Step 1: Methyl 5-(((2R,4R)-1-(tert-butoxycarbonyl)-2-methylpiperidin-4-yl)oxy)-6-methyl-7-(trifluoromethyl)thieno[3,2-b]pyridine-3-carboxylate To a stirred and cooled (0° C.) solution of Intermediate 13 (2.00 g, 6.87 mmol), tert-butyl (2R,4S)-4-hydroxy-2-methylpiperidine-1-carboxylate (2.59 g, 12.0 mmol) and triphenylphosphine (3.96 g, 15.1 mmol) in ethyl acetate (30 mL) was added, dropwise over 15 minutes, a solution of bis-(2-methoxyethyl)diazo-1,2-dicarboxylate (3.22 g, 13.7 mmol) in ethyl acetate (10 mL). The ice bath was allowed to slowly melt and the reaction was stirred overnight at room temperature. LCMS analysis indicated that the reaction was complete. The mixture was rinsed into a separatory funnel with ethyl acetate (~40 mL) and then washed with water (2×~100 mL). The organic layer was dried (Na$_2$SO$_4$) and concentrated. The crude material was subjected to automated flash chromatography (Combiflash system; 0 to 20% ethyl acetate in heptane; 120 g silica column). The title compound (R$_f$~0.3 with 8:2 heptane/ethyl acetate as the eluant) was obtained as a white solid (3.08 g, 92%). $^1$H NMR (400 MHz, CDCl$_3$) δ 8.50 (s, 1H), 5.65 (p, J=3.2 Hz, 1H), 4.47-4.38 (m, 1H), 4.00-3.90 (m, 4H), 3.26 (td, J=13.3, 2.7 Hz, 1H), 2.48 (q, J=1.9 Hz, 3H), 2.19-2.00 (m, 3H), 1.92-1.81 (m, 1H), 1.48 (s, 9H), 1.33 (d, J=7.1 Hz, 3H) ppm.

Step 2: Methyl 6-methyl-5-(((2R,4R)-2-methylpiperidin-4-yl)oxy)-7-(trifluoromethyl)thieno[3,2-b]pyridine-3-carboxylate Using the procedure described in step 2 of Example 175, the N-tert-butoxycarbonyl amine protecting group of the step 1 product was cleaved using a dichloromethane solution of trifluoroacetic acid. The crude product was deemed sufficiently pure to use, without purification, in the next step. $^1$H NMR (400 MHz, CDCl$_3$) δ 8.50 (s, 1H), 5.29 (tt, J=11.1, 4.6 Hz, 1H), 3.96 (s, 3H), 3.22 (ddd, J=12.5, 4.5, 2.4 Hz, 1H), 2.94-2.82 (m, 2H), 2.43 (q, J=2.0 Hz, 3H), 2.37-2.29 (m, 2H), 1.63-1.45 (m, 2H), 1.29 (q, J=11.5 Hz, 1H), 1.17 (d, J=6.3 Hz, 3H) ppm.

Step 3: N,6-Dimethyl-5-(((2R,4R)-2-methylpiperidin-4-yl)oxy)-7-(trifluoromethyl)thieno[3,2-b]pyridine-3-carboxamide Using the procedure described for step 2 of Example 25, the methyl ester functionality of the step 3 product was converted to the corresponding N-methyl carboxamide. The crude product was subjected to automated flash chromatography (Combiflash system; 0 to 10% 2N ammonia in methanol solution in chloroform; 80 g Gold silica column). The target component (R$_f$~0.4 with 9:1 chloroform/2N ammonia in methanol as the eluant) was obtained as a glassy, colorless solid. This material was co-evaporated with diethyl ether to afford a colorless foam, which was then ground with a spatula to provide the title compound as a white solid (2.34 g, 93%). $^1$H NMR (400 MHz, CDCl$_3$) δ 9.27-9.18 (m, 1H), 8.61 (s, 1H), 5.01 (tt, J=11.1, 4.4 Hz, 1H), 3.29 (ddd, J=12.5, 4.5, 2.5 Hz, 1H), 3.08 (d, J=4.9 Hz, 3H), 2.91-2.78 (m, 2H), 2.44 (q, J=2.0 Hz, 3H), 2.33-2.23 (m, 2H), 1.73-1.62 (m, 1H), 1.39 (q, J=11.5 Hz, 1H), 1.20 (d, J=6.3 Hz, 3H) ppm.

Step 4: (S)-1-(Trifluoromethoxy)propan-2-yl (2R,4R)-2-methyl-4-((6-methyl-3-(methylcarbamoyl)-7-(trifluoromethyl)thieno[3,2-b]pyridin-5-yl)oxy)piperidine-1-carboxylate Exchanging Intermediate 17 for the product of step 3 and Intermediate 11 for Intermediate 12, the reaction procedure described in Example 171 was used to prepare the title compound as a white solid (0.238 g, 83%). 1H NMR (400 MHz, CDCl$_3$) δ 9.07 (q, J=4.9 Hz, 1H), 8.64 (s, 1H), 5.40 (p, J=3.2 Hz, 1H), 5.14-5.05 (m, 1H), 4.58-4.48 (m, 1H), 4.12-3.96 (m, 3H), 3.36 (tt, J=13.5, 2.7 Hz, 1H), 3.06 (d, J=4.9 Hz, 3H), 2.51 (q, J=2.0 Hz, 3H), 2.24-2.07 (m, 3H), 1.99-1.87 (m, 1H), 1.38 (d, J=7.0 Hz, 3H), 1.34 (d, J=6.6 Hz, 3H) ppm. MS: 558 m/z (M+H$^+$).

Example 180. 2-(Trifluoromethoxy)ethyl (3S,4R)-3-fluoro-4-((6-methyl-3-(methylcarbamoyl)-7-(trifluoromethyl)thieno[3,2-b]pyridin-5-yl)oxy)piperidine-1-carboxylate Exchanging tert-butyl (2R,4S)-4-hydroxy-2-methylpiperidine-1-carboxylate for tert-butyl (3S,4S)-3-fluoro-4-hydroxypiperidine-1-carboxylate in step 1 and Intermediate 12 for Intermediate 11 in step 4, the four step synthetic sequence described in Example 176 was used to prepare the title compound as a white solid. $^1$H NMR (400 MHz, CDCl$_3$) δ 8.87 (q, J=4.9 Hz, 1H), 8.66 (s, 1H), 5.44-5.28 (m, 1H), 4.95 (br d, J=47.6 Hz, 1H), 4.38 (q, J=4.2 Hz, 2H), 4.26-4.11 (m, 3H), 4.05-3.81 (m, 1H), 3.78-3.57 (m, 1H), 3.54-3.37 (m, 1H), 3.08 (d, J=4.9 Hz, 3H), 2.51 (q, J=1.9 Hz, 3H), 2.35-2.23 (m, 1H), 2.12-2.00 (m, 1H) ppm. MS: 548 m/z (M+H$^+$).

Example 181. (S)-1-(Trifluoromethoxy)propan-2-yl (3S,4R)-3-fluoro-4-((6-methyl-3-(methylcarbamoyl)-7-(trifluoromethyl)thieno[3,2-b]pyridin-5-yl)oxy)piperidine-1-carboxylate

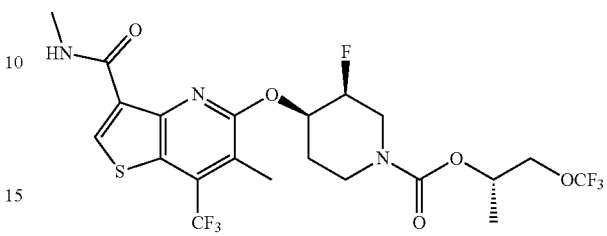

Exchanging tert-butyl (2R,4S)-4-hydroxy-2-methylpiperidine-1-carboxylate for tert-butyl (3S,4S)-3-fluoro-4-hydroxypiperidine-1-carboxylate in step 1, the four step synthetic sequence described in Example 176 was used to prepare the title compound as a white solid. $^1$H NMR (400 MHz, CDCl$_3$) δ 8.88 (q, J=4.9 Hz, 1H), 8.65 (s, 1H), 5.43-5.29 (m, 1H), 5.14-5.05 (m, 1H), 4.94 (br d, J=47.7 Hz, 1H), 4.22-3.54 (m, 5H), 3.54-3.35 (m, 1H), 3.08 (d, J=4.9 Hz, 3H), 2.51 (q, J=1.9 Hz, 3H), 2.34-2.22 (m, 1H), 2.12-1.98 (m, 1H), 1.35 (dd, J=6.6, 1.5 Hz, 3H) ppm. MS: 562 m/z (M+H$^+$).

Example 183. (S)-1-(Trifluoromethoxy)propan-2-yl (3R,4S)-3-fluoro-4-((6-methyl-3-(methylcarbamoyl)-7-(trifluoromethyl)thieno[3,2-b]pyridin-5-yl)oxy)piperidine-1-carboxylate

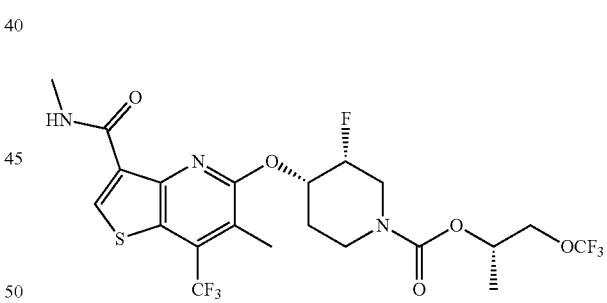

Exchanging tert-butyl (2R,4S)-4-hydroxy-2-methylpiperidine-1-carboxylate for tert-butyl (3R,4R)-3-fluoro-4-hydroxypiperidine-1-carboxylate in step 1, the four step synthetic sequence described in Example 176 was used to prepare the title compound as a foamy, white solid. $^1$H NMR (400 MHz, CDCl$_3$) δ 8.88 (q, J=4.9 Hz, 1H), 8.65 (s, 1H), 5.45-5.27 (m, 1H), 5.14-5.05 (m, 1H), 4.94 (br d, J=47.5 Hz, 1H), 4.24-3.54 (m, 5H), 3.54-3.36 (m, 1H), 3.08 (d, J=4.9 Hz, 3H), 2.51 (q, J=1.8 Hz, 3H), 2.35-2.22 (m, 1H), 2.12-1.98 (m, 1H), 1.35 (dd, J=6.6, 1.5 Hz, 3H) ppm. MS: 562 m/z (M+H$^+$).

Example 186. 1-(7-(Methylcarbamoyl)-4-(trifluoromethyl)thieno[3,2-d]pyrimidin-2-yl)piperidin-4-yl (S)-(1-methoxypropan-2-yl)carbamate

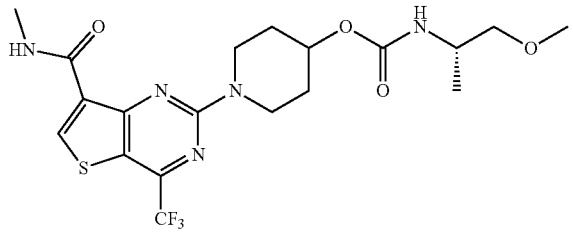

Step 1: tert-Butyl (4-methyl-2-(2,2,2-trifluoroacetyl)thiophen-3-yl)carbamate

To a stirred and cooled (~25 to ~30° C.) solution of tert-butyl (4-methylthiophen-3-yl)carbamate (5.63 g, 26.4 mmol) in tetrahydrofuran (100 mL) was added, dropwise over 15 minutes, a 2.5 M solution of n-butyllithium in hexanes (25.0 mL, 62.5 mmol). Following the addition, the mixture was stirred for another one hour at −20° C. before cooling to −25 to −30° C. and adding a solution of 2,2,2-trifluoro-N,N-dimethylacetamide (6.4 mL, 55 mmol) in tetrahydrofuran (12 mL), dropwise over 20 minutes. The reaction was then allowed to slowly warm to room temperature and stirred overnight. To quench any remaining n-butyllithium, ethyl acetate (10 mL) was slowly added to the stirred solution. The mixture was then partitioned between ethyl acetate (~100 mL) and an aqueous ammonium chloride solution (~150 mL). The organic layer was washed with brine (2×~150 mL), dried (Na$_2$SO$_4$) and concentrated onto ~25 g of silica. The impregnated media was subjected to automated flash chromatography (Combiflash system; 0 to 10% ethyl acetate in heptane; 220 g silica column). The purified title compound (Rf~0.42 with 9:1 heptane/ethyl acetate as the eluant) was obtained as a pale amber solid (3.89 g, 48%). $^1$H NMR (400 MHz, CDCl$_3$) δ 8.87 (br s, 1H), 7.46 (s, 1H), 2.27 (d, J=0.7 Hz, 3H), 1.52 (s, 9H) ppm.

Step 2: 1-(3-Amino-4-methylthiophen-2-yl)-2,2,2-trifluoroethan-1-one

Into a stirred solution of step 1 product (4.85 g, 15.7 mmol) in ethyl acetate (100 mL) was bubbled hydrogen chloride gas for approximately five minutes. The resulting suspension was stirred for 1.25 hour and was then concentrated. The residue was partitioned between chloroform (~75 mL) and aqueous sodium bicarbonate solution (~100 mL). The organic layer was combined with a second extract (chloroform, 1×~75 mL), dried (Na$_2$SO$_4$) and concentrated to afford the crude title compound as a grey-green solid (3.21 g, 98%). $^1$H NMR (400 MHz, CDCl$_3$) δ 7.27 (s, 1H), 6.59 (br s, 2H), 2.10 (s, 9H) ppm.

Step 3: 2-Chloro-7-methyl-4-(trifluoromethyl)thieno[3,2-d]pyrimidine

To a stirred and cooled (0° C.) solution of step 2 product (3.20 g, 15.30 mmol) in acetonitrile (20 mL) was added 2,2,2-trichloroacetyl isocyanate (2.5 mL, 20.98 mmol). After 2-3 minutes, the reaction became a thick suspension of off-white solid. The ice bath was removed and the reaction was allowed to warm to room temperature and then stirred for an additional one hour. Following this time, the mixture was concentrated to afford the crude acylurea as a grayish purple solid. The crude intermediate was loaded into a pressure vessel along with a 2.0 N solution of ammonia in methanol (130 mL, 260.00 mmol). The vessel was sealed and heated at 70° C. for 30 minutes and then allowed to cool to room temperature. The mixture was then concentrated to afford a moist, grayish purple solid. This material was triturated with ethyl acetate (~60 mL) and the suspended solid was recollected by suction filtration and air dried under house vacuum to afford the hydrate of the 7-methyl-4-(trifluoromethyl)thieno[3,2-d]pyrimidin-2(1H)-one intermediate as an off-white solid. This material was taken up in phosphorus oxychloride (15.0 mL, 161 mmol) and heated with stirring at 105° C. After two hours at this temperature the mixture was cooled to room temperature and slowly added, via pipet, to a stirred suspension of sodium bicarbonate (50 g) in water (200 mL). Following the addition, the mixture was transferred to a separatory funnel and extracted with ethyl acetate (3×~80 mL). The combined extracts were dried (Na$_2$SO$_4$) and concentrated onto ~15 g of silica. The impregnated media was subjected to automated flash chromatography (Combiflash system; 0 to 10% ethyl acetate in heptane; 120 g silica column). The title compound (R$_f$=0.4 with 9:1 heptane/ethyl acetate as the eluant) was obtained as a colorless, crystalline solid (2.86 g, 74% overall for three steps). $^1$H NMR (400 MHz, CDCl$_3$) δ 7.89 (q, J=1.2 Hz, 1H), 2.55 (d, J=1.2 Hz, 3H) ppm.

Step 4: 2-Chloro-7-(dibromomethyl)-4-(trifluoromethyl)thieno[3,2-d]pyrimidine

To a stirred solution of step 3 product (2.85 g, 11.3 mmol) in carbon tetrachloride (50 mL) was added N-bromosuccinimide (4.62 g, 26.0 mmol) and benzoyl peroxide (0.273 g, 1.13 mmol). The mixture was heated in an 80° C. oil bath for two hours. The reaction was cooled to room temperature and a small sample of clear solution was removed from the suspension and concentrated to afford a 1H NMR sample. Analysis of the obtained spectrum indicated that starting material had been fully consumed and, in its place, a mixture of the corresponding mono- and dibromomethyl derivatives (molar ratio of ~17:83, respectively) was observed. An additional portion of benzoyl peroxide (0.050 g, 0.206 mmol, 1.8 mole %) was added to the reaction and heating (80° C.) was continued for another 1.5 hours. The reaction was then cooled to room temperature and suction filtered. After rinsing the filtercake with diethyl ether (3×~20 mL), the combined filtrate was concentrated onto ~15 g of silica. The impregnated media was subjected to automated flash chromatography (Combiflash system; 0 to 10% ethyl acetate in heptane; 120 g silica column) to afford partially purified title compound as a viscous, faint amber oil (4.42 g, 96%). The material was carried into the next step without further purification. $^1$H NMR (400 MHz, CDCl$_3$) δ 8.68 (d, J=0.6 Hz, 1H), 7.25 (d, J=0.6 Hz, 1H) ppm.

Step 5: 1-(2-Chloro-4-(trifluoromethyl)thieno[3,2-d]pyrimidin-7-yl)ethan-1-one

To a stirred solution of impure step 4 product (4.40 g, 10.72 mmol) in 2:1 acetonitrile/water (60 mL), was added silver nitrate (5.46 g, 32.2 mmol). The resulting suspension was heated in a preheated oil bath (80° C.) for 30 minutes, cooled and suction filtered through a pad of Celite. The filtering agent/gray-green solid mixture was rinsed with ethyl acetate until the UV activity (as judged by TLC spotting) of the filtrate was faint. The combined filtrate was washed with aqueous sodium bicarbonate solution (1×~150 mL), dried (Na$_2$SO$_4$) and concentrated onto ~10 g of silica. The impregnated media was subjected to automated flash chromatography (Combiflash system; 0 to 10% ethyl acetate in heptane; 120 g silica column) to afford the purified title compound (R$_f$~0.2 with 9:1 heptane/ethyl acetate as eluant) as a white solid (2.17 g, 76%). $^1$H NMR (400 MHz, CDCl$_3$) δ 10.50 (s, 1H), 9.07 (s, 1H) ppm.

Step 6: Piperidin-4-yl (S)-(1-methoxypropan-2-yl)carbamate

Exchanging 2-(aminomethyl)-4-methylmorpholine for (S)-1-methoxypropan-2-amine, the O-(piperidin-4-yl) carbamate preparation described in steps 1 and 2 of Example 115 was used to prepare the crude title compound as a gray gum. This material was used, without characterization or purification, in the next step.

Step 7: 1-(7-Formyl-4-(trifluoromethyl)thieno[3,2-d]pyrimidin-2-yl)piperidin-4-yl (S)-(1-methoxypropan-2-yl)carbamate Into a 20 mL microwave reaction vial equipped with a stir bar was loaded step 5 product (0.250 g, 0.938 mmol), N,N-dimethylformamide (6 mL), step 6 product (0.355 g, 1.64 mmol) and N,N-diisopropylethylamine (0.33 mL, 1.9 mmol). The vessel was sealed and heated in a microwave reactor for one hour at 90° C. LCMS analysis indicated the reaction was complete. The mixture was concentrated and the residue was partitioned between aqueous sodium bicarbonate solution (~40 mL) and chloroform (~40 mL). The organic layer was combined with additional extracts (chloroform, 2×~30 mL), dried (Na$_2$SO$_4$) and concentrated onto ~4 g of silica. The impregnated media was subjected to automated flash chromatography (Combiflash system; 20 to 40% ethyl acetate in heptane; 80 g Gold silica column) to furnish the purified title compound (R$_f$~0.4 with 6:4 heptane/ethyl acetate as the eluant) as a yellow solid (0.332 g, 79%). $^1$H NMR (400 MHz, CDCl$_3$) δ 10.36 (s, 1H), 8.74 (s, 1H), 5.09-4.77 (m, 2H), 4.38-4.21 (m, 2H), 3.98-3.64 (m, 3H), 3.45-3.25 (m, 5H), 2.10-1.91 (m, 2H), 1.84-1.63 (m, 2H), 1.21 (d, J=6.7 Hz, 3H) ppm.

Step 8: (S)-2-(4-(((1-Methoxypropan-2-yl)carbamoyl)oxy)piperidin-1-yl)-4-(trifluoromethyl)-thieno[3,2-d]pyrimidine-7-carboxylic acid To a stirred solution of step 7 product (0.302 g, 0.676 mmol) in N,N-dimethylformamide (10 mL) was added Oxone (0.523 g, 0.851 mmol). The mixture was stirred at room temperature overnight and then analyzed by LCMS and found to be approximately 88% complete as determined by the relative peak areas of starting material and the putative product. Additional Oxone (0.208 g, 0.338 mmol) was added and stirring was continued for another night, though this resulted in no appreciable advancement in the reaction. The mixture was concentrated and the residue was taken up in water (~30 mL). The resulting suspension was sonicated until the undissolved solid was judged homogenous. The solid was collected by suction filtration and rinsed with additional water. The filtercake vacuum oven dried (~50° C.) to afford the crude title compound as a tan solid (0.280 g, 90%). 1H NMR (400 MHz, DMSO-d$_6$) δ 12.94 (br s, 1H), 9.14 (s, 1H), 7.04 (d, J=7.8 Hz, 1H), 4.92-4.71 (m, 1H), 4.43-4.05 (m, 2H), 3.75-3.47 (m, 2H), 3.27 (dd, J=9.4, 6.7 Hz, 1H), 3.15 (dd, J=9.4, 6.3 Hz, 1H), 2.06-1.86 (m, 2H), 1.71-1.45 (m, 2H), 1.03 (d, J=6.7 Hz, 3H) ppm.

Step 9: 1-(7-(Methylcarbamoyl)-4-(trifluoromethyl) thieno[3,2-d]pyrimidin-2-yl)piperidin-4-yl (S)-(1-methoxypropan-2-yl)carbamate Using the procedure for HATU mediated amide coupling described in step 3 of Example 10, step 8 product was condensed with methylamine hydrochloride. The resulting crude product was purified by automated flash chromatography (Combiflash system; 0 to 1% methanol in ethyl acetate; 80 g Gold silica column; see attached pdf for TLC). The target component (Rf~0.40 with 99:1 ethyl acetate/methanol as the eluant) was obtained as an off-white film. This material was ground with a spatula and vacuum oven dried (~60° C.) to afford the title compound as a beige solid (0.226 g, 82%). $^1$H NMR (400 MHz, CDCl$_3$) δ 9.07-8.94 (m, 1H), 8.85 (s, 1H), 5.10-4.70 (m, 2H), 4.30-4.10 (m, 2H), 3.90 (br s, 1H), 3.80-3.65 (m, 2H), 3.45-3.30 (m, 5H), 3.08 (d, J=4.9 Hz, 3H), 2.11-1.97 (m, 2H), 1.88-1.69 (m, 2H), 1.21 (d, J=6.7 Hz, 3H) ppm. MS: 476 m/z (M+H$^+$).

Example 187. 1-(7-(Methylcarbamoyl)-4-(trifluoromethyl)thieno[3,2-d]pyrimidin-2-yl)piperidin-4-yl-(S)-(1-cyclopropylethyl)carbamate

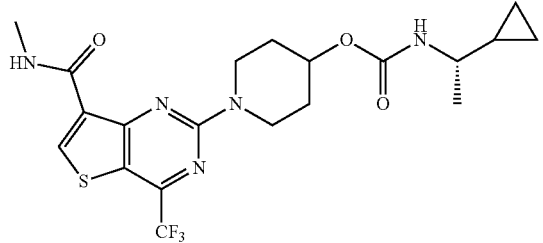

Step 1: Piperidin-4-yl (S)-(1-cyclopropylethyl)carbamate

Exchanging 4,5,6,7-tetrahydropyrazolo[1,5-a]pyrazine dihydrochloride for (S)-1-cyclopropylethan-1-amine, the O-(piperidin-4-yl) carbamate preparation described in step 1 of Example 95 was used to prepare the crude title compound as an off-white solid. This material was deemed sufficiently pure to use, without purification, in the next step. $^1$H NMR (400 MHz, CDCl$_3$) δ 4.83-4.50 (m, 2H), 3.19-2.98 (m, 3H), 2.69 (ddd, J=12.4, 10.2, 2.8 Hz, 2H), 2.01-1.84 (m, 2H), 1.68-1.38 (m, 2H), 1.20 (d, J=6.6 Hz, 3H), 0.80 (qt, J=8.2, 5.0 Hz, 1H), 0.53-0.40 (m, 2H), 0.40-0.30 (m, 1H), 0.25-0.16 (m, 1H) ppm.

Steps 2-4: 1-(7-(Methylcarbamoyl)-4-(trifluoromethyl)thieno[3,2-d]pyrimidin-2-yl)piperidin-4-yl (S)-(1-cyclopropylethyl)carbamate Exchanging piperidin-4-yl (S)-(1-methoxypropan-2-yl) carbamate for step 1 product, the reaction sequence described in steps 7-9 of Example 186 was used to prepare the title compound as a pale yellow solid. $^1$H NMR (400 MHz, CDCl$_3$) δ 9.06-8.95 (m, 1H), 8.85 (s, 1H), 4.98 (br s, 1H), 4.78-4.56 (m, 1H), 4.31-4.13 (m, 2H), 3.82-3.63 (m, 2H), 3.22-3.02 (m, 4H), 2.11-1.99 (m, 2H), 1.86-1.70 (m, 2H), 1.23 (d, J=6.6 Hz, 3H), 0.82 (qt, J=8.0, 4.9 Hz, 1H), 0.56-0.42 (m, 2H), 0.42-0.31 (m, 1H), 0.28-0.18 (m, 1H) ppm. MS: 472 m/z (M+H$^+$).

Example 190. 5-(3-((5-Fluoropyridin-3-yl)oxy)azetidin-1-yl)-N-methyl-7-(trifluoromethyl)thieno[3,2-b]pyridine-3-carboxamide

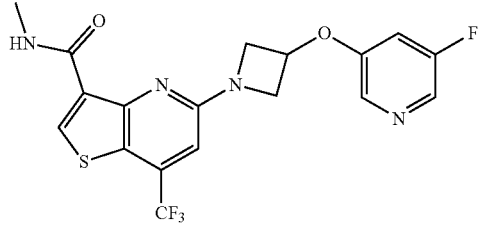 [SMILES: CNC(=O)c1csc2c(C(F)(F)F)cc(N3CC(Oc4cncc(F)c4)C3)nc12]

Step 1: tert-Butyl 3-((5-fluoropyridin-3-yl)oxy)azetidine-1-carboxylate

A stirred mixture of 5-fluoropyridin-3-ol (0.489 g, 4.33 mmol) and tert-butyl 3-hydroxyazetidine-1-carboxylate (0.500 g, 2.89 mmol) in toluene (5 mL) was sparged with nitrogen for 1-2 minutes. (Tributylphosphoranylidene)acetonitrile (1.1 mL, 4.3 mmol) was added and the mixture was heated at 90° C. for 14 hours. Following this time, the reaction was diluted with ethyl acetate (150 mL) and washed with dilute aqueous sodium bicarbonate solution and brine. The organic solution was then dried (Na$_2$SO$_4$) and concentrated to afford the crude product. This material was purified by automated flash chromatography (Biotage Isolera system; 20 to 100% ethyl acetate in heptane; 4 g silica column) to afford the title compound as a brown oil (0.460 g, 59%). $^1$H NMR (400 MHz, CDCl$_3$) δ 8.17 (d, J=2.3 Hz, 1H), 8.01 (br s, 1H), 6.82 (dt, J=9.8, 2.4 Hz, 1H), 4.99-4.87 (m, 1H), 4.40-4.27 (m, 2H), 4.09-3.95 (m, 2H), 1.45 (s, 9H) ppm.

Step 2: 3-(Azetidin-3-yloxy)-5-fluoropyridine

A stirred and cooled (0° C.) solution of step 1 product (0.460 g, 1.71 mmol) in dichloromethane (1 mL) was treated with trifluoroacetic acid (1.3 mL, 17 mmol). After one hour, the mixture was concentrated. The residue was purified by MPLC using a sulfonated polystyrene resin column that was pre-conditioned with dichloromethane and methanol and eluted with a 4M ammonia in methanol solution to afford the title compound as an amber oil (0.274 g, 95%). $^1$H NMR (400 MHz, CDCl$_3$) δ 8.13 (d, J=2.4 Hz, 1H), 8.03 (dd, J=2.5, 1.0 Hz, 1H), 6.81 (dt, J=10.0, 2.4, 2.4 Hz, 1H), 5.02 (p, 1H), 4.03-3.90 (m, 2H), 3.90-3.74 (m, 2H), 2.05 (s, 1H) ppm. MS: 427 m/z (M+H$^+$).

Step 3: 5-(3-((5-Fluoropyridin-3-yl)oxy)azetidin-1-yl)-N-methyl-7-(trifluoromethyl)thieno[3,2-b]pyridine-3-carboxamide Into a 5 mL microwave reaction vial was loaded Intermediate 5 (0.100 g, 0.339 mmol), step 2 product (0.114 g, 0.679 mmol), N,N-diisopropylethylamine (118 µL, 0.679 mmol) and N-methyl-2-pyrrolidinone (1.8 mL). The vessel was sealed and heated in a microwave reactor for 1.5 hours at 150° C. The mixture was poured into a vigorously stirred slurry of crushed ice and water. After the ice had fully melted, the precipitate was collected via filtration and purified by reversed phase HPLC (C18, 30×150 mm, 5 m Waters SunFire OBD column; 20 to 100% acetonitrile/water gradient) to afford the title compound as a white solid (0.046 g, 28%). 1H NMR (400 MHz, DMSO-d$_6$) δ 9.37-9.24 (m, 1H), 8.77 (s, 1H), 8.28 (d, J=2.2 Hz, 1H), 8.26-8.17 (m, 1H), 7.45 (dt, J=10.8, 2.4, 2.4 Hz, 1H), 7.07 (s, 1H), 5.46-5.30 (m, 1H), 4.81-4.61 (m, 2H), 4.34-4.17 (m, 2H), 2.93 (d, J=4.8 Hz, 3H) ppm. MS: 427 m/z (M+H$^+$).

Example 204. (R)-1-Cyclopropylethyl 6-((3-(methylcarbamoyl)-7-(trifluoromethyl)thieno[3,2-b]pyridin-5-yl)oxy)-2-azaspiro[3.3]heptane-2-carboxylate

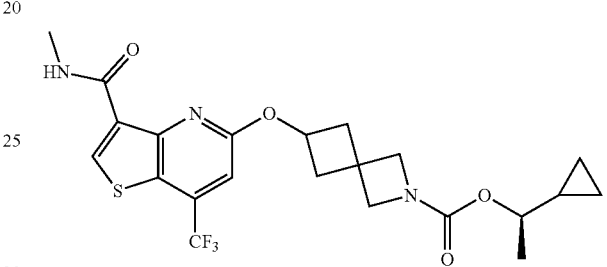

Step 1: (R)-1-Cyclopropylethyl (4-nitrophenyl) carbonate

To a stirred solution of (R)-1-cyclopropylethan-1-ol (197 mg, 2.29 mmol) and triethylamine (319 µL, 2.29 mmol) in dichloromethane (4 mL) was added 4-nitrophenyl chloroformate (461 mg, 2.29 mmol) at 0° C. The suspension was stirred at room temperature for 24 hours and then concentrated. The residue was purified by automated flash chromatography to afford the title product as a clear, colorless oil (330 mg, 57%). $^1$H NMR (400 MHz, CDCl$_3$) δ 8.35-8.23 (m, 2H), 7.45-7.33 (m, 2H), 4.47-4.19 (m, 1H), 1.46 (d, J=6.4 Hz, 3H), 1.22-1.06 (m, 1H), 0.69-0.60 (m, 2H), 0.58-0.48 (m, 1H), 0.38-0.26 (m, 1H) ppm.

Step 2: (R)-1-Cyclopropylethyl 6-((3-(methylcarbamoyl)-7-(trifluoromethyl)thieno[3,2-b]pyridin-5-yl)oxy)-2-azaspiro[3.3]heptane-2-carboxylate A mixture of Intermediate 25 (150 mg, 0.404 mmol), step 1 product (101 mg, 0.404 mmol) and triethylamine (56 µL, 0.40 mmol) in N,N-dimethylformamide (2 mL) was stirred at 90° C. for 30 minutes in a microwave reactor. The reaction was then concentrated and the residue was purified by reversed phase HPLC (C18, 30×150 mm, 5 m Waters SunFire OBD column; 20 to 100% acetonitrile/water gradient) to afford the title compound as a white solid (109 mg, 56%). $^1$H NMR (400 MHz, CDCl$_3$) δ 9.10 (br s, 1H), 8.75 (s, 1H), 7.08 (s, 1H), 5.14 (p, 1H), 4.25-4.20 (m, 1H), 4.09-4.04 (m, 4H), 3.11 (d, J=4.9 Hz, 3H), 2.90-2.73 (m, 2H), 2.59-2.39 (m, 2H), 1.29 (d, J=6.3 Hz, 3H), 0.99-0.93 (m, 1H), 0.58-0.18 (m, 4H) ppm. MS: 484 m/z (M+H$^+$).

Example 212. 2-(Trifluoromethoxy)ethyl 6-((3-(methylcarbamoyl)-7-(trifluoromethyl)thieno[3,2-b]pyridin-5-yl)oxy)-1-azaspiro[3.3]heptane-1-carboxylate

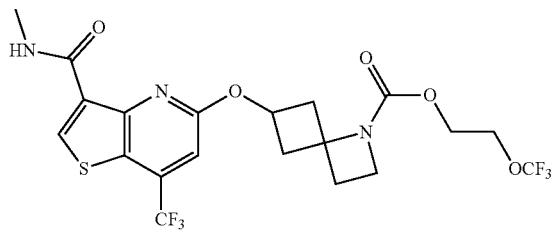 [SMILES: CNC(=O)c1csc2c(C(F)(F)F)cc(OC3CC4(CCN4C(=O)OCCOC(F)(F)F)C3)nc12]

Step 1: tert-Butyl 6-((3-(methylcarbamoyl)-7-(trifluoromethyl)thieno[3,2-b]pyridin-5-yl)oxy)-1-azaspiro[3.3]heptane-1-carboxylate To a stirred mixture of Intermediate 5 (265 mg, 0.899 mmol) and tert-butyl 6-hydroxy-1-azaspiro[3.3]heptane-1-carboxylate (249 mg, 1.17 mmol) in tetrahydrofuran (10 mL) was added potassium tert-butoxide (131 mg, 1.17 mmol). The reaction was stirred at 60° C. for two hours, cooled to room temperature and concentrated. The residue was dissolved in dichloromethane and this solution was washed with water and brine, dried ($Na_2SO_4$) and concentrated. The crude material was purified by automated flash chromatography (Biotage Isolera system; 0 to 100% ethyl acetate in dichloromethane; 10 g silica column) to afford the title compound as a beige solid (0.254 g, 60%). $^1$H NMR (400 MHz, $CDCl_3$) δ 9.19 (br s, 1H), 8.74 (s, 1H), 7.08 (s, 1H), 4.97 (p, J=7.2 Hz, 1H), 3.96-3.80 (m, 2H), 3.48-2.84 (m, 5H), 2.72 (s, 2H), 2.42-2.23 (m, 2H), 1.48 (s, 9H) ppm. MS: 472 m/z (M+H$^+$).

Step 2: 5-((1-Azaspiro[3.3]heptan-6-yl)oxy)-N-methyl-7-(trifluoromethyl)thieno[3,2-b]pyridine-3-carboxamide Using the procedure described in step 2 of Example 190, the step 1 product was N-deprotected to afford the title compound as a beige solid. MS: 372 m/z (M+H$^+$).

Step 3: 2-(Trifluoromethoxy)ethyl 6-((3-(methylcarbamoyl)-7-(trifluoromethyl)thieno[3,2-b]pyridin-5-yl)oxy)-1-azaspiro[3.3]heptane-1-carboxylate A stirred mixture of step 2 product (0.167 g, 0.450 mmol), Intermediate 11 (0.100 g, 0.450 mmol) and N-hydroxysuccinimide (0.053 g, 0.40 mmol) in acetonitrile (10 mL) was stirred overnight at 38° C. The reaction was then concentrated and residue was taken up in dichloromethane (20 mL). The solution was washed with water (10 mL), dried ($MgSO_4$) and concentrated. The crude material was purified by automated flash chromatography (Biotage Isolera system; 50 to 100% ethyl acetate in heptane; 4 g silica column) to afford the title compound as a white solid (0.142 g, 60%). $^1$H NMR (400 MHz, $CDCl_3$) δ 9.17 (br s, 1H), 8.74 (s, 1H), 7.10 (br s, 1H), 4.98 (p, 1H), 4.55-3.83 (m, 6H), 3.11 (d, J=4.9 Hz, 5H), 2.76 (s, 2H), 2.52-2.34 (m, 2H) ppm. MS: 528 m/z (M+H$^+$).

Example 218. Cyclopropylmethyl ((1S,3S)-3-((6-methyl-3-(methylcarbamoyl)-7-(trifluoromethyl)thieno[3,2-b]pyridin-5-yl)oxy)cyclobutyl)carbamate

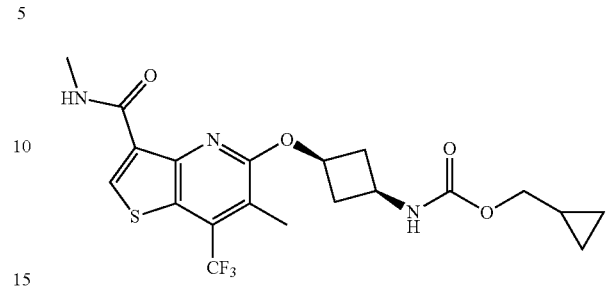

Step 1: 5-((1s,3s)-3-Aminocyclobutoxy)-N,6-dimethyl-7-(trifluoromethyl)thieno[3,2-b]pyridine-3-carboxamide Exchanging Intermediate 5 for Intermediate 15 and tert-butyl 6-hydroxy-1-azaspiro[3.3]heptane-1-carboxylate for tert-butyl ((1s,3s)-3-hydroxycyclobutyl)carbamate, the reaction sequence outlined in steps 1 and 2 of Example 212 was used to prepare the title compound. MS: 460 m/z (M+H$^+$).

Step 2: Cyclopropylmethyl ((1s,3s)-3-((6-methyl-3-(methylcarbamoyl)-7-(trifluoromethyl)thieno[3,2-b]pyridin-5-yl)oxy)cyclobutyl)carbamate To a stirred solution of step 1 product (74 mg, 0.208 mmol) and triethylamine (57 μL, 0.415 mmol) in chloroform (4 mL) added cyclopropylmethyl chloroformate (33 mg, 0.250 mmol). The mixture was stirred at room temperature for 30 minutes and then concentrated. The residue was partially purified by automated flash chromatography (Biotage Isolera system; 20 to 100% ethyl acetate in heptane; 4 g silica column). The resulting solid was triturated with diethyl ether and air dried on the frit under house vacuum to afford the title compound as a cream solid (65 mg, 68%). 1H NMR (400 MHz, DMSO-d$_6$) δ 8.74 (br d, 1H), 8.52 (s, 1H), 7.33 (d, J=8.1 Hz, 1H), 4.84 (p, 1H), 3.68 (q, 1H), 3.54 (d, J=7.2 Hz, 2H), 2.75 (d, J=4.8 Hz, 3H), 2.70-2.54 (m, 2H), 2.31-2.22 (m, 3H), 2.02-1.86 (m, 2H), 0.85-0.74 (m, 1H), 0.35-0.10 (m, 4H) ppm. MS: 458 m/z (M+H$^+$).

Example 220. (S)-1-Cyclopropylethyl ((1S,3R)-3-((6-methyl-3-(methylcarbamoyl)-7 (trifluoromethyl)thieno[3,2-b]pyridin-5-yl)oxy)cyclobutyl)carbamate

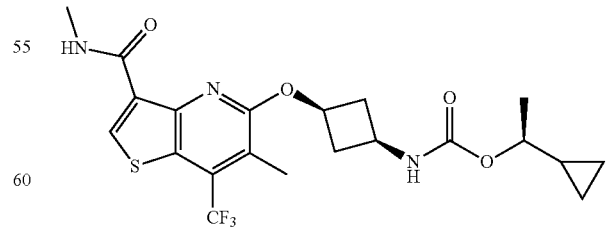

Exchanging Intermediate 27 for the step 1 product of Example 218 and (R)-1-cyclopropylethan-1-ol for (S)-1-cyclopropylethan-1-ol, the reaction sequence outlined in Example 204 was used to prepare the title compound as a white solid. ¹H NMR (400 MHz, CDCl₃) δ 9.14 (br s, 1H), 8.63 (s, 1H), 4.96 (p, 1H), 4.88 (br s, 1H), 4.23 (br s, 1H), 4.08 (br s, 1H), 3.26-2.96 (m, 5H), 2.47 (q, 3H), 2.28-2.06 (m, 2H), 1.30 (d, J=6.3 Hz, 3H), 1.05-0.89 (m, 1H), 0.66-0.15 (m, 4H) ppm. MS: 472 m/z (M+H⁺).

Example 254. 2-(Trifluoromethoxy)ethyl 3-methyl-3-((3-(methylcarbamoyl)-7-(trifluoromethyl)thieno[3,2-b]pyridin-5-yl)oxy)azetidine-1-carboxylate

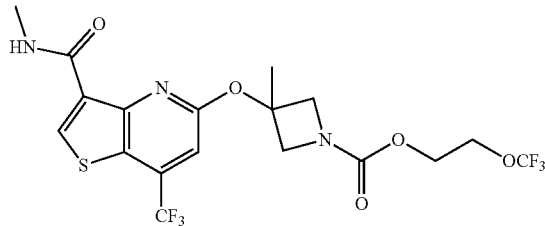 [SMILES: CNC(=O)c1csc2c(C(F)(F)F)cc(OC3(C)CN(C(=O)OCCOC(F)(F)F)C3)nc12]

Step 1: N-Methyl-5-((3-methylazetidin-3-yl)oxy)-7-(trifluoromethyl)thieno[3,2-b]pyridine-3-carboxamide Using the procedure described in step 2 of Example 190, the N-tert-butoxycarbonyl protecting group of the title compound of Example 269 was cleaved with trifluoroacetic acid in dichloromethane to afford the title compound as a beige solid. MS: 346 m/z (M+H⁺).

Step 2: 2-(Trifluoromethoxy)ethyl 3-methyl-3-((3-(methylcarbamoyl)-7 (trifluoromethyl)thieno[3,2-b]pyridin-5-yl)oxy)azetidine-1-carboxylate To a stirred mixture of step 1 product (188 mg, 0.544 mmol) and Intermediate 11 (134 mg, 0.599 mmol) in acetonitrile (5 mL) was added N-hydroxysuccinimide (63 mg, 0.544 mmol). After two hours at room temperature the reaction was concentrated and the crude material was purified by reversed phase HPLC (C18, 30×150 mm, 5 m Waters Sunfire OBD column; 20 to 100% acetonitrile/water) to afford the title compound as a tan solid (43 mg, 16%). ¹H NMR (400 MHz, CDCl₃) δ 8.78 (d, 1H), 8.72 (d, 1H), 7.17-7.08 (m, 1H), 4.43 (d, 2H), 4.32 (s, 2H), 4.22-4.08 (m, 4H), 3.10 (d, 3H), 1.92 (s, 3H) ppm. MS: 502 m/z (M+H⁺).

Example 256. 2-(Trifluoromethoxy)ethyl 3-((3-(methylcarbamoyl)-7-(trifluoromethyl)thieno[3,2-b]pyridin-5-yl)oxy)azetidine-1-carboxylate

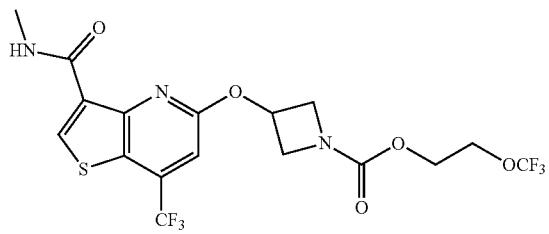 [SMILES: CNC(=O)c1csc2c(C(F)(F)F)cc(OC3CN(C(=O)OCCOC(F)(F)F)C3)nc12]

Step 1: tert-Butyl 3-((3-(methylcarbamoyl)-7-(trifluoromethyl)thieno[3,2-b]pyridin-5-yl)oxy)azetidine-1-carboxylate Exchanging tert-butyl 3-hydroxy-3-methylazetidine-1-carboxylate for tert-butyl 3-hydroxyazetidine-1-carboxylate, the same synthetic procedure described in Example 269 was used to prepare the title compound as a white solid. ¹H NMR (400 MHz, CDCl₃) δ 8.87-8.76 (m, 2H), 7.18 (s, 1H), 5.46-5.36 (m, 1H), 4.44-4.34 (m, 2H), 4.16-4.12 (m, 2H), 3.12 (d, J=4.9 Hz, 3H), 1.47 (s, 9H) ppm. MS: 432 m/z (M+H⁺).

Steps 2-3: 2-(Trifluoromethoxy)ethyl 3-((3-(methylcarbamoyl)-7-(trifluoromethyl)thieno[3,2-b]pyridin-5-yl)oxy)azetidine-1-carboxylate Exchanging the title compound of Example 269 for the present Example's step 1 product, the two-step reaction sequence described in Example 254 was used to prepare the title compound as a white solid. ¹H NMR (400 MHz, CDCl₃) δ 8.79 (br s, 1H), 8.74 (s, 1H), 7.19 (s, 1H), 5.52-5.41 (m, 1H), 4.56-4.42 (m, 2H), 4.42-4.28 (m, 2H), 4.28-4.10 (m, 4H), 3.12 (d, J=4.9 Hz, 3H) ppm. MS: 488 m/z (M+H⁺).

Example 269. tert-Butyl 3-methyl-3-((3-(methylcarbamoyl)-7-(trifluoromethyl)thieno[3,2-b]pyridin-5-yl)oxy)azetidine-1-carboxylate

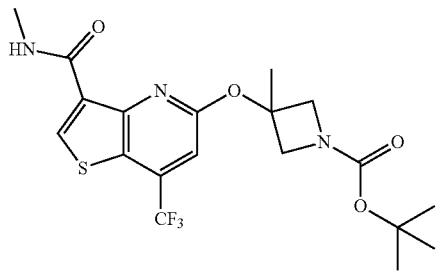 [SMILES: CNC(=O)c1csc2c(C(F)(F)F)cc(OC3(C)CN(C(=O)OC(C)(C)C)C3)nc12]

To a stirred mixture of Intermediate 5 (276 mg, 0.937 mmol) and tert-butyl 3-hydroxy-3-methylazetidine-1-carboxylate (277 mg, 1.40 mmol) in tetrahydrofuran (5 mL) was added potassium tert-butoxide (158 mg, 1.40 mmol). The mixture was heated at 70° C. for three hours and then cooled and concentrated. The residue was taken up in ethyl acetate (~50 mL) and this solution was washed with an aqueous ammonium chloride solution and brine, dried (Na₂SO₄) and concentrated. The crude material was purified by automated flash chromatography (Biotage Isolera system; 50 to 100% ethyl acetate in dichloromethane; 25 g silica column) to afford the title compound as a brown solid (710 mg, 74%). ¹H NMR (400 MHz, CDCl₃) δ 8.77 (br s, 2H), 7.12 (s, 1H), 4.41-4.25 (m, 2H), 4.11-3.94 (m, 2H), 3.10 (d, J=4.9 Hz, 3H), 1.89 (s, 3H), 1.46 (s, 9H) ppm. MS: 446 m/z (M+H⁺).

Example 274. Methyl 5-(1-(tert-butoxycarbonyl) piperidin-4-yl)-7-(trifluoromethyl)thieno[3,2-b]pyridine-3-carboxylate

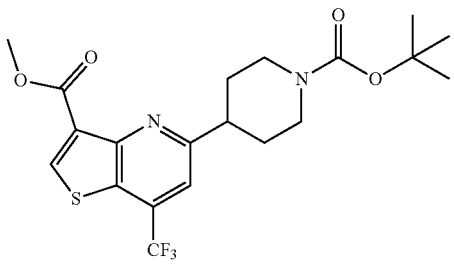 [SMILES: COC(=O)c1csc2c(C(F)(F)F)cc(C3CCN(C(=O)OC(C)(C)C)CC3)nc12]

Step 1: Methyl 5-(1-(tert-butoxycarbonyl)-1,2,3,6-tetrahydropyridin-4-yl)-7-(trifluoromethyl)-thieno[3,2-b]pyridine-3-carboxylate To a stirred solution of Intermediate 3 (2.00 g, 6.77 mmol) and (1-tert-butoxycarbonyl-1,2,3,6-tetrahydropyridin-4-yl) boronic acid pinacol ester (2.44 g, 7.49 mmol) in 1,2-dimethoxyethane (35 mL) was added a 2.0 M aqueous sodium carbonate solution (7.0 mL, 14 mmol). The mixture was sparged with nitrogen for ~10 minutes and then treated with [1,1'-bis(diphenylphosphino)ferrocene]dichloropalladium(II) (0.473 g, 0.639 mmol). The dark red-brown mixture was sparged with nitrogen a second time and then heated to reflux. After 19 hours, the reaction was analyzed by LCMS and found to contain comparable quantities of the desired product the corresponding carboxylic acid (via concomitant ester hydrolysis). The mixture was cooled to room temperature and then suction filtered through a pad of Celite. The filtrate was diluted with ethyl acetate (100 mL) and washed with water (2×50 mL) and brine (1×50 mL). The organic layer was then dried (MgSO4) and concentrated. The residue was purified by automated flash chromatography (Combiflash system; 0 to 30% ethyl acetate in heptane; 120 g silica column) to afford the title compound as a white solid (1.33 g, 44%). $^1$H NMR (400 MHz, CDCl$_3$) δ 8.70 (s, 1H), 7.70 (s, 1H), 6.82-6.89 (m, 1H), 4.17-4.25 (m, 2H), 4.01 (s, 3H), 3.66-3.76 (m, 2H), 2.79-2.89 (m, 2H), 1.50 (s, 9H) ppm. 19F NMR (376 MHz, CDCl$_3$) δ -64.0 (s) ppm. MS: 443 m/z (M+H$^+$).

Step 2: Methyl 5-(1-(tert-butoxycarbonyl)piperidin-4-yl)-7-(trifluoromethyl)thieno[3,2-b]pyridine-3-carboxylate A stirred suspension of step 1 product (1.27 g, 2.87 mmol) and 10% palladium on carbon (0.303 g) in tetrahydrofuran (30 mL) was repeatedly cycled between vacuum and a nitrogen atmosphere. The reaction flask was evacuated a final time and then refilled with hydrogen (via balloon). After 24 hours, the reaction was analyzed by LCMS and found to be incomplete. Additional palladium on carbon (0.440 g) was added and the reaction was restarted as before. After overnight stirring, the reaction was analyzed again and found to be near or at completion. The suspension was suction filtered through a pad of Celite, which was subsequently rinsed with additional tetrahydrofuran. The combined filtrate was concentrated and the resulting dark green, viscous oil was subjected to automated flash chromatography (Combiflash system; 0 to 20% ethyl acetate in heptane; 80 g silica column). The purified title compound was afforded as a yellow foam (0.633 g, 50%). $^1$H NMR (400 MHz, CDCl$_3$) δ 8.69 (s, 1H), 7.47 (s, 1H), 4.17-4.43 (m, 2H), 4.00 (s, 3H), 3.19 (tt, J=11.8, 3.7 Hz, 1H), 2.80-3.02 (m, 2H), 2.00-2.15 (m, 2H), 1.91-1.81 (m, 2H), 1.50 (s, 9H) ppm. 19F NMR (376 MHz, CDCl$_3$) δ -64.0 (s) ppm. MS: 445 m/z (M+H$^+$).

Example 297. Isobutyl (1-(3-(methylcarbamoyl)-7-(trifluoromethyl)thieno[3,2-b]pyridin-5-yl)piperidin-4-yl) carbamate

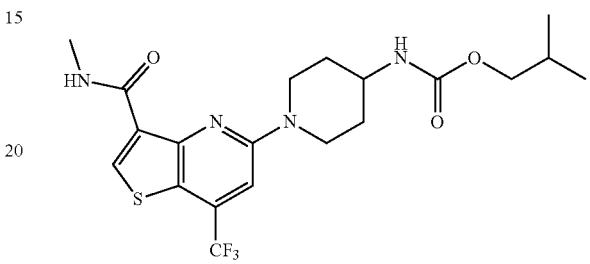

Step 1: Methyl 5-(4-((tert-butoxycarbonyl)amino) piperidin-1-yl)-7-(trifluoromethyl)thieno[3,2-b]pyridine-3-carboxylate Into a 10 mL microwave reaction vessel equipped with a stir bar was loaded 4-(tert-butoxycarbonylamino)piperidine (1.53 g, 7.50 mmol), Intermediate 3 (1.48 g, 5.00 mmol), N,N-dimethylformamide (3 mL) and N,N-diisopropylethylamine (1.31 mL, 7.50 mmol). The vessel was sealed and heated in a microwave reactor for seven hours at 100° C. The mixture diluted with ethyl acetate (10 mL) and then filtered to remove the solids. The filtercake was rinsed with additional ethyl acetate and the combined filtrate was diluted with ethyl acetate (100 mL), washed with an aqueous sodium bicarbonate solution (1×100 mL) and brine (1×100 mL). The organic layer was dried (MgSO$_4$) and concentrated. The resulting solid was purified by automated flash chromatography (Combiflash system; 0 to 10% methanol in dichloromethane; silica column) to afford the title compound as yellow solid (1.70 g, 74%). MS: 460 m/z (M+H$^+$).

Step 2: tert-Butyl (1-(3-(methylcarbamoyl)-7-(trifluoromethyl)thieno[3,2-b]pyridin-5-yl)piperidin-4-yl) carbamate Into a 10 mL microwave reaction vessel equipped with a stir bar was step 1 product (200 mg, 0.435 mmol) and a 2.0 M solution of methylamine in methanol (2.1 mL, 4.2 mmol). The vessel was sealed and heated in a microwave reactor for two hours at 100° C. The solution was then concentrated and the residue was triturated with a mixture of ethyl acetate and heptane to afford the title compound as yellow solid (199 mg, 100%). MS: 459 m/z (M+H$^+$).

Step 3: 5-(4-Aminopiperidin-1-yl)-N-methyl-7-(trifluoromethyl)thieno[3,2-b]pyridine-3-carboxamide trifluoroacetate salt To a stirred solution of step 2 product (199 mg, 0.435 mmol) in dichloromethane (3 mL) was added trifluoroacetic acid (0.67 mL, 8.7 mmol). The reaction was stirred overnight at room temperature and then concentrated. The residue was triturated with a mixture ethyl acetate and heptane to afford the title compound as yellow solid (200 mg, 97%). MS: 359 m/z (M+H⁺).

Step 4: Isobutyl (1-(3-(methylcarbamoyl)-7-(trifluoromethyl)thieno[3,2-b]pyridin-5-yl)piperidin-4-yl)carbamate To a stirred solution of step 3 product (100 mg, 0.212 mmol) and N,N-diisopropylethylamine (85 µL, 0.487 mmol) in dichloromethane (5 mL) was added isobutyl chloroformate (32 mg, 0.233 mmol). The reaction was maintained at room temperature overnight and then partitioned between an aqueous sodium bicarbonate solution (50 mL) and dichloromethane (50 mL). The organic layer was washed with brine (1×50 mL), dried (MgSO₄) and concentrated. The resulting crude material was purified by flash chromatography (Combiflash system; 0 to 20% ethyl acetate in dichloromethane; silica column) to afford the title compound as white solid (40 mg, 41%). 1H NMR (400 MHz, DMSO-d₆) δ 9.29 (br, 1H), 8.75 (s, 1H), 7.50 (s, 1H), 7.16 (d, J=7.7 Hz, 1H), 4.29 (d, J=13.1 Hz, 2H), 3.77-3.71 (m, 2H), 3.69-3.60 (m, 1H), 3.27-3.12 (m, 2H), 2.94 (d, J=4.5 Hz, 3H), 1.96-1.76 (m, 3H), 1.54-1.33 (m, 2H), 0.88 (d, J=6.7 Hz, 6H) ppm. MS: 459 m/z (M+H⁺).

Example 300. tert-Butyl (1-(3-(methylcarbamoyl)-7-(trifluoromethyl) thieno[3,2-b]pyridin-5-yl)azetidin-3-yl)carbamate

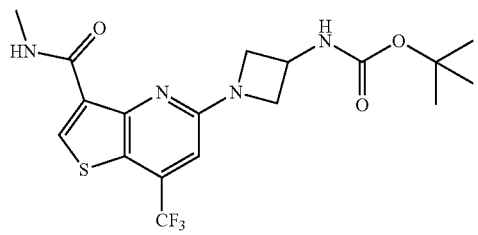 [SMILES: CNC(=O)c1csc2c(C(F)(F)F)cc(N3CC(NC(=O)OC(C)(C)C)C3)nc12]

Exchanging 4-(tert-butoxycarbonylamino)piperidine for tert-butyl 3-azetidinylcarbamate, the two-step reaction sequence outlined in steps 1-2 of Example 297 was used to prepare the title compound as a yellow solid. 1H NMR (400 MHz, DMSO-d₆) δ 9.38 (br, 1H), 8.76 (s, 1H), 7.65 (d, J=7.5 Hz, 1H), 6.99 (s, 1H), 4.56-4.47 (m, 1H), 4.41 (t, J=8.1 Hz, 2H), 4.03-3.94 (m, 2H), 2.93 (d, J=4.7 Hz, 3H), 1.40 (s, 9H) ppm. MS: 431 m/z (M+H⁺).

Example 339. Oxetan-3-yl 6-(3-(methylcarbamoyl)-7-(trifluoromethyl)thieno[3,2-b]pyridin-5-yl)-2,6-diazaspiro[3.3]heptane-2-carboxylate Step 1: 4-Nitrophenyl oxetan-3-yl carbonate To a stirred solution of oxetan-3-ol (0.500 g, 6.75 mmol) and triethylamine (1.42 mL, 10.1 mmol) in dichloromethane (4 mL) was added p-nitrophenyl chloroformate (1.43 g, 7.09 mmol). After four hours at room temperature, the mixture was diluted with dichloromethane and then washed with aqueous sodium bicarbonate solution and brine. The organic layer was dried (Na₂SO₄) and concentrated to afford the crude product as a viscous, clear yellow oil. This material was used without purification.

Step 2: Methyl 5-(6-((oxetan-3-yloxy)carbonyl)-2,6-diazaspiro[3.3]heptan-2-yl)-7-(trifluoromethyl)thieno[3,2-b]pyridine-3-carboxylate Into a 20 mL microwave reaction vessel equipped with a stir bar was loaded Intermediate 8 (0.150 g, 0.420 mmol), N,N-dimethylformamide (2 mL), step 1 product (0.151 g, 0.630 mmol), triethylamine (0.23 mL, 1.7 mmol) and 4-(dimethylamino)pyridine (7 mg, 59 mol). The vessel was sealed and then heated in a microwave reactor for one hour at 50° C. The mixture was then concentrated and the residue was partitioned between 4:1 chloroform/isopropanol and aqueous sodium bicarbonate solution. The organic layer was washed with brine, dried (Na₂SO₄) and concentrated. The crude material was purified by automated flash chromatography (Combiflash system; ethyl acetate/heptane; silica column) to afford the title compound as a white solid (118 mg, 62%). MS: 458 m/z (M+H⁺).

Step 3: Oxetan-3-yl 6-(3-(methylcarbamoyl)-7-(trifluoromethyl)thieno[3,2-b]pyridin-5-yl)-2,6-diazaspiro[3.3]heptane-2-carboxylate Into a 5 mL microwave reaction vessel equipped with a stir bar was loaded step 2 product (0.118 g, 0.258 mmol) and a 2.0 N solution of methylamine in methanol (0.64 mL, 1.29 mmol). The vessel was sealed and heated in a microwave reactor for five hours at 60° C. The mixture was then concentrated and the residue was purified by automated flash chromatography (Combiflash system; methanol/dichloromethane; silica column) to afford the title compound as a white solid (83 mg, 71%). ¹H NMR (400 MHz, CDCl₃) δ 9.46 (br s, 1H), 8.72 (s, 1H), 6.62 (s, 1H), 5.46-5.36 (m, 1H), 4.94-4.83 (m, 2H), 4.70-4.59 (m, 2H), 4.44-4.17 (m, 8H), 3.07 (d, J=4.7 Hz, 3H) ppm. MS: 457 m/z (M+H⁺).

Example 350. 1-Cyanopropan-2-yl 6-(3-(methylcarbamoyl)-7-(trifluoromethyl)thieno[3,2-b]pyridin-5-yl)-2,6-diazaspiro[3.3]heptane-2-carboxylate

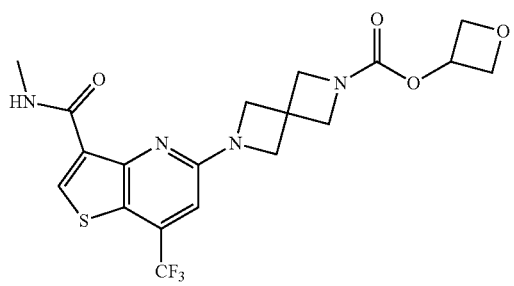 [SMILES: CNC(=O)c1csc2c(C(F)(F)F)cc(N3CC4(CN(C(=O)OC5COC5)C4)C3)nc12]

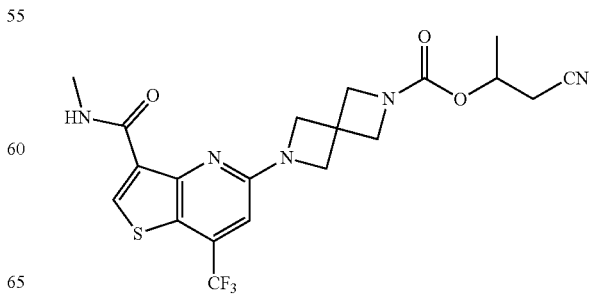

Exchanging oxetan-3-ol for 3-hydroxybutanenitrile, the three-step reaction sequence outlined in Example 339 was used to prepare the title compound. ¹H NMR (400 MHz, CDCl₃) δ 9.42 (s, 1H), 8.69 (s, 1H), 6.61 (s, 1H), 5.06-4.94 (m, 1H), 4.41-4.16 (m, 8H), 3.07 (d, J=4.8 Hz, 3H), 2.83-2.71 (m, 1H), 2.66-2.50 (m, 1H), 1.43 (d, J=6.4 Hz, 3H) ppm. MS: 468 m/z (M+H⁺).

Example 361. 5-(4-(2-(3,3-Difluoropyrrolidin-1-yl)ethoxy)piperidin-1-yl)-N-methyl-7-(trifluoromethyl)thieno[3,2-b]pyridine-3-carboxamide

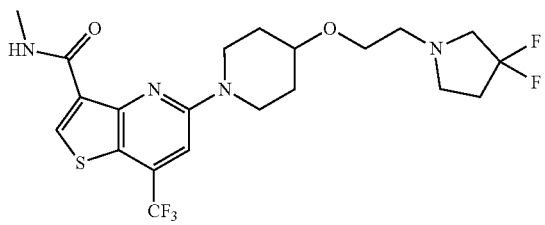 [SMILES: CNC(=O)c1csc2c(C(F)(F)F)cc(N3CCC(OCCN4CCC(F)(F)C4)CC3)nc12]

Step 1: tert-Butyl 4-(2-((methylsulfonyl)oxy)ethoxy)piperidine-1-carboxylate

To a stirred and cooled (0° C.) solution of tert-butyl 4-(2-hydroxyethoxy)piperidine-1-carboxylate (330 mg, 1.35 mmol) and triethylamine (377 μL, 2.69 mmol) in tetrahydrofuran (5 mL) was added methanesulfonyl chloride (136 μL, 1.75 mmol), dropwise over five minutes. The reaction was allowed to slowly warm to room temperature and stirred overnight. The mixture was then concentrated and the residue was taken up in dichloromethane. This solution was washed with aqueous sodium bicarbonate solution and brine and then dried (Na₂SO₄) and concentrated to afford the crude mesylate as a clear, pale yellow oil (0.360 g, 83%).

Step 2: tert-Butyl 4-(2-(3,3-difluoropyrrolidin-1-yl)ethoxy)piperidine-1-carboxylate To a stirred solution of crude step 1 product (0.360 g, 1.11 mmol) in acetonitrile (5 mL) was added N,N-diisopropylethylamine (1.4 mL, 8.0 mmol) and 3,3-difluoropyrrolidine hydrochloride (0.383 g, 2.67 mmol). The mixture was stirred at room temperature for two days and then concentrated. The residue was taken up in dichloromethane and this solution was washed with aqueous sodium bicarbonate solution and brine. The organic layer was then dried (Na₂SO₄) and concentrated. The resulting crude material was purified by automated flash chromatography (Combiflash system; methanol/dichloromethane; silica column) to afford the title compound as a colorless oil (0.108 g, 29%). ¹H NMR (400 MHz, CDCl₃) δ 3.82-3.68 (m, 2H), 3.58 (t, J=5.7 Hz, 2H), 3.50-3.38 (m, 1H), 3.15-3.03 (m, 2H), 2.97 (t, J=13.4 Hz, 2H), 2.84-2.65 (m, 4H), 2.32-2.19 (m, 2H), 1.86-1.76 (m, 2H), 1.57-1.40 (m, 11H) ppm.

Step 3: 4-(2-(3,3-Difluoropyrrolidin-1-yl)ethoxy)piperidine dihydrochloride

To a stirred solution of step 2 product (0.108 g, 0.323 mmol) in dichloromethane (2 mL) was added a 2.0 M solution of hydrogen chloride in diethyl ether (2 mL). The reaction was stirred at room temperature for two hours and then concentrated to afford the crude title compound as a tacky, red gum (0.099 g, 100%).

Step 4: 5-(4-(2-(3,3-Difluoropyrrolidin-1-yl)ethoxy)piperidin-1-yl)-N-methyl-7-(trifluoromethyl)thieno[3,2-b]pyridine-3-carboxamide Exchanging the step 2 product of Example 115 for crude step 3 product of the present Example and increasing the equivalents of N,N-diisopropylethylamine base used from 2.1 to 4.2, the procedure for the nucleophilic aromatic substitution of Intermediate 5 described in step 3 of Example 115 was used to prepare the title compound as a red-yellow solid. ¹H NMR (400 MHz, CDCl₃) δ 9.47 (br s, 1H), 8.65 (s, 1H), 7.06 (s, 1H), 3.98-3.88 (m, 2H), 3.70-3.60 (m, 3H), 3.53-3.42 (m, 2H), 3.08 (d, J=4.9 Hz, 3H), 2.99 (t, J=13.4 Hz, 2H), 2.87-2.69 (m, 4H), 2.34-2.19 (m, 2H), 2.06-1.96 (m, 2H), 1.84-1.71 (m, 2H) ppm. MS: 493 m/z (M+H⁺).

Example 368. (+/−)-tert-Butyl trans-2-methyl-4-((3-(methylcarbamoyl)-7-(trifluoromethyl)thieno[3,2-b]pyridin-5-yl)oxy)piperidine-1-carboxylate

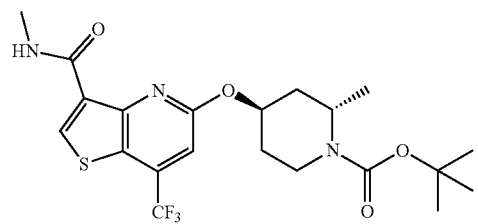 [SMILES: CNC(=O)c1csc2c(C(F)(F)F)cc(O[C@@H]3CCN(C(=O)OC(C)(C)C)[C@@H](C)C3)nc12]

Exchanging tert-butyl (2R,4R)-4-hydroxy-2-methylpiperidine-1-carboxylate for (+/−)-tert-butyl trans-4-hydroxy-2-methylpiperidine-1-carboxylate, the procedure described in step 1 of Example 175 was used to prepare the title compound as a white solid. ¹H NMR (400 MHz, CDCl₃) δ 8.96 (s, 1H), 8.76 (s, 1H), 7.08 (s, 1H), 5.43-5.33 (m, 1H), 4.69-4.56 (m, 1H), 4.21 (d, J=14.2 Hz, 1H), 3.22-2.95 (m, 4H), 2.29-2.18 (m, 1H), 2.13-2.06 (m, 1H), 1.83 (td, J=12.1, 5.8 Hz, 1H), 1.75-1.62 (m, 1H), 1.49 (s, 9H), 1.32 (d, J=7.1 Hz, 3H) ppm. MS: 474 m/z (M+H⁺).

Example 369. (+/−)-trans-2-(Trifluoromethoxy)ethyl-2-methyl-4-((3-(methylcarbamoyl)-7-(trifluoromethyl)thieno[3,2-b]pyridin-5-yl)oxy)piperidine-1-carboxylate

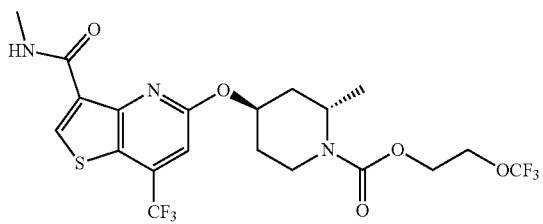 [SMILES: CNC(=O)c1csc2c(C(F)(F)F)cc(O[C@@H]3CCN(C(=O)OCCOC(F)(F)F)[C@@H](C)C3)nc12]

Step 1: N-Methyl-5-((trans-2-methylpiperidin-4-yl)oxy)-7-(trifluoromethyl)thieno[3,2-b]pyridine-3-carboxamide Into a stirred solution of the title compound of the title compound of Example 368 (0.090 g, 0.190 mmol) in ethyl acetate (6 mL) was bubbled hydrogen chloride gas for approximately two minutes. The mixture stirred for an additional 20 minutes and then concentrated to afford the crude title compound as a white solid (0.078 g, 100%). MS: 374 m/z (M+H$^+$).

Step 2: (+/−)-trans-2-(Trifluoromethoxy)ethyl-2-methyl-4-((3-(methylcarbamoyl)-7-(trifluoromethyl)thieno[3,2-b]pyridin-5-yl)oxy)piperidine-1-carboxylate To a stirred solution of step 1 product (0.075 g, 0.183 mmol) in acetonitrile (3 mL) was added triethylamine (33 μL, 0.24 mmol), a solution of Intermediate 11 (0.049 g, 0.220 mmol) in acetonitrile (2 mL) and N-hydroxysuccimide (0.026 g, 0.220 mmol). The mixture was heated at 50° C. for two hours and then cooled and concentrated. The residue was partitioned between dichloromethane (20 mL) and aqueous sodium bicarbonate solution (20 mL). The organic layer was combined with additional extracts (dichloromethane, 2×20 mL) and washed with brine. The organic layer was then dried (Na$_2$SO$_4$) and concentrated. The crude material was purified by automated flash chromatography (Combiflash system; 5 to 35% ethyl acetate in heptane; 12 g silica column) to afford the title compound as a glassy, colorless solid (0.058 g, 60%). $^1$H NMR (400 MHz, CDCl$_3$) δ 8.92 (s, 1H), 8.77 (s, 1H), 7.09 (s, 1H), 5.41 (tt, J=11.3, 4.4 Hz, 1H), 4.69 (s, 1H), 4.41-4.15 (m, 5H), 3.21-3.04 (m, 4H), 2.31-2.23 (m, 1H), 2.18-2.10 (m, 1H), 1.85 (td, J=12.4, 5.8 Hz, 1H), 1.81-1.67 (m, 1H), 1.36 (d, J=7.1 Hz, 3H) ppm. MS: 530 m/z (M+H$^+$).

Example 370. (+/−)-tert-Butyl cis-2-methyl-4-((3-(methylcarbamoyl)-7-(trifluoromethyl)thieno[3,2-b]pyridin-5-yl)oxy)piperidine-1-carboxylate

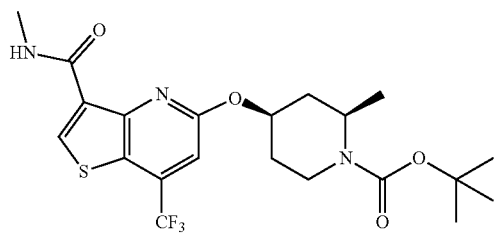 [SMILES: CNC(=O)c1csc2c(C(F)(F)F)cc(O[C@@H]3CCN(C(=O)OC(C)(C)C)[C@H](C)C3)nc12]

Exchanging tert-butyl (2R,4R)-4-hydroxy-2-methylpiperidine-1-carboxylate for (+/−)-tert-butyl cis-4-hydroxy-2-methylpiperidine-1-carboxylate, the procedure described in step 1 of Example 175 was used to prepare the title compound as a white solid. $^1$H NMR (400 MHz, CDCl$_3$) δ 9.04 (s, 1H), 8.75 (s, 1H), 7.11 (s, 1H), 5.40-5.34 (m, 1H), 4.50-4.39 (m, 1H), 3.99 (dd, J=13.7, 4.2 Hz, 1H), 3.29 (td, J=13.4, 2.9 Hz, 1H), 3.07 (d, J=4.9 Hz, 3H), 2.16-2.01 (m, 3H), 1.98-1.86 (m, 1H), 1.49 (s, 9H), 1.32 (d, J=7.1 Hz, 3H) ppm. MS: 474 m/z (M+H$^+$).

Example 371. (+/−)-cis-2-(Trifluoromethoxy)ethyl-2-methyl-4-((3-(methylcarbamoyl)-7-(trifluoromethyl)thieno[3,2-b]pyridin-5-yl)oxy)piperidine-1-carboxylate

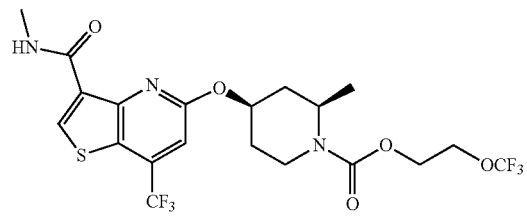 [SMILES: CNC(=O)c1csc2c(C(F)(F)F)cc(O[C@@H]3CCN(C(=O)OCCOC(F)(F)F)[C@H](C)C3)nc12]

Exchanging the title compound of Example 368 for the title compound of Example 370, the two-step reaction sequence outlined in Example 369 was used to prepare the title compound as a glassy, colorless solid. $^1$H NMR (400 MHz, CDCl$_3$) δ 9.01 (s, 1H), 8.76 (s, 1H), 7.12 (s, 1H), 5.47-5.35 (m, 1H), 4.60-4.45 (m, 1H), 4.42-4.30 (m, 2H), 4.19 (t, J=4.6 Hz, 2H), 4.05 (dd, J=14.2, 4.7 Hz, 1H), 3.39 (td, J=13.5, 2.8 Hz, 1H), 3.07 (d, J=4.9 Hz, 3H), 2.22-2.03 (m, 3H), 1.99-1.88 (m, 1H), 1.36 (d, J=7.1 Hz, 3H) ppm. MS: 530 m/z (M+H$^+$).

Example 373. tert-Butyl (2R,4R)-2-methyl-4-((3-(methylcarbamoyl)-7-(trifluoromethyl)thieno[3,2-b]pyridin-5-yl)oxy)piperidine-1-carboxylate

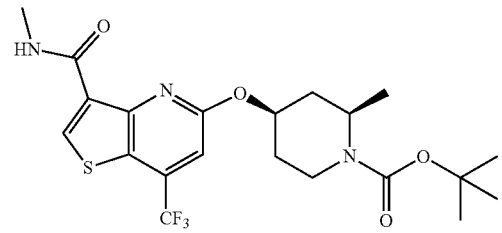

The procedure described in step 1 of Example 175 was used to prepare the title compound as a pale amber solid. $^1$H NMR (400 MHz, CDCl$_3$) δ 9.08-9.01 (m, 1H), 8.75 (s, 1H), 7.11 (s, 1H), 5.38 (p, J=3.1 Hz, 1H), 4.50-4.40 (m, 1H), 4.00 (ddd, J=13.8, 4.7, 1.8 Hz, 1H), 3.29 (td, J=13.4, 2.8 Hz, 1H), 3.07 (d, J=4.9 Hz, 3H), 2.18-2.01 (m, 3H), 1.97-1.85 (m, 1H), 1.49 (s, 9H), 1.32 (d, J=7.1 Hz, 3H) ppm. MS: 474 m/z (M+H$^+$).

Example 375. 2-(Trifluoromethoxy)ethyl (2R,4R)-2-methyl-4-((3-(methylcarbamoyl)-7-(trifluoromethyl)thieno[3,2-b]pyridin-5-yl)oxy)piperidine-1-carboxylate

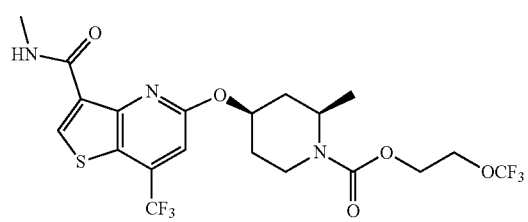 [SMILES: CNC(=O)c1csc2c(C(F)(F)F)cc(O[C@@H]3CCN(C(=O)OCCOC(F)(F)F)[C@H](C)C3)nc12]

Exchanging the title compound of Example 368 for the title compound of Example 373, the two-step reaction sequence outlined in Example 369 was used to prepare the title compound as a glassy, colorless solid. $^1$H NMR (400 MHz, CDCl$_3$) δ 9.00 (s, 1H), 8.76 (s, 1H), 7.12 (s, 1H), 5.47-5.34 (m, 1H), 4.57-4.44 (m, 1H), 4.45-4.28 (m, 2H), 4.19 (t, J=4.6 Hz, 2H), 4.05 (dd, J=13.3, 4.9 Hz, 1H), 3.39 (td, J=13.5, 2.9 Hz, 1H), 3.07 (d, J=4.9 Hz, 3H), 2.22-2.02 (m, 3H), 1.99-1.86 (m, 1H), 1.36 (d, J=7.1 Hz, 3H) ppm. MS: 530 m/z (M+H$^+$).

Example 387. (+/−)-tert-Butyl cis-3-fluoro-4-((6-methyl-3-(methylcarbamoyl)-7-(trifluoromethyl)thieno[3,2-b]pyridin-5-yl)oxy)piperidine-1-carboxylate

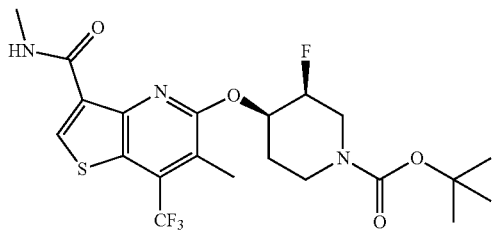 [SMILES: CNC(=O)c1csc2c(C(F)(F)F)c(C)c(O[C@@H]3CCN(C(=O)OC(C)(C)C)C[C@@H]3F)nc12]

Step 1: Methyl 5-((cis-1-(tert-butoxycarbonyl)-3-fluoropiperidin-4-yl)oxy)-6-methyl-7-(trifluoromethyl)thieno[3,2-b]pyridine-3-carboxylate To a stirred solution of Intermediate 13 (0.300 g, 1.03 mmol), (+/−)-tert-butyl cis-3-fluoro-4-hydroxypiperidine-1-carboxylate (0.339 g, 1.55 mmol) and triphenylphosphine (0.405 g, 1.55 mmol) in ethyl acetate (6 mL) was added bis-(2-methoxyethyl)diazo-1,2-dicarboxylate (0.362 g, 1.55 mmol). After four hours at room temperature, the mixture was diluted with additional ethyl acetate and washed with water. The organic layer was dried (Na$_2$SO$_4$) and concentrated to afford a residue which was then purified by automated flash chromatography (Combiflash system; 20 to 55% ethyl acetate in heptane; 12 g silica column). The title compound was obtained as a white solid (0.360 g, 71%). MS: 493 m/z (M+H$^+$).

Step 2: (+/−)-tert-Butyl cis-3-fluoro-4-((6-methyl-3-(methylcarbamoyl)-7-(trifluoromethyl)thieno[3,2-b]pyridin-5-yl)oxy)piperidine-1-carboxylate Using the procedure described in step 3 of Example 339, step 1 product was condensed with methylamine to afford the title compound as a white solid. $^1$H NMR (400 MHz, CDCl$_3$) δ 8.91 (br s, 1H), 8.65 (s, 1H), 5.40-5.28 (m, 1H), 4.91 (d, J=47.4 Hz, 1H), 4.15-4.04 (m, 1H), 3.94-3.73 (m, 1H), 3.71-3.54 (m, 1H), 3.44-3.33 (m, 1H), 3.08 (d, J=4.9 Hz, 3H), 2.51 (s, 3H), 2.32-2.20 (m, 1H), 2.06-1.96 (m, 1H), 1.50 (s, 9H) ppm. MS: 492 m/z (M+H$^+$).

Example 389. tert-Butyl 4-((6-methyl-3-(methylcarbamoyl)-7-(trifluoromethyl)thieno[3,2-b]pyridin-5-yl)oxy)piperidine-1-carboxylate

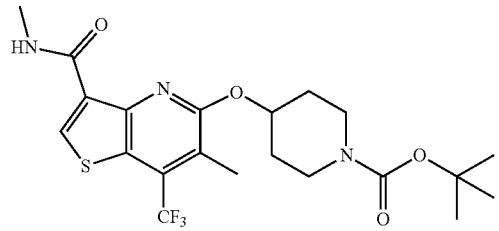 [SMILES: CNC(=O)c1csc2c(C(F)(F)F)c(C)c(OC3CCN(C(=O)OC(C)(C)C)CC3)nc12]

Step 1: Methyl 5-((1-(tert-Butoxycarbonyl)piperidin-4-yl)oxy)-6-methyl-7-(trifluoromethyl)thieno[3,2-b]pyridine-3-carboxylate Exchanging (+/−)-tert-butyl cis-3-fluoro-4-hydroxypiperidine-1-carboxylate for 4-hydroxypiperidine-1-carboxylate, the procedure described in step 1 of Example 387 was used to prepare the title compound. MS: 475 m/z (M+H$^+$).

Step 2: tert-Butyl 4-((6-methyl-3-(methylcarbamoyl)-7-(trifluoromethyl)thieno[3,2-b]pyridin-5-yl)oxy)piperidine-1-carboxylate Using the procedure described in step 3 of Example 339, step 1 product was condensed with methylamine to afford the title compound as a white solid. $^1$H NMR (400 MHz, CDCl$_3$) δ 9.10 (br s, 1H), 8.63 (s, 1H), 5.29-5.16 (m, 1H), 3.80-3.71 (m, 2H), 3.52-3.43 (m, 2H), 3.07 (d, J=4.9 Hz, 3H), 2.47 (s, 3H), 2.14-2.04 (m, 2H), 1.99-1.88 (m, 2H), 1.49 (s, 9H) ppm. MS: 474 m/z (M+H$^+$).

Example 390. 2-(Trifluoromethoxy)ethyl 4-((6-methyl-3-(methylcarbamoyl)-7-(trifluoromethyl)thieno[3,2-b]pyridin-5-yl)oxy)piperidine-1-carboxylate

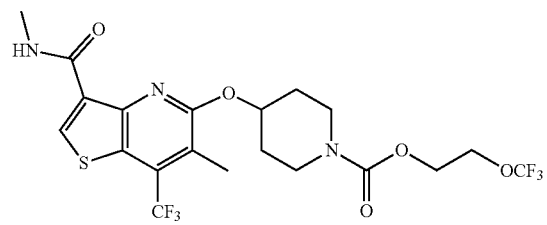 [SMILES: CNC(=O)c1csc2c(C(F)(F)F)c(C)c(OC3CCN(C(=O)OCCOC(F)(F)F)CC3)nc12]

Exchanging the title compound of Example 368 for the title compound of Example 389, the two-step reaction sequence outlined in Example 369 was used to prepare the title compound as a glassy, colorless solid. $^1$H NMR (400 MHz, CDCl$_3$) δ 9.06 (br s, 1H), 8.64 (s, 1H), 5.30-5.24 (m, 1H), 4.42-4.31 (m, 2H), 4.24-4.13 (m, 2H), 3.83-3.71 (m, 2H), 3.65-3.56 (m, 2H), 3.07 (d, J=4.9 Hz, 3H), 2.48 (s, 3H), 2.15-2.05 (m, 2H), 2.05-1.93 (m, 2H) ppm. MS: 530 m/z (M+H$^+$).

Example 408. 5-(4-(2-(Isopropylamino)-2-oxoethyl)piperazin-1-yl)-N,2-dimethyl-7-(trifluoromethyl)thieno[3,2-b]pyridine-3-carboxamide

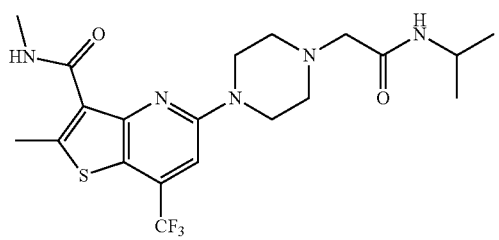 [SMILES: CNC(=O)c1c(C)sc2c(C(F)(F)F)cc(N3CCN(CC(=O)NC(C)C)CC3)nc12]

Using the conditions described in step 3 of Example 39, Intermediate 20 was subjected to SNAr displacement with a piperazine derivative, the step 2 product of Example 47 (N-isopropyl-2-(piperazin-1-yl)acetamide, to afford the title compound as an off-white solid. $^1$H NMR (400 MHz, CDCl$_3$) δ 9.72 (br s, 1H), 6.97 (s, 1H), 6.87 (d, J=8.3 Hz, 1H), 4.20-4.08 (m, 1H), 3.70-3.61 (m, 4H), 3.09 (s, 2H), 3.07-3.00 (m, 6H), 2.78-2.69 (m, 4H), 1.20 (d, J=6.6 Hz, 6H) ppm. MS: 458 m/z (M+H$^+$).

Example 415. 1-(2-Methyl-3-(methylcarbamoyl)-7-(trifluoromethyl)thieno[3,2-b]pyridin-5-yl)piperidin-4-yl (cyclopropylmethyl)carbamate

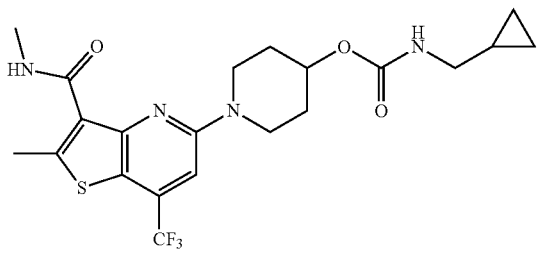 [SMILES: CNC(=O)c1c(C)sc2c(C(F)(F)F)cc(N3CCC(OC(=O)NCC4CC4)CC3)nc12]

Using the conditions described in step 3 of Example 39, Intermediate 20 was subjected to SNAr displacement with the amine component, Intermediate 24, to afford the title compound as a white solid. $^1$H NMR (400 MHz, CDCl$_3$) δ 9.82 (br s, 1H), 6.99 (s, 1H), 4.97 (br s, 1H), 4.79 (br s, 1H), 3.98-3.83 (m, 2H), 3.51 (t, J=10.7 Hz, 2H), 3.12-2.96 (m, 7H), 2.14-2.02 (m, 2H), 1.90-1.73 (m, 2H), 1.02-0.91 (m, 1H), 0.58-0.46 (m, 2H), 0.26-0.13 (m, 2H) ppm. MS: 471 m/z (M+H$^+$).

Example 418. (+/−)-trans-3-Fluoro-1-(3-(methylcarbamoyl)-7-(trifluoromethyl)thieno[3,2-b]pyridin-5-yl)piperidin-4-yl ((S)-1-(trifluoromethoxy)propan-2-yl)carbamate

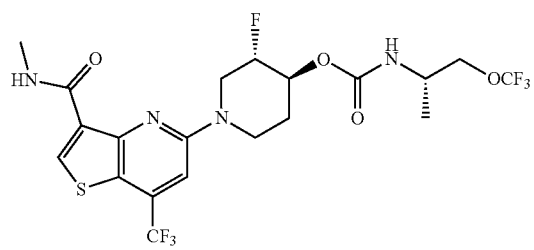 [SMILES: CNC(=O)c1csc2c(C(F)(F)F)cc(N3CC[C@H](OC(=O)N[C@@H](C)COC(F)(F)F)[C@@H](F)C3)nc12]

Step 1: (+/−)-trans-3-Fluoro-1-(3-(methylcarbamoyl)-7-(trifluoromethyl)thieno[3,2-b]pyridin-5-yl)piperidin-4-yl 1H-imidazole-1-carboxylate To a stirred solution of Intermediate 31 (0.126 g, 0.334 mmol) in dichloromethane (5 mL) was added 1,1'-carbonyldiimidazole (0.100 g, 0.617 mmol). The reaction was stirred at room temperature for five hours and then diluted with additional dichloromethane and washed with aqueous sodium bicarbonate solution and brine. The organic layer was dried (Na$_2$SO$_4$) and concentrated to afford the crude title compound as a colorless oil (157 mg, 100%). MS: 472 m/z (M+H$^+$).

Step 2: (+/−)-trans-3-Fluoro-1-(3-(methylcarbamoyl)-7-(trifluoromethyl)thieno[3,2-b]pyridin-5-yl)piperidin-4-yl ((S)-1-(trifluoromethoxy)propan-2-yl)carbamate To a stirred solution of step 1 product (0.157 g, 0.333 mmol) in acetonitrile (5 mL) was added Intermediate 11 (0.075 g, 0.416 mmol), N-hydroxysuccinimide (0.046 g, 0.400 mmol) and triethylamine (60 µL, 0.43 mmol). The reaction was heated overnight at 45° C. and then concentrated. The residue was partitioned between dichloromethane (20 mL) and aqueous sodium bicarbonate solution (20 mL). The organic layer was combined with additional extracts (dichloromethane, 2×20 mL), washed with brine and dried (Na$_2$SO$_4$). The solution was then concentrated and the resulting residue was subjected to automated flash chromatography (Combiflash system; 0.2 to 3% methanol in dichloromethane; 12 g silica column). The title compound was obtained as a white solid (0.101 g, 56%). $^1$H NMR (400 MHz, CDCl$_3$) δ 9.31 (br s, 1H), 8.72 (s, 1H), 7.08 (s, 1H), 5.07 (br s, 1H), 4.85 (br s, 1H), 4.76-4.59 (m, 1H), 4.20 (t, J=16.3 Hz, 1H), 4.11-3.99 (m, 2H), 3.98-3.83 (m, 2H), 3.72-3.54 (m, 2H), 3.09 (d, J=4.9 Hz, 3H), 2.38-2.27 (m, 1H), 1.86-1.76 (m, 1H), 1.29 (d, J=6.7 Hz, 3H) ppm. MS: 547 m/z (M+H$^+$).

Example 419. N-Isopropyl-7-(trifluoromethyl)-5-(3-((4-(trifluoromethyl)cyclohexyl)amino)pyrrolidin-1-yl)thieno[3,2-b]pyridine-3-carboxamide

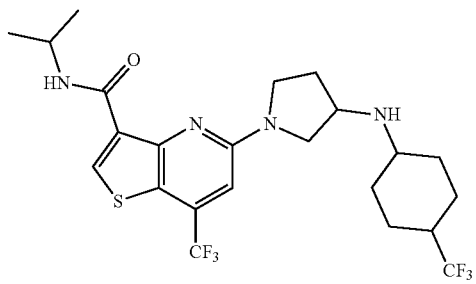 [SMILES: CC(C)NC(=O)c1csc2c(C(F)(F)F)cc(N3CCC(NC4CCC(C(F)(F)F)CC4)C3)nc12]

Step 1: 5-(3-Aminopyrrolidin-1-yl)-N-isopropyl-7-(trifluoromethyl)thieno[3,2-b]pyridine-3-carboxamide hydrochloride A 50 mL round-bottomed flask equipped with a stir bar was loaded with Example 642 (0.200 g, 423 µmo) and 2N hydrochloric acid in methanol (8 mL). The resulting solution was stirred at room temperature for 4 hours and concentrated to dryness to give the product as a yellow solid (0.173 g, 100%). MS: 373 m/z (M+H$^+$).

Step 2: N-Isopropyl-7-(trifluoromethyl)-5-(3-((4-(trifluoromethyl)cyclohexyl)amino)pyrrolidin-1-yl)thieno[3,2-b]pyridine-3-carboxamide A 100 mL round-bottomed flask equipped with a stir bar was loaded with step 1 product (0.050 g, 120 µmol), dichloroethane (8 mL), N,N-diisopropylethylamine (32 µL, 180 mol), 4-(trifluoromethyl)cyclohexan-1-one (0.040 g, 240 µmol) and acetic acid (14 µL, 240 mol). The resulting solution was stirred at room temperature for 30 minutes, then sodium triacetoxyborohydride (0.077 g, 370 µmol) was added. The reaction mixture was stirred at room temperature for 3 hours and then diluted with ethyl acetate (40 mL) and washed with water (20 mL) and brine (10 mL). The organic layer was dried (Na$_2$SO$_4$), filtered and concentrated to give a white solid which was triturated with ether to give the product as a white solid (0.035 g, 55%). $^1$H NMR (400 MHz, Methanol-d$_4$) δ 9.85 (d, J=7.5 Hz, 1H), 8.73 (s, 1H), 7.09 (d, J=3.0 Hz, 1H), 4.44-4.24 (m, 2H), 4.24-4.06 (m, 1H), 4.00-3.88 (m, 1H), 3.85-3.67 (m, 2H), 3.48 (s, 1H), 2.75-2.60 (m, 1H), 2.45-2.34 (m, 2H), 2.17 (s, 1H), 2.10-1.85 (m, 4H), 1.63-1.42 (m, 2H), 1.39 (dd, J=6.5, 1.1 Hz, 6H) ppm. MS: 523 m/z (M+H$^+$).

Example 420. 7-Cyclopropyl-N-ethyl-5-(4-(2-(isopropylamino)-2-oxoethyl)piperazin-1-yl)thieno[3,2-b]pyridine-3-carboxamide

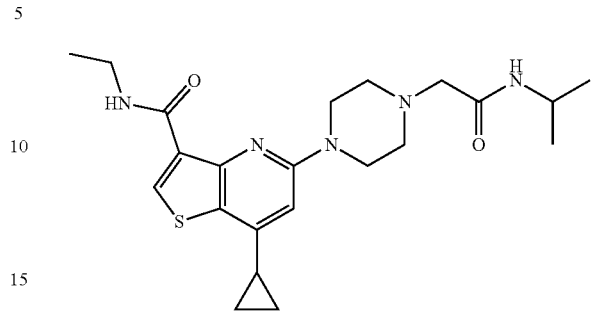

Step 1: Methyl 7-cyclopropyl-5-oxo-4,5-dihydrothieno[3,2-b]pyridine-3-carboxylate A 250 mL round-bottomed flask equipped with a stir bar was loaded with ethyl 3-cyclopropyl-3-oxopropanoate (7.95 g, 50 mmol), and methyl 4-aminothiophene-3-carboxylate (4.00 g, 25 mmol). The resulting solution was stirred at room temperature for 10 minutes. The mixture was placed into pre-heated oil bath (125° C.) and water (0.20 mL) was added via syringe every 30 minutes (up to 4 hours). After 6 hours at 125° C. (bath temperature), 1.0 mL of trifluoroacetic acid was added and stirred at 135° C. overnight. The solution was cooled to room temperature to give a black solid which was treated with ethyl acetate (80 mL), 1 gram of activated carbon and water (40 mL), and stirred at room temperature for 3 hours. The mixture was filtered through Celite to give a brown solution which was washed with brine (20 mL), dried (Na$_2$SO$_4$), filtered and concentrated to give a residue which was purified by chromatography using 0-100% ethyl acetate in heptane as eluant to give the title compound as a solid (0.349 g, 5%). $^1$H NMR (400 MHz, Acetone-d$_6$) 8.60 (s, 1H), 6.01 (s, 1H), 3.98 (s, 3H), 2.01 (m, 1H), 1.15 (m, 2H), 0.95 (m, 2H) ppm. MS: 250 m/z (M+H$^+$).

Step 2: Methyl 7-cyclopropyl-5-(((trifluoromethyl)sulfonyl)oxy)thieno[3,2-b]pyridine-3-carboxylate A stirred and cooled (0° C.) solution of step 1 product (0.349 g, 1.40 mmol) in pyridine (10 mL) were added trifluoromethanesulfonic anhydride (940 µL, 6 mmol) dropwise over 20 minutes. The reaction was allowed to slowly warm to room temperature and stirred overnight. The reaction was then concentrated and the residue was partitioned between water (50 mL) and dichloromethane (50 mL). The organic layer was combined with additional extracts, dried (MgSO$_4$) and concentrated to afford the title product as a brown solid (0.515 g, 96%).

Step 3: Methyl 7-cyclopropyl-5-(4-(2-(isopropylamino)-2-oxoethyl)piperazin-1-yl)thieno[3,2-b]pyridine-3-carboxylate A 25 mL microwave reaction vessel equipped with a stir bar was loaded with step 2 product (0.515 g, 1.4 mmol), N-isopropyl-2-(piperazin-1-yl)acetamide (0.300 g, 1.6 mmol), 1-methylpyrrolidin-2-one (8 mL) and N,N-diisopropylethylamine (940 µL, 5 mmol). The reaction was sealed and heated in a microwave reactor at 90° C. for 6 hours. The solution was diluted with ethyl acetate (60 mL) and washed with water (4×20 mL) and brine (10 mL). The organic layer was dried (Na$_2$SO$_4$) and concentrated. The crude product was purified by automated flash chromatography (Combiflash instrument; 50-100% ethyl acetate in heptane) to give the title compound as an amber solid (0.448 g, 80%). $^1$H NMR (400 MHz, CDCl$_3$) δ 8.45 (s, 1H), 7.00 (d, 1H), 6.37 (s, 1H), 4.26-4.06 (m, 1H), 3.94 (d, J=2.5 Hz, 4H), 3.70 (dd, J=6.2, 3.9 Hz, 4H), 3.04 (s, 2H), 2.66 (t, J=5.0 Hz, 4H), 2.17-1.98 (m, 2H), 1.18 (d, J=6.6 Hz, 6H), 1.15-1.09 (m, 2H), 0.95-0.88 (m, 2H) ppm. MS: 417 m/z (M+H$^+$).

Step 4: 7-Cyclopropyl-N-ethyl-5-(4-(2-(isopropylamino)-2-oxoethyl)piperazin-1-yl)thieno[3,2-b]pyridine-3-carboxamide A 25 mL microwave reaction vessel equipped with a stir bar was loaded with step 3 product (0.100 g, 240 µmol) and 2.0 M solution of ethylamine in methanol (5.0 mL, 10 mmol). The reaction was sealed and heated in a microwave reactor at 90° C. for 3 hours. The solution was concentrated to give a solid which was triturated with methanol to give the title compound as an amber solid (0.056 g, 54%). $^1$H NMR (400 MHz, CDCl$_3$) δ 9.70 (br t, J=5.1 Hz, 1H), 8.54 (s, 1H), 7.05-6.76 (m, 1H), 6.39 (s, 1H), 4.28-4.03 (m, 1H), 3.72-3.52 (m, 6H), 3.07 (s, 2H), 2.82-2.62 (m, 4H), 2.08 (tt, J=8.4, 5.1 Hz, 1H), 1.30 (t, J=7.3 Hz, 3H), 1.19 (d, J=6.6 Hz, 6H), 1.17-1.12 (m, 2H), 0.96-0.91 (m, 2H) ppm. MS: 430 m/z (M+H$^+$).

Example 422. 1-(3-(Azetidine-1-carbonyl)-7-(trifluoromethyl)thieno[3,2-b]pyridin-5-yl)piperidin-4-yl tert-butylcarbamate

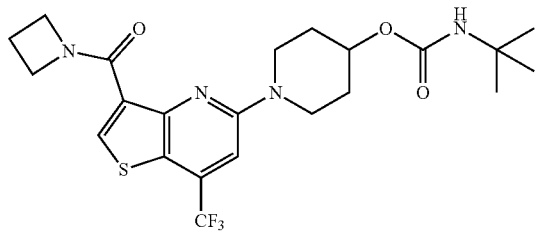 [SMILES: CC(C)(C)NC(=O)OC1CCN(c2cc(C(F)(F)F)c3scc(C(=O)N4CCC4)c3n2)CC1]

Step 1: Methyl 5-(4-hydroxypiperidin-1-yl)-7-(trifluoromethyl)thieno[3,2-b]pyridine-3-carboxylate A stirred solution of Intermediate 3 (10.0 g, 33.4 mmol) in N-methyl-2-pyrrolidinone (60 mL), were added piperidin-4-ol (6.00 g, 59 mmol) and N,N-diisopropylethylamine (11.8 mL, 68 mmol). The solution was heated at 130° C. for 3 hours and then left to stir at room temperature overnight. The mixture was concentrated and the brown solid was taken up in water (~200 mL). The chunks of suspended solid were dispersed with spatula agitation and sonication. When a nearly homogeneous suspension was achieved, the mixture was filtered. The filtercake was rinsed with water (2×40 mL) and diethyl ether (2×25 mL) and then dried under house vacuum. The filter cake was further dried in a vacuum oven (60° C.) to afford the title compound as a light brown solid (10.90 g, 89%). $^1$H NMR (400 MHz, CDCl3) □□8.54 (s, 1H), 7.02 (s, 1H), 4.30-4.20 (m, 2H), 4.08-3.88 (m, 4H), 3.48-3.29 (m, 2H), 2.10-1.99 (m, 2H), 1.67-1.56 (m, 2H) ppm. MS: 360 m/z (M+H$^+$).

Step 2: Methyl 5-(4-((tert-butylcarbamoyl)oxy)piperidin-1-yl)-7-(trifluoromethyl)thieno[3,2-b]pyridine-3-carboxylate A 25 mL microwave vial equipped with a stir bar was loaded with step 1 product (0.510 g, 1.4 mmol), N,N-dimethylformamide (10 mL), and tert-butyl isocyanate (1.40 g, 16.8 mmol). The mixture was heated at 130° C. for 6 hours in the microwave reactor. Additional tert-butyl isocyanate (0.550 g, 6.62 mmol) was added and the reaction was heated at 140° C. for 5 days. The solution was diluted with ethyl acetate (50 mL), washed with water (4×20 ml), saturated. ammonium chloride (20 mL), dried (Na$_2$SO$_4$), filtered and concentrated to give a brown solid which was purified by chromatography using 0-100% ethyl acetate in heptane as eluant to afford the title compound as a yellowish solid (0.800 g, 100%). MS: 460 m/z (M+H$^+$).

Step 3: 5-(4-((tert-Butylcarbamoyl)oxy)piperidin-1-yl)-7-(trifluoromethyl) thieno[3,2-b]pyridine-3-carboxylic acid A 50 mL round-bottom flask equipped with a stir bar was loaded with step 2 product (0.350 g, 760 µmol), methanol (8 mL, tetrahydrofuran (8 mL), water (8 mL) and lithium hydroxide (0.046 g, 1.9 mmol). The mixture was stirred at room temperature for 18 hours and then concentrated, diluted with water and acidified with 2N hydrochloric acid to pH=4-5 to give a precipitate, which was filtered and washed with water and dried in vacuo to give the product as pale yellow solid (0.338 g, 100%). MS: 446 m/z (M+H$^+$).

Step 4: 1-(3-(Azetidine-1-carbonyl)-7-(trifluoromethyl)thieno[3,2-b]pyridin-5-yl)piperidin-4-yl tert-butylcarbamate A 50 mL round-bottom flask equipped with a stir bar was loaded with step 3 product (0.120 g, 270 µmol), azetidine (0.046 g, 808 µmol), tetrahydrofuran (5 mL), and 2,4,6-tripropyl-1,3,5,2,4,6-trioxatriphosphorinane-2,4,6-trioxide (0.342 g, 540 µmol) and stirred under nitrogen at room temperature for 18 hours. The solution was diluted with ethyl acetate (40 mL), washed with water (20 mL) and brine (10 mL), dried (Na$_2$SO$_4$), filtered and concentrated to give a solid which was purified by chromatography using 0-100% ethyl acetate in heptane as eluant to afford the title compound as a white solid (0.100 g, 77 $^1$H NMR (400 MHz, CDCl$_3$) δ 8.06 (s, 1H), 6.99 (s, 1H), 4.92 (d, J=8.5 Hz, 1H), 4.64 (s, 1H), 4.27 (t, J=7.8 Hz, 2H), 4.21-4.14 (m, 2H), 4.12 (d, J=7.2 Hz, 1H), 4.10-4.02 (m, 2H), 3.49 (s, 2H), 2.38-2.26 (m, 2H), 2.09-1.99 (m, 3H), 1.34 (s, 9H) ppm. MS: 485 m/z (M+H$^+$).

Example 428. Methyl 5-(4-(((cyclopropylmethyl)carbamoyl)oxy)piperidin-1-yl)-7-(trifluoromethyl)thieno[3,2-b]pyridine-3-carboxylate

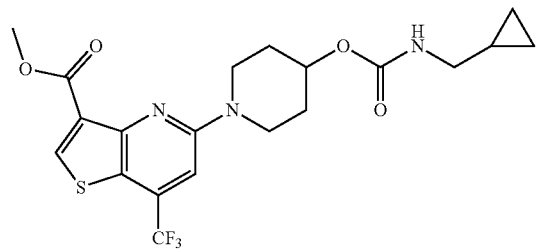 [SMILES: COC(=O)c1csc2c(C(F)(F)F)cc(N3CCC(OC(=O)NCC4CC4)CC3)nc12]

A 25 mL microwave reaction vessel equipped with a stir bar was loaded with Intermediate 3 (0.510 g, 1.7 mmol), Intermediate 24 (0.598 g, 3.0 mmol), N,N-diisopropylethylamine (602 µL, 3.5 mmol) and acetonitrile (12 mL). The vessel was sealed and heated in a microwave reactor at 130° C. for 5 hours. The solution was treated with ethyl acetate (40 mL) and washed with water (30 mL) and brine (20 mL). The organic layer was dried (Na$_2$SO$_4$), filtered and concentrated to give a brown residue which was purified by chromatography using 0-50% ethyl acetate in heptane as eluant to afford the title compound as a white solid (0.474 g, 60%). $^1$H NMR (400 MHz, CDCl$_3$) δ 8.55 (s, 1H), 7.02 (s, 1H), 5.04-4.89 (m, 1H), 4.86-4.73 (m, 1H), 4.18-4.04 (m, 2H), 3.95 (d, J=0.9 Hz, 3H), 3.62-3.46 (m, 2H), 3.07 (t, J=6.4 Hz, 2H), 2.16-2.01 (m, 2H), 1.90-1.67 (m, 2H), 1.09-0.90 (m, 1H), 0.61-0.43 (m, 2H), 0.24-0.11 (m, 2H) ppm. MS: 458 m/z (M+H$^+$).

Example 441. (+/−)-trans-1-(3-(Azetidine-1-carbonyl)-7-(trifluoromethyl)thieno[3,2-b]pyridin-5-yl)-3-fluoropiperidin-4-yl isopropylcarbamate

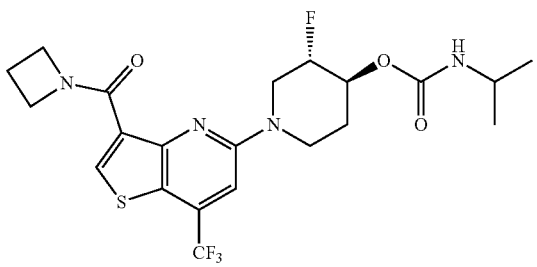 [SMILES: CC(C)NC(=O)O[C@H]1CCN(c2cc(C(F)(F)F)c3scc(C(=O)N4CCC4)c3n2)C[C@@H]1F]

Step 1: Methyl 5-((+/−)-trans-3-fluoro-4-hydroxypiperidin-1-yl)-7-(trifluoromethyl)thieno[3,2-b]pyridine-3-carboxylate A 25 mL microwave vial equipped with a stir bar was loaded with Intermediate 5 (3.75 g, 13 mmol), (+/−)-trans-3-fluoropiperidin-4-ol hydrochloride (1.80 g, 11.6 mmol), N,N-diisopropylethylamine (4.49 g, 35 mmol) and 1-methyl-2-pyrrolidinone (14 mL). The mixture was heated at 140° C. for 3 hours in a microwave reactor. The solution was diluted with ethyl acetate (100 mL), washed with water (4×20 mL) and saturated ammonium chloride (20 mL), dried (Na$_2$SO$_4$), filtered and concentrated to give a brown solid which was triturated with ether to give the product as a beige solid (3.50 g, 80%). MS: 404 m/z (M+H$^+$).

Step 2: Azetidin-1-yl(5-((+/−)-trans-3-fluoro-4-hydroxypiperidin-1-yl)-7-(trifluoromethyl)thieno[3,2-b]pyridin-3-yl)methanone A 25 mL microwave vial equipped with a stir bar was loaded with step 1 product (0.198 g, 520 µmol), azetidine (0.299 g, 5 mmol) and methanol (4 mL). The mixture was stirred at 100° C. for 3 hours and evaporated off to give a brown solid which was purified by chromatography using 0-10% methanol in dichloromethane as eluant to give the product as a yellowish solid (0.040 g, 19%). MS: 404 m/z (M+H$^+$).

Step 3. (+/−)-trans-1-(3-(Azetidine-1-carbonyl)-7-(trifluoromethyl)thieno[3,2-b]pyridin-5-yl)-3-fluoropiperidin-4-yl isopropylcarbamate A 25 mL microwave vial equipped with a stir bar was loaded with step 2 product (0.040 g, 100 µmol), 1,1'-carbonyldiimidazole (0.032 g, 200 µmol) and dichloromethane (8 mL). The mixture was stirred at room temperature for 3 hours and then concentrated to give a solid which was treated with acetonitrile (10 mL) and N-hydroxysuccinimide (0.023 g, 200 µmol). The solution was stirred at room temperature for 15 minutes, then isopropylamine (42 µL, 500 µmol) was added, and stirred at 40° C. for 16 hours. The solution was concentrated to give a residue. The residue was treated with ethyl acetate (50 mL), washed with water (20 mL) and brine (10 mL), dried (Na$_2$SO$_4$), filtered and concentrated to give a solid which was purified by chromatography using 0-100% ethyl acetate in heptane as eluant to give the product as a yellowish solid (0.034 g, 70%). $^1$H NMR (400 MHz, CDCl$_3$) δ 8.08 (s, 1H), 7.00 (s, 1H), 5.02 (s, 1H), 4.60 (d, J=42.1 Hz, 2H), 4.37-4.22 (m, 3H), 4.22-4.05 (m, 2H), 4.01-3.80 (m, 2H), 3.79-3.66 (m, 1H), 3.63-3.49 (m, 1H), 2.42-2.27 (m, 2H), 1.70 (s, 2H), 1.19 (d, J=6.5 Hz, 6H) ppm. MS: 489 m/z (M+H$^+$).

Example 449. 1-(7-Chloro-3-(methylcarbamoyl)thieno[3,2-b]pyridin-5-yl)piperidin-4-yl (cyclopropylmethyl)carbamate

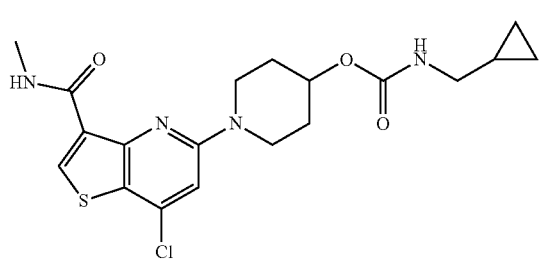 [SMILES: CNC(=O)c1csc2c(Cl)cc(N3CCC(OC(=O)NCC4CC4)CC3)nc12]

Using Intermediate 33 and Intermediate 24, the procedure described in step 3 of Example 420 was used to prepare the title compound as a white solid. $^1$H NMR (400 MHz, CDCl$_3$) δ 9.38 (br s, 1H), 8.59 (s, 1H), 6.66 (s, 1H), 5.11-4.85 (m, 2H), 3.80-3.67 (m, 2H), 3.54-3.34 (m, 2H), 3.17-3.01 (m, 5H), 2.21-2.04 (m, 2H), 2.01-1.80 (m, 2H), 1.07-0.92 (m, 1H), 0.60-0.48 (m, 2H), 0.29-0.15 (m, 2H) ppm. MS: 423 m/z (M+H$^+$).

Example 452. 1-(7-(Difluoromethyl)-3-(methylcarbamoyl)thieno[3,2-b]pyridin-5-yl)piperidin-4-yl isopropylcarbamate

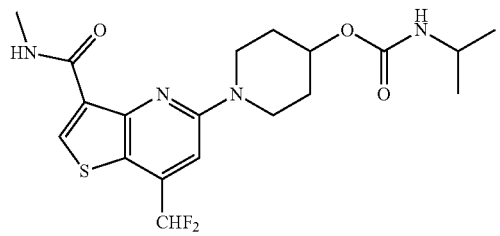 [SMILES: CNC(=O)c1csc2c(C(F)F)cc(N3CCC(OC(=O)NC(C)C)CC3)nc12]

Step 1: 1-(7-(Difluoromethyl)-3-(methylcarbamoyl)thieno[3,2-b]pyridin-5-yl)piperidin-4-yl isopropylcarbamate Using Intermediate 34 and piperidin-4-yl isopropylcarbamate, the procedure described in step 3 of Example 420 was used to prepare the title compound as a white solid. $^1$H NMR (400 MHz, CDCl$_3$) δ 8.52 (s, 1H), 6.97-6.57 (m, 2H), 4.93 (br s, 1H), 4.49 (br s, 1H), 4.10 (br d, J=12.9 Hz, 2H), 3.95 (s, 3H), 3.80 (br s, 2H), 3.52 (br s, 2H), 2.15-1.99 (m, 2H), 1.17 (d, J=6.5 Hz, 6H). ppm. MS: 428 m/z (M+H$^+$).

Step 2: 1-(7-(Difluoromethyl)-3-(methylcarbamoyl)thieno[3,2-b]pyridin-5-yl)piperidin-4-yl isopropylcarbamate Using step 1 product and methylamine, the procedure described in step 4 of Example 420 was used to prepare the title compound as a white solid. $^1$H NMR (400 MHz, CDCl$_3$) δ 9.51 (br s, 1H), 8.60 (s, 1H), 7.05-6.63 (m, 2H), 4.96 (br s, 1H), 4.68 (br s, 1H), 4.04-3.74 (m, 3H), 3.63-3.39 (m, 2H), 3.06 (d, J=4.8 Hz, 3H), 2.14-1.93 (m, 2H), 1.80 (s, 2H), 1.18 (d, J=6.7 Hz, 6H) ppm. MS: 427 m/z (M+H$^+$).

Example 473. 1-(3-(Methylcarbamoyl)-7-(trifluoromethyl)thieno[3,2-b]pyridin-5-yl)piperidin-4-yl cyclopropylcarbamate

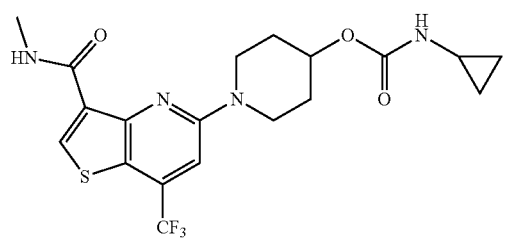 [SMILES: CNC(=O)c1csc2c(C(F)(F)F)cc(N3CCC(OC(=O)NC4CC4)CC3)nc12]

Using Intermediate 7 and isocyanatocyclopropane, the procedure described in step 2 of Example 422 was used to prepare the title compound as a white solid. $^1$H NMR (400 MHz, CDCl$_3$) δ 9.43 (s, 1H), 8.66 (s, 1H), 7.06 (s, 1H), 4.99 (br s, 2H), 4.00-3.86 (m, 2H), 3.55 (br s, 2H), 3.07 (d, J=4.8 Hz, 3H), 2.60 (d, J=7.8 Hz, 1H), 2.15-1.97 (m, 2H), 1.82 (br s, 2H), 0.86-0.70 (m, 2H), 0.62-0.43 (m, 2H) ppm. MS: 443 m/z (M+H$^+$).

Example 474. 1-(3-(Methylcarbamoyl)-7-(trifluoromethyl)thieno[3,2-b]pyridin-5-yl)piperidin-4-yl (cyclopropylmethyl)carbamate

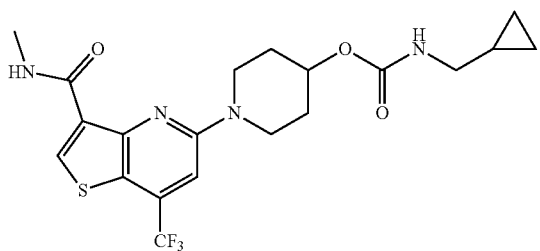

Using Intermediate 5 and Intermediate 24, the procedure described in step 3 of Example 420 was used to prepare the title compound as a white solid. $^1$H NMR (400 MHz, CDCl$_3$) δ 9.44 (br s, 1H), 8.66 (s, 1H), 7.07 (s, 1H), 5.18-4.91 (m, 1H), 4.91-4.74 (m, 1H), 4.06-3.86 (m, 2H), 3.71-3.49 (m, 2H), 3.16-3.01 (m, 5H), 2.20-2.02 (m, 2H), 1.95-1.73 (m, 2H), 1.09-0.89 (m, 1H), 0.63-0.43 (m, 2H), 0.20 (t, J=5.3 Hz, 2H) ppm. MS: 457 m/z (M+H$^+$).

Example 475. 1-(3-(Methylcarbamoyl)-7-(trifluoromethyl)thieno[3,2-b]pyridin-5-yl)piperidin-4-yl (cyclopropylmethyl)carbamate trifluoroacetate

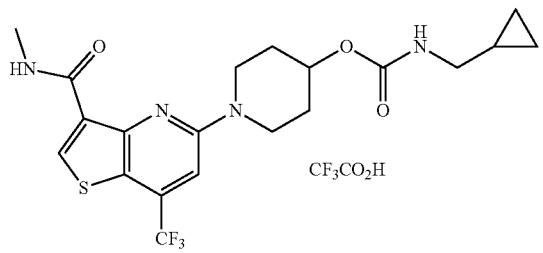

Using Intermediate 7 and (isocyanatomethyl)cyclopropane, the procedure described in step 2 of Example 422 was used to prepare the title compound as a white solid. $^1$H NMR (400 MHz, Methanol-d$_4$) δ 8.59 (s, 1H), 7.25 (s, 1H), 4.97-4.88 (m, 1H), 4.06-3.88 (m, 2H), 3.71-3.53 (m, 2H), 3.03 (s, 3H), 3.00 (d, J=6.9 Hz, 2H), 2.19-2.01 (m, 2H), 1.91-1.71 (m, 2H), 1.12-0.90 (m, 1H), 0.58-0.41 (m, 2H), 0.34-0.13 (m, 2H) ppm. MS: 457 m/z (M+H$^+$).

Example 488. (+/−)-trans-3-Fluoro-1-(3-(methylcarbamoyl)-7-(trifluoromethyl)thieno[3,2-b]pyridin-5-yl)piperidin-4-yl diisopropylcarbamate

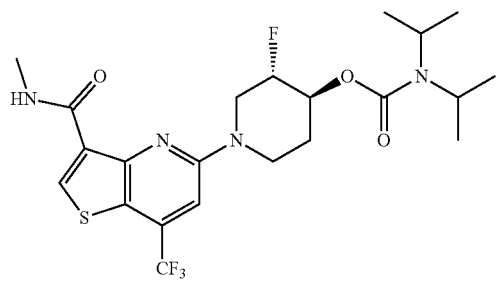 [SMILES: CNC(=O)c1csc2c(C(F)(F)F)cc(N3CC[C@H](OC(=O)N(C(C)C)C(C)C)[C@@H](F)C3)nc12]

Step 1: (+/−)-trans-3-Fluoro-1-(3-(methylcarbamoyl)-7-(trifluoromethyl)thieno[3,2-b]pyridin-5-yl)piperidin-4-yl 1H-imidazole-1-carboxylate To a stirred solution of 1,1'-carbonyldiimidazole (0.772 g, 4.76 mmol) in dichloromethane (10 mL) was added a solution of Intermediate 31 (1.33 g, 3.52 mmol) in dichloromethane (50 mL), dropwise over 20 minutes. The mixture was stirred overnight at at room temperature and then washed with water (3×20 mL) and brine (1×10 mL). The organic layer was dried (MgSO$_4$) and concentrated to afford the crude title compound as a pale pink solid (1.56 g, 94%). MS: 472 m/z (M+H$^+$).

Step 2: (+/−)-trans-3-Fluoro-1-(3-(methylcarbamoyl)-7-(trifluoromethyl)thieno[3,2-b]pyridin-5-yl)piperidin-4-yl diisopropylcarbamate A 100 mL round flask equipped with a stir bar was loaded with the crude step 1 product (0.300 g, 640 µmol), acetonitrile (20 mL) and N-hydroxysuccimide (0.088 g, 760 μmol), stirred at room temperature for 10 minutes, then diisopropylamine (0.257 g, 2.6 mmol) was added under nitrogen and stirred at 40° C. for 2 days. The reaction mixture was concentrated to give a residue. The residue was dissolved in ethyl acetate (50 mL) and washed with water (20 mL) and brine (10 mL). The organic layer was dried (Na$_2$SO$_4$), filtered, and concentrated to give a residue, which was purified by chromatography using 0-100% ethyl acetate in heptane as eluant to give the product as a white solid (0.240 g, 77%). $^1$H NMR (400 MHz, CDCl$_3$) δ 9.30 (br s, 1H), 8.68 (s, 1H), 7.08 (s, 1H), 5.24-5.08 (m, 1H), 4.92-4.63 (m, 1H), 4.27-4.02 (m, 2H), 3.96-3.75 (m, 3H), 3.75-3.58 (m, 2H), 3.09 (d, J=4.9 Hz, 3H), 2.46-2.27 (m, 1H), 1.93-1.73 (m, 1H), 1.25 (d, J=6.7 Hz, 12H) ppm. MS: 504 m/z (M+H$^+$).

Example 490. (+/−)-tran-3-Fluoro-1-(3-(methylcarbamoyl)-7-(trifluoromethyl)thieno[3,2-b]pyridin-5-yl)piperidin-4-yl isopropylcarbamate

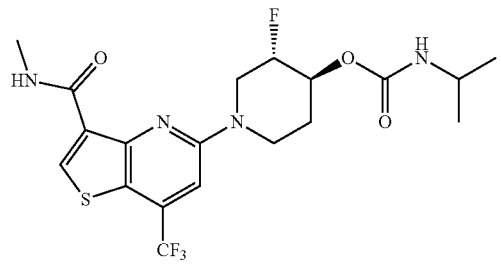 [SMILES: CNC(=O)c1csc2c(C(F)(F)F)cc(N3CC[C@H](OC(=O)NC(C)C)[C@@H](F)C3)nc12]

Exchanging diisopropylamine for iso-propylamine, the procedure described in Example 488 was used to prepare the title compound as a white solid. $^1$H NMR (400 MHz, CDCl$_3$) δ 9.30 (br s, 1H), 8.68 (s, 1H), 7.06 (s, 1H), 5.18-4.97 (m, 1H), 4.84-4.54 (m, 2H), 4.24-4.00 (m, 1H), 3.99-3.67 (m, 3H), 3.67-3.50 (m, 1H), 3.08 (d, J=4.8 Hz, 3H), 2.47-2.20 (m, 1H), 1.88-1.66 (m, 1H), 1.19 (d, J=6.6 Hz, 6H) ppm. MS: 463 m/z (M+H$^+$).

Example 492. (+/−)-trans-3-Fluoro-1-(3-(methylcarbamoyl)-7-(trifluoromethyl)thieno[3,2-b]pyridin-5-yl)piperidin-4-yl cyclopropylcarbamate

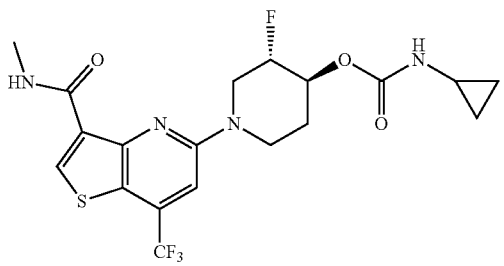 [SMILES: CNC(=O)c1csc2c(C(F)(F)F)cc(N3CC[C@H](OC(=O)NC4CC4)[C@@H](F)C3)nc12]

Exchanging diisopropylamine for cyclopropylamine, the procedure described in Example 488 was used to prepare the title compound as a white solid. $^1$H NMR (400 MHz, CDCl$_3$) δ 9.31 (br s, 1H), 8.67 (s, 1H), 7.06 (s, 1H), 5.32-4.96 (m, 1H), 4.88-4.51 (m, 1H), 4.26-4.03 (m, 1H), 3.95-3.53 (m, 3H), 3.08 (d, J=4.9 Hz, 3H), 2.72-2.52 (m, 1H), 2.49-2.21 (m, 1H), 1.88 (s, 1H), 0.95-0.67 (m, 2H), 0.67-0.48 (m, 2H) ppm. MS: 461 m/z (M+H$^+$).

Example 495 and Example 496. (3R,4R)-3-Fluoro-1-(3-(methylcarbamoyl)-7-(trifluoromethyl)thieno[3,2-b]pyridin-5-yl)piperidin-4-yl isopropylcarbamate and (3S,4S)-3-Fluoro-1-(3-(methylcarbamoyl)-7-(trifluoromethyl)thieno[3,2-b]pyridin-5-yl)piperidin-4-yl isopropylcarbamate (Separate Enantiomers of Known Absolute Stereochemistry)

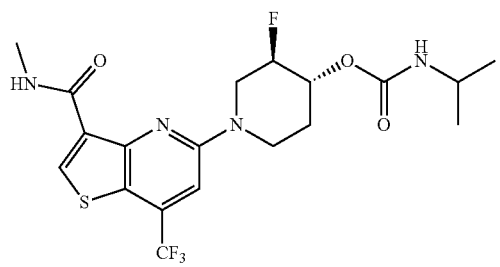

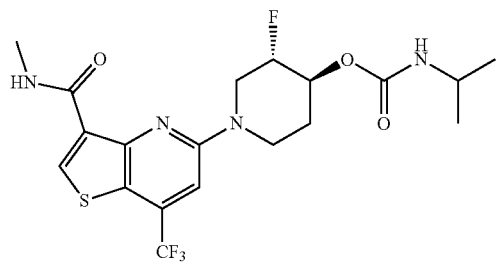

The title compounds were obtained by subjecting the title compound of Example 490 to chiral SFC separation (10× 250 mm CHIRALPAK IA column; 20% methanol modifier with 0.1% diethylamine additive). The absolute configurations of the individual enantiomers was determined by comparison of chiral SFC retention times to that of the authentic enantiomers prepared from optically active fluoropiperidin-4-ol starting materials of known stereochemistry (commercially available).

The early elution fraction was concentrated to afford the (3R,4R)-enantiomer as a white solid (Example 495). $^1$H NMR (400 MHz, CDCl$_3$) δ 9.31 (br s, 1H), 8.67 (s, 1H), 7.05 (s, 1H), 5.18-4.96 (m, 1H), 4.96-4.54 (m, 2H), 4.21-3.98 (m, 1H), 3.98-3.68 (m, 3H), 3.68-3.55 (m, 1H), 3.08 (d, J=4.8 Hz, 3H), 2.43-2.25 (m, 1H), 1.92-1.72 (m, 1H), 1.20 (d, J=6.5 Hz, 6H) ppm. MS: 463 m/z (M+H$^+$).

The late elution fraction was concentrated to afford the (3S,4S)-enantiomer as a white solid (Example 496). $^1$H NMR (400 MHz, CDCl$_3$) δ 9.31 (br s, 1H), 8.68 (s, 1H), 7.06 (s, 1H), 5.25-4.96 (m, 1H), 4.87-4.51 (m, 2H), 4.27-4.02 (m, 1H), 3.97-3.70 (m, 3H), 3.70-3.55 (m, 1H), 3.08 (d, J=4.9 Hz, 3H), 2.45-2.24 (m, 1H), 1.88-1.65 (m, 1H), 1.19 (d, J=6.5 Hz, 6H) ppm. MS: 463 m/z (M+H$^+$).

Example 505. 2-Cyanoethyl (1-(3-(methylcarbamoyl)-7-(trifluoromethyl)thieno[3,2-b]pyridin-5-yl)piperidin-4-yl)carbamate

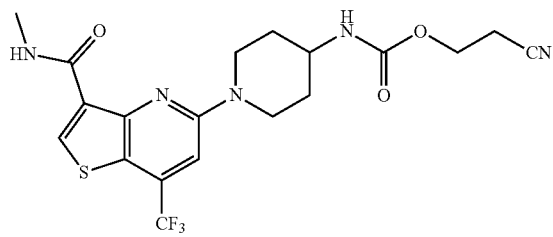 [SMILES: CNC(=O)c1csc2c(C(F)(F)F)cc(N3CCC(NC(=O)OCCC#N)CC3)nc12]

A 25 mL microwave reaction vial equipped with a stir bar was loaded with 3-hydroxypropanenitrile (0.079 g, 1.10 mmol), N-methyl-2-pyrrolidinone (8 mL), N,N-diisopropylethylamine (0.23 g, 1.8 mmol) and 4-nitrophenyl chloroformate (0.337 g, 1.70 mmol). The resulting solution was stirred at room temperature for two days and then treated with the step 3 product of Example 297 (0.080 g, 220 µmol). The mixture was heated at 90° C. for two hours and then cooled and diluted with EtOAc (50 mL). The solution was washed with water (2×20 mL) and brine (1×10 mL). The organic layer was dried ($Na_2SO_4$) and concentrated to give a residue which was purified by automated flash chromatography (0-100% EtOAc in heptane; silica column) to afford the title compound as an off-white solid (0.042 g, 41%). $^1$H NMR (400 MHz, $CDCl_3$) δ 9.40 (br s, 1H), 8.65 (s, 1H), 7.06 (s, 1H), 5.15-4.87 (m, 1H), 4.43-4.19 (m, 4H), 4.00-3.77 (m, 1H), 3.34-3.15 (m, 2H), 3.06 (d, J=4.8 Hz, 3H), 2.71 (t, J=6.2 Hz, 2H), 2.27-2.13 (m, 2H), 1.69-1.48 (m, 2H) ppm. MS: 456 m/z (M+H$^+$).

Example 520. 2-(Trifluoromethoxy)ethyl (1-(3-(methylcarbamoyl)-7-(trifluoromethyl)thieno[3,2-b]pyridin-5-yl)piperidin-4-yl)carbamate Exchanging 3-hydroxypropanenitrile for 2-(trifluoromethoxy)ethan-1-ol, the procedure described in Example 505 was used to prepare the title compound as a white solid. $^1$H NMR (400 MHz, $CDCl_3$) δ 9.39 (br s, 1H), 8.63 (s, 1H), 7.05 (s, 1H), 5.22-4.98 (m, 1H), 4.39-4.29 (m, 2H), 4.29-4.09 (m, 4H), 3.95-3.80 (m, 1H), 3.39-3.15 (m, 2H), 3.05 (d, J=4.9 Hz, 3H), 2.31-2.09 (m, 2H), 1.75-1.49 (m, 2H) ppm. MS: 515 m/z (M+H$^+$).

Example 528. 5-(4-((4-Isopropylthiazol-2-yl)methyl)piperazin-1-yl)-N-methyl-7-(trifluoromethyl)thieno[3,2-b]pyridine-3-carboxamide To a stirred solution of the hydrochloride salt of Intermediate 6 (0.110 g, 260 µmol) in methanol was added 4-isopropylthiazole-2-carboxaldehyde (0.122 g, 790 µmol), N,N-diisopropylethylamine (184 µl, 0.106 mmol), acetic acid (45 µl, 0.79 mmol) and sodium cyanoborohydride (0.049 g, 790 µmol). The reaction was heated overnight at 60° C. and then cooled and concentrated. The residue was partitioned between ethyl acetate (50 mL) and water (20 mL). The organic layer was washed with brine (10 mL) and concentrated. The resulting crude material was purified by automated flash chromatography (0-100% EtOAc in heptane; silica column) to afford the title compound as a white solid (0.095 g, 75%). $^1$H NMR (400 MHz, $CDCl_3$) δ 9.39 (br s, 1H), 8.66 (s, 1H), 7.04 (s, 1H), 6.86 (d, J=0.9 Hz, 1H), 3.94 (s, 2H), 3.70 (dd, J=4.5, 2.7 Hz, 3H), 3.24-3.02 (m, 4H), 2.80 (dd, J=6.0, 4.2 Hz, 4H), 1.32 (d, J=6.9 Hz, 6H) ppm. MS: 484 m/z (M+H$^+$).

Example 552. 5-(4-((4-Isopropylmorpholin-2-yl)methyl)piperazin-1-yl)-N-methyl-7-(trifluoromethyl)thieno[3,2-b]pyridine-3-carboxamide trifluoroacetate

Step 1: tert-Butyl 2-((4-(3-(methylcarbamoyl)-7-(trifluoromethyl)thieno[3,2-b]pyridin-5-yl)piperazin-1-yl)methyl)morpholine-4-carboxylate A 25 mL microwave vial equipped with a stir bar was loaded with the hydrochloride salt of Intermediate 6 (0.300 g, 660 µmol), N,N-dimethylformamide (4 mL), tert-butyl 2-(bromomethyl)morpholine-4-carboxylate (0.260 g, 920 µmol) and N,N-diisopropylethylamine (577 µL, 3.3 mmol) under nitrogen at room temperature. The solution was stirred at 90° C. for 2.5 days. The solution was diluted with ethyl acetate (40 mL), washed with water (4×10 mL) and brine (10 mL), dried ($Na_2SO_4$), filtered and concentrated to give a residue which was purified by chromatography using 20% acetone in ethyl acetate as eluant to afford the title compound as a foam solid (0.136 g, 38%). $^1$H NMR (400 MHz, CDCl$_3$) δ 9.49-9.34 (m, 1H), 8.66 (s, 1H), 7.03 (s, 1H), 4.09-3.79 (m, 3H), 3.79-3.60 (m, 5H), 3.60-3.46 (m, 1H), 3.08 (d, J=4.8 Hz, 3H), 2.94 (d, J=13.7 Hz, 1H), 2.78-2.56 (m, 6H), 2.42 (dd, J=13.2, 4.1 Hz, 1H), 1.48 (s, 9H) ppm. MS: 544 m/z (M+H$^+$).

Step 2: N-Methyl-5-(4-(morpholin-2-ylmethyl)piperazin-1-yl)-7-(trifluoromethyl)thieno[3,2-b]pyridine-3-carboxamide hydrochloride A 50 mL round flask equipped with a stir bar was loaded with step 1 product (0.136 g, 250 µmol), 2.0 M solution of hydrogen chloride in methanol (10 mL) at room temperature. The solution was stirred at room temperature for 18 hours and then evaporated to dryness to afford the title compound as a white solid (0.120 g, 87%). 1H NMR (400 MHz, Methanol-d$_4$) δ 8.75 (d, J=1.9 Hz, 1H), 7.50 (s, 1H), 4.70-4.38 (m, 3H), 4.33-4.16 (m, 1H), 4.02 (t, J=12.6 Hz, 1H), 3.87 (s, 3H), 3.62 (d, J=17.5 Hz, 2H), 3.54-3.20 (m, 9H), 3.14-3.01 (m, 4H) ppm. MS: 444 m/z (M+H$^+$).

Step 3: 5-(4-((4-Isopropylmorpholin-2-yl)methyl)piperazin-1-yl)-N-methyl-7-(trifluoromethyl)thieno[3,2-b]pyridine-3-carboxamide 2,2,2-trifluoroacetic acid A 100 mL round flask equipped with a stir bar was loaded with step 2 product (0.060 g, 110 µmol), methanol (4 mL), propan-2-one (0.025 g, 430 µmol), acetic acid (6 µL, 110 µmol) and N,N-diisopropylethylamine (94 µL, 540 µmol). The solution was stirred at room temperature for 30 minutes, then a solution of zinc chloride (0.030 g, 220 µmol) and sodium cyanoborohydride (0.014 g, 210 µmol) in methanol (1 mL) was added. The solution was stirred at room temperature for 3 days. The solution was concentrated to dryness to a residue which was treated with ethyl acetate (40 mL), washed with water (10 mL) and brine (10 mL), dried (Na$_2$SO$_4$), filtered and concentrated to give a solid which was purified by reverse HPLC using 10-100% acetonitrile in water (0.1% trifluoroacetic acid) as eluant to afford the title compound as a solid (0.008 g, 10%). 1H NMR (400 MHz, Methanol-d4) δ 8.75 (s, 1H), 7.49 (s, 1H), 4.55-4.41 (m, 1H), 4.32-4.22 (m, 1H), 4.14-3.91 (m, 5H), 3.75-3.40 (m, 9H), 3.27-3.16 (m, 1H), 3.11-2.95 (m, 4H), 1.41 (d, J=6.4 Hz, 6H). ppm. MS: 600 m/z (M+H$^+$).

Example 566. (S)-1-Cyclopropylethyl 4-(3-(methylcarbamoyl)-7-(trifluoromethyl)thieno[3,2-b]pyridin-5-yl)piperidine-1-carboxylate

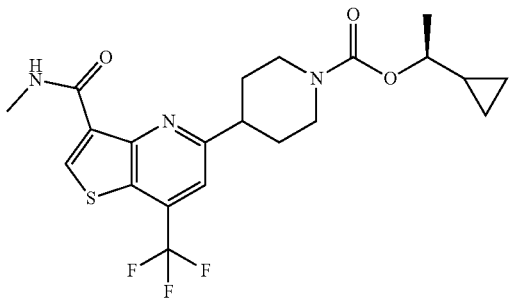 [SMILES: CNC(=O)c1csc2c(C(F)(F)F)cc(C3CCN(C(=O)O[C@@H](C)C4CC4)CC3)nc12]

A 25 mL microwave vial equipped with a stir bar was loaded with (S)-1-cyclopropylethan-1-ol (0.068 g, 790 µmol), 4-nitrophenyl chloroformate (0.159 g, 790 µmol), 1-methylpyrrolidin-2-one (5 mL) and N,N-diisopropylethylamine (0.136 g, 1.0 mmol). The mixture was stirred at 30° C. for 2 days. then Intermediate 29 (0.100 g, 260 µmol) was added and stirred at 90° C. for 2 hours. The reaction mixture was diluted with ethyl acetate (50 mL) and washed with water (3×20 mL) and brine (10 mL). The organic layer was dried (Na$_2$SO$_4$), filtered and concentrated to give a residue, which was purified by chromatography using 0-80% ethyl acetate in heptane as eluant to give the title compound (0.049 g, 41%). 1H NMR (400 MHz, CDCl3), 9.51 (br s, 1H), 8.82 (s, 1H), 7.50 (s, 1H), 4.52-4.24 (m, 3H), 3.07 (d, 3H), 3.05-2.88 (m, 2H), 2.12-2.05 (m, 2H), 1.96-1.76 (m, 2H), 1.31 (d, 3H), 1.08-0.96 (m, 1H), 0.92-0.83 (m, 1H), 0.63-0.38 (m, 3H), 0.33-0.18 (m, 1H) ppm. MS: 456 m/z (M+H$^+$).

Example 574. tert-Butyl 6-(3-(methylcarbamoyl)-7-(trifluoromethyl)thieno[3,2-b]pyridin-5-yl)-2-azaspiro[3.3]heptane-2-carboxylate

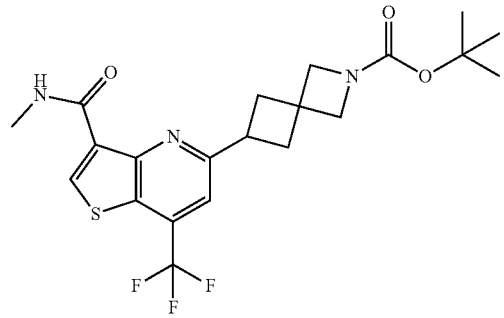 [SMILES: CNC(=O)c1csc2c(C(F)(F)F)cc(C3CC4(C3)CN(C(=O)OC(C)(C)C)C4)nc12]

Step 1: 5-Iodo-N-methyl-7-(trifluoromethyl)thieno[3,2-b]pyridine-3-carboxamide

A 100 mL round flask were charged with a stir bar, condenser, Intermediate 5 (2.00 g, 6.79 mmol) and sodium iodide (0.051 g, 339 µmol). The mixture was suspended in propiononitrile (20 mL). To it was added iodotrimethylsilane (1.93 mL, 14 mmol) to give dark amber mixture. The mixture was stirred at 90° C. for 2 hrs. Added water (60 mL) and solid sodium bisulfite (0.900 g) to remove excess iodine while stirring vigorously. The resulting yellow precipitate was collect via filtration, rinsed with water and air-dried. The solid was transferred into a flask and dissolved with ethyl acetate (80 mL), dried (Na$_2$SO$_4$), filtered and evaporated solvent to give a white solid which was purified by chromatography using 0-50% ethyl acetate in heptane as eluant to give the product as a white solid (1.523 g, 58%). MS: 387 m/z (M+H$^+$).

Step 2: tert-Butyl 6-(3-(methylcarbamoyl)-7-(trifluoromethyl)thieno[3,2-b]pyridin-5-yl)-2-azaspiro[3.3]heptane-2-carboxylate A 10 mL microwave vial were charged with a stir bar tert-butyl 6-iodo-2-azaspiro[3.3]heptane-2-carboxylate (0.502 g, 1.6 mmol) and N,N-dimethylacetamide (6 mL). The vial was kept under nitrogen environment and heated at 65° C. To it was then added zinc (0.101 g, 1.6 mmol) powder at once and stirred at 65° C. for 20 min. A separate 10-20 mL microwave vial were charged a stir bar, step 1 product (0.200 g, 520 μmol), copper (I) iodide (0.002 g, 13 μmol), palladiumCl2(dppf)₂ (0.0019 g, 30 μmol) and N,N-dimethylacetamide (6 mL). The vial was sealed a septum and was heated at 85° C. under nitrogen. While the second vial was heating the reaction mixture of the first vial was withdrawn into a syringe and added into the second vial. Upon addition reaction color changes to light amber then changed back to dark amber mixture. The solution was poured into saturated ammonium chloride (50 ml) and extracted with ethyl acetate (3×50 mL). The combined organic layer was back washed with water (2×30 ml) and brine (10 mL). The organic layer was dried (Na₂SO₄) and concentrated to a dark oil. The crude oil was purified on 10 g silica eluting with 0-80% ethyl acetate in heptane to give the title compound as a white solid (0.125 g, 53%). $^1$H NMR (400 MHz, CDCl₃) δ 9.57 (br s, 1H), 8.82 (s, 1H), 7.40 (s, 1H), 4.12 (s, 2H), 3.93 (s, 2H), 3.78 (p, J=8.6 Hz, 1H), 3.13 (d, J=4.9 Hz, 3H), 2.90-2.68 (m, 2H), 2.68-2.51 (m, 2H), 1.46 (s, 9H) ppm. MS: 456 m/z (M+H⁺).

Example 576. 2-(Trifluoromethoxy)ethyl 6-(3-(methylcarbamoyl)-7-(trifluoromethyl)thieno[3,2-b]pyridin-5-yl)-2-azaspiro[3.3]heptane-2-carboxylate

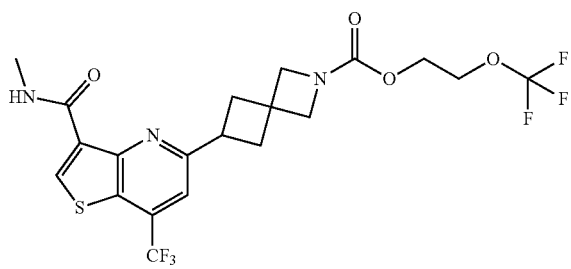 [SMILES: CNC(=O)c1csc2c(C(F)(F)F)cc(C3CC4(C3)CN(C(=O)OCCOC(F)(F)F)C4)nc12]

Step 1: N-Methyl-5-(2-azaspiro[3.3]heptan-6-yl)-7-(trifluoromethyl)thieno[3,2-b]pyridine-3-carboxamide hydrogen chloride A 10 mL microwave vial was charged with a stir bar and Example 574 (0.108 g, 237 mol) and 5-10% solution of hydrogen chloride in methanol (4 mL). The solution was stirred at room temperature for 16 hours and concentrated to give the title compound as a white solid (0.94 g, 100%). MS: 356 m/z (M+H⁺).

Step 2: 2-(Trifluoromethoxy)ethyl 6-(3-(methylcarbamoyl)-7-(trifluoromethyl)thieno[3,2-b]pyridin-5-yl)-2-azaspiro[3.3]heptane-2-carboxylate Using step 1 product and 2-(trifluoromethoxy)ethan-1-ol, the procedure described in Example 566 was used to prepare the title compound as a pale amber solid. $^1$H NMR (400 MHz, CDCl₃) δ 9.55 (br s, 1H), 8.83 (s, 1H), 7.41 (s, 1H), 4.30 (t, J=4.6 Hz, 2H), 4.21 (s, 2H), 4.20-4.11 (m, 2H), 4.02 (s, 2H), 3.80 (p, J=8.7 Hz, 1H), 3.13 (d, J=4.9 Hz, 3H), 2.84-2.73 (m, 2H), 2.68-2.56 (m, 2H) ppm. MS: 512 m/z (M+H⁺).

Example 585. tert-Butyl 3-(((3-(methylcarbamoyl)-7-(trifluoromethyl)thieno[3,2-b]pyridin-5-yl)oxy)methyl)azetidine-1-carboxylate

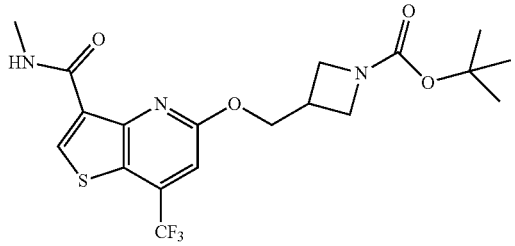 [SMILES: CNC(=O)c1csc2c(C(F)(F)F)cc(OCC3CN(C(=O)OC(C)(C)C)C3)nc12]

A 10 mL microwave vial equipped with a stir bar was loaded with Intermediate 5 (0.500 g, 1.7 mmol), tert-butyl 3-(hydroxymethyl)azetidine-1-carboxylate (0.381 g, 2.0 mmol), cesium carbonate (0.663 g, 2.0 mmol) and N,N-dimethylformamide (8 mL). The reaction mixture was stirred at 150° C. under microwave for 2.5 hours, then diluted with ethyl acetate (60 mL) and washed with water (4×15 mL) and brine (15 mL). the organic layer was dried (Na₂SO₄), filtered and concentrated to give a solid which was purified by chromatography using 10-100% ethyl acetate in heptane as eluant to give the product as a white solid (0.428 g, 57%). $^1$H NMR (400 MHz, CDCl₃) δ 9.01 (br s, 1H), 8.76 (s, 1H), 7.14 (s, 1H), 4.56 (d, J=6.5 Hz, 2H), 4.16 (t, J=8.5 Hz, 2H), 4.06-3.67 (m, 3H), 3.10 (d, J=4.9 Hz, 3H), 1.45 (d, J=12.9 Hz, 9H) ppm. MS: 446 m/z (M+H⁺).

Example 589. tert-Butyl 3-((3-(methylcarbamoyl)-7-(trifluoromethyl)thieno[3,2-b]pyridin-5-yl)oxy)pyrrolidine-1-carboxylate

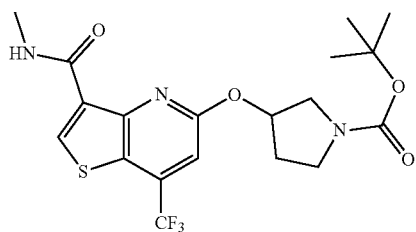 [SMILES: CNC(=O)c1csc2c(C(F)(F)F)cc(OC3CCN(C(=O)OC(C)(C)C)C3)nc12]

Exchanging tert-butyl 3-(hydroxymethyl)azetidine-1-carboxylate for tert-butyl 3-hydroxypyrrolidine-1-carboxylate, the procedure described in Example 585 was used to prepare the title compound as a white solid. $^1$H NMR (400 MHz, CDCl₃) δ 9.00 (br s, 1H), 8.76 (s, 1H), 7.13 (s, 1H), 5.60-5 48 (m, 1H), 3.90-3.74 (m, 2H), 3.74-3.50 (m, 2H), 3.09 (d, J=4.8 Hz, 3H), 2.44-2.26 (m, 2H), 1.48 (s, 9H) ppm. MS: 446 m/z (M+H⁺).

Example 590. 5-((1-(((Cyclopropylmethyl)carbamoyl)pyrrolidin-3-yl)oxy)-N-methyl-7-(trifluoromethyl)thieno[3,2-b]pyridine-3-carboxamide

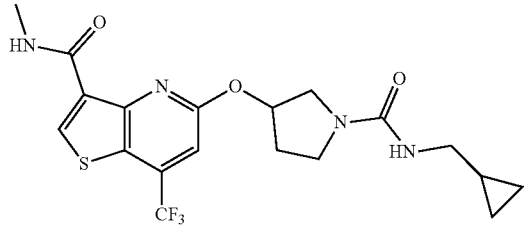 [SMILES: CNC(=O)c1csc2c(C(F)(F)F)cc(OC3CCN(C(=O)NCC4CC4)C3)nc12]

Step 1: N-Methyl-5-(pyrrolidin-3-yloxy)-7-(trifluoromethyl)thieno[3,2-b]pyridine-3-carboxamide hydrogen chloride A 25 mL microwave vial equipped with a stir bar was loaded with Example 589 (0.440 g, 988 μmol) and 2N hydrochloric acid (15 mL) in methanol. The solution was stirred at 80° C. for 3 hours and concentrated to dryness to give the product as a white solid (0.420 g, >99%). MS: 346 m/z (M+H$^+$).

Step 2: 5-((1-(((Cyclopropylmethyl)carbamoyl)pyrrolidin-3-yl)oxy)-N-methyl-7-(trifluoromethyl)thieno[3,2-b]pyridine-3-carboxamide Using step 1 product and (isocyanatomethyl)cyclopropane, the procedure described in step 2 of Example 422 was used to prepare the title compound as a white solid. 1H NMR (400 MHz, Methanol-d4) δ 8.77 (s, 1H), 7.29 (s, 1H), 5.73 (br s, 1H), 3.95-3.74 (m, 2H), 3.74-3.50 (m, 2H), 3.08 (d, J=1.0 Hz, 3H), 3.03 (d, J=6.8 Hz, 2H), 2.52-2.35 (m, 2H), 1.07-0.91 (m, 1H), 0.57-0.33 (m, 2H), 0.29-0.11 (m, 2H) ppm. MS: 443 m/z (M+H$^+$).

Example 593. tert-Butyl (S)-3-((3-(methylcarbamoyl)-7-(trifluoromethyl)thieno[3,2-b]pyridin-5-yl)oxy)pyrrolidine-1-carboxylate

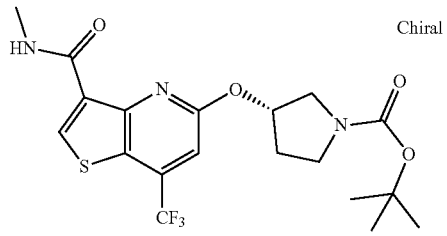 [SMILES: CNC(=O)c1csc2c(C(F)(F)F)cc(O[C@H]3CCN(C(=O)OC(C)(C)C)C3)nc12]

Exchanging tert-butyl 3-(hydroxymethyl)azetidine-1-carboxylate for tert-butyl (S)-3-hydroxypyrrolidine-1-carboxylate, the procedure described in Example 585 was used to prepare the title compound as a white solid. $^1$H NMR (400 MHz, CDCl$_3$) δ 9.00 (br s, 1H), 8.77 (s, 1H), 7.13 (s, 1H), 5.68-5.44 (m, 1H), 3.95-3.49 (m, 4H), 3.09 (d, J=4.8 Hz, 3H), 2.49-2.14 (m, 2H), 1.48 (s, 9H) ppm. MS: 446 m/z (M+H$^+$).

Example 594. (S)-5-((1-(((Cyclopropylmethyl)carbamoyl)pyrrolidin-3-yl)oxy)-N-methyl-7-(trifluoromethyl)thieno[3,2-b]pyridine-3-carboxamide

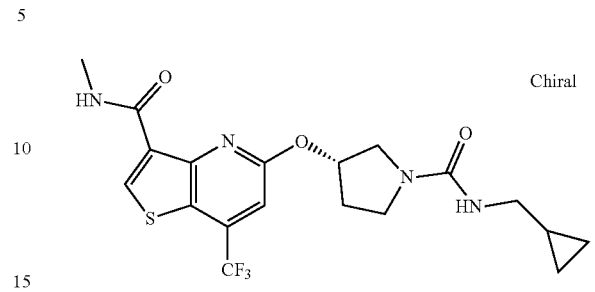

Step 1: (S)—N-Methyl-5-(pyrrolidin-3-yloxy)-7-(trifluoromethyl)thieno[3,2-b]pyridine-3-carboxamide hydrogen chloride Using Example 593 and 2N hydrochloric acid in methanol, the procedure described in step 1 of Example 590 was used to prepare the title compound as a white solid. MS: 346 m/z (M+H$^+$).

Step 2: (S)-5-((1-(((Cyclopropylmethyl)carbamoyl)pyrrolidin-3-yl)oxy)-N-methyl-7-(trifluoromethyl)thieno[3,2-b]pyridine-3-carboxamide Using step 1 product and (isocyanatomethyl)cyclopropane, the procedure described in step 2 of Example 422 was used to prepare the title compound as a white solid. 1H NMR (400 MHz, Methanol-d4) δ 8.75 (s, 1H), 7.28 (s, 1H), 5.87-5.61 (m, 1H), 3.94-3.76 (m, 2H), 3.75-3.50 (m, 2H), 3.39-3.29 (m, 1H), 3.08 (s, 3H), 3.06 (s, 2H), 2.47-2.35 (m, 2H), 1.12-0.91 (m, 1H), 0.60-0.36 (m, 2H), 0.36-0.12 (m, 2H) ppm. MS: 443 m/z (M+H$^+$).

Example 595. Cyclopropylmethyl (S)-3-((3-(methylcarbamoyl)-7-(trifluoromethyl)thieno[3,2-b]pyridin-5-yl)oxy)pyrrolidine-1-carboxylate

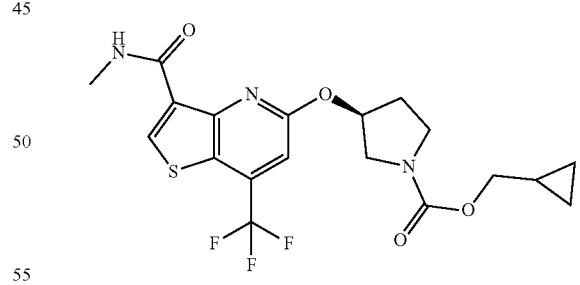

A 25 mL microwave vial equipped with a stir bar was loaded with cyclopropylmethanol (0.250 g, 3.5 mmol), 1-methylpyrrolidin-2-one (8 mL), N,N-diisopropylethylamine (0.089 g, 690 μmol) and 4-nitrophenyl chloroformate (1.05 g, 5.2 mmol). The solution was stirred at 20° C. for 2 days. Step 1 product of Example 594 (0.080 g, 230 μmol) was added and stirred at 90° C. for 16 hours. The reaction mixture was diluted with ethyl acetate (50 mL) and washed with water (3×20 mL) and brine (10 mL). The organic layer was dried (Na$_2$SO$_4$), filtered and concentrated to give a residue, which was purified by chromatography using 0-100% ethyl acetate in heptane as eluant to give the product as a white solid (0.095 g, 92%). $^1$H NMR (400 MHz, CDCl$_3$) δ 9.00 (br s, 1H), 8.77 (s, 1H), 7.13 (s, 1H), 5.72-5.43 (m, 1H), 4.01-3.89 (m, 2H), 3.87-3.77 (m, 2H), 3.77-3.68 (m, 1H), 3.68-3.58 (m, 1H), 3.10 (d, J=4.8 Hz, 3H), 2.48-2.20 (m, 2H), 1.79 (s, 1H), 1.22-1.06 (m, 1H), 0.65-0.46 (m, 2H), 0.38-0.21 (m, 2H) ppm. MS: 444 m/z (M+H$^+$).

Example 600. 2-(Trifluoromethoxy)ethyl (S)-3-((3-(methylcarbamoyl)-7-(trifluoromethyl)thieno[3,2-b]pyridin-5-yl)oxy)pyrrolidine-1-carboxylate

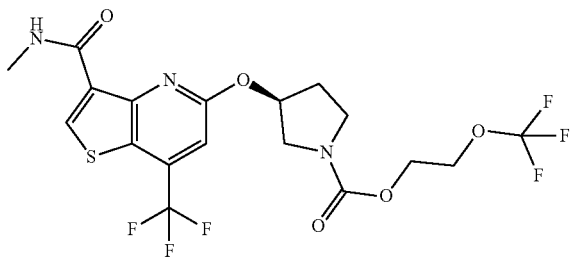 [SMILES: CNC(=O)c1csc2c(C(F)(F)F)cc(O[C@H]3CCN(C(=O)OCCOC(F)(F)F)C3)nc12]

Exchanging cyclopropylmethanol for 3-(trifluoromethoxy)ethan-1-ol, the procedure described in Example 595 was used to prepare the title compound as a white solid. $^1$H NMR (400 MHz, CDCl$_3$) δ 8.94 (br s, 1H), 8.77 (s, 1H), 7.13 (s, 1H), 5.66-5.48 (m, 1H), 4.48-4.27 (m, 2H), 4.27-4.14 (m, 2H), 3.97-3.61 (m, 4H), 3.10 (d, J=4.9 Hz, 3H), 2.53-2.25 (m, 2H) ppm. MS: 502 m/z (M+H$^+$).

Example 609. tert-Butyl (+/−)-cis-3-fluoro-4-((3-(methylcarbamoyl)-7-(trifluoromethyl)thieno[3,2-b]pyridin-5-yl)oxy)pyrrolidine-1-carboxylate

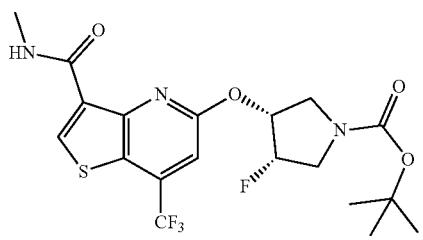 [SMILES: CNC(=O)c1csc2c(C(F)(F)F)cc(O[C@@H]3CN(C(=O)OC(C)(C)C)C[C@@H]3F)nc12]

Exchanging tert-butyl 3-(hydroxymethyl)azetidine-1-carboxylate for tert-butyl (+/−)-trans-3-fluoro-4-hydroxypyrrolidine-1-carboxylate, the procedure described in Example 585 was used to prepare the title compound as a white solid. $^1$H NMR (400 MHz, CDCl$_3$) δ 8.78 (br s, 2H), 7.25 (s, 1H), 5.51-5.29 (m, 2H), 4.18-4.01 (m, 1H), 3.95-3.56 (m, 3H), 3.08 (d, J=4.9 Hz, 3H), 1.50 (s, 9H) ppm. MS: 464 m/z (M+H$^+$).

Example 610. Cyclopropylmethyl (+/−)-cis-3-fluoro-4-((3-(methylcarbamoyl)-7-(trifluoromethyl)thieno[3,2-b]pyridin-5-yl)oxy)pyrrolidine-1-carboxylate

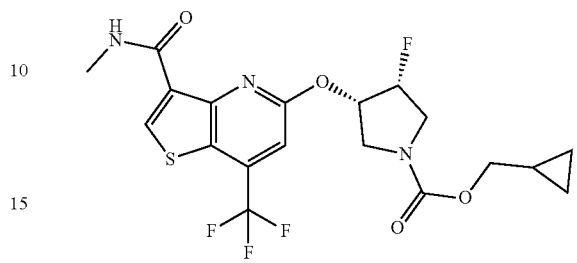

Step 1: 5-(((+/−)-cis-4-Fluoropyrrolidin-3-yl)oxy)-N-methyl-7-(trifluoromethyl)thieno[3,2-b]pyridine-3-carboxamide hydrogen chloride Using Example 609 and 2N hydrochloric acid in methanol, the procedure described in step 1 of Example 590 was used to prepare the title compound as a white solid. MS: 364 m/z (M+H$^+$).

Step 2: 2-(Trifluoromethoxy)ethyl (+/−)-cis-3-fluoro-4-((3-(methylcarbamoyl)-7-(trifluoromethyl)thieno[3,2-b]pyridin-5-yl)oxy)pyrrolidine-1-carboxylate Using step 1 product and cyclopropylmethanol, the procedure described in Example 595 was used to prepare the title compound as a white solid. $^1$H NMR (400 MHz, CDCl$_3$) δ 8.77 (br s, 2H), 7.25 (s, 1H), 5.58-5.23 (m, 2H), 4.29-4.10 (m, 1H), 3.98 (d, J=1.4 Hz, 1H), 3.97-3.56 (m, 4H), 3.08 (d, J=4.9 Hz, 3H), 1.23-1.03 (m, 1H), 0.65-0.52 (m, 2H), 0.46-0.22 (m, 2H) ppm. MS: 462 m/z (M+H$^+$).

Example 611. 2-(Trifluoromethoxy)ethyl (+/−)-cis-3-fluoro-4-((3-(methylcarbamoyl)-7-(trifluoromethyl)thieno[3,2-b]pyridin-5-yl)oxy)pyrrolidine-1-carboxylate

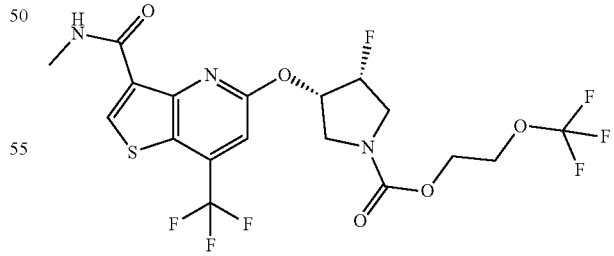

Using step 1 product of Example 610 and 3-(trifluoromethoxy)ethan-1-ol, the procedure described in Example 595 was used to prepare the title compound as a white solid. $^1$H NMR (400 MHz, CDCl$_3$) δ 8.78 (s, 1H), 8.71 (br s, 1H), 7.25 (s, 1H), 5.59-5.34 (m, 2H), 4.51-4.30 (m, 2H), 4.30-4.07 (m, 3H), 4.04-3.66 (m, 3H), 3.08 (t, J=4.4 Hz, 3H) ppm. MS: 520 m/z (M+H$^+$).

Example 628. tert-Butyl (+/−)-endo7-((3-(methyl-carbamoyl)-7-(trifluoromethyl)thieno[3,2-b]pyridin-5-yl)oxy)-3-oxa-9-azabicyclo[3.3.1]nonane-9-carboxylate

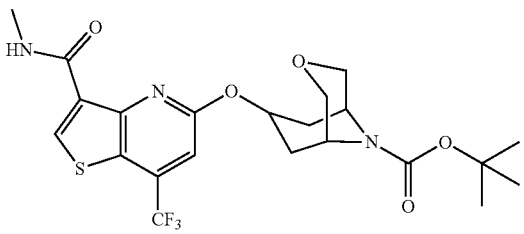 [SMILES: CNC(=O)c1csc2c(C(F)(F)F)cc(OC3CC4COCC(C3)N4C(=O)OC(C)(C)C)nc12]

A 10 mL microwave vial equipped with a stir bar was loaded with Intermediate 5 (0.200 g, 680 μmol), tert-butyl (+/−)-endo7-hydroxy-3-oxa-9-azabicyclo[3.3.1]nonane-9-carboxylate (0.165 g, 680 μmol), tetrahydrofuran (8 mL) and potassium 2-methylpropan-2-olate (0.084 g, 750 μmol). The solution was stirred at 70° C. for 2 hours, then diluted with ethyl acetate (40 mL) and washed with water (40 mL) and brine (10 mL). The organic layer was dried ($Na_2SO_4$), filtered and concentrated to give a red residue which was purified by reverse HPLC chromatography using 20-100% acetonitrile in water as eluant to give the title compound as a white solid (0.038 g, 11%). $^1$H NMR (400 MHz, $CDCl_3$) δ 9.03 (br s, 1H), 8.74 (s, 1H), 7.13 (t, J=0.8 Hz, 1H), 5.22-5.05 (m, 1H), 4.39-4.25 (m, 1H), 4.25-4.11 (m, 1H), 3.85-3.61 (m, 4H), 3.13 (d, J=4.8 Hz, 3H), 2.71-2.55 (m, 1H), 2.55-2.37 (m, 1H), 2.23-1.97 (m, 2H), 1.50 (s, 9H). ppm. MS: 502 m/z ($M+H^+$).

Example 629. 2-(Trifluoromethoxy)ethyl (+/−)-endo7-((3-(methylcarbamoyl)-7-(trifluoromethyl) thieno[3,2-b]pyridin-5-yl)oxy)-3-oxa-9-azabicyclo [3.3.]nonane-9-carboxylate

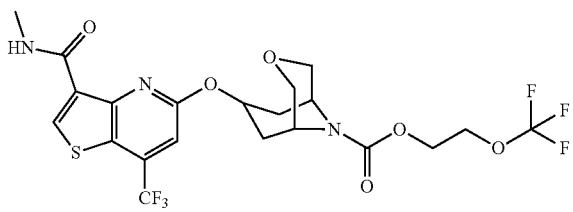 [SMILES: CNC(=O)c1csc2c(C(F)(F)F)cc(OC3CC4COCC(C3)N4C(=O)OCCOC(F)(F)F)nc12]

Step 1: (+/−)-5-((endo-3-Oxa-9-azabicyclo[3.3.1] nonan-7-yl)oxy)-N-methyl-7-(trifluoromethyl)thieno [3,2-b]pyridine-3-carboxamide hydrochloride Using the procedure described in step 2 of Example 552, the N-tert-butoxycarbonyl protecting group of the title compound of Example 628 was cleaved using a 2.0 M solution of hydrogen chloride in methanol.

Step 2: (+/−)-2-(Trifluoromethoxy)ethyl endo-7-((3-(methylcarbamoyl)-7-(trifluoromethyl)thieno[3,2-b] pyridin-5-yl)oxy)-3-oxa-9-azabicyclo[3.3.1]nonane-9-carboxylate A 25 mL round flask equipped with a stir bar was loaded with 2-(trifluoromethoxy)ethan-1-ol (0.026 g, 200 μmol), 1,1'-carbonyldiimidazole (0.033 g, 200 μmol) and dichloromethane (4 mL). The reaction mixture was stirred at rt for 16 hours and then concentrated. The residue was taken up in acetonitrile (6 mL). To this stirred solution was added N-hydroxysuccimide (0.023 g, 210 μmol), step 1 product (0.030 g, 70 μmol) and N,N-diisopropylethylamine (0.009 g, 70 μmol), in order. The reaction was heated overnight at 40° C. and then cooled and concentrated. The crude residue was purified by column chromatography using 0-100% EtOAc in heptane as eluant to give the title compound as a white solid (0.030 g, 78%). $^1$H NMR (400 MHz, $CDCl_3$) δ 9.01 (br s, 1H), 8.74 (s, 1H), 7.14 (s, 1H), 5.30-5.06 (m, 1H), 4.44-4.38 (m, 2H), 4.35-4.29 (m, 1H), 4.25 (d, J=8.0 Hz, 1H), 4.23-4.18 (m, 2H), 3.83-3.76 (m, 2H), 3.76-3.68 (m, 2H), 3.09 (d, J=4.9 Hz, 3H), 2.67-2.53 (m, 1H), 2.52-2.40 (m, 1H), 2.27-2.07 (m, 2H) ppm. MS: 558 m/z ($M+H^+$).

Example 632. 2-(Trifluoromethoxy)ethyl 4-((3-(methylcarbamoyl)-7-(trifluoromethyl)thieno[3,2-b] pyridin-5-yl)methyl)piperidine-1-carboxylate

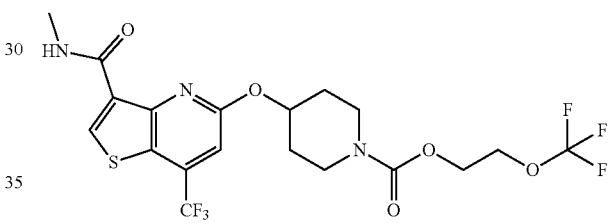

Step 1: N-methyl-5-(piperidin-4-ylmethyl)-7-(trifluoromethyl)thieno[3,2-b]pyridine-3-carboxamide hydrogen chloride Using Example 634 and 2N hydrochloric acid in methanol, the procedure described in step 1 of Example 590 was used to prepare the title compound as a white solid. MS: 358 m/z ($M+H^+$).

Step 2: 2-(Trifluoromethoxy)ethyl 4-((3-(methylcarbamoyl)-7-(trifluoromethyl)thieno[3,2-b]pyridin-5-yl)methyl)piperidine-1-carboxylate Using step 1 product and 3-(trifluoromethoxy)ethan-1-ol, the procedure described in Example 629 was used to prepare the title compound as a white solid. $^1$H NMR (400 MHz, $CDCl_3$) δ 9.52 (br s, 1H), 8.82 (s, 1H), 7.43 (s, 1H), 4.32 (t, J=4.6 Hz, 2H), 4.29-4.03 (m, 4H), 3.12 (d, J=4.8 Hz, 3H), 3.00 (d, J=7.1 Hz, 2H), 2.96-2.72 (m, 2H), 2.18-2.00 (m, 1H), 1.73 (d, J=12.0 Hz, 2H), 1.45-1.21 (m, 2H) ppm. MS: 514 m/z ($M+H^+$).

Example 634. tert-Butyl 4-((3-(methylcarbamoyl)-7-(trifluoromethyl)thieno[3,2-b]pyridin-5-yl)methyl)piperidine-1-carboxylate

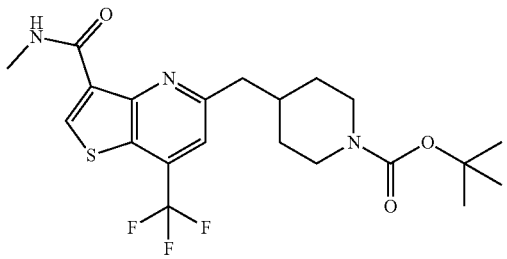 [SMILES: CNC(=O)c1csc2c(C(F)(F)F)cc(CC3CCN(C(=O)OC(C)(C)C)CC3)nc12]

Exchanging tert-butyl 6-iodo-2-azaspiro[3.3]heptane-2-carboxylate for tert-butyl 4-(iodomethyl)piperidine-1-carboxylate, the procedure described in Example 574 was used to prepare the title compound as a white solid. $^1$H NMR (400 MHz, CDCl$_3$) δ 9.73-9.29 (br s, 1H), 8.81 (s, 1H), 7.42 (s, 1H), 4.29-4.02 (m, 2H), 3.12 (d, J=4.8 Hz, 3H), 2.99 (d, J=7.1 Hz, 2H), 2.71 (t, J=12.6 Hz, 2H), 2.10-1.92 (m, 1H), 1.81-1.64 (m, 2H), 1.46 (s, 9H), 1.42-1.22 (m, 2H) ppm. MS: 458 m/z (M+H$^+$).

Example 636 and Example 637. 6-Chloro-5-[4-[2-(isopropylamino)-2-oxo-ethyl]piperazin-1-yl]-N-methyl-7-(trifluoromethyl)thieno[3,2-b]pyridine-3-carboxamide and 6-Chloro-5-[4-[2-(isopropylamino)-2-oxo-ethyl]piperazin-1-yl]-2-methoxy-N-methyl-7-(trifluoromethyl)thieno[3,2-b]pyridine-3-carboxamide (Two Compounds Isolated from One Reaction)

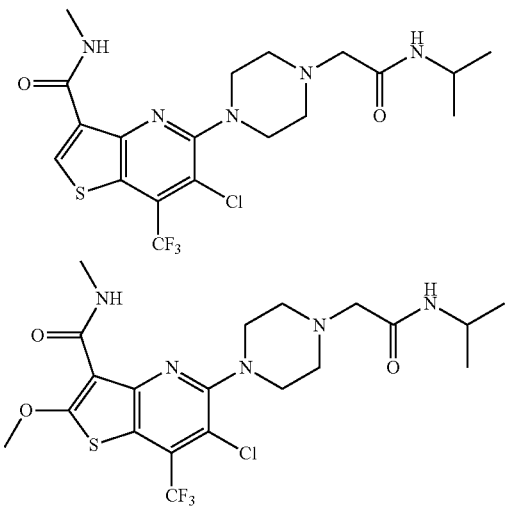

Step 1: 5,6-Dichloro-N-methyl-7-(trifluoromethyl)thieno[3,2-b]pyridine-3-carboxamide and 5,6-dichloro-2-methoxy-N-methyl-7-(trifluoromethyl)thieno[3,2-b]pyridine-3-carboxamide In a 50 mL round-bottomed flask were placed Intermediate 3 (800 mg, 2.71 mmol), 1-chloropyrrolidine-2,5-dione (3.25 g, 24.35 mmol), and acetic acid (5 mL). The mixture was heated at 130° C. for 20 hours, concentrated, and diluted with ethyl acetate (75 mL) and water (75 mL). The organic layer was separated, washed with saturated sodium bicarbonate (50 mL) and brine (50 mL), dried (Na$_2$SO$_4$), filtered, and concentrated to give a residue, which was triturated with acetonitrile to give 300 mg of products, methyl 6-chloro-5-hydroxy-7-(trifluoromethyl)thieno[3,2-b]pyridine-3-carboxylate (MS: 311 m/z (M+H$^+$)) and methyl 2,6-dichloro-5-hydroxy-7-(trifluoromethyl)thieno[3,2-b]pyridine-3-carboxylate (MS: 346 m/z (M+H$^+$)) appeared in LCMS. The mixture was used for a next step without further purification.

In a 20 mL vial were placed a mixture of above hydroxy pyridines (300 mg) and POCl3 (2.24 mL, 24.06 mmol). The mixture was heated at 110° C. for 2 hours and poured into a solution of dichloromethane and ice water. The organic layer was separated, washed with brine (20 mL), dried (Na$_2$SO$_4$), filtered, and concentrated to give a mixture of chlorinated products (~320 mg), methyl 5,6-dichloro-7-(trifluoromethyl)thieno[3,2-b]pyridine-3-carboxylate (MS: 330 m/z (M+H$^+$)) and methyl 2,5,6-trichloro-7-(trifluoromethyl)thieno[3,2-b]pyridine-3-carboxylate (MS: 364 m/z (M+H$^+$)), which were used for a next step without further purification. In a 50 mL round-bottomed flask were placed a mixture of above chlorinated products (~320 mg) and methanamine (4.81 mL, 9.63 mmol) in methanol (2M). After 12 hours at 20° C., the mixture was concentrated to give a mixture (~320 mg) of the title compounds, which was used for a next step without further purification.

Step 2: 6-Chloro-5-[4-[2-(isopropylamino)-2-oxo-ethyl]piperazin-1-yl]-N-methyl-7-(trifluoromethyl)thieno[3,2-b]pyridine-3-carboxamide and 6-chloro-5-[4-[2-(isopropylamino)-2-oxo-ethyl]piperazin-1-yl]-2-methoxy-N-methyl-7-(trifluoromethyl)thieno[3,2-b]pyridine-3-carboxamide In a 10 mL microwave vial were placed N,N-diisopropylethylamine (636 μL, 3.65 mmol), N-isopropyl-2-(piperazin-1-yl)acetamide (202 mg, 1.09 mmol), prepared in step 2 of Example 47, the products (~320 mg) of step 1, and N-methyl-2-pyrrolidinone (3 mL). The mixture was heated at 150° C. for 1 hour in a microwave reactor and diluted with ethyl acetate (25 mL) and water (25 mL). The organic layer was separated, washed with water (3×20 mL) and brine (20 mL), dried (MgSO4), filtered, and concentrated to give a residue, which was purified by automated flash chromatography (silica gel loading, 5:1 ethyl acetate:heptane to 10:1 ethyl acetate:methanol; 12S column) to afford a mixture of products which was further purified by HPLC to give the title compounds. Example 636 (48 mg, 100 μmol, 11% yield). $^1$H NMR (400 MHz, CDCl$_3$) δ 9.31-9.19 (m, 1H), 8.73 (s, 1H), 6.90 (d, J=8.8 Hz, 1H), 4.22-4.08 (m, 1H), 3.49 (t, J=4.9 Hz, 4H), 3.14-3.07 (m, 5H), 2.81 (t, J=4.8 Hz, 4H), 1.20 (d, J=6.5 Hz, 6H) ppm. MS: 478 m/z (M+H$^+$) and Example 637 (30 mg, 60 μmol, 6% yield). $^1$H NMR (400 MHz, CDCl$_3$) δ 8.6-8.52 (m, 1H), 7.18-6.94 (m, 1H), 4.19-4.04 (m, 1H), 3.93 (s, 3H), 3.55-3.43 (m, 4H), 3.15 (d, J=5.2 Hz, 3H), 3.07 (s, 2H), 2.74 (t, J=4.9 Hz, 4H), 1.18 (d, J=6.6 Hz, 6H) ppm. MS: 508 m/z (M+H$^+$).

Example 638. [1-[6-Chloro-3-(methylcarbamoyl)-7-(trifluoromethyl)thieno[3,2-b]pyridin-5-yl]-4-piperidyl] N-(cyclopropylmethyl)carbamate

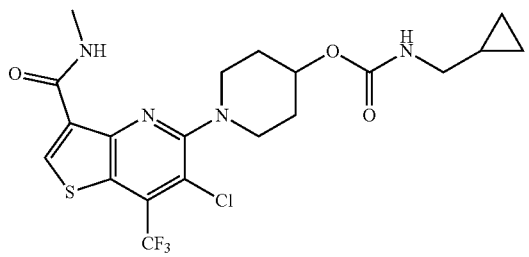 [SMILES: CNC(=O)c1csc2c(C(F)(F)F)c(Cl)c(N3CCC(OC(=O)NCC4CC4)CC3)nc12]

In a 5 mL vial were placed Example 669 (20 mg, 40 µmol) and N-methyl-2-pyrrolidinone (1 mL). 3-Chloroperbenzoic acid (15 mg, 60 µmol) was added at 20° C. After 1 hour at 20° C., the mixture was directly subjected to reversed phase HPLC for purification to give the title compound. $^1$H NMR (400 MHz, CDCl$_3$) δ 9.25 (brs, 1H), 8.70 (s, 1H), 4.97 (brs, 1H), 4.82 (brs, 1H), 3.68-56 (m, 2H), 3.30 (t, J=10.8 Hz, 2H), 3.07-3.1 (m, 5H), 2.15 (brs, 2H), 1.94 (brs, 2H), 1.06-0.93 (m, 1H), 0.59-0.42 (m, 2H), 0.23-0.21 (m, 2H) ppm. MS: 491 m/z (M+H$^+$).

Example 639. [1-[6-Fluoro-3-(methylcarbamoyl)-7-(trifluoromethyl)thieno[3,2-b]pyridin-5-yl]-4-piperidyl] N-[(1S)-1-cyclopropylethyl]carbamate

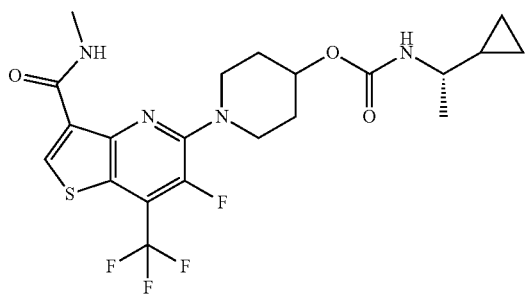 [SMILES: CNC(=O)c1csc2c(C(F)(F)F)c(F)c(N3CCC(OC(=O)N[C@@H](C)C4CC4)CC3)nc12]

In a 5 mL vial were placed Example 109 (62 mg, 131 µmol) and acetonitrile (2 mL). 1-Chloromethyl-4-fluoro-1,4-diazoniabicyclo[2.2.2]octane bis(tetrafluoroborate) (140 mg, 395 mol) was added at 20° C. After 15 hours at 20° C., the mixture was directly subjected to reversed phase HPLC providing the title compound (2 mg, 5 µmol, 3% yield) as a solid after lyophilization. $^1$H NMR (400 MHz, CDCl$_3$) δ 9.23 (brs, 1H), 8.62 (s, 1H), 4.95 (brs, 1H), 4.69 (brs, 1H), 3.87-3.75 (m, 2H), 3.47-3.3 (m, 2H), 3.25-3.11 (m, 1H), 3.07 (d, J=4.9 Hz, 3H), 2.10 (brs, 2H), 1.94-1.81 (m, 2H), 1.32-1.11 (m, 3H), 0.88-0.75 (m, 3H), 0.56-0.43 (m, 2H) ppm. MS: 489 m/z (M+H$^+$).

Example 640. [1-[6-Chloro-3-(methylcarbamoyl)-7-(trifluoromethyl)thieno[3,2-b]pyridin-5-yl]-4-piperidyl] N-cyclopropylcarbamate

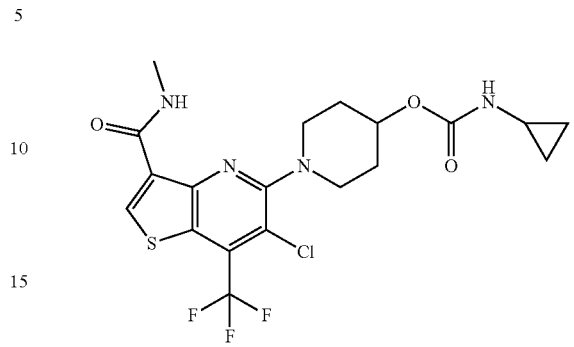

In a 5 mL vial were placed Example 473 (100 mg, 226 µmol) and N-methyl-2-pyrrolidinone (2 mL). Hydrogen chloride (113 µL, 452 µmol) in dioxane (4M) was added at 0° C. and after 10 minutes at room temperature, 3-chloroperbenzoic acid (83 mg, 339 µmol) was added at 0° C. After 1 hour at room temperature, the mixture was directly subjected to reversed phase HPLC to give the title compound (52 mg, 109 µmol, 48% yield) as a solid after lyophilization. 1H NMR (400 MHz, DMSO-d$_6$) δ 9.05 (brs, 1H), 8.85 (s, 1H), 7.32 (brs, 1H), 4.82 (brs, 1H), 3.63-3.5 (m, 5H), 2.95 (d, J=4.8 Hz, 3H), 2.12-2.01 (m, 2H), 1.87-0.62 (m, 2H), 0.57 (td, J=7.0, 4.7 Hz, 2H), 0.45-0.38 (m, 2H) ppm. MS: 477 m/z (M+H$^+$).

Example 641. [1-[6-fluoro-3-(methylcarbamoyl)-7-(trifluoromethyl)thieno[3,2-b]pyridin-5-yl]-4-piperidyl] N-cyclopropylcarbamate

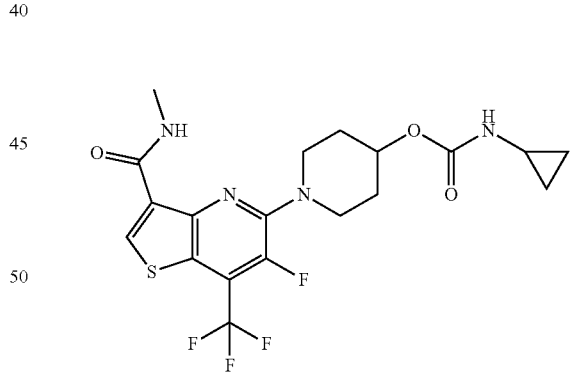

Using Example 473, the procedure described in Example 639 was used to prepare the title compound (8 mg, 18 µmol, 8% yield) as a solid after lyophilization. $^1$H NMR (400 MHz, CDCl$_3$) δ 9.22 (brs, 1H), 8.62 (s, 1H), 5.02-4.9 (m, 2H), 3.88-3.70 (m, 2H), 3.52-3.37 (m, 2H), 3.07 (d, J=4.9 Hz, 3H), 2.61 (brs, 1H), 2.19-2.06 (m, 2H), 1.94-1.7 (m, 2H), 0.76-0.68 (m, 2H), 0.62-0.51 (m, 2H) ppm. MS: 461 m/z (M+H$^+$).

Example 642. tert-Butyl N-[1-[3-(isopropylcarbamoyl)-7-(trifluoromethyl)thieno[3,2-b]pyridin-5-yl]pyrrolidin-3-yl]carbamate

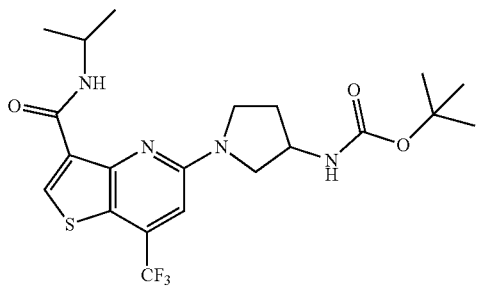 [SMILES: CC(C)NC(=O)c1csc2c(C(F)(F)F)cc(N3CCC(NC(=O)OC(C)(C)C)C3)nc12]

Using 5-(3-((tert-butoxycarbonyl)amino)pyrrolidin-1-yl)-7-(trifluoromethyl)thieno[3,2-b]pyridine-3-carboxylic acid, in which the ester in Example 659 was hydrolyzed by lithium hydroxide, and propan-2-amine, the procedure described in Example 649 was used to prepare the title compound (200 mg, 63%) as a solid. $^1$H NMR (400 MHz, CDCl$_3$) δ 9.59 (d, J=7.5 Hz, 1H), 8.58 (s, 1H), 6.68 (s, 1H), 5.49 (brs, 1H), 4.44 (brs, 1H), 4.34-4.17 (m, 1H), 3.88-3.7 (m, 1H), 3.74-3.53 (m, 2H), 3.45 (dd, J=10.6, 4.3 Hz, 1H), 2.45-2.31 (m, 1H), 2.23-2.11 (m, 1H), 1.47 (s, 9H), 1.35-1.16 (m, 6H) ppm. MS: 473 m/z (M+H$^+$).

Example 649. 2-[4-[3-(Azetidine-1-carbonyl)-7-(trifluoromethyl)thieno[3,2-b]pyridin-5-yl]piperazin-1-yl]-N-isopropyl-acetamide

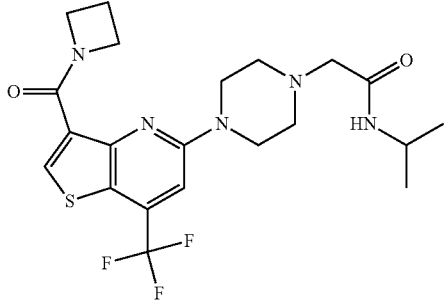 [SMILES: CC(C)NC(=O)CN1CCN(c2cc(C(F)(F)F)c3scc(C(=O)N4CCC4)c3n2)CC1]

Step 1: 5-(4-(2-(Isopropylamino)-2-oxoethyl)piperazin-1-yl)-7-(trifluoromethyl)thieno[3,2-b]pyridine-3-carboxylic acid In a 100 mL round-bottomed flask were placed Example 10 (143 mg, 321 µmol), methanol (3 mL), tetrahydrofuran (3 mL), and lithium hydroxide (77 mg, 3.22 mmol). After 3 hours at 60° C., the mixture was concentrated and diluted with ethyl acetate (50 mL) and water (50 mL), and its pH was adjusted to 1-2 with dilute hydrochloric acid solution. The insoluble product was filtered and dissolved in methanol/dichloromethane. The solution was dried (Na$_2$SO$_4$) and combined with extractive work-up solution. The organic phase of the filtrate was separated, washed with brine (25 mL), dried (MgSO$_4$), filtered and concentrated to give the title compound (110 mg, 255 µmol, 79% yield). MS: 431 m/z (M+H$^+$)

Step 2: 2-[4-[3-(Azetidine-1-carbonyl)-7-(trifluoromethyl)thieno[3,2-b]pyridin-5-yl]piperazin-1-yl]-N-isopropyl-acetamide In a 100 mL round-bottomed flask were placed step 1 product (110 mg, 255 µmol), N,N-diisopropylethylamine (357 µL, 2.04 mmol), and acetonitrile (10 mL). O-(Benzotriazol-1-yl)-N,N,N',N'-tetramethyluronium tetrafluoroborate (TBTU) (169 mg, 511 µmol) was added at 20° C., after 10 minutes, followed by addition of azetidine (44 mg, 767 µmol). After 2 hours at 20° C., the mixture was diluted with ethyl acetate (50 mL) and saturated sodium bicarbonate (20 mL). The organic layer was separated, washed ammonium chloride (20 mL) and brine (25 mL), dried (MgSO$_4$), filtered, and concentrated to give the residue, which was purified by automated flash chromatography (1:1 heptane/ethyl acetate to 0:100 heptane/ethyl acetate; 12S column, silica gel loading) to provide the title compound (63 mg, 134 µmol, 52% yield) as a solid. $^1$H NMR (400 MHz, CDCl$_3$) δ 8.06 (s, 1H), 7.01 (s, 1H), 6.94 (d, J=8 Hz, 1H), 4.28 (t, J=7.8 Hz, 2H), 4.22-4.06 (m, 3H), 3.84-3.64 (m, 4H), 3.07 (s, 2H), 2.79-2.62 (m, 4H), 2.37-2.29 (m, 2H), 1.20 (d, J=6.6 Hz, 6H) ppm. MS: 470 m/z (M+H$^+$).

Example 653. [1-[3-(Trideuteriomethylcarbamoyl)-7-(trifluoromethyl)thieno[3,2-b]pyridin-5-yl]-4-piperidyl] N-cyclopropylcarbamate

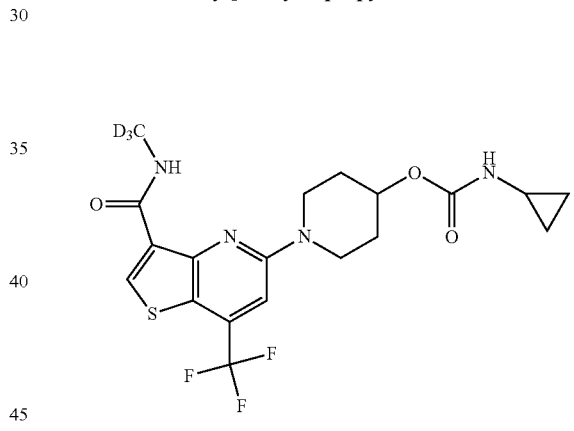

In a 20 mL microwave vial were placed methyl 5-(4-((cyclopropylcarbamoyl)oxy)piperidin-1-yl)-7-(trifluoromethyl)thieno[3,2-b]pyridine-3-carboxylate (120 mg, 270 µmol), which was prepared by a similar procedure as in Example 428, and methanol (5 mL). Methan-d3-amine (92 mg, 2.71 mmol) was bubbled into the reaction mixture for 2-3 minutes at room temperature. After 2 hours at 80° C., LCMS showed some product (~50% conversion) with remaining starting material. The mixture was bubbled again with methylamine-d3 and heated at 40° C. for 2 days (reaction completed). The mixture was concentrated to give a residue, which was suspended in acetonitrile and water and lyophilized to afford the title compound (101 mg, 228 µmol, 84% yield) as a solid. 1H NMR (400 MHz, DMSO-d$_6$) δ 9.24 (s, 1H), 8.75 (s, 1H), 7.51 (s, 1H), 7.33 (s, 1H), 4.82 (brs, 1H), 4.02 (brs, 2H), 3.50 (brs, 2H), 2.50-2.42 (m, 1H), 2.00-1.96 (m, 2H), 1.73-1.50 (m, 2H), 0.57 (dt, J=6.9, 3.3 Hz, 2H), 0.48-0.28 (m, 2H) ppm. MS: 446 m/z (M+H$^+$).

Example 659. Methyl 5-[3-(tert-butoxycarbonylamino)pyrrolidin-1-yl]-7-(trifluoromethyl)thieno[3,2-b]pyridine-3-carboxylate

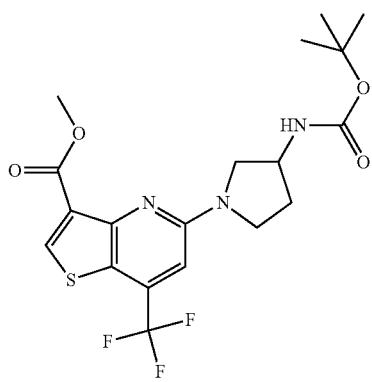 [SMILES: COC(=O)c1csc2c(C(F)(F)F)cc(N3CCC(NC(=O)OC(C)(C)C)C3)nc12]

In a 10 mL microwave vial were placed N,N-diisopropylethylamine (472 µL, 2.71 mmol), Intermediate 3 (400 mg, 1.35 mmol), and tert-butyl pyrrolidin-3-ylcarbamate (377 mg, 2.03 mmol) and N-methyl-2-pyrrolidinone (4 mL). After 30 minutes at 130° C. for in a microwave reactor, the mixture was diluted with ethyl acetate (50 mL) and water (50 mL). The organic layer was separated, washed with water (3×20 mL) and saturated ammonium chloride (20 mL), dried (MgSO$_4$), filtered, and concentrated to give a solid, which was purified by automated flash chromatography (5:1 heptane/ethyl acetate to 1:5 heptane/ethyl acetate; 12S column, solid loading) to afford the title compound (480 mg, 1.08 mmol, 79% yield). $^1$H NMR (400 MHz, CDCl$_3$) δ 8.54 (s, 1H), 6.72 (s, 1H), 4.70 (brs, 1H), 4.41 (brs, 1H), 3.96 (s, 3H), 3.89 (dd, J=10.9, 6.1 Hz, 1H), 3.74-3.70 (m, 2H), 3.51 (dd, J=11.0, 4.2 Hz, 1H), 2.44-2.25 (m, 1H), 2.06-2.01 (m, 1H), 1.46 (s, 9H) ppm. MS: 446 m/z (M+H$^+$).

Example 669. [1-[3-(Methylcarbamoyl)-7-(trifluoromethyl)thieno[3,2-b]pyridin-5-yl]-4-piperidyl] N-(cyclopropylmethyl)carbamate hydrochloride

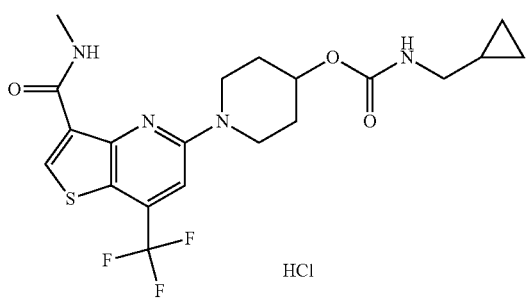 [SMILES: CNC(=O)c1csc2c(C(F)(F)F)cc(N3CCC(OC(=O)NCC4CC4)CC3)nc12 ; Cl]

In a 50 mL round-bottomed flask were placed Example 474 (35 mg, 76 µmol) and acetonitrile (5 mL). The mixture was treated with hydrochloric acid (958 µL, 3.83 mmol) in 4 M dioxane and concentrated to give a residue, which was diluted with acetonitrile and water, and lyophilized to afford the title compound (32 mg, 65 µmol, 85% yield) as a solid. 1H NMR (400 MHz, DMSO-d$_6$) δ 9.26 (q, J=4.8 Hz, 1H), 8.75 (s, 1H), 7.50 (s, 1H), 7.21 (t, J=5.8 Hz, 1H), 4.88-4.77 (m, 1H), 4.12-3.97 (m, 2H), 3.70-3.63 (m, 1H), 3.56-3.45 (m, 1H), 2.95 (d, J=4.7 Hz, 3H), 2.88 (t, J=6.3 Hz, 2H), 2.1-1.94 (m, 2H), 1.73-1.6 (m, 2H), 0.94-0.8 (m, 1H), 0.45-0.32 (m, 2H), 0.15 (d, J=4.9 Hz, 2H) ppm. MS: 493 m/z (M+H$^+$).

Example 670. [1-[3-(Methylcarbamoyl)-7-(trifluoromethyl)thieno[3,2-b]pyridin-5-yl]-4-piperidyl] N-(2,2-difluoro-1-methyl-ethyl)carbamate

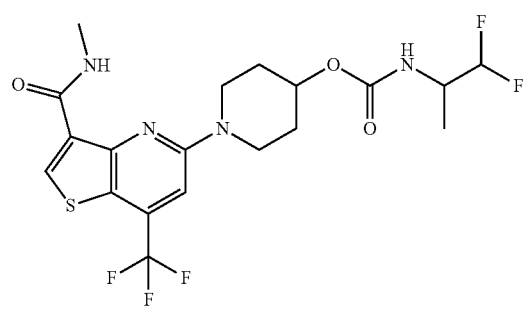 [SMILES: CNC(=O)c1csc2c(C(F)(F)F)cc(N3CCC(OC(=O)NC(C)C(F)F)CC3)nc12]

In a 5 mL vial were placed methyl 5-(4-hydroxypiperidin-1-yl)-7-(trifluoromethyl)thieno[3,2-b]pyridine-3-carboxylate (50 mg, 138 µmol), which was prepared in step 1 of Example 422, N,N-diisopropylethylamine (121 µL, 693 µmol), 4-nitrophenyl chloroformate (55 mg, 277 µmol) and N-methyl-2-pyrrolidinone (3 mL). After 15 hours at 20° C., 1,1-difluoropropan-2-amine hydrochloride (54 mg, 416 µmol) was added at room temperature. After 2 hours at room temperature, the mixture was diluted with ethyl acetate (20 mL) and saturated sodium bicarbonate (20 mL). The organic layer was separated, washed with water (3×15 mL), ammonium chloride (15 mL), and brine (20 mL), dried (Na$_2$SO$_4$), filtered, and concentrated to give a residue, which was purified by automated flash chromatography (5:1 heptane/ethyl acetate to 1:1 heptane/ethyl acetate; 4 g column) to afford methyl 5-(4-(((1,1-difluoropropan-2-yl)carbamoyl)oxy)piperidin-1-yl)-7-(trifluoromethyl)thieno[3,2-b]pyridine-3-carboxylate (60 mg, 124 µmol, 89% yield). MS: 482 m/z (M+H$^+$).

In a 25 mL round-bottomed flask were placed above methyl ester (60 mg, 124 µmol) and methanamine (6.23 mL, 12.46 mmol) in methanol (2M). After 5 hours at 50° C., the mixture was concentrated to give the residue, which was purified by reversed phase HPLC to give the title compound (27 mg, 57 µmol, 45% yield) as a solid. 1H NMR (400 MHz, DMSO-d$_6$) δ 9.26 (q, J=4.8 Hz, 1H), 8.75 (s, 1H), 7.52-7.51 (m, 2H), 5.91 (td, J=56.1, 3.2 Hz, 1H), 4.94-4.81 (m, 1H), 4.09-4.0 (m, 2H), 3.89 (brs, 1H), 3.59-3.48 (m, 2H), 2.95 (d, J=4.7 Hz, 3H), 2.00 (brs, 2H), 1.75-1.63 (m, 2H), 1.11 (d, J=7.0 Hz, 3H) ppm. MS: 481 m/z (M+H$^+$).

Example 671. [1-[3-(Methylcarbamoyl)-7-(trifluoromethyl)thieno[3,2-b]pyridin-5-yl]-4-piperidyl] N-(2-fluoro-1-methyl-ethyl)carbamate

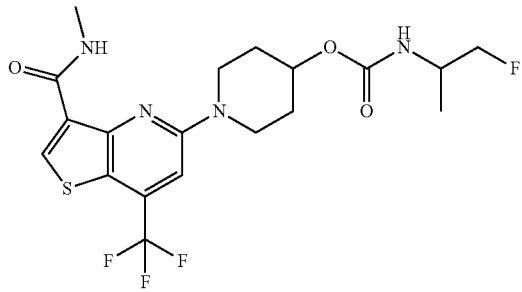 [SMILES: CNC(=O)c1csc2c(C(F)(F)F)cc(N3CCC(OC(=O)NC(C)CF)CC3)nc12]

Using 1-fluoropropan-2-amine hydrochloride, the procedure described in Example 670 was used to prepare the title compound as a solid. 1H NMR (400 MHz, DMSO-d$_6$) δ 9.30-9.22 (m, 1H), 8.75 (s, 1H), 7.51 (s, 1H), 7.26 (d, J=8.1 Hz, 1H), 4.84 (brs, 1H), 4.28 (dd, J=46.7, 5.1 Hz, 2H), 4.07-4.02 (m, 2H), 3.84-3.78 (m, 1H), 3.56-3.46 (m, 2H), 2.95 (d, J=4.7 Hz, 3H), 1.99 (brs, 2H), 1.68-1.62 (m, 2H), 1.07 (d, J=6.9 Hz, 3H) ppm. MS: 463 m/z (M+H$^+$).

Example 692 and Example 693. [1-[3-(Methylcarbamoyl)-7-(trifluoromethyl)thieno[3,2-b]pyridin-5-yl]-4-piperidyl] N-[(1R)-2-fluoro-1-methyl-ethyl] carbamate and [1-[3-(Methylcarbamoyl)-7-(trifluoromethyl)thieno[3,2-b]pyridin-5-yl]-4-piperidyl] N-[(1S)-2-fluoro-1-methyl-ethyl] carbamate (Separate Enantiomers of Known Absolute Configurations)

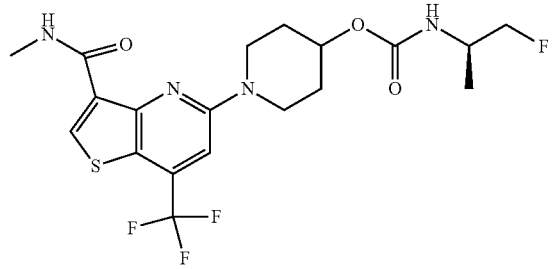

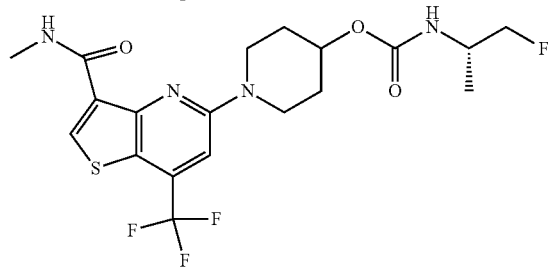

The title compounds were obtained by subjecting racemic Example 671 to chiral SFC (4.6×250 mm CHIRALPAK IC column; 15:85 ethanol/heptane modifier with 0.1% diethylamine additive). The absolute configurations of the individual enantiomers were determined by comparison of chiral SFC retention times to that of the authentic enantiomers prepared from optically active (S)-1-fluoropropan-2-amine hydrochloride starting materials of known stereochemistry (commercially available).

1st elution fraction Example 692, 1H NMR (400 MHz, DMSO-d$_6$) δ 9.26 (d, J=4.9 Hz, 1H), 8.75 (s, 1H), 7.51 (s, 1H), 7.25 (d, J=8.0 Hz, 1H), 4.83 (brs, 1H), 4.28 (dd, J=48, 4 Hz, 2H), 4.13-4.01 (m, 2H), 3.88-3.72 (m, 1H), 3.56-3.31 (m, 2H), 2.95 (d, J=4.8 Hz, 3H), 2.12-1.94 (m, 2H), 1.68-1.56 (m, 2H), 1.07 (dd, J=6.9, 1.4 Hz, 3H) ppm. MS: 463 m/z (M+H$^+$)

2nd elution fraction, Example 693, 1H NMR (400 MHz, DMSO-d$_6$) δ 9.27 (q, J=4 Hz, 1H), 8.76 (s, 1H), 7.51 (s, 1H), 7.26 (d, J=8.0 Hz, 1H), 4.84 (brs, 1H), 4.28 (dd, J=48, 4 Hz, 2H), 4.13-4.01 (m, 2H), 3.89-3.71 (m, 1H), 3.56-3.31 (m, 2H), 2.95 (d, J=4.8 Hz, 3H), 2.13-1.93 (m, 2H), 1.69-1.55 (m, 2H), 1.07 (dd, J=6.9, 1.4 Hz, 3H) ppm. MS: 463 m/z (M+H$^+$).

Example 780. Cyclopropylmethyl 4-(3-(methylcarbamoyl)-7-(trifluoromethyl)thieno[3,2-b]pyridin-5-yl)piperazine-1-carboxylate

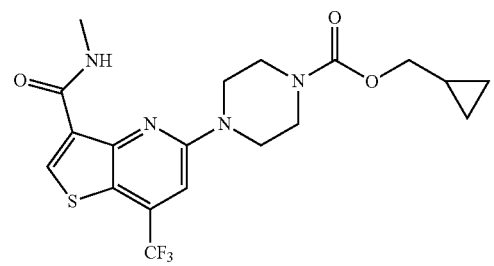 [SMILES: CNC(=O)c1csc2c(C(F)(F)F)cc(N3CCN(C(=O)OCC4CC4)CC3)nc12]

Using Intermediate 6 and cyclopropylmethanol, the procedure described in step 3 of Example 793 was used to prepare the title compound (160 mg, 43%) as white solid. $^1$H NMR (400 MHz, CDCl$_3$) δ 9.34 (br, 1H), 8.70 (s, 1H), 7.05 (s, 1H), 3.99 (d, J=7.2 Hz, 2H), 3.68-3.75 (m, 8H), 3.10 (d J=4.4 Hz, 3H), 1.15-1.19 (m, 1H), 0.61 (q, J=5.6 Hz, 2H), 0.34 (q, J=5.2 Hz, 2H) ppm. MS: 443 m/z (M+H$^+$)

Example 793 and Example 794. 1-(3-(Methylcarbamoyl)-7-(trifluoromethyl)thieno[3,2-b]pyridin-5-yl)piperidin-4-yl (2S,3S)-3-(dimethylamino)-2-methylazetidine-1-carboxylate and 1-(3-(Methylcarbamoyl)-7-(trifluoromethyl)thieno[3,2-b] pyridin-5-yl)piperidin-4-yl (2S,3R)-3-(dimethylamino)-2-methylazetidine-1-carboxylate (Separate Enantiomers of Known Absolute Configurations)

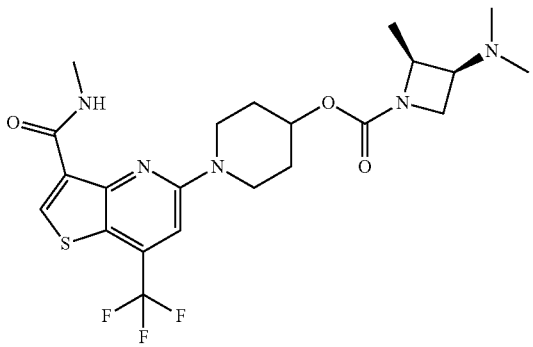

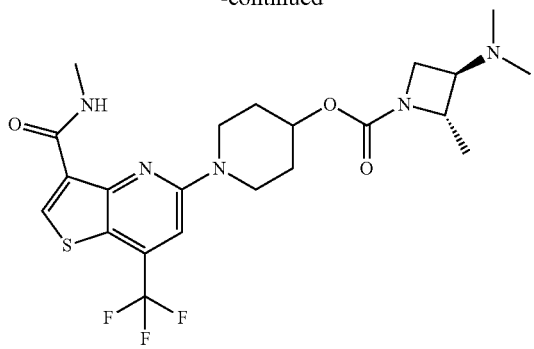

Step 1: Benzyl (2S)-3-(dimethylamino)-2-methylazetidine-1-carboxylate

Benzyl (S)-2-methyl-3-oxoazetidine-1-carboxylate (205 mg, 1.0 mmol) and dimethylamine (150 mg, 3.0 mmol) were dissolved in dichloromethane (10 mL). Acetic acid (2 drops) and sodium triacetoxyborohydride (736 mg, 3.0 mmol) were added and the reaction mixture was stirred at room temperature for 15 hours. The reaction mixture was diluted with ethyl acetate (100 mL) and saturated sodium bicarbonate solution (100 mL). The organic layer was separated and washed with saturated ammonium chloride solution (100 mL) and brine (100 mL), dried over $Na_2SO_4$, filtered and concentrated. The crude material was purified by silica gel column chromatography (pentane/ethyl acetate v/v=3:1) to give the title compound (150 mg, 60%) as colorless oil. MS; $(M^+1)$ 249.1

Step 2: (2S)—N,N,2-Trimethylazetidin-3-amine

To a solution of step 1 product (150 mg, 0.6 mmol) in methanol (15 mL) was added palladium on carbon (50 mg, 10%). The reaction mixture was stirred at room temperature under H2 overnight. After completion of the reaction, palladium on carbon was filtrated and the filtrate was concentrated to give crude the title compound (100 mg, crude) as a white solid.

Step 3: 1-(3-(Methylcarbamoyl)-7-(trifluoromethyl)thieno[3,2-b]pyridin-5-yl)piperidin-4-yl (2S,3S)-3-(dimethylamino)-2-methylazetidine-1-carboxylate and 1-(3-(methylcarbamoyl)-7-(trifluoromethyl)thieno[3,2-b]pyridin-5-yl)piperidin-4-yl (2S,3R)-3-(dimethylamino)-2-methylazetidine-1-carboxylate To a solution of Intermediate 7 (300 mg, 0.84 mmol) in dichloromethane (5 mL) were added N,N-diisopropylethylamine (215 mg, 1.67 mmol), 4-dimethylaminopyridine (105 mg, 0.84 mmol) and 4-nitrophenyl chloroformate (217 mg, 1.08 mmol). Then the mixture was stirred at room temperature for 4 hours. After completion of the reaction, the solvent was removed to give a crude intermediate. The intermediate was dissolved in dry N,N-dimethylformamide (3 mL) and then added N,N-diisopropylethylamine (325 mg, 2.46 mmol) and (2S)—N,N,2-trimethylazetidin-3-amine (430 mg, crude). The reaction mixture was stirred at 50° C. overnight. The resulting mixture was poured into water and extracted with dichloromethane (3×10 mL). The combined extracts were concentrated in vacuo. The residue was purified by reversed phase HPLC to afford the cis title compounds (19 mg, 4%)$^1$H NMR (400 MHz, $CDCl_3$) δ 9.45 (br, 1H), 8.66 (s, 1H), 7.06 (s, 1H), 4.99 (s, 1H), 4.30 (s, 1H), 3.90-3.59 (m, 4H), 3.60 (s, 2H), 3.07-3.01 (m, 4H), 2.10-2.02 (m, 8H), 1.83 (s, 2H), 1.43 (s, 3H) ppm. MS: 500 m/z $(M+H^+)$.

and the trans title compound (46 mg, 11%)$^1$H NMR (400 MHz, $CDCl_3$) δ 9.44 (br, 1H), 8.66 (s, 1H), 7.06 (s, 1H), 4.99 (s, 1H), 4.12 (s, 1H), 3.94-3.85 (m, 3H), 3.73-3.70 (m, 1H), 3.60 (s, 2H), 3.07 (d, J=4.8 Hz, 3H), 2.54 (s, 1H), 2.16 (s, 6H), 2.06-2.01 (m, 2H), 1.89-1.80 (m, 4H), 1.42 (s, 3H) ppm. MS: 500 m/z $(M+H^+)$.

Example 806. 1-(3-(Methylcarbamoyl)-7-(trifluoromethyl)thieno[3,2-b]pyridin-5-yl)piperidin-4-yl 1-methyl-1,6-diazaspiro[3.3]heptane-6-carboxylate

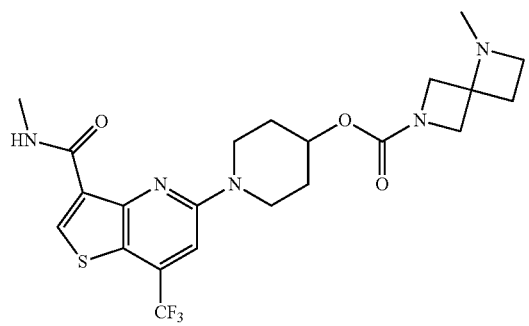 [SMILES: CNC(=O)c1csc2c(C(F)(F)F)cc(N3CCC(OC(=O)N4CC5(CCN5C)C4)CC3)nc12]

Using Intermediate 7 and 1-methyl-1,6-diazaspiro[3.3]heptane, the procedure described in step 3 of Example 793 was used to prepare the title compound (203 mg, crude) as brown oil. $^1$H NMR (400 MHz, $CDCl_3$) δ 9.46 (s, 1H), 8.67 (s, 1H), 7.07 (s, 1H), 4.96 (s, 1H), 4.26 (d, J=9.3 Hz, 2H), 3.95 (d, J=9.9 Hz, 2H), 3.90 (d, J=7.7 Hz, 1H), 3.61-3.51 (m, 2H), 3.18 (s, 2H), 3.08 (d, J=4.9 Hz, 2H), 2.38 (s, 2H), 2.35 (d, J=7.1 Hz, 2H), 2.04 (s, 3H) ppm. 0.0%; MS: 498 m/z $(M+H^+)$.

Example 809. (2S,3S)-1,2-Dimethylpyrrolidin-3-yl (1-(3-(methylcarbamoyl)-7-(trifluoromethyl)thieno[3,2-b]pyridin-5-yl)piperidin-4-yl)carbamate

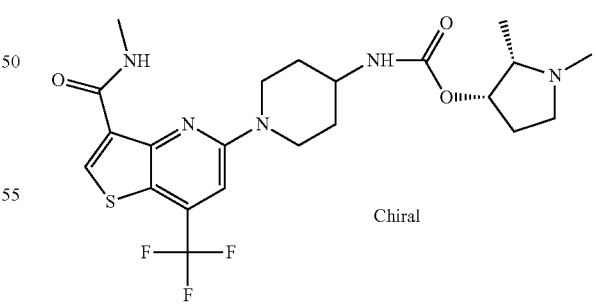

Chiral

Step 1: (2S,3S)-2-Methylpyrrolidin-3-ol

A mixture of benzyl (2S,3S)-3-hydroxy-2-methylpyrrolidine-1-carboxylate (300 mg, 1.28 mmol) and 10% palladium on carbon (100 mg) in methanol (20 mL) was flushed with hydrogen atmosphere and stirred at room temperature overnight. The resulting mixture was filtered through celite. The filtrate was concentrated in vacuo to afford the title compound (130 mg, >100%) as a yellow oil. LCMS UV absorption is weak; MS: 102 m/z (M+H$^+$).

Step 2: tert-Butyl (2S,3S)-3-hydroxy-2-methylpyrrolidine-1-carboxylate

To a solution of step 1 product (110 mg, 1.09 mmol), triethylamine (221 mg, 2.18 mmol) in dichloromethane (10 mL) was added di-tert-butyl pyrocarbonate (262 mg, 1.20 mmol) dropwise at 0-10° C. After stirring overnight at room temperature, the mixture was concentrated to afford the title compound (320 mg, >100%) as a yellow oil. MS: m/z 146 (M+H$^+$).

Step 3: tert-Butyl (2S,3S)-2-methyl-3-(((4-nitrophenoxy)carbonyl)oxy)pyrrolidine-1-carboxylate A mixture of step 2 product (320 mg, 1.09 mmol), 4-nitrophenyl chloroformate (285 mg, 1.42 mmol), N,N-diisopropylethylamine (281 mg, 2.18 mmol) and 4-dimethylaminopyridine (133 mg, 1.09 mmol) in dimethylformamide (5 mL) was stirred at 25° C. for 4 hours. The resulting mixture was concentrated and purified by silica gel chromatography (eluting with ethyl acetate) to afford the title compound (194 mg, 42%) as a yellow oil. MS: 311 m/z (M−55).

Step 4: tert-Butyl (2S,3S)-2-methyl-3-(((1-(3-(methylcarbamoyl)-7-(trifluoromethyl)thieno[3,2-b]pyridin-5-yl)piperidin-4-yl)carbamoyl)oxy)pyrrolidine-1-carboxylate A mixture of step 3 product of Example 297 (750 mg, 0.80 mmol), step 3 product (194 mg, 0.53 mmol), N,N-diisopropylethylamine (340 mg, 1.60 mmol), and 4-dimethylaminopyridine (105 mg, 0.53 mmol) in dimethylformamide (5 mL) was stirred at 50° C. overnight. The resulting mixture was poured into water and extracted with ethyl acetate (3×20 mL). The combined extracts were washed with brine (2×50 mL), dried over anhydrous sodium sulfate, concentrated and purified by reversed phase HPLC to afford the title compound (35 mg, 6%) as a white solid. MS: 586 m/z (M+H$^+$).

Step 5: (2S,3S)-2-Methylpyrrolidin-3-yl (1-(3-(methylcarbamoyl)-7-(trifluoromethyl)thieno[3,2-b]pyridin-5-yl)piperidin-4-yl)carbamate To a solution of step 4 product (35 mg, 0.06 mmol) in dichloromethane (5 mL) was added trifluoroacetic acid (1 mL). After stirring overnight at room temperature, the resulting mixture was concentrated in vacuo and was adjusted to pH=9-10 with ammonia-methanol solution. The solution was concentrated and purified by silica gel chromatography (eluting with dichloromethane/methanol, v/v, 1/2) to afford the title compound (136 mg, >100%) as a yellow oil. MS: 486 m/z (M+H$^+$).

Step 6: (2S,3S)-1,2-Dimethylpyrrolidin-3-yl (1-(3-(methylcarbamoyl)-7-(trifluoromethyl)thieno[3,2-b]pyridin-5-yl)piperidin-4-yl)carbamate A mixture of step 5 product (136 mg, 0.28 mmol), 37% formaldehyde aqueous solution (68 mg, 0.84 mmol) and sodium cyanoborohydride (53 mg, 0.84 mmol) in methanol (5 mL) was stirred overnight at room temperature. The mixture was concentrated and purified by reversed phase HPLC to afford the title compound (10 mg, 9%) as a brown solid. 1H NMR (400 MHz, MeOD) δ 8.69 (s, 1H), 7.36 (s, 1H), 5.14 (s, 1H), 4.33 (d, J=13.4 Hz, 2H), 3.74 (d, J=10.5 Hz, 1H), 3.26 (d, J=13.7 Hz, 2H), 3.15 (t, J=8.4 Hz, 1H), 3.07 (s, 3H), 2.40-2.22 (m, 5H), 2.23-2.13 (m, 1H), 2.07 (d, J=9.8 Hz, 2H), 1.76 (dd, J=20.2, 9.2 Hz, 1H), 1.59 (dd, J=20.3, 10.7 Hz, 2H), 1.14 (t, J=14.1 Hz, 3H) ppm. MS: 500 m/z (M+H$^+$).

Example 816. Isopropyl (1-(3-(methylcarbamoyl)-7-(trifluoromethyl)thieno[3,2-b]pyridin-5-yl)piperidin-4-yl)carbamate

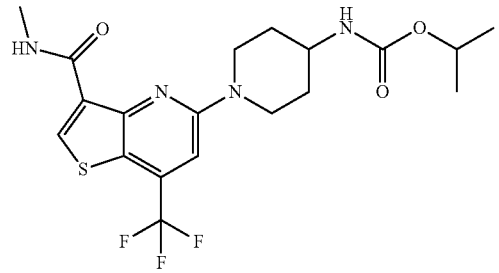 [SMILES: CNC(=O)c1csc2c(C(F)(F)F)cc(N3CCC(NC(=O)OC(C)C)CC3)nc12]

Using step 3 product of Example 297 and propan-2-ol, the procedure described in Example 809 was used to prepare the title compound (82 mg, 25%)) as a white solid. 1H NMR (400 MHz, CDCl3): δ 9.41 (br, 1H), 8.66 (s, 1H), 7.05 (s, 1H), 4.92 (s, 1H), 4.60 (s, 1H), 4.21 (d, J=13.2 Hz, 2H), 3.80 (s, 1H), 3.21 (m, 2H), 3.06 (d, J=4.8 Hz, 3H), 2.15 (d, J=18 Hz, 2H), 1.54 (m, 2H), 1.24 (d, J=6 Hz, 6H) ppm. MS: 445 m/z (M+H$^+$).

Example 822. (+/−)-cis-(1S,3S)-3-((3-(Methylcarbamoyl)-7-(trifluoromethyl)thieno[3,2-b]pyridin-5-yl)oxy)cyclobutyl oxetan-3-ylcarbamate

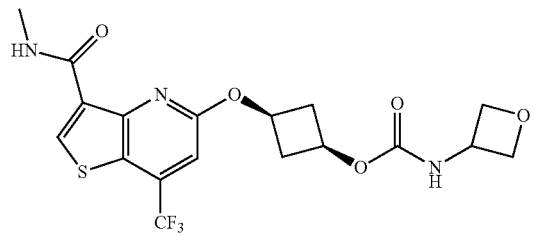 [SMILES: CNC(=O)c1csc2c(C(F)(F)F)cc(O[C@H]3C[C@@H](OC(=O)NC4COC4)C3)nc12]

Step 1: (+/−)-cis-(1s,3s)-3-(Benzyloxy)cyclobutan-1-ol

To a solution of 3-(benzyloxy)cyclobutan-1-one (10 g, 57.0 mmol) in tetrahydrofuran (75 mL) was added L-selectride (62.5 mL, 62.5 mmol) drop-wise at −78° C. and stirred at −78° C. for 1 hour. Then the mixture was warmed to room temperature for 1 hour. A saturated solution of sodium bicarbonate (30 mL) was added and then cooled to 0° C. and 30% hydrogen peroxide (10 mL) was added. The reaction mixture was diluted with water and extracted with ethyl acetate (100 mL×3). The combined extracts were dried over anhydrous Na₂SO₄ and concentrated to give the crude title compound (11.2 g, 100%) as a white solid. MS: 179 m/z (M+H⁺).

Step 2: (+/−)-cis-5-((1s,3s)-3-(Benzyloxy)cyclobu-toxy)-N-methyl-7-(trifluoromethyl)thieno[3,2-b]pyridine-3-carboxamide To a solution of Intermediate 5 (12 g, 40.8 mmol) in tetrahydrofuran (150 mL) was added step 1 product (11.2 g, crude) and potassium tert-butoxide (12 g, 107 mmol). The mixture was stirred at 90° C. for 2 hours. Then the reaction mixture was washed with water (100 mL) and extracted with dichloromethane (100 mL×3). The combined extracts were dried over anhydrous Na₂SO₄, concentrated and purified by chromatography to give the title compound (5.3 g, 30%) as white solid. MS: 347 m/z (M+H⁺).

Step 3: (+/−)-cis-5-((1s,3s)-3-Hydroxycyclobutoxy)-N-methyl-7-(trifluoromethyl)thieno[3,2-b]pyridine-3-carboxamide To a solution of step 2 product (5.3 g, 12.2 mmol) in methanol (100 mL) was added palladium on carbon (500 mg, 10%) and acetic acid (1 mL). The reaction mixture was stirred at room temperature under H2 overnight. After completion of the reaction, palladium on carbon was filtrated and the filtrate was concentrated to give the crude title compound (4.6 g) as a white solid.

Step 4: (+/−)-cis-(1s,3s)-3-((3-(Methylcarbamoyl)-7-(trifluoromethyl)thieno[3,2-b]pyridin-5-yl)oxy)cyclobutyl oxetan-3-ylcarbamate Using step 3 product and oxetan-3-amine, the procedure described in step 3 product of Example 793 was used to prepare the title compound (59 mg, 36%) as white solid. ¹H NMR (400 MHz, CDCl₃) δ 9.05 (br, 1H), 8.75 (s, 1H), 7.10 (s, 1H), 5.38 (s, 1H), 4.94-4.85 (m, 5H), 4.53 (s, 2H), 3.10-3.08 (m, 6H), 2.40-2.34 (m, 2H) ppm. MS: 445 m/z (M+H⁺).

Example 833. (+/−)-cis-(1S,3R)-3-((3-(Methylcarbamoyl)-7-(trifluoromethyl)thieno[3,2-b]pyridin-5-yl)oxy)cyclobutyl ((S)-1-(trifluoromethoxy)propan-2-yl)carbamate

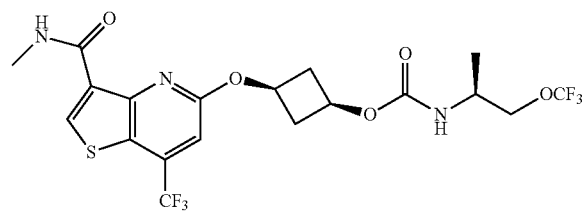 [SMILES: CNC(=O)c1csc2c(C(F)(F)F)cc(O[C@H]3C[C@@H](OC(=O)N[C@@H](C)COC(F)(F)F)C3)nc12]

Using Intermediate 28, the procedure described in Example 822 was used to prepare the title compound (60 mg, 24%) as a white solid. 1H NMR (400 MHz, CDCl3): δ 9.08 (br, 1H), 8.76 (s, 1H), 7.11 (s, 1H), 4.95-4.87 (m, 3H), 4.02-3.92 (m, 3H), 3.11 (d, J=4.8 Hz, 3H), 3.09-3.05 (m, 1H), 2.42-2.35 (m, 2H), 1.28 (d, J=6.8 Hz, 3H) ppm. MS: 516 m/z (M+H⁺).

Example 835. 4-Fluoro-1-methylpyrrolidin-3-yl 4-((3-(methylcarbamoyl)-7-(trifluoromethyl)thieno[3,2-b]pyridin-5-yl)oxy)piperidine-1-carboxylate

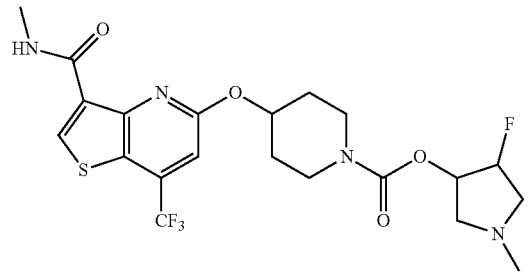 [SMILES: CNC(=O)c1csc2c(C(F)(F)F)cc(OC3CCN(C(=O)OC4CN(C)CC4F)CC3)nc12]

Step 1: 1-(tert-Butoxycarbonyl)-4-fluoropyrrolidin-3-yl 4-((3-(methylcarbamoyl)-7-(trifluoromethyl)thieno[3,2-b]pyridin-5-yl)oxy)piperidine-1-carboxylate To a solution of Intermediate 17 (205 mg, 1.00 mmol) in dichloromethane (5 mL) were added N,N-diisopropylethylamine (387 mg, 3.00 mmol), 4-dimethylaminopyridine (122 mg, 1.00 mmol) and 4-nitrophenyl chloroformate (200 mg, 1.00 mmol). After 4 hours at room temperature, the mixture was concentrated, dissolved in N,N-dimethylformamide (3 mL) and treated with N,N-diisopropylethylamine (387 mg, 3.00 mmol) and tert-butyl 3-fluoro-4-hydroxypyrrolidine-1-carboxylate (433 mg, 0.95 mmol). After stirring at 90° C. overnight, the resulting mixture was poured into water and extracted with dichloromethane (3×10 mL). The combined extracts were concentrated in vacuo to give a residue which was purified by silica gel column chromatography (pentane/ethyl acetate v/v=1:1) to afford the title compound (267 mg, 47%) as a yellow solid. Purity: >92% MS; 591 m/z (M+H⁺).

Step 2: 4-Fluoropyrrolidin-3-yl 4-((3-(methylcarbamoyl)-7-(trifluoromethyl)thieno[3,2-b]pyridin-5-yl)oxy)piperidine-1-carboxylate To a solution of step 1 product (267 mg, 0.46 mmol) in dichloromethane (5 mL) was added trifluoroacetic acid (2 mL). After stirring overnight at room temperature, the resulting mixture was concentrated in vacuo and the methanol solution was adjusted to pH=9-10 with ammonia-methanol solution. The solution was concentrated, triturated with dichloromethane, and filtered. The filtrate was concentrated to afford the title compound (205 mg, 92%) as a light-yellow solid. MS: 491 m/z (M+H⁺), Purity: 92%.)

Step 3: 4-Fluoro-1-methylpyrrolidin-3-yl 4-((3-(methylcarbamoyl)-7-(trifluoromethyl)thieno[3,2-b]pyridin-5-yl)oxy)piperidine-1-carboxylate A mixture of step 2 product (205 mg, 0.42 mmol), 37% formaldehyde aqueous solution (102 mg, 1.26 mmol), sodium cyanoborohydride (80 mg, 1.26 mmol), and methanol (5 mL) was stirred at room temperature overnight. The resulting mixture was concentrated and purified by reversed phase HPLC to afford the title compound (86 mg, 42%) as a white solid. 1H NMR (400 MHz, CDCl3): δ 9.05 (s, 1H), 8.78 (s, 1H), 7.15 (s, 1H), 5.22 (m, 3H), 3.83 (m, 2H), 3.56

(m, 2H), 3.18 (m, 5H), 2.83 (m, 1H), 2.77 (m, 1H), 2.45 (s, 3H), 2.11 (m, 4H) ppm. MS: 505 m/z (M+H⁺).

Example 853. (S)-1-(Trifluoromethoxy)propan-2-yl 6-((3-(methylcarbamoyl)-7-(trifluoromethyl)thieno[3,2-b]pyridin-5-yl)oxy)-2-azaspiro[3.3]heptane-2-carboxylate

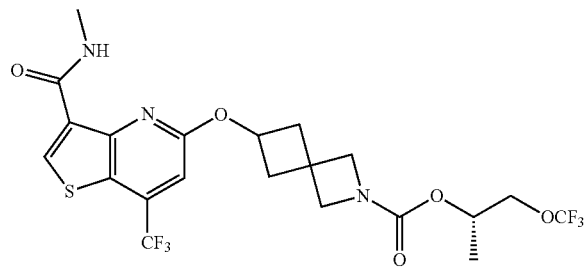 [SMILES: CNC(=O)c1csc2c(C(F)(F)F)cc(OC3CC4(C3)CN(C(=O)O[C@@H](C)COC(F)(F)F)C4)nc12]

Using Intermediate 25 and (S)-1-(trifluoromethoxy)propan-2-ol, the procedure described in step 1 of Example 835 was used to prepare the title compound (36 mg, 12%) as a white solid. 1H NMR (400 MHz, CDCl3): δ 9.13 (s, 1H), 8.76 (s, 1H), 7.10 (s, 1H), 5.19 (m, 1H), 5.04 (m, 1H), 4.03 (m, 6H), 3.13 (d, J=5.2 Hz, 3H), 2.38 (m, 2H), 1.35 (m, 3H) ppm. MS: 542 m/z (M+H⁺).

Example 858. (R)-2-(Trifluoromethoxy)propyl (S)-3-((3-(methylcarbamoyl)-7-(trifluoromethyl)thieno[3,2-b]pyridin-5-yl)oxy)pyrrolidine-1-carboxylate

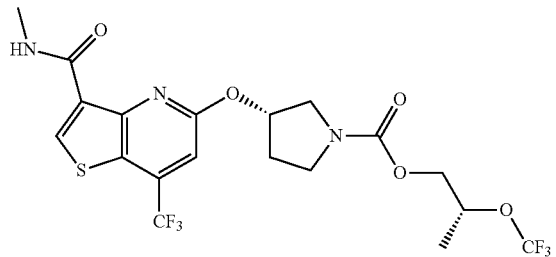 [SMILES: CNC(=O)c1csc2c(C(F)(F)F)cc(O[C@H]3CCN(C(=O)OC[C@@H](C)OC(F)(F)F)C3)nc12]

Step 1: (R)-2-(Trifluoromethoxy)propyl 1H-imidazole-1-carboxylate

A mixture of (R)-2-(trifluoromethoxy)propan-1-ol (260 mg, 1.81 mmol) and 1,1'-carbonyldiimidazole (440 mg, 2.72 mmol) was dissolved in dichloromethane (5 mL) After 16 hours at 25° C., the reaction mixture was quenched with saturated ammonium chloride (30 mL) and extracted with dichloromethane (30 mL). The organic layer was dried over Na2SO4, filtered, and concentrated and to give the title compound (300 mg, crude), which was used next step without further purification. MS: 239 m/z (M+H⁺).

Step 2: tert-Butyl (S)-3-((3-(methylcarbamoyl)-7-(trifluoromethyl)thieno[3,2-b]pyridin-5-yl)oxy)pyrrolidine-1-carboxylate To a solution of tert-butyl (S)-3-hydroxypyrrolidine-1-carboxylate (477 mg, 2.6 mmol) in tetrahydrofuran (10 mL) was added potassium tert-butoxide (286 mg, 2.6 mmol) in one portion. After 10 minutes, Intermediate 5 (500 mg, 1.7 mmol) was added and the reaction mixture was stirred at reflux for 1 hour. The reaction was quenched by addition of water (10 mL) and the mixture was diluted with saturated aqueous sodium bicarbonate (10 mL) and ethyl acetate (10 mL) and extracted with ethyl acetate (3×20 mL). The extracts were washed with brine (50 mL), dried (Na2SO4), filtered and concentrated in vacuo to give a yellow oil, which was purified by column chromatography on silica gel (pentane/ethyl acetate: 1/1) to give the title compound (655 mg, 87%) as a yellow oil. MS: 346 m/z (M+H⁺).

Step 3: (S)—N-Methyl-5-(pyrrolidin-3-yloxy)-7-(trifluoromethyl)thieno[3,2-b]pyridine-3-carboxamide A mixture of step 2 product (655 mg, 1.47 mmol) and hydrochloric acid dioxane solution (10 mL, 40 mmol, 4M) was stirred at room temperature for 2 hours. After concentration in vacuo the residue was stirred in ether (20 mL) at room temperature for 1 hour to give a solid which was filtered. The solid was dissolved in dichloromethane (20 mL) and its pH was adjusted to 8 with aqueous sodium bicarbonate solution. The organic layer was separated, dried over Na2SO4, and concentrated in vacuo to give the title compound (195 mg, yield: 64%) as a brown solid. MS: 346 m/z (M+H⁺).

Step 4: (R)-2-(Trifluoromethoxy)propyl (S)-3-((3-(methylcarbamoyl)-7-(trifluoromethyl)thieno[3,2-b]pyridin-5-yl)oxy)pyrrolidine-1-carboxylate A mixture of step 3 product (195 mg, 0.565 mmol), step 1 product (135 mg, 0.565 mmol), and N-hydroxysuccinimide (97 mg, 0.85 mmol) in acetonitrile (10 mL) was stirred at 60° C. under nitrogen atmosphere for 6 hours. After cooling down to room temperature, the solvent was removed in vacuo and the residue was purified by reversed phase HPLC to give the title compound (84 mg, yield: 24%) as light yellow solid. 1H NMR (400 MHz, CDCl3): δ 8.98 (d, J=3.4 Hz, 1H), 8.77 (s, 1H), 7.13 (d, J=4.1 Hz, 1H), 5.57 (s, 1H), 4.65-4.47 (m, 1H), 4.32-3.97 (m, 2H), 3.94-3.54 (m, 4H), 3.10 (d, J=4.8 Hz, 3H), 2.32 (m, 2H), 1.45-1.28 (m, 3H) ppm. MS: 516 m/z (M+H⁺).

Example 866. (S)-1-Cyclopropylethyl (2R,4R)-2-methyl-4-((6-methyl-3-(methylcarbamoyl)-7-(trifluoromethyl)thieno[3,2-b]pyridin-5-yl)oxy)piperidine-1-carboxylate

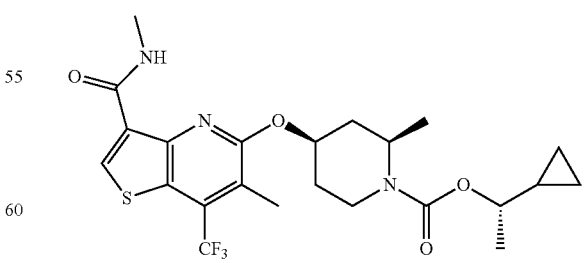

Using N,6-dimethyl-5-((((2S,4S)-2-methylpiperidin-4-yl)oxy)-7-(trifluoromethyl)thieno[3,2-b]pyridine-3-carboxamide (MS: 388 m/z (M+H⁺)), which was prepared from Intermediate 15 and tert-butyl (2R,4S)-4-hydroxy-2-methylpiperidine-1-carboxylate as in Intermediate 17, and (S)-1-cyclopropylethyl 1H-imidazole-1-carboxylate, the procedure described in Example 858 was used to prepare the title compound (43 mg, 68%) as a colorless oil. $^1$H NMR (400 MHz, CDCl$_3$) δ 9.14 (br, 1H), 8.65 (s, 1H), 5.41-5.40 (m, 1H), 4.57-4.54 (m, 1H), 4.36-4.28 (m, 1H), 4.10-4.06 (m, 1H), 3.38-3.31 (m, 1H), 3.10 (d, J=7.2 Hz, 3H), 2.51 (s, 3H), 2.21-2.06 (m, 3H), 1.99-1.90 (m, 1H), 1.39 (d, J=6.8 Hz, 3H), 1.35 (d, J=6.0 Hz, 3H), 1.04-0.98 (m, 1H), 0.55-0.40 (m, 3H), 0.23-0.26 (m, 1H) ppm. MS: No desired mass was detected.

UGT8 Activity
Assays for Detecting and measuring UGT8 Inhibition Properties of Compounds Example 871: In Vitro Assays for Sulfatide (SFT) Synthesis Inhibition For medium throughput screening, library compounds were dispensed into CellBIND 384 well plates to a final concentration of 10 μM. OE19 cells (Sigma) were grown in to 70-90% confluency in RPMI 1640+L-glutamine and XX % Hyclone; were trypsinized to achieve suspension and were aliquoted at 2,500 cells/well, total well volume 50 μl. Plates were incubated 72 hr at 37° C. in 5% CO2; supernatant was removed and plates were dried, heat-sealed and stored at −20° C. until analysis.

For IC50 determinations, the same procedure was followed except that test compounds were added to the plate as dose-downs in triplicate to yield concentration response curves.

Mass Spectrometer Analysis of Sulfatide (SFT):
Assay plates were thawed and 85 μl mobile phase B (5 mM ammonium formate$^+$0.2% formic acid in 50:50 methanol:acetonitrile). Fifteen μl 20 ng/ml C17 SFT in mobile phase B was added as an internal standard.

SFT was analyzed using an Applied Biosystems API-4000 triple quad mass spectrometer interfaced to a Thermo Scientific Multiplex system (LX-4) equipped with four pumps. Chromatography of OE19 cell samples or 2B5-mouse cells treated with compounds was performed using a Waters Acquity UPLC BEH C8 2.1×50 mm column with 1.7 um particle size. The chromatography was performed using the following mobile phases. Mobile phase A (MPA): 0.2% formic acid and 5 mM ammonium formate in deionized water; MPB: see above. The LC method was run in isocratic mode for 4 sequentially running columns using 95% MPB and 5% MPA with flow rate of 1 ml/min and a column temperature of 60° C.

The Triple quad mass spectrometer was run in Negative Ionization mode monitoring the following MRM transitions and using the following parameters:

Electrospray voltage was −4500 kV, and source temperature was 550° C.

| Sulfatide Isoforms | Q1 (m/z) | Q3 (m/z) | DP (V) | CE (eV) |
|---|---|---|---|---|
| C16 | 778.7 | 97.1 | −200 | −120 |
| C24 | 890.8 | 97.1 | −200 | −120 |
| IS | 792.8 | 97.1 | −200 | −120 |

Mass Spectrometer Analysis of Galactosylceramide (GalCer):
GalCer and glucosylceramide (GlcCer) were analyzed using Applied Biosystem API-5000 MS/MS System interfaced to a Thermo Scientific Multiplex system (LX-4) equipped with four pumps. Chromatography of cells treated with compounds was performed using Waters Cortecs HILIC 2.7 um, 2.1×100 mm column under the following conditions: Mobile phase A (MPA): 96% acetonitrile, 1% deionized water, 2% methanol, 1% acetic acid and 5 mM ammonium acetate; Mobile phase B: 80% methanol, 20% deionized water, 1% acetic acid and 5 mM ammonium acetate.

The liquid chromatography (LC) method was developed for 4 sequentially running columns. The initial gradient starts with 100% MPA going down to 75% MPA in 2 minutes, followed by a column wash step at 75% MPA for 0.08 minutes, and back to initial conditions at 2.28 minutes. Column was equilibrated for 2.54 minutes with total run time of 4.82 minutes. Flow rate was 0.5 ml/min and column was maintained at room temperature.

MS/MS Method: Positive Ionization Mode; Parameters:

| GalCer/GluCer Isoforms | Q1 (m/z) | Q3 (m/z) | DP (V) | CE (eV) |
|---|---|---|---|---|
| C16 | 700.7 | 264.3 | 120 | 50 |
| C24 | 812.8 | 264.3 | 120 | 50 |
| IS | 763.9 | 246.3 | 120 | 54 |

Electrospray voltage was 4500 kV, and source temperature was 50° C.

The IC$^{50}$ determinations for compounds disclosed herein are provided below in Table 3:

TABLE 3

| Example # | Potency range |
|---|---|
| Example 1 | B |
| Example 2 | B |
| Example 3 | B |
| Example 4 | A |
| Example 5 | B |
| Example 6 | B |
| Example 7 | C |
| Example 8 | B |
| Example 9 | A |
| Example 10 | A |
| Example 11 | A |
| Example 12 | C |
| Example 13 | B |
| Example 14 | B |
| Example 15 | B |
| Example 16 | B |
| Example 17 | B |
| Example 18 | C |
| Example 19 | B |
| Example 20 | B |
| Example 21 | B |
| Example 22 | B |
| Example 23 | C |
| Example 24 | C |
| Example 25 | B |
| Example 26 | B |
| Example 27 | A |
| Example 28 | B |
| Example 29 | B |
| Example 30 | B |
| Example 31 | B |
| Example 32 | B |
| Example 33 | A |
| Example 34 | B |
| Example 35 | A |
| Example 36 | B |
| Example 37 | A |
| Example 38 | B |

TABLE 3-continued

| Example # | Potency range |
|---|---|
| Example 39 | B |
| Example 40 | B |
| Example 41 | B |
| Example 42 | B |
| Example 43 | B |
| Example 44 | B |
| Example 45 | B |
| Example 46 | C |
| Example 47 | B |
| Example 48 | B |
| Example 49 | A |
| Example 50 | B |
| Example 51 | A |
| Example 52 | B |
| Example 53 | A |
| Example 54 | A |
| Example 55 | A |
| Example 56 | B |
| Example 57 | C |
| Example 58 | C |
| Example 59 | C |
| Example 60 | A |
| Example 61 | A |
| Example 62 | A |
| Example 63 | A |
| Example 64 | A |
| Example 65 | A |
| Example 66 | A |
| Example 67 | A |
| Example 68 | A |
| Example 69 | A |
| Example 70 | B |
| Example 71 | A |
| Example 72 | A |
| Example 73 | A |
| Example 74 | A |
| Example 75 | A |
| Example 76 | A |
| Example 77 | A |
| Example 78 | A |
| Example 79 | B |
| Example 80 | A |
| Example 81 | A |
| Example 82 | A |
| Example 83 | A |
| Example 84 | A |
| Example 85 | A |
| Example 86 | A |
| Example 87 | A |
| Example 88 | A |
| Example 89 | A |
| Example 90 | A |
| Example 91 | A |
| Example 92 | A |
| Example 93 | A |
| Example 94 | A |
| Example 95 | A |
| Example 96 | A |
| Example 97 | A |
| Example 98 | B |
| Example 99 | A |
| Example 100 | A |
| Example 101 | A |
| Example 102 | B |
| Example 103 | B |
| Example 104 | A |
| Example 105 | B |
| Example 106 | A |
| Example 107 | A |
| Example 108 | A |
| Example 109 | A |
| Example 110 | A |
| Example 111 | A |
| Example 112 | B |
| Example 113 | A |
| Example 114 | B |
| Example 115 | C |
| Example 116 | B |
| Example 117 | B |
| Example 118 | A |
| Example 119 | A |
| Example 120 | A |
| Example 121 | B |
| Example 122 | B |
| Example 123 | A |
| Example 124 | A |
| Example 125 | B |
| Example 126 | A |
| Example 127 | C |
| Example 128 | B |
| Example 129 | B |
| Example 130 | B |
| Example 131 | B |
| Example 132 | A |
| Example 133 | A |
| Example 134 | A |
| Example 135 | A |
| Example 136 | A |
| Example 137 | A |
| Example 138 | A |
| Example 139 | B |
| Example 140 | A |
| Example 141 | C |
| Example 142 | A |
| Example 143 | A |
| Example 144 | A |
| Example 145 | A |
| Example 146 | A |
| Example 147 | A |
| Example 148 | A |
| Example 149 | B |
| Example 150 | A |
| Example 151 | A |
| Example 152 | A |
| Example 153 | B |
| Example 154 | A |
| Example 155 | A |
| Example 156 | A |
| Example 157 | B |
| Example 158 | A |
| Example 159 | A |
| Example 160 | B |
| Example 161 | A |
| Example 162 | A |
| Example 163 | B |
| Example 164 | C |
| Example 165 | A |
| Example 166 | A |
| Example 167 | B |
| Example 168 | C |
| Example 169 | B |
| Example 170 | B |
| Example 171 | A |
| Example 172 | A |
| Example 173 | A |
| Example 174 | A |
| Example 175 | A |
| Example 176 | A |
| Example 177 | A |
| Example 178 | A |
| Example 179 | A |
| Example 180 | A |
| Example 181 | A |
| Example 182 | A |
| Example 183 | A |
| Example 184 | A |
| Example 185 | A |
| Example 186 | A |
| Example 187 | A |
| Example 188 | A |
| Example 189 | B |
| Example 190 | B |
| Example 191 | B |
| Example 192 | B |

TABLE 3-continued

| Example # | Potency range |
|---|---|
| Example 193 | B |
| Example 194 | B |
| Example 195 | C |
| Example 196 | A |
| Example 197 | A |
| Example 198 | A |
| Example 199 | A |
| Example 200 | B |
| Example 201 | A |
| Example 202 | B |
| Example 203 | A |
| Example 204 | A |
| Example 205 | A |
| Example 206 | A |
| Example 207 | A |
| Example 208 | B |
| Example 209 | B |
| Example 210 | B |
| Example 211 | B |
| Example 212 | B |
| Example 213 | C |
| Example 214 | B |
| Example 215 | A |
| Example 216 | A |
| Example 217 | A |
| Example 218 | A |
| Example 219 | A |
| Example 220 | A |
| Example 221 | A |
| Example 222 | C |
| Example 223 | A |
| Example 224 | A |
| Example 225 | A |
| Example 226 | A |
| Example 227 | A |
| Example 228 | A |
| Example 229 | B |
| Example 230 | B |
| Example 231 | A |
| Example 232 | A |
| Example 233 | B |
| Example 234 | A |
| Example 235 | B |
| Example 236 | A |
| Example 237 | A |
| Example 238 | B |
| Example 239 | B |
| Example 240 | A |
| Example 241 | A |
| Example 242 | C |
| Example 243 | A |
| Example 244 | B |
| Example 245 | A |
| Example 246 | C |
| Example 247 | C |
| Example 248 | B |
| Example 249 | C |
| Example 250 | B |
| Example 251 | B |
| Example 252 | A |
| Example 253 | C |
| Example 254 | A |
| Example 255 | A |
| Example 256 | A |
| Example 257 | C |
| Example 258 | A |
| Example 259 | B |
| Example 260 | B |
| Example 261 | A |
| Example 262 | B |
| Example 263 | B |
| Example 264 | A |
| Example 265 | A |
| Example 266 | A |
| Example 267 | B |
| Example 268 | A |
| Example 269 | B |
| Example 270 | A |
| Example 271 | B |
| Example 272 | A |
| Example 273 | A |
| Example 274 | B |
| Example 275 | A |
| Example 276 | B |
| Example 277 | B |
| Example 278 | C |
| Example 279 | C |
| Example 280 | A |
| Example 281 | A |
| Example 282 | B |
| Example 283 | B |
| Example 284 | A |
| Example 285 | B |
| Example 286 | A |
| Example 287 | A |
| Example 288 | A |
| Example 289 | A |
| Example 290 | B |
| Example 291 | B |
| Example 292 | B |
| Example 293 | B |
| Example 294 | C |
| Example 295 | A |
| Example 296 | A |
| Example 297 | A |
| Example 298 | A |
| Example 299 | A |
| Example 300 | A |
| Example 301 | A |
| Example 302 | A |
| Example 303 | A |
| Example 304 | B |
| Example 305 | A |
| Example 306 | B |
| Example 307 | B |
| Example 308 | B |
| Example 309 | B |
| Example 310 | A |
| Example 311 | B |
| Example 312 | A |
| Example 313 | A |
| Example 314 | A |
| Example 315 | B |
| Example 316 | B |
| Example 317 | A |
| Example 318 | A |
| Example 319 | B |
| Example 320 | A |
| Example 321 | A |
| Example 322 | A |
| Example 323 | A |
| Example 324 | A |
| Example 325 | A |
| Example 326 | A |
| Example 327 | B |
| Example 328 | B |
| Example 329 | B |
| Example 330 | B |
| Example 331 | C |
| Example 332 | B |
| Example 333 | A |
| Example 334 | A |
| Example 335 | A |
| Example 336 | B |
| Example 337 | A |
| Example 338 | A |
| Example 339 | A |
| Example 340 | C |
| Example 341 | A |
| Example 342 | A |
| Example 343 | A |
| Example 344 | B |
| Example 345 | A |
| Example 346 | A |

TABLE 3-continued

| Example # | Potency range |
|---|---|
| Example 347 | C |
| Example 348 | C |
| Example 349 | C |
| Example 350 | A |
| Example 351 | B |
| Example 352 | A |
| Example 353 | A |
| Example 354 | C |
| Example 355 | A |
| Example 356 | B |
| Example 357 | B |
| Example 358 | B |
| Example 359 | B |
| Example 360 | B |
| Example 361 | A |
| Example 362 | B |
| Example 363 | A |
| Example 364 | B |
| Example 365 | B |
| Example 366 | B |
| Example 367 | B |
| Example 368 | B |
| Example 369 | A |
| Example 370 | A |
| Example 371 | A |
| Example 372 | A |
| Example 373 | A |
| Example 374 | B |
| Example 375 | A |
| Example 376 | A |
| Example 377 | B |
| Example 378 | A |
| Example 379 | A |
| Example 380 | B |
| Example 381 | A |
| Example 382 | A |
| Example 383 | B |
| Example 384 | B |
| Example 385 | A |
| Example 386 | A |
| Example 387 | A |
| Example 388 | A |
| Example 389 | A |
| Example 390 | A |
| Example 391 | A |
| Example 392 | A |
| Example 393 | C |
| Example 394 | A |
| Example 395 | B |
| Example 396 | B |
| Example 397 | B |
| Example 398 | B |
| Example 399 | B |
| Example 400 | B |
| Example 401 | C |
| Example 402 | B |
| Example 403 | B |
| Example 404 | C |
| Example 405 | C |
| Example 406 | A |
| Example 407 | B |
| Example 408 | B |
| Example 409 | C |
| Example 410 | B |
| Example 411 | C |
| Example 412 | B |
| Example 413 | B |
| Example 414 | C |
| Example 415 | A |
| Example 416 | A |
| Example 417 | A |
| Example 418 | A |
| Example 419 | C |
| Example 420 | C |
| Example 421 | C |
| Example 422 | B |
| Example 423 | B |
| Example 424 | B |
| Example 425 | B |
| Example 426 | A |
| Example 427 | A |
| Example 428 | A |
| Example 429 | A |
| Example 430 | B |
| Example 431 | B |
| Example 432 | A |
| Example 433 | B |
| Example 434 | B |
| Example 435 | B |
| Example 436 | A |
| Example 437 | B |
| Example 438 | B |
| Example 439 | A |
| Example 440 | B |
| Example 441 | A |
| Example 442 | B |
| Example 443 | B |
| Example 444 | B |
| Example 445 | C |
| Example 446 | B |
| Example 447 | B |
| Example 448 | C |
| Example 449 | A |
| Example 450 | A |
| Example 451 | A |
| Example 452 | A |
| Example 453 | A |
| Example 454 | A |
| Example 455 | B |
| Example 456 | C |
| Example 457 | B |
| Example 458 | B |
| Example 459 | B |
| Example 460 | B |
| Example 461 | C |
| Example 462 | B |
| Example 463 | C |
| Example 464 | B |
| Example 465 | B |
| Example 466 | C |
| Example 467 | B |
| Example 468 | B |
| Example 469 | A |
| Example 470 | B |
| Example 471 | B |
| Example 472 | A |
| Example 473 | A |
| Example 474 | A |
| Example 475 | A |
| Example 476 | B |
| Example 477 | C |
| Example 478 | A |
| Example 479 | A |
| Example 480 | A |
| Example 481 | A |
| Example 482 | B |
| Example 483 | A |
| Example 484 | A |
| Example 485 | A |
| Example 486 | B |
| Example 487 | A |
| Example 488 | A |
| Example 489 | A |
| Example 490 | A |
| Example 491 | A |
| Example 492 | A |
| Example 493 | A |
| Example 494 | A |
| Example 495 | A |
| Example 496 | A |
| Example 497 | A |
| Example 498 | A |
| Example 499 | A |
| Example 500 | A |

TABLE 3-continued

| Example # | Potency range |
|---|---|
| Example 501 | A |
| Example 502 | A |
| Example 503 | A |
| Example 504 | A |
| Example 505 | A |
| Example 506 | A |
| Example 507 | A |
| Example 508 | B |
| Example 509 | A |
| Example 510 | A |
| Example 511 | B |
| Example 512 | A |
| Example 513 | C |
| Example 514 | C |
| Example 515 | A |
| Example 516 | A |
| Example 517 | A |
| Example 518 | A |
| Example 519 | A |
| Example 520 | A |
| Example 521 | A |
| Example 522 | C |
| Example 523 | B |
| Example 524 | B |
| Example 525 | C |
| Example 526 | B |
| Example 527 | C |
| Example 528 | A |
| Example 529 | B |
| Example 530 | B |
| Example 531 | B |
| Example 532 | B |
| Example 533 | B |
| Example 534 | C |
| Example 535 | B |
| Example 536 | B |
| Example 537 | B |
| Example 538 | B |
| Example 539 | B |
| Example 540 | C |
| Example 541 | B |
| Example 542 | C |
| Example 543 | C |
| Example 544 | A |
| Example 545 | B |
| Example 546 | C |
| Example 547 | C |
| Example 548 | B |
| Example 549 | A |
| Example 550 | C |
| Example 551 | C |
| Example 552 | C |
| Example 553 | C |
| Example 554 | C |
| Example 555 | B |
| Example 556 | B |
| Example 557 | B |
| Example 558 | A |
| Example 559 | A |
| Example 560 | A |
| Example 561 | A |
| Example 562 | A |
| Example 563 | B |
| Example 564 | C |
| Example 565 | B |
| Example 566 | A |
| Example 567 | A |
| Example 568 | A |
| Example 569 | A |
| Example 570 | C |
| Example 571 | B |
| Example 572 | B |
| Example 573 | A |
| Example 574 | A |
| Example 575 | B |
| Example 576 | A |
| Example 577 | A |
| Example 579 | B |
| Example 580 | C |
| Example 581 | C |
| Example 582 | C |
| Example 583 | C |
| Example 584 | B |
| Example 585 | B |
| Example 586 | C |
| Example 587 | C |
| Example 588 | B |
| Example 589 | B |
| Example 590 | B |
| Example 591 | B |
| Example 592 | B |
| Example 593 | B |
| Example 594 | B |
| Example 595 | A |
| Example 596 | B |
| Example 597 | B |
| Example 598 | B |
| Example 599 | B |
| Example 600 | A |
| Example 601 | B |
| Example 602 | A |
| Example 603 | A |
| Example 604 | A |
| Example 605 | A |
| Example 606 | A |
| Example 607 | B |
| Example 608 | A |
| Example 609 | A |
| Example 610 | A |
| Example 611 | A |
| Example 612 | A |
| Example 613 | A |
| Example 614 | A |
| Example 615 | B |
| Example 616 | B |
| Example 617 | A |
| Example 618 | B |
| Example 619 | A |
| Example 620 | B |
| Example 621 | B |
| Example 622 | A |
| Example 623 | A |
| Example 624 | B |
| Example 625 | C |
| Example 626 | B |
| Example 627 | B |
| Example 628 | B |
| Example 629 | A |
| Example 630 | C |
| Example 631 | A |
| Example 632 | A |
| Example 633 | A |
| Example 634 | B |
| Example 635 | B |
| Example 636 | B |
| Example 637 | B |
| Example 638 | A |
| Example 639 | A |
| Example 640 | A |
| Example 641 | A |
| Example 642 | B |
| Example 643 | C |
| Example 644 | C |
| Example 645 | C |
| Example 646 | C |
| Example 647 | B |
| Example 648 | A |
| Example 649 | B |
| Example 650 | C |
| Example 651 | C |
| Example 652 | A |
| Example 653 | A |
| Example 654 | B |
| Example 655 | A |

TABLE 3-continued

| Example # | Potency range |
|---|---|
| Example 656 | A |
| Example 657 | B |
| Example 658 | B |
| Example 659 | B |
| Example 660 | B |
| Example 661 | C |
| Example 662 | B |
| Example 663 | C |
| Example 664 | B |
| Example 665 | B |
| Example 666 | A |
| Example 667 | A |
| Example 668 | C |
| Example 669 | A |
| Example 670 | A |
| Example 671 | A |
| Example 672 | C |
| Example 673 | A |
| Example 674 | A |
| Example 675 | A |
| Example 676 | A |
| Example 677 | B |
| Example 678 | A |
| Example 679 | A |
| Example 680 | B |
| Example 681 | B |
| Example 682 | A |
| Example 683 | B |
| Example 684 | B |
| Example 685 | A |
| Example 686 | A |
| Example 687 | A |
| Example 688 | A |
| Example 689 | A |
| Example 690 | A |
| Example 691 | B |
| Example 692 | A |
| Example 693 | A |
| Example 694 | A |
| Example 695 | A |
| Example 696 | B |
| Example 697 | B |
| Example 698 | A |
| Example 699 | A |
| Example 700 | B |
| Example 701 | B |
| Example 702 | B |
| Example 703 | B |
| Example 704 | B |
| Example 705 | C |
| Example 706 | C |
| Example 707 | B |
| Example 708 | B |
| Example 709 | B |
| Example 710 | C |
| Example 711 | C |
| Example 712 | B |
| Example 713 | A |
| Example 714 | A |
| Example 715 | A |
| Example 716 | B |
| Example 717 | A |
| Example 718 | B |
| Example 719 | C |
| Example 720 | B |
| Example 721 | A |
| Example 722 | A |
| Example 723 | A |
| Example 724 | A |
| Example 725 | A |
| Example 726 | A |
| Example 727 | B |
| Example 728 | B |
| Example 729 | B |
| Example 730 | B |
| Example 731 | A |
| Example 732 | A |
| Example 733 | B |
| Example 734 | B |
| Example 735 | A |
| Example 736 | B |
| Example 737 | B |
| Example 738 | B |
| Example 739 | A |
| Example 740 | A |
| Example 741 | A |
| Example 742 | B |
| Example 743 | A |
| Example 744 | B |
| Example 745 | B |
| Example 746 | A |
| Example 747 | A |
| Example 748 | B |
| Example 749 | B |
| Example 750 | C |
| Example 751 | C |
| Example 752 | C |
| Example 754 | B |
| Example 755 | B |
| Example 756 | B |
| Example 757 | B |
| Example 758 | B |
| Example 759 | C |
| Example 760 | B |
| Example 761 | B |
| Example 762 | C |
| Example 763 | B |
| Example 764 | B |
| Example 765 | A |
| Example 766 | A |
| Example 767 | A |
| Example 768 | A |
| Example 769 | A |
| Example 770 | B |
| Example 771 | A |
| Example 772 | A |
| Example 773 | A |
| Example 774 | A |
| Example 775 | A |
| Example 776 | C |
| Example 777 | A |
| Example 778 | A |
| Example 779 | A |
| Example 780 | A |
| Example 781 | A |
| Example 782 | A |
| Example 783 | A |
| Example 784 | A |
| Example 785 | A |
| Example 786 | A |
| Example 787 | A |
| Example 788 | C |
| Example 789 | C |
| Example 790 | A |
| Example 791 | A |
| Example 792 | A |
| Example 793 | B |
| Example 794 | A |
| Example 795 | A |
| Example 796 | A |
| Example 797 | A |
| Example 798 | B |
| Example 799 | B |
| Example 800 | A |
| Example 801 | A |
| Example 802 | A |
| Example 803 | B |
| Example 804 | A |
| Example 805 | A |
| Example 806 | A |
| Example 807 | A |
| Example 808 | A |
| Example 809 | C |
| Example 810 | A |

TABLE 3-continued

| Example # | Potency range |
|---|---|
| Example 811 | C |
| Example 812 | A |
| Example 813 | B |
| Example 814 | A |
| Example 815 | B |
| Example 816 | A |
| Example 817 | A |
| Example 818 | B |
| Example 819 | A |
| Example 820 | A |
| Example 821 | A |
| Example 822 | B |
| Example 823 | C |
| Example 824 | A |
| Example 825 | A |
| Example 826 | A |
| Example 827 | A |
| Example 828 | A |
| Example 829 | A |
| Example 830 | B |
| Example 831 | B |
| Example 832 | C |
| Example 833 | A |
| Example 834 | C |
| Example 835 | B |
| Example 836 | B |
| Example 837 | A |
| Example 838 | A |
| Example 839 | A |
| Example 840 | A |
| Example 841 | A |
| Example 842 | A |
| Example 843 | A |
| Example 844 | A |
| Example 845 | A |
| Example 846 | C |
| Example 847 | C |
| Example 848 | B |
| Example 849 | A |
| Example 850 | A |
| Example 851 | A |
| Example 852 | A |
| Example 853 | A |
| Example 854 | A |
| Example 855 | A |
| Example 856 | A |
| Example 857 | A |
| Example 858 | A |
| Example 859 | A |
| Example 860 | A |
| Example 861 | A |
| Example 862 | A |
| Example 863 | A |
| Example 864 | A |
| Example 865 | A |
| Example 866 | A |
| Example 867 | A |
| Example 868 | A |
| Example 869 | B |
| Example 870 | A |

Potency of compounds, In-vitro SFT
Potency range: A < 0.1 uM; 0.1 uM < B < 1 uM; 1 uM < C Example 872: Acute In Vivo Models: Target Engagement in Mouse Kidney In vivo target engagement was initially assessed in an adult mouse kidney model assessing de novo synthesis inhibition. This model was selected because the high rate of GalCer and SFT synthesis and turnover in kidney facilitated development of an acute one-day model assessing the effect of a single administration of compound at different doses. Inhibition of de novo synthesis was determined by measuring the amount of 13C6 galactose (13C-Gal; CIL, cat #CLM-1570-pk) incorporated into GalCer and SFT.

Groups of 5 male C57Bl/6 mice, 6-9 wks of age (Charles River Laboratories) were maintained in an ALAAC-accredited vivarium with food and water ad libitum and were allowed to acclimate one week before initiating studies. Three to 5 dose groups received test article formulated in a clinically-acceptable formulation, administered by oral gavage; the control group received vehicle alone. One hr after administration of test article, animals received an intraperitoneal (i.p.) injection of 13C-Gal (3 g/kg); 5 hr after administration of test article, animals were euthanized and a kidney was removed and divided into two longitudinal samples that were snap-frozen and stored at −80° C. until processing for test article tissue exposure and lipid analysis (GalCer and SFT). Typically, brain and plasma samples were also collected for test article exposure. The resulting kidney tissue exposure and lipid analysis for individual compounds are presented in Table 4 below.

Example 873: Acute In Vivo Models: Target Engagement in Mouse Brain

Because MLD is a disease primarily of the central nervous system (CNS), it was essential to demonstrate target engagement in the brain. SFT biosynthesis and turnover in the myelin of adult mice is very low, necessitating development of a short-term acute model of de novo synthesis inhibition. To do this, we took advantage of the fact that unlike primates in which most developmental myelination occurs in utero, in rodents, peak myelination occurs between postnatal day 14 (P14) and P22.

Groups of 5 neonatal mice age-matched between P14 and P21 received test article formulated in a clinically-acceptable formulation, administered by oral gavage; the control group received vehicle alone. One hr after administration of test article, animals received an i.p. injection of 13C-Gal (3 g/kg); 5 hr after administration of test article, animals were euthanized, brains were removed and dissected for recovery of mid- and hind brain which was snap-frozen and stored at −80° C. until analysis. Plasma samples were also collected for test article exposure analysis. The resulting brain exposure and lipid analysis for individual compounds are presented in Table 4 below.

Mass Spectrometer Analysis of SFT

Quantitative analysis of sphingolipids (SLs) was performed using liquid chromatography with tandem mass spectrometry analysis (LC-MS/MS). Briefly, to extract glucosylceramide (GlcCer), galactosylceramide (GalCer), and sulfatide (ST), an aliquot of 10 μL of mouse tissue homogenate (100 mg/ml in water) was mixed with 1 mL of extraction solution (0.2% Formic Acid; 5 mM Ammonium formate in (50:50) Methanol:Acetonitrile (v/v) with internal standards (IS)). C17-ST and D35 labeled C18-GalCer were used for IS. The mixtures were vortexed and centrifuged. The resulting supernatants were transferred to HPLC vials for LC-MS/MS analysis. GlcCer and GalCer were separated using a Waters Acquity UPLC and Atlantis HILIC Silica column (2.1 mm×150 mm, 3 m particles, Waters Corp., Milford, Mass.) and analyzed by an API 5000 triple quadrupole mass spectrometer in MRM mode (Applied Biosystems, Foster City, Calif.). ST were analyzed using a Waters Acquity UPLC and BEH C18 column (2.1 mm×50 mm, 1.7 m particles, Waters Corp., Milford, Mass.) and analyzed by an API 6500 triple quadrupole mass spectrometer in MRM mode (Applied Biosystems, Foster City, Calif.).

Analytical Method for MLD Compounds

Plasma and tissue concentrations of the test compounds from MLD program were determined using exploratory liquid chromatography with tandem mass spectrometry (LC-MS/MS) methods. Briefly, tissue samples were first homogenized with a solution of 20% acetonitrile in water at a ratio of 1:4 (1.00 g of the tissue with 4.00 mL of the solution). Plasma and tissue homogenate samples were then processed using protein precipitation via the internal standard solution (RP-107 in acetonitrile). Chromatographic separation was performed using a Phenomenex Kinetex C8 column. Multiple mass transitions were monitored with tandem mass spectrometry (MS/MS). Calibration standards and quality control samples were prepared in blank control plasma or tissue homogenate. Calibration curves were generated using weighted linear regression analysis (1/×2) of peak area ratio (analyte to IS) versus analyte concentration. The appropriate calibration curve for each analyte was used to calculate the concentration of the analyte in plasma or tissue samples.

TABLE 4

| Example # | kidney PD dose (mg/kg) | kidney GalCer % inh | kidney Sulfatide % inh |
|---|---|---|---|
| 496 | 10, 30, 100 | A, A, A | A, A, A |
| 375 | 1, 3, 10, 30, 100 | C, C, B, A, A | C, C, B, A, A |
| 90 | 0.3, 1, 3, 10, 30 | C, C, A, A, A | C, B, A, A, A |
| 693 | 1, 3, 10 | C, C, B | C, C, A |
| 76 | 1, 3, 10 | C, B, B | C, B, B |
| 109 | 5, 10, 50 | C, B, A | |
| 473 | 3, 10, 50 | C, C, B | C, B, A |
| 475 | 3, 10, 50 | C, B, B | |

| Example # | brain PD dose (mg/kg) | brain GalCer % inh | brain Sulfatide % inh |
|---|---|---|---|
| 375 | 1, 3, 10 | B, B, A | B, B, A |
| 90 | 3, 10, 30 | A, A, A | A, A, A |
| 76 | 3, 10, 30 | B, A, A | B, A, A |
| 109 | 10, 30, 100 | B, B, B | A, A, A |
| 473 | 10, 30, 100 | A, A, A | A, A, A |

Potency of compounds, In-vivo GalCer and Sulfatide inhibition
Potency range: A > 80%; 40% < B < 80%; C < 40%

Dosing

Dosage regimens for the compounds described herein for monotherapy and combination therapy are generally determined by the skilled clinician and are expected to vary significantly depending the clinical status of the particular affected individual. The general principles for determining a dosage regimen for the treatment of cystic fibrosis or (and/or) CFTR modulation are well known to the skilled artisan. Guidance for dosage regimens can be obtained from any of the many well-known references in the art on this topic. Further guidance is available, inter alia, from a review of the specific references cited herein. In certain embodiments, such dosages may range from about 0.5 mg/kg to about 300 mg/kg, for example, from about 5 mg/kg to about 60 mg/kg (e.g., 5 mg/kg, 10 mg/kg, 15, mg/kg, 20 mg/kg, 25 mg/kg, 30 mg/kg, 35 mg/kg, 40 mg/kg, 45 mg/kg, 50 mg/kg, 55 mg/kg and 60 mg/kg) by intraperitoneal, oral or equivalent administration from one to five times daily. Such dosages may range from about 5 mg/kg to about 5 g/kg, preferably from about 10 mg/kg to about 1 g/kg by oral, intraperitoneal or equivalent administration from one to five times daily. In one embodiment, doses range from about 10 mg/day to about 500 mg/day (e.g., 10 mg/day, 20 mg/day, 30 mg/day, 40 mg/day, 50 mg/day, 60 mg/day, 70 mg/day, 80 mg/day, 90 mg/day, 100 mg/day, 110 mg/day, 120 mg/day, 130 mg/day, 140 mg/day, 150 mg/day, 160 mg/day, 170 mg/day, 180 mg/day, 190 mg/day, 200 mg/day, 210 mg/day, 220 mg/day, 230 mg/day, 240 mg/day, 250 mg/day, 260 mg/day, 270 mg/day, 280 mg/day, 290 mg/day, 300 mg/day). A particularly preferred Oral dose range is from about 50 mg to about 100 mg, wherein the dose is administered for example once daily. A particular oral dose range for a compound described herein is from about 5 mg/kg/day to about 600 mg/kg/day. In a particular oral dose range for a compound described herein is from about 1 mg/kg/day to about 120 mg/kg/day, e.g., 1 mg/kg/day, 5 mg/kg/day, 10 mg/kg/day, 15 mg/kg/day, 20 mg/kg/day, 25 mg/kg/day, 30 mg/kg/day, 35 mg/kg/day, 40 mg/kg/day, 45 mg/kg/day, 50 mg/kg/day, 55 mg/kg/day or 60 mg/kg/day, 65 mg/kg/day, 70 mg/kg/day, 75 mg/kg/day, 80 mg/kg/day, 85 mg/kg/day, 90 mg/kg/day, 95 mg/kg/day, 100 mg/kg/day, 105 mg/kg/day, 110 mg/kg/day, 115 mg/kg/day or 120 mg/kg/day.

The teachings of all patents, published applications and references cited herein are incorporated by reference in their entirety.

While the embodiments described herein have been particularly shown and described with references to example embodiments thereof, it will be understood by those skilled in the art that various changes in form and details may be made therein without departing from the scope encompassed by the appended claims.

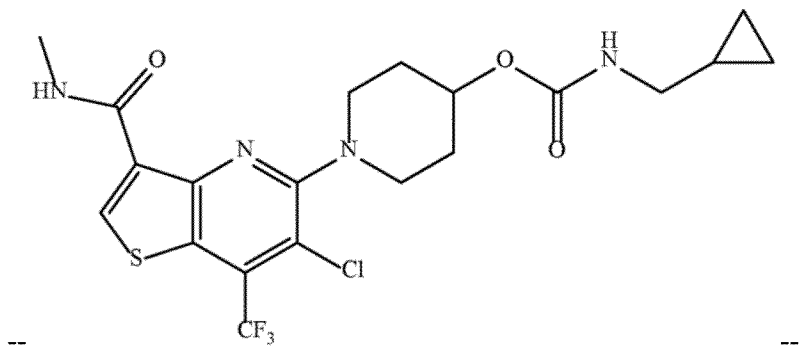

What is claimed is:

1. A compound of formula (I):

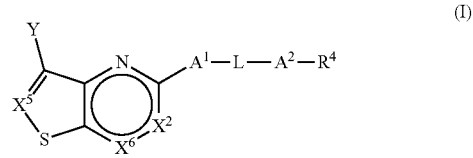

(I)

or a pharmaceutically acceptable salt or prodrug thereof, wherein:
(a) $X^2$ is $CR^2$ or N;
(b) $X^5$ is $CR^7$ or N;
(c) $X^6$ is $CR^1$ or N;
(d) Y is —CN, $C_{1-4}$ alkyl, —C(O)$NR^aR^b$, —$NR^a$—C(O)—$R^b$, —C(O)$OR^a$, —C(O)$R^a$, heteroaryl or —S(O)$_2NR^aR^b$, wherein the $C_{1-4}$ alkyl or heteroaryl may be substituted with 0-3 occurrences of $R^z$;
(e) each $R^a$ is independently H, $C_{1-4}$ alkyl, $C_{1-4}$ haloalkyl, —$C_{1-4}$ alkyl-$C_{3-9}$ cycloalkyl or $C_{3-9}$ cycloalkyl;
(f) each $R^b$ is independently $C_{1-4}$ alkyl, $C_{1-4}$ alkoxy, $C_{3-9}$ cycloalkyl or —$C_{1-4}$ alkyl-$C_{1-4}$ alkoxy; or when Y is —C(O)$NR^aR^b$, $R^a$ and $R^b$ can be taken together with the nitrogen atom to which they are attached to form a heterocycloalkyl ring substituted with 0-3 occurrences of $R^x$;
(g) $R^7$ is hydrogen, $C_{1-4}$ alkyl, $C_{1-4}$ alkoxy, —S(O)$_2$—$NR^aR^b$— or heteroaryl;
(h) $R^1$ is hydrogen, halo, —OH, $C_{1-4}$ alkyl, $C_{1-4}$ alkoxy, $C_{1-4}$ haloalkyl, $C_{1-4}$ haloalkoxy, —$NH_2$, —NH($C_{1-4}$ alkyl) or —N($C_{1-4}$ alkyl)$_2$, $C_{3-9}$ cycloalkyl or azetidinyl, wherein each —NH($C_{1-4}$ alkyl), cycloalkyl or azetidinyl is substituted with 0-5 occurrences of $R^x$;
(i) $R^2$ is hydrogen, halo, —OH, $C_{1-4}$ alkyl, $C_{1-4}$ alkoxy or $C_{3-9}$ cycloalkyl;
(j) $A^1$ is a bond, $C_{1-4}$ alkylene, —O—, —O—$C_{1-4}$ alkylene, —$C_{2-4}$ alkenylene, —$C_{2-4}$ alkynylene, —NR$^a$, —NR$^a$—C$_{1-4}$ alkylene-, —S—, —S(O)—, —S(O)$_2$—, —C(O)—, —C(O)—O— or —O—C(O)—;

(k) L is aryl, heteroaryl, C$_{3-12}$ cycloalkyl, a 3-12 membered heterocycloalkyl or a 3-12 membered heterocycloalkenyl each of which may be substituted with 0-4 occurrences of R$^x$;

(l) A$^2$ is a bond, —O—, —NR$^a$—, —C$_{1-4}$-alkyl-NR$^a$—, —C(O)—, —C$_{1-4}$ alkyl-C(O)—, —O—C(O)—, —C$_{1-4}$ alkyl-O—C(O)—, —C(O)—O—, —C$_{1-4}$ alkyl-C(O)—O—, —O—C(O)—O—, —S(O)$_2$—, —NR$^a$—S(O)—, —C$_{1-4}$-alkyl-NR$^a$—S(O)—, —NR$^a$—S(O)$_2$—, —C$_{1-4}$-alkyl-NR$^a$—S(O)$_2$—, —C(O)—NR$^a$—, —C$_{1-4}$ alkyl-C(O)—NR$^a$—, —NR$^a$—C(O)—, —C$_{1-4}$-alkyl-NR$^a$—C(O)—, —O—C(O)—NR$^a$—, —NR$^a$—C(O)—O—, —NR$^a$—C(O)—NR$^a$—, —NR$^a$—CH$_2$—C(O)—NR$^a$—, —O—CH$_2$—C(O)—NR$^a$—, —C(O)—O—CH$_2$—C(O)—, or —C(O)—NR$^a$—CH$_2$—C(O)—;

(m) R$^4$ is —OH, C$_{1-6}$ alkyl, C$_{2-6}$ alkenyl, C$_{2-6}$ alkynyl, C$_{3-9}$ cycloalkyl, heterocycloalkyl, aryl or heteroaryl, wherein each alkyl, cycloalkyl, heterocycloalkyl, aryl or heteroaryl of R$^4$ is substituted with 0-5 occurrences of R$^5$;

(n) R$^5$ is OH, halo, CO$_2$H, C$_{1-4}$ alkyl, C$_{2-6}$ alkynyl, C$_{1-4}$ alkoxy, C$_{1-4}$ haloalkyl, —O—C$_{1-4}$ haloalkyl, —C$_{1-4}$ alkyl-O—C$_{1-4}$ alkyl, —S—C$_{1-4}$ alkyl, —S(O)$_2$—C$_{1-4}$ alkyl, —S(O)—C$_{1-4}$ alkyl, —N(R$^a$)$_2$, —CH$_2$N(R$^a$)$_2$, —N(R$^a$)—S(O)—C$_{1-4}$ alkyl, -N-(R$^a$)—S(O)$_2$—C$_{1-4}$ alkyl, —NO$_2$, —CN, —CH$_2$CN, C$_{3-9}$ cycloalkyl, —O—C$_{3-9}$ cycloalkyl, —C$_{1-4}$ alkyl-C$_{3-9}$ cycloalkyl, —O—C$_{1-4}$ alkyl-C$_{3-9}$ cycloalkyl, —C$_{1-4}$ alkyl-O—C$_{1-4}$ haloalkyl, heterocycloalkyl, —C$_{1-4}$ alkyl-heterocycloalkyl, aryl, —O-aryl, heteroaryl, —O-heteroaryl, C$_{1-4}$-alkyl-heteroaryl, aralkyl or —O-aralkyl, wherein each alkyl, aryl, heteroaryl, cycloalkyl or heterocycloalkyl is substituted with 0-3 occurrences of R$^w$;

(o) each R$^w$ is independently halo, —OH, C$_{1-4}$ alkyl, C$_{1-4}$ haloalkyl or —C$_{1-4}$ alkoxy;

(p) each R$^x$ is independently halo, —OH, C$_{1-4}$ alkyl, —C$_{1-4}$ alkoxy, —C$_{1-4}$ alkyl-O—C$_{1-4}$ alkyl, —C(O)—N(R$^a$)$_2$, —O—C(O)—N(R$^a$)$_2$, —N(R$^a$)$_2$, —CH$_2$N(R$^a$)$_2$, heterocycloalkyl, —O—heterocycloalkyl, —O-aryl or —O-heteroaryl; and (q) each R$^z$ is independently hydrogen, halo, —OH, C$_{1-4}$ alkyl, C$_{1-4}$ alkoxy or C$_{3-9}$ cycloalkyl.

2. The compound of claim 1, wherein the compound is a compound of any one of formula Ia-If:

(Ia)

(Ib)

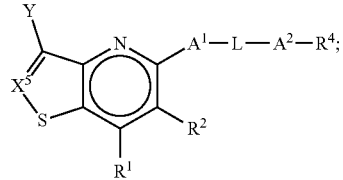
(Ic)

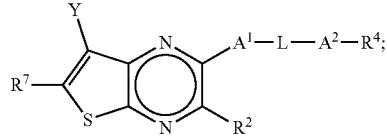
(Id)

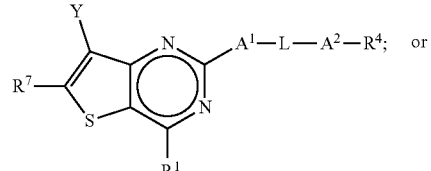
(Ie)

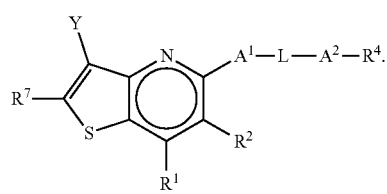
(If)

3. The compound of claim 1, wherein R$^2$ is hydrogen, C$_{1-4}$ alkyl or halo.

4. The compound of claim 1, wherein R$^7$ is C$_{1-4}$ alkyl or hydrogen.

5. The compound of claim 1, wherein Y is CN, —C(O)R$^a$, C$_{1-4}$ alkyl, —NR$^a$—C(O)—R$^b$, heteroaryl, Y is —C(O)OR$^a$, or —C(O)NR$^a$R$^b$.

6. The compound of claim 1, wherein the compound is a compound of formula II, IIa, IIb or IIc:

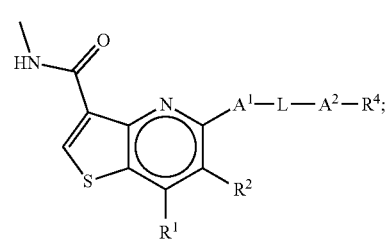
(II)

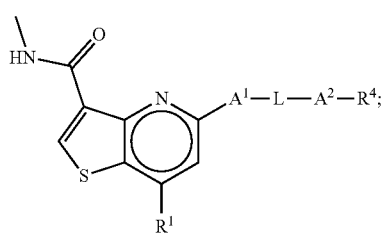
(IIa)

(IIb)
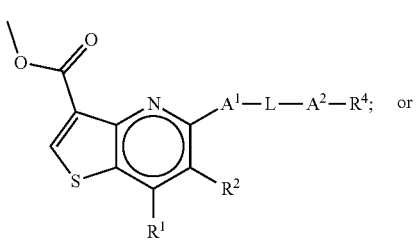

(IIc)
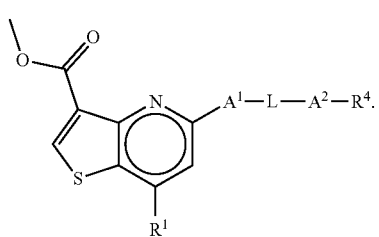

7. The compound of claim 1, wherein $R^1$ is hydrogen, —OH, halo, $C_{1-4}$ haloalkyl, $C_{1-4}$ alkoxy, $C_{1-4}$ haloalkoxy, —NH($C_{1-4}$ alkyl), —N($C_{1-4}$ alkyl)$_2$, $C_{3-9}$ cycloalkyl or azetidinyl.

8. The compound of claim 1, wherein the compound is a compound of formula III, IIa, IIIb or IIIc:

(III)
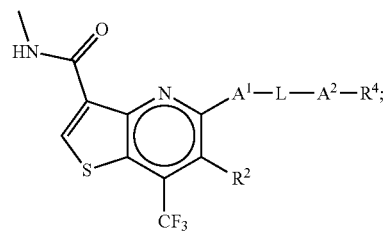

(IIIa)
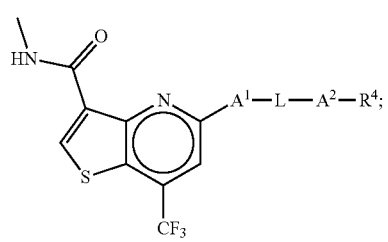

(IIIb)
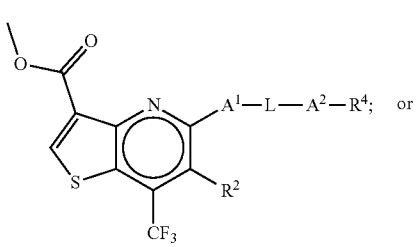

(IIIc)
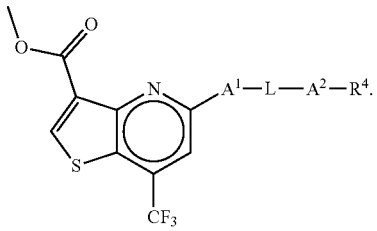

9. The compound of claim 1, wherein the $A^1$ is —O—, $C_{1-4}$ alkylene, a bond, —O—C(O)—, —C(O)—, —NR$^a$— or —NR$^a$—$C_{1-4}$ alkylene.

10. The compound of claim 1, wherein L is one of the following moieties:

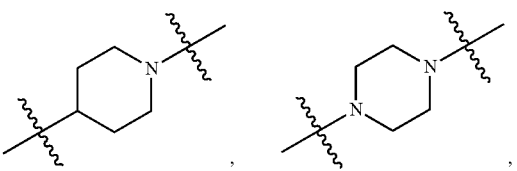

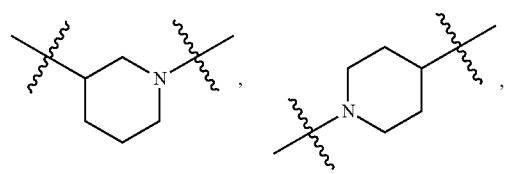

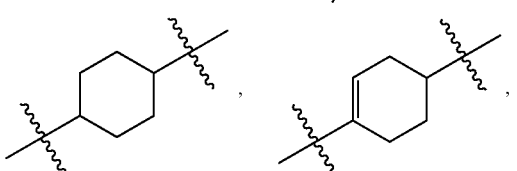

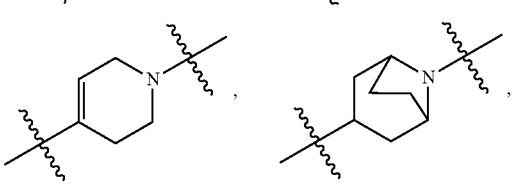

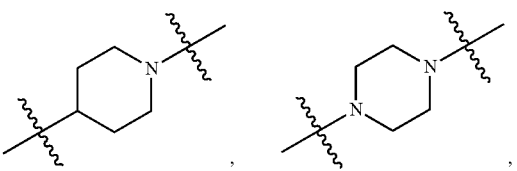

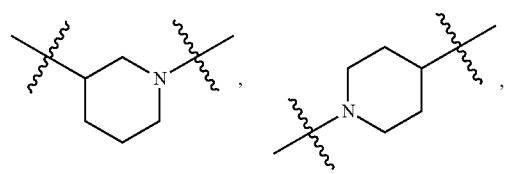

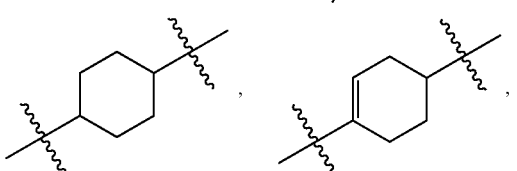

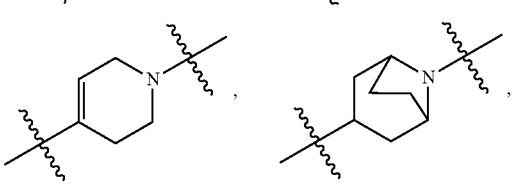

-continued
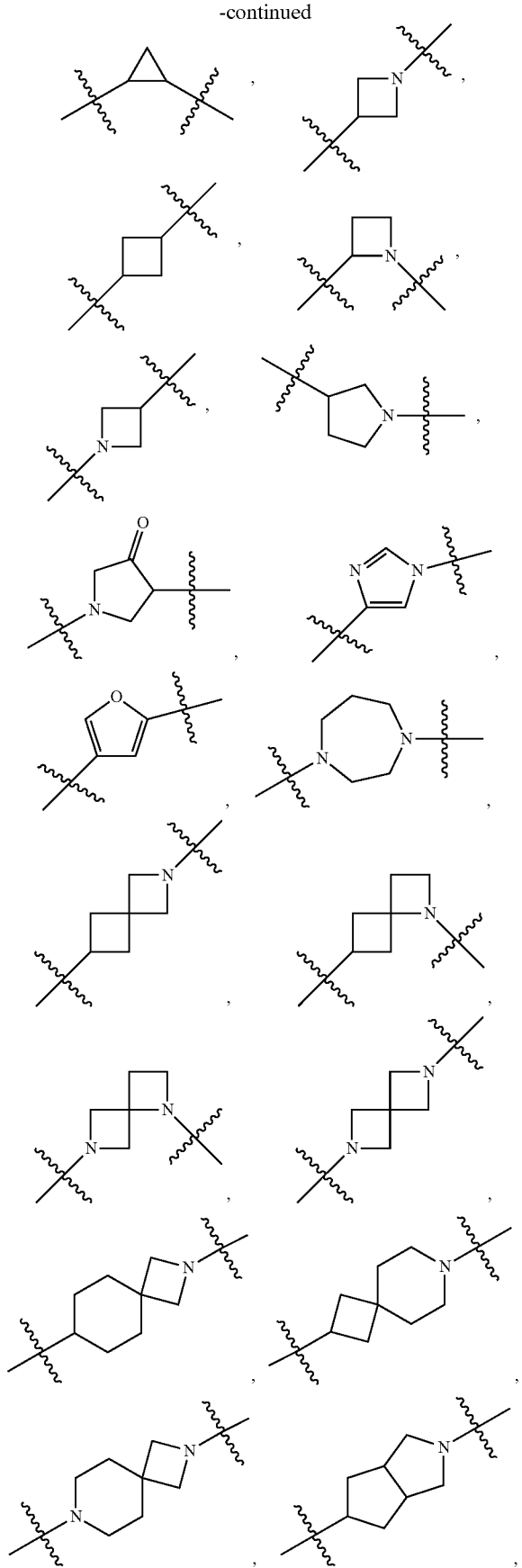
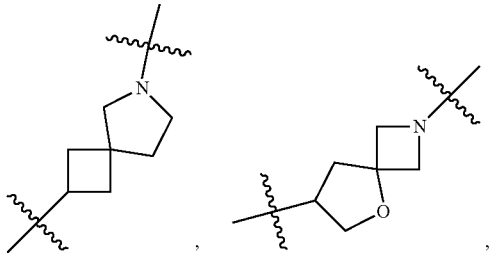
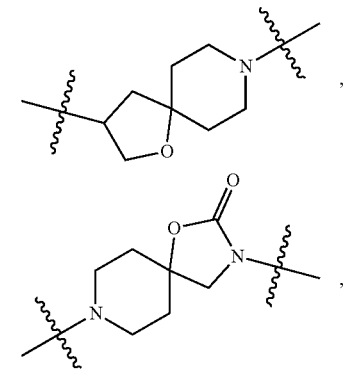
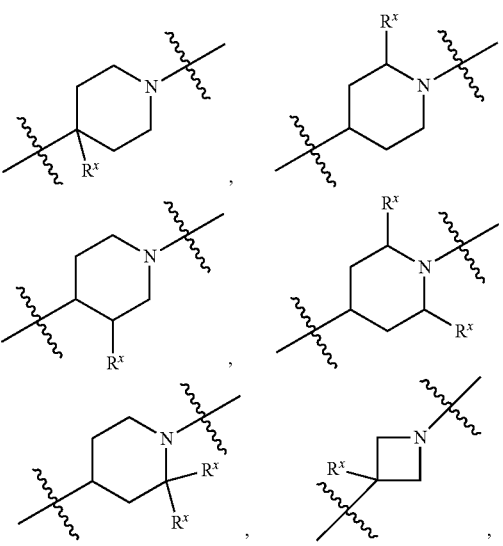
each of which is substituted with 0-4 occurrences of $R^x$.
11. The compound of claim 10, wherein L is one of the following moieties:

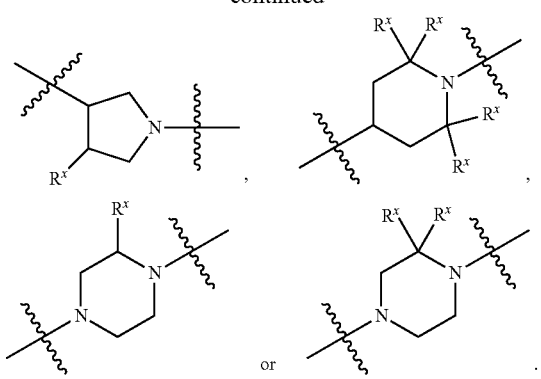
12. The compound of claim 10, wherein L is one of the following moieties:
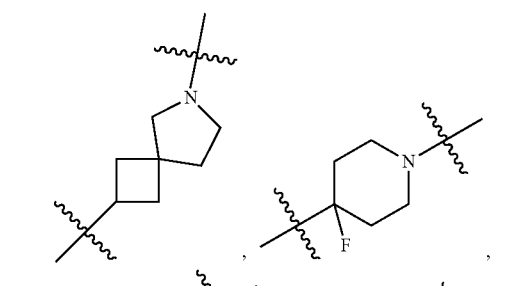
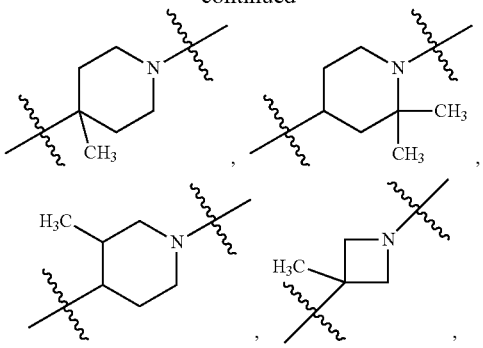
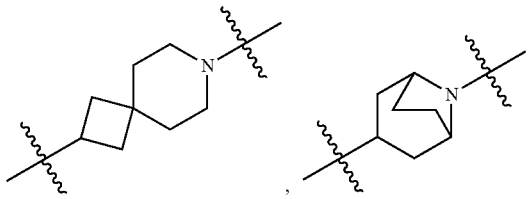
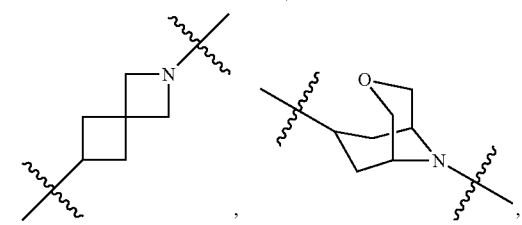
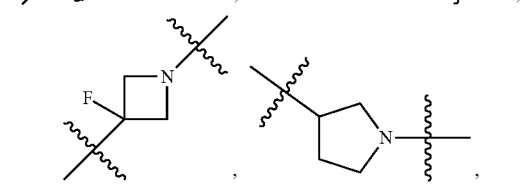
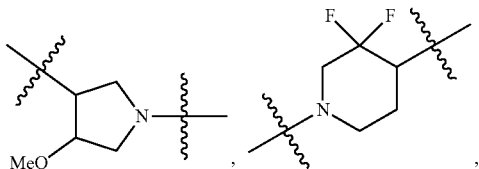
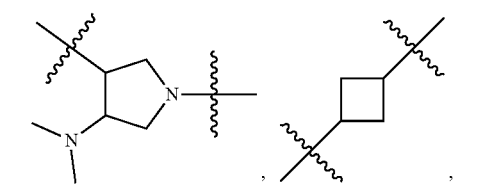
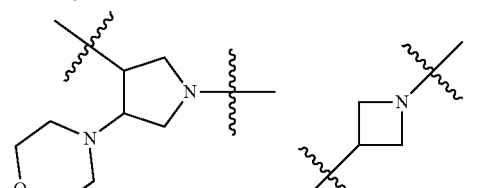
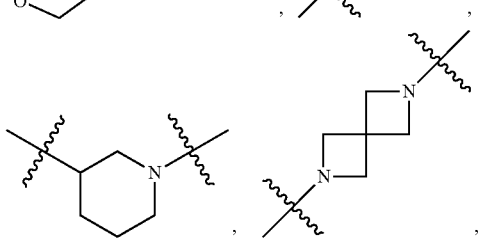

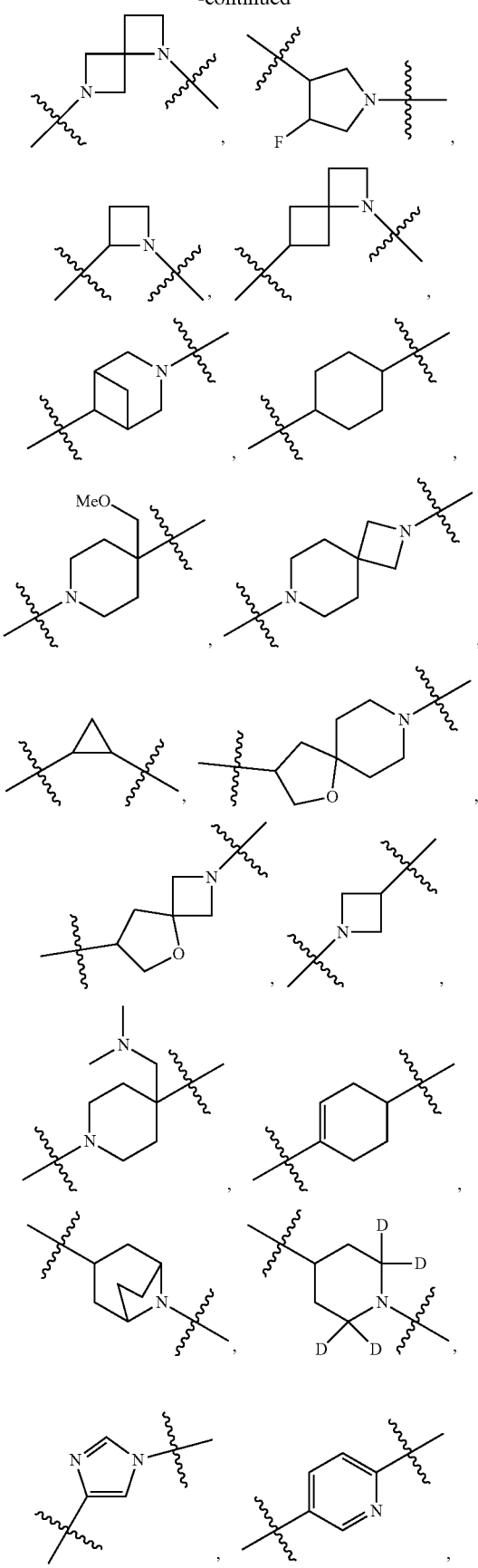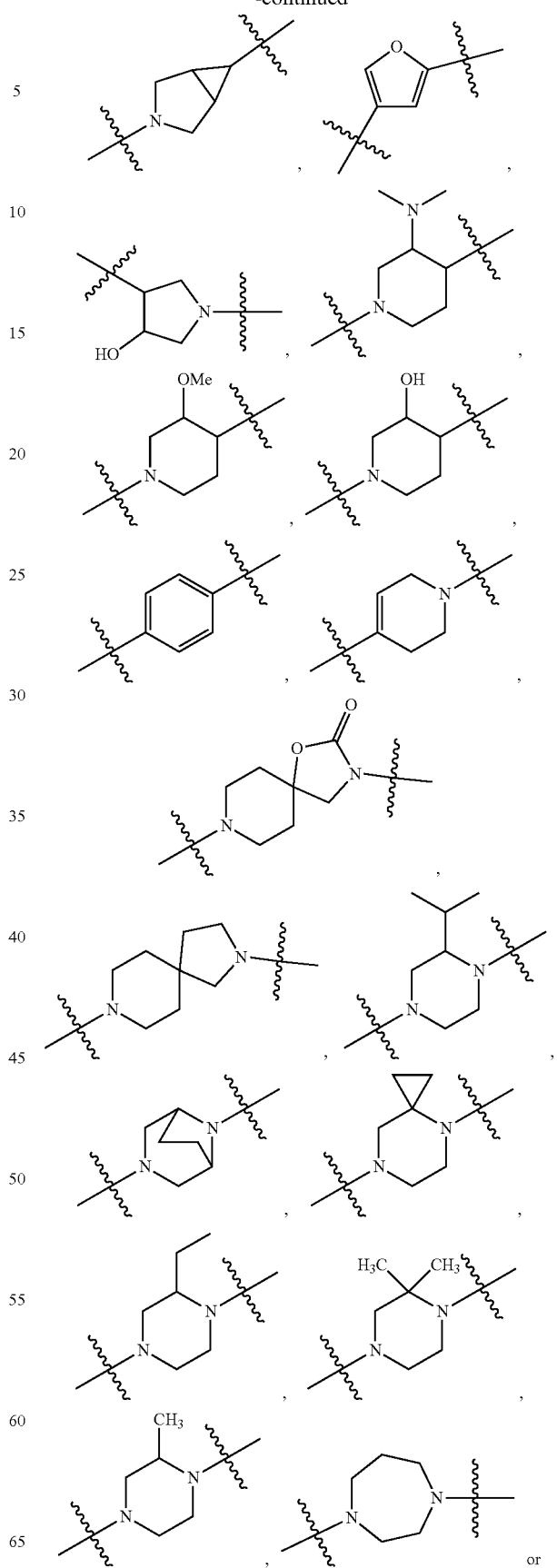

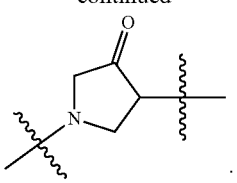
13. The compound of claim 12, wherein L is one of the following moieties:
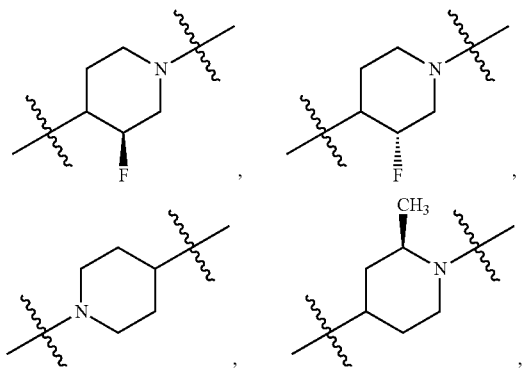
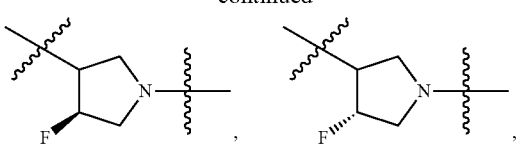
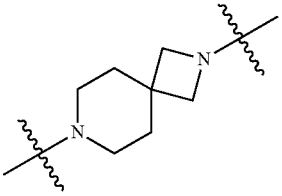
14. The compound of claim 13, wherein L is one of the following moieties:
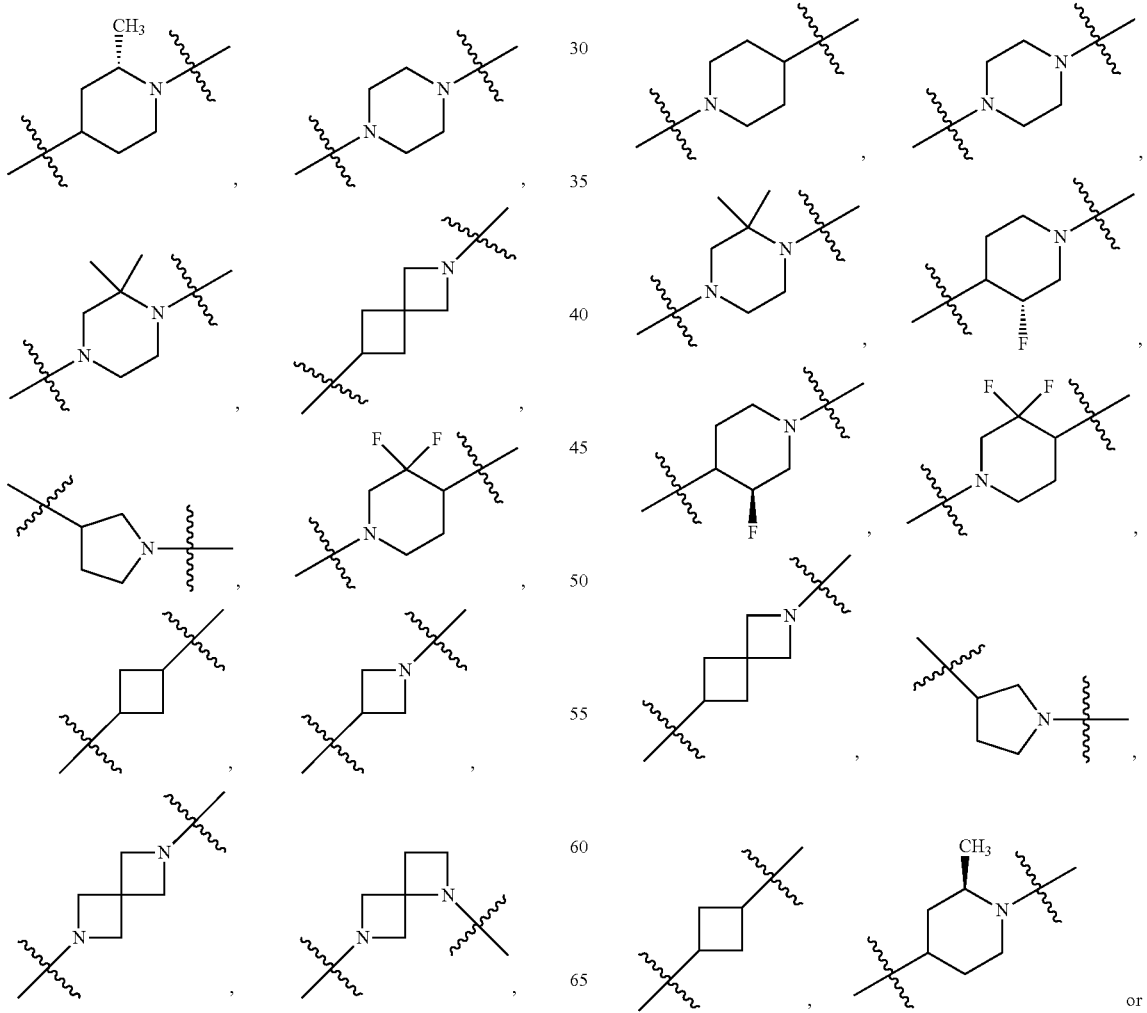
or -continued

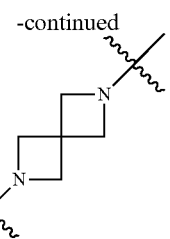

15. The compound of claim 1, wherein $A^2$ is a bond, —C(O)—O—, —OC(O)—NR$^a$—, —OC(O)—, —O—, —C(O)—, —NR$^a$—C(O)—O—, —NR$^a$—C(O)—NR$^a$—, —C(O)—NR$^a$—, —C$_{1-4}$ alkyl-C(O)—NR$^a$—, —O—C(O)—O—, —NR$^a$—C(O)—, —NR$^a$—, —S(O)$_2$—, —C$_{1-4}$ alkyl-C(O)—, —C$_{1-4}$ alkyl-NR$^a$—, —C$_{1-4}$ alkyl-NR$^a$—S(O)— or —C$_{1-4}$ alkyl-C(O)—O—.

16. The compound of claim 15, wherein $A^2$ is a bond, —C(O)—O—, —OC(O)—NR$^a$—, —OC(O)—, —O—, —NR$^a$—C(O)—O—, —C$_{1-4}$ alkyl-C(O)—NR$^a$—, or —NR$^a$—.

17. The compound of claim 1, wherein $R^4$ is —OH, C$_{1-6}$ alkyl substituted with 0-5 occurrences of $R^5$, heterocycloalkyl, C$_{3-9}$ cycloalkyl or heteroaryl.

18. The compound of claim 1, wherein $R^5$ is halo, C$_{1-4}$ alkyl, C$_{1-4}$ alkoxy, C$_{1-4}$ haloalkyl, —O—C$_{1-4}$ haloalkyl, cyano, C$_{3-9}$ cycloalkyl, C$_{1-4}$ alkyl-C$_{3-9}$ cycloalkyl, —O—C$_{1-4}$ alkyl-C$_{3-9}$ cycloalkyl or heterocycloalkyl, wherein each cycloalkyl, aryl, heteroaryl or heterocycloalkyl is substituted with 0-3 occurrences of $R^w$.

19. A pharmaceutical composition comprising a compound of claim 1 and one or more pharmaceutically acceptable salts thereof.

20. A method of treating a disease or disorder, wherein the disease or disorder is Krabbe's disease (KD) or Metachromatic leukodystrophy (MLD), wherein the method comprises administering a pharmaceutically effective amount of a compound of claim 1 to a patient in need thereof.

21. The method of claim 20, wherein the disease or disorder is Krabbe's disease (KD).

22. The method of claim 20, wherein the disease or disorder is Metachromatic leukodystrophy (MLD).

23. A compound selected from the group consisting of:
N-Methyl-5-(4-((5-methylpyridin-2-yl)methyl)piperazin-1-yl)-7-(trifluoromethyl)thieno[3,2-b]pyridine-3-carboxamide;
5-(4-Benzylpiperazin-1-yl)-N-methyl-7-(trifluoromethyl)thieno[3,2-b]pyridine-3-carboxamide;
N-Methyl-5-(4-((2-methylpyrimidin-4-yl)methyl)piperazin-1-yl)-7-(trifluoromethyl)thieno[3,2-b]pyridine-3-carboxamide;
5-(4-((6-Ethylpyridin-2-yl)methyl)piperazin-1-yl)-N-methyl-7-(trifluoromethyl)thieno[3,2-b]pyridine-3-carboxamide;
5-(4-((6-(Methoxymethyl)pyridin-2-yl)methyl)piperazin-1-yl)-N-methyl-7-(trifluoromethyl)thieno[3,2-b]pyridine-3-carboxamide;
N-Methyl-5-(4-((4-methylpyridin-2-yl)methyl)piperazin-1-yl)-7-(trifluoromethyl)thieno[3,2-b]pyridine-3-carboxamide;
N-Methyl-5-(4-((3-methylpyridin-2-yl)methyl)piperazin-1-yl)-7-(trifluoromethyl)thieno[3,2-b]pyridine-3-carboxamide;
5-(4-((6-Methoxypyridin-2-yl)methyl)piperazin-1-yl)-N-methyl-7-(trifluoromethyl)thieno[3,2-b]pyridine-3-carboxamide;
N-Methyl-5-(4-((6-methylpyridin-2-yl)methyl)piperazin-1-yl)-7-(trifluoromethyl)thieno[3,2-b]pyridine-3-carboxamide;
Methyl 5-(4-(2-(isopropylamino)-2-oxoethyl)piperazin-1-yl)-7-(trifluoromethyl)thieno[3,2-b]pyridine-3-carboxylate;
5-(4-(2-(Isopropylamino)-2-oxoethyl)piperazin-1-yl)-N-methyl-7-(trifluoromethyl)thieno[3,2-b]pyridine-3-carboxamide;
5-(4-(2-(Isopropylamino)-2-oxoethyl)piperazin-1-yl)-N,N-dimethyl-7-(trifluoromethyl)thieno[3,2-b]pyridine-3-carboxamide;
Methyl 5-(4-(2-(benzylamino)-2-oxoethyl)piperazin-1-yl)-7-(trifluoromethyl)thieno[3,2-b]pyridine-3-carboxylate;
Methyl 5-(4-(2-oxo-2-(phenylamino)ethyl)piperazin-1-yl)-7-(trifluoromethyl)thieno[3,2-b]pyridine-3-carboxylate;
Methyl 5-(4-(2-(cyclohexylamino)-2-oxoethyl)piperazin-1-yl)-7-(trifluoromethyl)thieno[3,2-b]pyridine-3-carboxylate;
Methyl 5-(4-(2-oxo-2-(piperidin-1-yl)ethyl)piperazin-1-yl)-7-(trifluoromethyl)thieno[3,2-b]pyridine-3-carboxylate;
Methyl 5-(4-(2-oxo-2-(pyrrolidin-1-yl)ethyl)piperazin-1-yl)-7-(trifluoromethyl)thieno[3,2-b]pyridine-3-carboxylate;
Methyl 5-(4-(2-(methylamino)-2-oxoethyl)piperazin-1-yl)-7-(trifluoromethyl)thieno[3,2-b]pyridine-3-carboxylate;
Methyl 5-(4-(4-methylpentanoyl)piperazin-1-yl)-7-(trifluoromethyl)thieno[3,2-b]pyridine-3-carboxylate;
Methyl 5-(4-(4-methylpentyl)piperazin-1-yl)-7-(trifluoromethyl)thieno[3,2-b]pyridine-3-carboxylate;
Isobutyl 4-(3-(methylcarbamoyl)-7-(trifluoromethyl)thieno[3,2-b]pyridin-5-yl)piperazine-1-carboxylate;
N-Methyl-5-(4-(pyridin-2-ylmethyl)piperazin-1-yl)-7-(trifluoromethyl)thieno[3,2-b]pyridine-3-carboxamide;
N-Methyl-5-(4-(pyridin-3-ylmethyl)piperazin-1-yl)-7-(trifluoromethyl)thieno[3,2-b]pyridine-3-carboxamide;
N-Methyl-5-(4-(pyridin-4-ylmethyl)piperazin-1-yl)-7-(trifluoromethyl)thieno[3,2-b]pyridine-3-carboxamide;
5-(4-(2-(Ethylamino)-2-oxoethyl)piperazin-1-yl)-N-methyl-7-(trifluoromethyl)thieno[3,2-b]pyridine-3-carboxamide;
5-(4-(2-(Cyclopropylamino)-2-oxoethyl)piperazin-1-yl)-N-methyl-7-(trifluoromethyl)thieno[3,2-b]pyridine-3-carboxamide;
5-(4-(2-(Isobutylamino)-2-oxoethyl)piperazin-1-yl)-N-methyl-7-(trifluoromethyl)thieno[3,2-b]pyridine-3-carboxamide;
(+/−)-5-(4-(1-(Isopropylamino)-1-oxobutan-2-yl)piperazin-1-yl)-N-methyl-7-(trifluoromethyl)thieno[3,2-b]pyridine-3-carboxamide;
5-(4-(1-(Isopropylamino)-2-methyl-1-oxopropan-2-yl)piperazin-1-yl)-N-methyl-7-(trifluoromethyl)thieno[3,2-b]pyridine-3-carboxamide;
tert-Butyl 2-(4-(3-(methylcarbamoyl)-7-(trifluoromethyl)thieno[3,2-b]pyridin-5-yl)piperazin-1-yl)acetate;
(+/−)-tert-Butyl 2-(4-(3-(methylcarbamoyl)-7-(trifluoromethyl)thieno[3,2-b]pyridin-5-yl)piperazin-1-yl)propanoate;
(+/−)-Isopropyl 2-(4-(3-(methylcarbamoyl)-7-(trifluoromethyl)thieno[3,2-b]pyridin-5-yl)piperazin-1-yl)propanoate;

(+/−)-5-(4-(1-(Isopropylamino)-1-oxopropan-2-yl)piperazin-1-yl)-N-methyl-7-(trifluoromethyl)thieno[3,2-b]pyridine-3-carboxamide;
Isopropyl 2-(4-(3-(methylcarbamoyl)-7-(trifluoromethyl)thieno[3,2-b]pyridin-5-yl)piperazin-1-yl)acetate;
5-(4-(2-(tert-butylamino)-2-oxoethyl)piperazin-1-yl)-N-methyl-7-(trifluoromethyl)thieno[3,2-b]pyridine-3-carboxamide;
(S)-5-(4-(1-(Isopropylamino)-1-oxopropan-2-yl)piperazin-1-yl)-N-methyl-7-(trifluoromethyl)thieno[3,2-b]pyridine-3-carboxamide;
(R)-5-(4-(1-(Isopropylamino)-1-oxopropan-2-yl)piperazin-1-yl)-N-methyl-7-(trifluoromethyl)thieno[3,2-b]pyridine-3-carboxamide;
N-Methyl-5-(4-((6-methylpyrazin-2-yl)methyl)piperazin-1-yl)-7-(trifluoromethyl)thieno[3,2-b]pyridine-3-carboxamide;
(+/−)-5-(4-(2-(Cyclopropylmethoxy)propyl)piperazin-1-yl)-N-methyl-7-(trifluoromethyl)thieno[3,2-b]pyridine-3-carboxamide;
(+/−)-5-(4-(1-(Cyclopropylmethoxy)propan-2-yl)piperazin-1-yl)-N-methyl-7-(trifluoromethyl)thieno[3,2-b]pyridine-3-carboxamide;
5-(4-(2-(Cyclopropylmethoxy)ethyl)piperazin-1-yl)-N-methyl-7-(trifluoromethyl)thieno[3,2-b]pyridine-3-carboxamide;
5-(4-(2-Cyclopropoxyethyl)piperazin-1-yl)-N-methyl-7-(trifluoromethyl)thieno[3,2-b]pyridine-3-carboxamide;
5-(4-(2-Isopropoxyethyl)piperazin-1-yl)-N-methyl-7-(trifluoromethyl)thieno[3,2-b]pyridine-3-carboxamide;
5-(4-(2-Isopropoxyacetyl)piperazin-1-yl)-N-methyl-7-(trifluoromethyl)thieno[3,2-b]pyridine-3-carboxamide;
5-(4-(2-(Isopropyl(methyl)amino)-2-oxoethyl)piperazin-1-yl)-N-methyl-7-(trifluoromethyl)thieno[3,2-b]pyridine-3-carboxamide;
5-(4-(1-isopropyl-2-oxopyrrolidin-3-yl)piperazin-1-yl)-N-methyl-7-(trifluoromethyl)thieno[3,2-b]pyridine-3-carboxamide;
5-(4-(2-(Isopropylamino)-2-oxoethyl)piperazin-1-yl)-N,6-dimethyl-7-(trifluoromethyl)thieno[3,2-b]pyridine-3-carboxamide;
5-(4-(2-(Isopropylamino)-2-oxoethyl)piperazin-1-yl)-N,7-dimethylthieno[3,2-b]pyridine-3-carboxamide;
5-(4-(2-(Isopropylamino)-2-oxoethyl)-3,3-dimethylpiperazin-1-yl)-N-methyl-7-(trifluoromethyl)thieno[3,2-b]pyridine-3-carboxamide;
(+/−)-5-(3-Isopropyl-4-(2-(isopropylamino)-2-oxoethyl)piperazin-1-yl)-N-methyl-7-(trifluoromethyl)thieno[3,2-b]pyridine-3-carboxamide;
(+/−)-5-(3-Ethyl-4-(2-(isopropylamino)-2-oxoethyl)piperazin-1-yl)-N-methyl-7-(trifluoromethyl)thieno[3,2-b]pyridine-3-carboxamide;
(+/−)-5-(4-(2-(Isopropylamino)-2-oxoethyl)-2-methylpiperazin-1-yl)-N-methyl-7-(trifluoromethyl)thieno[3,2-b]pyridine-3-carboxamide;
5-(8-(2-(Isopropylamino)-2-oxoethyl)-3,8-diazabicyclo[3.2.1]octan-3-yl)-N-methyl-7-(trifluoromethyl)thieno[3,2-b]pyridine-3-carboxamide;
5-(4-(2-(isopropylamino)-2-oxoethyl)-4,7-diazaspiro[2.5]octan-7-yl)-N-methyl-7-(trifluoromethyl)thieno[3,2-b]pyridine-3-carboxamide;
(+/−)-5-(4-(2-(Isopropylamino)-2-oxoethyl)-3-methylpiperazin-1-yl)-N-methyl-7-(trifluoromethyl)thieno[3,2-b]pyridine-3-carboxamide;
5-(4-(2-(Isopropylamino)-2-oxoethyl)-1,4-diazepan-1-yl)-N-methyl-7-(trifluoromethyl)thieno[3,2-b]pyridine-3-carboxamide;
N-Isopropyl-2-(4-(3-isopropyl-7-(trifluoromethyl)thieno[3,2-b]pyridin-5-yl)piperazin-1-yl)acetamide;
2-(4-(3-(Hydroxymethyl)-7-(trifluoromethyl)thieno[3,2-b]pyridin-5-yl)piperazin-1-yl)-N-isopropylacetamide;
5-(4-(2-(Isopropylamino)-2-oxoethyl)piperazin-1-yl)-7-(trifluoromethyl)thieno[3,2-b]pyridine-3-carboxylic acid;
1-(3-(Methylcarbamoyl)-7-(trifluoromethyl)thieno[3,2-b]pyridin-5-yl)piperidin-4-yl azetidine-1-carboxylate;
1-(3-(Methylcarbamoyl)-7-(trifluoromethyl)thieno[3,2-b]pyridin-5-yl)piperidin-4-yl (S)-pentan-2-ylcarbamate;
1-(3-(Methylcarbamoyl)-7-(trifluoromethyl)thieno[3,2-b]pyridin-5-yl)piperidin-4-yl (S)-(3-methylbutan-2-yl)carbamate;
1-(3-(Methylcarbamoyl)-7-(trifluoromethyl)thieno[3,2-b]pyridin-5-yl)piperidin-4-yl (S)-sec-butylcarbamate;
1-(3-(Methylcarbamoyl)-7-(trifluoromethyl)thieno[3,2-b]pyridin-5-yl)piperidin-4-yl cyclobutylcarbamate;
1-(3-(Methylcarbamoyl)-7-(trifluoromethyl)thieno[3,2-b]pyridin-5-yl)piperidin-4-yl (2-(trifluoromethoxy)ethyl)carbamate;
1-(3-(Methylcarbamoyl)-7-(trifluoromethyl)thieno[3,2-b]pyridin-5-yl)piperidin-4-yl 5-azaspiro[2.3]hexane-5-carboxylate;
1-(3-(Methylcarbamoyl)-7-(trifluoromethyl)thieno[3,2-b]pyridin-5-yl)piperidin-4-yl 1,1-difluoro-5-azaspiro[2.3]hexane-5-carboxylate;
1-(3-(Methylcarbamoyl)-7-(trifluoromethyl)thieno[3,2-b]pyridin-5-yl)piperidin-4-yl 3-(methoxymethyl)azetidine-1-carboxylate;
1-(3-(Methylcarbamoyl)-7-(trifluoromethyl)thieno[3,2-b]pyridin-5-yl)piperidin-4-yl 3-(dimethylamino)-3-methylazetidine-1-carboxylate;
1-(3-(Methylcarbamoyl)-7-(trifluoromethyl)thieno[3,2-b]pyridin-5-yl)piperidin-4-yl 3-((dimethylamino)methyl)azetidine-1-carboxylate;
1-(3-(Methylcarbamoyl)-7-(trifluoromethyl)thieno[3,2-b]pyridin-5-yl)piperidin-4-yl 3-(oxetan-3-yl)azetidine-1-carboxylate;
1-(3-(Methylcarbamoyl)-7-(trifluoromethyl)thieno[3,2-b]pyridin-5-yl)piperidin-4-yl 3-hydroxy-3-(trifluoromethyl)azetidine-1-carboxylate;
1-(3-(Methylcarbamoyl)-7-(trifluoromethyl)thieno[3,2-b]pyridin-5-yl)piperidin-4-yl (1R,6S)-5-methyl-2,5-diazabicyclo[4.1.0]heptane-2-carboxylate;
1-(3-(Methylcarbamoyl)-7-(trifluoromethyl)thieno[3,2-b]pyridin-5-yl)piperidin-4-yl (1S,6R)-5-methyl-2,5-diazabicyclo[4.1.0]heptane-2-carboxylate;
1-(3-(Methylcarbamoyl)-7-(trifluoromethyl)thieno[3,2-b]pyridin-5-yl)piperidin-4-yl 3-cyclopropylazetidine-1-carboxylate;
1-(3-(Methylcarbamoyl)-7-(trifluoromethyl)thieno[3,2-b]pyridin-5-yl)piperidin-4-yl isopropylcarbamate;
1-(3-(Methylcarbamoyl)-7-(trifluoromethyl)thieno[3,2-b]pyridin-5-yl)piperidin-4-yl (cyclobutylmethyl)carbamate;
1-(3-(Methylcarbamoyl)-7-(trifluoromethyl)thieno[3,2-b]pyridin-5-yl)piperidin-4-yl (S)-but-3-yn-2-ylcarbamate;
1-(3-(Methylcarbamoyl)-7-(trifluoromethyl)thieno[3,2-b]pyridin-5-yl)piperidin-4-yl (3S,5S)-3,5-dimethylmorpholine-4-carboxylate;
1-(3-(Methylcarbamoyl)-7-(trifluoromethyl)thieno[3,2-b]pyridin-5-yl)piperidin-4-yl (S)-2-methylpiperidine-1-carboxylate;

1-(3-(Methylcarbamoyl)-7-(trifluoromethyl)thieno[3,2-b]pyridin-5-yl)piperidin-4-yl (S)-2-methylpyrrolidine-1-carboxylate;

1-(3-(Methylcarbamoyl)-7-(trifluoromethyl)thieno[3,2-b]pyridin-5-yl)piperidin-4-yl (S)-(1-cyanoethyl)carbamate;

1-(3-(Methylcarbamoyl)-7-(trifluoromethyl)thieno[3,2-b]pyridin-5-yl)piperidin-4-yl 5,6,7,8-tetrahydro-[1,2,4]triazolo[1,5-a]pyrazine-7-carboxylate;

1-(3-(Methylcarbamoyl)-7-(trifluoromethyl)thieno[3,2-b]pyridin-5-yl)piperidin-4-yl 6-oxa-1-azaspiro[3.3]heptane-1-carboxylate;

1-(3-(Methylcarbamoyl)-7-(trifluoromethyl)thieno[3,2-b]pyridin-5-yl)piperidin-4-yl isopropyl(methyl)carbamate;

(1α,5α,6α)-3-(3-(Methylcarbamoyl)-7-(trifluoromethyl)thieno[3,2-b]pyridin-5-yl)-3-azabicyclo[3.1.0]hexan-6-yl (cyclopropylmethyl)carbamate;

1-(3-(Methylcarbamoyl)-7-(trifluoromethyl)thieno[3,2-b]pyridin-5-yl)piperidin-4-yl 3-(difluoromethoxy)azetidine-1-carboxylate;

1-(3-(Methylcarbamoyl)-7-(trifluoromethyl)thieno[3,2-b]pyridin-5-yl)piperidin-4-yl 3-(trifluoromethoxy)azetidine-1-carboxylate;

1-(3-(Methylcarbamoyl)-7-(trifluoromethyl)thieno[3,2-b]pyridin-5-yl)piperidin-4-yl 3-((trifluoromethoxy)methyl)azetidine-1-carboxylate;

1-(3-(Methylcarbamoyl)-7-(trifluoromethyl)thieno[3,2-b]pyridin-5-yl)piperidin-4-yl (S)-(1-(trifluoromethoxy)propan-2-yl)carbamate;

3,3-Difluoro-1-(3-(methylcarbamoyl)-7-(trifluoromethyl)thieno[3,2-b]pyridin-5-yl)piperidin-4-yl isopropylcarbamate;

3,3-Difluoro-1-(3-(methylcarbamoyl)-7-(trifluoromethyl)thieno[3,2-b]pyridin-5-yl)piperidin-4-yl 4-cyclopropylpiperazine-1-carboxylate;

3,3-Difluoro-1-(3-(methylcarbamoyl)-7-(trifluoromethyl)thieno[3,2-b]pyridin-5-yl)piperidin-4-yl (2S)-2,4-dimethylpiperazine-1-carboxylate;

3,3-Dimethyl-1-(3-(methylcarbamoyl)-7-(trifluoromethyl)thieno[3,2-b]pyridin-5-yl)piperidin-4-yl 4-methylpiperazine-1-carboxylate;

1-(3-(Methylcarbamoyl)-7-(trifluoromethyl)thieno[3,2-b]pyridin-5-yl)piperidin-4-yl 6,7-dihydropyrazolo[1,5-a]pyrazine-5(4H)-carboxylate;

1-(3-(methylcarbamoyl)-7-(trifluoromethyl)thieno[3,2-b]pyridin-5-yl)piperidin-4-yl 5,6-dihydroimidazo[1,5-a]pyrazine-7(8H)-carboxylate;

1-(3-(methylcarbamoyl)-7-(trifluoromethyl)thieno[3,2-b]pyridin-5-yl)piperidin-4-yl 5,6-dihydroimidazo[1,5-a]pyrazine-7(8H)-carboxylate;

1-(3-(Methylcarbamoyl)-7-(trifluoromethyl)thieno[3,2-b]pyridin-5-yl)piperidin-4-yl (3aR,6aS)-5-methylhexahydropyrrolo[3,4-c]pyrrole-2(1H)-carboxylate;

1-(3-(Methylcarbamoyl)-7-(trifluoromethyl)thieno[3,2-b]pyridin-5-yl)piperidin-4-yl 3-(dimethylamino)azetidine-1-carboxylate;

1-(3-(Methylcarbamoyl)-7-(trifluoromethyl)thieno[3,2-b]pyridin-5-yl)piperidin-4-yl (S)-(1-(thiazol-2-yl)ethyl)carbamate;

1-(3-(Methylcarbamoyl)-7-(trifluoromethyl)thieno[3,2-b]pyridin-5-yl)piperidin-4-yl (S)-2-ethyl-4-methylpiperazine-1-carboxylate;

(+/−)-trans-1-(3-(Methylcarbamoyl)-7-(trifluoromethyl)thieno[3,2-b]pyridin-5-yl)piperidin-4-yl 4-methoxy-1-methylpyrrolidin-3-yl)carbamate;

1-(3-(Methylcarbamoyl)-7-(trifluoromethyl)thieno[3,2-b]pyridin-5-yl)piperidin-4-yl (R)-2,4-dimethylpiperazine-1-carboxylate;

1-(3-(Methylcarbamoyl)-7-(trifluoromethyl)thieno[3,2-b]pyridin-5-yl)piperidin-4-yl (S)-2,4-dimethylpiperazine-1-carboxylate;

1-(3-(Methylcarbamoyl)-7-(trifluoromethyl)thieno[3,2-b]pyridin-5-yl)piperidin-4-yl (2-(pyrrolidin-1-yl)ethyl)carbamate;

(+/−)-1-(3-(Methylcarbamoyl)-7-(trifluoromethyl)thieno[3,2-b]pyridin-5-yl)piperidin-4-yl (2-(3-fluoropyrrolidin-1-yl)ethyl)carbamate;

1-(3-(Methylcarbamoyl)-7-(trifluoromethyl)thieno[3,2-b]pyridin-5-yl)piperidin-4-yl (2-(3,3-difluoropyrrolidin-1-yl)ethyl)carbamate;

1-(3-(Methylcarbamoyl)-7-(trifluoromethyl)thieno[3,2-b]pyridin-5-yl)piperidin-4-yl (R)-(1-cyclopropylethyl)carbamate;

1-(3-(Methylcarbamoyl)-7-(trifluoromethyl)thieno[3,2-b]pyridin-5-yl)piperidin-4-yl (S)-(1-cyclopropylethyl)carbamate;

1-(3-(Methylcarbamoyl)-7-(trifluoromethyl)thieno[3,2-b]pyridin-5-yl)piperidin-4-yl pyrrolidin-1-ylcarbamate;

1-(3-(Methylcarbamoyl)-7-(trifluoromethyl)thieno[3,2-b]pyridin-5-yl)piperidin-4-yl (cyclopropylmethyl)(methyl)carbamate;

1-(3-(Methylcarbamoyl)-7-(trifluoromethyl)thieno[3,2-b]pyridin-5-yl)piperidin-4-yl 4-(cyclopropylmethyl)piperazine-1-carboxylate;

1-(3-(Methylcarbamoyl)-7-(trifluoromethyl)thieno[3,2-b]pyridin-5-yl)piperidin-4-yl (2-isopropoxyethyl)carbamate;

1-(3-(Methylcarbamoyl)-7-(trifluoromethyl)thieno[3,2-b]pyridin-5-yl)piperidin-4-yl 4-methylpiperazine-1-carboxylate;

1-(3-(Methylcarbamoyl)-7-(trifluoromethyl)thieno[3,2-b]pyridin-5-yl)piperidin-4-yl ((4-methylmorpholin-2-yl)methyl)carbamate;

1-(3-(Methylcarbamoyl)-7-(trifluoromethyl)thieno[3,2-b]pyridin-5-yl)piperidin-4-yl (R)-3,4-dimethylpiperazine-1-carboxylate;

1-(3-(Methylcarbamoyl)-7-(trifluoromethyl)thieno[3,2-b]pyridin-5-yl)piperidin-4-yl (S)-3,4-dimethylpiperazine-1-carboxylate;

1-(3-(Methylcarbamoyl)-7-(trifluoromethyl)thieno[3,2-b]pyridin-5-yl)piperidin-4-yl (R)-2-(hydroxymethyl)-4-methylpiperazine-1-carboxylate;

1-(3-(Methylcarbamoyl)-7-(trifluoromethyl)thieno[3,2-b]pyridin-5-yl)piperidin-4-yl ((2S,3R)-3-hydroxybutan-2-yl)carbamate;

1-(3-(Methylcarbamoyl)-7-(trifluoromethyl)thieno[3,2-b]pyridin-5-yl)piperidin-4-yl (S)-3-methylmorpholine-4-carboxylate;

1-(3-(Methylcarbamoyl)-7-(trifluoromethyl)thieno[3,2-b]pyridin-5-yl)piperidin-4-yl cis-3-hydroxycyclobutyl)carbamate;

1-(3-(Methylcarbamoyl)-7-(trifluoromethyl)thieno[3,2-b]pyridin-5-yl)piperidin-4-yl trans-3-hydroxycyclobutyl)carbamate;

1-(3-(Methylcarbamoyl)-7-(trifluoromethyl)thieno[3,2-b]pyridin-5-yl)piperidin-4-yl (S)-(1-cyanopropan-2-yl)carbamate;

1-(3-(Methylcarbamoyl)-7-(trifluoromethyl)thieno[3,2-b]pyridin-5-yl)piperidin-4-yl (S)-(1-hydroxypropan-2-yl)carbamate;

1-(3-(Methylcarbamoyl)-7-(trifluoromethyl)thieno[3,2-b]pyridin-5-yl)piperidin-4-yl 3-hydroxyazetidine-1-carboxylate;

1-(3-(Methylcarbamoyl)-7-(trifluoromethyl)thieno[3,2-b]pyridin-5-yl)piperidin-4-yl (S)-(1-methoxypropan-2-yl)carbamate;

(+/−)-1-(3-(Methylcarbamoyl)-7-(trifluoromethyl)thieno[3,2-b]pyridin-5-yl)piperidin-4-yl trans-4-hydroxy-1-methylpyrrolidin-3-yl)carbamate;

1-(3-(Methylcarbamoyl)-7-(trifluoromethyl)thieno[3,2-b]pyridin-5-yl)piperidin-4-yl (2-hydroxy-2-methylpropyl)carbamate;

1-(3-(Methylcarbamoyl)-7-(trifluoromethyl)thieno[3,2-b]pyridin-5-yl)piperidin-4-yl (S)-2-methylpiperazine-1-carboxylate;

4-((Dimethylamino)methyl)-1-(3-(methylcarbamoyl)-7-(trifluoromethyl)thieno[3,2-b]pyridin-5-yl)piperidin-4-yl (S)-2-methylpyrrolidine-1-carboxylate;

4-((Dimethylamino)methyl)-1-(3-(methylcarbamoyl)-7-(trifluoromethyl)thieno[3,2-b]pyridin-5-yl)piperidin-4-yl isopropylcarbamate;

4-(Methoxymethyl)-1-(3-(methylcarbamoyl)-7-(trifluoromethyl)thieno[3,2-b]pyridin-5-yl)piperidin-4-yl isopropylcarbamate;

1-(3-(Dimethylcarbamoyl)-7-(trifluoromethyl)thieno[3,2-b]pyridin-5-yl)piperidin-4-yl (S)-(1-cyanopropan-2-yl)carbamate;

1-(3-(Azetidine-1-carbonyl)-7-(trifluoromethyl)thieno[3,2-b]pyridin-5-yl)piperidin-4-yl (S)-(1-cyanopropan-2-yl)carbamate;

(+/−)-trans-3-(Dimethylamino)-1-(3-(methylcarbamoyl)-7-(trifluoromethyl)thieno[3,2-b]pyridin-5-yl)piperidin-4-yl (cyclopropylmethyl)carbamate;

(+/−)-cis-3-Methyl-1-(3-(methylcarbamoyl)-7-(trifluoromethyl)thieno[3,2-b]pyridin-5-yl)piperidin-4-yl 4-methylpiperazine-1-carboxylate;

1-(3-(Methoxycarbamoyl)-7-(trifluoromethyl)thieno[3,2-b]pyridin-5-yl)piperidin-4-yl (cyclopropylmethyl)carbamate;

(+/−)-trans-1-(3-(Methylcarbamoyl)-7-(trifluoromethyl)thieno[3,2-b]pyridin-5-yl)piperidin-4-yl 4-fluoro-1-methylpyrrolidin-3-yl)carbamate;

(+/−)-cis-1-(3-(Methylcarbamoyl)-7-(trifluoromethyl)thieno[3,2-b]pyridin-5-yl)piperidin-4-yl 4-fluoro-1-methylpyrrolidin-3-yl)carbamate;

5-(3-Isopropyl-2-oxo-1-oxa-3,8-diazaspiro[4.5]decan-8-yl)-N-methyl-7-(trifluoromethyl)thieno[3,2-b]pyridine-3-carboxamide;

5-(2-Isopropyl-2,8-diazaspiro[4.5]decan-8-yl)-N-methyl-7-(trifluoromethyl)thieno[3,2-b]pyridine-3-carboxamide;

1-(3-(Methylcarbamoyl)thieno[3,2-b]pyridin-5-yl)piperidin-4-yl (S)-(1-(trifluoromethoxy)propan-2-yl)carbamate;

1-(7-Methyl-3-(methylcarbamoyl)thieno[3,2-b]pyridin-5-yl)piperidin-4-yl isopropylcarbamate;

1-(7-Methyl-3-(methylcarbamoyl)thieno[3,2-b]pyridin-5-yl)piperidin-4-yl (S)-(1-(trifluoromethoxy)propan-2-yl)carbamate;

N-Methyl-5-(4-((6-methylpyridin-2-yl)oxy)piperidin-1-yl)-7-(trifluoromethyl)thieno[3,2-b]pyridine-3-carboxamide;

5-(4-((6-Ethylpyridin-2-yl)oxy)piperidin-1-yl)-N-methyl-7-(trifluoromethyl)thieno[3,2-b]pyridine-3-carboxamide;

N-Methyl-5-(4-((2-methylpyrimidin-4-yl)oxy)piperidin-1-yl)-7-(trifluoromethyl)thieno[3,2-b]pyridine-3-carboxamide;

(+/−)-N-Methyl-5-(cis-3-methyl-4-((2-methylpyrimidin-4-yl)oxy)piperidin-1-yl)-7-(trifluoromethyl)thieno[3,2-b]pyridine-3-carboxamide;

(+/−)-N-Methyl-5-(trans-3-methyl-4-((2-methylpyrimidin-4-yl)oxy)piperidin-1-yl)-7-(trifluoromethyl)thieno[3,2-b]pyridine-3-carboxamide;

5-(4-((3-Cyclopropyl-1,2,4-thiadiazol-5-yl)oxy)piperidin-1-yl)-N-methyl-7-(trifluoromethyl)thieno[3,2-b]pyridine-3-carboxamide;

1-(6-Methyl-3-(methylcarbamoyl)-7-(trifluoromethyl)thieno[3,2-b]pyridin-5-yl)piperidin-4-yl (S)-(1-cyclopropylethyl)carbamate;

1-(3-(Methylcarbamoyl)-7-(trifluoromethyl)thieno[3,2-b]pyridin-5-yl)piperidin-4-yl (S)-(1-cyanopropan-2-yl)(methyl)carbamate;

1-(3-(Methylcarbamoyl)-7-(trifluoromethyl)thieno[3,2-b]pyridin-5-yl)piperidin-4-yl ((1-(2,2-difluoroethyl)azetidin-3-yl)methyl)carbamate;

Methyl 5-(4-(2-(isopropylamino)-2-oxoethyl)piperidin-1-yl)-7-(trifluoromethyl)thieno[3,2-b]pyridine-3-carboxylate;

5-(4-(2-(Isopropylamino)-2-oxoethyl)piperidin-1-yl)-N-methyl-7-(trifluoromethyl)thieno[3,2-b]pyridine-3-carboxamide;

5-(4-(2-((1-Methoxypropan-2-yl)amino)-2-oxoethyl)piperidin-1-yl)-N-methyl-7-(trifluoromethyl)thieno[3,2-b]pyridine-3-carboxamide;

5-(4-(2-((1,3-Dimethoxypropan-2-yl)amino)-2-oxoethyl)piperidin-1-yl)-N-methyl-7-(trifluoromethyl)thieno[3,2-b]pyridine-3-carboxamide;

(S)-1-Methoxypropan-2-yl (1-(3-(methylcarbamoyl)-7-(trifluoromethyl)thieno[3,2-b]pyridin-5-yl)piperidin-4-yl) carbonate;

Isopropyl (1-(3-(methylcarbamoyl)-7-(trifluoromethyl)thieno[3,2-b]pyridin-5-yl)piperidin-4-yl) carbonate;

(R)-1-Cyclopropylethyl 4-((3-(methylcarbamoyl)-7-(trifluoromethyl)thieno[3,2-b]pyridin-5-yl)oxy)piperidine-1-carboxylate;

(S)-1-Cyclopropylethyl 4-((3-(methylcarbamoyl)-7-(trifluoromethyl)thieno[3,2-b]pyridin-5-yl)oxy)piperidine-1-carboxylate;

Isopropyl 4-((3-(methylcarbamoyl)-7-(trifluoromethyl)thieno[3,2-b]pyridin-5-yl)oxy)piperidine-1-carboxylate;

tert-Butyl 3,3-difluoro-4-((3-(methylcarbamoyl)-7-(trifluoromethyl)thieno[3,2-b]pyridin-5-yl)oxy)piperidine-1-carboxylate;

N-Methyl-5-((1-(6-methylpyridin-2-yl)piperidin-4-yl)oxy)-7-(trifluoromethyl)thieno[3,2-b]pyridine-3-carboxamide;

2-Cyanoethyl 4-((3-(methylcarbamoyl)-7-(trifluoromethyl)thieno[3,2-b]pyridin-5-yl)oxy)piperidine-1-carboxylate;

2-Isopropoxyethyl 4-((3-(methylcarbamoyl)-7-(trifluoromethyl)thieno[3,2-b]pyridin-5-yl)oxy)piperidine-1-carboxylate;

2-(tert-Butoxy)ethyl 4-((3-(methylcarbamoyl)-7-(trifluoromethyl)thieno[3,2-b]pyridin-5-yl)oxy)piperidine-1-carboxylate;

(3-Fluoroazetidin-3-yl)methyl 4-((3-(methylcarbamoyl)-7-(trifluoromethyl)thieno[3,2-b]pyridin-5-yl)oxy)piperidine-1-carboxylate;

1-(Prop-2-yn-1-yl)azetidin-3-yl 4-((3-(methylcarbamoyl)-7-(trifluoromethyl)thieno[3,2-b]pyridin-5-yl)oxy)piperidine-1-carboxylate;

1-(Cyanomethyl)azetidin-3-yl 4-((3-(methylcarbamoyl)-7-(trifluoromethyl)thieno[3,2-b]pyridin-5-yl)oxy)piperidine-1-carboxylate;

2-(Trifluoromethoxy)ethyl 4-((3-(methylcarbamoyl)-7-(trifluoromethyl)thieno[3,2-b]pyridin-5-yl)oxy)piperidine-1-carboxylate;

2-(Trifluoromethoxy)ethyl 4-((6-chloro-3-(methylcarbamoyl)thieno[3,2-b]pyridin-5-yl)oxy)piperidine-1-carboxylate;

2-(Trifluoromethoxy)ethyl 4-((6-bromo-3-(methylcarbamoyl)thieno[3,2-b]pyridin-5-yl)oxy)piperidine-1-carboxylate;

2-(Trifluoromethoxy)ethyl 4-((6-cyclopropyl-3-(methylcarbamoyl)thieno[3,2-b]pyridin-5-yl)oxy)piperidine-1-carboxylate;

(S)-1-(Trifluoromethoxy)propan-2-yl (2R,4R)-2-methyl-4-((3-(methylcarbamoyl)-7-(trifluoromethyl)thieno[3,2-b]pyridin-5-yl)oxy)piperidine-1-carboxylate;

(S)-1-(Trifluoromethoxy)propan-2-yl (2R,4R)-2-methyl-4-((6-methyl-3-(methylcarbamoyl)-7-(trifluoromethyl)thieno[3,2-b]pyridin-5-yl)oxy)piperidine-1-carboxylate;

2-(Trifluoromethoxy)ethyl (2R,4R)-2-methyl-4-((6-methyl-3-(methylcarbamoyl)-7-(trifluoromethyl)thieno[3,2-b]pyridin-5-yl)oxy)piperidine-1-carboxylate;

(S)-1-(Trifluoromethoxy)propan-2-yl 4-((6-methyl-3-(methylcarbamoyl)-7-(trifluoromethyl)thieno[3,2-b]pyridin-5-yl)oxy)piperidine-1-carboxylate;

2-(Trifluoromethoxy)ethyl (2R,4S)-2-methyl-4-((6-methyl-3-(methylcarbamoyl)-7-(trifluoromethyl)thieno[3,2-b]pyridin-5-yl)oxy)piperidine-1-carboxylate;

2-(Trifluoromethoxy)ethyl (3S,4R)-3-fluoro-4-((6-methyl-3-(methylcarbamoyl)-7-(trifluoromethyl)thieno[3,2-b]pyridin-5-yl)oxy)piperidine-1-carboxylate;

(S)-1-(Trifluoromethoxy)propan-2-yl (3S,4R)-3-fluoro-4-((6-methyl-3-(methylcarbamoyl)-7-(trifluoromethyl)thieno[3,2-b]pyridin-5-yl)oxy)piperidine-1-carboxylate;

2-(Trifluoromethoxy)ethyl (3R,4S)-3-fluoro-4-((6-methyl-3-(methylcarbamoyl)-7-(trifluoromethyl)thieno[3,2-b]pyridin-5-yl)oxy)piperidine-1-carboxylate;

(S)-1-(Trifluoromethoxy)propan-2-yl (3R,4S)-3-fluoro-4-((6-methyl-3-(methylcarbamoyl)-7-(trifluoromethyl)thieno[3,2-b]pyridin-5-yl)oxy)piperidine-1-carboxylate;

(S)-1-(Trifluoromethoxy)propan-2-yl (2R,4S)-2-methyl-4-((6-methyl-3-(methylcarbamoyl)-7-(trifluoromethyl)thieno[3,2-b]pyridin-5-yl)oxy)piperidine-1-carboxylate;

1-(3-(Methylcarbamoyl)-7-(trifluoromethyl)isothiazolo[4,5-b]pyridin-5-yl)piperidin-4-yl (cyclopropylmethyl) carbamate;

1-(7-(Methylcarbamoyl)-4-(trifluoromethyl)thieno[3,2-d]pyrimidin-2-yl)piperidin-4-yl (S)-(1-methoxypropan-2-yl)carbamate;

1-(7-(Methylcarbamoyl)-4-(trifluoromethyl)thieno[3,2-d]pyrimidin-2-yl)piperidin-4-yl (S)-(1-cyclopropylethyl) carbamate;

1-(7-(Methylcarbamoyl)-4-(trifluoromethyl)thieno[3,2-d]pyrimidin-2-yl)piperidin-4-yl (S)-2,4-dimethylpiperazine-1-carboxylate;

1-(3-Propionyl-7-(trifluoromethyl)thieno[3,2-b]pyridin-5-yl)piperidin-4-yl 4-methylpiperazine-1-carboxylate dihydrochloride;

5-(3-((5-Fluoropyridin-3-yl)oxy)azetidin-1-yl)-N-methyl-7-(trifluoromethyl)thieno[3,2-b]pyridine-3-carboxamide;

N-Methyl-5-(3-((3-methylpyridin-2-yl)oxy)azetidin-1-yl)-7-(trifluoromethyl)thieno[3,2-b]pyridine-3-carboxamide;

5-(3-((3-Fluoropyridin-2-yl)oxy)azetidin-1-yl)-N-methyl-7-(trifluoromethyl)thieno [3,2b]pyridine-3-carboxamide;

N-Methyl-5-(3-((2-methylpyridin-3-yl)oxy)azetidin-1-yl)-7-(trifluoromethyl)thieno[3,2-b]pyridine-3-carboxamide;

Isopentyl 3-(3-(methylcarbamoyl)-7-(trifluoromethyl)thieno[3,2-b]pyridin-5-yl)azetidine-1-carboxylate;

Cyclopropylmethyl 3-(3-(methylcarbamoyl)-7-(trifluoromethyl)thieno[3,2-b]pyridin-5 yl)azetidine-1-carboxylate;

Isopropyl 6-((3-(methylcarbamoyl)-7-(trifluoromethyl)thieno[3,2-b]pyridin-5-yl)oxy)-2-azaspiro[3.3]heptane-2-carboxylate;

1-Fluoropropan-2-yl 6-((3-(methylcarbamoyl)-7-(trifluoromethyl)thieno[3,2-b]pyridin-5-yl)oxy)-2-azaspiro[3.3]heptane-2-carboxylate;

1-Methoxy-2-methylpropan-2-yl 6-((3-(methylcarbamoyl)-7-(trifluoromethyl)thieno[3,2-b]pyridin-5-yl)oxy)-2-azaspiro[3.3]heptane-2-carboxylate;

2,2-Difluoroethyl 6-((3-(methylcarbamoyl)-7-(trifluoromethyl)thieno[3,2-b]pyridin-5-yl)oxy)-2-azaspiro[3.3]heptane-2-carboxylate;

Oxetan-3-ylmethyl 6-((3-(methylcarbamoyl)-7-(trifluoromethyl)thieno[3,2-b]pyridin-5-yl)oxy)-2-azaspiro[3.3]heptane-2-carboxylate;

Cyclopropyl 6-((3-(methylcarbamoyl)-7-(trifluoromethyl)thieno[3,2-b]pyridin-5-yl)oxy)-2-azaspiro[3.3]heptane-2-carboxylate;

Oxetan-3-yl 6-((3-(methylcarbamoyl)-7-(trifluoromethyl)thieno[3,2-b]pyridin-5-yl)oxy)-2-azaspiro[3.3]heptane-2-carboxylate;

2-(Trifluoromethoxy)ethyl 6-((3-(methylcarbamoyl)-7-(trifluoromethyl)thieno[3,2-b]pyridin-5-yl)oxy)-2-azaspiro[3.3]heptane-2-carboxylate;

(R)-1-Cyclopropylethyl 6-((3-(methylcarbamoyl)-7-(trifluoromethyl)thieno[3,2-b]pyridin-5-yl)oxy)-2-azaspiro[3.3]heptane-2-carboxylate;

(S)-1-Cyclopropylethyl 6-((3-(methylcarbamoyl)-7-(trifluoromethyl)thieno[3,2-b]pyridin-5-yl)oxy)-2-azaspiro[3.3]heptane-2-carboxylate;

5-((2-(3-Fluoro-2,2-dimethylpropanoyl)-2-azaspiro[3.3]heptan-6-yl)oxy)-N-methyl-7-(trifluoromethyl)thieno[3,2-b]pyridine-3-carboxamide;

5-((2-(2,2-Dimethyl-3-(trifluoromethoxy)propanoyl)-2-azaspiro[3.3]heptan-6-yl)oxy)-N-methyl-7-(trifluoromethyl)thieno[3,2-b]pyridine-3-carboxamide;

5-((2-Isobutyryl-2-azaspiro[3.3]heptan-6-yl)oxy)-N-methyl-7-(trifluoromethyl)thieno[3,2-b]pyridine-3-carboxamide;

5-((2-(5-Fluoropyridin-3-yl)-2-azaspiro[3.3]heptan-6-yl)oxy)-N-methyl-7-(trifluoromethyl)thieno[3,2-b]pyridine-3-carboxamide;

5-((2-(6-Fluoropyridin-2-yl)-2-azaspiro[3.3]heptan-6-yl)oxy)-N-methyl-7(trifluoromethyl)thieno[3,2-b]pyridine-3-carboxamide;

N-Methyl-5-((2-(2,2,2-trifluoroethyl)-2-azaspiro[3.3]heptan-6-yl)oxy)-7-(trifluoromethyl)thieno[3,2-b]pyridine-3-carboxamide;

2-(Trifluoromethoxy)ethyl 6-((3-(methylcarbamoyl)-7-(trifluoromethyl)thieno[3,2-b]pyridin-5-yl)oxy)-1-azaspiro[3.3]heptane-1-carboxylate;

tert-Butyl 2-((3-(methylcarbamoyl)-7-(trifluoromethyl)thieno[3,2-b]pyridin-5-yl)oxy)-7-azaspiro[3.5]nonane-7-carboxylate;

2-(Trifluoromethoxy)ethyl 6-((3-(methylcarbamoyl)-7-(trifluoromethyl)thieno[3,2-b]pyridin-5-yl)oxy)-3-azabicyclo[3.1.1]heptane-3-carboxylate;

2-(Trifluoromethoxy)ethyl 3-((6-methyl-3-(methylcarbamoyl)-7-(trifluoromethyl)thieno[3,2-b]pyridin-5-yl)oxy)azetidine-1-carboxylate;

2-(Trifluoromethoxy)ethyl 6-((6-methyl-3-(methylcarbamoyl)-7-(trifluoromethyl)thieno[3,2-b]pyridin-5-yl)oxy)-2-azaspiro[3.3]heptane-2-carboxylate;

(S)-1-Cyclopropylethyl 6-((6-methyl-3-(methylcarbamoyl)-7-(trifluoromethyl)thieno[3,2-b]pyridin-5-yl)oxy)-2-azaspiro[3.3]heptane-2-carboxylate;

Cyclopropylmethyl ((1s,3s)-3-((6-methyl-3-(methylcarbamoyl)-7-(trifluoromethyl)thieno[3,2-b]pyridin-5-yl)oxy)cyclobutyl)carbamate;

Isopropyl ((1s,3s)-3-((6-methyl-3-(methylcarbamoyl)-7-(trifluoromethyl)thieno[3,2-b]pyridin-5-yl)oxy)cyclobutyl)carbamate;

(S)-1-Cyclopropylethyl ((1s,3R)-3-((6-methyl-3-(methylcarbamoyl)-7 (trifluoromethyl)thieno[3,2-b]pyridin-5-yl)oxy)cyclobutyl)carbamate;

(R)-1-Cyclopropylethyl ((1s,3S)-3-((6-methyl-3-(methylcarbamoyl)-7 (trifluoromethyl)thieno[3,2-b]pyridin-5-yl)oxy)cyclobutyl)carbamate;

Cyclopropylmethyl ((1r,3r)-3-((6-methyl-3-(methylcarbamoyl)-7(trifluoromethyl)thieno[3,2-b]pyridin-5-yl)oxy)cyclobutyl)carbamate;

2-(Trifluoromethoxy)ethyl (2R,4R)-4-((6-chloro-3-(methylcarbamoyl)-7-(trifluoromethyl)thieno[3,2-b]pyridin-5-yl)oxy)-2-methylpiperidine-1-carboxylate;

2-(Trifluoromethoxy)ethyl (2S,4S)-4-((6-chloro-3-(methylcarbamoyl)-7-(trifluoromethyl)thieno[3,2-b]pyridin-5-yl)oxy)-2-methylpiperidine-1-carboxylate;

2-(Trifluoromethoxy)ethyl 4-((6-chloro-3-(methylcarbamoyl)-7-(trifluoromethyl)thieno[3,2-b]pyridin-5-yl)oxy)piperidine-1-carboxylate;

tert-Butyl (2R,4R)-4-((6-fluoro-3-(methylcarbamoyl)-7-(trifluoromethyl)thieno[3,2-b]pyridin-5-yl)oxy)-2-methylpiperidine-1-carboxylate;

2-(Trifluoromethoxy)ethyl 6-((6-chloro-3-(methylcarbamoyl)-7-(trifluoromethyl)thieno[3,2-b]pyridin-5-yl)oxy)-2-azaspiro[3.3]heptane-2-carboxylate;

(S)-1-Cyclopropylethyl 6-((6-chloro-3-(methylcarbamoyl)-7-(trifluoromethyl)thieno[3,2-b]pyridin-5-yl)oxy)-2-azaspiro[3.3]heptane-2-carboxylate;

2-(Trifluoromethoxy)ethyl 6-((2-methyl-3-(methylcarbamoyl)-7-(trifluoromethyl)thieno[3,2-b]pyridin-5-yl)oxy)-2-azaspiro[3.3]heptane-2-carboxylate;

5-(cis-3-(3-(Cyclopropylmethyl)ureido)cyclobutoxy)-N,2-dimethyl-7 (trifluoromethyl)thieno[3,2-b]pyridine-3-carboxamide;

(S)-1-cyclopropylethyl ((1s,3R)-3-((3-(methylcarbamoyl)-7-(trifluoromethyl)thieno[3,2-b]pyridin-5-yl)oxy)cyclobutyl)carbamate;

(R)-1-cyclopropylethyl ((1s,3S)-3-((3-(methylcarbamoyl)-7-(trifluoromethyl)thieno[3,2-b]pyridin-5-yl)oxy)cyclobutyl)carbamate;

Oxetan-3-yl (cis-3-((3-(methylcarbamoyl)-7-(trifluoromethyl)thieno[3,2-b]pyridin-5-yl)oxy)cyclobutyl)carbamate;

(S)-1-Methoxypropan-2-yl (cis-3-((3-(methylcarbamoyl)-7-(trifluoromethyl)thieno[3,2-b]pyridin-5-yl)oxy)cyclobutyl)carbamate;

(R)-1-Methoxypropan-2-yl (cis-3-((3-(methylcarbamoyl)-7-(trifluoromethyl)thieno[3,2-b]pyridin-5-yl)oxy)cyclobutyl)carbamate;

2-(Trifluoromethoxy)ethyl (cis-3-((3-(methylcarbamoyl)-7-(trifluoromethyl)thieno[3,2-b]pyridin-5-yl)oxy)cyclobutyl)carbamate;

2,2-Difluoroethyl (cis-3-((3-(methylcarbamoyl)-7-(trifluoromethyl)thieno[3,2-b]pyridin-5-yl)oxy)cyclobutyl)carbamate;

2-(4-Chloro-1H-pyrazol-1-yl)ethyl (cis-3-((3-(methylcarbamoyl)-7-(trifluoromethyl)thieno[3,2-b]pyridin-5-yl)oxy)cyclobutyl)carbamate;

Thiazol-2-ylmethyl (cis-3-((3-(methylcarbamoyl)-7-(trifluoromethyl)thieno[3,2-b]pyridin-5-yl)oxy)cyclobutyl)carbamate;

Cyclopropylmethyl (cis-3-((3-(methylcarbamoyl)-7-(trifluoromethyl)thieno[3,2-b]pyridin-5-yl)oxy)cyclobutyl)carbamate;

Isopropyl (cis-3-((3-(methylcarbamoyl)-7-(trifluoromethyl)thieno[3,2-b]pyridin-5-yl)oxy)cyclobutyl)carbamate;

(+/−)-trans-4-Fluoro-1-methylpyrrolidin-3-yl (cis-3-((3-(methylcarbamoyl)-7-(tri fluoromethyl)thieno[3,2-b]pyridin-5-yl)oxy)cyclobutyl)carbamate;

2-Chloroethyl (cis-3-((3-(methylcarbamoyl)-7-(trifluoromethyl)thieno[3,2-b]pyridin-5-yl)oxy)cyclobutyl)carbamate;

cis-3-((3-(Methylcarbamoyl)-7-(trifluoromethyl)thieno[3,2-b]pyridin-5-yl)oxy)cyclobutyl 3,3-difluoroazetidine-1-carboxylate;

cis-3-((3-(Methylcarbamoyl)-7-(trifluoromethyl)thieno[3,2-b]pyridin-5-yl)oxy)cyclobutyl (2-(trifluoromethoxy)ethyl)carbamate;

cis-3-((3-(Methylcarbamoyl)-7-(trifluoromethyl)thieno[3,2-b]pyridin-5-yl)oxy)cyclobutyl 1-oxa-7-azaspiro[3.5]nonane-7-carboxylate;

cis-3-((3-(Methylcarbamoyl)-7-(trifluoromethyl)thieno[3,2-b]pyridin-5-yl)oxy)cyclobutyl (S)-2,4-dimethylpiperazine-1-carboxylate;

cis-3-((3-(Methylcarbamoyl)-7-(trifluoromethyl)thieno[3,2-b]pyridin-5-yl)oxy)cyclobutyl ((S)-1-cyclopropylethyl)carbamate;

cis-3-((3-(Methylcarbamoyl)-7-(trifluoromethyl)thieno[3,2-b]pyridin-5-yl)oxy)cyclobutyl 5,6-dihydro-[1,2,4]triazolo[1,5-a]pyrazine-7(8H)-carboxylate;

cis-3-((3-(Methylcarbamoyl)-7-(trifluoromethyl)thieno[3,2-b]pyridin-5-yl)oxy)cyclobutyl 3-chloroazetidine-1-carboxylate;

cis-3-((3-(Methylcarbamoyl)-7-(trifluoromethyl)thieno[3,2-b]pyridin-5-yl)oxy)cyclobutyl (S)-3-methylmorpholine-4-carboxylate;

cis-3-((3-(Methylcarbamoyl)-7-(trifluoromethyl)thieno[3,2-b]pyridin-5-yl)oxy)cyclobutyl (cyclopropylmethyl)carbamate;

N-Methyl-5-(cis-3-(pyridin-2-yloxy)cyclobutoxy)-7-(trifluoromethyl)thieno[3,2-b]pyridine-3-carboxamide;

2-(Trifluoromethoxy)ethyl 3-methyl-3-((3-(methylcarbamoyl)-7-(trifluoromethyl)thieno[3,2-b]pyridin-5-yl)oxy)azetidine-1-carboxylate;

3-(Trifluoromethoxy)propyl 3-methyl-3-((3-(methylcarbamoyl)-7-(trifluoromethyl)thieno[3,2-b]pyridin-5-yl)oxy)azetidine-1-carboxylate;

2-(Trifluoromethoxy)ethyl 3-((3-(methylcarbamoyl)-7-(trifluoromethyl)thieno[3,2-b]pyridin-5-yl)oxy)azetidine-1-carboxylate;

2-(Trifluoromethoxy)ethyl 2-(((3-(methylcarbamoyl)-7-(trifluoromethyl)thieno[3,2-b]pyridin-5-yl)oxy)methyl)azetidine-1-carboxylate;

(1-(Trifluoromethyl)cyclopropyl)methyl 4-((3-(methylcarbamoyl)-7-(trifluoromethyl)thieno[3,2-b]pyridin-5-yl)oxy)piperidine-1-carboxylate;

Cyclopropylmethyl (trans-3-((3-(methylcarbamoyl)-7-(trifluoromethyl)thieno[3,2-b]pyridin-5-yl)oxy)cyclobutyl)carbamate;

trans-3-((3-(Methylcarbamoyl)-7-(trifluoromethyl)thieno[3,2-b]pyridin-5-yl)oxy)cyclobutyl (cyclopropylmethyl)carbamate;

3-((3-(Methylcarbamoyl)-7-(trifluoromethyl)thieno[3,2-b]pyridin-5-yl)oxy)cyclobutyl (cyclopropylmethyl)carbamate;

3-(Methylcarbamoyl)-7-(trifluoromethyl)thieno[3,2-b]pyridin-5-yl 4-(3,3,3-trifluoropropoxy)piperidine-1-carboxylate;

1-(tert-Butyl) 4-(3-(methylcarbamoyl)-7-(trifluoromethyl)thieno[3,2-b]pyridin-5-yl) piperazine-1,4-dicarboxylate;

tert-Butyl (2R,4R)-4-((6-chloro-3-(methylcarbamoyl)-7-(trifluoromethyl)thieno[3,2-b]pyridin-5-yl)oxy)-2-methylpiperidine-1-carboxylate;

tert-Butyl 6-((3-(methylcarbamoyl)-7-(trifluoromethyl)thieno[3,2-b]pyridin-5-yl)oxy)-2-azaspiro[3.3]heptane-2-carboxylate;

tert-Butyl 6-((6-methyl-3-(methylcarbamoyl)-7-(trifluoromethyl)thieno[3,2-b]pyridin-5-yl)oxy)-2-azaspiro[3.3]heptane-2-carboxylate;

tert-Butyl 6-((2-methyl-3-(methylcarbamoyl)-7-(trifluoromethyl)thieno[3,2-b]pyridin-5-yl)oxy)-2-azaspiro[3.3]heptane-2-carboxylate;

tert-Butyl 6-((6-chloro-3-(methylcarbamoyl)-7-(trifluoromethyl)thieno[3,2-b]pyridin-5-yl)oxy)-2-azaspiro[3.3]heptane-2-carboxylate;

tert-Butyl 3-methyl-3-((3-(methylcarbamoyl)-7-(trifluoromethyl)thieno[3,2-b]pyridin-5-yl)oxy)azetidine-1-carboxylate;

tert-Butyl 4-((6-chloro-3-(methylcarbamoyl)-7-(trifluoromethyl)thieno[3,2-b]pyridin-5-yl)oxy)piperidine-1-carboxylate;

2-(Trifluoromethoxy)ethyl 4-((5-chloro-3-(methylcarbamoyl)-7 (trifluoromethyl)thieno[3,2-b]pyridin-6-yl)oxy)piperidine-1-carboxylate;

Methyl 6-fluoro-5-((1-((2-(trifluoromethoxy)ethoxy)carbonyl)piperidin-4-yl)oxy)-7-(trifluoromethyl)thieno[3,2-b]pyridine-3-carboxylate;

2-(Trifluoromethoxy)ethyl 4-((6-fluoro-3-(methylcarbamoyl)-7-(trifluoromethyl)thieno[3,2-b]pyridin-5-yl)oxy)piperidine-1-carboxylate;

Methyl 5-(1-(tert-butoxycarbonyl)piperidin-4-yl)-7-(trifluoromethyl)thieno[3,2-b]pyridine-3-carboxylate;

Isobutyl 4-(3-(methylcarbamoyl)-7-(trifluoromethyl)thieno[3,2-b]pyridin-5-yl)piperidine-1-carboxylate;

5-(1-(4-Fluorophenethyl)piperidin-4-yl)-N-methyl-7-(trifluoromethyl)thieno[3,2-b]pyridine-3-carboxamide hydrochloride;

Benzyl 4-(3-(methylcarbamoyl)-7-(trifluoromethyl)thieno[3,2-b]pyridin-5-yl)piperidine-1-carboxylate;

N-Methyl-5-(1-(4-methylpentyl)piperidin-4-yl)-7-(trifluoromethyl)thieno[3,2-b]pyridine-3-carboxamide;

5-(1-(2-(Benzyloxy)ethyl)piperidin-4-yl)-N-methyl-7-(trifluoromethyl)thieno[3,2-b]pyridine-3-carboxamide hydrochloride;

Isopentyl 4-(3-(methylcarbamoyl)-7-(trifluoromethyl)thieno[3,2-b]pyridin-5-yl)piperidine-1-carboxylate;

Isopropoxyethyl 4-(3-(methylcarbamoyl)-7-(trifluoromethyl)thieno[3,2-b]pyridin-5-yl)piperidine-1-carboxylate;

tert-Butyl 2,6-dimethyl-4-((3-(methylcarbamoyl)-7-(trifluoromethyl)thieno[3,2-b]pyridin-5-yl)oxy)piperidine-1-carboxylate;

tert-Butyl (2S,4r,6R)-2,6-dimethyl-4-((3-(methylcarbamoyl)-7-(trifluoromethyl)thieno[3,2-b]pyridin-5-yl)oxy)piperidine-1-carboxylate;

2-(Trifluoromethoxy)ethyl (2S,4r,6R)-2,6-dimethyl-4-((3-(methylcarbamoyl)-7-(trifluoromethyl)thieno[3,2-b]pyridin-5-yl)oxy)piperidine-1-carboxylate;

(+/−)-tert-Butyl (2R,6R)-2,6-dimethyl-4-((3-(methylcarbamoyl)-7-(trifluoromethyl)thieno[3,2-b]pyridin-5-yl)oxy)piperidine-1-carboxylate;

(+/−)-2-Trifluoromethoxy)ethyl (2R,6R)-2,6-dimethyl-4-((3-(methylcarbamoyl)-7-(trifluoromethyl)thieno[3,2-b]pyridin-5-yl)oxy)piperidine-1-carboxylate;

2-(Trifluoromethoxy)ethyl (2R,6R)-2,6-dimethyl-4-((3-(methylcarbamoyl)-7-(trifluoromethyl)thieno[3,2-b]pyridin-5-yl)oxy)piperidine-1-carboxylate;

2-(Trifluoromethoxy)ethyl (2S,6S)-2,6-dimethyl-4-((3-(methylcarbamoyl)-7-(trifluoromethyl)thieno[3,2-b]pyridin-5-yl)oxy)piperidine-1-carboxylate;

4-Nitrophenyl (2S,4r,6R)-2,6-dimethyl-4-((3-(methylcarbamoyl)-7-(trifluoromethyl)thieno[3,2-b]pyridin-5-yl)oxy)piperidine-1-carboxylate;

tert-Butyl 4-((7-methoxy-3-(methylcarbamoyl)thieno[3,2-b]pyridin-5-yl)oxy)piperidine-1-carboxylate;

Methyl 5-(4-(((cyclopropylmethyl)carbamoyl)oxy)piperidin-1-yl)-7-methoxythieno[3,2-b]pyridine-3-carboxylate;

Methyl 5-(4-((cyclopropylcarbamoyl)oxy)piperidin-1-yl)-7-methoxythieno[3,2-b]pyridine-3-carboxylate;

Isobutyl 4-((7-methoxy-3-(methylcarbamoyl)thieno[3,2-b]pyridin-5-yl)oxy)piperidine-1-carboxylate;

2-(Trifluoromethoxy)ethyl 4-((7-hydroxy-3-(methylcarbamoyl)thieno[3,2-b]pyridin-5-yl)oxy)piperidine-1-carboxylate;

2-(Trifluoromethoxy)ethyl 4-((7-(difluoromethoxy)-3-(methylcarbamoyl)thieno[3,2-b]pyridin-5-yl)oxy)piperidine-1-carboxylate;

tert-Butyl (1-(3-(methylcarbamoyl)-7-(trifluoromethyl)thieno[3,2-b]pyridin-5-yl)piperidin-4-yl)carbamate;

Isobutyl (1-(3-(methylcarbamoyl)-7-(trifluoromethyl)thieno[3,2-b]pyridin-5-yl)piperidin-4-yl) carbamate;

Cyclopropylmethyl (1-(3-(methylcarbamoyl)-7-(trifluoromethyl)thieno[3,2-b]pyridin-5-yl)piperidin-4-yl)carbamate;

Neopentyl (1-(3-(methylcarbamoyl)-7-(trifluoromethyl)thieno[3,2-b]pyridin-5-yl)piperidin-4-yl)carbamate;

tert-Butyl (1-(3-(methylcarbamoyl)-7-(trifluoromethyl)thieno[3,2-b]pyridin-5-yl)azetidin-3-yl)carbamate;

Isobutyl (1-(3-(methylcarbamoyl)-7-(trifluoromethyl)thieno[3,2-b]pyridin-5-yl)azetidin-3-yl) carbamate;

Cyclopropylmethyl (1-(3-(methylcarbamoyl)-7-(trifluoromethyl)thieno[3,2-b]pyridin-5-yl)azetidin-3-yl)carbamate;

Neopentyl (1-(3-(methylcarbamoyl)-7-(trifluoromethyl)thieno[3,2-b]pyridin-5-yl)azetidin-3-yl)carbamate;
tert-Butyl methyl(1-(3-(methylcarbamoyl)-7-(trifluoromethyl) thieno[3,2-b]pyridin-5-yl) piperidin-4-yl)carbamate;
Isobutyl methyl(1-(3-(methylcarbamoyl)-7-(trifluoromethyl)thieno[3,2-b]pyridin-5-yl) piperidin-4-yl) carbamate;
1-(7-Cyclopentyl-3-(methylcarbamoyl)thieno[3,2-b]pyridin-5-yl)piperidin-4-yl (cyclopropylmethyl)carbamate;
tert-Butyl (1-(7-cyclopentyl-3-(methylcarbamoyl)thieno[3,2-b]pyridin-5-yl)azetidin-3-yl)carbamate;
1-(7-(tert-Butyl)-3-(methylcarbamoyl)thieno[3,2-b]pyridin-5-yl)piperidin-4-yl (cyclopropylmethyl)carbamate;
1-(7-Isopropyl-3-(methylcarbamoyl)thieno[3,2-b]pyridin-5-yl)piperidin-4-yl (cyclopropylmethyl)carbamate;
tert-Butyl 4-fluoro-4-(((3-(methylcarbamoyl)-7-(trifluoromethyl)thieno[3,2-b]pyridin-5-yl)oxy)methyl)piperidine-1-carboxylate;
Isobutyl 4-fluoro-4-(((3-(methylcarbamoyl)-7-(trifluoromethyl)thieno[3,2-b]pyridin-5-yl)oxy)methyl)piperidine-1-carboxylate;
2,2,2-trifluoroethyl 4-fluoro-4-(((3-(methylcarbamoyl)-7-(trifluoromethyl)thieno[3,2-b]pyridin-5-yl)oxy)methyl)piperidine-1-carboxylate;
2-(Trifluoromethoxy)ethyl 4-fluoro-4-(((3-(methylcarbamoyl)-7-(trifluoromethyl)thieno[3,2-b]pyridin-5-yl)oxy)methyl)piperidine-1-carboxylate;
tert-Butyl 3-fluoro-3-(((3-(methylcarbamoyl)-7-(trifluoromethyl)thieno[3,2-b]pyridin-5-yl)oxy)methyl)azetidine-1-carboxylate;
Isobutyl 3-fluoro-3-(((3-(methylcarbamoyl)-7-(trifluoromethyl)thieno[3,2-b]pyridin-5-yl)oxy)methyl)azetidine-1-carboxylate;
2,2,2-Trifluoroethyl 3-fluoro-3-(((3-(methylcarbamoyl)-7-(trifluoromethyl)thieno[3,2-b]pyridin-5-yl)oxy)methyl)azetidine-1-carboxylate;
2-(Trifluoromethoxy)ethyl 3-fluoro-3-(((3-(methylcarbamoyl)-7-(trifluoromethyl)thieno[3,2-b]pyridin-5-yl)oxy)methyl)azetidine-1-carboxylate;
tert-Butyl 3-methyl-3-(((3-(methylcarbamoyl)-7-(trifluoromethyl)thieno[3,2-b]pyridin-5-yl)oxy)methyl)azetidine-1-carboxylate;
Isobutyl 3-methyl-3-(((3-(methylcarbamoyl)-7-(trifluoromethyl)thieno[3,2-b]pyridin-5-yl)oxy)methyl)azetidine-1-carboxylate;
2,2,2-Trifluoroethyl 3-methyl-3-(((3-(methylcarbamoyl)-7-(trifluoromethyl)thieno[3,2-b]pyridin-5-yl)oxy)methyl)azetidine-1-carboxylate;
2-(Trifluoromethoxy)ethyl 3-methyl-3-(((3-(methylcarbamoyl)-7-(trifluoromethyl)thieno[3,2-b]pyridin-5-yl)oxy)methyl)azetidine-1-carboxylate;
tert-Butyl 4-(((3-(methylcarbamoyl)-7-(trifluoromethyl)thieno[3,2-b]pyridin-5-yl)oxy)methyl)piperidine-1-carboxylate;
2,2,2-Trifluoroethyl 4-(((3-(methylcarbamoyl)-7-(trifluoromethyl)thieno[3,2-b]pyridin-5-yl)oxy)methyl)piperidine-1-carboxylate;
2-(Trifluoromethoxy)ethyl 4-(((3-(methylcarbamoyl)-7-(trifluoromethyl)thieno[3,2-b]pyridin-5-yl)oxy)methyl)piperidine-1-carboxylate;
tert-Butyl 4-methyl-4-(((3-(methylcarbamoyl)-7-(trifluoromethyl)thieno[3,2-b]pyridin-5-yl)oxy)methyl)piperidine-1-carboxylate;
2-(Trifluoromethoxy)ethyl 4-methyl-4-(((3-(methylcarbamoyl)-7-(trifluoromethyl)thieno[3,2-b]pyridin-5-yl)oxy)methyl)piperidine-1-carboxylate;
tert-Butyl (2r,4s)-2-((3-(methylcarbamoyl)-7-(trifluoromethyl)thieno[3,2-b]pyridin-5-yl)oxy)-6-azaspiro[3.4]octane-6-carboxylate;
tert-Butyl (2s,4r)-2-((3-(methylcarbamoyl)-7-(trifluoromethyl)thieno[3,2-b]pyridin-5-yl)oxy)-6-azaspiro[3.4]octane-6-carboxylate;
2-(Trifluoromethoxy)ethyl (2s,4r)-2-((3-(methylcarbamoyl)-7-(trifluoromethyl)thieno[3,2-b]pyridin-5-yl)oxy)-6-azaspiro[3.4]octane-6-carboxylate;
2-(Trifluoromethoxy)ethyl (2r,4s)-2-((3-(methylcarbamoyl)-7-(trifluoromethyl)thieno[3,2-b]pyridin-5-yl)oxy)-6-azaspiro[3.4]octane-6-carboxylate;
tert-Butyl (3aR,5r,6aS)-5-((3-(methylcarbamoyl)-7-(trifluoromethyl)thieno[3,2-b]pyridin-5-yl)oxy)hexahydrocyclopenta[c]pyrrole-2(1H)-carboxylate;
2-(Trifluoromethoxy)ethyl (3aR,5r,6aS)-5-((3-(methylcarbamoyl)-7-(trifluoromethyl)thieno[3,2-b]pyridin-5-yl)oxy)hexahydrocyclopenta[c]pyrrole-2(1H)-carboxylate;
trans-3-(Trifluoromethoxy)cyclobutyl (2R,4R)-4-((6-chloro-3-(methylcarbamoyl)-7-(trifluoromethyl)thieno[3,2-b]pyridin-5-yl)oxy)-2-methylpiperidine-1-carboxylate;
trans-3-((Trifluoromethoxy)methyl)cyclobutyl 4-((3-(methylcarbamoyl)-7-(trifluoromethyl)thieno[3,2-b]pyridin-5-yl)oxy)piperidine-1-carboxylate;
trans-3-(Trifluoromethoxy)cyclobutyl (2R,4R)-2-methyl-4-((3-(methylcarbamoyl)-7-(trifluoromethyl)thieno[3,2-b]pyridin-5-yl)oxy)piperidine-1-carboxylate;
cis-3-Hydroxycyclobutyl 4-((3-(methylcarbamoyl)-7-(trifluoromethyl)thieno[3,2-b]pyridin-5-yl)oxy)piperidine-1-carboxylate;
trans-3-(Trifluoromethoxy)cyclobutyl 4-((3-(methylcarbamoyl)-7-(trifluoromethyl)thieno[3,2-b]pyridin-5-yl)oxy)piperidine-1-carboxylate;
cis-3-(Trifluoromethoxy)cyclobutyl 4-((3-(methylcarbamoyl)-7-(trifluoromethyl)thieno[3,2-b]pyridin-5-yl)oxy)piperidine-1-carboxylate;
Oxetan-3-yl 6-(3-(methylcarbamoyl)-7-(trifluoromethyl)thieno[3,2-b]pyridin-5-yl)-2,6-diazaspiro[3.3]heptane-2-carboxylate;
N-Methyl-5-(6-(2-morpholinoacetyl)-2,6-diazaspiro[3.3]heptan-2-yl)-7-(trifluoromethyl)thieno[3,2-b]pyridine-3-carboxamide;
3-Methyloxetan-3-yl 6-(3-(methylcarbamoyl)-7-(trifluoromethyl)thieno[3,2-b]pyridin-5-yl)-2,6-diazaspiro[3.3]heptane-2-carboxylate;
1-Cyclopropylethyl 6-(3-(methylcarbamoyl)-7-(trifluoromethyl)thieno[3,2-b]pyridin-5-yl)-2,6-diazaspiro[3.3]heptane-2-carboxylate;
(R)-5-(6-(2-Methoxypropanoyl)-2,6-diazaspiro[3.3]heptan-2-yl)-N-methyl-7-(trifluoromethyl)thieno[3,2-b]pyridine-3-carboxamide;
(S)-5-(6-(2-Methoxypropanoyl)-2,6-diazaspiro[3.3]heptan-2-yl)-N-methyl-7-(trifluoromethyl)thieno[3,2-b]pyridine-3-carboxamide;
1-Methoxypropan-2-yl 6-(3-(methylcarbamoyl)-7-(trifluoromethyl)thieno[3,2-b]pyridin-5-yl)-2,6-diazaspiro[3.3]heptane-2-carboxylate;
Oxetan-3-ylmethyl 6-(3-(methylcarbamoyl)-7-(trifluoromethyl)thieno[3,2-b]pyridin-5-yl)-2,6-diazaspiro[3.3]heptane-2-carboxylate;
1-Methylpiperidin-3-yl 6-(3-(methylcarbamoyl)-7-(trifluoromethyl)thieno[3,2-b]pyridin-5-yl)-2,6-diazaspiro[3.3]heptane-2-carboxylate;

1-(1-Methylazetidin-3-yl)ethyl 6-(3-(methylcarbamoyl)-7-(trifluoromethyl)thieno[3,2-b]pyridin-5-yl)-2,6-diazaspiro[3.3]heptane-2-carboxylate;

1-Methylazetidin-3-yl 6-(3-(methylcarbamoyl)-7-(trifluoromethyl)thieno[3,2-b]pyridin-5-yl)-2,6-diazaspiro[3.3]heptane-2-carboxylate;

1-Cyanopropan-2-yl 6-(3-(methylcarbamoyl)-7-(trifluoromethyl)thieno[3,2-b]pyridin-5-yl)-2,6-diazaspiro[3.3]heptane-2-carboxylate;

1-(2-Fluoroethyl)azetidin-3-yl 6-(3-(methylcarbamoyl)-7-(trifluoromethyl)thieno[3,2-b]pyridin-5-yl)-2,6-diazaspiro[3.3]heptane-2-carboxylate;

1-(Cyanomethyl)azetidin-3-yl 6-(3-(methylcarbamoyl)-7-(trifluoromethyl)thieno[3,2-b]pyridin-5-yl)-2,6-diazaspiro[3.3]heptane-2-carboxylate;

2-(Trifluoromethoxy)ethyl 6-(3-(methylcarbamoyl)-7-(trifluoromethyl)thieno[3,2-b]pyridin-5-yl)-2,6-diazaspiro[3.3]heptane-2-carboxylate;

5-(4-((1-Isopropylpyrrolidin-3-yl)oxy)piperidin-1-yl)-N-methyl-7-(trifluoromethyl)thieno[3,2-b]pyridine-3-carboxamide;

5-(4-((1-(2,2-Difluoroethyl)pyrrolidin-3-yl)oxy)piperidin-1-yl)-N-methyl-7-(trifluoromethyl)thieno[3,2-b]pyridine-3-carboxamide;

5-(4-((1-(2-Fluoroethyl)pyrrolidin-3-yl)oxy)piperidin-1-yl)-N-methyl-7-(trifluoromethyl)thieno[3,2-b]pyridine-3-carboxamide;

5-(4-((1-(1,3-Difluoropropan-2-yl)pyrrolidin-3-yl)oxy)piperidin-1-yl)-N-methyl-7-(trifluoromethyl)thieno[3,2-b]pyridine-3-carboxamide;

5-(4-((1-(2,2-Difluoroethyl)azetidin-3-yl)oxy)piperidin-1-yl)-N-methyl-7-(trifluoromethyl)thieno[3,2-b]pyridine-3-carboxamide;

5-(4-((1-(2-Fluoroethyl)azetidin-3-yl)oxy)piperidin-1-yl)-N-methyl-7-(trifluoromethyl)thieno[3,2-b]pyridine-3-carboxamide;

5-(4-((1-(1,3-Difluoropropan-2-yl)azetidin-3-yl)oxy)piperidin-1-yl)-N-methyl-7-(trifluoromethyl)thieno[3,2-b]pyridine-3-carboxamide;

5-(4-(2-(3,3-Difluoropyrrolidin-1-yl)ethoxy)piperidin-1-yl)-N-methyl-7-(trifluoromethyl)thieno[3,2-b]pyridine-3-carboxamide;

5-(4-(2-(3-Fluoropyrrolidin-1-yl)ethoxy)piperidin-1-yl)-N-methyl-7-(trifluoromethyl)thieno[3,2-b]pyridine-3-carboxamide;

5-(4-(2-(4,4-Difluoropiperidin-1-yl)ethoxy)piperidin-1-yl)-N-methyl-7-(trifluoromethyl)thieno[3,2-b]pyridine-3-carboxamide;

5-(4-(2-(3-Hydroxypyrrolidin-1-yl)ethoxy)piperidin-1-yl)-N-methyl-7-(trifluoromethyl)thieno[3,2-b]pyridine-3-carboxamide;

5-(4-(2-(trans-3-Fluoro-4-hydroxypyrrolidin-1-yl)ethoxy)piperidin-1-yl)-N-methyl-7-(trifluoromethyl)thieno[3,2-b]pyridine-3-carboxamide;

N-Methyl-5-(4-(2-morpholinoethoxy)piperidin-1-yl)-7-(trifluoromethyl)thieno[3,2-b]pyridine-3-carboxamide;

5-(4-((6-Isopropylpyridin-2-yl)oxy)piperidin-1-yl)-N-methyl-7-(trifluoromethyl)thieno[3,2-b]pyridine-3-carboxamide;

(+/−)-tert-Butyl trans-2-methyl-4-((3-(methylcarbamoyl)-7-(trifluoromethyl)thieno[3,2-b]pyridin-5-yl)oxy)piperidine-1-carboxylate;

(+/−)-trans-2-(Trifluoromethoxy)ethyl-2-methyl-4-((3-(methylcarbamoyl)-7-(trifluoromethyl)thieno[3,2-b]pyridin-5-yl)oxy)piperidine-1-carboxylate;

(+/−)-tert-Butyl cis-2-methyl-4-((3-(methylcarbamoyl)-7-(trifluoromethyl)thieno[3,2-b]pyridin-5-yl)oxy)piperidine-1-carboxylate;

(+/−)-cis-2-(Trifluoromethoxy)ethyl-2-methyl-4-((3-(methylcarbamoyl)-7-(trifluoromethyl)thieno[3,2-b]pyridin-5-yl)oxy)piperidine-1-carboxylate;

(S)-1-Cyclopropylethyl (2R,4R)-2-methyl-4-((3-(methylcarbamoyl)-7-(trifluoromethyl)thieno[3,2-b]pyridin-5-yl)oxy)piperidine-1-carboxylate;

(S)-1-Cyclopropylethyl (2S,4S)-2-methyl-4-((3-(methylcarbamoyl)-7-(trifluoromethyl)thieno[3,2-b]pyridin-5-yl)oxy)piperidine-1-carboxylate;

tert-Butyl (2R,4R)-2-methyl-4-((3-(methylcarbamoyl)-7-(trifluoromethyl)thieno[3,2-b]pyridin-5-yl)oxy)piperidine-1-carboxylate;

tert-Butyl (2S,4S)-2-methyl-4-((3-(methylcarbamoyl)-7-(trifluoromethyl)thieno[3,2-b]pyridin-5-yl)oxy)piperidine-1-carboxylate;

2-(Trifluoromethoxy)ethyl (2R,4R)-2-methyl-4-((3-(methylcarbamoyl)-7-(trifluoromethyl)thieno[3,2-b]pyridin-5-yl)oxy)piperidine-1-carboxylate;

2-(Trifluoromethoxy)ethyl (2S,4S)-2-methyl-4-((3-(methylcarbamoyl)-7-(trifluoromethyl)thieno[3,2-b]pyridin-5-yl)oxy)piperidine-1-carboxylate;

(+/−)-tert-Butyl trans-3-fluoro-4-((3-(methylcarbamoyl)-7-(trifluoromethyl)thieno[3,2-b]pyridin-5-yl)oxy)piperidine-1-carboxylate;

(+/−)-2-(Trifluoromethoxy)ethyl trans-3-fluoro-4-((3-(methylcarbamoyl)-7-(trifluoromethyl)thieno[3,2-b]pyridin-5-yl)oxy)piperidine-1-carboxylate;

(S)-1-Cyclopropylethyl (3R,4R)-3-fluoro-4-((3-(methylcarbamoyl)-7-(trifluoromethyl)thieno[3,2-b]pyridin-5-yl)oxy)piperidine-1-carboxylate;

(S)-1-Cyclopropylethyl (3S,4S)-3-fluoro-4-((3-(methylcarbamoyl)-7-(trifluoromethyl)thieno[3,2-b]pyridin-5-yl)oxy)piperidine-1-carboxylate;

(+/−)-tert-Butyl cis-3-fluoro-4-((3-(methylcarbamoyl)-7-(trifluoromethyl)thieno[3,2-b]pyridin-5-yl)oxy)piperidine-1-carboxylate;

(+/−)-cis-2-(Trifluoromethoxy)ethyl-3-fluoro-4-((3-(methylcarbamoyl)-7-(trifluoromethyl)thieno[3,2-b]pyridin-5-yl)oxy)piperidine-1-carboxylate;

(S)-1-cyclopropylethyl (3R,4S)-3-fluoro-4-((3-(methylcarbamoyl)-7-(trifluoromethyl)thieno[3,2-b]pyridin-5-yl)oxy)piperidine-1-carboxylate;

(S)-1-cyclopropylethyl (3S,4R)-3-fluoro-4-((3-(methylcarbamoyl)-7-(trifluoromethyl)thieno[3,2-b]pyridin-5-yl)oxy)piperidine-1-carboxylate;

tert-Butyl (3S,4R)-3-fluoro-4-((3-(methylcarbamoyl)-7-(trifluoromethyl)thieno[3,2-b]pyridin-5-yl)oxy)piperidine-1-carboxylate;

tert-Butyl (3R,4S)-3-fluoro-4-((3-(methylcarbamoyl)-7-(trifluoromethyl)thieno[3,2-b]pyridin-5-yl)oxy)piperidine-1-carboxylate;

2-(Trifluoromethoxy)ethyl (3S,4R)-3-fluoro-4-((3-(methylcarbamoyl)-7-(trifluoromethyl)thieno[3,2-b]pyridin-5-yl)oxy)piperidine-1-carboxylate;

2-(Trifluoromethoxy)ethyl (3R,4S)-3-fluoro-4-((3-(methylcarbamoyl)-7-(trifluoromethyl)thieno[3,2-b]pyridin-5-yl)oxy)piperidine-1-carboxylate;

(+/−)-tert-Butyl cis-3-fluoro-4-((6-methyl-3-(methylcarbamoyl)-7-(trifluoromethyl)thieno[3,2-b]pyridin-5-yl)oxy)piperidine-1-carboxylate;

(+/−)-cis-2-(Trifluoromethoxy)ethyl-3-fluoro-4-((6-methyl-3-(methylcarbamoyl)-7-(trifluoromethyl)thieno[3,2-b]pyridin-5-yl)oxy)piperidine-1-carboxylate;

tert-Butyl 4-((6-methyl-3-(methylcarbamoyl)-7-(trifluoromethyl)thieno[3,2-b]pyridin-5-yl)oxy)piperidine-1-carboxylate;

2-(Trifluoromethoxy)ethyl 4-((6-methyl-3-(methylcarbamoyl)-7-(trifluoromethyl)thieno[3,2-b]pyridin-5-yl)oxy)piperidine-1-carboxylate;

tert-Butyl (2R,4R)-2-ethyl-4-((3-(methylcarbamoyl)-7-(trifluoromethyl)thieno[3,2-b]pyridin-5-yl)oxy)piperidine-1-carboxylate;

2-(Trifluoromethoxy)ethyl (2R,4R)-2-ethyl-4-((3-(methylcarbamoyl)-7-(trifluoromethyl)thieno[3,2-b]pyridin-5-yl)oxy)piperidine-1-carboxylate;

tert-Butyl (2R,4S)-2-ethyl-4-((3-(methylcarbamoyl)-7-(trifluoromethyl)thieno[3,2-b]pyridin-5-yl)oxy)piperidine-1-carboxylate;

2-(Trifluoromethoxy)ethyl-(2R,4S)-2-ethyl-4-((3-(methylcarbamoyl)-7-(trifluoromethyl)thieno[3,2-b]pyridin-5-yl)oxy)piperidine-1-carboxylate;

2-Hydroxyethyl 4-((3-(methylcarbamoyl)-7-(trifluoromethyl)thieno[3,2-b]pyridin-5-yl)oxy)piperidine-1-carboxylate;

tert-Butyl 7-((3-(methylcarbamoyl)-7-(trifluoromethyl)thieno[3,2-b]pyridin-5-yl)oxy)-2-azaspiro[3.5]nonane-2-carboxylate;

(R)-5-(4-(2-Cyclopropoxyethyl)-3-methylpiperazin-1-yl)-N-methyl-7-(trifluoromethyl)thieno[3,2-b]pyridine-3-carboxamide;

(S)-5-(4-(2-Cyclopropoxyethyl)-3-methylpiperazin-1-yl)-N-methyl-7-(trifluoromethyl)thieno[3,2-b]pyridine-3-carboxamide;

5-(cis-4-(2-Cyclopropoxyethyl)-3,5-dimethylpiperazin-1-yl)-N-methyl-7-(trifluoromethyl)thieno[3,2-b]pyridine-3-carboxamide;

5-(4-((4-Methoxy-6-methylpyridin-2-yl)methyl)piperazin-1-yl)-N-methyl-7-(trifluoromethyl)thieno[3,2-b]pyridine-3-carboxamide;

5-(4-(3-((Dimethylamino)methyl)benzyl)piperazin-1-yl)-N-methyl-7-(trifluoromethyl)thieno[3,2-b]pyridine-3-carboxamide;

5-(4-(1-((4-Methoxycyclohexyl)amino)-1-oxopropan-2-yl)piperazin-1-yl)-N-methyl-7-(trifluoromethyl)thieno[3,2-b]pyridine-3-carboxamide;

N-Methyl-5-(4-(1-oxo-1-((tetrahydro-2H-pyran-4-yl)amino)propan-2-yl)piperazin-1-yl)-7-(trifluoromethyl)thieno[3,2-b]pyridine-3-carboxamide;

N-Methyl-5-(4-((2-morpholinoethyl)sulfonyl)piperazin-1-yl)-7-(trifluoromethyl)thieno[3,2-b]pyridine-3-carboxamide;

N-Methyl-5-(4-((3-morpholinopropyl)sulfonyl)piperazin-1-yl)-7-(trifluoromethyl)thieno[3,2-b]pyridine-3-carboxamide;

(R)—N-(Cyclopropylmethyl)-2-(2-methyl-4-(3-propionyl-7-(trifluoromethyl)thieno[3,2-b]pyridin-5-yl)piperazin-1-yl)acetamide;

(S)—N-(Cyclopropylmethyl)-2-(2-methyl-4-(3-propionyl-7-(trifluoromethyl)thieno[3,2-b]pyridin-5-yl)piperazin-1-yl)acetamide;

5-(4-(2-(Isopropylamino)-2-oxoethyl)piperazin-1-yl)-N,2-dimethyl-7-(trifluoromethyl)thieno[3,2-b]pyridine-3-carboxamide;

5-(4-(2-(3-Fluoropyrrolidin-1-yl)-1-hydroxyethyl)piperidin-1-yl)-N-methyl-7-(trifluoromethyl)thieno[3,2-b]pyridine-3-carboxamide;

5-(4-(2-(4,4-Difluoropiperidin-1-yl)-1-hydroxyethyl)piperidin-1-yl)-N-methyl-7-(trifluoromethyl)thieno[3,2-b]pyridine-3-carboxamide;

5-(4-(1-Hydroxy-2-morpholinoethyl)piperidin-1-yl)-N-methyl-7-(trifluoromethyl)thieno[3,2-b]pyridine-3-carboxamide;

5-(4-(3-(4,4-Difluoropiperidin-1-yl)-2-hydroxypropyl)piperidin-1-yl)-N-methyl-7-(trifluoromethyl)thieno[3,2-b]pyridine-3-carboxamide;

5-(4-(3-(3,3-Difluoropyrrolidin-1-yl)-2-hydroxypropyl)piperidin-1-yl)-N-methyl-7-(trifluoromethyl)thieno[3,2-b]pyridine-3-carboxamide;

5-(4-(2-(1-(2,2-Difluoroethyl)pyrrolidin-3-yl)-2-hydroxyethyl)piperazin-1-yl)-N-methyl-7-(trifluoromethyl)thieno[3,2-b]pyridine-3-carboxamide;

1-(2-Methyl-3-(methylcarbamoyl)-7-(trifluoromethyl)thieno[3,2-b]pyridin-5-yl)piperidin-4-yl (cyclopropylmethyl)carbamate;

1-(3-(Methylcarbamoyl)-7-(trifluoromethyl)thieno[3,2-b]pyridin-5-yl)piperidin-4-yl (R)-2-(methoxymethyl)pyrrolidine-1-carboxylate;

1-(3-(Methylcarbamoyl)-7-(trifluoromethyl)thieno[3,2-b]pyridin-5-yl)piperidin-4-yl (S)-(1-(2,2-difluoroethoxy)propan-2-yl)carbamate;

(+/−)-trans-3-Fluoro-1-(3-(methylcarbamoyl)-7-(trifluoromethyl)thieno[3,2-b]pyridin-5-yl)piperidin-4-yl ((S)-1-(trifluoromethoxy)propan-2-yl)carbamate;

N-Isopropyl-7-(trifluoromethyl)-5-(3-((4-(trifluoromethyl)cyclohexyl)amino)pyrrolidin-1-yl)thieno[3,2-b]pyridine-3-carboxamide;

7-Cyclopropyl-N-ethyl-5-(4-(2-(isopropylamino)-2-oxoethyl)piperazin-1-yl)thieno[3,2-b]pyridine-3-carboxamide;

N-Butyl-7-cyclopropyl-5-(4-(2-(isopropylamino)-2-oxoethyl)piperazin-1-yl)thieno[3,2-b]pyridine-3-carboxamide;

1-(3-(Azetidine-1-carbonyl)-7-(trifluoromethyl)thieno[3,2-b]pyridin-5-yl)piperidin-4-yl tert-butylcarbamate;

1-(3-(3-Methoxyazetidine-1-carbonyl)-7-(trifluoromethyl)thieno[3,2-b]pyridin-5-yl)piperidin-4-yl tert-butylcarbamate;

1-(3-((3-Chloropropyl)carbamoyl)-7-(trifluoromethyl)thieno[3,2-b]pyridin-5-yl)piperidin-4-yl tert-butylcarbamate hydrochloride;

2-(4-(3-Acetamido-7-(trifluoromethyl)thieno[3,2-b]pyridin-5-yl)piperazin-1-yl)-N-isopropylacetamide;

1-(3-Acetamido-7-(trifluoromethyl)thieno[3,2-b]pyridin-5-yl)piperidin-4-yl (cyclopropylmethyl)carbamate;

1-(3-Acetyl-7-(trifluoromethyl)thieno[3,2-b]pyridin-5-yl)piperidin-4-yl (cyclopropylmethyl)carbamate;

Methyl 5-(4-(((cyclopropylmethyl)carbamoyl)oxy)piperidin-1-yl)-7-(trifluoromethyl)thieno[3,2-b]pyridine-3-carboxylate;

1-(3-(Ethylcarbamoyl)-7-(trifluoromethyl)thieno[3,2-b]pyridin-5-yl)piperidin-4-yl (cyclopropylmethyl)carbamate;

1-(3-(Cyclopropylcarbamoyl)-7-(trifluoromethyl)thieno[3,2-b]pyridin-5-yl)piperidin-4-yl (cyclopropylmethyl)carbamate;

2-(4-(3-Acetyl-7-(trifluoromethyl)thieno[3,2-b]pyridin-5-yl)piperazin-1-yl)-N-isopropylacetamide;

1-(3-(Azetidine-1-carbonyl)-7-(trifluoromethyl)thieno[3,2-b]pyridin-5-yl)piperidin-4-yl (cyclopropylmethyl)carbamate;

1-(3-((2-Methoxyethyl)carbamoyl)-7-(trifluoromethyl)thieno[3,2-b]pyridin-5-yl)piperidin-4-yl (cyclopropylmethyl)carbamate;

1-(3-Propionyl-7-(trifluoromethyl)thieno[3,2-b]pyridin-5-yl)piperidin-4-yl (S)-(1-cyclopropylethyl)carbamate;

1-(3-(1-Hydroxypropyl)-7-(trifluoromethyl)thieno[3,2-b]pyridin-5-yl)piperidin-4-yl ((S)-1-cyclopropylethyl)carbamate;
tert-Butyl 7-(3-acetyl-7-(trifluoromethyl)thieno[3,2-b]pyridin-5-yl)-2,7-diazaspiro[3.5]nonane-2-carboxylate;
1-(7-(3-Acetyl-7-(trifluoromethyl)thieno[3,2-b]pyridin-5-yl)-2,7-diazaspiro[3.5]nonan-2-yl)-3-methylbutan-1-one;
1-(3-(Azetidine-1-carbonyl)-7-(trifluoromethyl)thieno[3,2-b]pyridin-5-yl)piperidin-4-yl 3-fluoroazetidine-1-carboxylate;
1-(3-(Azetidine-1-carbonyl)-7-(trifluoromethyl)thieno[3,2-b]pyridin-5-yl)piperidin-4-yl 3-chloroazetidine-1-carboxylate;
1-(3-(3-Chloroazetidine-1-carbonyl)-7-(trifluoromethyl)thieno[3,2-b]pyridin-5-yl)piperidin-4-yl 3-chloroazetidine-1-carboxylate;
(+/−)-trans-1-(3-(Azetidine-1-carbonyl)-7-(trifluoromethyl)thieno[3,2-b]pyridin-5-yl)-3-fluoropiperidin-4-yl isopropylcarbamate;
7-Cyclopropyl-5-(4-(2-(isopropylamino)-2-oxoethyl)piperazin-1-yl)-N-methylthieno[3,2-b]pyridine-3-carboxamide;
7-Ethyl-5-(4-(2-(isopropylamino)-2-oxoethyl)piperazin-1-yl)-N-methylthieno[3,2-b]pyridine-3-carboxamide;
7-Chloro-5-(4-(2-(isopropylamino)-2-oxoethyl)piperazin-1-yl)-N-methylthieno[3,2-b]pyridine-3-carboxamide;
5-(4-(2-(Isopropylamino)-2-oxoethyl)piperazin-1-yl)-7-methoxy-N-methylthieno[3,2-b]pyridine-3-carboxamide;
7-(Difluoromethyl)-5-(4-(2-(isopropylamino)-2-oxoethyl)piperazin-1-yl)-N-methylthieno[3,2-b]pyridine-3-carboxamide;
7-(Dimethylamino)-5-(4-(2-(isopropylamino)-2-oxoethyl)piperazin-1-yl)-N-methylthieno[3,2-b]pyridine-3-carboxamide;
5-(4-(2-(Isopropylamino)-2-oxoethyl)piperazin-1-yl)-N-methyl-7-(2,2,2-trifluoroethoxy)thieno[3,2-b]pyridine-3-carboxamide;
1-(7-Chloro-3-(methylcarbamoyl)thieno[3,2-b]pyridin-5-yl)piperidin-4-yl (cyclopropylmethyl)carbamate;
1-(7-(Dimethylamino)-3-(methylcarbamoyl)thieno[3,2-b]pyridin-5-yl)piperidin-4-yl (cyclopropylmethyl)carbamate;
1-(7-(Difluoromethyl)-3-(methylcarbamoyl)thieno[3,2-b]pyridin-5-yl)piperidin-4-yl (cyclopropylmethyl)carbamate;
1-(7-(Difluoromethyl)-3-(methylcarbamoyl)thieno[3,2-b]pyridin-5-yl)piperidin-4-yl isopropylcarbamate;
1-(7-(Difluoromethyl)-3-(methylcarbamoyl)thieno[3,2-b]pyridin-5-yl)piperidin-4-yl cyclopropylcarbamate;
1-(7-Methoxy-3-(methylcarbamoyl)thieno[3,2-b]pyridin-5-yl)piperidin-4-yl isopropylcarbamate;
1-(3-(Methylcarbamoyl)-7-(trifluoromethyl)thieno[3,2-b]pyridin-5-yl)azetidin-3-yl (cyclopropylmethyl)carbamate trifluoroacetate;
5-(3-(2,2-Diethoxyethoxy)azetidin-1-yl)-N-methyl-7-(trifluoromethyl)thieno[3,2-b]pyridine-3-carboxamide;
5-(3-(2-Hydroxy-2-methylpropoxy)azetidin-1-yl)-N-methyl-7-(trifluoromethyl)thieno[3,2-b]pyridine-3-carboxamide trifluoroacetate;
5-(3-(2-(Cyclopropylmethoxy)ethoxy)azetidin-1-yl)-N-methyl-7-(trifluoromethyl)thieno[3,2-b]pyridine-3-carboxamide;
(1-(3-(Methylcarbamoyl)-7-(trifluoromethyl)thieno[3,2-b]pyridin-5-yl)azetidin-3-yl)methyl (cyclopropylmethyl)carbamate;
(1-(3-(Methylcarbamoyl)-7-(trifluoromethyl)thieno[3,2-b]pyridin-5-yl)azetidin-3-yl)methyl (1-cyanopropan-2-yl)carbamate;
5-(3-((2-(Isopropylamino)-2-oxoethyl)amino)pyrrolidin-1-yl)-N-methyl-7-(trifluoromethyl)thieno[3,2-b]pyridine-3-carboxamide;
5-(3-(2-(Isopropylamino)-2-oxoethoxy)pyrrolidin-1-yl)-N-methyl-7-(trifluoromethyl)thieno[3,2-b]pyridine-3-carboxamide;
5-(3-((2-(Isopropylamino)-2-oxoethyl)(methyl)amino)pyrrolidin-1-yl)-N-methyl-7-(trifluoromethyl)thieno[3,2-b]pyridine-3-carboxamide;
5-(3-(3-(tert-Butyl)ureido)pyrrolidin-1-yl)-N-methyl-7-(trifluoromethyl)thieno[3,2-b]pyridine-3-carboxamide;
5-(3-(((5-Isopropyloxazol-2-yl)methyl)amino)pyrrolidin-1-yl)-N-methyl-7-(trifluoromethyl)thieno[3,2-b]pyridine-3-carboxamide;
N-Methyl-5-(3-(((4-methylthiazol-2-yl)methyl)amino)pyrrolidin-1-yl)-7-(trifluoromethyl)thieno[3,2-b]pyridine-3-carboxamide;
1-(3-(Methylcarbamoyl)-7-(trifluoromethyl)thieno[3,2-b]pyridin-5-yl)pyrrolidin-3-yl (cyclopropylmethyl)carbamate;
5-(4-(2-(Cyclopropylamino)-2-oxoethyl)piperazin-1-yl)-N-methyl-7-(trifluoromethyl)thieno[3,2-b]pyridine-3-carboxamide hydrogen chloride;
5-(4-(3-(tert-Butyl)ureido)piperidin-1-yl)-N-methyl-7-(trifluoromethyl)thieno[3,2-b]pyridine-3-carboxamide;
5-(4-(3,3-Dimethyl-2-oxobutyl)piperazin-1-yl)-N-methyl-7-(trifluoromethyl)thieno[3,2-b]pyridine-3-carboxamide;
5-(4-(1-(Cyclopropylamino)-1-oxopropan-2-yl)piperazin-1-yl)-N-methyl-7-(trifluoromethyl)thieno[3,2-b]pyridine-3-carboxamide;
1-(3-(Methylcarbamoyl)-7-(trifluoromethyl)thieno[3,2-b]pyridin-5-yl)piperidin-4-yl tert-butylcarbamate;
1-(3-(Methylcarbamoyl)-7-(trifluoromethyl)thieno[3,2-b]pyridin-5-yl)piperidin-4-yl cyclopropylcarbamate;
1-(3-(Methylcarbamoyl)-7-(trifluoromethyl)thieno[3,2-b]pyridin-5-yl)piperidin-4-yl (cyclopropylmethyl)carbamate;
1-(3-(Methylcarbamoyl)-7-(trifluoromethyl)thieno[3,2-b]pyridin-5-yl)piperidin-4-yl (cyclopropylmethyl)carbamate trifluoroacetate;
((+/−)-cis-1-(3-(Methylcarbamoyl)-7-(trifluoromethyl)thieno[3,2-b]pyridin-5-yl)piperidine-3,4-diyl bis((cyclopropylmethyl)carbamate);
(+/−)-cis-4-Hydroxy-1-(3-(methylcarbamoyl)-7-(trifluoromethyl)thieno[3,2-b]pyridin-5-yl)piperidin-3-yl (cyclopropylmethyl)carbamate;
(+/−)-cis-3-Hydroxy-1-(3-(methylcarbamoyl)-7-(trifluoromethyl)thieno[3,2-b]pyridin-5-yl)piperidin-4-yl (cyclopropylmethyl)carbamate;
3-Fluoro-1-(3-(methylcarbamoyl)-7-(trifluoromethyl)thieno[3,2-b]pyridin-5-yl)piperidin-4-yl (cyclopropylmethyl)carbamate;
1-(3-(Methylcarbamoyl)-7-(trifluoromethyl)thieno[3,2-b]pyridin-5-yl)piperidin-4-yl ((tetrahydrofuran-2-yl)methyl)carbamate;
(+/−)-cis-3-methoxy-1-(3-(methylcarbamoyl)-7-(trifluoromethyl)thieno[3,2-b]pyridin-5-yl)piperidin-4-yl (cyclopropylmethyl)carbamate;

1-(3-(Methylcarbamoyl)-7-(trifluoromethyl)thieno[3,2-b]pyridin-5-yl)piperidin-4-yl (2-hydroxy-3-methoxypropyl)carbamate;

1-(3-(Methylcarbamoyl)-7-(trifluoromethyl)thieno[3,2-b]pyridin-5-yl)piperidin-4-yl 3-cyanoazetidine-1-carboxylate;

1-(3-(Methylcarbamoyl)-7-(trifluoromethyl)thieno[3,2-b]pyridin-5-yl)piperidin-4-yl 3-cyanomorpholine-4-carboxylate;

1-(3-(Methylcarbamoyl)-7-(trifluoromethyl)thieno[3,2-b]pyridin-5-yl)piperidin-4-yl ((1,4-dioxan-2-yl)methyl)carbamate;

1-(3-(Methylcarbamoyl)-7-(trifluoromethyl)thieno[3,2-b]pyridin-5-yl)piperidin-4-yl (5-fluoropyridin-3-yl)carbamate trifluoroacetate;

1-(3-(Methylcarbamoyl)-7-(trifluoromethyl)thieno[3,2-b]pyridin-5-yl)piperidin-4-yl 3-chloroazetidine-1-carboxylate;

(+/−)-trans-3-Fluoro-1-(3-(methylcarbamoyl)-7-(trifluoromethyl)thieno[3,2-b]pyridin-5-yl)piperidin-4-yl diisopropylcarbamate;

(+/−)-trans-3-Fluoro-1-(3-(methylcarbamoyl)-7-(trifluoromethyl)thieno[3,2-b]pyridin-5-yl)piperidin-4-yl oxetan-3-ylcarbamate;

(+/−)-tran-3-Fluoro-1-(3-(methylcarbamoyl)-7-(trifluoromethyl)thieno[3,2-b]pyridin-5-yl)piperidin-4-yl isopropylcarbamate;

(+/−)-trans-3-Fluoro-1-(3-(methylcarbamoyl)-7-(trifluoromethyl)thieno[3,2-b]pyridin-5-yl)piperidin-4-yl 3-methoxyazetidine-1-carboxylate;

(+/−)-trans-3-Fluoro-1-(3-(methylcarbamoyl)-7-(trifluoromethyl)thieno[3,2-b]pyridin-5-yl)piperidin-4-yl cyclopropylcarbamate;

(+/−)-trans-3-Fluoro-1-(3-(methylcarbamoyl)-7-(trifluoromethyl)thieno[3,2-b]pyridin-5-yl)piperidin-4-yl 4-methylpiperazine-1-carboxylate;

(+/−)-trans-3-Fluoro-1-(3-(methylcarbamoyl)-7-(trifluoromethyl)thieno[3,2-b]pyridin-5-yl)piperidin-4-yl ((S)-1-cyclopropylethyl)carbamate;

(3R,4R)-3-Fluoro-1-(3-(methylcarbamoyl)-7-(trifluoromethyl)thieno[3,2-b]pyridin-5-yl)piperidin-4-yl isopropylcarbamate;

(3S,4S)-3-Fluoro-1-(3-(methylcarbamoyl)-7-(trifluoromethyl)thieno[3,2-b]pyridin-5-yl)piperidin-4-yl isopropylcarbamate;

(+/−)-trans-3-Fluoro-1-(3-(methylcarbamoyl)-7-(trifluoromethyl)thieno[3,2-b]pyridin-5-yl)piperidin-4-yl (3-fluorocyclobutyl)carbamate;

(+/−)-cis-3-Fluoro-1-(3-(methylcarbamoyl)-7-(trifluoromethyl)thieno[3,2-b]pyridin-5-yl)piperidin-4-yl isopropylcarbamate;

(+/−)-trans-3-Fluoro-1-(3-(methylcarbamoyl)-7-(trifluoromethyl)thieno[3,2-b]pyridin-5-yl)piperidin-4-yl cyclopropylcarbamate;

(+/−)-trans-3-Fluoro-1-(3-(methylcarbamoyl)-7-(trifluoromethyl)thieno[3,2-b]pyridin-5-yl)piperidin-4-yl (2-(trifluoromethoxy)ethyl)carbamate;

(3R,4R)-3-Fluoro-1-(3-(methylcarbamoyl)-7-(trifluoromethyl)thieno[3,2-b]pyridin-5-yl)piperidin-4-yl cyclopropylcarbamate;

(3S,4S)-3-Fluoro-1-(3-(methylcarbamoyl)-7-(trifluoromethyl)thieno[3,2-b]pyridin-5-yl)piperidin-4-yl cyclopropylcarbamate;

(+/−)-trans-3-Fluoro-1-(3-(methylcarbamoyl)-7-(trifluoromethyl)thieno[3,2-b]pyridin-5-yl)piperidin-4-yl (2-(trifluoromethoxy)ethyl)carbamate;

(+/−)-trans-3-Fluoro-1-(3-(methylcarbamoyl)-7-(trifluoromethyl)thieno[3,2-b]pyridin-5-yl)piperidin-4-yl 3-(trifluoromethoxy)azetidine-1-carboxylate;

2-Cyanoethyl (1-(3-(methylcarbamoyl)-7-(trifluoromethyl)thieno[3,2-b]pyridin-5-yl)piperidin-4-yl)carbamate;

3-Cyanocyclobutyl (1-(3-(methylcarbamoyl)-7-(trifluoromethyl)thieno[3,2-b]pyridin-5-yl)piperidin-4-yl)carbamate;

1-Cyanopropan-2-yl (1-(3-(methylcarbamoyl)-7-(trifluoromethyl)thieno[3,2-b]pyridin-5-yl)piperidin-4-yl)carbamate;

4-Methyl-N-(1-(3-(methylcarbamoyl)-7-(trifluoromethyl)thieno[3,2-b]pyridin-5-yl)piperidin-4-yl)morpholine-2-carboxamide;

1-Methoxypropan-2-yl (1-(3-(methylcarbamoyl)-7-(trifluoromethyl)thieno[3,2-b]pyridin-5-yl)piperidin-4-yl)carbamate;

1,3-Dimethoxypropan-2-yl (1-(3-(methylcarbamoyl)-7-(trifluoromethyl)thieno[3,2-b]pyridin-5-yl)piperidin-4-yl)carbamate;

(1,4-Dioxan-2-yl)methyl (1-(3-(methylcarbamoyl)-7-(trifluoromethyl)thieno[3,2-b]pyridin-5-yl)piperidin-4-yl)carbamate;

Oetan-3-ylmethyl (1-(3-(methylcarbamoyl)-7-(trifluoromethyl)thieno[3,2-b]pyridin-5-yl)piperidin-4-yl)carbamate;

(4-Methylmorpholin-3-yl)methyl (1-(3-(methylcarbamoyl)-7-(trifluoromethyl)thieno[3,2-b]pyridin-5-yl)piperidin-4-yl)carbamate;

1-Methylpyrrolidin-3-yl (1-(3-(methylcarbamoyl)-7-(trifluoromethyl)thieno[3,2-b]pyridin-5-yl)piperidin-4-yl)carbamate trifluoroacetate;

Oxetan-3-yl (1-(3-(methylcarbamoyl)-7-(trifluoromethyl)thieno[3,2-b]pyridin-5-yl)piperidin-4-yl)carbamate;

4-Methylpentan-2-yl (1-(3-(methylcarbamoyl)-7-(trifluoromethyl)thieno[3,2-b]pyridin-5-yl)piperidin-4-yl)carbamate;

(S)-1-Cyclopropylethyl (1-(3-(methylcarbamoyl)-7-(trifluoromethyl)thieno[3,2-b]pyridin-5-yl)piperidin-4-yl)carbamate;

(R)-1-Cyclopropylethyl (1-(3-(methylcarbamoyl)-7-(trifluoromethyl)thieno[3,2-b]pyridin-5-yl)piperidin-4-yl)carbamate trifluoroacetate;

1-Cyclopropylpropan-2-yl (1-(3-(methylcarbamoyl)-7-(trifluoromethyl)thieno[3,2-b]pyridin-5-yl)piperidin-4-yl)carbamate;

2-(Trifluoromethoxy)ethyl (1-(3-(methylcarbamoyl)-7-(trifluoromethyl)thieno[3,2-b]pyridin-5-yl)piperidin-4-yl)carbamate;

N-Methyl-5-(4-((4-methylthiazol-2-yl)methyl)piperazin-1-yl)-7-(trifluoromethyl)thieno[3,2-b]pyridine-3-carboxamide;

5-(4-((4,5-Dimethyloxazol-2-yl)methyl)piperazin-1-yl)-N-methyl-7-(trifluoromethyl)thieno[3,2-b]pyridine-3-carboxamide;

5-(4-((5-Isopropyloxazol-2-yl)methyl)piperazin-1-yl)-N-methyl-7-(trifluoromethyl)thieno[3,2-b]pyridine-3-carboxamide;

5-(4-((5-Isopropyl-1,3,4-oxadiazol-2-yl)methyl)piperazin-1-yl)-N-methyl-7-(trifluoromethyl)thieno[3,2-b]pyridine-3-carboxamide;

5-(4-((4,5-Dimethyl-1H-imidazol-2-yl)methyl)piperazin-1-yl)-N-methyl-7-(trifluoromethyl)thieno[3,2-b]pyridine-3-carboxamide;

5-(4-((1-((4,5-dimethyl-1H-imidazol-2-yl)methyl)-4,5-dimethyl-1H-imidazol-2-yl)methyl)piperazin-1-yl)-N-methyl-7-(trifluoromethyl)thieno[3,2-b]pyridine-3-carboxamide;

N-Methyl-5-(4-((5-methyl-1,3,4-oxadiazol-2-yl)methyl)piperazin-1-yl)-7-(trifluoromethyl)thieno[3,2-b]pyridine-3-carboxamide;

5-(4-((4-Isopropylthiazol-2-yl)methyl)piperazin-1-yl)-N-methyl-7-(trifluoromethyl)thieno[3,2-b]pyridine-3-carboxamide;

N-Methyl-5-(4-(1-(4-methylthiazol-2-yl)ethyl)piperazin-1-yl)-7-(trifluoromethyl)thieno[3,2-b]pyridine-3-carboxamide;

N-Methyl-5-(4-(1-(5-methylthiazol-2-yl)ethyl)piperazin-1-yl)-7-(trifluoromethyl)thieno[3,2-b]pyridine-3-carboxamide;

N-Methyl-5-(1-((4-methylthiazol-2-yl)methyl)piperidin-4-yl)-7-(trifluoromethyl)thieno[3,2-b]pyridine-3-carboxamide;

N-Methyl-5-(4-((5-methyl-1,3,4-oxadiazol-2-yl)methoxy)piperidin-1-yl)-7-(trifluoromethyl)thieno[3,2-b]pyridine-3-carboxamide;

N-Methyl-5-(4-(1-(6-methylpyridin-2-yl)ethyl)piperazin-1-yl)-7-(trifluoromethyl)thieno[3,2-b]pyridine-3-carboxamide;

N-Methyl-5-(4-(2-methylthiazole-4-carbonyl)piperazin-1-yl)-7-(trifluoromethyl)thieno[3,2-b]pyridine-3-carboxamide;

5-(4-(5-Cyclopropyl-1,3,4-oxadiazol-2-yl)piperidin-1-yl)-N-methyl-7-(trifluoromethyl)thieno[3,2-b]pyridine-3-carboxamide;

5-(4-((2-(Cyclopropylamino)ethyl)sulfonyl)piperazin-1-yl)-N-methyl-7-(trifluoromethyl)thieno[3,2-b]pyridine-3-carboxamide trifluoroacetate;

5-(4-((2-Isopropoxyethyl)sulfonyl)piperazin-1-yl)-N-methyl-7-(trifluoromethyl)thieno[3,2-b]pyridine-3-carboxamide;

5-(4-((2-(Cyclopropylmethoxy)ethyl)sulfonyl)piperazin-1-yl)-N-methyl-7-(trifluoromethyl)thieno[3,2-b]pyridine-3-carboxamide;

5-(4-((2-(Cyclopropyl(methyl)amino)ethyl)sulfonyl)piperazin-1-yl)-N-methyl-7-(trifluoromethyl)thieno[3,2-b]pyridine-3-carboxamide;

5-(4-((2-(3-Methoxyazetidin-1-yl)ethyl)sulfonyl)piperazin-1-yl)-N-methyl-7-(trifluoromethyl)thieno[3,2-b]pyridine-3-carboxamide;

5-(4-((2-(Isopropylamino)-2-oxoethyl)amino)piperidin-1-yl)-N-methyl-7-(trifluoromethyl)thieno[3,2-b]pyridine-3-carboxamide trifluoroacetate;

5-(4-(((tert-Butylsulfinyl)amino)methyl)piperidin-1-yl)-N-methyl-7-(trifluoromethyl)thieno[3,2-b]pyridine-3-carboxamide;

5-(4-(((Cyclopropylmethyl)amino)methyl)piperidin-1-yl)-N-methyl-7-(trifluoromethyl)thieno[3,2-b]pyridine-3-carboxamide trifluoroacetate;

5-(4-(2-Isopropoxyethoxy)piperidin-1-yl)-N-methyl-7-(trifluoromethyl)thieno[3,2-b]pyridine-3-carboxamide;

5-(4-(1-(Cyclopropylmethoxy)-3-hydroxypropan-2-yl)piperazin-1-yl)-N-methyl-7-(trifluoromethyl)thieno[3,2-b]pyridine-3-carboxamide;

5-(4-(3-Formamidopropyl)piperazin-1-yl)-N-methyl-7-(trifluoromethyl)thieno[3,2-b]pyridine-3-carboxamide;

5-(4-(2-(Bis(cyclopropylmethyl)amino)ethyl)piperazin-1-yl)-N-methyl-7-(trifluoromethyl)thieno[3,2-b]pyridine-3-carboxamide;

5-(4-(3-(Cyclopropanecarboxamido)propyl)piperazin-1-yl)-N-methyl-7-(trifluoromethyl)thieno[3,2-b]pyridine-3-carboxamide trifluoroacetate;

5-(4-(2-(Cyclopropylmethoxy)ethoxy)piperidin-1-yl)-N-methyl-7-(trifluoromethyl)thieno[3,2-b]pyridine-3-carboxamide;

5-(4-(2-(Isopropylsulfonyl)ethyl)piperazin-1-yl)-N-methyl-7-(trifluoromethyl)thieno[3,2-b]pyridine-3-carboxamide;

5-(4-(2-Hydroxy-3-morpholinopropoxy)piperidin-1-yl)-N-methyl-7-(trifluoromethyl)thieno[3,2-b]pyridine-3-carboxamide;

5-(4-((4-Isopropylmorpholin-2-yl)methyl)piperazin-1-yl)-N-methyl-7-(trifluoromethyl)thieno[3,2-b]pyridine-3-carboxamide trifluoroacetate;

Methyl 5-(4-((3-isopropoxyazetidin-1-yl)methyl)piperidin-1-yl)-7-(trifluoromethyl)thieno[3,2-b]pyridine-3-carboxylate;

5-(4-((3-Isopropoxyazetidin-1-yl)methyl)piperidin-1-yl)-N-methyl-7-(trifluoromethyl)thieno[3,2-b]pyridine-3-carboxamide;

5-(4-(3-(3,3-Difluoropyrrolidin-1-yl)-2-hydroxypropoxy)piperidin-1-yl)-N-methyl-7-(trifluoromethyl)thieno[3,2-b]pyridine-3-carboxamide;

5-(4-(2-hydroxy-3-isopropoxypropoxy)piperidin-1-yl)-N-methyl-7-(trifluoromethyl)thieno[3,2-b]pyridine-3-carboxamide;

5-(4-((5-Isopropyl-1,3,4-oxadiazol-2-yl)methoxy)piperidin-1-yl)-N-methyl-7-(trifluoromethyl)thieno[3,2-b]pyridine-3-carboxamide;

(S)-1-Cyclopropylethyl 7-(3-(methylcarbamoyl)-7-(trifluoromethyl)thieno[3,2-b]pyridin-5-yl)-2,7-diazaspiro[3.5]nonane-2-carboxylate;

Cyclopropyl 7-(3-(methylcarbamoyl)-7-(trifluoromethyl)thieno[3,2-b]pyridin-5-yl)-2,7-diazaspiro[3.5]nonane-2-carboxylate;

Oxetan-3-yl 7-(3-(methylcarbamoyl)-7-(trifluoromethyl)thieno[3,2-b]pyridin-5-yl)-2,7-diazaspiro[3.5]nonane-2-carboxylate;

Isopropyl 7-(3-(methylcarbamoyl)-7-(trifluoromethyl)thieno[3,2-b]pyridin-5-yl)-2,7-diazaspiro[3.5]nonane-2-carboxylate;

5-(2-(Ethyl(isopropyl)carbamoyl)-2,7-diazaspiro[3.5]nonan-7-yl)-N-methyl-7-(trifluoromethyl)thieno[3,2-b]pyridine-3-carboxamide;

tert-Butyl 4-(3-(methylcarbamoyl)-7-(trifluoromethyl)thieno[3,2-b]pyridin-5-yl)piperidine-1-carboxylate;

5-(1-(1-(Cyclopropylamino)-1-oxopropan-2-yl)piperidin-4-yl)-N-methyl-7-(trifluoromethyl)thieno[3,2-b]pyridine-3-carboxamide;

N-Methyl-5-(1-((4-methylthiazol-2-yl)methyl)piperidin-4-yl)-7-(trifluoromethyl)thieno[3,2-b]pyridine-3-carboxamide hydrogen chloride;

(S)-1-Cyclopropylethyl 4-(3-(methylcarbamoyl)-7-(trifluoromethyl)thieno[3,2-b]pyridin-5-yl)piperidine-1-carboxylate;

4-Methylpentan-2-yl 4-(3-(methylcarbamoyl)-7-(trifluoromethyl)thieno[3,2-b]pyridin-5-yl)piperidine-1-carboxylate;

4-(3-(Methylcarbamoyl)-7-(trifluoromethyl)thieno[3,2-b]pyridin-5-yl)cyclohex-3-en-1-yl (cyclopropylmethyl)carbamate;

2-Cyclopropylethyl 4-(3-(methylcarbamoyl)-7-(trifluoromethyl)thieno[3,2-b]pyridin-5-yl)piperidine-1-carboxylate;

tert-Butyl (3S,4S)-3,4-dihydroxy-4-(3-(methylcarbamoyl)-7-(trifluoromethyl)thieno[3,2-b]pyridin-5-yl)piperidine-1-carboxylate;

2-Cyclopropyl-2-oxoethyl 4-(3-(methylcarbamoyl)-7-(trifluoromethyl)thieno[3,2-b]pyridin-5-yl)piperidine-1-carboxylate;

4-(3-(Methylcarbamoyl)-7-(trifluoromethyl)thieno[3,2-b]pyridin-5-yl)cyclohexyl (cyclopropylmethyl)carbamate;

2-(Trifluoromethoxy)ethyl 4-(3-(methylcarbamoyl)-7-(trifluoromethyl)thieno[3,2-b]pyridin-5-yl)piperidine-1-carboxylate;

tert-Butyl 6-(3-(methylcarbamoyl)-7-(trifluoromethyl)thieno[3,2-b]pyridin-5-yl)-2-azaspiro[3.3]heptane-2-carboxylate;

tert-Butyl 2-(3-(methylcarbamoyl)-7-(trifluoromethyl)thieno[3,2-b]pyridin-5-yl)-7-azaspiro[3.5]nonane-7-carboxylate;

2-(Trifluoromethoxy)ethyl 6-(3-(methylcarbamoyl)-7-(trifluoromethyl)thieno[3,2-b]pyridin-5-yl)-2-azaspiro[3.3]heptane-2-carboxylate;

2-(Trifluoromethoxy)ethyl 2-(3-(methylcarbamoyl)-7-(trifluoromethyl)thieno[3,2-b]pyridin-5-yl)-7-azaspiro[3.5]nonane-7-carboxylate;

tert-Butyl 4-((3-(methylcarbamoyl)-7-(trifluoromethyl)thieno[3,2-b]pyridin-5-yl)thio)piperidine-1-carboxylate;

tert-Butyl 4-((3-(methylcarbamoyl)-7-(trifluoromethyl)thieno[3,2-b]pyridin-5-yl)sulfinyl)piperidine-1-carboxylate;

tert-butyl 4-((3-(methylcarbamoyl)-7-(trifluoromethyl)thieno[3,2-b]pyridin-5-yl)sulfonyl)piperidine-1-carboxylate;

5-(4-(2-(Cyclopropylamino)-2-oxoethoxy)phenyl)-N-methyl-7-(trifluoromethyl)thieno[3,2-b]pyridine-3-carboxamide;

(1-(3-(Methylcarbamoyl)-7-(trifluoromethyl)thieno[3,2-b]pyridin-5-yl)-1H-imidazol-4-yl)methyl (cyclopropylmethyl)carbamate;

tert-Butyl 3-(((3-(methylcarbamoyl)-7-(trifluoromethyl)thieno[3,2-b]pyridin-5-yl)oxy)methyl)pyrrolidine-1-carboxylate;

tert-Butyl 3-(((3-(methylcarbamoyl)-7-(trifluoromethyl)thieno[3,2-b]pyridin-5-yl)oxy)methyl)azetidine-1-carboxylate;

5-((6-Methoxypyridin-3-yl)methoxy)-N-methyl-7-(trifluoromethyl)thieno[3,2-b]pyridine-3-carboxamide trifluoroacetate;

5-((1-(Cyclopropylcarbamoyl)azetidin-3-yl)methoxy)-N-methyl-7-(trifluoromethyl)thieno[3,2-b]pyridine-3-carboxamide;

tert-Butyl 3-((3-(methylcarbamoyl)-7-(trifluoromethyl)thieno[3,2-b]pyridin-5-yl)oxy)azetidine-1-carboxylate;

tert-Butyl 3-((3-(methylcarbamoyl)-7-(trifluoromethyl)thieno[3,2-b]pyridin-5-yl)oxy)pyrrolidine-1-carboxylate;

5-((1-((Cyclopropylmethyl)carbamoyl)pyrrolidin-3-yl)oxy)-N-methyl-7-(trifluoromethyl)thieno[3,2-b]pyridine-3-carboxamide;

tert-Butyl (R)-3-((3-(methylcarbamoyl)-7-(trifluoromethyl)thieno[3,2-b]pyridin-5-yl)oxy)pyrrolidine-1-carboxylate;

(R)-5-((1-((Cyclopropylmethyl)carbamoyl)pyrrolidin-3-yl)oxy)-N-methyl-7-(trifluoromethyl)thieno[3,2-b]pyridine-3-carboxamide;

tert-Butyl (S)-3-((3-(methylcarbamoyl)-7-(trifluoromethyl)thieno[3,2-b]pyridin-5-yl)oxy)pyrrolidine-1-carboxylate;

(S)-5-((1-((Cyclopropylmethyl)carbamoyl)pyrrolidin-3-yl)oxy)-N-methyl-7-(trifluoromethyl)thieno[3,2-b]pyridine-3-carboxamide;

Cyclopropylmethyl (S)-3-((3-(methylcarbamoyl)-7-(trifluoromethyl)thieno[3,2-b]pyridin-5-yl)oxy)pyrrolidine-1-carboxylate;

1-Methoxypropan-2-yl (3S)-3-((3-(methylcarbamoyl)-7-(trifluoromethyl)thieno[3,2-b]pyridin-5-yl)oxy)pyrrolidine-1-carboxylate;

1-Cyanoethyl (3R)-3-((3-(methylcarbamoyl)-7-(trifluoromethyl)thieno[3,2-b]pyridin-5-yl)oxy)pyrrolidine-1-carboxylate;

1,3-Difluoropropan-2-yl (S)-3-((3-(methylcarbamoyl)-7-(trifluoromethyl)thieno[3,2-b]pyridin-5-yl)oxy)pyrrolidine-1-carboxylate;

tert-Butyl 3-hydroxy-4-((3-(methylcarbamoyl)-7-(trifluoromethyl)thieno[3,2-b]pyridin-5-yl)oxy)pyrrolidine-1-carboxylate;

2-(Trifluoromethoxy)ethyl (S)-3-((3-(methylcarbamoyl)-7-(trifluoromethyl)thieno[3,2-b]pyridin-5-yl)oxy)pyrrolidine-1-carboxylate;

Isopropyl (S)-3-((3-(methylcarbamoyl)-7-(trifluoromethyl)thieno[3,2-b]pyridin-5-yl)oxy)pyrrolidine-1-carboxylate;

(S)-1-Cyclopropylethyl (S)-3-((3-(methylcarbamoyl)-7-(trifluoromethyl)thieno[3,2-b]pyridin-5-yl)oxy)pyrrolidine-1-carboxylate;

3-(Trifluoromethoxy)propyl (S)-3-((3-(methylcarbamoyl)-7-(trifluoromethyl)thieno[3,2-b]pyridin-5-yl)oxy)pyrrolidine-1-carboxylate;

2,2,2-Trifluoroethyl (S)-3-((3-(methylcarbamoyl)-7-(trifluoromethyl)thieno[3,2-b]pyridin-5-yl)oxy)pyrrolidine-1-carboxylate;

tert-Butyl (+/−)-trans-3-fluoro-4-((3-(methylcarbamoyl)-7-(trifluoromethyl)thieno[3,2-b]pyridin-5-yl)oxy)pyrrolidine-1-carboxylate;

2-(Trifluoromethoxy)ethyl (+/−)-trans-3-fluoro-4-((3-(methylcarbamoyl)-7-(trifluoromethyl)thieno[3,2-b]pyridin-5-yl)oxy)pyrrolidine-1-carboxylate;

Cyclopropylmethyl (+/−)-trans-3-fluoro-4-((3-(methylcarbamoyl)-7-(trifluoromethyl)thieno[3,2-b]pyridin-5-yl)oxy)pyrrolidine-1-carboxylate;

2-Cyclopropylethyl (S)-3-((3-(methylcarbamoyl)-7-(trifluoromethyl)thieno[3,2-b]pyridin-5-yl)oxy)pyrrolidine-1-carboxylate;

tert-Butyl (+/−)-cis-3-fluoro-4-((3-(methylcarbamoyl)-7-(trifluoromethyl)thieno[3,2-b]pyridin-5-yl)oxy)pyrrolidine-1-carboxylate;

Cyclopropylmethyl (+/−)-cis-3-fluoro-4-((3-(methylcarbamoyl)-7-(trifluoromethyl)thieno[3,2-b]pyridin-5-yl)oxy)pyrrolidine-1-carboxylate;

2-(Trifluoromethoxy)ethyl (+/−)-cis-3-fluoro-4-((3-(methylcarbamoyl)-7-(trifluoromethyl)thieno[3,2-b]pyridin-5-yl)oxy)pyrrolidine-1-carboxylate;

3,3,3-Trifluoropropyl (S)-3-((3-(methylcarbamoyl)-7-(trifluoromethyl)thieno[3,2-b]pyridin-5-yl)oxy)pyrrolidine-1-carboxylate;

(2,2-Difluorocyclopropyl)methyl (3S)-3-((3-(methylcarbamoyl)-7-(trifluoromethyl)thieno[3,2-b]pyridin-5-yl)oxy)pyrrolidine-1-carboxylate;

4,4,4-Trifluorobutyl (S)-3-((3-(methylcarbamoyl)-7-(trifluoromethyl)thieno[3,2-b]pyridin-5-yl)oxy)pyrrolidine-1-carboxylate;

tert-Butyl (+/−)-trans-3-((3-(methylcarbamoyl)-7-(trifluoromethyl)thieno[3,2-b]pyridin-5-yl)oxy)-4-morpholinopyrrolidine-1-carboxylate;
(5-(Trifluoromethyl)isoxazol-3-yl)methyl (S)-3-((3-(methylcarbamoyl)-7-(trifluoromethyl)thieno[3,2-b]pyridin-5-yl)oxy)pyrrolidine-1-carboxylate;
2-(Trifluoromethoxy)ethyl (R)-3-((3-(methylcarbamoyl)-7-(trifluoromethyl)thieno[3,2-b]pyridin-5-yl)oxy)pyrrolidine-1-carboxylate;
tert-Butyl ((+/−)-trans-3-(dimethylamino)-4-((3-(methylcarbamoyl)-7-(trifluoromethyl)thieno[3,2-b]pyridin-5-yl)oxy)pyrrolidine-1-carboxylate;
2-(Trifluoromethoxy)ethyl (+/−)-trans-3-(dimethylamino)-4-((3-(methylcarbamoyl)-7-(trifluoromethyl)thieno[3,2-b]pyridin-5-yl)oxy)pyrrolidine-1-carboxylate;
tert-Butyl (S)-3-((6-methyl-3-(methylcarbamoyl)-7-(trifluoromethyl)thieno[3,2-b]pyridin-5-yl)oxy)pyrrolidine-1-carboxylate;
tert-Butyl (+/−)-trans-3-methoxy-4-((3-(methylcarbamoyl)-7-(trifluoromethyl)thieno[3,2-b]pyridin-5-yl)oxy)pyrrolidine-1-carboxylate;
2-(Trifluoromethoxy)ethyl ((+/−)-trans-3-methoxy-4-((3-(methylcarbamoyl)-7-(trifluoromethyl)thieno[3,2-b]pyridin-5-yl)oxy)pyrrolidine-1-carboxylate;
2-(Trifluoromethoxy)ethyl (S)-3-((6-methyl-3-(methylcarbamoyl)-7-(trifluoromethyl)thieno[3,2-b]pyridin-5-yl)oxy)pyrrolidine-1-carboxylate;
tert-Butyl 4-((3-(methylcarbamoyl)-7-(trifluoromethyl)thieno[3,2-b]pyridin-5-yl)oxy)piperidine-1-carboxylate;
5-((1-(2-(Isopropylamino)-2-oxoethyl)piperidin-4-yl)oxy)-N-methyl-7-(trifluoromethyl)thieno[3,2-b]pyridine-3-carboxamide;
tert-Butyl (+/−)-cis-4-((3-(methylcarbamoyl)-7-(trifluoromethyl)thieno[3,2-b]pyridin-5-yl)oxy)cyclohexyl)carbamate;
Isopropyl (+/−)-cis-4-((3-(methylcarbamoyl)-7-(trifluoromethyl)thieno[3,2-b]pyridin-5-yl)oxy)cyclohexyl)carbamate;
tert-Butyl (+/−)-endo7-((3-(methylcarbamoyl)-7-(trifluoromethyl)thieno[3,2-b]pyridin-5-yl)oxy)-3-oxa-9-azabicyclo[3.3.1]nonane-9-carboxylate;
2-(Trifluoromethoxy)ethyl (+/−)-endo7-((3-(methylcarbamoyl)-7-(trifluoromethyl)thieno[3,2 b]pyridin-5-yl)oxy)-3-oxa-9-azabicyclo[3.3.1]nonane-9-carboxylate;
tert-Butyl (+/−)-exo-3-((3-(methylcarbamoyl)-7-(trifluoromethyl)thieno[3,2-b]pyridin-5-yl)oxy)-8-azabicyclo[3.2.1]octane-8-carboxylate;
tert-Butyl (+/−)-endo3-((3-(methylcarbamoyl)-7-(trifluoromethyl)thieno[3,2-b]pyridin-5-yl)oxy)-8-azabicyclo[3.2.1]octane-8-carboxylate;
2-(Trifluoromethoxy)ethyl 4-((3-(methylcarbamoyl)-7-(trifluoromethyl)thieno[3,2-b]pyridin-5-yl)methyl)piperidine-1-carboxylate;
5-(4-((Cyclopropylmethyl)carbamoyl)piperazin-1-yl)-N-methyl-7-(trifluoromethyl)thieno[3,2-b]pyridine-3-carboxamide trifluoroacetate;
tert-Butyl 4-((3-(methylcarbamoyl)-7-(trifluoromethyl)thieno[3,2-b]pyridin-5-yl)methyl)piperidine-1-carboxylate;
2-(Trifluoromethoxy)ethyl (+/−)-exo-3-((3-(methylcarbamoyl)-7-(trifluoromethyl)thieno[3,2-b]pyridin-5-yl)oxy)-8-azabicyclo[3.2.1]octane-8-carboxamide;
6-Chloro-5-[4-[2-(isopropylamino)-2-oxo-ethyl]piperazin-1-yl]-N-methyl-7-(trifluoromethyl)thieno[3,2-b]pyridine-3-carboxamide;
6-Chloro-5-[4-[2-(isopropylamino)-2-oxo-ethyl]piperazin-1-yl]-2-methoxy-N-methyl-7-(trifluoromethyl)thieno[3,2-b]pyridine-3-carboxamide;
[1-[6-Chloro-3-(methylcarbamoyl)-7-(trifluoromethyl)thieno[3,2-b]pyridin-5-yl]-4-piperidyl] N-(cyclopropylmethyl)carbamate;
[1-[6-Fluoro-3-(methylcarbamoyl)-7-(trifluoromethyl)thieno[3,2-b]pyridin-5-yl]-4-piperidyl] N-[(1S)-1-cyclopropylethyl]carbamate;
[1-[6-Chloro-3-(methylcarbamoyl)-7-(trifluoromethyl)thieno[3,2-b]pyridin-5-yl]-4-piperidyl] N-cyclopropylcarbamate;
[1-[6-fluoro-3-(methylcarbamoyl)-7-(trifluoromethyl)thieno[3,2-b]pyridin-5-yl]-4-piperidyl]N-cyclopropylcarbamate;
tert-Butyl N-[1-[3-(isopropylcarbamoyl)-7-(trifluoromethyl)thieno[3,2-b]pyridin-5-yl]pyrrolidin-3-yl]carbamate;
N-Isopropyl-2-[4-[3-(5-methyloxazol-2-yl)-7-(trifluoromethyl)thieno[3,2-b]pyridin-5-yl]piperazin-1-yl]acetamide;
N-[(4-Fluorophenyl)methyl]-5-[4-[2-(isopropylamino)-2-oxo-ethyl]piperazin-1-yl]-7-(trifluoromethyl)thieno[3,2-b]pyridine-3-carboxamide;
5-[4-[2-(Isopropylamino)-2-oxo-ethyl]piperazin-1-yl]-7-(trifluoromethyl)thieno[3,2-b]pyridine-3-carboxamide;
N-Isopropyl-2-[4-[3-(4-methyloxazol-2-yl)-7-(trifluoromethyl)thieno[3,2-b]pyridin-5-yl]piperazin-1-yl]acetamide;
2-[4-[3-(1-Hydroxypropyl)-7-(trifluoromethyl)thieno[3,2-b]pyridin-5-yl]piperazin-1-yl]-N-isopropyl-acetamide;
N-Isopropyl-2-[4-[3-propanoyl-7-(trifluoromethyl)thieno[3,2-b]pyridin-5-yl]piperazin-1-yl]acetamide;
2-[4-[3-(Azetidine-1-carbonyl)-7-(trifluoromethyl)thieno[3,2-b]pyridin-5-yl]piperazin-1-yl]-N-isopropyl-acetamide;
N-Isopropyl-2-[4-[3-(methoxymethyl)-7-(trifluoromethyl)thieno[3,2-b]pyridin-5-yl]piperazin-1-yl]acetamide;
N-Isopropyl-2-[4-[3-methyl-7-(trifluoromethyl)thieno[3,2-b]pyridin-5-yl]piperazin-1-yl]acetamide;
[1-[3-Propanoyl-7-(trifluoromethyl)thieno[3,2-b]pyridin-5-yl]-4-piperidyl] N-(cyclopropylmethyl)carbamate;
[1-[3-(Trideuteriomethylcarbamoyl)-7-(trifluoromethyl)thieno[3,2-b]pyridin-5-yl]-4-piperidyl] N-cyclopropylcarbamate;
7-(1,1-Difluoroethyl)-5-[4-[2-(isopropylamino)-2-oxo-ethyl]piperazin-1-yl]-N-methyl-thieno[3,2-b]pyridine-3-carboxamide;
[1-[7-(1,1-Difluoroethyl)-3-(methylcarbamoyl)thieno[3,2-b]pyridin-5-yl]-4-piperidyl] N-(cyclopropylmethyl)carbamate hydrochloride;
[1-[3-(Methylcarbamoyl)-7-(2,2,2-trifluoroethoxy)thieno[3,2-b]pyridin-5-yl]-4-piperidyl] N-isopropylcarbamate;
5-[3-(4-Hydroxy-4-methyl-pent-2-ynoxy)azetidin-1-yl]-N-methyl-7-(trifluoromethyl)thieno[3,2-b]pyridine-3-carboxamide;
5-[3-[3-(Cyclopropylmethoxy)azetidin-1-yl]azetidin-1-yl]-N-methyl-7-(trifluoromethyl)thieno[3,2-b]pyridine-3-carboxamide;
Methyl 5-[3-(tert-butoxycarbonylamino)pyrrolidin-1-yl]-7-(trifluoromethyl)thieno[3,2-b]pyridine-3-carboxylate;

5-[3-[[(1R,2R)-2-Hydroxycyclohexyl]amino]pyrrolidin-1-yl]-N-methyl-7-(trifluoromethyl)thieno[3,2-b]pyridine-3-carboxamide;

5-[3-(2-Isopropoxyethylamino)pyrrolidin-1-yl]-N-methyl-7-(trifluoromethyl)thieno[3,2-b]pyridine-3-carboxamide;

5-[3-(3-Hydroxy-3-methyl-but-1-ynyl)pyrrolidin-1-yl]-N-methyl-7-(trifluoromethyl)thieno[3,2-b]pyridine-3-carboxamide;

5-[3-(Cyclopropylmethoxy)pyrrolidin-1-yl]-N-methyl-7-(trifluoromethyl)thieno[3,2-b]pyridine-3-carboxamide;

Methyl 5-[4-(tert-butoxycarbonylamino)-1-piperidyl]-7-(trifluoromethyl)thieno[3,2-b]pyridine-3-carboxylate;

5-[4-[2-[(2-Hydroxy-1,1-dimethyl-ethyl)amino]-1-methyl-2-oxo-ethyl]piperazin-1-yl]-N-methyl-7-(trifluoromethyl)thieno[3,2-b]pyridine-3-carboxamide;

[1-[3-(Methylcarbamoyl)-7-(trifluoromethyl)thieno[3,2-b]pyridin-5-yl]-4-piperidyl] N-(2-methoxy-2-methyl-propyl)carbamate;

[1-[3-(Methylcarbamoyl)-7-(trifluoromethyl)thieno[3,2-b]pyridin-5-yl]-4-piperidyl] N-(3-methoxy-2,2-dimethyl-propyl)carbamate;

[1-[3-(Methylcarbamoyl)-7-(trifluoromethyl)thieno[3,2-b]pyridin-5-yl]-4-piperidyl] 3,3-dimethylpiperazine-1-carboxylate;

[1-[3-(Methylcarbamoyl)-7-(trifluoromethyl)thieno[3,2-b]pyridin-5-yl]-4-piperidyl] N-(cyclopropylmethyl)carbamate hydrochloride;

[1-[3-(Methylcarbamoyl)-7-(trifluoromethyl)thieno[3,2-b]pyridin-5-yl]-4-piperidyl] N-(2,2-difluoro-1-methyl-ethyl)carbamate;

[1-[3-(Methylcarbamoyl)-7-(trifluoromethyl)thieno[3,2-b]pyridin-5-yl]-4-piperidyl] N-(2-fluoro-1-methyl-ethyl)carbamate;

[1-[3-(Methylcarbamoyl)-7-(trifluoromethyl)thieno[3,2-b]pyridin-5-yl]-4-piperidyl] N-[2-hydroxy-1-(hydroxymethyl)ethyl]carbamate;

[1-[3-(Methylcarbamoyl)-7-(trifluoromethyl)thieno[3,2-b]pyridin-5-yl]-4-piperidyl] N-tetrahydrofuran-3-yl-carbamate;

[1-[3-(Methylcarbamoyl)-7-(trifluoromethyl)thieno[3,2-b]pyridin-5-yl]-4-piperidyl] N-(oxetan-3-yl)carbamate;

[1-[3-(Methylcarbamoyl)-7-(trifluoromethyl)thieno[3,2-b]pyridin-5-yl]-4-piperidyl] N-(3-methyloxetan-3-yl)carbamate;

[1-[3-(methylcarbamoyl)-7-(trifluoromethyl)thieno[3,2-b]pyridin-5-yl]-4-piperidyl] 3-methylthiomorpholine-4-carboxylate;

[1-[3-(Methylcarbamoyl)-7-(trifluoromethyl)thieno[3,2-b]pyridin-5-yl]-4-piperidyl] 3-methyl-1-oxo-1,4-thiazinane-4-carboxylate;

[1-[3-(Methylcarbamoyl)-7-(trifluoromethyl)thieno[3,2-b]pyridin-5-yl]-4-piperidyl] 3-methyl-1,1-dioxo-1,4-thiazinane-4-carboxylate;

[1-[3-(Methylcarbamoyl)-7-(trifluoromethyl)thieno[3,2-b]pyridin-5-yl]-4-piperidyl] N-[(1S)-1-methyl-2-methylsulfanyl-ethyl]carbamate;

[1-[3-(Methylcarbamoyl)-7-(trifluoromethyl)thieno[3,2-b]pyridin-5-yl]-4-piperidyl] N-[(1S)-1-methyl-2-methylsulfinyl-ethyl]carbamate;

[1-[3-(methylcarbamoyl)-7-(trifluoromethyl)thieno[3,2-b]pyridin-5-yl]-4-piperidyl] N-[(1S)-1-methyl-2-methylsulfonyl-ethyl]carbamate;

[1-[3-(Methylcarbamoyl)-7-(trifluoromethyl)thieno[3,2-b]pyridin-5-yl]-4-piperidyl] N-(1,1-dioxothiolan-3-yl)carbamate;

[1-[3-(Methylcarbamoyl)-7-(trifluoromethyl)thieno[3,2-b]pyridin-5-yl]-4-piperidyl] 3-(3-pyridyloxy)azetidine-1-carboxylate;

[1-[3-(Methylcarbamoyl)-7-(trifluoromethyl)thieno[3,2-b]pyridin-5-yl]-4-piperidyl] 3-(2-pyridyl)azetidine-1-carboxylate;

[1-[3-(Methylcarbamoyl)-7-(trifluoromethyl)thieno[3,2-b]pyridin-5-yl]-4-piperidyl] N-(1-cyclopropyl-1-deuterio-ethyl)carbamate;

[1-[3-(Methylcarbamoyl)-7-(trifluoromethyl)thieno[3,2-b]pyridin-5-yl]-4-piperidyl] N-(1-deuterio-1-methyl-ethyl)carbamate;

[2,2,6,6-Tetradeuterio-1-[3-(methylcarbamoyl)-7-(trifluoromethyl)thieno[3,2-b]pyridin-5-yl]-4-piperidyl] N-cyclopropylcarbamate;

[2,2,6,6-Tetradeuterio-1-[3-(methylcarbamoyl)-7-(trifluoromethyl)thieno[3,2-b]pyridin-5-yl]-4-piperidyl] N-isopropylcarbamate;

[(1R,5S)-8-[3-(Methylcarbamoyl)-7-(trifluoromethyl)thieno[3,2-b]pyridin-5-yl]-8-azabicyclo[3.2.1]octan-3-yl] N-cyclopropylcarbamate;

[1-[3-(Methylcarbamoyl)-7-(trifluoromethyl)thieno[3,2-b]pyridin-5-yl]-4-piperidyl] N-[(1S)-2,2-dideuterio-1-methyl-2-(trideuteriomethoxy)ethyl]carbamate;

[(1R,5S)-8-[3-(Methylcarbamoyl)-7-(trifluoromethyl)thieno[3,2-b]pyridin-5-yl]-8-azabicyclo[3.2.1]octan-3-yl] N-cyclopropylcarbamate;

[1-[3-(Methylcarbamoyl)-7-(trifluoromethyl)thieno[3,2-b]pyridin-5-yl]-4-piperidyl] N-[(1R)-2-fluoro-1-methyl-ethyl]carbamate;

[1-[3-(Methylcarbamoyl)-7-(trifluoromethyl)thieno[3,2-b]pyridin-5-yl]-4-piperidyl] N-[(1S)-2-fluoro-1-methyl-ethyl]carbamate;

[1-[3-(methylcarbamoyl)-7-(trifluoromethyl)thieno[3,2-b]pyridin-5-yl]-4-piperidyl] N-[cyclopropyl(dideuterio)methyl]carbamate;

[1-[3-(Methylcarbamoyl)-7-(trifluoromethyl)thieno[3,2-b]pyridin-5-yl]-4-piperidyl] N-[2-fluoro-1-(fluoromethyl)ethyl]carbamate;

[1-[3-(Methylcarbamoyl)-7-(trifluoromethyl)thieno[3,2-b]pyridin-5-yl]-4-piperidyl] 6-hydroxy-8-oxa-2-azaspiro[3.4]octane-2-carboxylate;

[1-[3-(Methylcarbamoyl)-7-(trifluoromethyl)thieno[3,2-b]pyridin-5-yl]-4-piperidyl] 6-[(2,2,2-trifluoro-1-methyl-ethyl)amino]-8-oxa-2-azaspiro[3.4]octane-2-carboxylate;

[1-[3-(Methylcarbamoyl)-7-(trifluoromethyl)thieno[3,2-b]pyridin-5-yl]-4-piperidyl] 3-(2,2,2-trifluoroethoxy)azetidine-1-carboxylate;

[2-Fluoro-1-(fluoromethyl)ethyl] N-[1-[3-(methylcarbamoyl)-7-(trifluoromethyl)thieno[3,2-b]pyridin-5-yl]-4-piperidyl]carbamate;

5-[4-[(2-Ethylthiazol-4-yl)methyl]piperazin-1-yl]-N-methyl-7-(trifluoromethyl)thieno[3,2-b]pyridine-3-carboxamide;

N-Methyl-5-[4-[(4-methyl-2-thienyl)methyl]piperazin-1-yl]-7-(trifluoromethyl)thieno[3,2-b]pyridine-3-carboxamide;

N-Methyl-5-[4-[(2-methyloxazol-4-yl)methyl]piperazin-1-yl]-7-(trifluoromethyl)thieno[3,2-b]pyridine-3-carboxamide;

5-[4-(Isobutylcarbamoyl)-1-piperidyl]-N-methyl-7-(trifluoromethyl)thieno[3,2-b]pyridine-3-carboxamide;

5-[4-(2-Hydroxy-4,4-dimethyl-pentyl)piperazin-1-yl]-N-methyl-7-(trifluoromethyl)thieno[3,2-b]pyridine-3-carboxamide;

5-[4-[1-(4,4-Dimethyl-5H-oxazol-2-yl)ethyl]piperazin-1-yl]-N-methyl-7-(trifluoromethyl)thieno[3,2-b]pyridine-3-carboxamide;
5-[4-[3-(Cyclopropylmethoxy)pyrrolidin-1-yl]-1-piperidyl]-N-methyl-7-(trifluoromethyl)thieno[3,2-b]pyridine-3-carboxamide;
5-[4-(2-Hydroxy-3-isopropoxy-propyl)piperazin-1-yl]-N-methyl-7-(trifluoromethyl)thieno[3,2-b]pyridine-3-carboxamide;
5-[4-(2-Isopropoxyethylamino)-1-piperidyl]-N-methyl-7-(trifluoromethyl)thieno[3,2-b]pyridine-3-carboxamide;
5-[4-(3-tert-Butoxy-2-hydroxy-propyl)piperazin-1-yl]-N-methyl-7-(trifluoromethyl)thieno[3,2-b]pyridine-3-carboxamide;
5-[4-(3-Isopropoxypyrrolidin-1-yl)-1-piperidyl]-N-methyl-7-(trifluoromethyl)thieno[3,2-b]pyridine-3-carboxamide;
5-[4-(4-Hydroxy-4-methyl-pent-2-ynyl)piperazin-1-yl]-N-methyl-7-(trifluoromethyl)thieno[3,2-b]pyridine-3-carboxamide;
5-[4-(3-Hydroxy-3-methyl-but-1-ynyl)-1-piperidyl]-N-methyl-7-(trifluoromethyl)thieno[3,2-b]pyridine-3-carboxamide;
5-[4-(5-Hydroxy-5-methyl-hexa-1,3-diynyl)-1-piperidyl]-N-methyl-7-(trifluoromethyl)thieno[3,2-b]pyridine-3-carboxamide;
5-[4-(4-Hydroxy-4-methyl-pent-2-ynoxy)-1-piperidyl]-N-methyl-7-(trifluoromethyl)thieno[3,2-b]pyridine-3-carboxamide;
[1,1-Dimethyl-4-[[1-[3-(methylcarbamoyl)-7-(trifluoromethyl)thieno[3,2-b]pyridin-5-yl]-4-piperidyl]oxy]but-2-ynyl] acetate;
5-[4-Hydroxy-4-(5-hydroxy-5-methyl-hexa-1,3-diynyl)-1-piperidyl]-N-methyl-7-(trifluoromethyl)thieno[3,2-b]pyridine-3-carboxamide;
5-[2-(Cyclopropylmethoxy)-4-oxa-8-azaspiro[4.5]decan-8-yl]-N-methyl-7-(trifluoromethyl)thieno[3,2-b]pyridine-3-carboxamide;
5-[2-(2-Hydroxy-2-methyl-propoxy)-4-oxa-8-azaspiro[4.5]decan-8-yl]-N-methyl-7-(trifluoromethyl)thieno[3,2-b]pyridine-3-carboxamide;
5-(2-Hydroxy-4-oxa-8-azaspiro[4.5]decan-8-yl)-N-methyl-7-(trifluoromethyl)thieno[3,2-b]pyridine-3-carboxamide;
5-[6-(Cyclopropylmethoxy)-8-oxa-2-azaspiro[3.4]octan-2-yl]-N-methyl-7-(trifluoromethyl)thieno[3,2-b]pyridine-3-carboxamide;
5-[6-(3,3-Difluoropyrrolidin-1-yl)-8-oxa-2-azaspiro[3.4]octan-2-yl]-N-methyl-7-(trifluoromethyl)thieno[3,2-b]pyridine-3-carboxamide;
N-Methyl-7-(trifluoromethyl)-5-[6-[(2,2,2-trifluoro-1-methyl-ethyl)amino]-8-oxa-2-azaspiro[3.4]octan-2-yl]thieno[3,2-b]pyridine-3-carboxamide trifluoroacetate;
tert-Butyl 2-[3-(methylcarbamoyl)-7-(trifluoromethyl)thieno[3,2-b]pyridin-5-yl]-2,6-diazaspiro[3.3]heptane-6-carboxylate;
tert-Butyl 7-[3-(Methylcarbamoyl)-7-(trifluoromethyl)thieno[3,2-b]pyridin-5-yl]-2,7-diazaspiro[3.5]nonane-2-carboxylate;
5-[6-(2-tert-Butoxyacetyl)-2,6-diazaspiro[3.3]heptan-2-yl]-N-methyl-7-(trifluoromethyl)thieno[3,2-b]pyridine-3-carboxamide;
5-[2-(2-tert-Butoxyacetyl)-2,7-diazaspiro[3.5]nonan-7-yl]-N-methyl-7-(trifluoromethyl)thieno[3,2-b]pyridine-3-carboxamide;
tert-butyl 2-[3-(Methylcarbamoyl)-7-(trifluoromethyl)thieno[3,2-b]pyridin-5-yl]-2,7-diazaspiro[3.5]nonane-7-carboxylate;
5-[7-(2-tert-butoxyacetyl)-2,7-diazaspiro[3.5]nonan-2-yl]-N-methyl-7-(trifluoromethyl)thieno[3,2-b]pyridine-3-carboxamide;
5-[2-[2-(Isopropylamino)-2-oxo-ethyl]-2,7-diazaspiro[3.5]nonan-7-yl]-N-methyl-7-(trifluoromethyl)thieno[3,2-b]pyridine-3-carboxamide;
N-Methyl-5-[2-(4-methylpyrimidin-2-yl)-2,7-diazaspiro[3.5]nonan-7-yl]-7-(trifluoromethyl)thieno[3,2-b]pyridine-3-carboxamide;
5-[2-(Cyclopropylmethylcarbamoyl)-2,7-diazaspiro[3.5]nonan-7-yl]-N-methyl-7-(trifluoromethyl)thieno[3,2-b]pyridine-3-carboxamide;
Cyclopropylmethyl 7-[3-(methylcarbamoyl)-7-(trifluoromethyl)thieno[3,2-b]pyridin-5-yl]-2,7-diazaspiro[3.5]nonane-2-carboxylate;
N-Methyl-5-[2-[(2S)-1-methylpyrrolidine-2-carbonyl]-2,7-diazaspiro[3.5]nonan-7-yl]-7-(trifluoromethyl)thieno[3,2-b]pyridine-3-carboxamide;
N-methyl-5-[2-(4-methylpiperazine-1-carbonyl)-2,7-diazaspiro[3.5]nonan-7-yl]-7-(trifluoromethyl)thieno[3,2-b]pyridine-3-carboxamide;
5-[2-[2-(3,3-Difluoropyrrolidin-1-yl)acetyl]-2,7-diazaspiro[3.5]nonan-7-yl]-N-methyl-7-(trifluoromethyl)thieno[3,2-b]pyridine-3-carboxamide;
5-[2-[2-[(3R)-3-Fluoropyrrolidin-1-yl]acetyl]-2,7-diazaspiro[3.5]nonan-7-yl]-N-methyl-7-(trifluoromethyl)thieno[3,2-b]pyridine-3-carboxamide;
5-[2-(2-Hydroxy-3,3-dimethyl-butyl)-2,7-diazaspiro[3.5]nonan-7-yl]-N-methyl-7-(trifluoromethyl)thieno[3,2-b]pyridine-3-carboxamide;
5-[2-(3-Hydroxy-3-methyl-butanoyl)-2,7-diazaspiro[3.5]nonan-7-yl]-N-methyl-7-(trifluoromethyl)thieno[3,2-b]pyridine-3-carboxamide hydrochloride;
N-Methyl-5-[2-[2-(trifluoromethoxy)acetyl]-2,7-diazaspiro[3.5]nonan-7-yl]-7-(trifluoromethyl)thieno[3,2-b]pyridine-3-carboxamide;
5-[2-(2-Methoxypropanoyl)-2,7-diazaspiro[3.5]nonan-7-yl]-N-methyl-7-(trifluoromethyl)thieno[3,2-b]pyridine-3-carboxamide;
(2-Methoxy-1,1-dimethyl-ethyl) 7-[3-(methylcarbamoyl)-7-(trifluoromethyl)thieno[3,2-b]pyridin-5-yl]-2,7-diazaspiro[3.5]nonane-2-carboxylate;
N-Methyl-5-[6-(4-methylpiperazine-1-carbonyl)-2,6-diazaspiro[3.3]heptan-2-yl]-7-(trifluoromethyl)thieno[3,2-b]pyridine-3-carboxamide;
N-Methyl-5-[2-(3,3,3-trifluoro-2-hydroxy-propanoyl)-2,7-diazaspiro[3.5]nonan-7-yl]-7-(trifluoromethyl)thieno[3,2-b]pyridine-3-carboxamide;
(3-Hydroxy-3-methyl-butyl) 4-[3-(methylcarbamoyl)-7-(trifluoromethyl)thieno[3,2-b]pyridin-5-yl]piperidine-1-carboxylate;
tert-Butyl 7-[3-(methylcarbamoyl)-7-(trifluoromethyl)thieno[3,2-b]pyridin-5-yl]-2-azaspiro[3.5]nonane-2-carboxylate;
2-(Trifluoromethoxy)ethyl 4-[1-[3-(methylcarbamoyl)-7-(trifluoromethyl)thieno[3,2-b]pyridin-5-yl]ethyl]piperazine-1-carboxylate;
2-(Trifluoromethoxy)ethyl 7-[3-(methylcarbamoyl)-7-(trifluoromethyl)thieno[3,2-b]pyridin-5-yl]-2-azaspiro[3.5]nonane-2-carboxylate;
Methyl 5-[(1-tert-butoxycarbonyl-4-piperidyl)amino]-7-(trifluoromethyl)thieno[3,2-b]pyridine-3-carboxylate;

Methyl 5-[(1-tert-butoxycarbonylpyrrolidin-3-yl)amino]-7-(trifluoromethyl)thieno[3,2-b]pyridine-3-carboxylate;

Methyl 5-[(1-tert-butoxycarbonyl-4-piperidyl)methylamino]-7-(trifluoromethyl)thieno[3,2-b]pyridine-3-carboxylate;

5-[2-(2-Isopropylthiazol-4-yl)ethylamino]-N-methyl-7-(trifluoromethyl)thieno[3,2-b]pyridine-3-carboxamide;

Methyl 5-[2-(1-tert-butoxycarbonylpyrrolidin-3-yl)ethynyl]-7-(trifluoromethyl)thieno[3,2-b]pyridine-3-carboxylate;

tert-Butyl 4-hydroxy-4-[2-[3-(methylcarbamoyl)-7-(trifluoromethyl)thieno[3,2-b]pyridin-5-yl]ethynyl]piperidine-1-carboxylate;

[(1S)-1-Cyclopropylethyl] 3-[[3-(methylcarbamoyl)-7-(trifluoromethyl)thieno[3,2-b]pyridin-5-yl]oxymethyl]azetidine-1-carboxylate;

tert-Butyl 6-[3-(methylcarbamoyl)-7-(trifluoromethyl)thieno[3,2-b]pyridin-5-yl]oxy-8-oxa-2-azaspiro[3.4]octane-2-carboxylate;

tert-Butyl 2-[3-(methylcarbamoyl)-7-(trifluoromethyl)thieno[3,2-b]pyridin-5-yl]oxy-4-oxa-8-azaspiro[4.5]decane-8-carboxylate;

N-Methyl-5-[5-[3-(3-pyridyl)azetidine-1-carbonyl]-3-furyl]-7-(trifluoromethyl)thieno[3,2-b]pyridine-3-carboxamide;

5-[4-[4-(2-Hydroxy-2-methyl-propyl)piperazin-1-yl]phenyl]-N-methyl-7-(trifluoromethyl)thieno[3,2-b]pyridine-3-carboxamide;

5-[6-(6-Chloro-3-pyridyl)-3-pyridyl]-N-methyl-7-(trifluoromethyl)thieno[3,2-b]pyridine-3-carboxamide;

5-[6-(3-Isopropoxyazetidin-1-yl)-3-pyridyl]-N-methyl-7-(trifluoromethyl)thieno[3,2-b]pyridine-3-carboxamide; trifluoroacetate;

5-[6-[2-(1-hydroxycyclohexyl)ethynyl]-3-pyridyl]-N-methyl-7-(trifluoromethyl)thieno[3,2-b]pyridine-3-carboxamide; trifluoroacetate;

1-(3-(Methylcarbamoyl)-7-(trifluoromethyl)thieno[3,2-b]pyridin-5-yl)piperidin-4-yl (1-(1H-imidazol-1-yl)propan-2-yl)carbamate;

1-(3-(Methylcarbamoyl)-7-(trifluoromethyl)thieno[3,2-b]pyridin-5-yl)piperidin-4-yl 2-methyl-4-(1H-1,2,4-triazol-1-yl)piperidine-1-carboxylate;

1-(3-(Methylcarbamoyl)-7-(trifluoromethyl)thieno[3,2-b]pyridin-5-yl)piperidin-4-yl (1-(methylsulfonyl)azetidin-3-yl)carbamate;

1-(3-(Methylcarbamoyl)-7-(trifluoromethyl)thieno[3,2-b]pyridin-5-yl)piperidin-4-yl 2-methyl-4-(methylsulfonyl)piperazine-1-carboxylate;

1-(3-(Methylcarbamoyl)-7-(trifluoromethyl)thieno[3,2-b]pyridin-5-yl)piperidin-4-yl (S)-(1-cyclopropylpropan-2-yl)carbamate;

1-(3-(Methylcarbamoyl)-7-(trifluoromethyl)thieno[3,2-b]pyridin-5-yl)piperidin-4-yl (R)-(1-cyclopropylpropan-2-yl)carbamate;

1-(3-(Methylcarbamoyl)-7-(trifluoromethyl)thieno[3,2-b]pyridin-5-yl)piperidin-4-yl (oxetan-3-ylmethyl)carbamate;

1-(3-(Methylcarbamoyl)-7-(trifluoromethyl)thieno[3,2-b]pyridin-5-yl)piperidin-4-yl ((3-hydroxyoxetan-3-yl)methyl)carbamate;

1-(3-(Methylcarbamoyl)-7-(trifluoromethyl)thieno[3,2-b]pyridin-5-yl)piperidin-4-yl ((3-fluorooxetan-3-yl)methyl)carbamate;

1-(3-(Methylcarbamoyl)-7-(trifluoromethyl)thieno[3,2-b]pyridin-5-yl)piperidin-4-yl (R)-2-methylazetidine-1-carboxylate;

1-(3-(Methylcarbamoyl)-7-(trifluoromethyl)thieno[3,2-b]pyridin-5-yl)piperidin-4-yl (S)-2-methylazetidine-1-carboxylate;

1-(3-(Methylcarbamoyl)-7-(trifluoromethyl)thieno[3,2-b]pyridin-5-yl)piperidin-4-yl 3-methoxyazetidine-1-carboxylate;

1-(3-(Methylcarbamoyl)-7-(trifluoromethyl)thieno[3,2-b]pyridin-5-yl)piperidin-4-yl 2-oxa-6-azaspiro[3.3]heptane-6-carboxylate;

1-(3-(Methylcarbamoyl)-7-(trifluoromethyl)thieno[3,2-b]pyridin-5-yl)piperidin-4-yl 6-methyl-2,6-diazaspiro[3.3]heptane-2-carboxylate;

1-(3-(Methylcarbamoyl)-7-(trifluoromethyl)thieno[3,2-b]pyridin-5-yl)piperidin-4-yl 5,8-dioxa-2-azaspiro[3.4]octane-2-carboxylate;

1-(3-(methylcarbamoyl)-7-(trifluoromethyl)thieno[3,2-b]pyridin-5-yl)piperidin-4-yl (2S)-3-cyclopropyl-3-hydroxy-2-methylazetidine-1-carboxylate;

1-(3-(Methylcarbamoyl)-7-(trifluoromethyl)thieno[3,2-b]pyridin-5-yl)piperidin-4-yl (2S,3S)-3-hydroxy-2-methylpyrrolidine-1-carboxylate;

Cyclopropylmethyl 4-(3-(methylcarbamoyl)-7-(trifluoromethyl)thieno[3,2-b]pyridin-5-yl)piperazine-1-carboxylate;

1-(3-(Methylcarbamoyl)-7-(trifluoromethyl)thieno[3,2-b]pyridin-5-yl)piperidin-4-yl (2-fluoroethyl)carbamate;

1-(3-(Methylcarbamoyl)-7-(trifluoromethyl)thieno[3,2-b]pyridin-5-yl)piperidin-4-yl (2,2-difluoroethyl)carbamate;

1-(3-(Methylcarbamoyl)-7-(trifluoromethyl)thieno[3,2-b]pyridin-5-yl)piperidin-4-yl (methyl-d3)carbamate;

1-(3-(Methylcarbamoyl)-7-(trifluoromethyl)thieno[3,2-b]pyridin-5-yl)piperidin-4-yl (3-methoxycyclobutyl)carbamate;

(+/−)-1-(3-(Methylcarbamoyl)-7-(trifluoromethyl)thieno[3,2-b]pyridin-5-yl)piperidin-4-yl ((1r,3r)-3-cyanocyclobutyl)carbamate;

(+/−)-1-(3-(Methylcarbamoyl)-7-(trifluoromethyl)thieno[3,2-b]pyridin-5-yl)piperidin-4-yl ((1s,3s)-3-cyanocyclobutyl)carbamate;

1-(3-(Methylcarbamoyl)-7-(trifluoromethyl)thieno[3,2-b]pyridin-5-yl)piperidin-4-yl (3-ethoxycyclobutyl)carbamate;

(+/−)-1-(3-(Methylcarbamoyl)-7-(trifluoromethyl)thieno[3,2-b]pyridin-5-yl)piperidin-4-yl ((1r,3r)-3-(methylsulfonyl)cyclobutyl)carbamate;

(+/−)-1-(3-(Methylcarbamoyl)-7-(trifluoromethyl)thieno[3,2-b]pyridin-5-yl)piperidin-4-yl ((1s,3s)-3-(methylsulfonyl)cyclobutyl)carbamate;

1-(3-(Methylcarbamoyl)-7-(trifluoromethyl)thieno[3,2-b]pyridin-5-yl)piperidin-4-yl (2-oxaspiro[3.3]heptan-6-yl)carbamate;

1-(3-(Methylcarbamoyl)-7-(trifluoromethyl)thieno[3,2-b]pyridin-5-yl)piperidin-4-yl ((2-methyltetrahydrofuran-2-yl)methyl)carbamate;

Cyclopropyl (1-(3-(methylcarbamoyl)-7-(trifluoromethyl)thieno[3,2-b]pyridin-5-yl)piperidin-4-yl)carbamate;

1-(3-(Methylcarbamoyl)-7-(trifluoromethyl)thieno[3,2-b]pyridin-5-yl)piperidin-4-yl (2S,3S)-3-(dimethylamino)-2-methylazetidine-1-carboxylate;

1-(3-(Methylcarbamoyl)-7-(trifluoromethyl)thieno[3,2-b]pyridin-5-yl)piperidin-4-yl (2S,3R)-3-(dimethylamino)-2-methylazetidine-1-carboxylate;

1-(3-(Methylcarbamoyl)-7-(trifluoromethyl)thieno[3,2-b]pyridin-5-yl)piperidin-4-yl (S)-(1-(oxetan-3-yl)ethyl)carbamate;

1-(3-(Methylcarbamoyl)-7-(trifluoromethyl)thieno[3,2-b]pyridin-5-yl)piperidin-4-yl (R)-(1-(oxetan-3-yl)ethyl)carbamate;

1-(3-(Methylcarbamoyl)-7-(trifluoromethyl)thieno[3,2-b]pyridin-5-yl)piperidin-4-yl (2S,3S)-3-methoxy-2-methylazetidine-1-carboxylate;

1-(3-(Methylcarbamoyl)-7-(trifluoromethyl)thieno[3,2-b]pyridin-5-yl)piperidin-4-yl [1,3'-biazetidine]-1'-carboxylate;

1-(3-(Methylcarbamoyl)-7-(trifluoromethyl)thieno[3,2-b]pyridin-5-yl)piperidin-4-yl (2'S,3'S)-2'-methyl-[1,3'-biazetidine]-1'-carboxylate;

1-(3-(Methylcarbamoyl)-7-(trifluoromethyl)thieno[3,2-b]pyridin-5-yl)piperidin-4-yl (2S,3R)-3-hydroxy-2-methylpyrrolidine-1-carboxylate;

1-(3-(Methylcarbamoyl)-7-(trifluoromethyl)thieno[3,2-b]pyridin-5-yl)piperidin-4-yl (2S,3S)-3-hydroxy-2,3-dimethylpyrrolidine-1-carboxylate;

1-(3-(Methylcarbamoyl)-7-(trifluoromethyl)thieno[3,2-b]pyridin-5-yl)piperidin-4-yl (2S,3S)-3-cyano-2-methylazetidine-1-carboxylate;

1-(3-(Methylcarbamoyl)-7-(trifluoromethyl)thieno[3,2-b]pyridin-5-yl)piperidin-4-yl 6-(cyanomethyl)-2,6-diazaspiro[3.3]heptane-2-carboxylate;

1-(3-(Methylcarbamoyl)-7-(trifluoromethyl)thieno[3,2-b]pyridin-5-yl)piperidin-4-yl (2S,3R)-3-(cyanomethyl)-2-methylazetidine-1-carboxylate;

1-(3-(Methylcarbamoyl)-7-(trifluoromethyl)thieno[3,2-b]pyridin-5-yl)piperidin-4-yl (2S,3S)-3-(cyanomethyl)-2-methylazetidine-1-carboxylate;

1-(3-(Methylcarbamoyl)-7-(trifluoromethyl)thieno[3,2-b]pyridin-5-yl)piperidin-4-yl 1-methyl-1,6-diazaspiro[3.3]heptane-6-carboxylate;

1-(3-(Methylcarbamoyl)-7-(trifluoromethyl)thieno[3,2-b]pyridin-5-yl)piperidin-4-yl (S)-pent-3-yn-2-ylcarbamate;

1-(3-(Methylcarbamoyl)-7-(trifluoromethyl)thieno[3,2-b]pyridin-5-yl)piperidin-4-yl (R)-pent-3-yn-2-ylcarbamate;

(2S,3S)-1,2-Dimethylpyrrolidin-3-yl (1-(3-(methylcarbamoyl)-7-(trifluoromethyl)thieno[3,2-b]pyridin-5-yl)piperidin-4-yl)carbamate;

(S)-1-(2,2-Difluoroethyl)pyrrolidin-3-yl (1-(3-(methylcarbamoyl)-7-(trifluoromethyl)thieno[3,2-b]pyridin-5-yl)piperidin-4-yl)carbamate;

1-(3-(Methylcarbamoyl)-7-(trifluoromethyl)thieno[3,2-b]pyridin-5-yl)piperidin-4-yl 6-methyl-1,6-diazaspiro[3.3]heptane-1-carboxylate;

1-(3-(Methylcarbamoyl)-7-(trifluoromethyl)thieno[3,2-b]pyridin-5-yl)piperidin-4-yl (2S,3R)-2-methyl-3-(1H-1,2,4-triazol-1-yl)azetidine-1-carboxylate;

1-(3-(methylcarbamoyl)-7-(trifluoromethyl)thieno[3,2-b]pyridin-5-yl)piperidin-4-yl (S)-(5-hydroxy-5-methylhex-3-yn-2-yl)carbamate;

1-(3-(Methylcarbamoyl)-7-(trifluoromethyl)thieno[3,2-b]pyridin-5-yl)piperidin-4-yl (R)-(5-hydroxy-5-methylhex-3-yn-2-yl)carbamate;

1-Methylazetidin-3-yl (1-(3-(methylcarbamoyl)-7-(trifluoromethyl)thieno[3,2-b]pyridin-5-yl)piperidin-4-yl)carbamate;

Isopropyl (1-(3-(methylcarbamoyl)-7-(trifluoromethyl)thieno[3,2-b]pyridin-5-yl)piperidin-4-yl)carbamate;

2,2-Difluoroethyl (1-(3-(methylcarbamoyl)-7-(trifluoromethyl)thieno[3,2-b]pyridin-5-yl)piperidin-4-yl)carbamate;

1-(1,3-Difluoropropan-2-yl)azetidin-3-yl (1-(3-(methylcarbamoyl)-7-(trifluoromethyl)thieno[3,2-b]pyridin-5-yl)piperidin-4-yl)carbamate;

Methyl-d3 (1-(3-(methylcarbamoyl)-7-(trifluoromethyl)thieno[3,2-b]pyridin-5-yl)piperidin-4-yl)carbamate;

2-Fluoroethyl (1-(3-(methylcarbamoyl)-7-(trifluoromethyl)thieno[3,2-b]pyridin-5-yl)piperidin-4-yl)carbamate;

1-Fluoropropan-2-yl (1-(3-(methylcarbamoyl)-7-(trifluoromethyl)thieno[3,2-b]pyridin-5-yl)piperidin-4-yl)carbamate;

(+/−)-cis-(1s,3s)-3-((3-(Methylcarbamoyl)-7-(trifluoromethyl)thieno[3,2-b]pyridin-5-yl)oxy)cyclobutyl oxetan-3-ylcarbamate;

(1s,3s)-3-((3-(Methylcarbamoyl)-7-(trifluoromethyl)thieno[3,2-b]pyridin-5-yl)oxy)cyclobutyl 3-methoxyazetidine-1-carboxylate;

1-(3-(Methylcarbamoyl)-7-(trifluoromethyl)thieno[3,2-b]pyridin-5-yl)piperidin-4-yl 1-oxa-6-azaspiro[3.3]heptane-6-carboxylate;

1-(3-(Methylcarbamoyl)-7-(trifluoromethyl)thieno[3,2-b]pyridin-5-yl)piperidin-4-yl ((S)-1-((S)-oxetan-2-yl)ethyl)carbamate;

1-(3-(Methylcarbamoyl)-7-(trifluoromethyl)thieno[3,2-b]pyridin-5-yl)piperidin-4-yl ((R)-1-((S)-oxetan-2-yl)ethyl)carbamate;

1-(3-(Methylcarbamoyl)-7-(trifluoromethyl)thieno[3,2-b]pyridin-5-yl)piperidin-4-yl (2S,3R)-3-cyano-2-methylpyrrolidine-1-carboxylate;

(S)-1-((S)-Oxetan-2-yl)ethyl (1-(3-(methylcarbamoyl)-7-(trifluoromethyl)thieno[3,2-b]pyridin-5-yl)piperidin-4-yl)carbamate;

(S)-1-((R)-Oxetan-2-yl)ethyl (1-(3-(methylcarbamoyl)-7-(trifluoromethyl)thieno[3,2-b]pyridin-5-yl)piperidin-4-yl)carbamate;

(+/−)-cis-(1s,3s)-3-((3-(Methylcarbamoyl)-7-(trifluoromethyl)thieno[3,2-b]pyridin-5-yl)oxy)cyclobutyl isopropylcarbamate;

(+/−)-cis-(1s,3s)-3-((3-(Methylcarbamoyl)-7-(trifluoromethyl)thieno[3,2-b]pyridin-5-yl)oxy)cyclobutyl 3-(trifluoromethoxy)azetidine-1-carboxylate;

(+/−)-cis-(1s,3s)-3-((3-(Methylcarbamoyl)-7-(trifluoromethyl)thieno[3,2-b]pyridin-5-yl)oxy)cyclobutyl 3-hydroxy-3-methylazetidine-1-carboxylate;

(+/−)-cis-(1s,3R)-3-((3-(Methylcarbamoyl)-7-(trifluoromethyl)thieno[3,2-b]pyridin-5-yl)oxy)cyclobutyl ((S)-1-(trifluoromethoxy)propan-2-yl)carbamate;

(+/−)-cis-(1s,3s)-3-((3-(Methylcarbamoyl)-7-(trifluoromethyl)thieno[3,2-b]pyridin-5-yl)oxy)cyclobutyl 3-(dimethylamino)azetidine-1-carboxylate;

4-Fluoro-1-methylpyrrolidin-3-yl 4-((3-(methylcarbamoyl)-7-(trifluoromethyl)thieno[3,2-b]pyridin-5-yl)oxy)piperidine-1-carboxylate;

1-(3-(Methylcarbamoyl)-7-(trifluoromethyl)thieno[3,2-b]pyridin-5-yl)piperidin-4-yl 3-(1H-imidazol-1-yl)azetidine-1-carboxylate;

1-(3-(Methylcarbamoyl)-7-(trifluoromethyl)thieno[3,2-b]pyridin-5-yl)piperidin-4-yl 3-(1H-1,2,3-triazol-1-yl)azetidine-1-carboxylate;

1-(3-(Methylcarbamoyl)-7-(trifluoromethyl)thieno[3,2-b]pyridin-5-yl)piperidin-4-yl 3-(1H-1,2,4-triazol-1-yl)azetidine-1-carboxylate;

(+/−)-trans-3-Fluoro-1-(3-(methylcarbamoyl)-7-(trifluoromethyl)thieno[3,2-b]pyridin-5-yl)piperidin-4-yl 3-(1H-1,2,4-triazol-1-yl)azetidine-1-carboxylate;

(+/−)-cis-3-Fluoro-1-(3-(methylcarbamoyl)-7-(trifluoromethyl)thieno[3,2-b]pyridin-5-yl)piperidin-4-yl 3-(1H-1,2,4-triazol-1-yl)azetidine-1-carboxylate;

1-(3-(Methylcarbamoyl)-7-(trifluoromethyl)thieno[3,2-b]pyridin-5-yl)piperidin-4-yl 1-cyclopropyl-1,6-diazaspiro[3.3]heptane-6-carboxylate;

1-(3-(Methylcarbamoyl)-7-(trifluoromethyl)thieno[3,2-b]pyridin-5-yl)piperidin-4-yl 1-ethyl-1,6-diazaspiro[3.3]heptane-6-carboxylate;

1-(3-(Methylcarbamoyl)-7-(trifluoromethyl)thieno[3,2-b]pyridin-5-yl)piperidin-4-yl 1-(2,2,2-trifluoroethyl)-1,6-diazaspiro[3.3]heptane-6-carboxylate;

(+/−)-trans-2-(Trifluoromethoxy)ethyl 3-methyl-4-((3-(methylcarbamoyl)-7-(trifluoromethyl)thieno[3,2-b]pyridin-5-yl)oxy)piperidine-1-carboxylate;

(+/−)-cis-2-(Trifluoromethoxy)ethyl 3-methyl-4-((3-(methylcarbamoyl)-7-(trifluoromethyl)thieno[3,2-b]pyridin-5-yl)oxy)piperidine-1-carboxylate;

2-(Trifluoromethoxy)ethyl (R)-3-((3-(methylcarbamoyl)-7-(trifluoromethyl)thieno[3,2-b]pyridin-5-yl)oxy)piperidine-1-carboxylate;

2-(Trifluoromethoxy)ethyl (S)-3-((3-(methylcarbamoyl)-7-(trifluoromethyl)thieno[3,2-b]pyridin-5-yl)oxy)piperidine-1-carboxylate;

tert-Butyl 2,2-dimethyl-4-((3-(methylcarbamoyl)-7-(trifluoromethyl)thieno[3,2-b]pyridin-5-yl)oxy)piperidine-1-carboxylate;

(S)-1-(Trifluoromethoxy)propan-2-yl 4-((3-(methylcarbamoyl)-7-(trifluoromethyl)thieno[3,2-b]pyridin-5-yl)oxy)piperidine-1-carboxylate;

(R)-1-(Trifluoromethoxy)propan-2-yl 4-((3-(methylcarbamoyl)-7-(trifluoromethyl)thieno[3,2-b]pyridin-5-yl)oxy)piperidine-1-carboxylate;

(S)-2-(Trifluoromethoxy)propyl 4-((3-(methylcarbamoyl)-7-(trifluoromethyl)thieno[3,2-b]pyridin-5-yl)oxy)piperidine-1-carboxylate;

(R)-2-(Trifluoromethoxy)propyl 4-((3-(methylcarbamoyl)-7-(trifluoromethyl)thieno[3,2-b]pyridin-5-yl)oxy)piperidine-1-carboxylate;

(S)-1-(Trifluoromethoxy)propan-2-yl 6-((3-(methylcarbamoyl)-7-(trifluoromethyl)thieno[3,2-b]pyridin-5-yl)oxy)-2-azaspiro[3.3]heptane-2-carboxylate;

(S)-1-(Trifluoromethoxy)propan-2-yl (S)-3-((3-(methylcarbamoyl)-7-(trifluoromethyl)thieno[3,2-b]pyridin-5-yl)oxy)pyrrolidine-1-carboxylate;

(3S,4S)-3-Methyl-1-(3-(methylcarbamoyl)-7-(trifluoromethyl)thieno[3,2-b]pyridin-5-yl)piperidin-4-yl isopropylcarbamate;

(3R,4R)-3-Methyl-1-(3-(methylcarbamoyl)-7-(trifluoromethyl)thieno[3,2-b]pyridin-5-yl)piperidin-4-yl 3-(trifluoromethoxy)azetidine-1-carboxylate;

(S)-2-(Trifluoromethoxy)propyl (S)-3-((3-(methylcarbamoyl)-7-(trifluoromethyl)thieno[3,2-b]pyridin-5-yl)oxy)pyrrolidine-1-carboxylate;

(R)-2-(Trifluoromethoxy)propyl (S)-3-((3-(methylcarbamoyl)-7-(trifluoromethyl)thieno[3,2-b]pyridin-5-yl)oxy)pyrrolidine-1-carboxylate;

(S)-2-(Trifluoromethoxy)propyl 6-((3-(methylcarbamoyl)-7-(trifluoromethyl)thieno[3,2-b]pyridin-5-yl)oxy)-2-azaspiro[3.3]heptane-2-carboxylate;

(R)-2-(Trifluoromethoxy)propyl 6-((3-(methylcarbamoyl)-7-(trifluoromethyl)thieno[3,2-b]pyridin-5-yl)oxy)-2-azaspiro[3.3]heptane-2-carboxylate;

2-Trifluoromethoxy)ethyl 2,2-dimethyl-4-((3-(methylcarbamoyl)-7-(trifluoromethyl)thieno[3,2-b]pyridin-5-yl)oxy)piperidine-1-carboxylate;

(3R,4S)-3-methyl-1-(3-(Methylcarbamoyl)-7-(trifluoromethyl)thieno[3,2-b]pyridin-5-yl)piperidin-4-yl isopropylcarbamate;

(3R,4S)-3-Methyl-1-(3-(methylcarbamoyl)-7-(trifluoromethyl)thieno[3,2-b]pyridin-5-yl)piperidin-4-yl 3-(trifluoromethoxy)azetidine-1-carboxylate;

(S)-1-Cyanopropan-2-yl 4-((3-(methylcarbamoyl)-7-(trifluoromethyl)thieno[3,2-b]pyridin-5-yl)oxy)piperidine-1-carboxylate;

(S)-1-Cyanopropan-2-yl (2R,4R)-2-methyl-4-((3-(methylcarbamoyl)-7-(trifluoromethyl)thieno[3,2-b]pyridin-5-yl)oxy)piperidine-1-carboxylate;

(S)-1-Cyclopropylethyl (2R,4R)-2-methyl-4-((6-methyl-3-(methylcarbamoyl)-7-(trifluoromethyl)thieno[3,2-b]pyridin-5-yl)oxy)piperidine-1-carboxylate;

2-Hydroxy-2-methylpropyl (2R,4R)-2-methyl-4-((3-(methylcarbamoyl)-7-(trifluoromethyl)thieno[3,2-b]pyridin-5-yl)oxy)piperidine-1-carboxylate;

1-(2,2,2-Trifluoroethyl)pyrrolidin-3-yl 4-((3-(methylcarbamoyl)-7-(trifluoromethyl)thieno[3,2-b]pyridin-5-yl)oxy)piperidine-1-carboxylate;

2-(Fluoromethoxy)ethyl 4-((3-(methylcarbamoyl)-7-(trifluoromethyl)thieno[3,2-b]pyridin-5-yl)oxy)piperidine-1-carboxylate; and (S)-1-(3-Fluoroazetidin-1-yl)propan-2-yl (2R,4R)-2-methyl-4-((3-(methylcarbamoyl)-7-(trifluoromethyl)thieno[3,2-b]pyridin-5-yl)oxy)piperidine-1-carboxylate.

24. The compound of claim 1, wherein the compound is selected from the group consisting of:

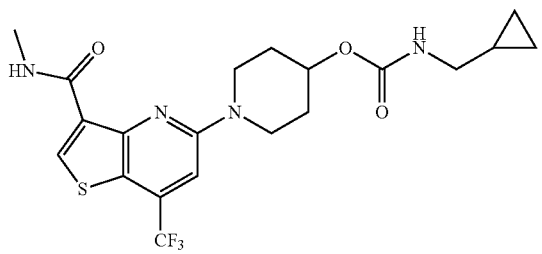

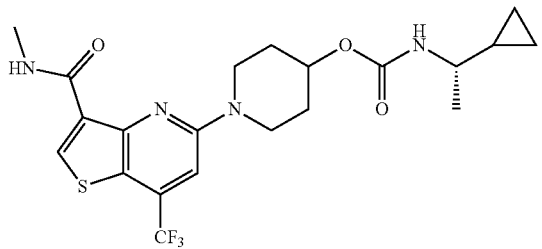

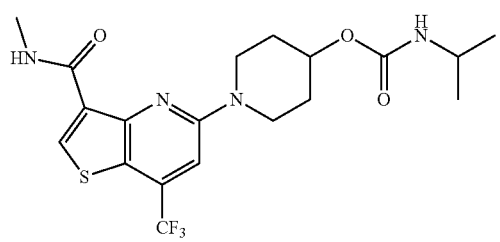

279
-continued
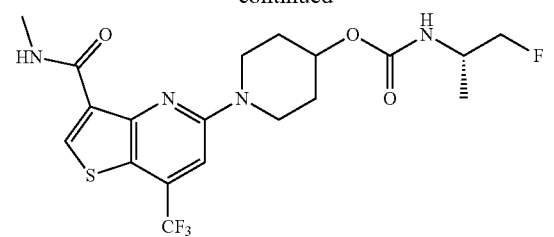
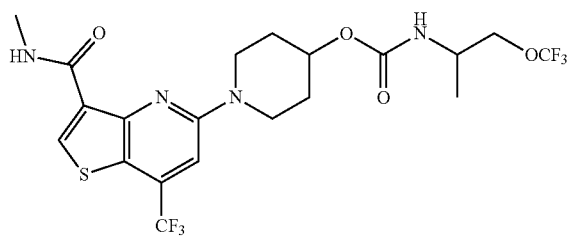
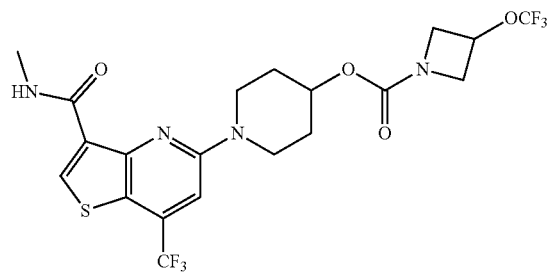
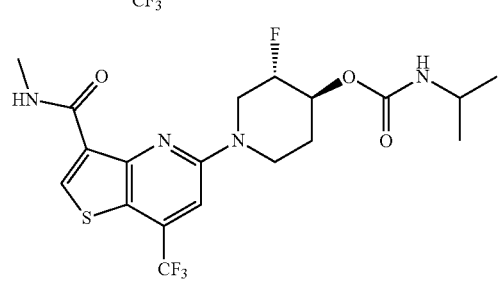
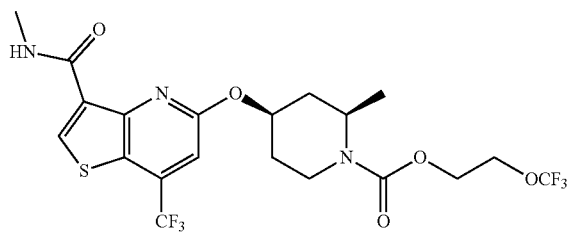
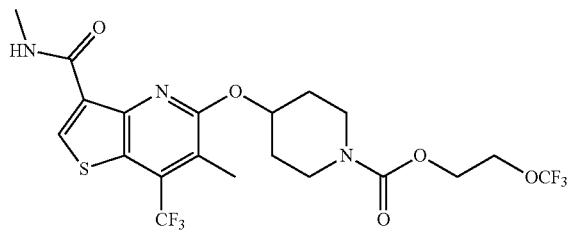
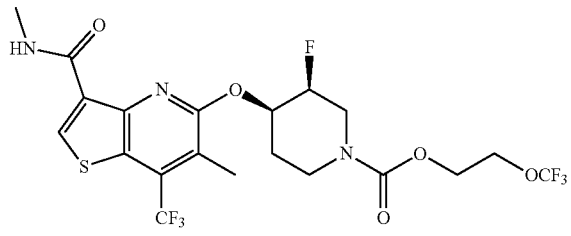
280
-continued
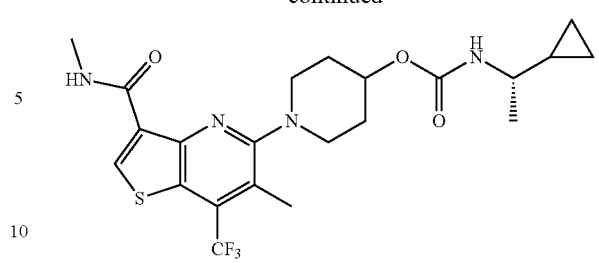
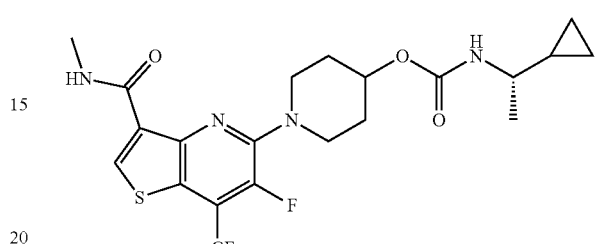
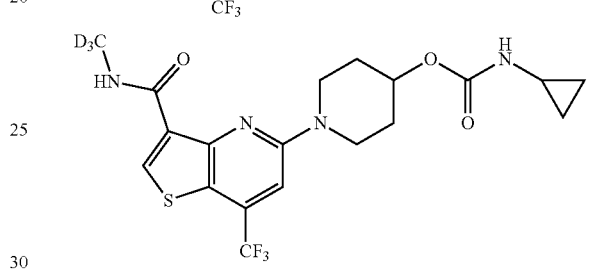
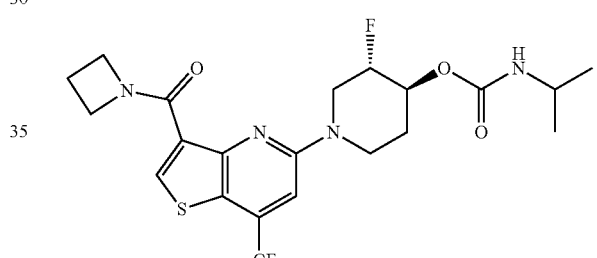
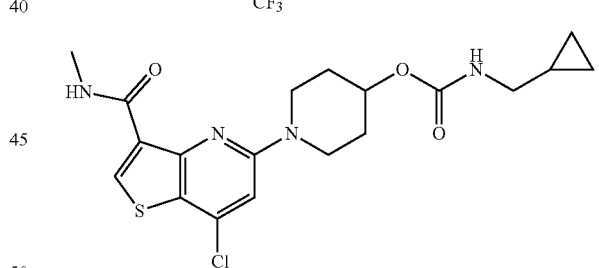
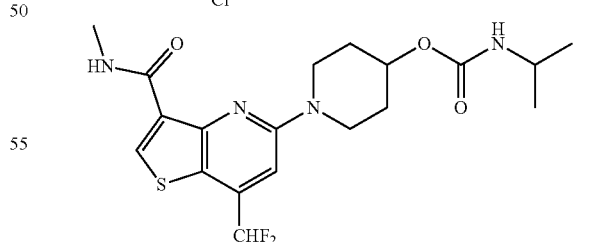
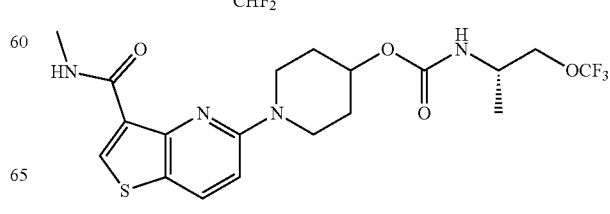

281
-continued
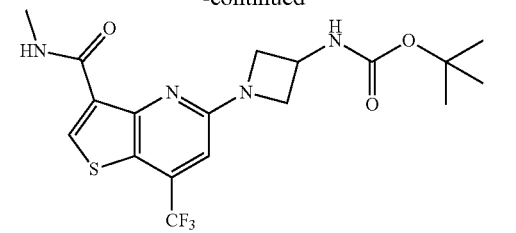
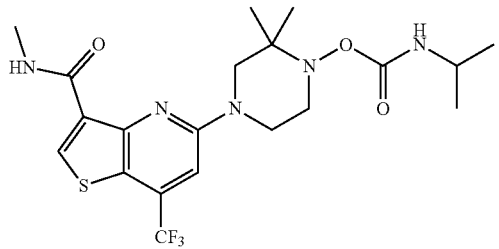
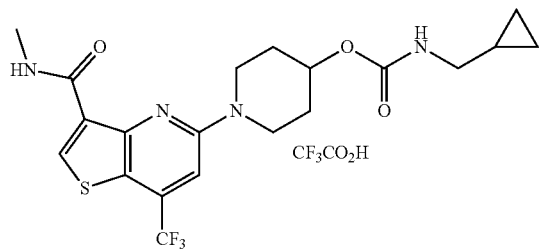
CF₃CO₂H
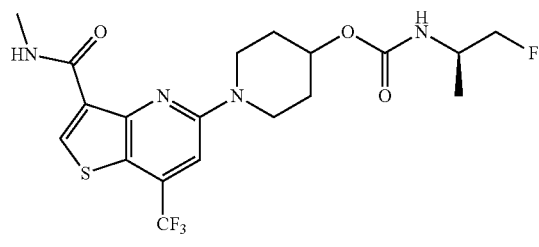
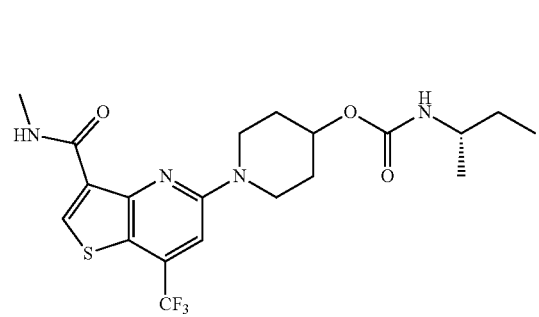
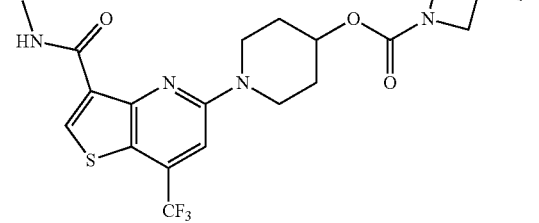
282
-continued
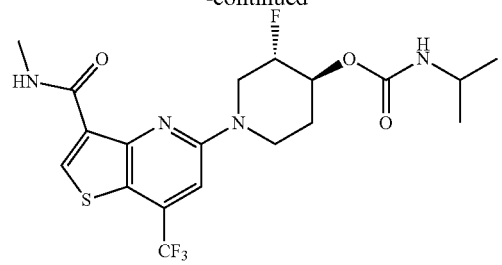
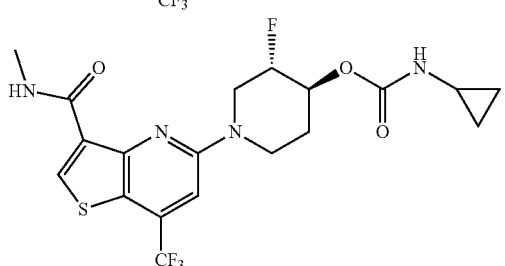
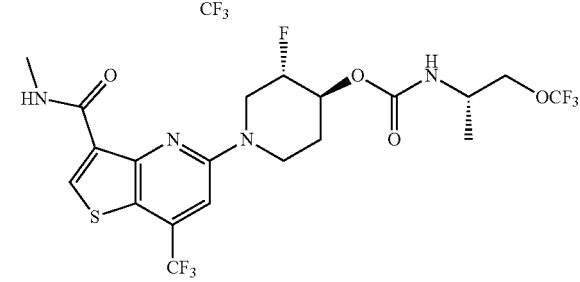
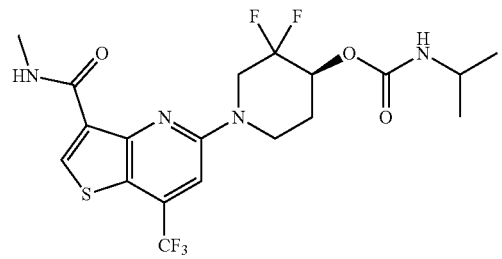
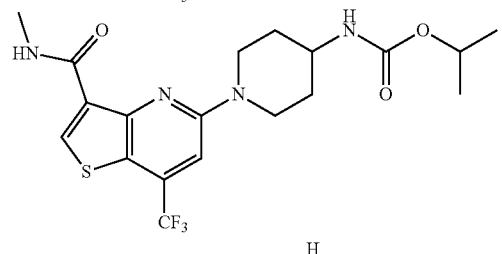
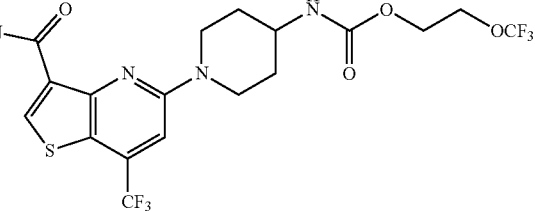
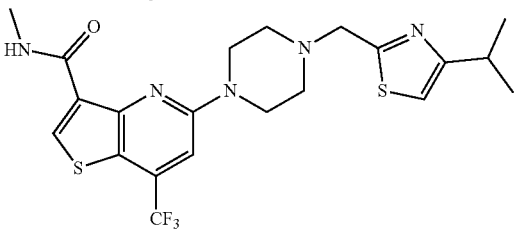

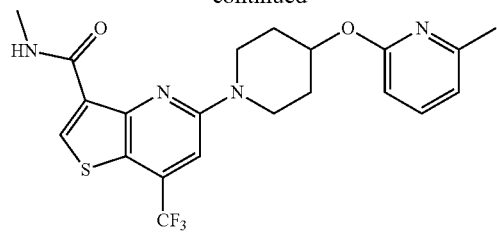
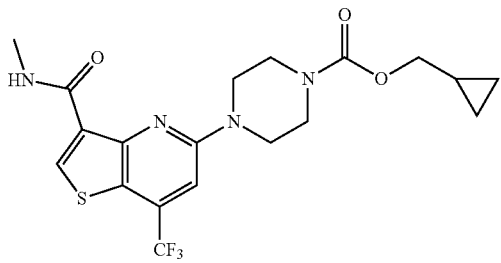
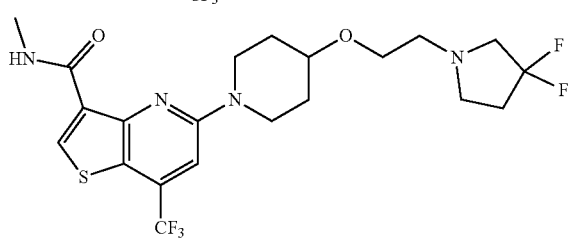
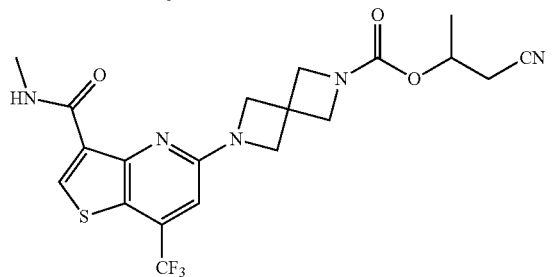
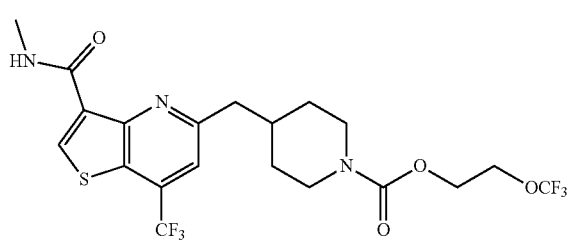
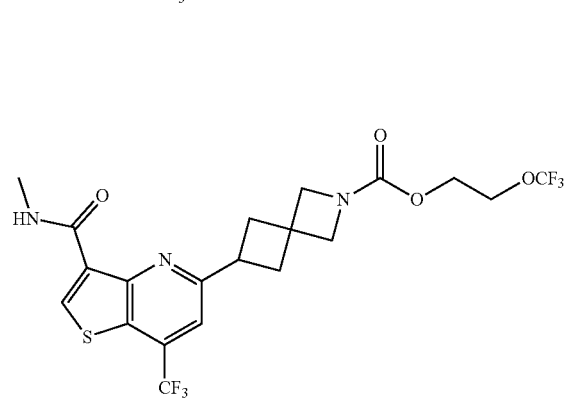
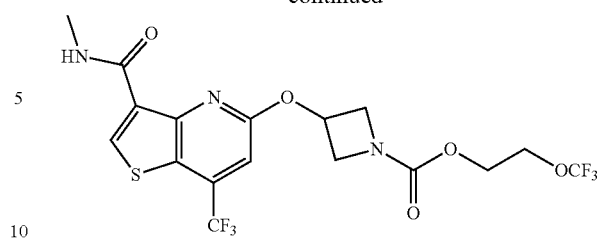
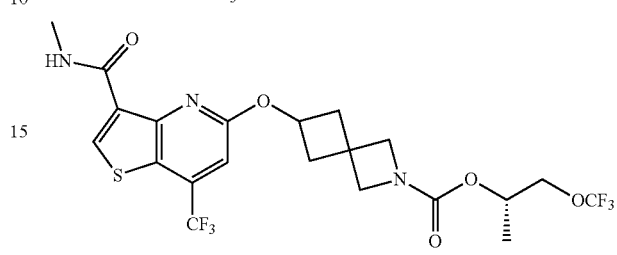
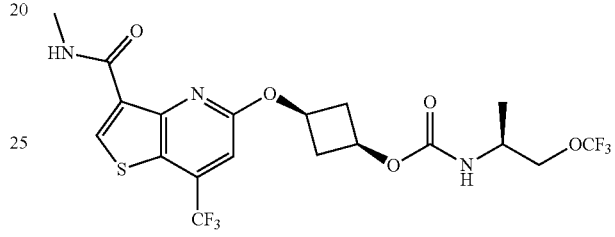
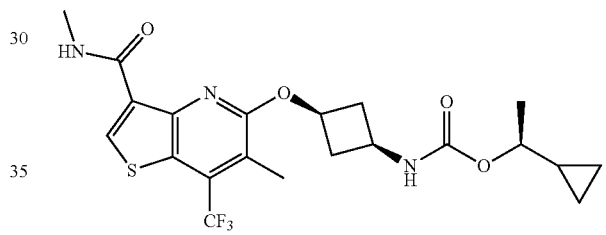
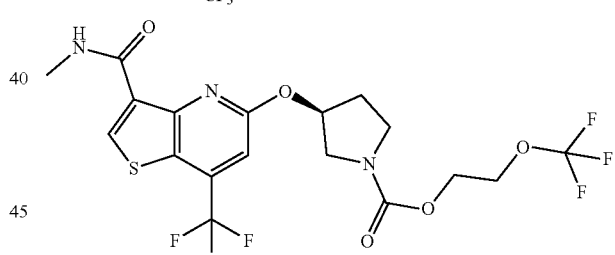
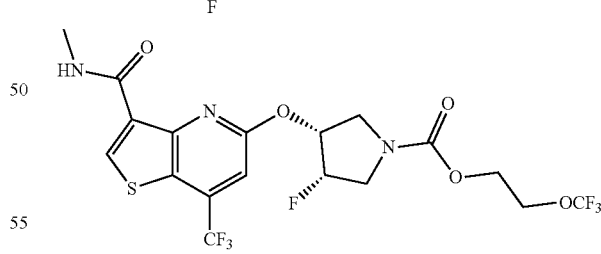
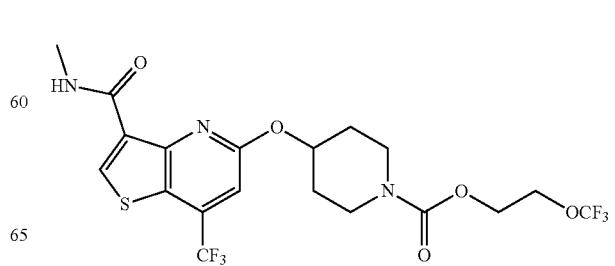

285
-continued
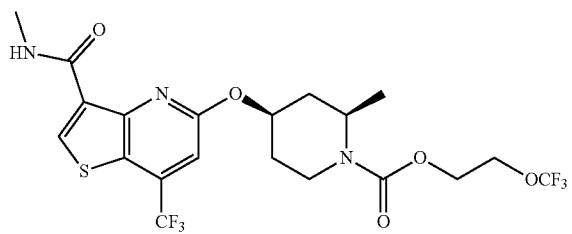
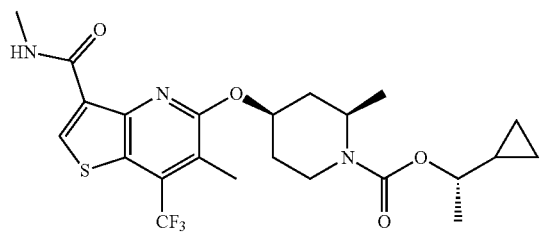
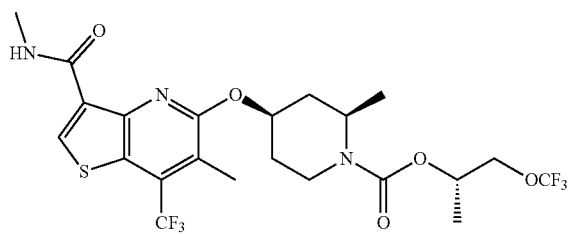
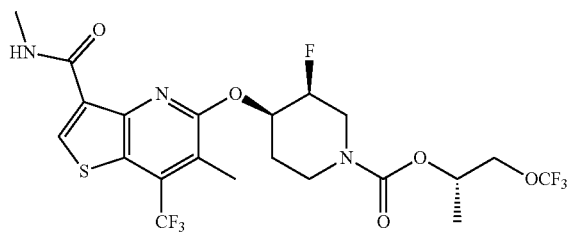
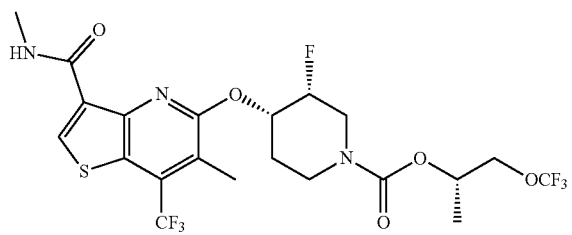
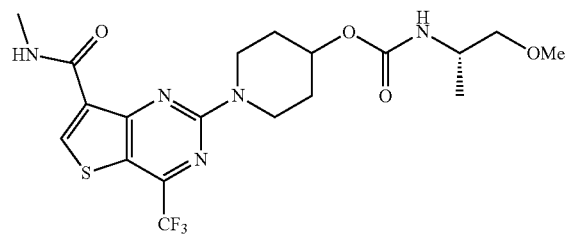
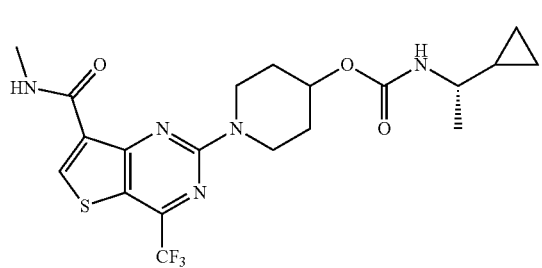
286
-continued
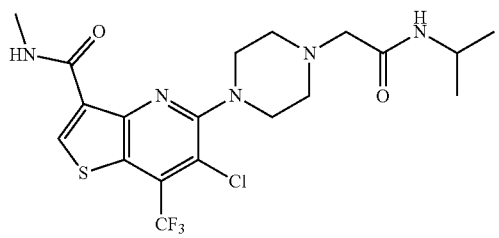
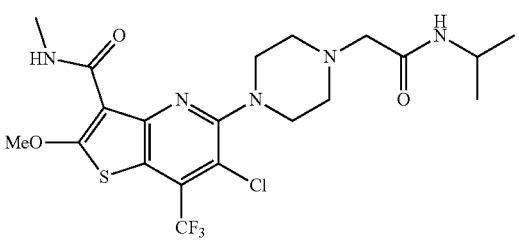
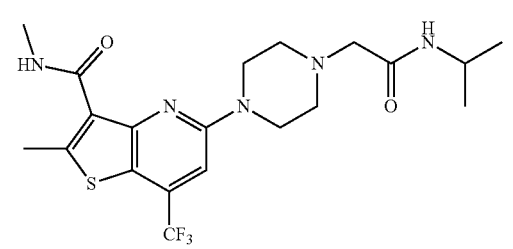
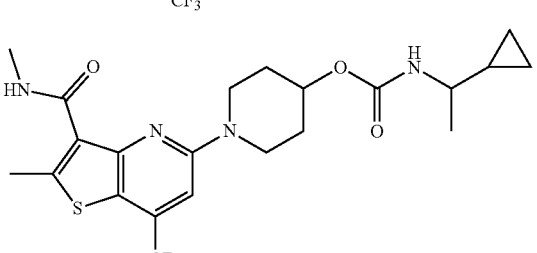
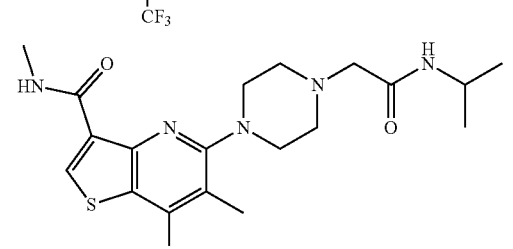
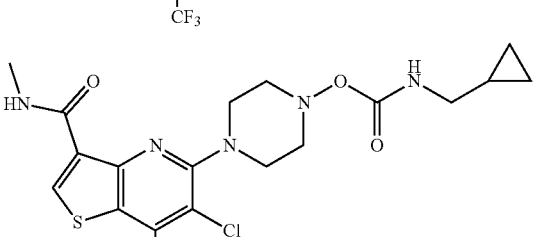
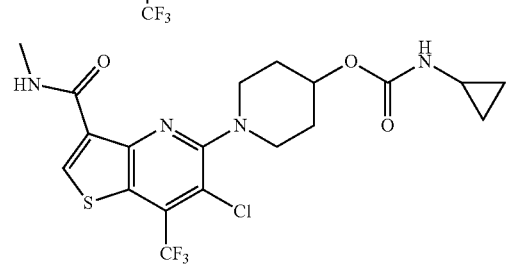

287
-continued
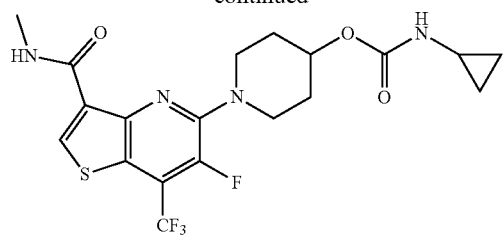
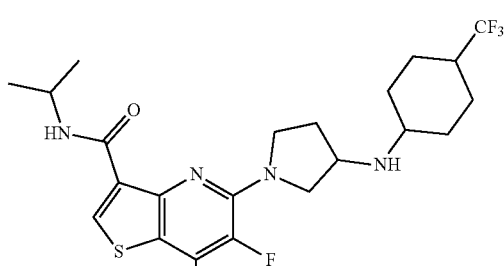
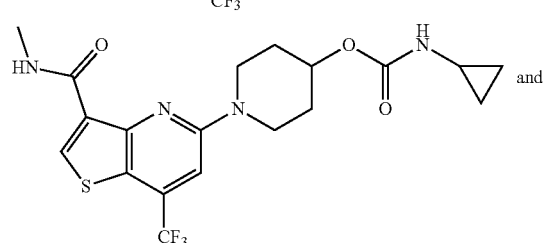 and
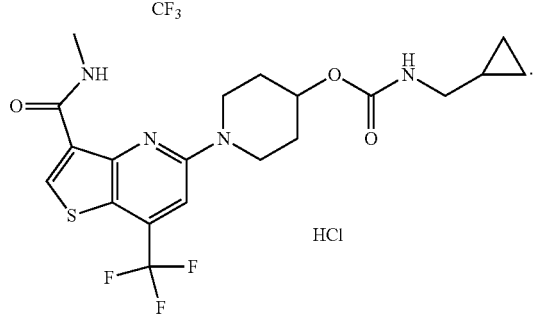
HCl
25. The compound of claim 1, wherein the compound is selected from the group consisting of:
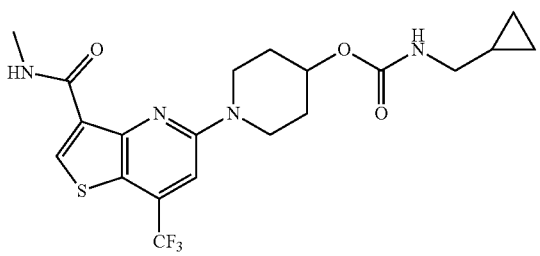
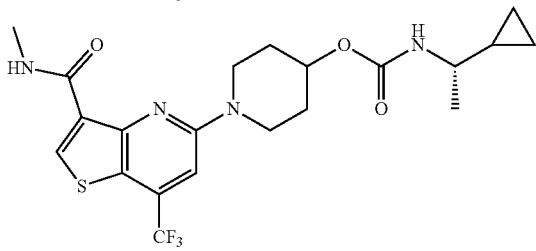
288
-continued
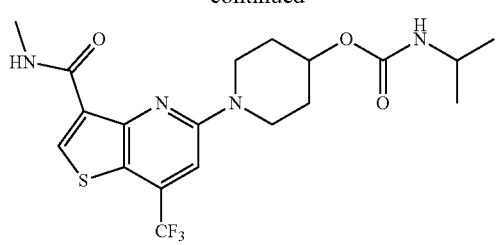
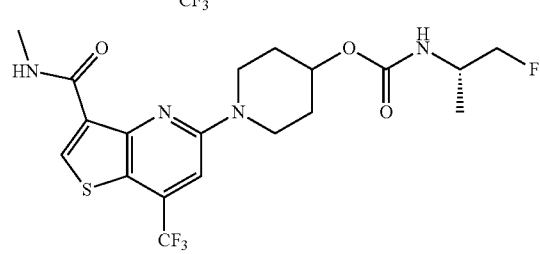
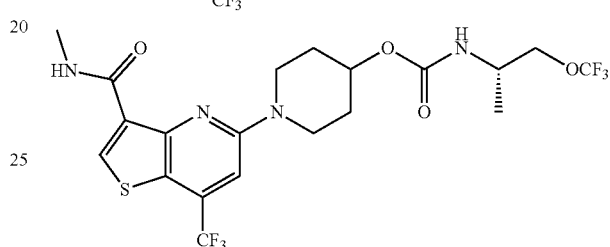
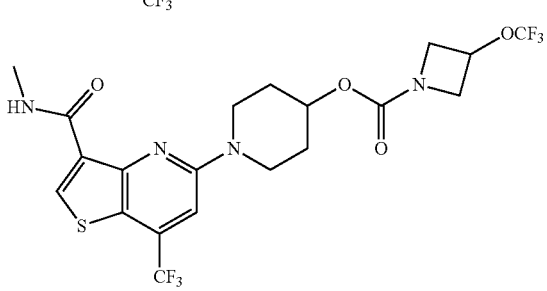
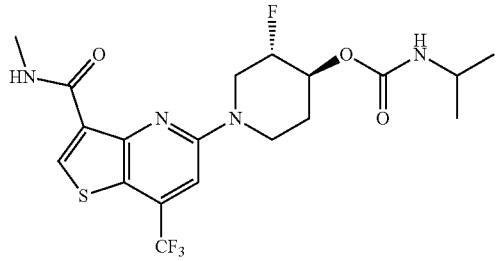
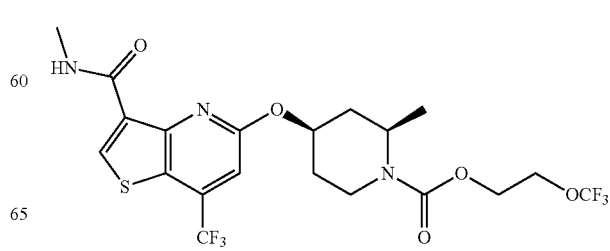

-continued
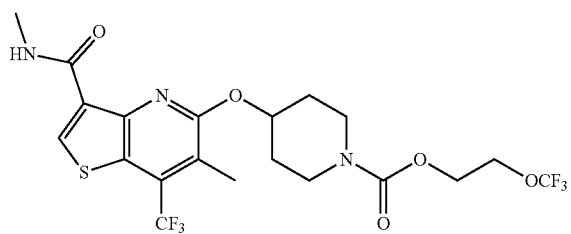
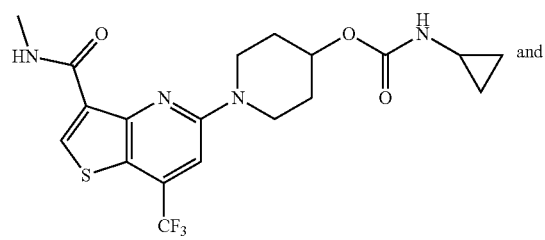
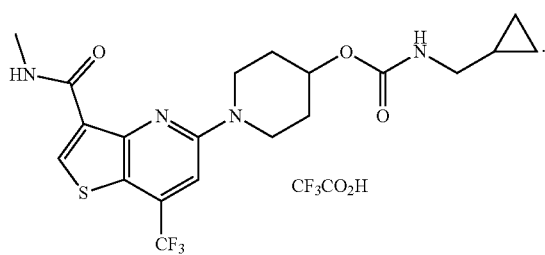
and
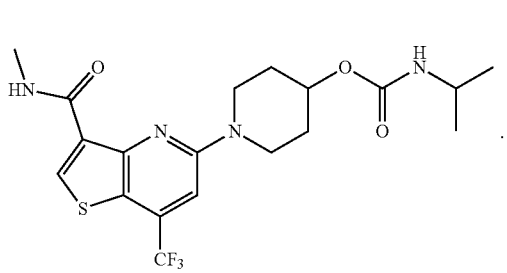 [SMILES: CNC(=O)c1csc2c(C(F)(F)F)cc(N3CCC(OC(=O)NC(C)C)CC3)nc12]
26. The compound of claim 25, wherein the compound is
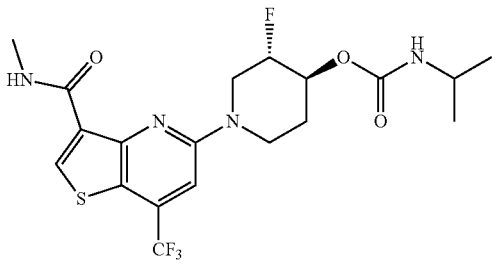
27. The compound of claim 25, wherein the compound is
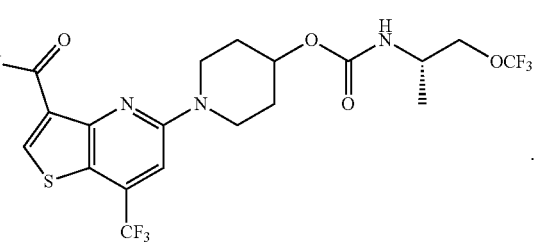
28. The compound of claim 25, wherein the compound is
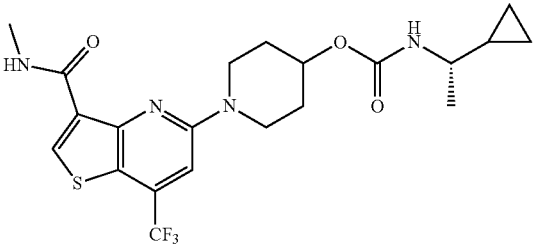
29. The compound of claim 25, wherein the compound is
30. The compound of claim 25, wherein the compound is
* * * * *

UNITED STATES PATENT AND TRADEMARK OFFICE
CERTIFICATE OF CORRECTION

PATENT NO. : 11,098,056 B2
APPLICATION NO. : 16/590027
DATED : August 24, 2021
INVENTOR(S) : Sungtaek Lim et al.

Page 1 of 3

It is certified that error appears in the above-identified patent and that said Letters Patent is hereby corrected as shown below:

In the Specification

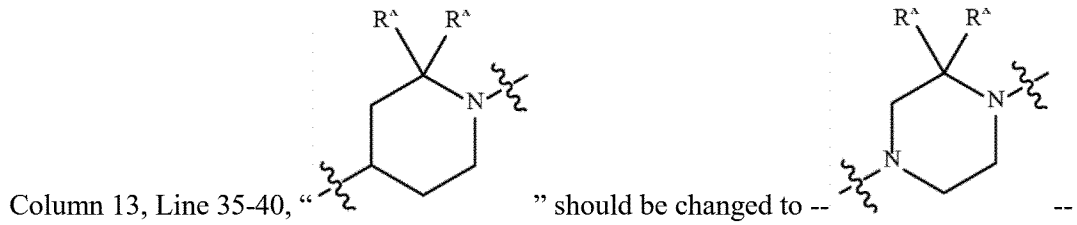

Column 13, Line 35-40, " " should be changed to -- --

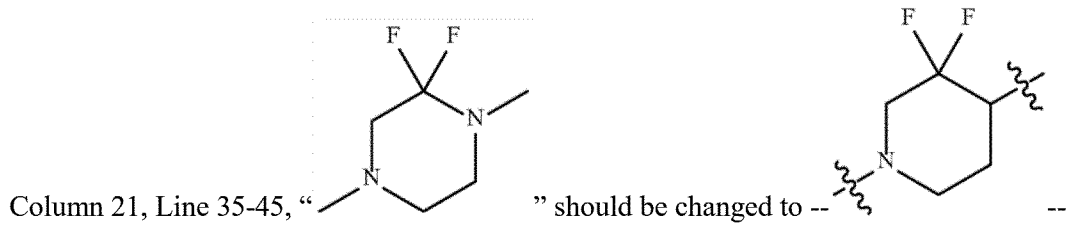

Column 21, Line 35-45, " " should be changed to -- --

Column 154, Line 59, "5 m Waters" should be changed to --5 µM Waters--

Column 162, Line 22, "7 mg, 59 mol" should be changed to --7 mg, 59 µmol--

Column 171, Line 37, "423 µmo" should be: --423 µmol--

Column 171, Line 52, "180 mol" should be changed to --180 µmol--

Column 171, Line 53, "240 mol" should be changed to --240 µmol--

Column 173, Line 64, "☐ ☐" should be: --δ--

Column 195, Line 58, "395 mol" should be changed to --395 µmol--

Signed and Sealed this
Eighteenth Day of October, 2022

Katherine Kelly Vidal
*Director of the United States Patent and Trademark Office*

CERTIFICATE OF CORRECTION (continued)
U.S. Pat. No. 11,098,056 B2

Column 224, Line 60, "3 m particles" should be changed to --3 μm particles--

Column 224, Line 64-65, "1.7 m particles" should be changed to --1.7 μm particles--

In the Claims

Claim 24, Column 286, Line 30-35,

" 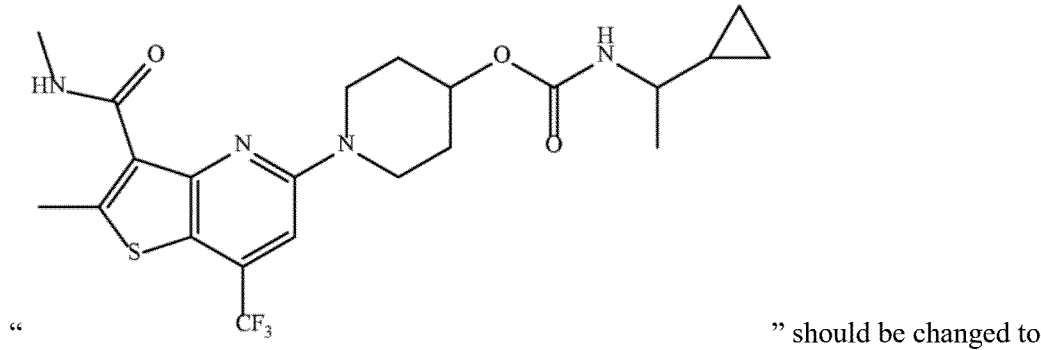 " should be changed to

-- 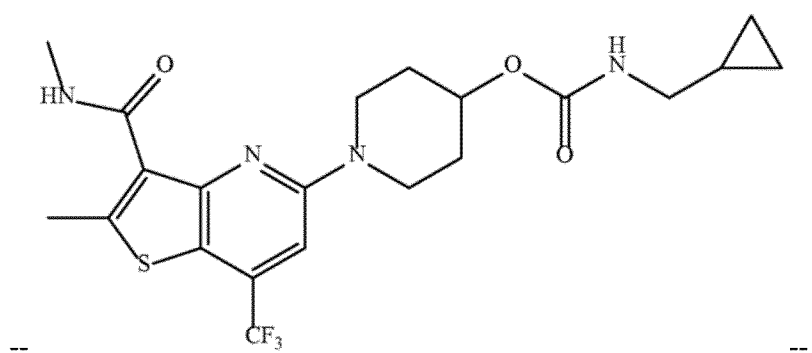 --

Claim 24, Column 286, Line 50-55,

" 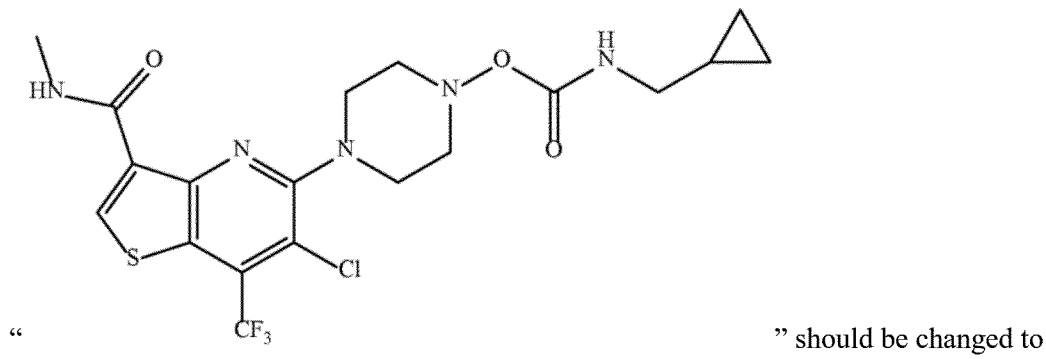 " should be changed to